US011981906B2

(12) United States Patent
Nadzan et al.

(10) Patent No.: US 11,981,906 B2
(45) Date of Patent: May 14, 2024

(54) NUCLEOTIDE SEQUENCES AND CORRESPONDING POLYPEPTIDES CONFERRING MODIFIED PHENOTYPE CHARACTERISTICS IN PLANTS

(71) Applicant: Ceres, Inc., Thousand Oaks, TX (US)

(72) Inventors: Gregory Nadzan, Woodland Hills, CA (US); Richard Schneeberger, Carlsbad, CA (US); Han Suk Kim, Camarillo, CA (US); David Van-dinh Dang, San Diego, CA (US); Kenneth A. Feldmann, Tucson, AZ (US); Roger Pennell, Malibu, CA (US); Shing Kwok, Woodland Hills, CA (US); Hongyu Zhang, Thousand Oaks, CA (US); Cory Christensen, Sherwood, OR (US); Jack Okamuro, Oak Park, CA (US); Fasong Zhou, Oxnard, CA (US); Wuyi Wang, Newbury Park, CA (US); Emilio Margolles-Clark, Miami, FL (US); Gerard Magpantay, Calabasas, CA (US); Julissa Sosa, Northridge, CA (US); Nestor Apuya, Culver City, CA (US); Kerstin Piccolo, Woodland Hills, CA (US); Bonnie Hund, Denver, CO (US); Nickolai Alexandrov, Thousand Oaks, CA (US); Vyacheslav Brover, Simi Valley, CA (US); Peter Mascia, Thousand Oaks, CA (US)

(73) Assignee: Ceres, Inc., Thousand Oaks, CA (US)

( * ) Notice: Subject to any disclaimer, the term of this patent is extended or adjusted under 35 U.S.C. 154(b) by 935 days.

(21) Appl. No.: 16/991,897

(22) Filed: Aug. 12, 2020

(65) Prior Publication Data

US 2021/0087576 A1 Mar. 25, 2021

Related U.S. Application Data

(60) Division of application No. 15/689,941, filed on Aug. 29, 2017, now Pat. No. 10,815,494, which is a division of application No. 13/644,359, filed on Oct. 4, 2012, now Pat. No. 9,777,287, which is a continuation-in-part of application No. 13/465,846, filed on May 7, 2012, now abandoned, which is a division of application No. 10/572,827, filed on Mar. 7, 2007, now Pat. No. 8,193,409, said application No. 13/644,359 is a continuation-in-part of application No. 11/779,266, filed on Jul. 17, 2007, now abandoned, which is a continuation-in-part of application No. 11/778,060, filed on Jul. 15, 2007, now abandoned, which is a continuation-in-part of application No. 11/248,547, filed on Oct. 12, 2005, now Pat. No. 7,244,879, said application No. 13/644,359 is a continuation-in-part of application No. 12/514,991, filed as application No. PCT/US2007/085007 on Nov. 16, 2007, now abandoned, said application No. 13/644,359 is a continuation-in-part of application No. 12/445,005, filed as application No. PCT/US2007/081301 on Oct. 12, 2007, now abandoned, said application No. 13/644,359 is a continuation-in-part of application No. 12/515,707, filed as application No. PCT/US2007/085439 on Nov. 21, 2007, now abandoned, said application No. 13/644,359 is a continuation-in-part of application No. 12/615,920, filed on Nov. 10, 2009, now Pat. No. 8,471,099, (Continued)

(51) Int. Cl.
*C12N 15/82* (2006.01)
*C07K 14/415* (2006.01)

(52) U.S. Cl.
CPC ........ *C12N 15/8271* (2013.01); *C07K 14/415* (2013.01); *C12N 15/8201* (2013.01); *C12N 15/8241* (2013.01); *C12N 15/8261* (2013.01); *C12N 15/8269* (2013.01); *Y02A 40/146* (2018.01)

(58) Field of Classification Search
None
See application file for complete search history.

(56) References Cited

U.S. PATENT DOCUMENTS 7,696,409 B2  4/2010  Schneeberger et al.
8,471,099 B2  6/2013  Schneeberger et al.

(Continued)

FOREIGN PATENT DOCUMENTS

EP         1033405         9/2000
EP         1033405 A2 *    9/2000  ............ C07H 21/04
WO    WO 2009/105612       8/2009

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495, 1994).*
Thornton et al. (Nature structural Biology, structural genomics supplement, Nov. 2000).*

(Continued)

*Primary Examiner* — Vinod Kumar
(74) *Attorney, Agent, or Firm* — Dentons US LLP

(57) ABSTRACT

Methods and materials for modulating low-nitrogen tolerance levels in plants are disclosed. For example, nucleic acids encoding low nitrogen tolerance-modulating polypeptides are disclosed as well as methods for using such nucleic acids to transform plant cells. Also disclosed are plants having increased[RCL2] low-nitrogen tolerance levels and plant products produced from plants having increased low-nitrogen tolerance levels.

9 Claims, 165 Drawing Sheets

Specification includes a Sequence Listing.

Related U.S. Application Data which is a division of application No. 11/114,963, filed on Apr. 25, 2005, now Pat. No. 7,696,409, said application No. 13/644,359 is a continuation-in-part of application No. 12/605,261, filed on Oct. 23, 2009, now abandoned, which is a division of application No. 11/298,391, filed on Dec. 8, 2005, now Pat. No. 7,663,027, said application No. 13/644,359 is a continuation-in-part of application No. 12/377,106, filed as application No. PCT/US2007/075747 on Aug. 10, 2007, now abandoned, said application No. 13/644,359 is a continuation of application No. 12/541,607, filed on Aug. 14, 2009, now abandoned, which is a continuation of application No. 11/140,347, filed on May 27, 2005, now Pat. No. 7,576,260, said application No. 13/644,359 is a continuation-in-part of application No. 13/184,361, filed on Jul. 15, 2011, now Pat. No. 8,962,921, which is a division of application No. 11/140,450, filed on May 27, 2005, now Pat. No. 8,022,273, said application No. 13/644,359 is a continuation-in-part of application No. 11/654,357, filed on Jan. 16, 2007, now abandoned, said application No. 13/644,359 is a continuation-in-part of application No. 13/465,841, filed on May 7, 2012, now Pat. No. 9,765,355, which is a division of application No. 11/858,117, filed on Sep. 19, 2007, now abandoned, which is a continuation-in-part of application No. PCT/US2007/006544, filed on Mar. 14, 2007, said application No. 13/644,359 is a continuation-in-part of application No. 12/922,143, filed as application No. PCT/US2009/037025 on Mar. 12, 2009, now abandoned, said application No. 13/644,359 is a continuation-in-part of application No. 11/241,685, filed on Sep. 30, 2005, now Pat. No. 8,481,814, said application No. 13/644,359 is a continuation-in-part of application No. 12/863,773, filed as application No. PCT/US2009/031609 on Jan. 21, 2009, now abandoned, said application No. 13/644,359 is a continuation-in-part of application No. 12/282,342, filed as application No. PCT/US2007/006544 on Mar. 14, 2007, now Pat. No. 8,324,454, said application No. 13/644,359 is a continuation-in-part of application No. 12/911,698, filed on Oct. 25, 2010, now Pat. No. 9,914,935, which is a division of application No. 11/324,098, filed on Dec. 29, 2005, now Pat. No. 7,884,261, which is a continuation-in-part of application No. 11/172,740, filed on Jun. 30, 2005, now Pat. No. 7,396,979, said application No. 13/644,359 is a continuation-in-part of application No. 13/609,176, filed on Sep. 10, 2012, now abandoned, which is a division of application No. 12/139,269, filed on Jun. 13, 2008, now abandoned, which is a division of application No. 11/172,740, filed on Jun. 30, 2005, now Pat. No. 7,396,979, said application No. 13/644,359 is a continuation-in-part of application No. 12/918,609, filed as application No. PCT/US2009/034638 on Feb. 20, 2009, now abandoned, said application No. 13/644,359 is a continuation-in-part of application No. 12/776,319, filed on May 7, 2010, now abandoned, which is a division of application No. 11/324,093, filed on Dec. 29, 2005, now Pat. No. 7,803,983, which is a continuation-in-part of application No. 11/172,740, filed on Jun. 30, 2005, now Pat. No. 7,396,979.

(60) Provisional application No. 61/036,396, filed on Mar. 13, 2008, provisional application No. 61/030,152, filed on Feb. 20, 2008, provisional application No. 61/022,786, filed on Jan. 22, 2008, provisional application No. 60/860,296, filed on Nov. 21, 2006, provisional application No. 60/859,467, filed on Nov. 16, 2006, provisional application No. 60/851,585, filed on Oct. 12, 2006, provisional application No. 60/837,434, filed on Aug. 11, 2006, provisional application No. 60/782,735, filed on Mar. 14, 2006, provisional application No. 60/778,568, filed on Mar. 1, 2006, provisional application No. 60/758,831, filed on Jan. 13, 2006, provisional application No. 60/635,140, filed on Dec. 8, 2004, provisional application No. 60/635,115, filed on Dec. 8, 2004, provisional application No. 60/615,080, filed on Sep. 30, 2004, provisional application No. 60/583,621, filed on Jun. 30, 2004, provisional application No. 60/584,829, filed on Jun. 30, 2004, provisional application No. 60/584,800, filed on Jun. 30, 2004, provisional application No. 60/575,309, filed on May 27, 2004, provisional application No. 60/575,253, filed on May 27, 2004, provisional application No. 60/564,659, filed on Apr. 23, 2004.

(56) References Cited

U.S. PATENT DOCUMENTS

| | | | |
|---|---|---|---|
| 9,777,287 B2 | 10/2017 | Nadzan et al. | |
| 10,428,344 B2 | 10/2019 | Nadzan et al. | |
| 10,815,494 B2 | 10/2020 | Nadzan et al. | |
| 11,396,659 B2 | 7/2022 | Nadzan et al. | |
| 11,624,075 B2 | 4/2023 | Nadzan et al. | |
| 2002/0160378 A1 | 10/2002 | Harper et al. | |
| 2004/0009476 A9 | 1/2004 | Harper et al. | |
| 2006/0107345 A1* | 5/2006 | Alexandrov | C07K 14/415 536/23.6 |
| 2011/0061124 A1 | 3/2011 | Nadzan et al. | |
| 2015/0259699 A1* | 9/2015 | Nadzan | C07K 14/415 800/267 |
| 2017/0037426 A1 | 2/2017 | Alexandrov et al. | |
| 2020/0048653 A1 | 2/2020 | Nadzan et al. | |
| 2020/0056199 A1 | 2/2020 | Nadzan et al. | |
| 2021/0079416 A1 | 3/2021 | Nadzan et al. | |

OTHER PUBLICATIONS

Keskin et al. (Protein Science, 13:1043-1055, 2004).*
Doerks et al., (TIG, 14:248-250, 1998).*
Smith et al. (Nature Biotechnology, 15:1222-1223, 1997).*
Bork et al. (TIG, 12:425-427, 1996).*
USPTO: Corrected Notice of Allowability for U.S. Appl. No. 15/689,941, dated Aug. 25, 2020.
UniProt Accession No. Q9C9V8_ARATH, dated Jun. 1, 2001.
Forde, "Local and long-range signaling pathways regulating plant responses to nitrate," Annu Rev Plant Biol, 53:203-224, 2002.
Gazzarrini et al., "Three functional transporters for constitutive, diurnally regulated, and starvation-induced uptake of ammonium into *Arabidopsis* roots," Plant Cell, 11:937-948, 1999.
GenBank Gene ID: 4914437, CD630_27000 sigma-54 dependent transcriptional regulator [Clostridioides difficile 630], Available at https://www.ncbi.nlm.nih.gov/gene/?term=4914437, Retrieved Jan. 12, 2017.
GenBank Gene ID: 7981380, DMR_t00510 [Desulfovibrio magneticus RS-1], Available at https://www.ncbi.nlm.nih.gov/gene/7981380, Retrieved Jan. 12, 2017.
Huber et al., "Regulation of maize leaf nitrate reductase activity involves both gene expression and protein phosphorylation," Plant Physiol, 106:1667-1674, 1994.
Hwang et al., "Sequences necessary for nitrate-dependent transcription of *Arabidopsis* nitrate reductase genes," Plant Physiol, 113:853-862, 1997.

(56) References Cited

OTHER PUBLICATIONS

Okamoto et al., "Regulation of NRT1 and NRT2 gene families of *Arabidopsis thaliana*: responses to nitrate provision," Plant Cell Physiol, 44:304-317, 2003.
Redinbaugh et al., "Higher plant responses to environmental nitrate," Physiol Plant, 82:640-650, 1991.
Good et al., "Can less yield more? Is reducing nutrient input into the environment compatible with maintaining crop production?," *TRENDS in Plant Science* 9(12):597-605, 2004.
Guerois et al., "Predicting Changes in the Stability of Proteins and Protein Complexes: A Study of More Than 1000 Mutations," *J. Mol. Biol.* 320:369-387, 2002.
Kumar et al., "Predicting the effects of coding non-synonymous variants on protein function using the SIFT algorithm," *Nature Protocols* 4(8):1073-1082, 2009.
Ng et al., "Predicting the Effects of Amino Acid Substitutions on Protein Function," *Annu. Rev. Genom. Hum. Genet.* 7:61-80, 2006.
Reva et al., "Predicting the functional impact of protein mutations: application to cancer genomics," *Nucleic Acids Research* 39(17):e118, 2011.
Sandhya et al., "CUSP: an algorithm to distinguish structurally conserved and unconserved regions in protein domain alignments and its application in the study of large length variations," BMS Structural Biology; 14 pages; May 31, 2008.
Bowie et al., Science 247:1306-1310, 1990.
Mcconnell et al., Nature 411 (6838): 709-713, 2001.
Kano-Murakami et al., (1993, FEBS 334:365-368).
Eddy, 2004, Nature Biotechnology 22(10):1315-1316.
Falcon-Perez et al., Functional Domain Analysis of the Yeast ABC Transporter Yof1p by Site-Directed Mutagenesis, The Journal of Biological Chemistry 274(33):23584-23590, 1999.
Hill and Preiss, Functional Analysis of Conserved Histidines in ADP-Glucose Pyrophosphorylase from *Escherichia coli*1, Biochemical and Biophysical Research Communications 244:573-577, 1998.
Guo et al., Protein Tolerance to Random Amino Acid Change, PNAS 101(25):9205-9210, 2004.
Lazar et al., Transforming Growth Factor alpha: Mutation of Aspartic Acid 47 and Leucine 48 Results in Different Biological Activities, Molecular and Cellular Biology 8(3):1247-1252, 1988.
Sweetlove et al., Starch Metabolism in Tubers of Transgenic Potato (*Solanum tuberosum*) with Increased ADPglucose Pyrophosphorylase, Biochemical Journal 320:493-498, 1996.
Fourgoux-Nicol et al., Isolation of Rapeseed Genes Expressed Early and Specifically During Development of the Male Gametophyte, Plant Molecular Biology 40:857-872, 1999.
U.S. Appl. No. 16/991,904, filed Aug. 12, 2020, Nadzan et al.

* cited by examiner

Figure 1

| | | |
|---|---|---|
| SEQ_ID_NO_21 | ---------- ---MTNLYLT L---------- ---------- ---------- | 8 |
| SEQ_ID_NO_36 | ---------- ---MNPLA-- ---------- ---------- ---------- | 5 |
| SEQ_ID_NO_47 | ---------- ---MGLWIV F--------- ---------- ---------- | 8 |
| SEQ_ID_NO_4 | -----MENRR SSGSGWWVC VLP------L FTKDGPAYFL HSSSDDVSAW | 39 |
| SEQ_ID_NO_46 | ---------- ---------- ---------- ---------- ---------- | 0 |
| SEQ_ID_NO_39 | --MDSSPSTD DCGGVLLYVS LAAKC---G GDPCRVVGFV ---------- | 34 |
| SEQ_ID_NO_40 | MDMDSSPSTD DCGGVLLYVS LAAKC---G GDPCRVVGFV ---------- | 36 |
| SEQ_ID_NO_27 | -----MAPSE KC-GWLLYVS LAAKCCGNGD GKPYRVVGFV ---------- | 34 |
| SEQ_ID_NO_29 | -----MAPPTE DC-GWLLYLS LAAKC---- GDPQRLLGFA ---------- | 30 |
| SEQ_ID_NO_38 | -----MAPSE DC-GWLLYLS LAAKC---- GDPHRLLGFA ---------- | 29 |
| SEQ_ID_NO_3 | --------MAI KLDTSSLLLA LSKC---SL LTQTNLALSL ---------- | 30 |
| SEQ_ID_NO_25 | --------MSI NL-DNLWIFA LASKC---- -TQENLAYSL ---------- | 26 |
| SEQ_ID_NO_22 | --------MTS HDDNLWIALL TSKC---- -TQENLAWL ---------- | 27 |
| SEQ_ID_NO_6 | --------MGS DL-ESVWLFA LASKC--KA FSQQNTAWPL ---------- | 29 |
| SEQ_ID_NO_10 | --------MRT DL-DSFWIFA LASKC--RA FTQENLAWSL ---------- | 29 |
| | | |
| SEQ_ID_NO_21 | -----LLPT FIFLIVLVLS ---------- ---------- ---RRRNNR | 28 |
| SEQ_ID_NO_36 | -----LIFC TALFCILYH FL-------- ---------- ---TRRSVR | 27 |
| SEQ_ID_NO_47 | -----VTIV AAIINRLLN LI-------- ---------- ---KKPTLP | 30 |
| SEQ_ID_NO_4 | RQWPLYALL IVANCAVLVS MLSPGGCAWA GRH------- ----KRGRVA | 78 |
| SEQ_ID_NO_46 | ---------- ---------- ---------- ---------- ---------- | 0 |
| SEQ_ID_NO_39 | -----AVAV VAFAMTSLLH MLSPGGPAWG RYWW------ ----NRRGGLG | 69 |
| SEQ_ID_NO_40 | -----AVAV VAFAMTSLLH MLSPGGPAWG RYWW------ ----NRRGGLG | 71 |
| SEQ_ID_NO_27 | -----VVLL AAFVVTSLLH MASQGGAAWG RYWW------ ----RRKGLG | 68 |
| SEQ_ID_NO_29 | -----AVFV AACVVTSLLH MASPGGPAWG WYWW------ ----TRRAGLG | 65 |
| SEQ_ID_NO_38 | -----AVLA TAFVVTALLH MASPGGPAWG RYWW------ ----TRRAGLG | 64 |
| SEQ_ID_NO_3 | -----LVAS LASLALSLFF MSHPGGPAWG KYFL------ ----HRRQTT | 65 |
| SEQ_ID_NO_25 | -----LIMA LLWITMFFY MSHPGGPAWG KYYYSSNYST TKTNNKNNLN | 70 |
| SEQ_ID_NO_22 | -----LIMG SLWLTMTFYY MSHPGGPAWG KYYT------ ----YSPPLS | 61 |
| SEQ_ID_NO_6 | -----LIIA LAWLVMTIVY MVHPGGPAWG KYRF------ ----KKCAIT | 63 |
| SEQ_ID_NO_10 | -----LIIG LAWIVVTLIY MAYPGGPAWG KYKL------ ----KNTSLT | 63 |

Figure 1 (continued)

| | | | | | | | |
|---|---|---|---|---|---|---|---|
| SEQ_ID_NO_21 | L--------- | ----PPGPNP | APIIGNLPHM | -GPKPHQTLA | AMVTT---YG | | 81 |
| SEQ_ID_NO_36 | L--------- | ----PPGPKP | MPIVGNLPHL | -GPVPHHSIA | ALAKT---YG | | 80 |
| SEQ_ID_NO_47 | L--------- | ----PPGPSP | MPIVGNLPHM | -GPVPHHALA | ALALK---HG | | 63 |
| SEQ_ID_NO_4 | --------- | ----IPGPKG | MPIIGSLMDM | SVGLPHRKLE | SLARL-HGAK | | 113 |
| SEQ_ID_NO_46 | --------- | ---------- | ---------- | ---------- | ---------- | | 0 |
| SEQ_ID_NO_39 | AAA------ | ----PGPRG | LPVLGSMSLM | -AGLAHRKLA | AAAGGSPARR | | 108 |
| SEQ_ID_NO_40 | AAA------ | ----PGPRG | LPVLGSMSLM | -AGLAHRKLA | AAAGGSPARR | | 110 |
| SEQ_ID_NO_27 | GEAR----- | ----PGPRG | FPVIGSMGLM | -TGLAHRKLA | AAAAGNVRRR | | 108 |
| SEQ_ID_NO_29 | VRAA----- | ----PGPRG | LPVVGSMGLM | -TGLAHRKLS | AAAEROASRR | | 105 |
| SEQ_ID_NO_38 | GAA------ | ----PGPRG | LPVLGSMGLM | -TGLAHRKLA | AAASK--ARR | | 101 |
| SEQ_ID_NO_3 | V-------- | ----PGPRG | LPEVGSMSLM | SNTLAHRCIA | ATAEK-FRAE | | 101 |
| SEQ_ID_NO_25 | SSTKPSTTTS | SSIFIPGPKG | YPLEGSMNLM | SSSLAHHRIA | STAKT-CKAT | | 119 |
| SEQ_ID_NO_22 | D-------- | ----PGPKG | FPLIGSMGLM | -TGLAHHRIA | AAAAT-CRAK | | 96 |
| SEQ_ID_NO_6 | TINKP---- | ----PGPRG | LPLIGSMNMV | ANSLAHHLIA | TIAKT-CKAK | | 103 |
| SEQ_ID_NO_10 | SNP------ | ----PGPRG | FPITGSMKLM | -TGLAHHKIA | AAADA-CKAR | | 101 |

| | | | | | | | |
|---|---|---|---|---|---|---|---|
| SEQ_ID_NO_21 | PLLHLRLCFA | DVVVAASKSM | AEQFLKVHDA | NFASRPPNSG | AKHMAYNYDD | | 111 |
| SEQ_ID_NO_36 | PLMHLRMCFV | DVVVAASASM | AADFLKTHDA | NFSNRPPNSG | AKHIAYNYDD | | 110 |
| SEQ_ID_NO_47 | PLMHLQLGFV | DVIVAASASM | AEQFLKVHDA | NFSSRPPNSG | AKYIAYNYDD | | 113 |
| SEQ_ID_NO_4 | QLMSFSLCCT | PAVITSDPEV | ARELLL-TSP | HFANRPLKQS | AQQLLFG-RA | | 160 |
| SEQ_ID_NO_46 | --MAFSYGLT | REIVSSHPKT | AKEILL-SSP | AFADRPIKES | AYELLFN-RA | | 45 |
| SEQ_ID_NO_39 | RLMALSLGET | RVVVTADPGM | ARELLL-ASA | AFADRPVKES | AYGMLFH-RA | | 155 |
| SEQ_ID_NO_40 | RLMALSLGET | RVVVTADPGM | ARELLL-ASA | AFADRPVKES | AYGMLFH-RA | | 157 |
| SEQ_ID_NO_27 | RLMSFSMGET | RVVVTADPDV | ARELLL-ASP | AFADRPVKES | AYGLMFH-RA | | 155 |
| SEQ_ID_NO_29 | RLMAFSLGET | RVVVTADLDV | ARELLL-ASA | AFADRPVKES | AYGLLFH-RA | | 152 |
| SEQ_ID_NO_38 | RLMAFSLGET | RVVVTADPDV | ARELLL-ASA | TFADRPVKES | AYGLLFH-RA | | 148 |
| SEQ_ID_NO_3 | RLMAFSLGET | RVIVTCNPDV | AKEILL-NSP | VFADRPVKES | AYSLMFN-RA | | 148 |
| SEQ_ID_NO_25 | RLMAFSLGDT | RAMVTCNPDV | AKEILL-HSS | VFADRPIKES | AYSLMFN-RA | | 166 |
| SEQ_ID_NO_22 | RLMAFSLGDT | RVIVTCHPDV | AKEILL-NSS | VFADRPVKES | AYSLMFN-RA | | 143 |
| SEQ_ID_NO_6 | RLMAFSLGDT | RVIVTCNPEV | AKEILL-NSS | VFADRPVKES | AYSLMFN-RA | | 150 |
| SEQ_ID_NO_10 | RLMAFSLGDT | RVIVTCNPDV | AKEILL-NSS | VFADRPVKES | AYSLMFN-RA | | 148 |

Figure 1 (continued)

```
SEQ_ID_NO_21   LVFAPYGDRW RMLRKISSVH LFSAKALEDF KHVRDEEVGT LMRE--LARA   159
SEQ_ID_NO_36   LVFAPYGPRW RMLRKICSVH LFSGDALDDF RHIRDEEVLA LMRA--LARE   158
SEQ_ID_NO_47   LVFAPYGPRW RLLRKISYVH MFSSKALDDF RHIRDDEVAS LIRN--LSNS   161
SEQ_ID_NO_4    IGFAPNGDYW RLLRRIASAH LFAPRRIAAH EAQRDADVVA MLDD--QKE    208
SEQ_ID_NO_46   MGFAPFGDYW RNLRRISSTY LFSPRRVSSF EKQRSE GEG  MVRD--MKRM   93
SEQ_ID_NO_39   IGFAPYGIYW RALRRVASTH LFSPRQVSAS AAQRAM ARD  MVEAMRSAAA  205
SEQ_ID_NO_40   IGFAPYGIYW RALRRVASTH LFSPRQVSAS AAQRAM ARD  MVEAMRSAAA  207
SEQ_ID_NO_27   IGFAPYGAYW RTLRRVSSSH LFSPRQVAAS AAQRAM AHD  MVDA--MRPV  203
SEQ_ID_NO_29   IGFAPHGAYW RALRRVASAH LFSPRQIAAS AAQRAA ARD  MVDA--TTTA  200
SEQ_ID_NO_38   IGFAPHGAYW RALRRVASAH LFSPRQIAAS AAQRAM ARD  MVDAMMNEQG  198
SEQ_ID_NO_3    IGFAPYGVYW QTLRKIASNH LFSPKQIKRS ETQRSV AND  IVKC--LTKQ  196
SEQ_ID_NO_25   IGFAPYGVYW RTLRKISTNH LFSPMQIKSS GPDRSE AID  MIDL--FRNR  214
SEQ_ID_NO_22   IGFASYGVYW RSLRRIASNH LFCPRQIKAS ELDRSD AAD  MVHI--LNNK  191
SEQ_ID_NO_6    IGFAPYGVYW RELRRIAATH LFCPKQIKNS EEDRRF ADE  MVNL--FGRH  198
SEQ_ID_NO_10   IGFAPYGVYW RTLRKIASTH LFCPKQIKAA ESQRLQLASD MVST--FNDR  196

SEQ_ID_NO_21   NTKP---VNL GQLVNMCVLN ALQREM GRR  LFGAD---- ADHKAEEFRS  201
SEQ_ID_NO_36   GQTP---VKL GQLLNVCTIN ALBRVM GRR  VFGDGSGG-- EDPKADEFKE  203
SEQ_ID_NO_47   GSKA---ANL GQMLNVCTIN ALARVM GRR  VENEGNGGCE CDPRADEFKS  208
SEQ_ID_NO_4    YHSK-GVVRV RRHLQDAALN NIMGSVFGRR FDMSH---- ENEEVKKLRE  252
SEQ_ID_NO_46   MERN-GVVEV RRMLHYGBLN NIMLTVFGKK FDF------ AKDEGLELEL  135
SEQ_ID_NO_39   AAAG-GGVAA RPFLKRASLH NVMASVFGRK YELAAP---- ESEETAELRS  250
SEQ_ID_NO_40   AAAG-GGVAA RPFLKRASLH NVMASVFGRK YELAAP---- ESEETAELRS  252
SEQ_ID_NO_27   GGAGVKHVEA RRFLKRASLH NVMASVFGRR YELDEA---  GSDEAAELKS  249
SEQ_ID_NO_29   AAHA-PVVVA RRFLKRASLH NVMASVFGRR YDLMA----- DSREAEELKA  244
SEQ_ID_NO_38   AAAP-GVVTA RRFLKRASLH SVMASVFGRR YELLQAAD-- GGEEAAELQS  245
SEQ_ID_NO_3    SNIK-GLCFA RDLIKHASLN NMMCSVFGKE YELEE----- EHEEVSELRE  240
SEQ_ID_NO_25   HLHG-GFC-V RDVLKKASLN NMMCSVFGQR FKIDE----- VNERMMELSG  257
SEQ_ID_NO_22   RHRS---LRV RQVLKKASLS NMMCSVFGQE YKLHD----- PNSGMEDLGI  233
SEQ_ID_NO_6    GHER--SFIV REVVKRASLN NMMVSIFGRK YKLDC----- DNNEVDELRG  241
SEQ_ID_NO_10   EKSS---FSV REVLKRASLN NMMCSVFGRE YKLDS----- FNNEVEELRA  238
```

Figure 1 (continued)

| | | |
|---|---|---|
| SEQ_ID_NO_21 | MVTEMMALAG VFNLGDFVPA DCLDLQGVA GKMKRLHKRF DAFLSSLEE | 251 |
| SEQ_ID_NO_36 | MVVELMVLAG VFNLGDFVPA EWLDLQGVA SKMKKLHARF DAFLGAVEE | 253 |
| SEQ_ID_NO_47 | MVVELMVLAG VFNLGDFVPB EWLDLQGVQ SKMKKLHKRF DSFLTSIED | 258 |
| SEQ_ID_NO_4 | MVDEGFDLLG AFNWADHLPW RPLDFLRIH ARCARLVPRV TTFVSNIEQ | 302 |
| SEQ_ID_NO_46 | LKEGYELLG IFNWGDHLPL GWLDLQSVR RKCRTLVAKV NVFVKKIDE | 185 |
| SEQ_ID_NO_39 | MVDEGYDLLG QLNWSDHLPW APFDLQKTR SRCSSLVPRV NRFVTRIDE | 300 |
| SEQ_ID_NO_40 | MVDEGYDLLG QLNWSDHLPW APFDLKKTR SRCSSLVPRV NRFVTRIDE | 302 |
| SEQ_ID_NO_27 | LVDEGYDLLG QLNWSDHLPW ARFDLQKIR SRCSALVPRV NRFVGRIDE | 299 |
| SEQ_ID_NO_29 | LVDEGYDLLG QLNWSDHLPW ARFDLQKTR ARCCALVPRV NRFVGNIGE | 294 |
| SEQ_ID_NO_38 | LVDQGYDLLG QLNWSDHLPW LARFDLQRTR ARCAALVPRV NRFVGRIDE | 295 |
| SEQ_ID_NO_3 | LVEEGYDLLG TLNWTDHLPW LSEFDPQRIR SRCSNLVPKV NRFVNRISD | 290 |
| SEQ_ID_NO_25 | LVEQGYDLLG QLNWGDHLPF LKDFDVQKIR FSCSELVPKV NRFVGSISD | 307 |
| SEQ_ID_NO_22 | LVDQGYDLLG LFNWADHLPF LAHFDAQNIR FRCSNLVPMV NRFVGTIAE | 283 |
| SEQ_ID_NO_6 | LVDEGYDLLG TLNWSDHLPW LADFDPQNIR VRCSNLVPKV NGFVGGIAQ | 291 |
| SEQ_ID_NO_10 | LVEEGYDLLG TLNWSDHLPW LADFDPQKIR FRCSNLVPKV NRFVGRLAE | 288 |

| | | |
|---|---|---|
| SEQ_ID_NO_21 | HEAMK----N GCDQKHTDML STLISLK--- --ETDFDGEG GTLTDTEIKA | 292 |
| SEQ_ID_NO_36 | HKISG----S AGSERHVDLL STLISLKDNA DGEGG----- -KLTDMEIKA | 293 |
| SEQ_ID_NO_47 | HMVSK----- --SEKHNDLL STLLSLKEKV DEDGD----- -KLNDTEIKA | 295 |
| SEQ_ID_NO_4 | HRREE---QR RESGDQCDFV DVLLSLQ--- --GED----- -KLDEEDMIA | 338 |
| SEQ_ID_NO_46 | HKRRA-NGVG IDEGEGEDFV DVLLSLE--- --EKD----- -RLSESDMVA | 223 |
| SEQ_ID_NO_39 | HRARL----S LAVDAAVDFT DVLLSLH--- --GGD----- -KLSDADMVA | 335 |
| SEQ_ID_NO_40 | HRARL----S LAVDAAVDFT DVLLSLH--- --GGD----- -KLSDADMVA | 337 |
| SEQ_ID_NO_27 | HRAAL----N DDDDAVVDFT DVLLSLG--- --GSD----- -KLSDADMIA | 334 |
| SEQ_ID_NO_29 | HRARL---GR GGDTAVMDFT DVLLSLG--- --GDD----- -KLSDADMIA | 330 |
| SEQ_ID_NO_38 | HRAARLHLGG DGAAVVDFT DVLLSLG--- --GSD----- -RLSDADMIA | 334 |
| SEQ_ID_NO_3 | HREQT----- --RDSPSDFV DVLLSLD--- --GPD----- -KLSDPDIIA | 322 |
| SEQ_ID_NO_25 | HRADK----- --NDTNKDFV HVLLSLG--- --EPD----- -KLSDSDMIA | 339 |
| SEQ_ID_NO_22 | HRASK----- --TETNRDFV DVLLSLF--- --EPD----- -QLSDSDMIA | 315 |
| SEQ_ID_NO_6 | HRART----- --NEEARDLV DVLLSLG--- --GAD----- -KLSDSDMIA | 223 |
| SEQ_ID_NO_10 | HRALT----- --RSENPDFV DVLLSLG--- --GHD----- -KLSDSDMIA | 320 |

Figure 1 (continued)

| | | | | | | | |
|---|---|---|---|---|---|---|---|
| SEQ_ID_NO_21 | LLLNMFTAGT | DTSASTVDWA | AELIRHPEI | MRKAQEELDS | VV- | GRGRP N | 341 |
| SEQ_ID_NO_36 | LLLNLFTAGT | DTSSSTVEWA | AELIRHPEM | MAQAQOELDA | VV- | GRGRLVT | 342 |
| SEQ_ID_NO_47 | LLLNMFTAGT | DTSSSTTEWA | AELIKNPKL | MIHIQNELDT | VV- | GRDRLVT | 344 |
| SEQ_ID_NO_4 | VLWEMIFRGT | DTTALLTEWT | MAELVLHPEA | DKKADAELDA | VV- | GHDRSVK | 387 |
| SEQ_ID_NO_46 | VLWEMIFRGT | DTVAILLEVT | LARMVLHPDI | QSKADVEIDS | VV- | DSSRPVL | 272 |
| SEQ_ID_NO_39 | VLWEMIFRGT | DTVAVLIEVV | AARLVLHQDV | QARVHDELDR | VV- | GSDRAVT | 384 |
| SEQ_ID_NO_40 | VLWEMIFRGT | DTVAVLIEVV | AARLVLHQDV | QARVHDELDR | VV- | GSDRAVT | 386 |
| SEQ_ID_NO_27 | VLWEMIFRGT | DTVAVVIEVV | LARLMLHQDV | QARVHEELDR | VV- | GPNRAVT | 383 |
| SEQ_ID_NO_29 | VLWEMIFRGT | DTVAVLIEVV | LARLVLHQDV | QSKVQEELDR | VV- | GL GQAVT | 379 |
| SEQ_ID_NO_38 | VLWEMIFRGT | DTVAVLMEVV | LARLVLHQDV | QRRVQEELDR | VV- | GPGRAVT | 383 |
| SEQ_ID_NO_3 | VLWEMIFRGT | DTVAVLIEVA | LARMVLHPDI | QSTVHNELDQ | IV- | GRSRAVE | 371 |
| SEQ_ID_NO_25 | VLWEMIFRGT | DTVAVLIEVA | LARLVIHPDV | QKKVQTELDE | VASGESCAIT | | 389 |
| SEQ_ID_NO_22 | VLWEMIFRGT | DTVAVLIEVA | LARMALHPHM | QSKVQEELDA | VV- | GKARAVA | 364 |
| SEQ_ID_NO_6 | VLWEMIFRGT | DTVAVLIEVV | LARIVVHPDV | QSRVHDELDK | VV- | GKSKAVY | 372 |
| SEQ_ID_NO_10 | VLWEMIFRGT | DTVAVLIEVA | LARMVLHPDV | QSKVHDELVK | VV- | GRSRAVA | 369 |

| | | | | | | | |
|---|---|---|---|---|---|---|---|
| SEQ_ID_NO_21 | ESDLSQLPYL | DAVIKENFRL | HPPTPLLSLP | HIASESCEI- | NGYHIPKGST | | 389 |
| SEQ_ID_NO_36 | DLDLPKLTYL | QAIVKETFRL | HPSTPLLSLP | RMAAESCEI- | NGYHIPKNAT | | 390 |
| SEQ_ID_NO_47 | EQDLTHLPYL | EAVIKETFRL | HPSTPLLSLP | RVATNSCEI- | FNYHIPKGAT | | 392 |
| SEQ_ID_NO_4 | DSDIPKLPYI | QAVVKEALRM | HPPGPLLSWA | RLSTEDVNMG | DGMCVPAGTT | | 437 |
| SEQ_ID_NO_46 | DSDIQRLPYL | QSIVKETLRM | HPPGPLLSWA | RLAIHDVPV- | DGHMPAGTT | | 321 |
| SEQ_ID_NO_39 | ESDASKLVYL | DAVIKEVLRL | HPPGPLLSWA | RLATSDVHM- | GGFLPSGTT | | 433 |
| SEQ_ID_NO_40 | ESDASKLVYL | DAVIKEVLRL | HPPGPLLSWA | RLATSDVHM- | GGFLPSGTT | | 435 |
| SEQ_ID_NO_27 | ESDAASLVFL | DAVVKEVLRL | HPPGPLLSWA | RLATSDVHM- | DGLHVPAGTT | | 432 |
| SEQ_ID_NO_29 | ESDITASLPYL | DAVIKEVLRL | HPPGPLLSWA | RLATSDVYM- | SGYLVPAGTT | | 428 |
| SEQ_ID_NO_38 | EPDGASLAYL | HAVIREVLRL | HPPGPLLSWA | RLATSDVHM- | GGYLVPAGTT | | 432 |
| SEQ_ID_NO_3 | ESDVSLMYL | TAVVKEVLRL | HPPGPLLSWA | RLAITDTII- | DGRRVPAGTT | | 420 |
| SEQ_ID_NO_25 | EEDVAAMYL | PAVIKEVLRL | HPPGPLLSWA | RLAITDTTI- | DGYHVPAGTT | | 438 |
| SEQ_ID_NO_22 | EDDVAMTYL | PAVVKEVLRL | HPPGPLLSWA | RLSINDTTI- | DGYHVPAGTT | | 413 |
| SEQ_ID_NO_6 | ESDVMNITYL | MAVIKEVLRL | HPPGPLLSWA | RLAITDTTV- | DGYHVPKGTM | | 421 |
| SEQ_ID_NO_10 | ESDITAMYL | DAVVKEVLRL | HPPGPLLSWA | RLAITDTTI- | DGYHVPKGTT | | 418 |

| | | | |
|---|---|---|---|
| SEQ_ID_NO_21 | YGITLDRAVP LVHPKLRLD | MSAYGLGSA | 511 |
| SEQ_ID_NO_36 | YGLTLDRAAP LMVHPRPRLS | PQVFGK--- | 509 |
| SEQ_ID_NO_47 | YQLTLDRAVP LAHPRPRLS | PHLYL---- | 510 |
| SEQ_ID_NO_4 | LKLSCEMARP LHCVPVTRVP | FAKFSD--- | 553 |
| SEQ_ID_NO_46 | LKMSLEMKNP LVCVAVPRFE | -------- | 426 |
| SEQ_ID_NO_39 | LKLSCEMATP LEARLRPRRK | VMSV---- | 552 |
| SEQ_ID_NO_40 | LKLSCEMATP LEARLRPRRK | V------- | 551 |
| SEQ_ID_NO_27 | LRLSCEMAAP LEARLRPRRA | V------- | 552 |
| SEQ_ID_NO_29 | LRLSCEMAAP LEARVVPRHA | VC------ | 543 |
| SEQ_ID_NO_38 | LRLSCEMAAP LEARLVPRRA | V------- | 548 |
| SEQ_ID_NO_3 | LRLSCEMANP LAAKLRPRRS | FSV----- | 534 |
| SEQ_ID_NO_25 | LRLSCEMANP LTVQVRPRR- | -------- | 546 |
| SEQ_ID_NO_22 | LKLSSEMANP LIVKVRPRRG | -------- | 523 |
| SEQ_ID_NO_6 | LKLSCEMANP LXVRIRPRRK | LT------ | 533 |
| SEQ_ID_NO_10 | LRLSCEMANP LTVKVRPRRS | SOSPLY-- | 535 |

Figure 2

| | | | | | | | |
|---|---|---|---|---|---|---|---|
| SEQ_ID_NO_67 | ---------- | MQLQPAVAN- | -------P | NTPSGAA--- | ---------- | | 17 |
| SEQ_ID_NO_65 | MDTSHWPQGI | GLVKAVEPS- | ----KPVPT | ERKPRPQ--- | ----KEQ-- | | 34 |
| SEQ_ID_NO_63 | MGMDSSSGQQ | QQMSNQSLES | MLTCSKGE-Q | DKKPKPP--- | ----QPE-- | | 39 |
| SEQ_ID_NO_73 | -----MDQQQ | QEMSSQTLES | MLVCTKPDQD | QKKPRPA--- | ----EQQ-- | | 35 |
| SEQ_ID_NO_69 | ------MQEE | PGRRPVPPF- | -----AGVDL | RRPKGYP--- | -VAVAKEERP | | 34 |
| SEQ_ID_NO_70 | -------MQE | AGRRPAPQF- | -----AGVDL | RRPKGYPAAA | QLTPAAEEAA | | 37 |
| SEQ_ID_NO_71 | -------MQE | AGRRPAPQF- | -----AGVDL | RRPKGYPAAA | QLTPAAEEAA | | 37 |
| SEQ_ID_NO_64 | -----MPSSD | SGESRRS-K- | --------P | QNRPGAP--- | --APEQE-- | | 27 |
| SEQ_ID_NO_75 | -------MEA | GQVPDGRAL- | -----MAAVT | TTGGGGR--- | ----EPE-- | | 27 |
| SEQ_ID_NO_51 | -------MQD | ----PTGFH- | ---------Q | MKAPAFQ--- | ----EQEQQ- | | 21 |
| SEQ_ID_NO_53 | -------MQD | ----PSTAF- | ---------H | TIKPQFP--- | ----EQE-- | | 19 |
| SEQ_ID_NO_60 | -------MQD | ----PLTLF- | ---------Q | PMKPHFP--- | ----EQE-- | | 18 |
| SEQ_ID_NO_58 | -------MQE | DLTSAAAYYH | HQSMIMTAKQ | QQQPELP--- | ----EQE-- | | 33 |
| SEQ_ID_NO_49 | -------MQD | ----PAAYY- | -QTMMAKQQQ | QQQPQFA--- | ----EQE-- | | 27 |

| | | | | | | | |
|---|---|---|---|---|---|---|---|
| SEQ_ID_NO_67 | ---REQCPRC | ASHDTKFCYY | NNYNLSQPRH | FCRACRRYWT | LGGSLRNVPI | | 64 |
| SEQ_ID_NO_65 | ---ANCPRC | NSTNTKFCYY | NNYSLSQPRY | FCKTCRRYWT | EGGSLRNVPV | | 61 |
| SEQ_ID_NO_63 | ---ALKCPRC | DSNNTKFCYY | NNYSLSQPRY | FCKSCRRYWT | KGGTLRNVPV | | 86 |
| SEQ_ID_NO_73 | ---PQKCPRC | DSANTKFCYY | NNYSLTQPRY | FCKSCRRYWT | KGGTLRNVPV | | 82 |
| SEQ_ID_NO_69 | APGGDPCPRC | GSRDTKFCYY | NNYNLSQPRH | LCKSCRRYWT | KGGSLRNVPV | | 84 |
| SEQ_ID_NO_70 | AGVGDPCPRC | ESRDTKFCYY | NNYNLSQPRH | FCKSCRRYWT | KGGSLRNVPV | | 87 |
| SEQ_ID_NO_71 | AGVGDPCPRC | ESRDTKFCYY | NNYNLSQPRH | FCKSCRRYWT | KGGSLRNVPV | | 87 |
| SEQ_ID_NO_64 | ---NLPCPRC | DSTNTKFCYY | NNYNYSQPRH | LCKACRRYWT | HGGTLRDIPV | | 74 |
| SEQ_ID_NO_75 | ---GLPCPRC | ESVNTKFCYY | NNYNLSQPRY | FCKTCRRYWT | RGGALRNVPV | | 74 |
| SEQ_ID_NO_51 | ---QLKCPRC | DSTNTKFCYY | NNYNLSQPRH | FCKNCRRYWT | KGGALRNIPV | | 68 |
| SEQ_ID_NO_53 | ---QLKCPRC | DSNNTKFCYY | NNYNLSQPRH | FCKNCRRYWT | KGGALRNIPV | | 66 |
| SEQ_ID_NO_60 | ---QLKCPRC | DSTNTKFCYY | NNYNLSQPRH | FCKNCRRYWT | KGGALRNIPV | | 65 |
| SEQ_ID_NO_58 | ---QLNCPRC | ASPNTKFCYY | NNYNLSQPRH | FCKNCRRYWT | KGGSLRNIPV | | 80 |
| SEQ_ID_NO_49 | ---QLKCPRC | DSPNTKFCYY | NNYNLSQPRH | FCKSCRRYWT | KGGALRNVPV | | 74 |

Figure 2 (continued)

| | | | | | | | |
|---|---|---|---|---|---|---|---|
| SEQ_ID_NO_67 | GGSTRKRLRP | APQQTMRRPP | VHFGAP- - P | PPPMPA- - - | - - - - - - - - - - | | 97 |
| SEQ_ID_NO_65 | GGGSRKNKRS | SSSSNNSSSS | - - -TSS- - -S | YKKIPDLT- - | - - - - - - - - - - | | 113 |
| SEQ_ID_NO_63 | GGGCRKNKRS | SSASSKRSQD | - - - -QPFQTN | PNPLTCFPSL | SYDSNDLTLA | | 132 |
| SEQ_ID_NO_73 | GGGCRKNKKL | SSTTSAKRSS | QDNISPNISN | PIPSYDSSTD | LSLAFARLQK | | 132 |
| SEQ_ID_NO_69 | GGGTRKSSSS | SSSSSAAAAA | - - - -TTTTTS | TSPGAAPK- - | -ATKRSKNSK | | 127 |
| SEQ_ID_NO_70 | GGGSRKSSTS | SSSSSSAAAA | - - - -SS- - -S | SSPSSPAK- - | -SPKRSKNSK | | 127 |
| SEQ_ID_NO_71 | GGGSRKSSTS | SSSAAAAAAS | - - - - -S- - -S | SSPSSPAK- - | -SPKRSKNSK | | 126 |
| SEQ_ID_NO_64 | GGGTRKNAKR | SRTHHVAVTS | - - - -SS- - -S | SSAVT- - - - | - - - - - - - - - - | | 102 |
| SEQ_ID_NO_75 | GGNTRKATPA | TGRRKRSTPA | - - - - -P- - -V | NVTVPAP- - - | - - - - - - - - - - | | 103 |
| SEQ_ID_NO_51 | GGGTRKGTKR | SSSSTNKPKR | - - - -QP- - -N | PSPDPTPNQK | -IPDPSPPPP | | 110 |
| SEQ_ID_NO_53 | GGGSRKNTKR | SSNTKRANPD | - - - - -P- - -N | PDPVKPTR- - | - - - - - - - - - - | | 96 |
| SEQ_ID_NO_60 | GGGSRKNTKR | SSSSNNNTKR | - - - - - - - - - - | ASPSPPVS- - | - - - - - - - - - - | | 93 |
| SEQ_ID_NO_58 | GGGTRKNSSK | RSSVGSSSSA | - - - -PS- - -S | SSPKSKTV- - | - - - - - - - - - - | | 111 |
| SEQ_ID_NO_49 | GGGSRKNATK | RSTSSSSSAS | - - - -SP- - -S | NSSQNKKT- - | - - - - - - - - - - | | 105 |

| | | | | | | | |
|---|---|---|---|---|---|---|---|
| SEQ_ID_NO_67 | -QSHSQQAPQ | GGLLSSLFAF | GAAPLFEGRV | GF- - - -D- - | LGLGLPGLSQ | | 139 |
| SEQ_ID_NO_65 | -IPTSSQNPK | IINEPHDLNL | AFNPSATSNF | SNISEFMA- - | LPLMNPNSTT | | 160 |
| SEQ_ID_NO_63 | LARLQKGHLG | FDHEHDFSIL | GNQTNTSCG | LNN- - - - - - | HGMNHSSNNQ | | 175 |
| SEQ_ID_NO_73 | QTNAHLEIDQ | EHDNNNMSMM | YNTGNNCTST | TELDALRGG- | FLENAPNHPG | | 181 |
| SEQ_ID_NO_69 | RRRVAPAPDP | AAPGTDASTA | DVASTAPSTV | - - - - - - - - - - | AASEKPSATE | | 167 |
| SEQ_ID_NO_70 | RRRVSPPPPQ | PAP- - - - - - - | APPPPTTADA | - - - - - - - - - - | ADVAAPTAPE | | 160 |
| SEQ_ID_NO_71 | RRRVSPPPPQ | PVP- - - - - - - | APPPPTTADA | - - - - - - - - - - | ADVAAPTAPE | | 159 |
| SEQ_ID_NO_64 | -SAPEQNYP | - - - - - - - - - - | SMFPIQGGSF | PY- - - - - - - | GGVDGEGKQN | | 132 |
| SEQ_ID_NO_75 | -ATASPPPPP | ALHGGSLLRP | YGGGGGSGLL | SFAAPALASP | LAAADPDRRL | | 152 |
| SEQ_ID_NO_51 | KSSSSSMFPQ | QIVLNSGAQN | SDSDIDSTRM | -Y- - - -L- - | LPVDHQDGKM | | 152 |
| SEQ_ID_NO_53 | -RVADSSSSS | ATSSTSGQQL | AGNGNQDPTR | VY- - - - - - - | GVEADPDRKI | | 137 |
| SEQ_ID_NO_60 | -SAPAPEPDP | TRI- - - - - - - | - - - - - - - - - - | - - - - - - - - - - | GPTPVVG- - - | | 112 |
| SEQ_ID_NO_58 | -AVSDQESRT | TGN- - - - - - | SGQEMDPTRM | LY- - - -G- - | LPVGDPS- - | | 143 |
| SEQ_ID_NO_49 | -KNPDPDPDP | RNS- - - - - - | QKPDLDPTRM | LY- - - -G- - | FPLSDQDVKG | | 140 |

Figure 2 (continued)

| | | | | | | | | |
|---|---|---|---|---|---|---|---|---|
| SEQ_ID_NO_67 | VGLGGGAG- | - - - E- - - - - - - | - - FGLHSLGL | RGGHAGT- - - | - - - - - SA- - - | | | 165 |
| SEQ_ID_NO_65 | SFMSSIMP- - | - - QLSDSNNI | M- YSSSSTGL | PNLHDLK- - - | - - - - - PTLNF | | | 197 |
| SEQ_ID_NO_63 | GFFEALMG- - | - - SQNNVQNL | YYMGEVDNGN | ANGNGNGEMM | LPYDHEMSI A | | | 221 |
| SEQ_ID_NO_73 | LFHHNMYNYA | NMGQLVENGE | MGMSYQQDQM | SIGTSTTMMT | TI VKQEMCNM | | | 231 |
| SEQ_ID_NO_69 | HAAAAVAT- - | - - EKPPAAPP | VSVGAFADTS | PAPDAGS- - - | - - - - - - - - - - | | | 209 |
| SEQ_ID_NO_70 | DTTKKAPE- - | - - DLTAAAAT | QPAVALGLGV | ADGGGGG- - - | - - - - - K- - - - | | | 194 |
| SEQ_ID_NO_71 | ATTKKAPE- - | - - DLTAAAAT | QPAVALGLGV | ADGGGGG- - - | - - - - - - - - - - | | | 192 |
| SEQ_ID_NO_64 | MSVCGSFT- - | - - SLLNNNPQ | QNSGFLALGG | FGLGLGH- - - | - - - - - GL- - - | | | 167 |
| SEQ_ID_NO_75 | LDFGGSFT- - | - - SLIAPGVA | DYGVHFSAGF | LMGGLAP- - - | - - - - - AALPR | | | 190 |
| SEQ_ID_NO_51 | MDIGGSFS- - | - - SLLASTGQ | - - FGNLLEGF | NSNGSGL- - - | - - - - - KT- - L | | | 186 |
| SEQ_ID_NO_53 | LDMGGSFS- - | - - SLLASSGQ | - - FGSIFEGL | DSGGSGL- - - | - - - - - KMVRM | | | 173 |
| SEQ_ID_NO_60 | - - - GGSFS- - | - - SLLASSGH | LGLGNLLEGL | NSSGSNL- - - | - - - - - KTVQM | | | 147 |
| SEQ_ID_NO_58 | - - - GGRFS- - | - - SLLVSNMQ | QI RGVNYET- | - - - GSG- - - | - - - - - - - - - - | | | 168 |
| SEQ_ID_NO_49 | MEIGGSFS- - | - - SLLANNMQ | - - LGLGGGGI | MLDGSG- - - - | - - - - - - - - - - | | | 170 |

| | | | | | | | | |
|---|---|---|---|---|---|---|---|---|
| SEQ_ID_NO_67 | - - - - - - - - - - | - - - - - - - - - - | PMLM- PTAFL | D- - - - - - - - - | - NGNVDTAKV | | | 184 |
| SEQ_ID_NO_65 | SL- - DGFDNN | - - - - - NGYGS | LQGE- TAGXK | LFFPLDDLKN | VSTPNDDHEF | | | 239 |
| SEQ_ID_NO_63 | TTQAVTVTTM | KQEMCNVREQ | NENRVLLGFP | WQFNNGDTNM | AEMDH- - - - - | | | 266 |
| SEQ_ID_NO_73 | ARSTEGHDLN | - - - - NSNNN | NKV- - LCGFP | WQQMNGDHHV | NNMNTNDFFY | | | 274 |
| SEQ_ID_NO_69 | - - - - GGVREL | - - - - - LPHPS | RFEM- PSGCN | LG- - - - - - - - | - - - - - - - - - - | | | 222 |
| SEQ_ID_NO_70 | - - - - EHLDTS | - - - - - P- - - - | - FEM- PSGCD | L- - - - - - - - - | - - - - - - - - - - | | | 210 |
| SEQ_ID_NO_71 | - - - KEHLDTS | - - - - - P- - - - | - FEM- PSGCD | L- - - - - - - - - | - - - - - - - - - - | | | 209 |
| SEQ_ID_NO_64 | - - - - GDMGFG | - - - - - I GR- - | - - EMSFPGMM | DGSNMGVPVV | SSGI GNSMQL | | | 204 |
| SEQ_ID_NO_75 | AP- - GSVAAL | - - - - - PPPPP | QQQP- TVSQA | L- - - - - - - - - | - - - - - - - - - - | | | 213 |
| SEQ_ID_NO_51 | NHFGGNFDSG | - - - - - CEMDQ | NSGR- DPLFG | E- - - - - - - - - | SSKNGESYLD | | | 221 |
| SEQ_ID_NO_53 | GGFGEDLNAG | - - - - - PSR- - | - - - - - NPGLD | LQGSSNNNTT | NDGGGESY- - | | | 209 |
| SEQ_ID_NO_60 | EEFGENVSSG | - - - - - PVADP | DSGR- NPGLE | MD- - - - - - - - | SNGNAENFLS | | | 183 |
| SEQ_ID_NO_58 | - - - - - - - - - - | - - - - - - - - - - | - - - M- YPGME | LG- - - - - - - - | - - - - - - - - - - | | | 176 |
| SEQ_ID_NO_49 | - - - - - - - - - - | - - - - - - - - - - | - - - MDHPGMG | LGL- - - - - - - | - - - - - - - - - - | | | 180 |

Figure 2 (continued)

| | | | | | | |
|---|---|---|---|---|---|---|
| SEQ_ID_NO_67 | ----SGGGAA | AMWAPEFSPA | PTVADVGGNG | MFHGGAQIMG | QL | 222 |
| SEQ_ID_NO_65 | D------EQN | RGQAAESHGF | WNG------- | ML GGGS---- | -- | 262 |
| SEQ_ID_NO_63 | -------LGR | AGWNGLTSSW | GHGL------ | LNSPLM----- | -- | 289 |
| SEQ_ID_NO_73 | STN----KQS | WNGFGGSSNW | HGL------- | INSPLM----- | -- | 299 |
| SEQ_ID_NO_69 | -------PPY | WGWGTSVFAD | TDPA------ | LFLNLP----- | -- | 245 |
| SEQ_ID_NO_70 | ---------G | PYWPTGVFAD | TDPS------ | LFLNLP----- | -- | 231 |
| SEQ_ID_NO_71 | ---------G | PYWPTGVFAD | TDPS------ | LFLNLP----- | -- | 230 |
| SEQ_ID_NO_64 | EGGE---TGF | VGGGDCFSW | PGLA------ | STPGNGLK--  | -- | 234 |
| SEQ_ID_NO_75 | -------PEG | MVW---SMGW | PDLS------ | L---------- | -- | 228 |
| SEQ_ID_NO_51 | V---QGGRDT | SCWSGDSNGW | PDLS------ | YTPGSSLRR-- |    | 252 |
| SEQ_ID_NO_53 | -------LQG | GEWGNSNNGW | PGLA------ | YTPGSSFQ--  | -- | 235 |
| SEQ_ID_NO_60 | LQN----GDS | SCW-NGTSGW | SHLA------ | FTPGSSFQ--  | -- | 211 |
| SEQ_ID_NO_58 | -------LGS | GIRRNDDAAL | TDLA------ | MNRVEKN---  | -- | 200 |
| SEQ_ID_NO_49 | -------RRT | EPGNNNNPW | TDLA------ | WNRAEKN---  | -- | 204 |

Figure 3

| | | | | | | | | | |
|---|---|---|---|---|---|---|---|---|---|
| SEQ_ID_NO_88 | MAST----- | ---------- | ------ | RRVQ | C--LMRRFYR | ---GSRTFGV | | | 23 |
| SEQ_ID_NO_95 | MTSL----- | ----QSFLAI | KPAAAGWAAG | ARPAAAPQSR | RARVSACLAA | | | | 40 |
| SEQ_ID_NO_90 | MNSL----- | ----QSFLAV | APVK--PAAA | A--ARLPSSR | RARVSACLAT | | | | 36 |
| SEQ_ID_NO_93 | MNSL----- | ----QSFLAL | NPPAAAAALG | G--ARLRPSR | ---VTACLAT | | | | 35 |
| SEQ_ID_NO_80 | MGSL----- | ----KLFPSF | SLSV--SPAT | N--LRRPLNN | GR-VNASLNM | | | | 35 |
| SEQ_ID_NO_87 | MGAVYFSOSC | YKPRQFNLE | REBTLVGRCP | V--VQLRCRR | V--VSACLNV | | | | 46 |
| SEQ_ID_NO_77 | MASL----- | ---GQITLPR | APS---SEIG | L--LRRRFER | PI-IRTRIGF | | | | 35 |
| SEQ_ID_NO_92 | MASL----- | ---GQITLPR | APS---LQKG | L--LRRP--- | ---IRTPIRF | | | | 30 |
| SEQ_ID_NO_78 | MTSL----- | ----QYFSLN | RPV---FPAT | H--LHRPGIR | HLQVSACANV | | | | 35 |
| SEQ_ID_NO_82 | MGSL----- | ----QHFLNS | PISVPFSPNL | N--HRRSFF- | ---LRACLNL | | | | 34 |

| | | | | | | | |
|---|---|---|---|---|---|---|---|
| SEQ_ID_NO_88 | ATQPNA---- | ---------- | ----SSSSQT | IDKEFQHSA | HNYHPLPIVF | | 55 |
| SEQ_ID_NO_95 | PPPPPT---- | -TAASAVGPA | RRELSAASRA | VMDDEARYLV | GTYKRSRVVF | | 85 |
| SEQ_ID_NO_90 | PAPAPT---- | ------APAAA | RRELSAASRA | VMADEAKYIV | GTYKRAQVVE | | 77 |
| SEQ_ID_NO_93 | PTPTPPPPTS | APLAPAAAAA | RRELSAASRA | VVEDEARYIV | GTYNRSRVVL | | 85 |
| SEQ_ID_NO_80 | DVEAPN---- | --------P | LKLKSNGSNE | VIEKDAKFIV | GTYARAPVVL | | 72 |
| SEQ_ID_NO_87 | DVDAPN---- | -------TGN | TTSEKKKTKD | VIEMEGMYLV | GTYARTPVVL | | 85 |
| SEQ_ID_NO_77 | NGRIAS---- | -VLTNAGDQA | VSVKASVSQK | VIEEEAKVI | GTYARAPVVL | | 80 |
| SEQ_ID_NO_92 | NGRIAS---- | -VLTNAG--- | -SVKASVSQK | VIEEEAKVLV | GTYARAPVVL | | 71 |
| SEQ_ID_NO_78 | EVQAPS---- | ---------- | SVKKDGVSKE | VMEAAGRVLV | GTYARVPVVL | | 71 |
| SEQ_ID_NO_82 | DVHAPD---- | --------SV | KPKTHLKSRE | VMEMEGKVLV | GTYARNPVVI | | 72 |

| | | | | | | |
|---|---|---|---|---|---|---|
| SEQ_ID_NO_88 | AHAKGSAVWD | PEGNKYIDFL | SGYSAVNQGH | CHPKILKALK | NQAGRLTVSS | 105 |
| SEQ_ID_NO_95 | EYGRGCKLYD | VDGREYLDMS | AGIAVTALGH | ADPDVCATIA | EQSGKIVHVS | 135 |
| SEQ_ID_NO_90 | VAGRGCKLYD | IDGREYLDMA | AGIAVNALGH | GDPDVDAAAA | DQRSRLVHAS | 127 |
| SEQ_ID_NO_93 | VAGRGCKLYD | ADGREYLDMA | AGIAVNALGH | ADPDWAAVS | AQAATLVHAS | 135 |
| SEQ_ID_NO_80 | SSGKGCKLYD | PEGREFLDCA | AGIAVNALGH | GDPDWLRAVT | EQASILTHVS | 122 |
| SEQ_ID_NO_87 | ERGEGCKLYD | VEGNEYLDLS | AGIAVNALGH | GDADWLKAVV | EQAGTLTHTS | 135 |
| SEQ_ID_NO_77 | SSGKGCKLFD | PEGKEYLDCA | BGIAVNALGH | GDPDWLRAVT | EQAGVLAHVS | 130 |
| SEQ_ID_NO_92 | SSGKGCKLMD | AEGKEYLDCA | BGIAVNALGH | GDPDWLQAVT | DQASVLSHVS | 121 |
| SEQ_ID_NO_78 | SRGKGCKLYD | PEGREYLDLS | AGIAVNVLGH | ADSDWLRAVT | EQAATLTHVS | 121 |
| SEQ_ID_NO_82 | SSGKGCKLYD | PEGREYLDCT | SGIAVNALGH | GDPDWKAVV | EQANLLTHVS | 122 |

Figure 3 (continued)

| | | | | | | | |
|---|---|---|---|---|---|---|---|
| SEQ_ID_NO_88 | RAFYNDRFPV | FAEYSTALFG | YDMVLPINTG | AEGVETALKL | ARKAGYDKKK | | 155 |
| SEQ_ID_NO_95 | NVFYTTPQVE | LAKRLVEVSF | ADRAFFASTG | TEANEAAIKF | SRK--FQRVA | | 183 |
| SEQ_ID_NO_90 | NVGYTVPQVE | LAKRLVEASF | ADRAFFANSG | TEANEAAIKF | ARK--YQRVA | | 175 |
| SEQ_ID_NO_93 | NVQYTVPQVA | LAKRLVEASF | ADRVFFANTG | TEANEAAIKF | ARK--FQRVA | | 183 |
| SEQ_ID_NO_80 | NAYYSIPQ- | ---------- | ---------- | ---------- | ---------- | | 130 |
| SEQ_ID_NO_87 | NIFHTIPQVE | LAKRLVASSF | ADRVFFANSG | TEANEAAIKF | ARK--YQRHT | | 183 |
| SEQ_ID_NO_77 | NVYYTIPQIE | LAKRLVASSF | ADRVFFCNSG | TEANEAAIKF | SRK--FQRFT | | 178 |
| SEQ_ID_NO_92 | NVYYTIPQIE | LAKRLVASSF | ADRVFFCNSG | TEANEAAIKF | SRK--FQRFT | | 169 |
| SEQ_ID_NO_78 | NVFYSIPQVE | LAKRLVASSF | ADRVFFSNSG | TEANEAAIKF | ARK--FQRFT | | 169 |
| SEQ_ID_NO_82 | NVFYSVPQVE | LAKRLVACSF | ADRVFFTNSG | TEANEAAIKF | ARK--YQRFT | | 170 |
| | | | | | | | |
| SEQ_ID_NO_88 | IPNDEAL--- | IVSCCGCFNG | RTLGVI SMSC | DNEATRGFGP | LIPGHLKVDF | | 202 |
| SEQ_ID_NO_95 | HPDSDDPPME | FLAFSSSFHG | RTMGAVALTS | KSQYREPFAP | VMPGVTFVDY | | 233 |
| SEQ_ID_NO_90 | HPNGDAPI TE | FMSFTNCFHG | RTIGSLALTS | KVQYREPFEP | VMPGSTFVEY | | 224 |
| SEQ_ID_NO_93 | RPDGDAPI TE | FMSFTNCFHG | RTMGSLALTS | KVQYREPFAP | VMPGATFAEY | | 232 |
| SEQ_ID_NO_80 | ---------- | ---------- | ---------- | ---------- | ---------- | | 130 |
| SEQ_ID_NO_87 | TSNGKVPATE | FIAFSNCFHG | RTLGALALTS | KVQYRMPFEP | VMPGVTFLEY | | 233 |
| SEQ_ID_NO_77 | HPEDKEVATG | FIAFTNSFHG | RTLGALALTS | KEQYRTPFEP | IMPGVTFLEY | | 228 |
| SEQ_ID_NO_92 | HPEDKEVATG | FIAFTNSFHG | RTLGALALTS | KEQYRTPFEP | IMPGVTFLEY | | 219 |
| SEQ_ID_NO_78 | RPDEKQPATE | FVSFSNSFHG | RTMGSLALTS | KENYRSPFEP | VMPGVTFLEY | | 219 |
| SEQ_ID_NO_82 | NPEKQQA-TE | FISFSNSFHG | RTMGALALTS | KEQYRFPFEP | VMPGVNFLEY | | 219 |
| | | | | | | | |
| SEQ_ID_NO_88 | GDAEALEKIL | KEKGDAI AAF | ILEPIQGEAG | VKIPPDGYLK | AVRDLCSKYN | | 252 |
| SEQ_ID_NO_95 | GDLEAAKKF | --QSGRVAAV | FVEPVQGEGG | HSATQEFLQ | GLREACDEAG | | 281 |
| SEQ_ID_NO_90 | GNLEEAKKVI | --QSGKIAAV | FVEPVQGEGG | HSATNEFLQ | GLRDACDEAG | | 272 |
| SEQ_ID_NO_93 | GNLEEAKKVI | --QSGKIAAV | FVEPVQGEGG | HSATKEFLQ | GLRDACDEAG | | 280 |
| SEQ_ID_NO_80 | ---------- | ---------- | ---------- | ---------- | ---------- | | 130 |
| SEQ_ID_NO_87 | GNAQAAVELI | --KQGKIAAV | FVEPIQGEGG | YSATKEFLQ | SLRNACDETG | | 281 |
| SEQ_ID_NO_77 | GNIQAATDLI | --RSGKIAAV | FVEPIQGEGG | YSATKEFLQ | SLRSACDAAG | | 276 |
| SEQ_ID_NO_92 | GNTQAATDLI | --RSGKIAAV | FVEPIQGEGG | VYSATKEFLQ | SLRSACDAAG | | 267 |
| SEQ_ID_NO_78 | GNIEAATQLI | --QRRKIAAV | FVEPIQGEGG | VYSATKEFLY | ALRKACDDSG | | 267 |
| SEQ_ID_NO_82 | GDVQAATELI | --KSGRIAAV | FVEPIQGEGG | YSATKEFLQ | SLRSACDDAG | | 267 |

Figure 3 (continued)

| | | | | | | | |
|---|---|---|---|---|---|---|---|
| SEQ_ID_NO_88 | VLMIADEIQT | GLARTGKMLA | CEWEEVRPDV | VVLGKALGGG | I PVSAVLAD | 302 |
| SEQ_ID_NO_95 | ALLVFDEVQC | GFGRTGYLWA | HEAYGVEPDI | MTLAKPLANG | -LPIGVVLVK | 330 |
| SEQ_ID_NO_90 | ALLVFDEVQC | GLGRTGYLWA | HEVYGVLPDI | MTLAKPLANG | -LPIGVALVT | 321 |
| SEQ_ID_NO_93 | ALLVFDEVQC | GLGRTGYLWA | YEAYGVLPDI | MTLAKPLAGG | -LPIGVLVT | 329 |
| SEQ_ID_NO_80 | -------VQC | GLGRTGYLWA | HEAYGVFPDM | MTLAKPLAGG | -LPIGATLVS | 172 |
| SEQ_ID_NO_87 | ALLVFDEVQC | GLGRSGFLWA | HEAYGVFPDM | MTLAKPLAGG | -LPIGALLVT | 330 |
| SEQ_ID_NO_77 | SLLVFDEVQC | GLGRTGLMWA | YEAFGVTPDI | MTVAKPLAGG | -LPIGAVLVT | 325 |
| SEQ_ID_NO_92 | SLLVFDEVQC | GLGRTGNLWA | YEAFGVTPDI | MTVAKPLAGG | -LPIGAVLVT | 316 |
| SEQ_ID_NO_78 | TLLVFDEVQC | GLGRTGYLWA | HELYDVFPDI | MTLAKPLAGG | -LPIGAVLVT | 316 |
| SEQ_ID_NO_82 | SLLVFDEVQC | GLGRTGYLWA | HEAYGVVPDI | MTLAKPLAGG | -LPIGAALVS | 316 |

| | | | | | | | |
|---|---|---|---|---|---|---|---|
| SEQ_ID_NO_88 | KEVMLCIKPG | QHGSTFGGNP | LASAVAIABL | EVIKEERLAE | RSTKLGGELL | 352 |
| SEQ_ID_NO_95 | EKVAAAINYG | DHGTTFGGGP | LACQTAITVF | DKIMKPGFLA | EVSKKGENFK | 380 |
| SEQ_ID_NO_90 | EKVAAAIHYG | DHGTTFGGGP | FVCHAALATL | DKIQKPGFLA | EVTKKGEYFK | 371 |
| SEQ_ID_NO_93 | EKVASAINFG | DHGTTFGGGP | LVCQAALTTL | DKIQKPGFLA | EVAKKGENFK | 379 |
| SEQ_ID_NO_80 | ERVASAIAHG | DHGSTFAGSP | FVCSAAICVF | NKISNPSFLS | SVLKKGDYMK | 222 |
| SEQ_ID_NO_87 | ERVASAINYG | DHGSTFAGSP | LVCSAALAVL | DKISKPDFLS | SVSKKGLYFK | 380 |
| SEQ_ID_NO_77 | EKVAETINYG | DHGSTFAGSP | LVCSAAIAVM | DKVSKPSFLS | SVSNKGRYFR | 375 |
| SEQ_ID_NO_92 | EKVAETIKYG | DHGSTFAGNP | LVCSAAIAVF | DKVSKSSFLA | SVSSKGLYFK | 366 |
| SEQ_ID_NO_78 | ERVASAITYG | DHGTTFAGGP | LVCKAALTVL | DKILRPGFLA | SVSKKGHYFK | 366 |
| SEQ_ID_NO_82 | EKVAAAIKYG | DHGSTFAGGP | LVCNAAIAVL | DKISKPGFLA | SVSEKGQYFK | 366 |

| | | | | | | | |
|---|---|---|---|---|---|---|---|
| SEQ_ID_NO_88 | GLLEKIQKQY | PDHVKEVRGR | GLFIGVELNS | ESLSPVSFFE | LSEKLKDRGV | 402 |
| SEQ_ID_NO_95 | QLLRTKLSGN | P-HVKEVRGV | GLLVGIELD | -----VPAGP | LVDACLDAGV | 423 |
| SEQ_ID_NO_90 | QLLKTKLGGN | P-HVKEIRGA | GLIVGIELD | -----VPAGP | LVDACLDAGV | 414 |
| SEQ_ID_NO_93 | QLLSTKLSGN | A-HVKEIRGI | GLIVGIELD | -----VPAGP | LVDACLDRGV | 422 |
| SEQ_ID_NO_80 | ELLNQKLGGN | P-HVKEIRGW | GLMIGIELD | -----VSASP | LVDACRNSGL | 265 |
| SEQ_ID_NO_87 | ELLREKLGEN | R-HVKEIRGV | GLIIGIDLD | -----VPASP | LVDACRSSGL | 423 |
| SEQ_ID_NO_77 | DLLVKKLGGN | S-YVKEVRGE | GLIIGVELD | -----VPASS | LVDACRDSGL | 418 |
| SEQ_ID_NO_92 | DLLVKKLGGN | L-HVKEVRGE | GLIIGVELD | -----VPAGP | LVDACRDSGL | 409 |
| SEQ_ID_NO_78 | EMLINKLGGN | S-HVREVRGV | GLIVGIELD | -----VSASP | LVNACLNSGL | 409 |
| SEQ_ID_NO_82 | ELLIHKLGGN | S-HVREVRGL | GLIIGIELD | -----VSASP | LVDACRDSSL | 409 |

Figure 3 (continued)

| | | | | | | | |
|---|---|---|---|---|---|---|---|
| SEQ_ID_NO_88 | LAKST-HDT | RFTPPLCIS | ADEIQQGSKA | LADVLEIDLP | MLKKMKPKDA | | 451 |
| SEQ_ID_NO_95 | IVLTAGKGNV | VRLVPPLIIS | EKELEHA--- | -ADVIRDCLP | VLDVAAA--- | | 466 |
| SEQ_ID_NO_90 | FLLTAGKGNV | VRLVPALIVS | EKELEQA--- | -AEVIRECLP | ALEASTS--- | | 457 |
| SEQ_ID_NO_93 | IVLTAGKGNV | VRLVPPLIIS | EKELEQA--- | -AEVIRDCLP | ALDASTS--- | | 465 |
| SEQ_ID_NO_80 | LVLTAGKGNV | VRLVPPLIIS | EEELKHA--- | -AEILHECLP | ALDNSN---- | | 307 |
| SEQ_ID_NO_87 | LVLTAGKGNV | VRLVPPLIIT | EKELEQA--- | -ASILCQTLP | VLDN------ | | 463 |
| SEQ_ID_NO_77 | LILTAGKGNV | VRIVPPLVIS | EEEIERA--- | -VEIMADNLT | ALD------- | | 457 |
| SEQ_ID_NO_92 | LILTAGKGNV | VRIVPPLIIS | EEEIERA--- | -VEIIFHDLT | ALD------- | | 448 |
| SEQ_ID_NO_78 | LVLTAGKGNV | VRIVPPLIIT | EQELEKA--- | -AEILLQCLP | ALDRHG---- | | 451 |
| SEQ_ID_NO_82 | LILTAGKGNV | VRLVPPLIIS | EQELERA--- | -AEIILECLP | ALDKTS---- | | 451 |

| | | | |
|---|---|---|---|
| SEQ_ID_NO_88 | APPAGPSACD | RCGRVVYG | 469 |
| SEQ_ID_NO_95 | ---------- | -------- | 466 |
| SEQ_ID_NO_90 | ---------- | -------- | 457 |
| SEQ_ID_NO_93 | ---------- | -------- | 465 |
| SEQ_ID_NO_80 | ---------- | -------- | 307 |
| SEQ_ID_NO_87 | ---------- | -------- | 463 |
| SEQ_ID_NO_77 | ---------- | -------- | 457 |
| SEQ_ID_NO_92 | ---------- | -------- | 448 |
| SEQ_ID_NO_78 | ---------- | -------- | 451 |
| SEQ_ID_NO_82 | ---------- | -------- | 451 |

Figure 4

```
SEQ_ID_NO_101    -MSETEAAPV VA------- -----PAAEA APAAEAPK-- AKAPKAKAPK   34
SEQ_ID_NO_102    --MATTEAVE EP------- ----VPVEAT ANEDAKPTE- EKPAKEKKPK   35
SEQ_ID_NO_150    --MASTDPPA DT------V PAEPVANEDV KAAEEKP--- VKAPKEKKVK   38
SEQ_ID_NO_118    --MALDTPVS AP------- -----VVPEV TERKSKRG-- TKAAAVKVPK   32
SEQ_ID_NO_145    --MATTVAIE TP------- --------AFT PVAVDPPA-- AKPAKAKKAK   31
SEQ_ID_NO_149    --MSAAVAIE TP------- -----AFAPV PVARDEPV-- AKPGKVTKAK   33
SEQ_ID_NO_144    --MATDETTD PR------- --------- ------PV-- AKSKKAKAPK   22
SEQ_ID_NO_125    --MSTDVAAD VP----APEV EVAADPVVET TAEAAAGD-- AKPAKETKAK   42
SEQ_ID_NO_137    --MATEVAET PA------- ---PLAEAVP ETPAEAPA-- APAAEANST-   34
SEQ_ID_NO_146    --MATDVAAT EP------- -----EVAAE EAAAAPETT ATAGDSKPAK   35
SEQ_ID_NO_147    --MATDVAAT EP------- -----EVAAE EAAAAPETT ATAGDSKPAK   35
SEQ_ID_NO_119    -MAAVEDPIV PM-----EGV EEEVPVTVTE APEEAAPP-- AEDPAPKKGK   42
SEQ_ID_NO_100    --MSIEEENV PT------T VDSGAADTTV KSPEKKPA-- AKGGKSKKTT   39
SEQ_ID_NO_113    --MSTEEETK VV------- --VESGDAEA TVTEKKPA-- AKGGAKAKKT   36
SEQ_ID_NO_104    --MATEEPAV VA------- -DPAPETEED KTAETKAT-- SKSGRAKKTK   37
SEQ_ID_NO_108    --MSSDEPTV AV------- -DGSTEPTSA EPADDKPA-- AKPSRAKKTK   37
SEQ_ID_NO_116    MTSSVEEPTV SAVEQTIVEE PAAVDPLPPV VNESDEPT-- AAKPK----   43
SEQ_ID_NO_117    --MASEEPTT VAVEQPIVEE PEAVDTFPPV VNESEEPT-- AKPKKAPK-   44
SEQ_ID_NO_122    --MATEEPLV VT-----EIV TEAVVVEAEP AKEENSPA-- AEPDEPKKEK   41
SEQ_ID_NO_120    --MATEEPVI VN-------E VVEEQAAPET VKDEANPP-- AKSGKAKKET   39

SEQ_ID_NO_101    QPKAPKAPKE PKAPKEKKPK AAPTHPPYE MVKDAITTLK ERNGSSLPAL   84
SEQ_ID_NO_102    TP----KEKK PRAAKGS--K PPAHPPYVQ MIAEAITALK ERGGSSPYAI   79
SEQ_ID_NO_150    TP----KEKK PKAAKGS--K PPPAHPPYFQ MISEAIVALK ERGGSSPYAI   82
SEQ_ID_NO_118    -----EKKK VIAAKKPKSK GTSSHPSFFE MISDAISTLK ERTGSSQYAI   76
SEQ_ID_NO_145    VP----KEKK ASVAK----- -PALHPTYLE MISEAIASLK ERTGSSQIAI   71
SEQ_ID_NO_149    AP----KEKK ASVAKKP--- --ALHPTYLE MISEAIASLK ERTGSSQYAI   74
SEQ_ID_NO_144    EA----RAKK AAAPRKP--- --SAHPPYAE MIKEAITTLK ERTGSSPYAI   63
SEQ_ID_NO_125    AA----KAKK PSAPRKP--R ATPAHPTYAE MVSEAITALK ERTGSSQYAI   86
SEQ_ID_NO_137    -----KAKK ASAPKK---R ANPTHPPYAE MISEAVTSLK ERTGSSQYAI   75
SEQ_ID_NO_146    EA----KAKK AAAPRKA--R STATHPPYAE MISEAIATLK ERTGSSQYAI   79
SEQ_ID_NO_147    EA----KAKK AAAPRKA--R STATHPPYAE MISEAIATLK ERTGSSQYAI   79
SEQ_ID_NO_119    EL----KPKK AAAPRKP--R SAPAHPPYLE MITDAITSLK ERTGSSQQAI   86
SEQ_ID_NO_100    TAKATKKPVK AAAPTKK--K TTSSHPTYEE MIKDAIVTLK ERTGSSQYAI   87
SEQ_ID_NO_113    PA----KKKP AAAPRK---R TTGSHPYEE MIKDAIVTLK ERTGSSQYAI   79
SEQ_ID_NO_104    EP----KTKK AAAPRKP--R AAPTHPPYEE MIKDAIVTLK ERTGSSQYAI   81
SEQ_ID_NO_108    EP----KAKK APAPKKPRHR TPSSHPPYEE MIKDAIVTLK ERTGSSQYAI   83
SEQ_ID_NO_116    -----KAPK EPKPRKPASK NTRTHPTYEE MVTDAIVTLK EKNGSSQYAL   87
SEQ_ID_NO_117    -----EPKA KKAPAKP--- --RTHPTYEE MVKEAIVALK ERNGSSQYAI   83
SEQ_ID_NO_122    EI----EAKK PAAPRK---R NPPTHPSYFE MIKDAIVTLK DKTGSSQHAI   84
SEQ_ID_NO_120    -----KAKK PAAPRKR--S ATPTHPPYFE MIKDAIVTLK ERTGSSQHAI   81
```

Figure 4 (continued)

| | | | | | | | |
|---|---|---|---|---|---|---|---|
| SEQ_ID_NO_101 | KKFIENKYGK | DIHDKNFAKT | LSQVVKTFVK | GGKLVKVKGS | FKLSE---- | | 129 |
| SEQ_ID_NO_102 | AKFLGDKYK | ADLPPNFKKQ | LNVQLKNLTK | SGKLTKVKAS | YKLTA---- | | 123 |
| SEQ_ID_NO_150 | AKFLSEKYK | SDLPPVFKKK | LNVQLRNLTN | SGKLTKVKGS | YKLAE---- | | 126 |
| SEQ_ID_NO_118 | NKFVEDKHK | Q-LPSNFRKL | LFHLKKLVA | SGKLVKVKNS | FKLPS---- | | 119 |
| SEQ_ID_NO_145 | SKFVENKHK | AHLPANFKKL | LLVQLRKLTA | AGKLTKVKNS | YKISA---- | | 115 |
| SEQ_ID_NO_149 | AKFVEDKHK | SHLPANFKKL | LLVQLQKLTA | AGKLTKVKNS | YKISA---- | | 118 |
| SEQ_ID_NO_144 | GKFIEDKHK | AHLPSNFRKI | LFLQLKKLAA | AGKLTKVKSS | YKLST---- | | 107 |
| SEQ_ID_NO_125 | AKFVEDKHK | AHLPANFRKI | LSVQLKKLVA | SGKLTKVKAS | YKLSA---- | | 130 |
| SEQ_ID_NO_137 | AKFVEDKHK | DKLPPNFRKL | LLGQLKKLVA | AGKLTKVKNS | YKLPA---- | | 119 |
| SEQ_ID_NO_146 | GKFLEDKHK | DHLPSNFRKQ | LLVQIKKLVA | AGKLTKVKNS | YKLPP---- | | 123 |
| SEQ_ID_NO_147 | GKFLEDKHK | DHLPSNFRKQ | LLVQIKKLVA | AGKLTKVKNS | YKLPP---- | | 123 |
| SEQ_ID_NO_119 | QKFLEAKHK | D-LPAVFRKM | LSNNLKKLVA | AGKLVKVKAS | YKLPS---- | | 129 |
| SEQ_ID_NO_100 | QKFIEEKHK | S-LPPTFRKL | LLVNLKRLVA | SEKLVKVKAS | FKIPS---A- | | 131 |
| SEQ_ID_NO_113 | QKFIEEKQ-K | S-LPPTFRKL | LLVNLRRLVA | SGKLVKVKAS | FKIPS---- | | 122 |
| SEQ_ID_NO_104 | AKFIEEKQ-K | N-LPGNFKKL | LLVHLKKLVA | AGKLVKVKAS | YKLPS---A- | | 125 |
| SEQ_ID_NO_108 | TKFLEEKHK | Q-LPSNFKKL | LFHLKKLVL | SDKIVKVKGS | FKLPS---- | | 126 |
| SEQ_ID_NO_116 | AKFIEEKHK | N-LPANFKKI | LLVQIKKLVA | SGKLVKVKGS | YKLPA--KS | | 132 |
| SEQ_ID_NO_117 | AKFIEEKHK | Q-LPSNFKKI | LLVQIRKLVA | SGKLVKVKAS | YKLPA---- | | 126 |
| SEQ_ID_NO_122 | TKFIEDKQ-K | N-LPSNFRKL | LLVQLKKLVA | SGKLVKVKSS | YKLPA-AR- | | 129 |
| SEQ_ID_NO_120 | TKFIEEKQ-K | S-LPSNFKKL | LLTQLKKFVA | SEKLVKVKNS | YKLPSGSKP- | | 128 |

| | | | | | | | |
|---|---|---|---|---|---|---|---|
| SEQ_ID_NO_101 | ---ALKAKAK | KSTPKK-AKA | DG----EAKP | KK-SE-AKPK | ----KAEAVK | | 165 |
| SEQ_ID_NO_102 | -----PKAPA | APKPKK-EKK | TVAKKKAPKP | KV-PA-AKPK | -APAAKAAKP | | 164 |
| SEQ_ID_NO_150 | ----KEKKAD | APKPKT-EKK | PA----AKKP | KA-PA-AKAP | -AKAPSKAS | | 163 |
| SEQ_ID_NO_118 | -------ARA | APAPAL-AKK | PT----IPKP | KV-------- | --AAKPKTAK | | 147 |
| SEQ_ID_NO_145 | ----KPTTAT | KPKKTS-AKS | TT----VAKP | KS-AA-AKPK | --STAAKVKK | | 152 |
| SEQ_ID_NO_149 | ----KPTPAA | KPKSA----- | ------AVKP | KS-AA-TKLK | -SAAKKVKK | | 149 |
| SEQ_ID_NO_144 | ---IVHAAPA | EPKS------ | ------AAGP | KK-PA-AVQT | --KLKAKAKP | | 138 |
| SEQ_ID_NO_125 | -------AAA | KPKP------ | ------AAKK | KPAAK-KKAP | --AKKTATKT | | 158 |
| SEQ_ID_NO_137 | ----RAPAAA | KPKPKS-KTA | ------VKKP | KA-------- | --GAKKPKAA | | 148 |
| SEQ_ID_NO_146 | ---TRAPAAA | KPKAKP-AAA | A----KPKP | KPKAA-AKPK | --AAAKPKAK | | 161 |
| SEQ_ID_NO_147 | ---TRAPAAA | KPKAKP-AAA | A----KPKP | KPKAA-AKPK | --AAAKPKAK | | 161 |
| SEQ_ID_NO_119 | -AKSSAPAKK | KPAAAP-AKK | KA----AAAP | AKKKT-AAAP | --KKKAAAAP | | 170 |
| SEQ_ID_NO_100 | -RSAATPKPA | APVKKK-ATV | VA----KPKG | KV-AA-AVAP | --AKAKAAAK | | 171 |
| SEQ_ID_NO_113 | --AAKPAATT | KPVNKK-PAA | A-----VTKP | KG----KAP | --AKAKPAAK | | 157 |
| SEQ_ID_NO_104 | -RSSKTATAA | SAPAKK-KTA | TT----KSKS | KP--A-SKPK | --EGKSTKAT | | 164 |
| SEQ_ID_NO_108 | ---AKSSAPA | KPAAASPAKK | KTATAAKPKA | KSKPAYSKAK | ETKSAKSTAK | | 173 |
| SEQ_ID_NO_116 | AAPAKKPAAA | KPKPKPKAKA | PVAKAPAAKS | KAKAA-PAKA | KAKAKAKAAP | | 181 |
| SEQ_ID_NO_117 | -KSSAAKPAK | KPAAAK-SKA | KPKAKAATKS | KAKPA-AKAK | --PAAKAKPA | | 171 |
| SEQ_ID_NO_122 | -SAAPKAAAT | APAKKK-PGA | KPKAT-KAKP | KPKPK-TVAP | --KAKTATKP | | 173 |
| SEQ_ID_NO_120 | -AAAAVPAKK | KPAAAK-SKP | AAKPKAAVKP | KAKPA-AKAK | --PAAKAKPA | | 173 |

Figure 4 (continued)

| | | | | | | | |
|---|---|---|---|---|---|---|---|
| SEQ_ID_NO_101 | KTKAPKEKVE | RPKKEKKEKV | EKKKATPKAE | KPKK----AA | TPKSAGKKK- | | 210 |
| SEQ_ID_NO_102 | KAAKKAAPAK | PAAPAPP--- | ------KKEE | KPAA-AA-PK | KAAPAAKPKK | | 203 |
| SEQ_ID_NO_150 | KPAAPKKAEK | PMAPKK---A | AAPKKAAKPA | APKAAAPKAK | KPAAAAKPE- | | 208 |
| SEQ_ID_NO_118 | IGAKPKAKAK | VAAKTKA--T | TKTVA---- | ---------- | KKIPAAKPKA | | 180 |
| SEQ_ID_NO_145 | A--------- | ---------A | VKPKPKSAAV | KPKAEPA-AP | KPKAVSKPKA | | 183 |
| SEQ_ID_NO_149 | AAVKPKPKSA | ---------A | VKPKAPAVNM | KSKP-A-AL | KPNTVTKSKT | | 187 |
| SEQ_ID_NO_144 | AAASKTKAK | IATTAKA--K | SKHVASTVKP | KPKA--A-AA | KPRVAPKRKS | | 183 |
| SEQ_ID_NO_125 | KAKAPAKKAL | ---------A | AKPKA-KAPA | KPKA----AA | KPKAAAKPKA | | 193 |
| SEQ_ID_NO_137 | TKPKPKAKAK | SPAKAKP--A | AKPKA-AAKP | KPAA----A | KPKAAAKPKA | | 190 |
| SEQ_ID_NO_146 | APAKSKAAAK | PKAAAKP--A | AKPKAAAKPK | SPAK--P-AA | KPKAAPKAKA | | 206 |
| SEQ_ID_NO_147 | APAKSKAAAK | PKAAAKP--A | AKPKAAAKPK | SPAK--P-AA | KPKAAPKAKA | | 206 |
| SEQ_ID_NO_119 | KKKAPVAKAK | PAAKPKAKAV | VKPKA-KAAV | KPKA-KP-AA | KPAAKAKPA- | | 216 |
| SEQ_ID_NO_100 | GTKKPAAKVV | AKAKV----T | AKPKAKVTAA | KPKS----K | SVAAVSKTKA | | 212 |
| SEQ_ID_NO_113 | GAKKPAAAAK | PKAKT----T | ATTKA-AAKP | KPKT----K | SVAAVSKTKA | | 197 |
| SEQ_ID_NO_104 | PKAKAKTKTT | SKAKSKP--A | AKPKA---TS | KAKAAPA-KT | KAVASVKPKT | | 208 |
| SEQ_ID_NO_108 | SPAKSKAAAK | PKAKPKAA-A | AKPKV-TAKA | KPKA-AP-AK | AKTSVAKPKA | | 219 |
| SEQ_ID_NO_116 | AKAKPAAKAK | PAAKAKP--A | AKAKP-VAKA | KPKAKAP-VA | KANAVPVA-- | | 225 |
| SEQ_ID_NO_117 | AKAKPAAKAK | PAAKAKP--A | AKAKPAAKPV | KTAAAKP-AA | KAKPAAKPKA | | 218 |
| SEQ_ID_NO_122 | KAKQRQVKAK | LVAKAKP--A | VKPKA----- | -----AA-VA | MPKAAEKPK- | | 209 |
| SEQ_ID_NO_120 | AKAKPAAKAK | PAAKAKP--A | AKAKP-VAKA | KPKA-AA-AA | KPKAAVKPKA | | 218 |

| | | | | | | | |
|---|---|---|---|---|---|---|---|
| SEQ_ID_NO_101 | -ATPKPKAAP | ---------- | ---------- | -------K | SPAKKDAKPK | KATPGKKAAP | 240 |
| SEQ_ID_NO_102 | -PAAKPKKAA | ---------- | ---------- | ---TPKKPAP | KPKPAKKAAT | | 229 |
| SEQ_ID_NO_150 | -AAPKRSST- | ---------- | ---------- | ---RTAAKPA | APKAAKKPTP | | 233 |
| SEQ_ID_NO_118 | KTAGKPKTVA | ---------- | ---------- | -------A | KPAKVAKTAA | VASPGKKKAV | 211 |
| SEQ_ID_NO_145 | -VAPKPKTAG | ---------- | ---------- | -PAKKAKTSA | KPSPSKKAAP | | 211 |
| SEQ_ID_NO_149 | -VALKGKTAG | ---------- | ---------- | RPAKAAKTSV | KAAPGKKAAP | | 216 |
| SEQ_ID_NO_144 | PVKPKPKPKP | ---------- | ---------- | RPTRAAKTAA | KDSPGKKAAK | | 213 |
| SEQ_ID_NO_125 | KAAAKPKAAA | ---------- | ------KPKG | RPAKAAKTSA | KDAPGKKAPA | | 227 |
| SEQ_ID_NO_137 | KPAAKAKPKA | -------VAA | KPKPAAKKAG | RPAKAAKTSA | KDTPGKKAAP | | 233 |
| SEQ_ID_NO_146 | KPAAKPKAKA | APKPKAAVVT | KTKATSAPAR | RPAKAAKTSA | KDTPSKKAAP | | 256 |
| SEQ_ID_NO_147 | KPAAKPKAKA | APKPKAAAVT | KTKATSAPAR | RPAKAAKTSA | KDTPSKKAAP | | 256 |
| SEQ_ID_NO_119 | -AKAKPAAKP | ---------- | KAK-----A | KPAKVARTST | RTTPGKKAPA | | 249 |
| SEQ_ID_NO_100 | -VAAKPKAKE | ---------- | ---------- | RPAKASRTST | RTSPGKKVAA | | 241 |
| SEQ_ID_NO_113 | -VAAKPKAKE | ---------- | ---------- | RPVKASRTST | RTSPGKKAAA | | 226 |
| SEQ_ID_NO_104 | TAATKPKAAA | ---------- | KPK-----D | KPVKASRTST | RTSPGKRAAA | | 242 |
| SEQ_ID_NO_108 | -APAKPKAKE | ---------- | ---------- | RPAKASRTST | RTSPGKKAAA | | 248 |
| SEQ_ID_NO_116 | -AKAKPAAKA | ---------- | KPAAKAKPAA | RPAKASRTST | RTSPGKRAAA | | 264 |
| SEQ_ID_NO_117 | AAKAKPAAKA | ---------- | KPAAKAKPAA | KPAKAARTST | RTSPAAAAAA | | 259 |
| SEQ_ID_NO_122 | -TPVKTKAAA | ---------- | KP--KAK--E | KPAKVARTAT | RSTPSRKAAP | | 244 |
| SEQ_ID_NO_120 | -APAKTKAAV | ---------- | KPNLKAK--T | TTAKVAKTAT | RTTPSRKAAP | | 255 |

Figure 4 (continued)

| SEQ_ID_NO_101 | - - KKAPAKKS | T - PKAKEA - - | | | | 255 |
|---|---|---|---|---|---|---|
| SEQ_ID_NO_102 | - - - - - - - - - - | - - PKKKAG - - | | | - - - - - - RP - - | 237 |
| SEQ_ID_NO_150 | - - - - - - - - - - | - - - - KKAG - - | | | - - - - - - GA - - - | 239 |
| SEQ_ID_NO_118 | - - - - - PVKKV | K - TVKSPA - - | | | | 223 |
| SEQ_ID_NO_145 | - - - - VASKKA | K - PVKKATA - | | | | 225 |
| SEQ_ID_NO_149 | - - - - VALKKA | K - AGKKVTT - | | | | 230 |
| SEQ_ID_NO_144 | - - - - RSSSRS | A - PTKKPK - - | | | - - - - PAVKKA | 232 |
| SEQ_ID_NO_125 | - - - - AAAPKK | A - AARKPPT - | - - - - - - - - - - | KRSTPVKKAA | PAKKAAPAKK | 261 |
| SEQ_ID_NO_137 | - - - - - AKKPA | A - AAKKAPA - | - - - - - - - - - - | KKAAPAKKA - | - - - - PTPSRK | 261 |
| SEQ_ID_NO_146 | - - - - AAKKPA | A - AAKKAPA - | - - - - - - - - - - | KKAAPAKKA - | - - - - AAPARK | 285 |
| SEQ_ID_NO_147 | - - - - AAKKPA | A - AAKKAPA - | - - - - - - - - - - | KKAAPAKKA - | - - - - AAPARK | 285 |
| SEQ_ID_NO_119 | KPAAAPVKKA | T - PVKKATAT | PVKKAAPVKK | AAPAKGKSV - | - - - - KTPVKR | 293 |
| SEQ_ID_NO_100 | - - - - - PAKKV | A - VTKKAP - - | | - - - AKSAKV - | - - - - KSPAKR | 265 |
| SEQ_ID_NO_113 | - - - - PAKKAA | AAATKKAP - - | | - - - AKSVKV - | - - - - KSPAKR | 252 |
| SEQ_ID_NO_104 | - - PKPAAKKA | P - AAKKAP - - | | AKSVKPKSV - | - - - - KSPAKK | 272 |
| SEQ_ID_NO_108 | - - TKVAPKKA | A - TPKKAP - - | | AKTVKLKSV - | - - - - KTPTKK | 278 |
| SEQ_ID_NO_116 | - - AKPAVKKA | ATPVKKAVPA | - - - - - - - - - - | KKAATPVKK - | - - - - AAPARK | 297 |
| SEQ_ID_NO_117 | - - PKPAAKKA | A - PVKKTPV - | | KAAAKAKTA - | - - - - KSPAKK | 289 |
| SEQ_ID_NO_122 | - - - KPVAKKV | P - VKKAAPA - | | AKSVKAKTA - | - - - - KSPAKR | 274 |
| SEQ_ID_NO_120 | - - KATPAKKE | - - PVKKAP - - | | - - - - - AKNV - | - - - - KSPAKK | 279 |

| SEQ_ID_NO_101 | - - - KSKGKK | 261 |
|---|---|---|
| SEQ_ID_NO_102 | - - - AKKAKK | 243 |
| SEQ_ID_NO_150 | - - - AKKAKK | 245 |
| SEQ_ID_NO_118 | - - - GKRTRK | 229 |
| SEQ_ID_NO_145 | - - - PKKAKK | 231 |
| SEQ_ID_NO_149 | - - - PKKAKK | 236 |
| SEQ_ID_NO_144 | AAAAKKAKK | 241 |
| SEQ_ID_NO_125 | APAAKKAKK | 270 |
| SEQ_ID_NO_137 | VP - SRKAKK | 269 |
| SEQ_ID_NO_146 | VP - ARKAKK | 293 |
| SEQ_ID_NO_147 | VP - ARKAKK | 293 |
| SEQ_ID_NO_119 | TSARKAGKK | 302 |
| SEQ_ID_NO_100 | AS - TRKAKK | 273 |
| SEQ_ID_NO_113 | ASTRKK - - - | 258 |
| SEQ_ID_NO_104 | AT - SRRGKK | 280 |
| SEQ_ID_NO_108 | AA - VKKGKK | 286 |
| SEQ_ID_NO_116 | APAKRGGRK | 306 |
| SEQ_ID_NO_117 | AA - AKRGKK | 297 |
| SEQ_ID_NO_122 | AS - ARKGRK | 282 |
| SEQ_ID_NO_120 | AT - PKRGRK | 287 |

Figure 5

| | | | | | | | |
|---|---|---|---|---|---|---|---|
| SEQ_ID_NO_164 | MENM----- | KMNNDERFA- | ------QKGV | PVHSQVMKIK | QESEKIVDWS | | 37 |
| SEQ_ID_NO_158 | MENN----- | SSNDDSRGRN | GDGDHGYVGF | PIHSQVIKIR | QEFDKIKHPS | | 44 |
| SEQ_ID_NO_154 | MEQKKISSSS | SSNNNAVIRD | EDE---YKGV | PIHSQVMKIK | QEFEKIKHPS | | 47 |
| SEQ_ID_NO_152 | MENK----- | TDNGN----- | ------EDGP | IIHSQVEKIK | KEFEKIRQPS | | 33 |
| SEQ_ID_NO_162 | MENK----- | TNNGN----- | ------EDG- | PKHSQVVKIK | REFEKISQPS | | 32 |

| | | | | | | |
|---|---|---|---|---|---|---|
| SEQ_ID_NO_164 | PGKPEIRSVL | REIS-RQISR | SPLGISGDPI | SVGES | | 71 |
| SEQ_ID_NO_158 | LQQLEVRGVV | KCRINRQRSR | SPLGLAERPI | SVGN- | | 78 |
| SEQ_ID_NO_154 | LQQPDMRRVL | REIT-RQRSR | SPLGLAERPI | SVGNS | | 81 |
| SEQ_ID_NO_152 | LQQPEMRRVL | SEIKRRQRSR | SPLGLGERSI | SVGN- | | 67 |
| SEQ_ID_NO_162 | LKQPEMRRVL | SEITRRQRSR | SPLGLGERSI | SVGH- | | 66 |

Figure 6

| | | | | | | | |
|---|---|---|---|---|---|---|---|
| SEQ_ID_NO_184 | | | | | MG | L | 3 |
| SEQ_ID_NO_168 | | | | | MS | S PTQVLQG LLGEFHSRRL | 22 |
| SEQ_ID_NO_177 | | | | | ME | YPRRTLLH-- ---------- | 10 |
| SEQ_ID_NO_181 | | | | | MG | TPLRMPHMST CSNVAPAP- | 20 |
| SEQ_ID_NO_182 | | | | | MA | MSPHDQHEHE PDHAHRSP- | 20 |
| SEQ_ID_NO_183 | | | | | MA | MSPHDQHEHE PDHAHRSP- | 20 |
| SEQ_ID_NO_170 | | | | | MR | PAPLEAEAAA ANT SHLSP- | 20 |
| SEQ_ID_NO_166 | | | | | MR | LLVAEAA--- ---------- | 9 |
| SEQ_ID_NO_174 | MWMMI SQEGQ | RSNPI IYHNN | I HLLCEVDQK | REKASVIVLK | IQTKHPNPES | | 50 |

| | | | | | | | |
|---|---|---|---|---|---|---|---|
| SEQ_ID_NO_184 | ------SSLP | GPSEGMLCVI | LVN------- | TALSIS FKG | VRSVLHVLG | 40 |
| SEQ_ID_NO_168 | LLTP- TTAS | PPSSE HHNS | SDLYTRNNGF | DANI VMVLSV | LLCALICSLG | 70 |
| SEQ_ID_NO_177 | --TPF SGHPG | GPSQPLDGAT | A---TDGSNF | DANVVMILAV | LLCALICALG | 55 |
| SEQ_ID_NO_181 | --APEAPRAP | PSSP------ | ----------L | DYDVVVILAA | MLCALVCALG | 53 |
| SEQ_ID_NO_182 | ------SNGT | AATSTIATNR | NGPYSGAGDF | ASNMAVILAA | LLAALALALA | 64 |
| SEQ_ID_NO_183 | ------SNGT | AATSTIATNR | NGPYSGAGDF | ASNMAVILAA | LLAALALALA | 64 |
| SEQ_ID_NO_170 | --PPLHSRAP | SCDPQVHSCK | NAPYSNSNDF | GANTAMILII | LLCALICALV | 68 |
| SEQ_ID_NO_166 | --SPLSSFAA | TPTCNSHTCR | NKPYSNSTDF | TANASVLLIL | VISALICALS | 56 |
| SEQ_ID_NO_174 | FKTSLEP-SP | PLSPHSLCIR | NKPYSNSSEF | QANASVLLIL | FVSALICSLS | 99 |

| | | | | | | | |
|---|---|---|---|---|---|---|---|
| SEQ_ID_NO_184 | IRLSQSSSSP | SSVTASSEIP | ASEPFDFRVS | HPESFLEEFR | NKTPTLRYES | 90 |
| SEQ_ID_NO_168 | LNSIIRCALR | CSSLIASEGG | ATTSSRLANK | ---GVKRKAL | KTFPTYNYS- | 116 |
| SEQ_ID_NO_177 | LNSIVRCALR | CSSRVVGPE | PNQVTRLVQS | ---GLRRKAL | RANPVLVYS- | 101 |
| SEQ_ID_NO_181 | LNSMLQCMVR | CTRRAVADPV | GWAHRRABA | ---GLKREDV | VALPVVTYSL | 99 |
| SEQ_ID_NO_182 | LNAAVRYLLR | RHRRARQQPA | AAAAAAEDPE | KPPVQEADPP | PPPPALVYSA | 114 |
| SEQ_ID_NO_183 | LNAAVRYLLR | RHRRARQQPA | AAAAAAEDPE | KPPVQEADPP | PPPPALVYSA | 114 |
| SEQ_ID_NO_170 | LNTAI RAFLR | SNNNNSSDRL | GELEEDRKPK | --DEADMATL | VLATTQVYS- | 115 |
| SEQ_ID_NO_166 | LYAAI RCFLR | --------PT | LETEDDHKPD | --PEAAASST | PTTPTLVYS- | 95 |
| SEQ_ID_NO_174 | LCAAI RCFLR | PN------L | QTDDNEHKPD | --PEEDVSST | VPTPTLVYS- | 139 |

| | | | | | | | |
|---|---|---|---|---|---|---|---|
| SEQ_ID_NO_184 | LCRCKKHEDN | ECSVCLSKFE | EDSEINKLK- | -C----GHL | FHKTCLEKW- | 132 |
| SEQ_ID_NO_168 | ADLKLPGLDS | ECII CLSDFT | AGDRVRLLPK | -C----NHG | FHVRCI DKW- | 159 |
| SEQ_ID_NO_177 | PGLRINAANP | TCAI CLSDFE | AGEHVRVLPK | -C----NHG | FHVRCI DRW- | 144 |
| SEQ_ID_NO_181 | -ASPPAAAAA | GCAI CLSDFA | DGERMRVLPV | -C----GHR | FHVVCI DRW- | 141 |
| SEQ_ID_NO_182 | AGTKLAGA-A | ECAI CLAEFV | DGDTVRVMPC | WCQEI PLESG | LRFAQI KVYQ | 163 |
| SEQ_ID_NO_183 | AGTKLAGA-A | ECAI CLAEFV | DGDTVRVMPV | -C----GHG | FHARCI ERW- | 156 |
| SEQ_ID_NO_170 | AGMKLGGVEA | DCAI CLSEFV | EGEGI RVLGR | -C----DHG | FHVLCI EKW- | 158 |
| SEQ_ID_NO_166 | SDLELAGAEA | ECAI CLSEFE | QGESI QVLEK | -C----QHG | FHVKCI HKW- | 138 |
| SEQ_ID_NO_174 | SDLELAGAQA | ECAI CLSEFE | PGESI HVLEK | -C----HHG | FHI KCI HKW- | 182 |

Figure 6 (continued)

| | | | | | | | | | |
|---|---|---|---|---|---|---|---|---|---|
| SEQ_ID_NO_184 | | · · · · · · · · · · | -L- DYWN TC | PL CRT- | PLVV | · · · · · · · · · · | · · · · · · · · V | 150 |
| SEQ_ID_NO_168 | | · · · · · · · · · · | -L- SAHSSC | PKCRH- | CLVD | TCDKI VGCT- | --QASSSEPP | 192 |
| SEQ_ID_NO_177 | | · · · · · · · · · · | -L- LARSTC | PTCRD- | SLFG | VPQKASGCSE | ASRAAEPEPA | 180 |
| SEQ_ID_NO_181 | | · · · · · · · · · · | -L- ASHKSC | PTCRR- | RLSS | · · · · · · · · · · | · · · · · · · · ES | 159 |
| SEQ_ID_NO_182 | TGPFNVEAAN | LL- PTPGIC | TTCRF- | VYRG | VVKHLHFL-- | --YGDWRD L | 206 |
| SEQ_ID_NO_183 | | · · · · · · · · · · | -LAGGRRSSC | PTCRA- | PAAT | · · · · · · · · · · | · · · · · · · · PP | 176 |
| SEQ_ID_NO_170 | | · · · · · · · · · · | -L- SSHSSC | PTCRRG | CLAS | SPSSPEPDNC | SAGNGHDSNS | 195 |
| SEQ_ID_NO_166 | | · · · · · · · · · · | -L- STRSSC | PTCRT- | SIFS | · · · · · · · · · · | · · · · · · · · · · | 154 |
| SEQ_ID_NO_174 | | · · · · · · · · · · | -L- SSRSSC | PTCRT- | SIFS | · · · · · · · · · · | --QNTL DSAT | 206 |

| | | | | | |
|---|---|---|---|---|---|
| SEQ_ID_NO_184 | AAAEDQKQLS | SNVW- · · · · · | · · · · | 164 |
| SEQ_ID_NO_168 | PVQETI LSI I | TPVDREGFI H | SYR- | 215 |
| SEQ_ID_NO_177 | PAPAPARSVL | VPLRPEGLVT | HYDF | 204 |
| SEQ_ID_NO_181 | GGGHRHL QVL | TAV- · · · · · · | · · · · | 172 |
| SEQ_ID_NO_182 | ACFVKGKKNT | NS- · · · · · · · | · · · · | 218 |
| SEQ_ID_NO_183 | GATATEPAAV | AP- · · · · · · · | · · · · | 188 |
| SEQ_ID_NO_170 | SQSAEPERAA | DNLSTNGNL P | V- · · | 216 |
| SEQ_ID_NO_166 | QHSETPSSHI | NA- · · · · · · · | · · · · | 166 |
| SEQ_ID_NO_174 | SAVAPSTNEI | NA- · · · · · · · | · · · · | 218 |

Figure 7

```
SEQ_ID_NO_194    MLKSKSCREE MRSSS AYK- YHCLTNGGTP EAVAAPSPTN PQLPVMLRSY    49
SEQ_ID_NO_199    -MAAADYDRA YRPYAPSSAA DYDRPYRNE- ---------- ------VPY    32
SEQ_ID_NO_204    -MAAADADYE YRAYG-APA- DHDRPYHG-- ---------- RE----VVPY    31
SEQ_ID_NO_186    ---MANYYE- -PPAS-GNRR DAVKGYNS-- -G-------- ---------SF    25
SEQ_ID_NO_201    ---MD--RS- -KSYA-GGR- MQIEPYYD-- -G----GGAR PD----FRSY    30
SEQ_ID_NO_203    ---MDDFRS- -RSFN-DGK- MQLEVYGGRR SGAVPAPPVL HD----YRSY    39
SEQ_ID_NO_188    ---MEHFRS- -KSCR-EGR- IEMEGYDEDK AA----PTNM QD----LRSY    35
SEQ_ID_NO_196    ---MEEFRS- -KSYG-DGR- MQIEAYRG-- -------ANI QD----LRCV    30
SEQ_ID_NO_197    ---MEDYNKQ IRPYG-NSCM MQMEGYYG-- -A----TNPN YD----LRSY    35
SEQ_ID_NO_193    ---MEDYNRQ -RAYG-DTG- MQIQPYHG-- -G----GPGT GD----FRKY    33

SEQ_ID_NO_194    S-------- TSTYS---- ---------- ----PHKNPT TVRDNPNS-K    70
SEQ_ID_NO_199    G-------- DRRIDLVVKP PPP------- ----TRSPPP PLPVTKSG--    60
SEQ_ID_NO_204    G-------- DRRIDVVVKP PGTTTTTT-- ----TRSPPP PLPVTKVG-G    65
SEQ_ID_NO_186    D-------- DSSGDQSQ-- ---------- ----TNDYQL KIKKSKSVPN    50
SEQ_ID_NO_201    SYSAGGSGMG TSSYAYQYEY S--------- ----GAGAGE EMKRSKS---   64
SEQ_ID_NO_203    S-------- -ASYFYTYD- ---------- ----GSGVGY GDFKGKPDHG    64
SEQ_ID_NO_188    S-------- -VSYAVSVQP N--------- ----QSGKEG KMKKGKSN--    60
SEQ_ID_NO_196    S-------- -ASYASSVHP TTTTTTTTQT QMGGNNNNEA KFKKGKST--    68
SEQ_ID_NO_197    S-------- DFSYAQTQRG ---------- ----PNNKDL KLKKGKS-S    61
SEQ_ID_NO_193    S-------- -TSYA----- ---------- ----TENNIX NIKKEKS---   52

SEQ_ID_NO_194    SNGKVKKGL- --KEAEIQRK KRVAAYNVYG VEGKVKGSIR KNFKWEKETC    117
SEQ_ID_NO_199    GGGGIGSAWC F-SDPEVKRR RRVASYKAYS VEGKVKASFR RGFRWIKDKC    109
SEQ_ID_NO_204    GGGGMGSAWC F-SDPEMKRR RRVASYKAYS VEGKVKSSLR RGFRWIKAKC    114
SEQ_ID_NO_186    ADRAASRSWS E-SDPESRRK RRYAGYKVYS VEDKMKGSIR KSFKWFKDL-    97
SEQ_ID_NO_201    -----KRRML ALADPDMERK RRVAYKAYG VEGKMKGSFR KSFKWIKDRY    109
SEQ_ID_NO_203    SSASNKGGRV F-KDPEFQRK RRVASYKAYA VEGKVKGSLR RSLRWFKDKY    113
SEQ_ID_NO_188    -LESSKSWS F-NDPELQRK RRVANYKVYA IEGKMKGSLR KSFRWIKDTC    108
SEQ_ID_NO_196    -NGSTSKSWS F-SDPELQRK KRVASYKVYA VEGKLKGSLR KSFKWLKDRC    116
SEQ_ID_NO_197    SRSSISKSWG FGDDPEFQRK KRVASYKMYS VEGKVKGSFR KSFKWLKNRY    111
SEQ_ID_NO_193    ---ARSKSWG I-TDPELQRK KRVASYKMYS VEGKVKGSFR KSFRWLKQRY    98
```

Figure 7 (continued)

| | | |
|---|---|---|
| SEQ_ID_NO_194 | SNAVNGLW | 125 |
| SEQ_ID_NO_199 | TGFIHG | 115 |
| SEQ_ID_NO_204 | SELIHGWYGS LLLPLSFSLD DFIITSKQAL S | 145 |
| SEQ_ID_NO_186 | ---IGLS | 102 |
| SEQ_ID_NO_201 | LNLVYGWS | 117 |
| SEQ_ID_NO_203 | TRAVYGWW | 121 |
| SEQ_ID_NO_188 | TQVVYGWR | 116 |
| SEQ_ID_NO_196 | NRVVYG | 122 |
| SEQ_ID_NO_197 | WHVVYSLW | 119 |
| SEQ_ID_NO_193 | TQVVYGWW | 106 |

Figure 8

```
SEQ_ID_NO_216    MGKGEAWVNG QRIGRYWPTY VASDASCTDS CNYRGPYSAS KCRKNCEKPS    50
SEQ_ID_NO_208    .......... .......... ....METLQ  CRHQHVFIL  .........C    15
SEQ_ID_NO_214    .......... .......... ....MDTTHS CRRG--VIL  .........C    14

SEQ_ID_NO_216    QTLYHVPRSW LKPSGNILVL FFFRGGDPTQ ISIVTKQTES LCAHVSDSHP   100
SEQ_ID_NO_208    LVLFHS-SL  FVLASKIDVS DDARGIRIDG ---GQKRFLT NSPQHSKEHA    60
SEQ_ID_NO_214    LVLSYS-SV  FGLASNMSIS NDTSGNKTDS FFESQSTSTE WGTDMGDKYI    62

SEQ_ID_NO_216    PPVDLWNSET ESGRKVGPVL SLTCPHDNQV SSIKFASYG  TPLSTCGNFY   150
SEQ_ID_NO_208    .......ACT NEEPDLGPLT RISCNEPEYV LTKINFADYG NPTGTCGHFR   103
SEQ_ID_NO_214    .......MCT ESNMEIPWM- -ISCKKSKEV FTRINFADYG NPSGKCEHYR   103

SEQ_ID_NO_216    HGRCSSNKAL SIVQKACIGS SSCSVGVSBD TFGDP-CRGM AKSLAVEATC   199
SEQ_ID_NO_208    RDNCGARATM RIVKKNCLGK EKCHLLVTDE MFGPSKCKGA PM-LAVETTC   152
SEQ_ID_NO_214    HGNCGAKTTM EVAKKNCLGK HDCVFKVSDE MFGTSHCKKE AK-FFVQLTC   152

SEQ_ID_NO_216    A--    200
SEQ_ID_NO_208    TIA    155
SEQ_ID_NO_214    TKA    155
```

Figure 9

| | | | | | | | |
|---|---|---|---|---|---|---|---|
| SEQ_ID_NO_218 | ----MDEEAA | KPRDSTVNQQ | H--------- | ---------- | QYY | YGTFQGVANF | 30 |
| SEQ_ID_NO_225 | ----MDEEAA | KPRDTTVNQQ | Q--------- | ---------- | QYY | YGTFQGVANY | 30 |
| SEQ_ID_NO_227 | -MGDGEEDKS | KGFADEADTH | H--------- | ---------- | Q   | YGTFQGVSNY | 31 |
| SEQ_ID_NO_220 | ----MSGDEK | NPAVVVDHQH | H--------- | ---------- | Q   | YGTFQGVSNY | 28 |
| SEQ_ID_NO_222 | ----MSDQEK | NRGVVVDHRH | HEDQPPPPP  | -----PPDPQ | YGTFQGVANY | | 40 |
| SEQ_ID_NO_231 | MAGEMPDADG | KPRSASSGFQ | PSAPPQPQ-- | -----AQQYQ | YGTFGA---- | | 39 |
| SEQ_ID_NO_230 | -MGGGREEEA | ASKL-VGYSS | GDLPPSAPPH | LQGQDPQQYQ | YGTFQ----- | | 42 |
| SEQ_ID_NO_229 | -MGGGDEQEA | DAGKSGGYSS | SGLPPSEPL- | -----SQQYG | YGTFQG---- | | 38 |
| SEQ_ID_NO_1052 | -MGGRHEAEA | DGGKAGGYSS | SGLPPSEAPH | LQGQPSQEYG | YGTFQG---- | | 45 |

| | | | | | | | |
|---|---|---|---|---|---|---|---|
| SEQ_ID_NO_218 | PTPAPPPQFM | QPQHPITTF- | ---PGHAY-- | ---------Q | NLQGHG---- | | 61 |
| SEQ_ID_NO_225 | PPPAPPP--- | LPHQPIVTSP | LLPP------ | ---------- | ---------- | | 51 |
| SEQ_ID_NO_227 | PPPRP----- | QNSPPVTGFP | QPSAPPRV-- | ---------Y | D-SAPP---- | | 60 |
| SEQ_ID_NO_220 | PPPPPP---- | QHHGPAIGFP | QPVPPPGL-- | ---------H | EPSAPP---- | | 59 |
| SEQ_ID_NO_222 | PPPS------ | --QSHVIGFP | QPVPPPGL-- | ---------- | --TAEP---- | | 64 |
| SEQ_ID_NO_231 | PSSAPG---- | EVPQPAVGFP | QPAPPPGL-- | ---------R | HYPQPPPPSY | | 74 |
| SEQ_ID_NO_230 | PPPHHHAASG | ELARPPVGFP | QPAPPPGFAG | ASGGGGHYHH | HHQQQP---- | | 89 |
| SEQ_ID_NO_229 | SRAGSG---- | EFRKPPVGFP | QPAPPPGF-- | --GGGG---Y | HNQQQP---- | | 73 |
| SEQ_ID_NO_1052 | P--------- | --RQPPVGFP | QPAPPPGF-- | --GGGG---Y | HNQQKP---- | | 73 |

| | | | | | | | |
|---|---|---|---|---|---|---|---|
| SEQ_ID_NO_218 | ---------- | ---GGVNYAQ | GFPVVVPDYT | -VVEVRP--M | IEHELPCCGL | | 95 |
| SEQ_ID_NO_225 | ---------- | --------VH | GYQ-TLQEYT | -VVEVRP--V | REHDVPCCGF | | 79 |
| SEQ_ID_NO_227 | ---------- | ------HYAH | GYQ-TVPVHG | -IAEGRPVHV | RQRRLPCCGI | | 92 |
| SEQ_ID_NO_220 | ---------- | ----PQYYPQ | GYQ-TVPGYA | -VAEGRP--V | RERRLPCCGI | | 91 |
| SEQ_ID_NO_222 | ---------- | -------YAQ | GYQ-TVPGYA | -VAEGRP--V | RQRRLPCCGC | | 93 |
| SEQ_ID_NO_231 | AVYPPLPPQT | YPAAAPYYAL | GYQ-AVQGYL | PVVEGRP--V | RMRRLPFCGL | | 121 |
| SEQ_ID_NO_230 | ---------- | YAPAEPYYAQ | GYQ-TSPGYG | SIAEGRP--V | RMRRLPCCGL | | 125 |
| SEQ_ID_NO_229 | ---------- | YTPEEPYYAQ | GYQ-AVPGYG | QVAEGRP--V | RMRRLPCCGL | | 110 |
| SEQ_ID_NO_1052 | ---------- | YAPAEPYYAQ | GYQ-AVPGYG | PVAEGRP--V | RMRRLPCCGL | | 110 |

| | | | | | | | |
|---|---|---|---|---|---|---|---|
| SEQ_ID_NO_218 | GMGWFLFIMG | FLFGGIPWYL | GAFIVLVT-S | VDHREKAGYV | ACSIA----- | | 139 |
| SEQ_ID_NO_225 | GMGWFLFIMG | FLFGGIPWYL | GAVIILFT-S | VDHREKAGYV | ACSVA----- | | 123 |
| SEQ_ID_NO_227 | GLGWFLFIVG | FFLGAIPWYV | GMFIMIVGRR | DHREKPGYI  | ACTIA----- | | 137 |
| SEQ_ID_NO_220 | GFGWFLFIIG | FFLGAIPWYI | GLFVLLCA-R | DYREKPGYI  | ACTIA----- | | 135 |
| SEQ_ID_NO_222 | GVGWFLFIIG | FFLGAIPWYI | GLFIIACM-R | DPREKPGYV  | ACTIALRKHL | | 142 |
| SEQ_ID_NO_231 | GMGWFLFIIG | FFLAAIPWYI | GAFVLICVRV | HDYREKPGYV | ACTIA----- | | 166 |
| SEQ_ID_NO_230 | GLGWLLFIAG | FFLAAIPWYV | GAFILICVRV | HDYREKPGYV | ACTVA----- | | 170 |
| SEQ_ID_NO_229 | GLGWCLFITG | FFLAAIPWYI | GAFIMICVRV | HDHREKPGYV | ACTIAVSS-- | | 158 |
| SEQ_ID_NO_1052 | GLGWCLFITG | FFLAAIPWYI | GAFILICVRV | HDQREKPGYV | ACTIA----- | | 155 |

Figure 9 (continued)

| | | | | |
|---|---|---|---|---|
| SEQ_ID_NO_218 | ---------- ---------- S | VVYLI AVMLG | MTGD N | W | 158 |
| SEQ_ID_NO_225 | ---------- ---------- S | VVYLI AVMLG | MAGN N | W | 143 |
| SEQ_ID_NO_227 | ---------- ---------- A | I LATI AVI LG | VTKGAE DW | 156 |
| SEQ_ID_NO_220 | ---------- ---------- A | VLATI AI I LG | VTKGI D DF | 153 |
| SEQ_ID_NO_222 | VEHECHI EI R CLLHNLCVK A | I LATI AI I LG | ATKGAD EW | 180 |
| SEQ_ID_NO_231 | ---------- ---------- A | SLAAI AI LLG | VTRGEE W | 185 |
| SEQ_ID_NO_230 | ---------- ---------- A | VI AAI VI PLG | LTKGAH VW | 189 |
| SEQ_ID_NO_229 | ---------- ---------- F | LL QCNL TVY | FTSGI --- | 174 |
| SEQ_ID_NO_1052 | ---------- ---------- A | VVAAVAI LLG | VTKGTH VW | 174 |

Figure 10

```
SEQ_ID_NO_244    MEYQRTNNLS LAFQFFRKAF EMCDSDPLLF NEYGVLRYRQ G-NYEEAVEN   49
SEQ_ID_NO_234    MEYMRTHSYK LADQFFMQAK AICPSDPLVY NELGVVAYHM KEYGKAVRW    49
SEQ_ID_NO_236    MEYMRTHSYK LAEQFFMQAK TICPSDPLVY NELGVVAYNM KEYNKAVLA    49
SEQ_ID_NO_241    MQYVRMHNFK LAEQFFTQAK SICPSDPLIH NELGVVAYNM KEEYQKAVSY   50
SEQ_ID_NO_242    MQYLRMHNFK LAEQFFTQAK SICPSDPLIY NEMGVVAYNM KEYQKAVQW    49

SEQ_ID_NO_244    FERALDLAPK PVGSRMESL  VNLAQAFRKI GRYDEAIATF QSALLISPRN   99
SEQ_ID_NO_234    FEKTLAH PS ALTESMEPTV VNLAHAYRKL RKDREAISYY ERALTLSTKS   99
SEQ_ID_NO_236    FEKTLKH PS -LSQLMEPTV INLAHAYRKL KIYHEAISCY ERALALSTRS   98
SEQ_ID_NO_241    YAKALTFPTK SLSL----AF AGLAYIYHLM DDFEAAINYY HKALMLKPDD   95
SEQ_ID_NO_242    FELTLEHTSS SLNEMMEPTL VNLGHALRKL KKYQKAISYY EKALTFQTKS   99

SEQ_ID_NO_244    ASTYAALAFT YQMKSRCSEP VSLGLAIEYY HKALSLRADD AFSQHHLELA   149
SEQ_ID_NO_234    LSTYSGLAYT YHLQGNFS- ----AAISYY HKALMLKPDD QFCTEMLNVA   143
SEQ_ID_NO_236    LSTYAGLAYT YHLQDNFT- ----AAITCY HKALMLKPDD QFCTEMLSLA   142
SEQ_ID_NO_241    QFCTDMLTYA LESICQIT- ---------- ---------- --------A    114
SEQ_ID_NO_242    LSAFAGLAYT YHLMAMYH- ----V----- HRA------- ----EVLQI    127

SEQ_ID_NO_244    LIDQSAITIP RHQQVEWDTM FPKVEDINAV TPTFGIASSP QGGILFPTPS   199
SEQ_ID_NO_234    LMDE------ ---------- ---------- ---------- ----------   147
SEQ_ID_NO_236    LVDE------ ---------- ---------- ---------- ----------   146
SEQ_ID_NO_241    RRKP------ ---------- ---------- ---------- ----------   118
SEQ_ID_NO_242    TKEP------ ---------- ---------- ---------- ----------   131

SEQ_ID_NO_244    PHSFQGTPTF GQTPFSARVD RMDESVDMDQ SVDMDESE    237
SEQ_ID_NO_234    ---------- CQNGVDSKV- ---------- ----ELC     159
SEQ_ID_NO_236    ---------- GRRGIDPKI- ---------- ----EFR     158
SEQ_ID_NO_241    ---------- GRGLLTATGG ---------- ----VTC     131
SEQ_ID_NO_242    ---------- GR-------- ---------- -------     133
```

Figure 11

```
SEQ_ID_NO_268   ---MEEQQAA AABGG---GG BGGASMCANG CGFFGSEATK KLCSKCYRDQ   44
SEQ_ID_NO_298   ---MAER-QE VSG------- GMAAPMCANA CGFFGSAATK NLCSKCYK--   37
SEQ_ID_NO_260   ---MSSEQNN STSFP----- PTEPKLCDNG CGFFGSPSNM NLCSKCYR--   40
SEQ_ID_NO_249   ---MAEELHR CQA------- P---DLCAHN CGFFGSPTTC NLCSECYR--   34
SEQ_ID_NO_255   ---MAEEQHR CQE------- P---RLCVNN CGFFGSPATC NLCSKCYG--   35
SEQ_ID_NO_265   ---MAEELHR CQA------- ---ADRLCANN CGFFGSPAMC DLCSKCYR--   36
SEQ_ID_NO_262   ---MAEELHR CQA------- PEGHRLCSNN CGFFGSPATM NLCSKCYR--   37
SEQ_ID_NO_251   ---MAEELHR CQA------- PEGHRLCVNN CGFFGSSATM NLCSKCYR--   37
SEQ_ID_NO_246   ---MAEELHR CET------- PEGHRLCVNN CGFFGSSATM NLCSNCYG--   37
SEQ_ID_NO_274   ---MAEELHP CQT------- PEGHRLCVHN CGFFGSSATM NLCSNCYG--   37
SEQ_ID_NO_248   MAQRDKEETE MKV------- SEBLSLCIHN CGFSGNPATK NMCDSCYK--   41
SEQ_ID_NO_279   ---MAQESWK QESEETRVHA PEAPILCINN CGFFGSSMTN NMCSKCYR--   46
SEQ_ID_NO_295   ---MAQESWK QESHA----- PEAPILCINN CGFFGSSMTN NMCSKCYR--   40
SEQ_ID_NO_270   ---MDHDKTG CQSP------ PEGPKLCINN CGFFGSAATM NMCSKCHK--   39
SEQ_ID_NO_267   ---MEQNETG CQVP------ PDAPMCVNN CGFFGSAATM NPCSKCHK--   39
SEQ_ID_NO_277   ---MEHEETG CQPH------ PEGPILCVHN CGFFGSVATR NMCSKCHK--   39
SEQ_ID_NO_286   ---MEHKETG CQQ------- PKGPILCIHN CGFFGSAATM NMCSKCHK--   38
SEQ_ID_NO_290   ---MEHKETG CQQ------- PEGPILCIHN CGFFGSAATM NMCSKCHK--   38

SEQ_ID_NO_268   LKAAPSSPPA APDLVANEEE EASTAAAAAA DECLALCSSG CGFFGSKETN   94
SEQ_ID_NO_298   ---------- --EHLIKTAK DEASAAVVMG GAIVKCAADB CGFFGSSATN   75
SEQ_ID_NO_260   ---------- --SLRAEEDQ TAVAKAAVEK SLKLPSCSL- TAPAPKD-PL   77
SEQ_ID_NO_249   ---------- --GLQLKEQQ BSSAKQAFMH TLVPSSSSLP ------SS   64
SEQ_ID_NO_255   ---------- --DLRDSCPL NCLLAPSBSA SVSSFSSPL- ----------   61
SEQ_ID_NO_265   ---------- --DLQMKEQR SSAKLVLHD TLIPDSNSB SLPTG-HP   72
SEQ_ID_NO_262   ---------- --DIRLKEEE DAKTKSTIET ALSGSSSATV -------T   66
SEQ_ID_NO_251   ---------- --DLCLKEQE ASSKSALSS SPSSSSTMM ----------   64
SEQ_ID_NO_246   ---------- --DLCLKQQQ DASMKSTVES SLSPVIAPV- ----------   64
SEQ_ID_NO_274   ---------- --DLCLKNQQ DASMKSTVES SLSAASPPS- ----------   64
SEQ_ID_NO_248   ---------- ------STGI MTQPHLTFSG KEKARSSELR -------LP   68
SEQ_ID_NO_279   ---------- --DFI----- KLMEAPVVEK KVTTSASSS- ----------   67
SEQ_ID_NO_295   ---------- --DFV---KL MEMDAPVVDK KLITTASS- ----------   63
SEQ_ID_NO_270   ---------- ---LFDQEQ GAKLASAVSG SPSNLKETF -------TA   69
SEQ_ID_NO_267   ---------- --DLMLKQQQ TELAASSIGS ANGGSGSPB KEPDSAIT--   75
SEQ_ID_NO_277   ---------- --DMMLKEEQ AKLAASSFGN VNGTSNSNG NEPV----VA   73
SEQ_ID_NO_286   ---------- --EMINKQEQ AKLAASSIDS VNGGDSGKE PIIAG--HA   73
SEQ_ID_NO_290   ---------- --EMINKQEQ AKLAASSIDS VNGGDSGKE PIIAG--HA   73
```

Figure 11 (continued)

| SEQ ID | col1 | col2 | col3 | col4 | col5 | col6 | # |
|---|---|---|---|---|---|---|---|
| SEQ_ID_NO_269 | NMCSKCYRDH | LKATSPLFSS | SSSPATASTT | DITVPIAPAT | TAPTPSLKGK | | 144 |
| SEQ_ID_NO_298 | NMCSGCYMDF | LKDAH----- | ----ASPAVA | DKWVVLAAEK | QPAAAQISAA | | 116 |
| SEQ_ID_NO_260 | E--------- | ---------- | ----TKPASV | ETWVLAETSS | VPPVATSCDE | | 104 |
| SEQ_ID_NO_249 | S--------- | ---------- | ----SARSSF | SASLPAKEFP | SAGTKETKVV | | 91 |
| SEQ_ID_NO_255 | ---------- | ---------- | ----TVDVIK | NQIAPVLVVE | GDEKGEFKAE | | 87 |
| SEQ_ID_NO_265 | S--------- | ---------- | ----STSPSV | MYSSSTPTV | ELVAAAAGPS | | 99 |
| SEQ_ID_NO_262 | A--------- | ---------- | ----TAVVAS | SVESPSAPVE | SLPPPVLIS | | 93 |
| SEQ_ID_NO_251 | ---------- | ---------- | ----ESGQV | PLLALHEVNR | ESAVPEIASA | | 90 |
| SEQ_ID_NO_246 | ---------- | ---------- | ----LENYAA | ELEPTFKKT | EEKKPQIPT | | 90 |
| SEQ_ID_NO_274 | ---------- | ---------- | ----SPEDS | ISTST APVV | QIVAAEIQIE | | 90 |
| SEQ_ID_NO_248 | E--------- | ---------- | ----RSDYCR | --RDLITQDD | KKGDDDAK | | 93 |
| SEQ_ID_NO_279 | ---------- | ---------- | ----TAPLET | KRDDAPAAAA | TEAVAEKQAE | | 93 |
| SEQ_ID_NO_296 | ---------- | ---------- | ----STVPFE | TAKQDDTVPD | AAAMDDKQPA | | 89 |
| SEQ_ID_NO_270 | D--------- | ---------- | ----LVDAT | KSIEPVAVSV | DAVAEVVAPE | | 96 |
| SEQ_ID_NO_267 | ---------- | ---------- | ----TVHVDA | GESDSMIVSM | QASHESLLNE | | 101 |
| SEQ_ID_NO_277 | A--------- | ---------- | ----GVDVQA | HLVEPKTLSL | QPSFSFGSGS | | 100 |
| SEQ_ID_NO_288 | E--------- | ---------- | ----VAVAQV | EVKTLVAQPA | EIAGPSEGVT | | 100 |
| SEQ_ID_NO_290 | E--------- | ---------- | ----VAVAQV | EVKTLVAQPA | EIAGPSEGVT | | 100 |

| SEQ ID | col1 | col2 | col3 | col4 | col5 | # |
|---|---|---|---|---|---|---|
| SEQ_ID_NO_269 | EEEATARASS | SAAAAKPNR | CVACRKKVGL | LGFECRCGGT | FCSTHRHADK | 194 |
| SEQ_ID_NO_298 | TSSTAPAA- | -VKAAAAPNR | CASCRKKVGL | LGFPCRCGGT | FCALHRYAEK | 163 |
| SEQ_ID_NO_260 | GEP------- | --SKPARPNR | CFSCNKKVGV | MSFKCKCGST | FCGSHRYPEK | 145 |
| SEQ_ID_NO_249 | EEE------- | --EVQVFPNR | CLSCKKRVGL | TGFKCRCGMV | FCGLHRYPGT | 132 |
| SEQ_ID_NO_255 | PTI------- | -VVPQQKPNR | CLTCRRRVGL | TGFNCRCGMV | FCGTHRYPEQ | 129 |
| SEQ_ID_NO_265 | EAE------- | --PPKVQPNR | CGTCRRRVGL | TGFKCRCGLT | LCGTHRYPEQ | 140 |
| SEQ_ID_NO_262 | PDI------- | --AAPVQANR | CGACRKRVGL | TGFKCRCGTT | FCGSHRYPEK | 134 |
| SEQ_ID_NO_251 | AED------- | --REQQPNR | CMVCRKRVGL | TGFRCKCGVT | FCGSHRYPEN | 131 |
| SEQ_ID_NO_246 | EQP------- | --SPPQRPNR | CTVCRKRVGL | TGFMCRCGTT | FCGSHRYPEV | 131 |
| SEQ_ID_NO_274 | KQI------- | ---CQQRPNR | CTVCRKRVGL | TGFMCRCGTT | FCGTHRYPEV | 130 |
| SEQ_ID_NO_248 | NDSTTKI-- | -VEKKQEVNR | CSGCRRKVGL | TGFRCRCGDM | FCSEHRYSDR | 140 |
| SEQ_ID_NO_279 | QEP------- | ---PKPPSNR | CLTCRKKVGL | TGFLCRCGDT | FCSTHRYTDS | 133 |
| SEQ_ID_NO_296 | QEP------- | ---PKPPSNR | CSTCRKKVGL | TGFQCRCGGT | FCSLHRYTDS | 129 |
| SEQ_ID_NO_270 | EAA------- | -AKPKEGPSR | CTTCNKRVGL | TGFKCRCGDL | FCGTHRYADV | 138 |
| SEQ_ID_NO_267 | NNV------- | -LVKEVPPNR | CSACRKKVGL | TGFNCRCGNL | FCAVHRYSDK | 143 |
| SEQ_ID_NO_277 | GSS------- | GEAKPEGPKR | CGTCNKRVGL | TGFNCRCGHL | FCAVHRYSDK | 143 |
| SEQ_ID_NO_288 | VNP------- | --KGREGPNR | CSTCRKRVGL | TGFNCRCGNL | YCAMHRYSDK | 141 |
| SEQ_ID_NO_290 | VNP------- | --KGREGPNR | CSTCRKRVGL | TGFNCRCGNL | YCAMHRYSDK | 141 |

Figure 11 (continued)

| SEQ_ID_NO_268 | HACTFDFKKS | DREKIAKENP | LIVAPK TKF   | 224 |
|---------------|------------|------------|--------------|-----|
| SEQ_ID_NO_298 | HACDFDFKAA | GREKIAKNNP | LVVAAK NKI   | 193 |
| SEQ_ID_NO_260 | HECSFDFKEV | GRGAIAKANP | VVKADKVQRI   | 175 |
| SEQ_ID_NO_249 | TCLCF      |            |              | 137 |
| SEQ_ID_NO_255 | HDCEFDFKSL | GKEQIAKANP | VVKGEKLQRI   | 159 |
| SEQ_ID_NO_265 | HGCGFDFKGM | GREEIKKANP | VVKGEKLNKI   | 170 |
| SEQ_ID_NO_262 | HACGFDFKAV | GREEIARANP | VIKGEKLRRI   | 164 |
| SEQ_ID_NO_251 | HGCTFDFKKV | GREEIARANP | LVKAEKLEKI   | 161 |
| SEQ_ID_NO_246 | HGCTFDFKSA | GREEIAKANP | LV AAKLQKI   | 161 |
| SEQ_ID_NO_274 | HGCTFDFKSA | GREEIAKANP | LVVAAKLQKI   | 160 |
| SEQ_ID_NO_249 | HDCSFDYKAA | GREEIARQNP | VVKAAK RL    | 170 |
| SEQ_ID_NO_279 | HQCTFDYKKV | AREQIAKQNP | VVMAEK NKI   | 163 |
| SEQ_ID_NO_298 | HECTFDYKKV | AREQIAKQNP | VV AEK NKI   | 159 |
| SEQ_ID_NO_270 | HNCSFDYHVA | AQEAIAKANP | VVKADKLDKI   | 166 |
| SEQ_ID_NO_267 | HDCPFDYRSA | AQDAIAKANP | VVKAEKLDKL   | 173 |
| SEQ_ID_NO_277 | HDCPYDYHTA | ARDVIAKANP | VVKADKLEKI   | 173 |
| SEQ_ID_NO_286 | HDCQFDYRTA | ARDAIAKANP | VVKAEKLDKI   | 171 |
| SEQ_ID_NO_290 | HDCQFDYRTA | ARDAIAKANP | VVKAEKLDKI   | 171 |

Figure 12

```
SEQ_ID_NO_310         -------MAE AKGAAAPL- --LAREDGRR RGGMGGATWA Q--TLGNVVV   37
SEQ_ID_NO_316         MGFGMG-NDG ASSSSSRLDP APLLPHHGSA GGEIG--LSS QPKTFANVFI   47
SEQ_ID_NO_325         MGFGMGNNNG ASSSSSRLDP APLLPHHGSG SREVG--LSS QPKTFANVFI   48
SEQ_ID_NO_312         MGF----DKE ASSSSSRLDA APLLPQHG-- GGGAGGHLSS QPKTFANVFI   44
SEQ_ID_NO_319         MGL----HKE ASSSSSRLDA APLLPHHGHG GGGAGHHLSS QPKTFANVFI   46
SEQ_ID_NO_321         MGL----HKE ASSSSSRLDA APLLPHHGHG GGGAGHHLSS QPKTFANVFI   46
SEQ_ID_NO_300         MGF----QNE ASSSSYTLKI PPPAREDTPL LGK-GPPLSS QFKTFANVFI   45
SEQ_ID_NO_302         MGFG---RKK ASSSAKTF-- --PPREDTPL IAK-STPLSS QSKTFANVFI   42

SEQ_ID_NO_310         SIVGTGVLGL PYAFRAAGWV AGSLGVAAAG FALLYCMLLL VDCKDKLQEE   87
SEQ_ID_NO_316         AVVGAGVLGL PYTFSHTGWA AGSLLLFAVA VLTFYCMMLL VACRRLAD-   96
SEQ_ID_NO_325         AVVGAGVLGL PYTFSHTGWA AGTLLLFSVA ALTFYCMMLL VACRRRLAD-   97
SEQ_ID_NO_312         AVVGSGVLGL PYTFSRTGWA AGTLLLLAVA ALTFHCMMLL VAARRRIAD-   93
SEQ_ID_NO_319         AVVGSGVLGL PYTFSRTGWV AGSVLLLAVA ALTFHCMMLL VACRRRLAY-   95
SEQ_ID_NO_321         AVVGSGVLGL PYTFSRTGWV AGSVLLLAVA ALTFHCMMLL VACRRRLAY-   95
SEQ_ID_NO_300         AVVGAGVLGL PYAFKRTGWL MGVLLLVSVS VLTHHCMMLL VYTRRKLDSF   95
SEQ_ID_NO_302         AIVGAGVLGL PYAFKRTGWL MSLIMLFSVA GLTHYCMMLL VNTRGKLQSF   92

SEQ_ID_NO_310         ETDEPKNYTY GDFGEKCFGT IGRCLTEILI LISQAGGSVA YLVFIGENLH  137
SEQ_ID_NO_316         --ERPKIASF GDLGDAVFGA HGRFAVDVML VLSQASFCIG YLIFISNTMA  144
SEQ_ID_NO_325         --EHPKIASF GDLGDAVFGA HGRFAVDVML VLSQVSFCVG YLIFISNTMA  145
SEQ_ID_NO_312         --AHPKIASF GDLGHAIYGA PGRHAVDAML VLSQASFCVG YLIFISNTMA  141
SEQ_ID_NO_319         --DHPKIASF GDLGAAVCGP AGRHVVDAML VLSQASFCVG YLIFISNTMA  143
SEQ_ID_NO_321         --DHPKIASF GDLGAAVCGP AGRHVVDAML VLSQASFCVG YLIFISNTMA  143
SEQ_ID_NO_300         NAGISKIGSF GDLGFAVCGS LGRIVVDLFI ILSQAGFCVG YLIFIGTTLA  145
SEQ_ID_NO_302         SGGFSKITSF GDVGFTVCGS IGRFVVDVMI VLSQAGFCIG YLIFIANTLA  142

SEQ_ID_NO_310         SVFS------ ---------- -----QSMS PAGFIFAVLL PVQIALSFL   165
SEQ_ID_NO_316         HLYP----IF APSSS----- ------ALLS PKALFIWAML PFQLGLNSIK  179
SEQ_ID_NO_325         HLYP----IT APSSS----- ------ALLS PKALVIWAML PFQLGLNSIK  180
SEQ_ID_NO_312         HLYPAIGAQ SPAS------ ------PLLT AKALFIWAML PFQLGLNSIR  179
SEQ_ID_NO_319         HLYP-VGDS SPSS------ ------PLLT AKAIFIWVML PFQLGLNSIK  179
SEQ_ID_NO_321         HLYP-VGDS SPSS------ ------PLLT AKAIFIWVML PFQLGLNSIK  179
SEQ_ID_NO_300         NLSD----PE SPTSLRHQFT RLGSEFLGVS SKSLYIWGCF PFQLGLNSIK  191
SEQ_ID_NO_302         NLFN----SP SPNGLASQIL A-----LSMS AKSMYMWGCF PFQLGLNSIA  183
```

Figure 12 (continued)

| | | | | | | | |
|---|---|---|---|---|---|---|---|
| SEQ_ID_NO_310 | SLSSLSPESI | FADVCNVLAA | AVVIRKDLDL | IDHPFANRSA | FNGVLAIPFA | 215 |
| SEQ_ID_NO_316 | TLTLLAPLSI | FADVVDLGAM | GVVLGQDVAA | M.AMPPPVVA | FGGPAALLYG | 229 |
| SEQ_ID_NO_325 | TLTLLAPLSI | FADVVDLGAM | GVVLGQDVAA | WAKPVPVAA | FGGPAALLYG | 230 |
| SEQ_ID_NO_312 | TLTLLAPLSI | FADVVDLGAM | GVVLGQDABV | MLADRPPVFA | FAGPAQLLYG | 229 |
| SEQ_ID_NO_319 | TLTLLAPLSI | FADVVDLGAM | GVVLGQDVST | MLANKPPVFA | SAGPTELLYG | 229 |
| SEQ_ID_NO_321 | TLTLLAPLSI | FADVVDLGAM | GVVLGQDVST | MLANKPPVFA | SAGPTELLYG | 229 |
| SEQ_ID_NO_300 | TLTHLAPLSI | FADIVDLGAM | AVVIVEDSM | ILKQRPDVVA | FGGMSLFLYG | 241 |
| SEQ_ID_NO_302 | TLTHLAPLSI | FADVVDLAAM | GVVIVKDVF | MVENRAEVRA | FGGLSVFFYG | 233 |

| | | | | | | | |
|---|---|---|---|---|---|---|---|
| SEQ_ID_NO_310 | FGVAVFCFEG | FSMTLALESS | MAERRKFRWV | LSDAVVGILV | VYACFGVCGY | 265 |
| SEQ_ID_NO_316 | LGVSVYAFEG | VGMVLPLEAE | AANKRKFGVT | LGLSMAFIAV | MYGLFGVMGY | 279 |
| SEQ_ID_NO_325 | LGVSVYAFEG | VGMVLPLEAE | AANKKKFGVT | LGLSMAFIAV | MYGLFGVMGY | 280 |
| SEQ_ID_NO_312 | LGVAVYAFEG | IGMVLPLEAE | AADKRRFGAT | LALSMAFIAV | MYGLFGAMGY | 279 |
| SEQ_ID_NO_319 | LGVAVYAFEG | IGMVLPLEAE | AADKRKFGGT | LALSMAFIAV | MYGLFGAMGY | 279 |
| SEQ_ID_NO_321 | LGVAVYAFEG | IGMVLPLEAE | AADKRKFGGT | LALSMAFIAV | MYGLFGAMGY | 279 |
| SEQ_ID_NO_300 | MGVAVYSFEG | VGMVLPLESE | MKDKDKFGKV | LALGNGFISL | IYLAFGILGY | 291 |
| SEQ_ID_NO_302 | MGVAVYAFEG | IGMVLPIESE | MREREKFGRI | LGLSMGLISV | IYGAFGVLGY | 283 |

| | | | | | | | |
|---|---|---|---|---|---|---|---|
| SEQ_ID_NO_310 | LAYGEATKDI | TLNLPNSMS | SAAVKVGLCI | ALAFTEPVMM | HPIHEIVETR | 315 |
| SEQ_ID_NO_316 | VAFGDATRDI | TTNLGAGWL | SAAVQLGLCI | NLFFTMPVMM | NPVYEVAERL | 329 |
| SEQ_ID_NO_325 | VAFGDATRDI | TTNLGAGWL | SAAVQLGLCI | NLFFTMPVMM | NPVYEVAERL | 330 |
| SEQ_ID_NO_312 | LAFGAATRDI | TTNLGTGWL | SVLVQLGLCI | NLFFTMPVMM | NPVYEVAERL | 329 |
| SEQ_ID_NO_319 | LAFGAATRDI | TTNLGTGWL | SVAVQLGLCI | NLFFTMPVMM | NPVYEVAERL | 329 |
| SEQ_ID_NO_321 | LAFGAATRDI | TTNLGTGWL | SVTVQLGLCI | NLFFTMPVMM | NPVYEVAERL | 329 |
| SEQ_ID_NO_300 | LAFGEDTKDI | TANLGAGLV | STVVQLGLCI | NLFFTFPLMM | NPVFEIVERR | 341 |
| SEQ_ID_NO_302 | FAFGNDTQDI | TANLGPGLL | SLLVQLGLCI | NLFFTFPLMM | NPVYEILERR | 333 |

| | | | | | | | |
|---|---|---|---|---|---|---|---|
| SEQ_ID_NO_310 | LRSSGCFQKL | SHGVPGAEWL | GLHSSRLLMV | TLLVMASCI | PAFGSFVSFV | 365 |
| SEQ_ID_NO_316 | L-------- | -HGKRYCWWL | -----RWLLV | VVVGLAAMYV | PNFTDFLALV | 354 |
| SEQ_ID_NO_325 | L-------- | -HGKRYCWWL | -----RWLLV | IVVGLAAMYV | PNFTDFLALV | 355 |
| SEQ_ID_NO_312 | L-------- | -CGKRYAWWL | -----RWILV | VLVGLLAMLV | PNFADFLSLV | 354 |
| SEQ_ID_NO_319 | L-------- | -CRKRYAWWL | -----RWLLV | MVVGLMAMLV | PNFADFLSLV | 354 |
| SEQ_ID_NO_321 | L-------- | -CRKRYAWWL | -----RWLLV | MVVGLMAMLV | PNFADFLSLV | 354 |
| SEQ_ID_NO_300 | F-------- | -SRGMYSAWL | -----RWLLV | LAVTLVALFV | PNFADFLSLV | 376 |
| SEQ_ID_NO_302 | F-------- | -WGGRYCLWL | -----RWVSV | LLVTLVALMV | PNFADFMSLV | 368 |

Figure 12 (continued)

| | | | | | | | |
|---|---|---|---|---|---|---|---|
| SEQ_ID_NO_310 | GCTVCALLSF | VLPTFFHLN | VGSSMSLWRR | VLDYGFLLFG | LGFAGYGLFT | 415 |
| SEQ_ID_NO_316 | GSSVCVLLGF | VLPASFHLKV | FGAEMAMPGV | LSDALLVVLG | LALAVFGTYT | 414 |
| SEQ_ID_NO_325 | GSSVCVLLGF | VLPASFHLKV | FGREMEMPGV | VSDVLVVIG | LSLAVFGTYT | 415 |
| SEQ_ID_NO_312 | GSSVCVVLGF | VLPAVFHLKV | FGTEIGWAGL | VADVAIIVTG | LALAVSGTWT | 414 |
| SEQ_ID_NO_319 | GSSVCVLLGF | VLPAAFHLKV | FGAEVGWPGL | AGDVAVIVVG | TALAVSGTWT | 414 |
| SEQ_ID_NO_321 | GSSVCVLLGF | VLPAAFHLKV | FGAEVGWPGL | AGDVAVIVVG | TALAVSGTWT | 414 |
| SEQ_ID_NO_300 | GSSTCCVLGF | VLPALFHLLV | FKEEMGWLQW | SSDTAIVVLG | VVLAVSGTWS | 426 |
| SEQ_ID_NO_302 | GSSVCCGLGF | VLPALFHLLV | FKEEMSWKGW | SIDVGVALG | LVLAVSGTWY | 418 |

| | | |
|---|---|---|
| SEQ_ID_NO_310 | ALSSH----- | 420 |
| SEQ_ID_NO_316 | SLLQIFHSSSA | 425 |
| SEQ_ID_NO_325 | SLLQIFHSSSA | 426 |
| SEQ_ID_NO_312 | SLVQIFSSSDL | 425 |
| SEQ_ID_NO_319 | SLAQIFSSSDV | 425 |
| SEQ_ID_NO_321 | SLAQIFSSSDV | 425 |
| SEQ_ID_NO_300 | SLSEIFSVKV- | 436 |
| SEQ_ID_NO_302 | ALMEIFAVKV- | 428 |

Figure 13

| SEQ_ID_NO | | | | | | | |
|---|---|---|---|---|---|---|---|
| SEQ_ID_NO_366 | - - - - - MEAEM | LYSALALTFA | LMVHRILSN | SQNK- - - - - | RSLINLPPSP | 39 |
| SEQ_ID_NO_348 | - - - - - MEAEM | LYSALALTFA | FMVYRILSN | SCDK- - - - - | RSLTKLPPSP | 39 |
| SEQ_ID_NO_365 | - - - - - MEAEM | LYSALALTFA | FMVYRILSN | SCEK- - - - - | SSLIKLPPSP | 39 |
| SEQ_ID_NO_346 | - - - - - - - - MV | LLSELAAATL | FLTTHFIS | TLLS- - - - -I | TNGRRLPPGP | 37 |
| SEQ_ID_NO_2546 | - - - MAPKKSK | TTAMKPCTVS | PPYLSKKLPR | NLKCSYSLKS | HKKIFLPPSP | 47 |
| SEQ_ID_NO_332 | - - - - - - - - - - | - - - - - - - - - - | - - - - - - - - - - | - - - - - - - - - - | - - - - - - - - - - | 0 |
| SEQ_ID_NO_338 | - - - MEALMNV | DFQNCLTLIL | LCLLSFLCYS | FFFK- - -KP | KDSENLPPSP | 43 |
| SEQ_ID_NO_341 | - - - - - - - - - - | MEMIVFLFL | VLLISLILSS | SSNN- - - - - | - -SLQLPKSP | 32 |
| SEQ_ID_NO_2549 | - - - - - MGTFT | DLOMYTIFFI | LSFISTLLLR | SFLN-EITTP | TTRLRLPPSP | 44 |
| SEQ_ID_NO_2544 | - - - - - - - - MLL | EIALGLLVLG | LFLHLRPTPS | AKSK- - - -A | LRHLPNPPSP | 38 |
| SEQ_ID_NO_2541 | - - - - - - - - MLL | ELALGLLVLA | LFLHLRPTPT | AKSK- - - -A | LRHLPNPPSP | 38 |
| SEQ_ID_NO_358 | - - - - - - - - MLL | ELALGLLVLA | LFLHLRPTPT | AKSK- - - -A | LRHLPNPPSP | 38 |
| SEQ_ID_NO_360 | - - - - - - - - MLL | ELALGLLVLA | LFLHLRPTPT | AKSK- - - -A | LRHLPNPPSP | 38 |
| SEQ_ID_NO_339 | - - - - - - -MRLV | EIAVTLVLIA | LFIHFRPTPT | AKSK- - - -A | LRHLPNPPSP | 39 |
| SEQ_ID_NO_2550 | - - - - - - - - MLV | ELALALLAIA | LFLHLRPTPT | AKSK- - - -A | LRHLPNPPSP | 38 |
| SEQ_ID_NO_2543 | - - - - - - - - - ML | EIQGYVVLFL | LWFISSIFIR | SLFK- - - -K | SVCYKLPPGP | 37 |
| SEQ_ID_NO_2551 | - - - - - - - - - ML | DIQGYLVLFL | LWFISTILIR | SIFK- - - -K | SQCYKLPPGP | 37 |
| SEQ_ID_NO_2548 | MEVATSRELI | NPTAFPILVL | VRGLTTVFYV | LRRR- -CSG | NGGLRLPPSP | 47 |
| SEQ_ID_NO_353 | - - - - - MDHQL | VARGLFKPLL | LFVAGLIVLY | ALRRRRHRR | SSDLRLPPSP | 44 |
| SEQ_ID_NO_354 | - - - - - MDHQL | VARGLFKPLL | LFVAGLIVLY | ALRRRRHRR | SSGLRLPPSP | 45 |
| SEQ_ID_NO_324 | - - - - - - - - - MA | DIQGYILLFL | LWLLSTILVR | AILN- - -KF | RAKPRLPPSP | 38 |
| SEQ_ID_NO_356 | - - - -MEPCLV | AVSVLVSALI | CVFFFRPYFH | RYGK- - - - - | - - - -NLPPSP | 36 |
| SEQ_ID_NO_349 | - - - -MNIFEV | FQSVSPAIIA | IFFISSLFTY | LVLL- - -RN | QKSLSLPPSP | 42 |
| SEQ_ID_NO_351 | - - - - - -MNTL | QLFLLFFFP | TLLFLYCLPY | KRNQ- - - - - | -NHRRLPPSP | 37 |
| SEQ_ID_NO_2553 | - - - -MNIFVL | FQSLSPAVIA | AVWLPSLFLY | LLSK- - - -S | KQNHRLPPSP | 41 |
| SEQ_ID_NO_364 | - - - - - - - - - - | - - - -MALYAA | LFLLSAAVVR | SVLD- - - -RK | RGRPPYPPGP | 32 |
| SEQ_ID_NO_347 | - - - - - - - - - - | - -MSTLVYST | LFILSTLLLT | LLTR- - - - - | TRRKTRPPGP | 32 |
| SEQ_ID_NO_359 | - - - - - - - - -M | DTVLITLYTA | LFVITTTFLF | LLRR- - - - - | -RGPPSPPGP | 34 |

Figure 13 (continued)

| | | | | | | | |
|---|---|---|---|---|---|---|---|
| SEQ_ID_NO_368 | PGWLPIIGH | -LHLIK NPL | HRTLYDCSQK | LGSIFSVWFG | --SRLVVVVS | 84 |
| SEQ_ID_NO_348 | PGWLPVIGH | -AHLMK NLL | HRTLYDFSQK | LGPIFSIRFG | --SRLVVVVS | 84 |
| SEQ_ID_NO_365 | PGWLPVIGH | -VHLMK NLL | HRTLYDFSQK | LGPIFSLRFG | --TRLVVVVS | 84 |
| SEQ_ID_NO_346 | -RSQPVIGA- | -LPLLG AMP | HVSLAKMAKK | YGAL MYLKVG | --TCGMVVAS | 81 |
| SEQ_ID_NO_2546 | -PALPFIGH | -LHILG SLW | HQSFQKLALR | YGPFMLIHAS | --ASTSYVVS | 91 |
| SEQ_ID_NO_332 | ---------- | ---------- | ---------- | ---------- | ---------- | 0 |
| SEQ_ID_NO_338 | -PSLPIIGH | -LHHL SLFM | HRSLQKLSSK | YGPLLYLHVF | --NVP LLVG | 88 |
| SEQ_ID_NO_341 | -PSIPLLGH | -LHHLT-PSL | YKSLYTLSSK | HGPLLLLRLG | PSRRLLLVS | 78 |
| SEQ_ID_NO_2549 | -PALPIIGH | RLHFL-S-SSI | YKSFHSLSTC | YGPLLYLHFG | --ASRCLLVS | 90 |
| SEQ_ID_NO_2544 | KPRLPLIGH | -LHLLKDQLL | HHSLIDLSKR | YGPLYSLYFG | --SMPTVVAS | 84 |
| SEQ_ID_NO_2541 | KPRLPFIGH | -LHLLKDKLL | HYALIDLSKK | HGPLFSLYFG | --SMPTVVAS | 84 |
| SEQ_ID_NO_358 | KPRLPFIGH | -LHLLKDKLL | HYALIDLSKK | HGPLFSLYFG | --SMPTVVAS | 84 |
| SEQ_ID_NO_360 | KPRLPFIGH | -LHLLKDKLL | HYALIDLSKK | HGPLFSLYFG | --SMPTVVAS | 84 |
| SEQ_ID_NO_339 | KPRLPFVGH | -LHLLDHPLL | HQSLIRLGER | YGPLYSLYFG | --SMPTIVAS | 85 |
| SEQ_ID_NO_2550 | KPRLPFVGH | -LHLLDDPLL | HHSLIKLGER | YGPLYSLYFG | --SMPTVVAS | 84 |
| SEQ_ID_NO_2543 | PISFPILGH | -APYLR SLL | HKSLYKLSNR | YGPLMHIMLG | --SQHVVVAS | 82 |
| SEQ_ID_NO_2551 | PISLPLIGH | -APYLR SLL | HQALYKLSTR | YGPLMHVLIE | --SQHVIVAS | 82 |
| SEQ_ID_NO_2548 | -LALPVLGH | -FHLLA PLP | HQALHRLASR | HGPLLYLRLG | --SMPA AAC | 91 |
| SEQ_ID_NO_353 | -FGLPILGH | -LHLLA PLP | HQALHRLAAR | HGPLLFLRLG | --SVPCVAAC | 88 |
| SEQ_ID_NO_354 | -FGLPILGH | -LHLLA PLP | HQALHRLAAR | HGPLLFLRLG | --SVPCVAAC | 89 |
| SEQ_ID_NO_324 | -LALPIIGH | -LHLLA PIP | HQALHKLSTR | YGPLIHLFLG | --SVPCVVAS | 82 |
| SEQ_ID_NO_355 | FFRLPIIGH | -VHMLG PLL | HQSFHNLSHR | YGPLFSLNFG | --SVLCVVAS | 81 |
| SEQ_ID_NO_349 | -PALPIIGH | -LHHLG PLI | HHSFHQLSTR | YGPLIHLRLG | --SVPCVVAS | 86 |
| SEQ_ID_NO_351 | -PSFPIIGH | -LHHLG PLI | HQSFHAL STR | YGSLIHLRLG | --SVPCVVVS | 81 |
| SEQ_ID_NO_2553 | -PSLPIIGH | -LHHLG PLI | HQSFHNLSTR | YGPLIHLRLG | --SVPCVVAS | 85 |
| SEQ_ID_NO_364 | -FPLPIIGH | -LHLLG PRL | HQTFHDLSQR | YGPLMQLRLG | --SIRCVIAA | 76 |
| SEQ_ID_NO_347 | -LALPLIGH | -LHLLG PKL | HHTFHQFSQR | YGPLIQLYLG | --SVPCVVAS | 78 |
| SEQ_ID_NO_359 | -LSLPIIGH | -LHLLG PRL | HHTFHEFSLK | YGPLIQLKLG | --SIPCVVAS | 78 |

Figure 13 (continued)

| | | | | | | | |
|---|---|---|---|---|---|---|---|
| SEQ_ID_NO_368 | SSSLVEECFT | KYD I VLANR | PDL HLDL RSL | GASTL SVI GA | PYGDHWRNLR | 133 |
| SEQ_ID_NO_349 | SSSLVEECFT | KYD I VLANR | PCA SVDRRSL | GFSTTSVI GA | PYGDHWRNLR | 133 |
| SEQ_ID_NO_365 | SSSLVEECFT | KYD I VLANR | PQPSVDRRSL | GFSTTSVI GA | PYGDHWRNLR | 133 |
| SEQ_ID_NO_346 | TPDAAKA FLK | TLD LNFSNR | PPNA BATH L | A GAQD WFA | H GPR WK LR | 129 |
| SEQ_ID_NO_2546 | NGA I AKEVFK | TND I NFANR | PEF SSE Y-Q | I NDI FS M | D NKL W FLK | 139 |
| SEQ_ID_NO_332 | | | | | | 0 |
| SEQ_ID_NO_338 | SPSI A EI FR | T D VN SSR | DFPT EGS- | LFGS SF TA | PYGE YWKFMK | 136 |
| SEQ_ID_NO_341 | SAAVA DVFK | THD LAFSSR | PA FAFAER L | PFGTSGFVTA | PYGPYWRFMK | 126 |
| SEQ_ID_NO_2549 | SAAMA EI FK | TND LAFASR | PRLAFADK L | PYGTSSFI TA | E GDYWRFMK | 138 |
| SEQ_ID_NO_2544 | TPELFKLFLQ | THEAASFNTR | FQTSA KR L | TYDNS VAMV | PFGPYWKF R | 132 |
| SEQ_ID_NO_2541 | TPELFKLFLQ | THEATSFNTR | FQTSA RR L | TYDSS VAMV | PFGPYWKFVR | 132 |
| SEQ_ID_NO_358 | TPELFKLFLQ | THEATSFNTR | FQTSA RR L | TYDSS VAMV | P GPYWKFVR | 132 |
| SEQ_ID_NO_360 | TPELFKLFLQ | THEATSFNTR | FQTSA RR L | TYDSS VAMV | PFGPYWKFVR | 132 |
| SEQ_ID_NO_339 | TPDLFKLFLQ | THEAVSFNTR | FQTSA RR L | TYDNS VAMV | PFAPYWKF R | 133 |
| SEQ_ID_NO_2550 | TPELFKLFLQ | THEA S SFNTR | FQTSA RR L | TYDNS VAMV | PFAPYWKF R | 132 |
| SEQ_ID_NO_2543 | TAES AKQI LK | T EF ESFTNR | PI MI ASEN L | TYGAADYFFI | PYGN YWRFLK | 130 |
| SEQ_ID_NO_2551 | SAEMAKQI LK | TYE ESFCNR | PI MI ASEN L | TYGAADYFFI | PYGTYWRFLK | 130 |
| SEQ_ID_NO_2548 | SPDAAREVLK | THE AAFLDR | A PTAVHR L | M GGQDF FS | AYGPYWRFMK | 139 |
| SEQ_ID_NO_353 | SPDAAREVLK | THE AAFLDR | PKPAAVHR L | TYGGQDFSFS | AYGPYWRFMK | 136 |
| SEQ_ID_NO_354 | SPDAAREVLK | THE AAFLDR | PKPAAVHR L | TYGGQDFSFS | AYGPYWRFMK | 137 |
| SEQ_ID_NO_334 | TPE T AKEFLK | THE N SFCDR | PKSTAVDF- | TYGSADFSFA | PYGPYWKFMK | 130 |
| SEQ_ID_NO_355 | TP HF AKC L Q | TNE L AFN CR | I ESTAVKK L | TYE SS L AFA | PYGDYWRF K | 128 |
| SEQ_ID_NO_342 | TPDLARDFLK | TNE LAFSSR | KHSLA DH V | TYGVS FAFA | PYGPYWKF K | 133 |
| SEQ_ID_NO_351 | TPDLAKDFLK | TNE LAFSSR | KHSLA DH I | TYGVA FAFA | PYGTYWKF K | 128 |
| SEQ_ID_NO_2553 | TPDLARDFLK | TNE LAFSSR | KHSLA DH I | TYGVA FAFA | PYGPYWKF K | 132 |
| SEQ_ID_NO_364 | SPELAKECLK | THE LVFSSR | KHSTA DI V | TYDSS FAFS | PYGPYWKF K | 123 |
| SEQ_ID_NO_347 | TPELAREFLK | THE L DF SSR | KHSTA DI V | TYDSS FAFA | PYGPYWKF K | 123 |
| SEQ_ID_NO_359 | TPELAREFLK | TNE LAFSSR | KHSTA DI V | TYDSS FAFS | PYGPYWKY K | 125 |

Figure 13 (continued)

| | | | | | | | |
|---|---|---|---|---|---|---|---|
| SEQ_ID_NO_366 | KLCDLEVFAP | TRLASFLSIR | RDERDRMISG | LYKISSAGLA | KVNLEAKIAE | | 183 |
| SEQ_ID_NO_348 | KLCDLEVFAP | TRLASFLSIR | LDERDRMISA | LYKISSAGFA | KVNLEAKIVE | | 183 |
| SEQ_ID_NO_365 | KLCDLEVFAP | TRLASFLSIR | LDERDRMISS | LYKISSAGFA | KVNLETKIVE | | 183 |
| SEQ_ID_NO_346 | KLSNLHMLGG | KALENWANVR | ANELSHMLKS | MFDMGREGE | RVNVAEMLTF | | 178 |
| SEQ_ID_NO_2546 | KICMTEILSA | QQISKFADVR | KEEMKVLQF | F-LKCSEQGD | ACDVGIQLMD | | 188 |
| SEQ_ID_NO_332 | - - - - - - - - - - | - - - - - - - - - - | - - - - - - - - - - | - - - - - - - - - - | - - - - - - - - MK | | 2 |
| SEQ_ID_NO_338 | KLIVTKFLGP | QALERSQKVR | - - - - RSYYLN | LLDKAVKKE | SVEIAEEAMK | | 181 |
| SEQ_ID_NO_341 | KLCVTELLST | RQLERSRSIR | REEILRSKR | VIDNARETV | ALDLGSEFTK | | 175 |
| SEQ_ID_NO_2549 | KLCVTELLGV | KQLERSRVVR | REELDCFLKK | LLVESGENGE | AVDVRAEVMK | | 187 |
| SEQ_ID_NO_2544 | KLIMNDLLNA | TTVNKLRPLR | SHEIRKVLRV | LLAQSAEAQC | PLNVTEELLK | | 181 |
| SEQ_ID_NO_2541 | KLIMNDLFNA | TTVNKLRPLR | TQQIRKFLRV | MAQGAEAQK | PLDLTEELLK | | 181 |
| SEQ_ID_NO_359 | KLIMNDLLNA | TTVNKLRPLR | TQQIRKFLRV | MAQGAEAQK | PLDLTEELLK | | 181 |
| SEQ_ID_NO_360 | KLIMNDLLNA | TTVNKLRPLR | TQQIRKFLRV | MAQGAEAQK | PLDLTEELLK | | 181 |
| SEQ_ID_NO_339 | KLIMNDLLNA | TTVNKLRPLR | SQEIRKVLM | MAKSAQTQE | PLNVTEELLK | | 182 |
| SEQ_ID_NO_2550 | KIIMNDLLNA | TTVNKLRPLR | SQEIRKVLKA | MAHSAESQQ | PLNVTEELLK | | 181 |
| SEQ_ID_NO_2543 | KLCMTELLSG | KTLEHFVHIR | EDEIKCFMGT | LLLEISKNGK | PIEMRHELIR | | 179 |
| SEQ_ID_NO_2551 | KLCMTELLSG | KTLEHFVNIR | EDEIQCFLRN | VLEISKTGK | GMEMRQELIR | | 179 |
| SEQ_ID_NO_2548 | RACVHELLDS | RTLERLRHVR | REEVSRLVRS | LBRSAGDDSA | AVDVDANLMG | | 189 |
| SEQ_ID_NO_353 | RACVHELLAG | RTLDRLRHVR | REEVARLVGS | LLRASADGGE | RVDVDAALMG | | 185 |
| SEQ_ID_NO_354 | RACVHELLAG | RTLDRLRHVR | REEVARLVGS | LLRASADGGE | RVDVDAALMG | | 186 |
| SEQ_ID_NO_334 | KICMTELLGG | RMDCLLPVK | HEEIROFLOF | LLKKANARE | SIDVGSOLIR | | 179 |
| SEQ_ID_NO_356 | KLSMNELLGS | RSINNFQHLR | AQETHQLLRL | LSNRARAFE | AVNITEELLK | | 177 |
| SEQ_ID_NO_349 | KTSIVELLGN | QNLSNFLPIR | TQEVHELLQT | LLMVKSKKNE | SVNLSEELLK | | 182 |
| SEQ_ID_NO_351 | KLFITVELLGT | QNLSHFLPIR | THEIRELLRT | LLMVKSRAKE | RVNLTEELLK | | 177 |
| SEQ_ID_NO_2553 | KLSTVELLGN | QNLGHFLPIR | TQEIHELLHT | LLMEKSKRKE | SVNLTEELLK | | 181 |
| SEQ_ID_NO_364 | KLCTYELLGA | RNLAHFQPIR | TLEVKSFLQI | LLMRKGESGE | SFNVTEELVK | | 172 |
| SEQ_ID_NO_347 | KLCTYELLGA | RNLSHFQPIR | ALEVMSFLRI | LLYEKFEQKC | SVNVTEELVK | | 172 |
| SEQ_ID_NO_359 | KLCTYELLGA | RNLGHFQPIR | NLEVRSFLQL | LLMHKSFKGE | SVNVTDELVR | | 174 |

Figure 13 (continued)

| | | | | | | | | |
|---|---|---|---|---|---|---|---|---|
| SEQ_ID_NO_366 | LTFNNLMRML | AGK  YYGEEA | EDEEEAKRFR | DMTKEALELM | N TFNLAEIFP | 233 |
| SEQ_ID_NO_348 | LTFNNIMRMV | A A KRYYGEEA | EDDEEAKRFR | DLTKEALELT | SASNPGEIFP | 233 |
| SEQ_ID_NO_365 | LTFNNIMRMV | AGKRYYGEEA | EDDEEAKRFR | DLTKEALELT | SASNPGEIFP | 233 |
| SEQ_ID_NO_346 | A M A NMI G QVI | LSKR V FVN -- | K G V-EVN E FK | DMV V ELM T T A | G V FNIGDFIP | 226 |
| SEQ_ID_NO_2546 | MTNNLICRLI | MSTR T S N -- | VN --ES A EIR | EIAK G V L A | GQL S -GEIFG | 234 |
| SEQ_ID_NO_332 | LVNNTVCQMI | MGRSCSEE-- | NG --EAERVR | GLVTKTDALT | KKFILAGILR | 48 |
| SEQ_ID_NO_338 | LVNNTVCQMI | MGRSCSEE-- | NG --EAERVR | GLVTKTDALT | KKFILAGILR | 227 |
| SEQ_ID_NO_341 | F T NNVTCR T A | MSTSCAE K -- | C E --DAERIR | KLVKE S F ELA | A K L D -GDVLG | 221 |
| SEQ_ID_NO_2542 | LTNH S T CRVI | LS A RCSED-- | N D --EAERL L | EMVTE N VELA | V K M S FGDVFG | 233 |
| SEQ_ID_NO_2544 | WTNNTISMLM | LG------- | ----EAEEVR | DLARETVKIF | GEYSLTDFIW | 219 |
| SEQ_ID_NO_2541 | WTNSTISMMM | LG------- | ----EAEEIR | DIAREVLKIF | GEYSLTDFIW | 219 |
| SEQ_ID_NO_358 | WTNSTISMMM | LG------- | ----EAEEIR | DIAREVLKIF | GEYSLTDFIW | 219 |
| SEQ_ID_NO_360 | WTNSTISMMM | LG------- | ----EAEEIR | DIAREVLKIF | GEYSLTDFIW | 219 |
| SEQ_ID_NO_339 | WTNSTISRMM | LG------- | ----EAEEIR | DIARDVLKIF | GEYSLTDFIW | 220 |
| SEQ_ID_NO_2550 | WTNNTISRMM | LG------- | ----EAEEVR | DIAREVLKIF | GEYSLTDFIW | 219 |
| SEQ_ID_NO_2543 | HTNNIISRMT | MGKKSSG M -- | N D --EVGQLR | KVVREIGELL | GAFNLGDIIG | 226 |
| SEQ_ID_NO_2551 | HTNNIISRMT | MGKKSNG T -- | N D --EVGQVR | KLVREIGELL | GAFNLGDIIG | 226 |
| SEQ_ID_NO_2548 | VTGDIVSRMV | MSRRWTGD-- | DS A TD T EEMR | SVIAETA V T | GTFNLQDYIG | 237 |
| SEQ_ID_NO_353 | LTGDIVSRMV | MGRRWTGD-- | DN --DAEEMR | SVVAETAELT | GTFNLQDYIG | 231 |
| SEQ_ID_NO_354 | LTGDIVSRMV | MGRRWTGD-- | DN --DAEEMR | SVVAETAELT | GTFNLQDYIG | 232 |
| SEQ_ID_NO_324 | LTNNVISRMA | MSQRCS D N -- | DD --EADEVR | NLV H EVADLT | GKFNLSDFIW | 226 |
| SEQ_ID_NO_356 | LTNNVIS I MM | VG------- | ----EAEEAR | DVVRDVTEIF | GEFNVSDFIW | 215 |
| SEQ_ID_NO_349 | LTNNVICQMM | MSIRCSG T -- | NN --EADEAK | NLVREVTKIF | GEFN I SDF I C | 228 |
| SEQ_ID_NO_351 | LTNNVISQMM | MSIRCSG T -- | NS --EADEAK | NLVREVTKIF | GQFNVSDFIW | 223 |
| SEQ_ID_NO_2553 | LTNNVICQMM | MSIRCSG T -- | NS --EADEAK | NLVREVTTIF | GQFNVSDFIW | 227 |
| SEQ_ID_NO_364 | LTSNVISHMM | LSIRCSET-- | ES --EAEAAR | TVIREVTQIF | GEFDVSDIIW | 218 |
| SEQ_ID_NO_347 | LTSNVIS N MM | LGIRCSG T -- | EG --EAE V AR | TVIREVTQIF | GEFDVSEIVW | 218 |
| SEQ_ID_NO_359 | LTSNVISHMM | LSIRCSED-- | EG --DAEAAR | TVIREVTQIF | GEFDVTDIIW | 220 |

Figure 13 (continued)

| SEQ_ID | Sequence | # |
|---|---|---|
| SEQ_ID_NO_366 | - LRW GCNG FEKQLPVHSR KTDEI MQGLL DEHR- - - - - - - - - - - - - - | 266 |
| SEQ_ID_NO_348 | - LRWL GCNG LEKKLAVHSR KTDEFMQGLL DEHR- - - - - - - - - - - - - - | 266 |
| SEQ_ID_NO_365 | - LRWL GFNG LEKKLAVHAR KTDEFMQGLL DEHR- - - - - - - - - - - - - - | 266 |
| SEQ_ID_NO_346 | - CLAMMDLQG LEKEMKRLHK KFDALLTKMF DEHK- - - - - - - - - ATSY | 262 |
| SEQ_ID_NO_2546 | - PLKKYDLQG AGRKAKALLL KFDFLMDGIT KKHE- - DER R- - - - - - V | 272 |
| SEQ_ID_NO_332 | KPLQKI GI SL FKKELMDASC KFNEVLEKIL VEYK- - - - - - - - - - EKVE | 86 |
| SEQ_ID_NO_338 | KPLQKI GI SL FKKELMDASC KFNEVLEKIL VEYK- - - - - - - - - - EKVE | 265 |
| SEQ_ID_NO_341 | - PFKELSFW YGKKADMST RYDELLEEVL KEHE- - - HKR L - - - - SRAN | 262 |
| SEQ_ID_NO_2549 | - PLKRLGFW YGRKAVELT RYDEILEKML KEHE- - ER- - - - - - - - - - | 268 |
| SEQ_ID_NO_2544 | - PLKKLKFGK YEKRI DEI FN KFDPV EKVI KKRQEI VRRR KN- - - - GEVV | 264 |
| SEQ_ID_NO_2541 | - PLKHLKVGK YEKRI DDI LN KFDPVVERVI KKRREI VRRR KN- - - - GEVV | 264 |
| SEQ_ID_NO_358 | - PLKHLKVGK YEKRI DDI LN KFDPVVERVI KKRREI VRRR KN- - - - GEVD | 264 |
| SEQ_ID_NO_360 | - PLKHLKVGK YEKRI DDI LN KFDPVVERVI KKRREI VRRR KN- - - - GEVV | 264 |
| SEQ_ID_NO_339 | - PLKKLKVGK YEKKI EEI FN RFDPV EKVI KKRQDVRRRR KERN- - GELE | 267 |
| SEQ_ID_NO_2550 | - PLKKLKVGD YEKRI DEI FN KFDPV EKVI KKRQEI KRR KERD- - GELE | 266 |
| SEQ_ID_NO_2543 | - FMRPLDLQG FGKRNKDTHH KMDVMMEKVL KEHE- - EAR AL- - - - KEGA | 266 |
| SEQ_ID_NO_2551 | - FMRPFDLQG FGKKNRDAHH NMDVMMEKVL KEHE- - EAR AKE- - - KGGA | 268 |
| SEQ_ID_NO_2548 | - VFKYWDMQG LGKRI DAVHR KFDAMMERI L TARDALRRRR RKEP- - ADGA | 284 |
| SEQ_ID_NO_353 | - VFKYWDVQG LGKRI DAVHR KFDAMMERI L TPREAKRKLR RQ- - - - AAAD | 276 |
| SEQ_ID_NO_354 | - VFKYWDVQG LGKRI DAVHR KFDAMMERI L TAREAKRKLR RQ- - - - AAAD | 277 |
| SEQ_ID_NO_334 | - FCKNLDLQG FGKRLKEVRK RFDTMTERI I VEHE- - EAR KKK- - - KETG | 268 |
| SEQ_ID_NO_356 | - LFKKMDLQG FGKRI EDLFQ RFDTLVERI I SKREQTRKDR RRNSKKGEDG | 264 |
| SEQ_ID_NO_349 | - LFKNI DLQG FKKRYVDTHT RYNALLEKMI FERE- - EKR KQ- - - KKSE | 270 |
| SEQ_ID_NO_351 | - FCKNI DLQG FKKRYEST HR RYDALLERI I VGRE- - ENR RR- - - GK K | 265 |
| SEQ_ID_NO_2553 | - FCKNLDLQG FKKRYEDTHR RYDALLEKI I SERE- - EKR RK- - - GGKR | 269 |
| SEQ_ID_NO_364 | - LCKNFDFQG I RKRSEDI QR RYDALLEKI I TDRE- - KQR RTH- - GGGG | 261 |
| SEQ_ID_NO_347 | - FCKNLDLQG I RKRSEDI RR RYDALLEKI I SDRE- - RLR LRS- - GGGG | 261 |
| SEQ_ID_NO_359 | - FCKKFDLQG I KKRSEDI QR RYDALLEKI I SDRE- - RSR RQNRDKHGGG | 266 |

Figure 13 (continued)

| | | | | | | | | |
|---|---|---|---|---|---|---|---|---|
| SEQ_ID_NO_366 | RGERQNTMVG | HLLSL--QE | SQPDYYTDEI | TGLIISIII | AGTDASVVTT | 313 |
| SEQ_ID_NO_348 | RGERQNTMVD | HLLSL--QE | SQPEYYTDEI | TGLIVALII | AGTDASVVTT | 313 |
| SEQ_ID_NO_365 | RGERQNTMVD | HLLSL--QE | SQPEYYTDEI | TGLIVALII | AGTDASVVTT | 313 |
| SEQ_ID_NO_346 | ERKGKPDFLD | CVMENRD-NG | EGEFRLSTTN | KALLLNLFT | AGTDTSSSAI | 310 |
| SEQ_ID_NO_2546 | GGKERRDMMD | ILLEIAD-DE | NAEMKLTRNG | KGLFLDLFL | GGTDTTSVAL | 321 |
| SEQ_ID_NO_332 | EHHQGTDMMD | KLLEVYG-DE | KAEYKITRDH | KSLFVDLFF | AGTDTSTHAI | 135 |
| SEQ_ID_NO_338 | EHHQGTDMMD | KLLEVYG-DE | KAEYKITRDH | KSLFVDLFF | AGTDTMTHAI | 314 |
| SEQ_ID_NO_341 | GDCSERDLMD | ILLDVYH-DA | HAEFKITMAH | KAFFMDLFI | AGTHTSAEAT | 311 |
| SEQ_ID_NO_2549 | GKREDKDLMD | VLLEVYQ-DD | KAGMKLTRTH | KAFILDLFM | AGTNTSAESM | 317 |
| SEQ_ID_NO_2544 | EGEQSGIFLD | TLLEFAE-DE | TMEIKITKEC | KGLVVDFFS | AGTDSTAVAT | 313 |
| SEQ_ID_NO_2541 | EGEVSGVFLD | TLLEFAE-DE | TMEIKITKDH | KGLVVDFFS | AGTDSTPVAT | 313 |
| SEQ_ID_NO_358 | EGEVSGVFLD | TLLEFAE-DE | TTEIKITKDH | KGLVVDFFS | AGTDSTAVAT | 313 |
| SEQ_ID_NO_360 | EGEVSGVFLD | TLLEFAE-DE | TMEIKITKDH | KGLVVDFFS | AGTDSTAEAT | 313 |
| SEQ_ID_NO_339 | EGEQSVVFLD | TLLDFAE-DE | TMEIKITKEC | KGLVVDFFS | AGTDSTAVAT | 316 |
| SEQ_ID_NO_2550 | EGEQSVVFLD | TLLEFAE-DE | TMEIKITKEC | KGLVVDFFS | AGTDSTAVAT | 316 |
| SEQ_ID_NO_2543 | GSDRKKDLFD | ILLNLIEADD | GAESKLTRES | AKAFALDMFI | AGTNGPASVL | 316 |
| SEQ_ID_NO_2551 | ESDRKKDLFD | ILLNLIEAD | GADNKLTRES | AKAFALDMFI | AGTNGPASVL | 317 |
| SEQ_ID_NO_2548 | GEGAKKDLLD | MLFDMHE-DE | AAEMRLTRDN | KAFMLDIFS | AGTDTTAITL | 333 |
| SEQ_ID_NO_353 | GEDDEKDLLD | MLFDMHE-DE | AAEMRLTRDN | KAFMLDIFA | AGTDTTTITL | 325 |
| SEQ_ID_NO_354 | GEDDEKDLLD | MLFDMHE-DE | AAEMRLTRDN | KAFMLDIFA | AGTDTTTITL | 326 |
| SEQ_ID_NO_334 | EGDPVKDLLD | ILLDISE-DD | SSEMKLTREN | KAFILDIFA | AGTDTSAVTM | 317 |
| SEQ_ID_NO_356 | SDGIRDFLD | ILLDCTE-DE | NSEIKIQRVH | KALIMDFFT | AGTDTTAIST | 313 |
| SEQ_ID_NO_349 | DGIKGKDFLD | ILLDVLE-DE | NAEIKITRDH | KALILDFFT | AATDTTAISI | 316 |
| SEQ_ID_NO_351 | DGIEGKDFLD | MLLDVLE-DG | KAEIKITRDH | KALILDFLT | AGTDTTAIAI | 313 |
| SEQ_ID_NO_2553 | DDVKGTDFLD | MLLDVLE-DG | KAEIKITRDH | KALILDFFT | AATDTTAIAV | 318 |
| SEQ_ID_NO_364 | GGGEAKDFLD | VFLDIME-SG | KAEVKFTREH | LKALILDFFT | AGTDTTAIVC | 310 |
| SEQ_ID_NO_347 | GGGEVKDFLD | MLLDVME-SE | KSEVEFTREH | LKALILDFFT | AGTDTTAITT | 310 |
| SEQ_ID_NO_359 | NNEEAKDFLD | MLLDVME-SG | DTEVKFTREH | LKALILDFFT | AGTDTTAIAT | 315 |

Figure 13 (continued)

| | | | | | | | |
|---|---|---|---|---|---|---|---|
| SEQ_ID_NO_366 | EWAMSLLLNH | PKVLEKARQE | MDTLVGHERM | VEEDDLPKLR | YLHVILETL | 363 |
| SEQ_ID_NO_348 | EWAMSLLLNH | PKVLEKARKE | LDTLVGHERM | VDEHDLPKLR | YLHCIVLETL | 363 |
| SEQ_ID_NO_365 | EWAMSLILNH | PQVLEKARKE | LDTLVGHERM | VDEHDLPKLR | YLHCIVLETL | 363 |
| SEQ_ID_NO_346 | EWALAEMMKN | PALKKAGGE | MDQVIGNNRR | LLESDIPNLP | YLRAICKETF | 360 |
| SEQ_ID_NO_2546 | QWEAEVLNH | PKALKKLQEE | IDRVVGPNRL | VDDSDIPNLP | YLQAVVKETL | 371 |
| SEQ_ID_NO_332 | QWMAEIINN | SYILERLREE | DSVVGKTRL | QETDLPNLP | CLQATVKEGL | 185 |
| SEQ_ID_NO_338 | QWMAEIINN | SYILERLREE | DSVVGKTRL | QETDLPNLP | CLQATVKEGL | 364 |
| SEQ_ID_NO_341 | QWAMAELLNH | PEAFQKVRKE | ELVFGNVRL | VDESDITNLP | YLQAVVKETL | 361 |
| SEQ_ID_NO_2549 | QWTIAELINH | PDVFKKVREE | DLAVGRTRL | VEESDIPNLP | YLQAVVKETL | 367 |
| SEQ_ID_NO_2544 | EWALAELINN | PRVLQKAREE | VYSVVGKDRL | VDEVDTQNLP | YIRAIVKETF | 363 |
| SEQ_ID_NO_2541 | EWALAELINN | PKVLEKAREE | VYSVVGKDRL | VDEVDTPNLP | YISAIVKETF | 363 |
| SEQ_ID_NO_359 | EWALAELINN | PKVLEKAREE | VYSVVGKDRL | VDEVDTQNLP | YIRAIVKETF | 363 |
| SEQ_ID_NO_360 | EWALAELINN | PKVLEKAREE | VYSVVGKDRL | VDEVDTQNLP | YIRAIVKETF | 363 |
| SEQ_ID_NO_339 | QWDSELINN | PRVMKKAREE | VDSVVGKDRL | VDESDIQNLP | YIRAVVKETF | 366 |
| SEQ_ID_NO_2550 | DWALSELINN | PRVLKKAREE | VESVVGKDRL | VDEADIQNLP | YIRAIVKETF | 365 |
| SEQ_ID_NO_2543 | EWALAELIRN | PHVFKKAREE | DSTVGKERL | FKESDIPNLP | YLQAVVKETL | 366 |
| SEQ_ID_NO_2551 | EWSLAELIRN | PQVFKKAREE | DSVVGKERL | VKESDIPNLP | YLQAVVKETL | 367 |
| SEQ_ID_NO_2548 | EWALSELINN | PDILRRAQAE | LDAIVGASRL | ADESDIPRLP | YLQAIAKETL | 383 |
| SEQ_ID_NO_353 | EWALSELINN | PPVLRKLQAE | LDAVVGGARL | ADESDIPSLP | YLQAVAKETL | 375 |
| SEQ_ID_NO_354 | EWALSELINN | PPVLRKLQAE | LDAVVGGARL | ADESDIPSLP | YLQAVAKETL | 376 |
| SEQ_ID_NO_324 | EWALAELINN | PNILERAREE | DSVVGQSRL | VQESDIANLP | YVQAILKETL | 367 |
| SEQ_ID_NO_356 | EWALVELVKK | PSVLQKVREE | IDNVVGKDRL | VEESDCPNLP | YLQAILKETF | 363 |
| SEQ_ID_NO_349 | EWTLVELTNN | PKVLENARKE | AEVVGDERL | VQESDIPNLP | YIQAIIKETL | 368 |
| SEQ_ID_NO_351 | EWALVELINN | PNALEKARQE | DQVIGDERL | VQESDTPNLP | YIQAIIKEAL | 363 |
| SEQ_ID_NO_2553 | EWTMVELINN | PKVLEKAKKE | VDNVIGNSRL | VQESDAPNLP | YIQAIIKETL | 368 |
| SEQ_ID_NO_364 | EWAIAEVINN | PNVLKKAQEE | IANIVGFDRI | LQESDAPNLP | YLQALIKETF | 360 |
| SEQ_ID_NO_347 | EWAIAELISN | PNVLKKAQEE | MDKVIGSQRL | QESDAPNLP | YLNAIIKETF | 360 |
| SEQ_ID_NO_359 | EWAIAELINN | PNVLKKAQEE | SRIIGTKRI | VQESDAPDLP | YLQAIIKETF | 365 |

Figure 13 (continued)

| | | | | | | | |
|---|---|---|---|---|---|---|---|
| SEQ_ID_NO_366 | RLFPSVPTLV | PHEPSEDCN | GGYNVPKGTM | LVNAWAIHR | DPKVV | DDPM | 412 |
| SEQ_ID_NO_348 | RLFPSVPTLV | PHEPSEDCKI | GGYNVPKGTM | VLVNAWAIHR | DPKVV | DDPL | 412 |
| SEQ_ID_NO_365 | RLFPSVPTLV | PHEPSEDCKI | GGYNVPKGTM | LVNAWAIHR | DPKVV | DDPL | 412 |
| SEQ_ID_NO_346 | RKHPSTPLNL | PRISNEPCIV | DGYYIPKNTR | LSVNIWAIGR | DPEVV | ENPL | 409 |
| SEQ_ID_NO_2546 | RVHPSLPLI | FRKCREDCVV | NGYTIPKNSR | LVLNIYAINR | DPNEV | RDAD | 419 |
| SEQ_ID_NO_332 | RLHPPVP V | LRTFKEGCTI | GGFYVPEKTT | LVVHGYAMMR | DPEYV | EDPQ | 233 |
| SEQ_ID_NO_338 | RLHPPVP LV | LRTFKEGCTI | GGFYVPEKTT | LVVNGYAMMR | DPEYV | EDPQ | 412 |
| SEQ_ID_NO_341 | RLYPPAP F | TRECROHCKI | NSFDVPPKTA | VAINLYAIMR | DPDSV | DNPN | 409 |
| SEQ_ID_NO_2549 | RLHPPAP VA | TRECRKNCKI | GGFNIPEKTA | VAINLYAIMR | DPEIV | DDPT | 416 |
| SEQ_ID_NO_2544 | RMHPPLP VV | KRKCVEECEI | EGCVIPEGAL | LFNVWAVGR | DPKYV | DRPS | 411 |
| SEQ_ID_NO_2541 | RMHPPLP VV | KRKCTEECEI | NGYVIPEGAL | LFNVWQVGR | DPKYV | DRPS | 411 |
| SEQ_ID_NO_358 | RMHPPLP VV | KRKCTEECEI | NGYVIPEGAL | LFNVWQVGR | DPKYV | DRPS | 411 |
| SEQ_ID_NO_360 | RMHPPLP VV | KRKCTEECEI | NGYVIPEGAL | LFNVWQVGR | DPKYV | DRPS | 411 |
| SEQ_ID_NO_339 | RMHPPLP VV | KRKCTEECEI | NGYVIPEGAL | VLFNVWAVGR | DPKYV | DRPL | 414 |
| SEQ_ID_NO_2550 | RMHPPLP VV | KRKCVQECEL | NGYVIPEGAL | LFNVWAVDR | DPKYV | ESPS | 413 |
| SEQ_ID_NO_2543 | RMHPPTP F | AREATRSCQV | DGYDVPAFSK | FINAWAIGR | DPNYV | DNPL | 414 |
| SEQ_ID_NO_2551 | RMHPPTP F | AREAIRGCQV | DGYDIPANSK | FINAWAIGR | DPKYV | DNPQ | 415 |
| SEQ_ID_NO_2548 | RLHPAFP LV | VRRSTEPCKV | SGYDVPAGST | VFVNVWAIGR | DPACW | ADPL | 432 |
| SEQ_ID_NO_353 | RLHPTGP LV | VRRSLERATV | AGYDVPAGAT | VFVNVWAIGR | DAAWV | PEPT | 423 |
| SEQ_ID_NO_354 | RLHPTGP LV | VRRSLERATV | AGYDVPAGAT | VFVNVWAIGR | DAAWV | PEPT | 424 |
| SEQ_ID_NO_334 | RLHPTGP I | LRESSESCTI | NGYEIPARTR | LFVNVWAINR | DPNYV | ENPL | 415 |
| SEQ_ID_NO_356 | RLHPPVP MV | TRRCVAECTV | ENYVIPEDSL | LFVNVWSIGR | NPKFV | DNPL | 411 |
| SEQ_ID_NO_349 | RMHPPIP MV | RKSIDNVTV | DGYDIRAGTM | LFVNIWSIGR | NPLYV | ESPL | 416 |
| SEQ_ID_NO_351 | RLHPPIP ML | IRKSTEHVIV | DGYDIPAGTL | LFVNIWSIGR | NPQCV | ETPL | 411 |
| SEQ_ID_NO_2553 | RLHPPIP ML | IRKSIEKVTV | DGYEIPAGTM | LFVNIWSIGR | NAQYV | ESPL | 416 |
| SEQ_ID_NO_364 | RLHPPIP ML | ARKSISDCVI | DGYMPANTL | LFVNLWSMGR | NPKIV | DFPT | 408 |
| SEQ_ID_NO_347 | RLHPPIP ML | TRKSISDVVV | NGYTIPAKTL | LFVNLWSMGR | NPNYV | ENPM | 408 |
| SEQ_ID_NO_359 | RLHPPIP ML | SRKSTSDCTV | NGYKQAKSL | LFVNIWSIGR | NPNYV | ESPM | 413 |

Figure 13 (continued)

| | | | | | | | | |
|---|---|---|---|---|---|---|---|---|
| SEQ_ID_NO_366 | EFKPDRFET | ---------- | -------ME | LE | VETHKLLPFG | MGRRGCPGAG | 443 |
| SEQ_ID_NO_348 | EFKPDRFEI | ---------- | -------ME | ME | VETHKLLPFG | MGRRACPGAG | 443 |
| SEQ_ID_NO_365 | EFKPDRFET | ---------- | -------ME | ME | VETHKLLPFG | MGRRACPGAG | 443 |
| SEQ_ID_NO_346 | EFVPERFLS | ---SRNSKI | -D----PR | | GNDFELIPFG | AGRRCAGTR | 447 |
| SEQ_ID_NO_2546 | EFLPERYLVN | SGGGEEHQLA | EPDELEAMK | | GQNFCYVPFG | GGRRGCPGAG | 469 |
| SEQ_ID_NO_332 | EFKPERFLAS | SRSSQND-- | -E-----R | | DELLKYLPFG | NGRRACPGAN | 273 |
| SEQ_ID_NO_338 | EFKPERFLAS | SRSSQND-- | -E-----R | | DELLKYLPFG | NGRRACPGAN | 452 |
| SEQ_ID_NO_341 | EFDPERFLQE | CDHEDLSD-- | -D-----GK | | RMKFNFVPFG | GGRRGCPGTA | 450 |
| SEQ_ID_NO_2549 | EFRPERFLVP | SKFDVDLD-- | -Q-----TK | | GQNFNFVPFG | GGRRGCPGTL | 456 |
| SEQ_ID_NO_2544 | EFRPERFLEN | GGEGAVGPI | -D-----LR | | GQHFQLLPFG | SGRRMCPGVN | 453 |
| SEQ_ID_NO_2541 | EFRPERFLET | GAEGEAGPL | -D-----LR | | GQHFQLLPFG | SGRRMCPGVN | 453 |
| SEQ_ID_NO_358 | EFRPERFLET | GAEGEARPL | -D-----LR | | GQHFQLLPFG | SGRRMCPGVN | 453 |
| SEQ_ID_NO_360 | EFRPERFLET | GAEGEARPL | -D-----LR | | GQHFQLLPFG | SGRRMCPGVN | 453 |
| SEQ_ID_NO_339 | EFRPERFLEN | AGEGDAGSI | -D-----LR | | GQHFQLLPFG | SGRRMCPGVN | 456 |
| SEQ_ID_NO_2550 | EFRPERFLT | -AEGGATSI | -D-----LR | | GQNFELLPFG | SGRRMCPGVN | 463 |
| SEQ_ID_NO_2543 | VFNPERFLQ | SDDPSKSKI | -D-----VR | | GQYYQLLPFG | SGRRSCPGSS | 465 |
| SEQ_ID_NO_2551 | VYEPERFLI | TDEPGKSKI | -D-----VR | | GQYYQLLPFG | SGRRSCPGSS | 456 |
| SEQ_ID_NO_2548 | AFRPERFLE | GGEGRGDSAG | LD-----VR | | GQHFHLLPFG | SGRRCPGAS | 475 |
| SEQ_ID_NO_353 | AFRPERFVS | GGGGGGTAA | -D-----VR | | GQHFHLLPFG | SGRRCPGAS | 464 |
| SEQ_ID_NO_354 | AFRPERFVS | GGGGGGTAA | -D-----VR | | GQHFHLLPFG | SGRRCPGAS | 465 |
| SEQ_ID_NO_334 | EFEPERFLC- | AGENGKSQL | -D-----VR | | GQHFHFLPFG | SGRRGCPGTT | 456 |
| SEQ_ID_NO_356 | EFRPERFLK | LESDSSSMV | -D-----VR | | GSHFQLLPFG | SGRRMCPGVS | 462 |
| SEQ_ID_NO_349 | EFKPHRFLD | ---SHARHL | -D-----VK | | GCCFQLLPFG | TGRRGCPGS | 454 |
| SEQ_ID_NO_351 | EFKPHRFLD | -GGDLKSSL | -D-----K | | GHNFQLLPFG | TGRRGCPGVN | 451 |
| SEQ_ID_NO_2553 | EFEPDRFFE | -GDI-KSSL | -D-----K | | GCSFQLLPFG | TGRRGCPGIN | 458 |
| SEQ_ID_NO_364 | AFQPERFLE | ---KEKAAI | -D-----VK | | GQHFELLPFG | TGRRGCPGML | 446 |
| SEQ_ID_NO_347 | EFRPERFLEK | GLSSI---- | -D-----VK | | GQHFELLPFG | TGRRGCPGML | 446 |
| SEQ_ID_NO_359 | EFRPERFLEK | GRESI---- | -D-----VK | | GQHFELLPFG | TGRRGCPGML | 451 |

Figure 13 (continued)

| | | | | | | | | |
|---|---|---|---|---|---|---|---|---|
| SEQ_ID_NO_366 | LAKKFVGLAL | ASLIQCFDWE | R | SA- -EKI | - - - - - - - | DLK | EGASRITLPK | 483 |
| SEQ_ID_NO_349 | LAQKFVGLAL | GSLIQCFDWE | R | TSP- -EKI | - - - - - - - | DLN | EGSC- TLPK | 482 |
| SEQ_ID_NO_365 | LAQKFVGLAL | GSLIQCFEWE | R | MSA- -EKI | - - - - - - - | DLN | EGSG- TLPK | 482 |
| SEQ_ID_NO_346 | MGIVMVEYL | GTLVHSFDWK | L | PSEV EL- | - - - - - - - | NME | EAFG- LALQK | 487 |
| SEQ_ID_NO_2546 | LANAVLHRTL | GVLIQCFDWK | I | KGA- -EKL | - - - - - - - | NME | QGVG- FSSAM | 508 |
| SEQ_ID_NO_332 | LAYISVGTAI | GVMVQCFDWE | I | - - -KGDKI | - - - - - - - | NMD | EAPGKITLTM | 312 |
| SEQ_ID_NO_338 | LAYISVGTAI | GVMVQCFDWE | I | - - -KGDKI | - - - - - - - | NMD | EAPGKITLTM | 491 |
| SEQ_ID_NO_341 | LAFSLMNTAV | AAMVQCFDWK | I | GKDGKGEKV | - - - - - - - | DME | SGSC- MSLSM | 492 |
| SEQ_ID_NO_2549 | LAFAMMNTTV | AAIVQCFDWK | L | GGDGDGSSKV | - - - - - - - | DMC | SGPG- LTLSM | 498 |
| SEQ_ID_NO_2544 | LSTSGMATLL | ASVIQCFDLQ | V | LDPQGHVL | KGDDAKVSME | ERAG- LTVPR | 501 |
| SEQ_ID_NO_2541 | LATSGMATLL | ASLIQCFDLQ | V | LGPQGQIL | KGGDAKVSME | ERAG- LTVPR | 501 |
| SEQ_ID_NO_358 | LATSGMATLL | ASLIQCFDLQ | V | LGPQGQIL | KGGDAKVSME | ERAG- LTVPR | 501 |
| SEQ_ID_NO_360 | LATSGMATLL | ASLIQCFDLQ | V | LGPQGQIL | KGGDAKVSME | ERAG- LTVPR | 501 |
| SEQ_ID_NO_339 | LATAGMATLL | SSVLQCFELQ | V | AGPNGQIL | KGADAKVSMD | ERPG- LTVPR | 504 |
| SEQ_ID_NO_2550 | LATAGMATLL | ASVIQCFDLQ | V | VGLKGKLL | KGSDAKVSME | ESPG- LTVPR | 501 |
| SEQ_ID_NO_2543 | LALLVIQATL | ASLIQCFDW | V | NDGKSHD | - - - - - - - | DMS | EVGR- VTVFL | 496 |
| SEQ_ID_NO_2551 | LALLVIQATL | ASLVQCFDWW | V | NDGKNSE | - - - - - - - | DMS | EEGR- VTVFL | 497 |
| SEQ_ID_NO_2548 | LAMLVVQAAL | AAMLQCFEWA | P | VGG- -ATV | - - - - - - - | DME | EGPG- LTLPR | 514 |
| SEQ_ID_NO_353 | LAMLVVQAAL | AAMVQCFEWS | P | VGG- -APV | - - - - - - - | DME | EGPG- LTLPR | 503 |
| SEQ_ID_NO_354 | LAMLVVQAAL | AAMVQCFEWS | P | VGG- -APV | - - - - - - - | DME | EGPG- LTLPR | 504 |
| SEQ_ID_NO_334 | LALQMVQTS- | AAMIQCFDWK | V | NGFVL- - - | - - - - - - - | DMC | EGI- TLPR | 493 |
| SEQ_ID_NO_356 | LAMQEVPALL | GAIIQCFDFH | V | VGPKGEIL | KGDD VLNVD | ERPG- LTAPR | 500 |
| SEQ_ID_NO_349 | LAMRELPVVI | AGLIQCFEWN | A- | NDK- -EVL | - - - - - - - | SMD | ERAG- LTAPR | 493 |
| SEQ_ID_NO_351 | LAMRELSVVI | ANLIQCFDWD | V | VGE- -RLL | - - - - - - - | NTD | ERAG- LTAPR | 490 |
| SEQ_ID_NO_2553 | LAMRELPVVI | AGLIQCFEWD | V | NNK- -EBL | - - - - - - - | ITD | ERAG- LTAPR | 495 |
| SEQ_ID_NO_364 | LAIQEVV- I | GTMIQCFDWK | L | PDGSGHV- | - - - - - - - | DMA | ERPG- LTAPR | 486 |
| SEQ_ID_NO_347 | LGMQELFS-I | GAMVQCFDWK | L | PDGVKSV | - - - - - - - | DMT | ERPG- LTAPR | 488 |
| SEQ_ID_NO_359 | LAIQEVVS-I | GTMVQCFDWK | L | ADGSGHNV | - - - - - - - | DMT | ERSG- LTAPR | 492 |

Figure 13 (continued)

| SEQ_ID_NO | | | | | |
|---|---|---|---|---|---|
| SEQ_ID_NO_366 | ATTLEAMCKP | RHVMEKVLRQ | VSNV | | 507 |
| SEQ_ID_NO_348 | AKTLEAMCKP | RHVMEKVLRQ | VSNV | | 506 |
| SEQ_ID_NO_365 | AKTLEAMCKP | RHIMERVLRQ | VSNV | | 506 |
| SEQ_ID_NO_346 | AVPLEAMVTP | RLPLDVYAPL | A--- | | 508 |
| SEQ_ID_NO_2548 | VHPLICVPVV | R----VNPL | ETAN | | 527 |
| SEQ_ID_NO_332 | AHPLNCTLVP | RTLIPVTSTV | QIPSS | | 337 |
| SEQ_ID_NO_338 | AHPLNCTLVP | RTLIPVTSTV | QIPSS | | 516 |
| SEQ_ID_NO_341 | VHPLICVPVV | H----FDPY | D | | 509 |
| SEQ_ID_NO_2549 | LHPLKCHPIV | H----FNPF | EC | | 515 |
| SEQ_ID_NO_2544 | KHNLVCLPLA | K--TTLAAKL | LSP | | 522 |
| SEQ_ID_NO_2541 | AHSLVCVPLA | R--IGVASKL | LS | | 521 |
| SEQ_ID_NO_358 | AHSLVCVPLA | R--IGVASKL | LS | | 521 |
| SEQ_ID_NO_360 | AHSLVCVPLA | R--IGVASKL | LS | | 521 |
| SEQ_ID_NO_339 | AHNLVCVPLA | R--PGAAAKL | LSS | | 525 |
| SEQ_ID_NO_2550 | AHNLMCVPLA | R--TNVTSE | LSS | | 522 |
| SEQ_ID_NO_2543 | AKPLKCKPVP | H----FVPF | SSA | | 514 |
| SEQ_ID_NO_2551 | AKPLKCKPVP | R----FVPF | SA | | 514 |
| SEQ_ID_NO_2548 | KRPLVCTYKA | R----LHPV | PVPTAAAADN | GVDGTLHCA | 546 |
| SEQ_ID_NO_353 | KRPLVCTVSP | R----IHPL | PAAASASLT | | 527 |
| SEQ_ID_NO_354 | KRPLVCTVSP | R----IHPL | PAAASASLT | | 528 |
| SEQ_ID_NO_324 | AHPLICVPVA | R----LNPF | PSF | | 511 |
| SEQ_ID_NO_356 | AHNLVCVPVD | RTSGGGPLKI | EC | | 523 |
| SEQ_ID_NO_349 | AVDLEFVPLM | RF-CNCPNDF | VSA | | 514 |
| SEQ_ID_NO_351 | AVDFVCVPLE | R--GNTLKI | LGSN | | 511 |
| SEQ_ID_NO_2553 | AVDFVCVPSM | R--ENCPKVF | | | 513 |
| SEQ_ID_NO_364 | ETDLFCRVVP | R----VDPL | VVSTD | | 506 |
| SEQ_ID_NO_347 | ANDLVCDLVP | R----IDPV | VVSGP | | 506 |
| SEQ_ID_NO_359 | AFDLVCRLVP | R----VDPA | TLSGA | | 512 |

Figure 14

| SEQ_ID | Sequence | # |
|---|---|---|
| SEQ_ID_NO_475 | ----------MSS------------------RL------YVGN | 9 |
| SEQ_ID_NO_436 | MAFCNKLGNL LRQGATQS------SHAP VSSMLNYLRH MSSSKLFIGG | 42 |
| SEQ_ID_NO_420 | MAFLSKVGKI FRQTSAHVTA SNSMLQSI--------RC MSSSKIFVGG | 40 |
| SEQ_ID_NO_473 | ----------MAASDV------EF---------RC------FVGG | 14 |
| SEQ_ID_NO_369 | ----------MAGGE-------EF---------RC------FVGG | 13 |
| SEQ_ID_NO_371 | ----------MASADV------EF---------RC------FVGG | 14 |
| SEQ_ID_NO_372 | ----------MASADV------EF---------RC------FVGG | 14 |
| SEQ_ID_NO_373 | ------------MAEV------EY---------RC------FVGG | 12 |
| SEQ_ID_NO_458 | ------------MADV------EY---------RC------FVGG | 12 |
| SEQ_ID_NO_597 | ------------MADV------EY---------RC------FVGG | 12 |
| SEQ_ID_NO_455 | ----------MAAADV------EY---------RC------FVGG | 14 |
| SEQ_ID_NO_477 | ----------MAAADV------EY---------RC------FVGG | 14 |
| SEQ_ID_NO_465 | ----------MAASDV------EY---------RC------FVGG | 14 |
| SEQ_ID_NO_488 | ----------MAAPDV------EY---------RC------FVGG | 14 |
| SEQ_ID_NO_494 | ----------MAAPDV------EY---------RC------FVGG | 14 |
| SEQ_ID_NO_374 | -----------MDAEV------EY---------RC------FVGG | 13 |
| SEQ_ID_NO_441 | ------------MAEV------EY---------RC------FVGG | 12 |
| SEQ_ID_NO_444 | ----------MASADV------EY---------RC------FVGG | 14 |
| SEQ_ID_NO_451 | ------------MGDV------EY---------RC------FVGG | 12 |
| SEQ_ID_NO_595 | ------------MAEV------EY---------RC------FVGG | 12 |
| SEQ_ID_NO_474 | ------------MAEV------EY---------RC------FVGG | 12 |
| SEQ_ID_NO_447 | ------------MAEV------EY---------SC------FVGG | 12 |
| SEQ_ID_NO_450 | -----------MAAEV------EY---------SC------FVGG | 13 |
| SEQ_ID_NO_434 | -----------MGSSDV------EY---------RC------FVGG | 14 |
| SEQ_ID_NO_437 | -----------MAAADI------EY---------RC------FVGG | 14 |
| SEQ_ID_NO_438 | ------------MSADI------EY---------RC------FVGG | 13 |
| SEQ_ID_NO_454 | -------------MAE------EY---------RC------FVGG | 11 |
| SEQ_ID_NO_392 | ------------MSAEV------EY---------RC------FVGG | 13 |
| SEQ_ID_NO_425 | ----------MASAEV------EF---------RC------FVGG | 14 |
| SEQ_ID_NO_504 | ----------MASAEI------EF---------RC------FVGG | 14 |
| SEQ_ID_NO_368 | ----------MASGDV------EY---------RC------FVGG | 14 |
| SEQ_ID_NO_422 | ----------MASPDV------EY---------RC------FVGG | 14 |
| SEQ_ID_NO_596 | ----------MASADV------EF---------RC------FVGG | 14 |
| SEQ_ID_NO_433 | ----------M--ADV------ED---------RC------FVGG | 12 |
| SEQ_ID_NO_376 | ----------MASADV------EY---------RC------FVGG | 14 |
| SEQ_ID_NO_440 | ----------MASADV------EY---------RC------FVGG | 14 |

Figure 14 (continued)

| SEQ_ID | | | | | | | |
|---|---|---|---|---|---|---|---|
| SEQ_ID_NO_475 | LSWNAKEEDL | RTYFGKFGEV | EEASIALDRE | SGRSRGFGFV | TLPADVA-KD | 58 |
| SEQ_ID_NO_436 | LSYGVDDQSL | KDAFASYGEV | VEARVITDRD | TGRSRGFGFV | NFTSDESATS | 92 |
| SEQ_ID_NO_420 | ISYSTDEFGL | REAFSKYGEV | VDAKIIVDRE | TGRSRGFAFV | TFTSTEEASN | 90 |
| SEQ_ID_NO_473 | LAWATDDASL | ERAFSTYGDI | VESKIINDRE | TGRSRGFGFV | TFRDEQSMRD | 64 |
| SEQ_ID_NO_369 | LAWATTDGRL | EGAFRPFGEV | VQSKVISDRE | TGRSRGFGFV | TFADENSMNA | 63 |
| SEQ_ID_NO_371 | LAWSTDDRSL | QEAFSPYGEV | VESKIISDRE | TGRSRGFGFV | TFNDEQSMRD | 64 |
| SEQ_ID_NO_372 | LSWSTDDRSL | KDAFTAFGEV | MDSKVVSDRE | TGRSRGFGFV | TFMDEQSMRD | 64 |
| SEQ_ID_NO_373 | LSWGTDDRSL | AEAFNKFGEV | TDSKIINDRE | TGRSRGFGFV | TFANEQSMRD | 62 |
| SEQ_ID_NO_458 | LAWATDDQSL | DNAFSKYGDV | IDSKIITDRE | TGRSRGFGFV | TFASDEAMRD | 62 |
| SEQ_ID_NO_507 | LRWATDDQSL | QNAFSKYGDV | IDSKIITDRE | TGRSRGFGFV | TFASDEAMRD | 62 |
| SEQ_ID_NO_455 | LAWATNNETL | EQAFANFGQV | IDSKVITDRE | TGRSRGFGFV | IFSSEQSMLD | 64 |
| SEQ_ID_NO_477 | LAWATDNASL | QQAFASYGDV | LDSKVITDRE | TGRSRGFGFV | TFSSEQSMLD | 64 |
| SEQ_ID_NO_465 | LAWATDDHSL | HNAFSTYGEV | LESKIILDRE | TDRSRGFGFV | TFSTEEAMRN | 64 |
| SEQ_ID_NO_488 | LAWATDDRSL | EAAFSTYGEI | LDSKIINDRE | TGRSRGFGFV | TFSSEQSMRD | 64 |
| SEQ_ID_NO_494 | LAWATDDRSL | EAAFSTYGEI | LDSKIINDRE | TGRSRGFGFV | TFSSEQSMRD | 64 |
| SEQ_ID_NO_374 | LAWATDDQSL | ERAFSNYGQV | LESKIINDRE | TGRSRGFGFV | TFSSEQAMRD | 63 |
| SEQ_ID_NO_441 | LAWATNDESL | EQAFSQFGDI | TDSKIINDRE | TGRSRGFGFV | TFKDEKSMRD | 62 |
| SEQ_ID_NO_444 | LAWATTDQSL | SEAFSQYGEI | LESKIINDRE | TGRSRGFGFV | TFKDEQSMRD | 64 |
| SEQ_ID_NO_451 | LAWATTDNTL | SEAFSQYGEV | VESKIINDRE | TGRSRGFGFV | TFKDEQAMRD | 62 |
| SEQ_ID_NO_505 | LAWATTDQTL | GDAFSQFGEI | LDSKIINDRE | TGRSRGFGFV | TFKDEKAMRD | 62 |
| SEQ_ID_NO_474 | LAWATTDQTL | GDAFSQYGEI | LDSKIINDRE | TGRSRGFGFV | TFKDEQAMRD | 62 |
| SEQ_ID_NO_447 | LAWATTDRTL | ADAFGTYGEV | LDSKIINDRE | TGRSRGFGFV | TFKDEKCMRD | 62 |
| SEQ_ID_NO_450 | LAWATTDRTL | SDAFSTYGEV | VDSKIINDRE | TGRSRGFGFV | TFKDEKSMKE | 63 |
| SEQ_ID_NO_434 | LAWATDSQAL | EQAFSKFGEI | TDSKVINDRE | TGRSRGFGFV | TFAEEKSMRD | 64 |
| SEQ_ID_NO_437 | LAWATSDKAL | EEAFSAYGEV | LESKIINDRE | TGRSRGFGFV | TFNNEKSMRD | 64 |
| SEQ_ID_NO_438 | LAWATTDQSL | DEAFSPYGEI | LDSKIINDRE | TGRSRGFGFV | TFNNEKSMRD | 63 |
| SEQ_ID_NO_454 | LAWATNDQSL | EQAFSQFGEI | TDCKIINDRE | TGRSRGFGFV | TFSSESMKN | 61 |
| SEQ_ID_NO_392 | LAWATTDQVL | DEAFSQYGEI | IDSKIINDRE | TGRSRGFGFV | TFGNEKAMRD | 63 |
| SEQ_ID_NO_425 | LAWATDHDAL | EKAFSQFGEI | VESKVINDRE | TGRSRGFGFV | TFATEQAMRD | 64 |
| SEQ_ID_NO_504 | LAWATDNDAL | ERAFSPFGEI | IESKIINDRE | TGRSRGFGFV | TFSNEKAMRD | 64 |
| SEQ_ID_NO_368 | LAWATDDRAL | ETAFAQYGDV | IDSKIINDRE | TGRSRGFGFV | TFKDEKAMKD | 64 |
| SEQ_ID_NO_422 | LAWATDDRAL | ETAFSQYGEV | LDSKIINDRE | TGRSRGFGFV | TFKDEKSMKD | 64 |
| SEQ_ID_NO_506 | LAWATTDSSL | HEAFSAYGDI | LESKIINDRE | TGRSRGFGFV | TFRDEKSMRD | 64 |
| SEQ_ID_NO_433 | LAWATDNDAL | EKAFSQYGEI | VDSKIINDRE | TGRSRGFGFV | TFANEKSMND | 62 |
| SEQ_ID_NO_376 | LAWATDDRAL | EEAFSVYGEI | VESKIINDRE | SGRSRGFGFV | TFRDEKSMRD | 64 |
| SEQ_ID_NO_440 | LAWATDDHAL | EQAFSQYGEV | VESKIINDRE | TGRSRGFGFV | TFSNEKSMND | 64 |

Figure 14 (continued)

| SEQ_ID | col1 | col2 | col3 | col4 | col5 | col6 | col7 | # |
|---|---|---|---|---|---|---|---|---|
| SEQ_ID_NO_475 | AI EKTNGAEF | MGRNI KVNEA | SPPGER- PPR | TNN- - - - - - | Y | GGGY | GDFN- - | 99 |
| SEQ_ID_NO_436 | ALSAMDGQDL | NGRNI RVSYA | NDRPSA- - - - | - - - - - - - - - - - - - | | - - - - P- - - - | | 119 |
| SEQ_ID_NO_420 | AMQLLDGQDL | HGRRI RVNYA | TERGSGFGGR | G- - - - - - - - | F | GGP- - - - - - - - | | 124 |
| SEQ_ID_NO_473 | AI KGMNGQTL | DGRNI TVNEA | EVFAAA- VAA | - - - - - - - - - - | G | TAAAAEVAVT | | 104 |
| SEQ_ID_NO_369 | AI KEMNGQEL | DGRNI TVNQA | QSRGGG- GGG | GG- - - - - - - | G | GGGY | GR- - - - | 101 |
| SEQ_ID_NO_371 | AI DAMNGKML | DGRSI TVNPA | QSRGNG- GGG | GGG- - - - - - | G | SRGYR- - - - - | | 102 |
| SEQ_ID_NO_372 | AI EGMNGRDL | DGRNI TVNRA | QARGGG- GGG | GG- - - - - - - | G | GGGY | RG- - - - | 102 |
| SEQ_ID_NO_373 | AI DEMNGKEL | DGRSI TVNEA | QSRGSG- GGG | - - - - - - - - - | G | GGGY | RS- - - - | 98 |
| SEQ_ID_NO_458 | AI EAMNGQDL | HSRNI TVNEA | HSRRSG- GGG | GGFSGG- - - | G | GGGY | GGQRRE | 108 |
| SEQ_ID_NO_507 | AI EAMNGQDL | DGRNI TVNEA | QSRRSD- GGG | GFGG- - - - - | G | GGGY | GGQRRE | 106 |
| SEQ_ID_NO_455 | AI ENMNGKEL | DGRNI TVNQA | QSRGGG- GGG | GGYGG- - - - | G | GGGY | - - - - - | 103 |
| SEQ_ID_NO_477 | AI EAMNGKDL | DGRNI TVNQA | QSRGGG- - - - | - - - - - - - - - | G | GGGY | - - - - - | 95 |
| SEQ_ID_NO_465 | AI EGMNGKEL | DGRNI TVNEA | QSRGGR- GGL | - - - - - - - - - | G | GGGY | G- - - - | 98 |
| SEQ_ID_NO_488 | AI EGMNGKEL | DGRNI TVNEA | QSRRSG- GGG | - - - - - - - - - | G | GGGY | - - - - - | 98 |
| SEQ_ID_NO_494 | AI EGMNGKEL | DGRNI TVNEA | QSRRSG- GGG | GGYGG- - - - | G | GGGY | - - - - - | 103 |
| SEQ_ID_NO_374 | AI EGMNGQDL | DGRNI TVNEA | QSRGSG- GGG | GGYRGG- - - | G | GGGY | - - - - - | 103 |
| SEQ_ID_NO_441 | AI EGMNGQEL | DGRNI TVNEA | QSRGSG- GGG | GRREG- - - - | G | GGGY | - - - - - | 101 |
| SEQ_ID_NO_444 | AI EGMNGQTL | DGRNI TVNEA | QSRGSG- GN- | - - - - - - - - - | G | GGGF | RGPRRD | 103 |
| SEQ_ID_NO_451 | AI EGMNGQDL | DGRNI TVNEA | QSRGGG- GGG | GGR- - - - - - | G | GGGY | GGGRRE | 105 |
| SEQ_ID_NO_505 | AI EGMKGQDL | DGRNI TVNEA | QSRGSG- GGG | - - - - - - - - - | G | GGGY | R- - - - - | 97 |
| SEQ_ID_NO_474 | AI EGMNGQDL | DGRNI TVNEA | QSRGSG- GGG | GG- - - - - - - | Y | RGG- - R- - - - | | 98 |
| SEQ_ID_NO_447 | AI EGMNGQEL | DGRSI TVNEA | QARGSG- GGG | GG- - - - - - - | Y | GGGR | RE- - - - | 100 |
| SEQ_ID_NO_450 | AI SGMNGSEL | DGRSI TVNEA | QARGSG- GGG | G- - - - - - - - | G | GGGF | GGGRRR | 104 |
| SEQ_ID_NO_434 | AI EEMNGQDI | DGRNI TVNEA | QSRGSG- GGG | RGGGGGGYGG | | GGGY | GG- - - - | 109 |
| SEQ_ID_NO_437 | AI EGMNGQNL | DGRNI TVNEA | QSRGGG- GGL | - - - - - - - - - | G | GGGY | R- - - - - | 98 |
| SEQ_ID_NO_438 | AI QGMNSQEL | DGRNI TVNEA | QSRGSG- GGG | - - - - - - - - - | G | GGGY | SR- - - - | 99 |
| SEQ_ID_NO_454 | AI EGMNGQDL | DGRNI TVNEA | QSRSGG- - - - | - - - - - - - - - | G | GGGY | - - - - - | 92 |
| SEQ_ID_NO_392 | AI DGMNGQDL | DGRNI TVNEA | QSRGSG- GGG | G- - - - - - - - | G | GGGY | NR- - - - | 100 |
| SEQ_ID_NO_425 | AI EGMNGQNL | DGRNI TVNEA | QSRGKGGGGG | GGGYGG- - - | G | GGGY | - - - - - | 105 |
| SEQ_ID_NO_504 | AI EGMNGQNL | DGRNI TVNEA | QSRGSG- GGG | GG- - - - - - - | N | GGGY | SR- - - - | 102 |
| SEQ_ID_NO_368 | AI EGMNGQDL | DGRSI TVNEA | QSRGSG- GGG | GHRGG- - - - | G | GGGY | LR- - - - | 104 |
| SEQ_ID_NO_422 | AI EGMNGQDL | DGRSI TVNEA | QSRGSG- GGG | GGRG- - - - - | G | GGGY | R- - - - - | 103 |
| SEQ_ID_NO_506 | AI EGMNGQNL | DGRNI TVNEA | QSRGSG- GGG | GGGYGSR- - | G | GGGY | - - - - - | 105 |
| SEQ_ID_NO_433 | VI EAMNGQDL | DGRNI TVNQA | QSRGSG- GGG | GGR- - - - - - | G | GGGY | - - - - - | 99 |
| SEQ_ID_NO_376 | AI EGMNGQNL | DGRNI TVNEA | QSRRSG- GGG | GEGYGG- - - | G | SGGY | KR- - - - | 106 |
| SEQ_ID_NO_440 | AI EGMNGQNL | DGRNI TVNEA | QSRGSG- GGG | GRREGG- - - | G | GGGY | GR- - - - | 106 |

Figure 14 (continued)

| SEQ_ID | Sequence | Length |
|---|---|---|
| SEQ_ID_NO_475 | GNGGGRDYG---------RGGYGRG------NGGY GGRNAG YGG | 128 |
| SEQ_ID_NO_436 | RGGG GGY ----------GGGY-------------G-DGF | 134 |
| SEQ_ID_NO_420 | GGGNAGGYGA P--------SGGYGGG-------GGY-----G-GGA | 149 |
| SEQ_ID_NO_473 | EVVG--------------TAATAGTA-------------V-DRR | 120 |
| SEQ_ID_NO_369 | REQGGGGY----------GGGYGGSR------GGG-----D-REG | 124 |
| SEQ_ID_NO_371 | GGGG--------------GGGYGGSRD RG----DRGY-----G-GGG | 125 |
| SEQ_ID_NO_372 | GGGG--------------SGGYGGGG-------SGGY ESRRSG-GGG | 127 |
| SEQ_ID_NO_373 | GGGG--------------GGGYGGG-------GGGY GGRREG-GGG | 122 |
| SEQ_ID_NO_458 | GGGGGGGY---------GGGRSGG-------GGGY GS---R-EGG | 133 |
| SEQ_ID_NO_507 | GGGG-GYGG G--------GGGYGGGR-----------S-GGG | 127 |
| SEQ_ID_NO_455 | GGREGGGYGG G--------GGGYGGRRE G----GGGY GGGGYG-GGG | 137 |
| SEQ_ID_NO_477 | GGGRQGGYGG G--------GGGYGGGGG------GGGY GG---G-RRE | 125 |
| SEQ_ID_NO_465 | GGRGGGGYGG GGRRDG----GGGYGGG-------GGGY--------GGG | 128 |
| SEQ_ID_NO_488 | GGGG GGYGG GRG-------GGGYGGGG------GGGY GRREGGYGGG | 132 |
| SEQ_ID_NO_494 | GGGGGGGYGR R--------EGGYGGG--------------G-GYG | 125 |
| SEQ_ID_NO_374 | GGRREGGYNR GG-------GGGYGGG-------GGGY-----G-GGG | 130 |
| SEQ_ID_NO_441 | -GGG GGYGG RREGGG----GGGYGGRR-----------E-GGG | 127 |
| SEQ_ID_NO_444 | GGGG GGYGG GRR-------DGGYGGN------GGY GG---G-RRE | 131 |
| SEQ_ID_NO_451 | GGGG-GYGG----------GGGYGGGRR E----------G-GGG | 127 |
| SEQ_ID_NO_505 | GGGG GGYGG GGRR------EGGYGGG-------GGY GG---G-RRE | 126 |
| SEQ_ID_NO_474 | GGGG GGYGG GGRR------EGGYGGG-------GGGY GG---G-RRE | 128 |
| SEQ_ID_NO_447 | GGGG-GYGG G--------GGGYGGGRR-----------E-GGG | 122 |
| SEQ_ID_NO_450 | EGGG GGYGG----------GGGYRGGG-------GGGY-------GGG | 128 |
| SEQ_ID_NO_434 | GGGCYGGGGC RRDGGYSRSG GGGGYGGGG-----DRGY G---G-GGG | 147 |
| SEQ_ID_NO_437 | NGGG GGYGG GRR-------EGGYGGG-------GGY-----S-RGG | 124 |
| SEQ_ID_NO_438 | GGGG GGYGG GGRR------EGGYGGG-------GGGY NSRS-S-GGG | 131 |
| SEQ_ID_NO_454 | SRGG-------------------------------------- | 96 |
| SEQ_ID_NO_392 | NSGG GGYGG GGRREG----GGGYSRG-------GGGY GG---G-GGG | 132 |
| SEQ_ID_NO_425 | GGGG-GYSR G--------GGGYGGGGG RR----EGGY NR---N-GGG | 135 |
| SEQ_ID_NO_504 | GGGG GGYGG----------GGGYGGGGR R----EGCG GGYSRG-GGG | 134 |
| SEQ_ID_NO_368 | SGGG GGYSG --G------GGSYGGGG---------------- | 122 |
| SEQ_ID_NO_422 | SGGG GGYGG G--------GGGYGGGGR-----EGGY-----S-GGG | 130 |
| SEQ_ID_NO_506 | GGGGRRESGG---------GGGYGGSR---------GY-----G-GGG | 129 |
| SEQ_ID_NO_433 | GGGG-------------------------------------- | 103 |
| SEQ_ID_NO_376 | SGGC GGYGR --R------EGGYGGGRR EGVFWNGGGY DG---G-GGG | 141 |
| SEQ_ID_NO_440 | REGG GGYSR GGG-------GGGYGGG-------GGGY G---G-GNG | 134 |

Figure 14 (continued)

```
SEQ_ID_NO_475    RGNFG - GQG ------ GYGD NRFGNDNFGG SYGGRGGYRG -PRGPSAEEN   169
SEQ_ID_NO_436    SNRGG - GGG ------ ---- -------- -- ------- --- ----------   142
SEQ_ID_NO_420    GGYGA - -PGG ------ GYGX ---WWWL-RR RCWWLRC--- ----------   174
SEQ_ID_NO_473    MGTGG - --- ------ ---- --------AK AVVRLPR--- ----------   134
SEQ_ID_NO_369    SGYGG - SRG G----- GYG -------- GG GGGGYGG - R -GG-------   148
SEQ_ID_NO_371    GGYGG - GGG ------ GYG -------- GG GGSRYGG--- -GG-------   147
SEQ_ID_NO_372    SGGGGYSGGG RERSERGYGG GSRN---- GG GYSGYSG GG -GGGSRYGGG   171
SEQ_ID_NO_373    GGYGG - GSG G----- GYGG ---RRE--GG GGGGYGG - G -GGGGYRG--   155
SEQ_ID_NO_458    GGYGG - GGG ------ GYGG SRGGS---GG GGGGYGGSRG -G--------   163
SEQ_ID_NO_507    GGYGSRDGGG G----- GYL- -------- GG GGGGYGG - S RGG-------   153
SEQ_ID_NO_455    GGYGGREGGG ------ GYGG -------- GG GYGGNRG--- ----------   160
SEQ_ID_NO_477    GGYGG - GGG GGRREGGYG -------- GG GYGSRG--- ----------   150
SEQ_ID_NO_465    GGYGG - GGG ------ GYGG -------- GN RGGGYGN--- ----------   149
SEQ_ID_NO_488    GGYGGGRGGG G----- GYG -------- GS RGGGYGG--- ----------   155
SEQ_ID_NO_494    GGRGG - GGG ------ GYG -------- GS RGGGYGG--- ----------   145
SEQ_ID_NO_374    GGYGG - GGG ------ GYGG -------- GR REGGYGG - G -GGDRYARG-   160
SEQ_ID_NO_441    GGYGG - GGG ------ GYGG RR----- EG GDGGYGG--- ----------   150
SEQ_ID_NO_444    GGYGG - GDR ------ GYG -------- GG GGGGSRYSRG -GG-------   156
SEQ_ID_NO_451    GGYSG - GGG ------ GYGG GRREGGY- GG GGGGYGGGDR YSDRSSRGGG   168
SEQ_ID_NO_505    GGYGG - GGG G----- GYGG -------- GR REGGYGG--- ----------   148
SEQ_ID_NO_474    GGYGG - GGG ------ YGG -------- GR REGGYGG--- ----------   148
SEQ_ID_NO_447    GGYGG - GRR ------ ---- -------- EG GGGGYGG--- ----------   139
SEQ_ID_NO_450    RREGG - GGG ------ GYGG GRRE---- GG GGGGYGG--- ----------   153
SEQ_ID_NO_434    GGYGG - GRD R----- GYGG -------- GG GDRGYGG GG -GGDRYSRGG   180
SEQ_ID_NO_437    GGYGG - GGG ------ GYG -------- GG RDRGYGGGGD -GGSRYSRGG   156
SEQ_ID_NO_438    GGYGG - GRD Q----- GYGG -------- GG GGSRYSR - G -GG-------   156
SEQ_ID_NO_454    ------- GGG ------ ---- -------- -- ------- --- ----------    99
SEQ_ID_NO_392    YGSGG - GGG ------ GYG -------- GG RDRGYGD--- -GGSRYSSR   160
SEQ_ID_NO_425    GGYGG - GGG GYGGGGYGG -------- GG RDRGYGG - D -GGSRYSRGG   172
SEQ_ID_NO_504    GGYGS - - GGG ------ GYGG G------ GR REGGYGGGEG -GGARYSRGS   168
SEQ_ID_NO_368    -GRRE - GGG ------ GYG -------- GG EGGGYGG - S -GG-------   144
SEQ_ID_NO_422    GGYSSRGGGG G----- GYGG GGRRD--- GG EGGGYGG - S -GG-------   162
SEQ_ID_NO_506    GGYGGRREGG YSRDG- GYG -------- GD GGSRYSR - S -GA-------   159
SEQ_ID_NO_433    ------- --- ------ ---- -------- -- ------- --- ----------   103
SEQ_ID_NO_376    GGYGG - GGG ------ GYG -------- GG GGGGY---- ----------   159
SEQ_ID_NO_440    GGYGG - GRE QR---- GYGD -------- SG GGSRYSR--- ----------   157
```

Figure 14 (continued)

| SEQ ID | Sequence | # |
|---|---|---|
| SEQ_ID_NO_475 | NSNNYGGY- | 177 |
| SEQ_ID_NO_436 | ----GGGW- | 146 |
| SEQ_ID_NO_420 | --SSWWLWRR WLQCSRWWLR RWLILWWKCC WWRLWR | 208 |
| SEQ_ID_NO_473 | ----SEGWAS | 140 |
| SEQ_ID_NO_369 | --PSSGNWRN DRQPEY---- | 162 |
| SEQ_ID_NO_371 | --SEGGSWRR | 155 |
| SEQ_ID_NO_372 | GVSDDGGWRS | 181 |
| SEQ_ID_NO_373 | --NSDGNWRN | 163 |
| SEQ_ID_NO_458 | --SGGNWRE | 171 |
| SEQ_ID_NO_507 | --SGGNWRE | 181 |
| SEQ_ID_NO_455 | --DSGGNWRN | 168 |
| SEQ_ID_NO_477 | --DSGGNWRN | 158 |
| SEQ_ID_NO_465 | ---SDGNWRN | 156 |
| SEQ_ID_NO_488 | --DSGGNWRN | 163 |
| SEQ_ID_NO_494 | --DSGGNWRN | 153 |
| SEQ_ID_NO_374 | --NSDSDWRN | 168 |
| SEQ_ID_NO_441 | ----GGGGSR W- | 157 |
| SEQ_ID_NO_444 | --ASDGNWRN | 164 |
| SEQ_ID_NO_451 | GGSSDGNWRN | 178 |
| SEQ_ID_NO_505 | --GSES---- | 152 |
| SEQ_ID_NO_474 | --GSEGNWRN | 156 |
| SEQ_ID_NO_447 | --GGYGGGR Y- | 148 |
| SEQ_ID_NO_450 | --GGYGGGDR Y- | 162 |
| SEQ_ID_NO_434 | GADSGGNWRD | 190 |
| SEQ_ID_NO_437 | G-ASEGNWRS | 165 |
| SEQ_ID_NO_438 | --ESDGNWKN | 164 |
| SEQ_ID_NO_454 | --DSGGNWRN | 107 |
| SEQ_ID_NO_392 | GESEGGSWRS | 170 |
| SEQ_ID_NO_425 | GCSDGGSWRN | 182 |
| SEQ_ID_NO_504 | GCSEGGSWRS | 178 |
| SEQ_ID_NO_366 | ----GGGW- | 148 |
| SEQ_ID_NO_422 | ----GGGW- | 166 |
| SEQ_ID_NO_506 | --SDGGSWRN | 167 |
| SEQ_ID_NO_433 | ----GG--- | 105 |
| SEQ_ID_NO_376 | ----GG---- | 161 |
| SEQ_ID_NO_440 | -DSDGGNWRS | 166 |

Figure 15

```
SEQ_ID_NO_527    ---MAGISVI VVVVAFLHI LAFVLAIGAE MRRST----- ----------   32
SEQ_ID_NO_529    MGDVGRSSIL VHILVIALCL AAFGFAIAAE RRRST----- ----------   35
SEQ_ID_NO_530    MGDTERSSIL VHILVIALCL TAFGFAIAAE RRRSTVKSTY LRYILNFVFE   50
SEQ_ID_NO_531    MGDTERSSIL VHILVIALCL TAFGFAIAAE RRRST----- ----------   35
SEQ_ID_NO_510    MGE-GKASTL VFILVVALSL VAFGFSIAAE RRRS------ ----------   34
SEQ_ID_NO_525    MGE-GKGSTL VFILVIALCL VAFGFSIAAE RRRS------ ----------   34
SEQ_ID_NO_521    MAE-GRGSTL VHLLVVVLCL VAFGFAIAAE RRRSV----- ----------   34
SEQ_ID_NO_513    MGE-GKGSTL VHLLVVVLSL VAFGFAIAAE RRRSV----- ----------   34
SEQ_ID_NO_517    MFE-GKGSTL VHLLVVVLSL VAFGFAIAAE RRRS------ ----------   33
SEQ_ID_NO_511    ----MASKLL LIAVFVLDL IAFGLAVAAE QRRST----- ----------   30
SEQ_ID_NO_523    ----MASIL VQVSALLNL IAFGLAVAAE QRRSK----- ----------   30

SEQ_ID_NO_527    ---------- ---GKVVPDE YDERTFCAYD SDASTAYGLS AFGLLLLSQA   69
SEQ_ID_NO_529    ---------- ---GSIVTDS S-NTTFCVYD SDIATGYGVG AFLFLLSGHS   71
SEQ_ID_NO_530    FMDGVFFTIY IVQGSIVTDS F-NSTFCVYD SDIATGYGVG AFLFLLSGDS   99
SEQ_ID_NO_531    ---------- ---GSIVTDS F-NSTFCVYD SDIATGYGVG AFLFLLSGDS   71
SEQ_ID_NO_510    ---------- ---GKSIQDP ITNTTFCVYD SDVATGYGVG AFLFLLSSES   71
SEQ_ID_NO_525    ---------- ---GKSIQDP ITNATYCVYS SDVATGYGVG AFLFLLSSES   71
SEQ_ID_NO_521    ---------- ---GTMHKIE GTNETFCSYS SDVATGYGVG AFLFLLSXES   71
SEQ_ID_NO_513    ---------- ---GTVVKDD ITNSTYCVYN SDVATGYGVG AFLFLLSGES   71
SEQ_ID_NO_517    ---------- ---------- ---------- ------YGVG AFLFLLSSES   47
SEQ_ID_NO_511    ---------- ---AKIVQDS EVNYNYCVYD SYISTGYGVG AFLFLMVSQA   67
SEQ_ID_NO_523    ---------- ---ATVFPDL AKEYDYCVYD SDVATGYGVG ALLLLVAAQA   67

SEQ_ID_NO_527    VMSAATRCLC FGRGLSAGGP RTCAIASFVV SWISFLVAEV CLLAGSARNA   119
SEQ_ID_NO_529    LLMGLTKCMC FGAPLAPGGS RAWSIIYFAS SWTFAIAEA CLIAGATKNA   121
SEQ_ID_NO_530    LLMVVTKCMC FGKPLAPGGS RAWSIIYFAS SWTFMIAES CLIAGATKNA   149
SEQ_ID_NO_531    LLMVVTKCMC FGKPLAPGGS RAWSIIYFAS SWTFMIAES CLIAGATKNA   121
SEQ_ID_NO_510    LLMSVTKCMC FGRPLAPGSD RAWSIIYFIS SWMTFLVAEA CVIAGATKNA   121
SEQ_ID_NO_525    LLMGVTKCMC FGRPLSPGSD RAWSIIYFIS SWMTFLVAEA CLIAGATKNA   121
SEQ_ID_NO_521    LXMGVTKCMC FGRPLTPGVN RAXSIXYFLS SWTFXVAEA CLIAGATKNA   121
SEQ_ID_NO_513    LLMGVTKCMC FGRPLAPGSD RAWSIIYFVS SWLTFLVAEA CLIAGATRNA   121
SEQ_ID_NO_517    LLMGITKCMC FGRSLAPGGD RAWAIIYFVS SWATFLVAEG CLIAGAKKNA   97
SEQ_ID_NO_511    LIMAASKCFC CGKGLNPSGS RAWAVILFIV CMLEFLIAE CLLAGSVRNA   117
SEQ_ID_NO_523    VVMLASRCFC CGRGLKPGGS RACALMLFLF SWLTFLVAAA CLLAGSVRNA   117
```

Figure 15 (continued)

| | | | | | | | | |
|---|---|---|---|---|---|---|---|---|
| SEQ_ID_NO_527 | YHTKYVGYYA | KKDLSSCTAL | RKGVFAAGAT | FVLLSMISSL | LYYWSYSKA- | 168 |
| SEQ_ID_NO_529 | YHTKYRDMVY | AGNW-TCQSL | RKGVFIAGAV | FVVFTMILDV | YFYMYYAKA- | 169 |
| SEQ_ID_NO_530 | YHTRYRHMVY | VGSW-TCESL | RKGVFIAGAV | FVVFTMILNV | YFYMYYTKS- | 197 |
| SEQ_ID_NO_531 | YHTRYRHMVY | VGSW-TCESL | RKGVFIAGAV | FVVFTMILNV | YFYMYYTKS- | 169 |
| SEQ_ID_NO_510 | YHTKY--LS | SCTF-SCASL | RKGIFIAGAV | FIVATMVLNV | YYYMYFTKS- | 167 |
| SEQ_ID_NO_525 | YHTKY--LS | AGAF-SCESL | RKGIFIAGAV | FTVATMILNV | YYYFHFTKF- | 167 |
| SEQ_ID_NO_521 | YHTKYRGMIY | AHNF-SCEAL | RKGXFIAGAV | VVVATMILNV | YYYMYFTKAM | 170 |
| SEQ_ID_NO_513 | YHTKYRGMIY | AQNF-SCETL | RKGVFIAGAV | FVVATMILNV | YYYMYFAKAT | 170 |
| SEQ_ID_NO_517 | YHTKYRGMIY | AQNF-TCETL | RKGVFIAGAV | FVVATMILNV | YYYMYFSKAT | 146 |
| SEQ_ID_NO_511 | YHTKYRTIFS | EQPP-SCETV | RKGVFGAGAA | FIFLNAIVNK | FYYICYSSA- | 185 |
| SEQ_ID_NO_523 | YHTRYRGLFN | GDPL-SCETL | RKGVFAAGAA | FTFFTALLSE | FYYISYSKS- | 165 |

| | | | | | |
|---|---|---|---|---|---|
| SEQ_ID_NO_527 | -DMGGWKHQ | NEGGVGMAEF | GPEKRGLGNT NG | 199 |
| SEQ_ID_NO_529 | TSQAAKKLSK | TTPSVGMIGY | A-  -- | 190 |
| SEQ_ID_NO_530 | TSQAAKKLNK | TTPNVGMIGY | A-  -- | 218 |
| SEQ_ID_NO_531 | TSQAAKKLNK | TTPNVGMIGY | A-  -- | 190 |
| SEQ_ID_NO_510 | SSPPAHKANR | SSSNIGMAGY | A-  -- | 188 |
| SEQ_ID_NO_525 | FFPPTHKANR | SGSNIGMAGY | A-  -- | 188 |
| SEQ_ID_NO_521 | TXPVXHKANR | VSSTVGMAGY | A-  -- | 191 |
| SEQ_ID_NO_513 | TTMPAHKANR | TNSTVGMIGY | A-  -- | 191 |
| SEQ_ID_NO_517 | ASKAAHKTNR | TSSL-VGMIGN | P-  -- | 166 |
| SEQ_ID_NO_511 | -RDKSFQAYG | GETGVGMGTY | K-  -- | 185 |
| SEQ_ID_NO_523 | -RDAAGGAPY | GGSSIGMGPY | T-  -- | 185 |

Figure 16

```
SEQ_ID_NO_546    ----MSSSLE RKKGKTVI-- ---------- M LRSCSQCGSN GHN-----    28
SEQ_ID_NO_542    ---------- ---------- ---------M GRKCSHCGNI GHN-----    14
SEQ_ID_NO_547    ---------- ---------- ---------M TRRCSHCSTN GHN-----    14
SEQ_ID_NO_533    ----MESVVA T--------- ---------W SREEEKAFEN AIALHCV---    25
SEQ_ID_NO_539    ----MSSGGT I--------- ---------W SYDEEKAFEN AIAMHM---    25
SEQ_ID_NO_535    ----MAGSVS ---------- ---------W SREEEKAFEN AIAMHM---    24
SEQ_ID_NO_538    ----MASVGT ---------- ---------W TRDEEKTFEN AIAMHM---    24
SEQ_ID_NO_553    ----MTSQAA TTTTTAAAAA A-------W TREDDKAFEN ALAACAAPPP    38
SEQ_ID_NO_550    ----MAAEEA SSSGGGEEGS GAGAGG---W TREQEKAFEN ALATV-----    38
SEQ_ID_NO_552    ----MAVNEA SSSGGGEEGC GS------W TREQEKAFEN AVATMGG---    36
SEQ_ID_NO_536    ----METLYP SSHLSSSAWF VLDNPS-TKW TKEENKMFES ALAIY-----    40
SEQ_ID_NO_543    MDRGEILSP ASYLQNSNWL FPETRA-TKW TPEENKQFEN ALALY-----    44
SEQ_ID_NO_548    ----MEILAP SSYFSSSSWF LEESRSTTRW TAAENKAFEN ALAVF-----    41

SEQ_ID_NO_546    --SRTCGESS SAAGNGAGDG EFMLFGVRVK VDPMRKSVSM NDLSD-YELP    75
SEQ_ID_NO_542    ---------- SR-TCNSLRG SGBFVGVRLF GVQLDLSSSC VSMKKSFSMD    53
SEQ_ID_NO_547    --SRTCPNRG VK-LFGVRLT -DGL RKSAS MGNLTHFASG SGGGS-TPLN    59
SEQ_ID_NO_533    -EEEI TEDQW NK-MSSMVPS -KALEEVKKH YQLLEDVKA IENGQ-VPLP    71
SEQ_ID_NO_539    --EESSKEQW EK-I ASAVPS -KSMEEVKQH YQVLVEDVSA IEAGH-SFP    70
SEQ_ID_NO_535    -DKEECEEQW EK-I ASTVPT -KSLEELKLH YELLVEDVTA IEAGH-VPLP    70
SEQ_ID_NO_538    --DEDSNEQW EK-I ASMVPS -KSLEELKLH YKI LVEDVCA IEAGN-VPIP    69
SEQ_ID_NO_553    ADGGAPDDDW FAALAASVPG ARSAEEVRRH YEALVEDVAA IDAGR-VPLP    87
SEQ_ID_NO_550    -DEEEGEAMM DK-I ADAVES -KTPEEVRRH YELLVEDVDG IEAGR-VPLL    84
SEQ_ID_NO_552    --EEDGDARW EK-LAEAVES -KTPEEVRRH YELLVEDVDG IESGR-VPLP    81
SEQ_ID_NO_536    --DKETPDRW FK-VAAL PG -KTVSDVI KQ YKELEEDVCE IEAGR-FPVP    85
SEQ_ID_NO_543    --DKDEPDRW DK-VAAM PG -KTVGDVI KQ YRELEEDVSD IEAGL-IPIP    89
SEQ_ID_NO_548    --DENTPNRW ER-VAERVPG -KTVGDVMRQ YKELEDDVSS IEAGF-VPVP    86
```

Figure 16 (continued)

| | | | | | | | |
|---|---|---|---|---|---|---|---|
| SEQ_ID_NO_546 | SNVN------ | QNGVDNSKNS | NDSDKVVADD | VVTAGAGYV- | ---------S | 109 |
| SEQ_ID_NO_542 | SFPT------ | ---SSSSPTS | SFSSSRLTID | DRASIGYLSD | GL-------- | 86 |
| SEQ_ID_NO_547 | GVVH------ | DSPGDTPDHP | A-VGGGSADG | YASEDFVAG- | ---------- | 91 |
| SEQ_ID_NO_533 | RYHHRKGLIV | DEAAAAATSP | ANRDHSSGS | SEKKPNPGTS | GIS------S | 115 |
| SEQ_ID_NO_539 | NYAS------ | DETTSSNKD- | FHGSSKATSS | DKRSNCNYGS | GFSGLGLDST | 113 |
| SEQ_ID_NO_535 | CYKG------ | EEPSSSAKDY | FHGPSMAPNS | DRRSNSGYGN | GFSGLTLDST | 114 |
| SEQ_ID_NO_538 | NYEG------ | EEAASSTKD- | LHGLSGTMTT | VKKLNCGYGS | GFVGLGHESS | 112 |
| SEQ_ID_NO_553 | RYAG------ | EESAAPPDGA | GAAAASKDG | GHRRDERKGG | G--------G | 123 |
| SEQ_ID_NO_550 | VYAG------ | DGDEGGSGGG | AGGSGGGGGG | GGKKSGGGG | ---------G | 118 |
| SEQ_ID_NO_552 | AYAA------ | ---------- | -DGAAEEGGG | GGKKGSGGG | ---------G | 104 |
| SEQ_ID_NO_536 | GYDL------ | ----ASSFSF | EFVDDRNFDV | YRRKSSVG-- | ---------- | 113 |
| SEQ_ID_NO_543 | GYSS------ | ----SDAFTLE | WFNNNQGYDG | FRHYYTPGG- | ---------- | 119 |
| SEQ_ID_NO_548 | GYST------ | ----SSPFTL | EWGSGHGFDG | FKQSYGTGG- | ---------- | 115 |

| | | | | | | | |
|---|---|---|---|---|---|---|---|
| SEQ_ID_NO_546 | ADDAVQHQ-- | STGGRERKRG | IPWTEEEHKL | FLLGLDKVGK | GDWRGI SRNF | 157 |
| SEQ_ID_NO_542 | ---------- | IVRTQERKKG | VPWTEEEHRK | FLVGLEKLGK | GDWRGI SRNY | 126 |
| SEQ_ID_NO_547 | ---------- | SSSSRERKKG | VPWTEEEHRM | FLLGLDKLGK | GDWRGI ARNY | 131 |
| SEQ_ID_NO_533 | SNGGRSGG-- | SRAEQERRKG | IPWTEEEHRL | FLLGLDKFGK | GDWRSI SRNF | 163 |
| SEQ_ID_NO_539 | THSSGKGGLS | RSSEQERRKG | IPWTEEEHRL | FLLGLDKFGK | GDWRSI SRNF | 163 |
| SEQ_ID_NO_535 | GHGGKQS--- | SRSDQERRKG | IPWTEEEHRL | FLLGLDKFGK | GDWRSI SRNF | 161 |
| SEQ_ID_NO_538 | GHGGKGA--- | SRSEQERRKG | IPWTEEEHRL | FLLGLDKFGK | GDWRSI SRNF | 159 |
| SEQ_ID_NO_553 | GYDGGKSC-- | SKAEQERRKG | IPWTEEEHRL | FLLGLDKFGK | GDWRSI SRNF | 171 |
| SEQ_ID_NO_550 | GHGEKGSS-- | KSAEQERRKG | AWTEDEHRL | FLLGLEKYGK | GDWRSI SRNF | 166 |
| SEQ_ID_NO_552 | THGDKRSA-- | KSAEQERRKG | AWTEDEHRL | FLLGLEKYGK | GDWRSI SRNF | 152 |
| SEQ_ID_NO_536 | ---------- | RGSEHERKKG | VPWTEEEHKQ | FLRLLKYGK | GDWRNI SRNF | 153 |
| SEQ_ID_NO_543 | ----KRTTAA | RSSEQERKKG | VPWTEEEHRQ | FLMGLQKYGK | GDWRNI SRNF | 165 |
| SEQ_ID_NO_548 | ----RKSSSG | RPSEQERKKG | VPWTEEEHKL | FLMGLKKYGK | GDWRNI SRNF | 161 |

Figure 16 (continued)

| | | | | | | | |
|---|---|---|---|---|---|---|---|
| SEQ_ID_NO_546 | VKTRTPTQVA | SHAQKYYLRK | NNLNRRRRRS | SLFDITTDSV | PGGLPMDDVK | | 207 |
| SEQ_ID_NO_542 | VTTRTPTQVA | SHAQKYFIRL | ATLNKKKRRS | SLFDMVGSGK | TN-KTVD--- | | 172 |
| SEQ_ID_NO_547 | VISRTPTQVA | SHAQKYFIRQ | SNMSRRKRRS | SLFDIVADES | GDTPMVSR-- | | 179 |
| SEQ_ID_NO_533 | VISRTPTQVA | SHAQKYFIRL | NSMNRDRRRS | SIHDITTVNN | QA-------- | | 205 |
| SEQ_ID_NO_539 | VISRTPTQVA | SHAQKYFIRL | NSMNRDRRRS | SIHDITSVNN | GD-------- | | 205 |
| SEQ_ID_NO_535 | VISRTPTQVA | SHAQKYFIRL | NSMNRDRRRS | SIHDITSVNN | GD-------- | | 203 |
| SEQ_ID_NO_538 | VISRTPTQVA | SHAQKYFIRL | NSMNRDRRRS | SIHDITSLNN | GD-------- | | 201 |
| SEQ_ID_NO_553 | VISRTPTQVA | SHAQKYFIRL | NSMNRDRRRS | SIHDITSVTA | GDQV------ | | 215 |
| SEQ_ID_NO_550 | VISRTPTQVA | SHAQKYFIRL | NSMNRERRRS | SIHDITSVN- | GE-------- | | 207 |
| SEQ_ID_NO_552 | VISRTPTQVA | SHAQKYFIRL | NSMNRERRRS | SIHDITSVNN | GD-------- | | 194 |
| SEQ_ID_NO_536 | VNSKTPTQVA | SHAQKYFMRQ | LSGGKDKRRP | SIHDITTVNL | TE-------- | | 195 |
| SEQ_ID_NO_543 | VTTRTPTQVA | SHAQKYFIRQ | STGGKDERRS | SIHDITTVNL | PDTKS----- | | 210 |
| SEQ_ID_NO_548 | VITRTPTQVA | SHAQKYFIRQ | LSGGKDKRRA | SIHDITTVNL | SDNQTPS--- | | 208 |

| | | | | | | |
|---|---|---|---|---|---|---|
| SEQ_ID_NO_546 | NHQDKSVPKV | LQHSQVPHAE | KPNMNGYTIA | PFPLAVGPIL | LPVQVHNPME | 257 |
| SEQ_ID_NO_542 | ---------- | ------PNNS | SKSKSGDSVC | RHDHEVEKDA | TLSL---LIN | 203 |
| SEQ_ID_NO_547 | ---------- | ------DFLA | DDPAQAEMQS | ----NNLLPP | TPAVDEECES | 209 |
| SEQ_ID_NO_533 | ---------- | ------PANT | GGGQQPQVVK | ----HRPAQP | QPQP---Q-- | 230 |
| SEQ_ID_NO_539 | ---------- | ------VASS | QAPITGLHSS | -----TISSN | TMGV------ | 228 |
| SEQ_ID_NO_535 | ---------- | ------TSH- | QAPITGQQAN | --------TN | SPGA---AVM | 225 |
| SEQ_ID_NO_538 | ---------- | ------VSSH | QAPITGQQAN | ----TSPAGP | APAM------ | 225 |
| SEQ_ID_NO_553 | ---------- | ------AAQQ | GAPITGHQAT | ----GNPAAA | ALGP---PGM | 242 |
| SEQ_ID_NO_550 | ---------- | ------ASAA | QGPITG---- | ----TNGQAA | VPGK---S-- | 228 |
| SEQ_ID_NO_552 | ---------- | ------PSTA | QGPITGQ--- | ----TNGQAA | NPGK---P-- | 216 |
| SEQ_ID_NO_536 | ---------- | ------PTAS | ENEKLSSMDQ | ---FSKLPSL | QKSP---CYQ | 223 |
| SEQ_ID_NO_543 | ---------- | ------PSPD | EKKSSPDHST | TSLQSQPQQK | MVGM---A-- | 239 |
| SEQ_ID_NO_548 | ---------- | ------PDNK | KPPSSPDHSM | ----AQQQTS | STSI---H-- | 233 |

Figure 16 (continued)

| | | |
|---|---|---|
| SEQ_ID_NO_546 | NKAFHWGDHQ L-QNGPGMLL RTVPFIPVAN S---------- -----SSAIR | 292 |
| SEQ_ID_NO_542 | SLQQQTKSDD Y-DMQKIEDD SEEAEHKDVP D---------- -----WLHPL | 238 |
| SEQ_ID_NO_547 | MGSAASANSI DGEHALPIPE SSQYQHPLVY PAYVAPFYPM PYPCWPGYTA | 259 |
| SEQ_ID_NO_533 | PQPQQHHPPT --MAGLGMYG GAPVGQPIIA P--------- -----PDHMG | 264 |
| SEQ_ID_NO_539 | GQSLKHRVQG HIPPGLGMYG TIPVGHPVAA P--------- -----PGHMA | 263 |
| SEQ_ID_NO_535 | GQSVKHRAQP H-LPGLGMYG AIPVGRPIAA A--------- -----PGHIG | 259 |
| SEQ_ID_NO_538 | GPPVKHRTQA H-MPGLAMYG P-PLGHPVAP P--------- -----PGHMA | 259 |
| SEQ_ID_NO_553 | KHHHHHHPGG A-PPPMPMYS AAPMGHPVA- ---------- ------GHMV | 274 |
| SEQ_ID_NO_550 | PKQSPHQPGN L-PPGVDAFG TIT GQPVGG P--------- -----LV--- | 259 |
| SEQ_ID_NO_552 | SKQSP-QPAN T-PPGVDAYG TITGQPVGG P--------- -----LV--- | 246 |
| SEQ_ID_NO_536 | KLLFDWNRSS --NGGLLGLG S-NYGDRLMS F--------- -----PSGIA | 256 |
| SEQ_ID_NO_543 | KGLIDWKPQN EGGGAAGVFS Q-ANGNLLMA P--------- -----LCGI- | 273 |
| SEQ_ID_NO_548 | KLPFQWDQTS N-ETIMGFAS SGHHGNMFQS N--------- -----PFGM- | 267 |

| | | |
|---|---|---|
| SEQ_ID_NO_546 | DLNLN-QRVL ----EGEPSS P--------- ---------LS LKLSLSSSDN | 319 |
| SEQ_ID_NO_542 | TKSLN-MTLV IIPNSSNVAP P--------- ---------DL ELTLAGSKSN | 269 |
| SEQ_ID_NO_547 | EPAIAETHEV LKPIAVHSKS PINVDELVGM SKLSLGESIG DAAKPPSLSL | 309 |
| SEQ_ID_NO_533 | -SAVG-TPVM LPPPMGTHHH H--------- ---------HH HHLGVAPYAV | 295 |
| SEQ_ID_NO_539 | -SAVG-TPVM LPPGPHPHPH P--------- ---------HH HAHPHPPYVL | 294 |
| SEQ_ID_NO_535 | -SAVG-TPVM LIPPAHHPHS P--------- ---------- ----PPYIV | 282 |
| SEQ_ID_NO_538 | -SAVG-TPVM LPPPGHHPH- ---------- ---------- ----PPYVV | 281 |
| SEQ_ID_NO_553 | PAAVG-TPVV F-PPGH---- ---------- ---------- ----APYVV | 293 |
| SEQ_ID_NO_550 | -SAVG-TPVT LIPVAAPPHM G--------- ---------YA MHAPVPGTVV | 289 |
| SEQ_ID_NO_552 | -SAVG-TPVT LIPVSAPPHL A--------- ---------YG MRAPVPGAVV | 276 |
| SEQ_ID_NO_536 | ANGK-N--- --EQDQELNS A--------- ---------YY GTYSKPHKSI | 283 |
| SEQ_ID_NO_543 | -SSYG-QRLI --QEQNLLRG T--------- ---------LP GYQFAPYNLI | 301 |
| SEQ_ID_NO_548 | -NSYG-FKM- --QGQQMQRG G--------- ---------FC DTYLGSQNMA | 295 |

Figure 16 (continued)

| | | | | |
|---|---|---|---|---|
| SEQ_ID_NO_546 | SQSSSTRHST GFQAMAATSF SKGGDSIISV A-- | 350 |
| SEQ_ID_NO_542 | NMEQDKTSSS SFLIGPI SVT ---------- --- | 289 |
| SEQ_ID_NO_547 | KLVEGSSRQS AFHANPSSGS SGMNSSHNPI HAV | 342 |
| SEQ_ID_NO_533 | PA-------- -YPVPPLPQQ HPAPSTMH-- --- | 314 |
| SEQ_ID_NO_539 | PLA------- -YPMAPPTMH Q--------- --- | 307 |
| SEQ_ID_NO_535 | PVA------- -YPMAPPPMH Q--------- --- | 295 |
| SEQ_ID_NO_538 | PVA------- -YPTAPPKTA ---------- --- | 293 |
| SEQ_ID_NO_553 | PVG------- -YPAPPAKMH Q--------- --- | 306 |
| SEQ_ID_NO_550 | PRAPM----- -YPMPPPPSR ---------- --- | 303 |
| SEQ_ID_NO_552 | PGAPVNIAPM PYPMPPPPSH G--------- --- | 297 |
| SEQ_ID_NO_536 | ---------- -FQFEPSRYQ IYG------- --- | 295 |
| SEQ_ID_NO_543 | ---------- -FQMQPMQRQ ---------- --- | 310 |
| SEQ_ID_NO_548 | ---------- -FQMQSGLHF PNA------- --- | 307 |

Figure 17

| | | | | | | | |
|---|---|---|---|---|---|---|---|
| SEQ_ID_NO_559 | -----MENK | -------TP | FFSLS FLS | LNCA GG--- | -------NDL | 27 |
| SEQ_ID_NO_586 | -----MQTA | ----------LFF LVT CT | ITCTLGD--- | -------VNL | 23 |
| SEQ_ID_NO_591 | ---------- | -------MLG | ICILL VFLNN | FTCA ID--- | -------DDL | 23 |
| SEQ_ID_NO_581 | -----MART | PRTTILHLV | TLCC LWVQN | TPSLAST--- | ---ASAI DEF | 38 |
| SEQ_ID_NO_588 | -----MARA | PR--ILHLL | ALCSL SSSSV | AVAVASA--- | ---SGAADAF | 36 |
| SEQ_ID_NO_589 | -----MTTT | SR-ALALVL | SSCCL LVAVD | AAYAKKP--- | --NLSKNDF | 37 |
| SEQ_ID_NO_590 | MARTSMTTTS | RA--LALVL | SSCCL LVAVD | AAYAKKP--- | --NLSKNDF | 42 |
| SEQ_ID_NO_584 | -----MANS | RA---FALV | LFCAL SSCQ | VAFSYFP--- | --PPAAKEDF | 36 |
| SEQ_ID_NO_583 | -----MATS | RP--LALAL | LLCAL SACSH | AAI SYPPSAM | STAAPANNGF | 41 |
| SEQ_ID_NO_585 | -----MARS | RA--FAFAL | LICAV AASCH | VAL SAPP--- | PYAKQVERDF | 38 |
| SEQ_ID_NO_560 | -----MNCB | A----FSFWF | VCKI IFFLS | FNI QISI--- | ---ANPQENF | 34 |
| SEQ_ID_NO_577 | -----MKTL | -----SCYYT | FATV ALLFS | FTPSSAD--- | ------THENF | 31 |
| SEQ_ID_NO_569 | -----MPNP | -----MRPYL | ILSV FFFNL | YHSMAVP--- | ---DPTHQAL | 33 |
| SEQ_ID_NO_575 | -----MEKS | -----NSLPF | LSVI VLLHV | SNSLTTP--- | -TRESI HDTF | 35 |
| SEQ_ID_NO_576 | -----MDTM | GK---LFFLT | ATLT VLFNS | TTAATSP--- | ------IQHF | 32 |
| SEQ_ID_NO_578 | -----MANI | TSSFNMQTS | LTLL LLLST | QSSATSR--- | ----SITDRF | 37 |
| SEQ_ID_NO_579 | -----MAIT | YS-FNFKSY | FPLL VLLST | HSSATST--- | ----SII DRF | 36 |
| SEQ_ID_NO_558 | -----MTS | -----LTTQT | LIIT FLLT | PTSFASP--- | ---PSLEDVF | 32 |
| SEQ_ID_NO_571 | -----MKSP | -------FVF | FSVL ISVSL | PNSI ALP--- | -------DNF | 27 |

| | | | | | | | |
|---|---|---|---|---|---|---|---|
| SEQ_ID_NO_559 | LSCLTFNGVR | N------HT | VFSADSDSDF | NRFLHLSI QN | PLFQNSLI SK | 70 |
| SEQ_ID_NO_586 | SSCLTSNGVS | N-----FTA | LSTSSDS-DY | HRLLYVSMQN | QIFTRPKYPR | 66 |
| SEQ_ID_NO_591 | PSCLTHGVH | N-----YTT | HQSTSNSDAY | HRLLYVSMQN | QIFTRSIFPD | 67 |
| SEQ_ID_NO_581 | LGCLSAD-IP | S------GL | IQTPATPSSY | SALLSTTRN | LRYVLPDTSK | 80 |
| SEQ_ID_NO_588 | VGCLTAAGVP | P------GL | LQTPASP-SY | DALLRSSVRN | LRYVAPGTPW | 78 |
| SEQ_ID_NO_589 | LSCLAAG-IP | A------RQ | LYAKGSP-SY | GSVLTSTI RN | LRYLSSKTCN | 78 |
| SEQ_ID_NO_590 | LSCLAAG-IP | A------RQ | LYAKGSP-SY | GSVLTSTI RN | LRYLSSKTCN | 83 |
| SEQ_ID_NO_584 | LGCLVKE-IP | P------RL | LYAKSSP-AY | PSVLGQTI RN | SRWSSPDNVK | 77 |
| SEQ_ID_NO_583 | LSCLI KS-VP | P------RL | LHGKSSR-AY | GSI MESTVRN | VKFVSDKTVK | 82 |
| SEQ_ID_NO_585 | LTCLTKD-IP | P------RQ | LYAKSSP-AY | ASVWSSTVRN | IKFLSDKTVK | 79 |
| SEQ_ID_NO_560 | LKCFSEY-IP | NNPANP--KF | YTQDDQ-LY | MSVLNSTI QN | LRFTSDTTPK | 80 |
| SEQ_ID_NO_577 | LDCLYSYPHN | T---NSI SSV | LYTQTNS-SY | FSVLDATMQN | LRF--SDSRK | 75 |
| SEQ_ID_NO_569 | LDCLTDS-IP | T---DTASSI | VSKSNP-SY | TSVLRAVI RN | ARFNTSSTPK | 78 |
| SEQ_ID_NO_575 | LHCLQSH-TT | NQPDH-VSNI | VYAQTNT-SY | TSVLRAFARN | ARFSAPSTCK | 82 |
| SEQ_ID_NO_576 | LNCLPHSLVS | E--------V | TYTPNNA-SF | STI LNMKI QN | KRFKTATTPK | 73 |
| SEQ_ID_NO_578 | LQCLHDRADP | S---FPI TGE | VYTPGNS-SF | PTVLQNYI RN | LRFNETTTPK | 83 |
| SEQ_ID_NO_579 | TQCLNNRADP | S---FPLSGQ | LYTPDNS-SF | PSVLQAYI RN | LRFNESTTPK | 82 |
| SEQ_ID_NO_558 | AQCVTDF-KP | SNPKSPI QNY | YTQRSP-NF | LTI LNNYVRN | LRYFNNMTRK | 80 |
| SEQ_ID_NO_571 | LDCLTENSQP | T---NPI SDA | HTPDNP-SF | TTVLQSYARN | LRFLTLSTPK | 73 |

Figure 17 (continued)

| | | | | | | | | |
|---|---|---|---|---|---|---|---|---|
| SEQ_ID_NO_559 | PSAILPGSK | EELSNTIRC | RKGSWTIRLR | SGGHSYEGLS | YTS---DTP | 116 |
| SEQ_ID_NO_586 | PSMILPQSK | EELAASYVCS | NRGLWTIRLR | SGGHSYEGLS | YVA---DTP | 112 |
| SEQ_ID_NO_591 | PRVILPESM | DQLANVISCC | TRGSWTIRLR | SGGHSYEGLS | HIA---DNP | 113 |
| SEQ_ID_NO_581 | PLGIAATEH | AHAQTTVRCG | RRHGVRVRVR | SGGHDYEGLS | YASVHLHNRN | 130 |
| SEQ_ID_NO_588 | PLAYAATEP | AHAQAAVRCG | RRHGVRVRTR | SGGHDYEGLS | YASL---DPR | 125 |
| SEQ_ID_NO_589 | PLYIVTPTDV | KHIQVAVSCG | RRHNVRIRVR | SGGHDYEGLS | YRS---EIP | 124 |
| SEQ_ID_NO_590 | PLYIVTPTDV | KHIQVAVSCG | RRHNVRIRVR | SGGHDYEGLS | YRS---EIP | 129 |
| SEQ_ID_NO_584 | PLYITPTNV | SHIQSAVVCG | RRHSVRIRVR | SGGHDYEGLS | YRS---LQP | 123 |
| SEQ_ID_NO_583 | PVYITPTEA | AHIQATVACG | RXHGLRVRVR | SGGHDYEGLS | YRS---AKP | 128 |
| SEQ_ID_NO_585 | PLYITPTNA | SHIQAAVVCG | RRHGMRIRVR | SGGHDYEGLS | YRS---EKP | 125 |
| SEQ_ID_NO_560 | PLVVTPSNV | SHIQASILCS | KKVGLQIRTR | SGGHDAEGLS | YIS---QVP | 126 |
| SEQ_ID_NO_577 | PLVVTPQVV | SHIQATIKCS | QRHGLQIRTR | SGGHDYEGLS | YVA---RVP | 121 |
| SEQ_ID_NO_569 | PLIITPLDE | SHVSAAVICS | QKLGFDLKIR | SGGHDYEGLS | YVF---DNP | 124 |
| SEQ_ID_NO_575 | PLLVTPLSE | NQVQATYVCA | KSIGLQLKIR | SGGHDFEGVS | YIS---QVP | 128 |
| SEQ_ID_NO_576 | PLAITAKDD | SHIQETIKCA | KSNNQIRIR | SGGHDYEGFS | YVS---DVP | 119 |
| SEQ_ID_NO_578 | PELITAEHV | SHIQAAVVCG | KQNRLLLKTR | SGGHDYEGLS | YLT---NTN | 129 |
| SEQ_ID_NO_579 | PILITALHP | SHIQAAVVCA | KTHRLLMKTR | SGGHDYEGLS | YVT---NSN | 128 |
| SEQ_ID_NO_558 | PVAVAAADV | THIQATITCA | KKLGLQLRIR | SGGHDYDGMS | YLS---TID | 126 |
| SEQ_ID_NO_571 | PLAIAAKHE | SHVQATIICS | KKLGLQIRIR | SGGHDYDGLS | YVS---DVA | 119 |

| | | | | | | | | |
|---|---|---|---|---|---|---|---|---|
| SEQ_ID_NO_559 | --FILIDLMN | LNRVSIDLES | ETAWESGST | LGELYYAIIE | SSSKL-GFTA | 163 |
| SEQ_ID_NO_586 | --FVVIDLMN | LNRISIDLES | KTAWESGAT | LGEIYCASE | ASDTL-GFSG | 159 |
| SEQ_ID_NO_591 | --FVIIDLMN | LNGSIDLDT | QTAWESGAT | LGEIYHAIGK | SSGTM-AFSA | 160 |
| SEQ_ID_NO_581 | EPFAVLDLAA | LRAIHVDAAR | AEAWESGAT | VGELYYANGA | ASRSL-GFPA | 179 |
| SEQ_ID_NO_588 | ESFAVLDLAA | FREVRVDAAR | AEAWAGSGAT | LGEVYYANGA | ASRAL-AFPA | 174 |
| SEQ_ID_NO_589 | EPFAIVDLVN | MRNVTVDGKA | RTAWESGAQ | GELYYGISK | ASPTL-AFPA | 173 |
| SEQ_ID_NO_590 | EPFAIVDLVN | MRNVTVDGKA | RTAWESGAQ | GELYYGISK | ASPTL-AFPA | 178 |
| SEQ_ID_NO_584 | ETFAVVDLNK | MRAVVVDGKA | RTAWDSGAQ | LGELYYAIYK | ASPTL-AFPA | 172 |
| SEQ_ID_NO_583 | ETFAVVDLSM | MRQVRIDGKA | ATAWDSGAQ | LGELYYAVAK | MTPSL-GFPA | 177 |
| SEQ_ID_NO_585 | EPFAVVDMNK | MRAVSIDGKA | ATAWDSGAQ | LGDLYYGIAK | ASPKL-GFPA | 174 |
| SEQ_ID_NO_560 | --FAIVDLRN | MHTVKVDIHS | QTAWEAGAT | LGEVYYWNE | MNENF-SFPG | 173 |
| SEQ_ID_NO_577 | --FVILDLLN | FREIKVDVEN | RTAWQVGAT | LGELYYTSQ | ASKTL-GFPA | 168 |
| SEQ_ID_NO_569 | --FFVLDMFN | LRSITVNMAD | ETAWGAGAT | LGELYYNWK | NSKVH-GFPA | 171 |
| SEQ_ID_NO_575 | --FILDMFN | FQDVTVDVQN | EIAVQAGAS | LGQVYYRIME | KSKVH-GFPA | 175 |
| SEQ_ID_NO_576 | --FILDMFH | LNSVDINLQE | STAWESGAT | LGKIYYNIAN | KSNKL-AFPS | 166 |
| SEQ_ID_NO_578 | QPFFIVDMFN | LRSINVDIEQ | ETAWQAGAT | LGEVYYRIAE | KSNKH-GFPA | 178 |
| SEQ_ID_NO_579 | QPFFVVDMFN | LRSINVSLED | ETAWQAGAT | LGEVYYRIAE | KSNSH-AFPA | 177 |
| SEQ_ID_NO_558 | --FVVLDMFN | LRSINIDPKL | DTAWQSGAT | LGEIYYGVAN | KSNDLRGFPA | 174 |
| SEQ_ID_NO_571 | --FILDMFN | LRSINIDIED | ESAWQAGAT | LGEVYYRIAE | KSNVH-GFPA | 166 |

Figure 17 (continued)

| | | | | | | | |
|---|---|---|---|---|---|---|---|
| SEQ_ID_NO_559 | GWCPTVGTGG | HISGGGFGMM | SRKYGLAADN | VVDALIDAN | GALLDRQAMG | 213 |
| SEQ_ID_NO_586 | GYCPTVGSGG | HISGGGFGMM | SRKYGLAADN | VIDALIVDAN | GAVLDRSSMG | 209 |
| SEQ_ID_NO_591 | GYCPTGSGG | HIAPGGFGMM | SRKYGLAADN | VVDALLVDAN | GVVLDRESMG | 210 |
| SEQ_ID_NO_581 | GSCPTMGVGG | HLSGGGFGSL | ARKYGLSADN | VLDAVVVDAD | GRLVNRSTMG | 229 |
| SEQ_ID_NO_588 | GVCPTVGVGG | HLGGGGFGTL | MRRYGLAADN | VLDAVLVDAD | GRLLNRTTMG | 224 |
| SEQ_ID_NO_589 | GVCPTIGVGG | HFSGGGFGML | LRKFGLASDN | VLDVKVVDAN | GKVQDRKSMG | 223 |
| SEQ_ID_NO_590 | GVCPTIGVGG | HFSGGGFGML | LRKFGLASDN | VLDVKVVDAN | GKVQDRKSMG | 228 |
| SEQ_ID_NO_584 | GVCPTIGVGG | NFAGGGFGML | LRKYGIAAEN | VIDVKLYDAN | GKLHDKKSMG | 222 |
| SEQ_ID_NO_583 | GVCATIGVGG | HFSGGGFGML | LRKYGTAGDN | VIDAKVVDAN | GTLLDRKSMG | 227 |
| SEQ_ID_NO_585 | GVCITIGVGG | HFSGGGFGML | LRKYGTAADN | VIDAKVVDAQ | GRLLDRKAMG | 224 |
| SEQ_ID_NO_580 | GYCPTVGVGG | HFSGGGYGAL | MRNYGLAADN | IDAHLVNVD | GKVLDRKSMG | 223 |
| SEQ_ID_NO_577 | GVCYSVGAGG | HISGGGYGFL | MRKYGLAADN | VIDAHIIDVN | GNLLDRKAMG | 218 |
| SEQ_ID_NO_569 | GVCPTVGVGG | HLSGAGYGTL | IRKYGLSVDH | VVDAKLVDVN | GKILDRKTMG | 221 |
| SEQ_ID_NO_575 | GACPTVGVGG | HLSGGGYGNM | IRKYGLSVDH | VVDAKIVDVK | GRILDKESMG | 225 |
| SEQ_ID_NO_576 | GVCFTLGAGG | HFSGGGYGNL | MRKFGLSVDN | IDAKMVDVK | GNLLDRKSMG | 216 |
| SEQ_ID_NO_578 | GVCPTVGVGG | HFSGGGYGNL | MRKYGLSVDN | VDAQIIDVN | GKLLDRKSMG | 228 |
| SEQ_ID_NO_579 | GVCPTVGVGG | HFSGGGYGNL | MGKYGLSVDN | VDAQLIDVN | GKLLNRKSMG | 227 |
| SEQ_ID_NO_558 | GICPGLGAGG | HFSGGGYGNM | MRKYGLSIDN | IDAKIVDAK | GKVLDRSSMG | 224 |
| SEQ_ID_NO_571 | GVCPTLGVGG | HFSGGGYGNM | MRKYGLSVDN | VDAQIIDVR | GRILDRKSMG | 216 |

| | | | | | | | |
|---|---|---|---|---|---|---|---|
| SEQ_ID_NO_559 | EDVFWAIRGG | GGGVWGAIYA | WKIKLLPVPE | KVTVFRVTKN | VAIDE--ATS | 261 |
| SEQ_ID_NO_586 | EDVFWAIRGG | GGGVWGAIYA | WKLQLLPVPK | QVTVFKLMKN | FDNIE-EASK | 258 |
| SEQ_ID_NO_591 | EDVFWAIRGG | GGGVWGAVYA | WKLQLVPVPK | NVTIFRLMKH | SEVED--ASK | 258 |
| SEQ_ID_NO_581 | EDHFWALCGG | GGESFGVVLS | MKVRLVPVPE | TVTVFSIVRS | RSQS---AVE | 276 |
| SEQ_ID_NO_588 | EDLFWAIRGG | GGESFGVVLS | AKLRLVPVPE | TVTVFTVRRS | RNQS---ASE | 271 |
| SEQ_ID_NO_589 | EDYLWAVRGG | GGSSFGIVVS | WKLRLLPVPA | TVTVIQMPKM | VNEG---AVD | 270 |
| SEQ_ID_NO_590 | EDYLWAVRGG | GGSSFGIVVS | AKLRLLPVPA | TVTVLQMPKM | VNEG---AVD | 275 |
| SEQ_ID_NO_584 | DDHFWAVRGG | GGESFGVVVA | NQVKLLPVPP | TVTIFKISKT | VSEG---AVD | 269 |
| SEQ_ID_NO_583 | EDYFWAIRGG | GGESFGIMVS | MQVQLVPVPP | KVTVFQIHRG | VKDG---AID | 274 |
| SEQ_ID_NO_585 | EDHFWAIRGG | GGESFGIVAS | NQVKLLPVPP | KVTVFQVHKG | IKES---AID | 271 |
| SEQ_ID_NO_580 | EDLFWAIRGG | GGENFGIIAA | WKIKLVVVPS | KATIFSVKKN | MELHG--LVK | 271 |
| SEQ_ID_NO_577 | EDLFWAIRGG | GGASFGIVVS | WKIKLVPVPS | TVTVFNVERI | LEEN---ATE | 265 |
| SEQ_ID_NO_569 | EDLFWAIRGG | GAASFGVVLS | YKIKLVPVPE | TVTVFRIERL | LTEN---ATD | 268 |
| SEQ_ID_NO_575 | EDLFWAIRGG | GGASFGVILS | YTVKLVPVPE | NVTVFQIDKT | LEEN---ATD | 272 |
| SEQ_ID_NO_576 | EDLFWAIRGG | GGASFGILSL | AKLQLVPVTP | QVVFDVKRN | VSEG---ATD | 283 |
| SEQ_ID_NO_578 | EDLFWAITGG | GGVSFGVVLA | YKIKLVRVPE | VVTVFTIERR | EEQN---LST | 275 |
| SEQ_ID_NO_579 | EDLFWAITGG | GGVSFGVVVA | YKIKLVRVPT | TVTVFNVQRT | SEQN---LST | 274 |
| SEQ_ID_NO_558 | EDLFWALRGG | GAASFCVVLA | WKIKLVPVPA | KVTVFNIETF | GNTGSVNTTE | 274 |
| SEQ_ID_NO_571 | EDLFWAIRGG | GAASFGVILS | WKIKLVPVPE | IVTVFSVDRT | LEEG---VSD | 263 |

Figure 17 (continued)

| SEQ_ID_NO | | | | | | | |
|---|---|---|---|---|---|---|---|
| SEQ_ID_NO_559 | LLHKWQFVLA | EELEEDFTLS | VLGGADEK-- | -------QVW | LTMLGFHFGL | | 301 |
| SEQ_ID_NO_586 | MLHKWQVVLA | PALEDDFTLS | VLAGADTN-- | -------GLW | FSFLGLYLGP | | 298 |
| SEQ_ID_NO_591 | LLHKWQLVLA | PKLEDDFSLA | VLAGTNKDS- | -------SIW | LTFLGLYLGP | | 299 |
| SEQ_ID_NO_581 | LITKWQEMA | PASPQELYLR | VLVL------ | -------NQQ | ANFQALFLGR | | 312 |
| SEQ_ID_NO_588 | LITKWQELA | PALPRDLLLR | VVVQ------ | -------GRH | AQFEALFLGR | | 307 |
| SEQ_ID_NO_589 | LLTKWQSLA | PTFPEDLMR | VMAQ------ | -------ADK | AVFEGLYLGT | | 306 |
| SEQ_ID_NO_590 | LLTKWQSLA | PTFPEDLMR | VMAQ------ | -------ADK | AVFEGLYLGT | | 311 |
| SEQ_ID_NO_584 | INKWQVVA | PQLPADLMR | IAQ------- | -------GPK | ATFEAMYLGT | | 305 |
| SEQ_ID_NO_583 | LINKWQQVA | PSLPDDLMR | MAM------- | -------EQD | AMFEALYLGT | | 310 |
| SEQ_ID_NO_585 | LVTKWQTVA | PALPDDLMR | MAM------- | -------GQG | AMFEALYLGT | | 307 |
| SEQ_ID_NO_560 | LFNKWQNA | YKYDKDLMLT | THFRTRNITD | NHGKNKTTVH | GYFSSIFLGG | | 320 |
| SEQ_ID_NO_577 | IEKWQLVA | NKLDERFLR | NDLARANSS- | QHGKL--ALQ | ANFVAMFQGG | | 311 |
| SEQ_ID_NO_569 | ITFKWQTA | PTTDENLFMR | MLLQPVTRN- | --KKK--TAR | ISVIALYLGD | | 312 |
| SEQ_ID_NO_575 | LVWQWQKVA | PHTDDRLYLR | LVLQPVSSNF | VKGKK--TIR | ASVEALFLGE | | 319 |
| SEQ_ID_NO_576 | IVYKWQLA | PKLHKDLFLR | AQPNVVQIG- | QEGKK--VVQ | ISFIGQFLGK | | 309 |
| SEQ_ID_NO_578 | IAERWQVA | DKLDRDLFLR | MTFSVINDT- | NGG-K--TVR | AIFPTLYLGN | | 320 |
| SEQ_ID_NO_579 | AHRWQVA | DKLDNDLFLR | MTFNVINNT- | NGE-K--TIR | GLFPTLYLGN | | 319 |
| SEQ_ID_NO_558 | LVAKWQEA | DKIDNDLFR | LTLGSSNK-- | -------TVK | ASFMGMYLGN | | 314 |
| SEQ_ID_NO_571 | LAWKWQQAA | DKLDNDLFR | LMLQPVNGT- | QEGKK--TIQ | ASFVAMFLGR | | 310 |

| SEQ_ID_NO | | | | | | | |
|---|---|---|---|---|---|---|---|
| SEQ_ID_NO_559 | KTVAKSTFDL | LFPELGLVEE | DYLEMSWGES | FAYLAGLE-- | ------TVSQL | | 344 |
| SEQ_ID_NO_586 | KELAISSVDQ | NFPELNLVME | DCKEMSWVES | FAHLAGLN-- | ------SVEEM | | 341 |
| SEQ_ID_NO_591 | KELASSSMHK | KFPELNLLLE | DCMEMSWVEA | TAELAGLK-- | ------SVSEL | | 342 |
| SEQ_ID_NO_581 | CGGLHRLMQD | RFPELGMTEQ | DCEEVSWQS | TAFFGFSTTS | V----PPEDL | | 358 |
| SEQ_ID_NO_588 | CSRVLEHMRA | HFPELGVARA | DCEEISWIQS | TVYFAFYSSS | K----PPELL | | 353 |
| SEQ_ID_NO_589 | CDALLPLVTS | RFPELGVNRS | HCNEMSWYQS | IAFIHLGKNA | T----VKDI | | 351 |
| SEQ_ID_NO_590 | CDALLPLVTS | RFPELGVNRS | HCNEMSWYQS | IAFIHLGKNA | T----VKDI | | 356 |
| SEQ_ID_NO_584 | CKTLTPLMSG | KFPELGMNPD | HCNEMSWIQS | IPFVHLGHRD | A----LEDDL | | 351 |
| SEQ_ID_NO_583 | CKDLLPLMAS | RFPELGVKQE | DCNEMPWMQS | VAFIPMGKSA | T----VMDL | | 355 |
| SEQ_ID_NO_585 | CKDLVLLMTA | RFPELGMNAT | HCKEMTWIES | VPYIPMGPKG | T----VRDL | | 352 |
| SEQ_ID_NO_560 | VDSLVDLMNK | SFPELGIKKT | DCKELSWIDT | TIFYSGVVNY | NTANFKKEL | | 370 |
| SEQ_ID_NO_577 | VEELIPLMQK | NFPELGLKRK | DCTETSWIES | AVFTNGALIG | SSGHEAPEVL | | 361 |
| SEQ_ID_NO_569 | SDSLVSLLQK | DFPELSIGKS | NCNETTWIDS | VLWWANFNLG | T----PPTAL | | 358 |
| SEQ_ID_NO_575 | ADELVKLLGD | EFPLIGLKKE | LCHEMRWIDS | VVWWANYNDG | S----SVNAL | | 365 |
| SEQ_ID_NO_576 | IERLLTLMNK | EFPELGLNKS | DCFSMPMNS | TLFWYGEPIG | T----PLEVL | | 355 |
| SEQ_ID_NO_578 | SRNLVTLLNK | DFPELGLQES | DCTEMSWVES | VLYYTGFPSG | T----PTTAL | | 366 |
| SEQ_ID_NO_579 | STALVALLNK | DFPELGVEIS | DCIEMSWIES | VLFYTNFPIG | T----PTTAL | | 365 |
| SEQ_ID_NO_558 | SSNLLEIMNA | KFPELGLIKR | ECIEMKWIES | VLFWLGIPPG | TA---PTTSM | | 361 |
| SEQ_ID_NO_571 | AERLLSVMNE | SFPELGLQAK | DCAEMPWIES | VLSWGMPKG | T----PLEVL | | 356 |

| SEQ_ID_NO | | | | | | |
|---|---|---|---|---|---|---|
| SEQ_ID_NO_559 | EFMKPFVSKN | PRLGYVNHID | LDLGGIDW-- | -GNKTVVNN- | AIEISRS-WG | 486 |
| SEQ_ID_NO_586 | NYMGQFLPSD | PRIAYVNHVD | LDLGRLDW-- | -TNSTIASN- | AIEIART-WG | 483 |
| SEQ_ID_NO_591 | DYMGKFVSNN | PRVGYVNHVD | LDLGRIDW-- | -VNKTISSGR | AIELART-WG | 485 |
| SEQ_ID_NO_581 | KEMEPYVSKN | PRAVYVNYRD | LDLGTNELD- | -GDVT----- | SYEKARVSWG | 498 |
| SEQ_ID_NO_588 | REMEPYVSKN | PRTGYVNYRD | LDLGTNELE- | -GNVT----- | SYAKARI-WG | 491 |
| SEQ_ID_NO_589 | AFMEPYVTKN | PRQAYVNYRD | LDLGVNAVEA | GANVS----- | CYQVGKV-WG | 491 |
| SEQ_ID_NO_590 | AFMEPYVTKN | PRQAYVNYRD | LDLGVNAVEA | GANVS----- | CYQVGKV-WG | 496 |
| SEQ_ID_NO_584 | NYMEPYVSKN | PRQAYANYRD | IDLGRNEVV- | -NDVS----- | TYASGKV-WG | 488 |
| SEQ_ID_NO_583 | AFMEPYVSKN | PRQAYANYRD | LDLGVNEVV- | -GDVS----- | TYDSGRV-WG | 491 |
| SEQ_ID_NO_585 | DFMTPYVSKN | PRQAYVNYRD | LDLGVNQVV- | -GNVS----- | TYASGKV-WG | 488 |
| SEQ_ID_NO_560 | NFTTPYVSQN | PRLAYLNYRD | LDLGKTNP-- | -ESPN----- | NYTQARI-WG | 507 |
| SEQ_ID_NO_577 | KYMEPYVSNS | PRAAYVNYRD | LDIGVNN--- | -NGYT----- | SYHQAS--WG | 499 |
| SEQ_ID_NO_569 | DFMTPFVSKN | PRSAYFNYRD | DVG--S--- | -TKKW----- | SYEEGKV-YG | 492 |
| SEQ_ID_NO_575 | NYMTPFVSKN | PRSAYFNYRD | LDIGINS--- | -HGKD----- | NFEDGKV-YG | 501 |
| SEQ_ID_NO_576 | EFMTPYVSTS | PREAFLNYRD | ADIGANHP-- | -SNVT----- | RFDIAKT-YG | 493 |
| SEQ_ID_NO_578 | DYMTPFVSKN | PREAFLNYRD | LDIGINS--- | -HGRN----- | AYTEGMV-YG | 502 |
| SEQ_ID_NO_579 | DYMTPFVSKN | PREAFLNYRD | LDIGVNS--- | -HGKN----- | AYGEGMV-YG | 501 |
| SEQ_ID_NO_558 | EAMSPYVSKN | PREAFLNYRD | VDIGK----- | -SLNS----- | TYEEGKV-YG | 495 |
| SEQ_ID_NO_571 | EAMTPYVSKN | PREAFLNYRD | DIGSIGS-- | -HGNG----- | TFQEASV-YG | 493 |

| SEQ_ID_NO | | | | | | |
|---|---|---|---|---|---|---|
| SEQ_ID_NO_559 | ESYFLS-NYE | RLIRAKTLID | PNNVFNHPQS | PPMANFDYL | EKTLGSDGGE | 535 |
| SEQ_ID_NO_586 | EKYFLS-NYE | RLVRAKTLID | PKNVFHHPQS | PPMPQDDLR | PNGIWRTEEM | 532 |
| SEQ_ID_NO_591 | EKYFMS-NYD | RLVRAKTMID | PKNVFNHPQS | PPLLEIMLD | NVKENDVIYK | 534 |
| SEQ_ID_NO_581 | DKYFKG-NFK | RLAAVKTMVD | PHDFFRNEQS | PPLPTAKMM | IDSI------ | 541 |
| SEQ_ID_NO_588 | EKYFRG-NFE | RLAAVKAMVD | PDDFFRNEQS | PPLPAAKGW | SSI------- | 533 |
| SEQ_ID_NO_589 | EKYFKG-NFE | RLARTKAKVD | PTDFFRNEQS | PPLLA---- | ---------- | 526 |
| SEQ_ID_NO_590 | EKYFKG-NFE | RLARTKAKVD | PTDFFRNEQS | PPLLA---- | ---------- | 531 |
| SEQ_ID_NO_584 | QKYFKG-NFE | RLAITKGKVD | PTDYFRNEQS | PPLIKKY-- | ---------- | 525 |
| SEQ_ID_NO_583 | EKYYNG-NFE | RLARTKAKVD | PCDYFRNEQS | PPLLK---- | ---------- | 526 |
| SEQ_ID_NO_585 | EKYFKG-NFE | RLARTKGKID | PEDYFRNEQS | PPLL----- | ---------- | 522 |
| SEQ_ID_NO_560 | EKYFGK-NFN | RLVKVKTKAD | PNNFFRNEQS | PPLPPHHH- | ---------- | 545 |
| SEQ_ID_NO_577 | LKYFSN-NFK | RLATVKTKVD | PHNFFRNEQS | PTLSKE--- | ---------- | 535 |
| SEQ_ID_NO_569 | ESYFNG-NYE | RLVDVKTAVD | ANNFFRNEQS | PPRSSKI-- | ---------- | 529 |
| SEQ_ID_NO_575 | IKYFNK-NFE | RLVKVKSAID | PENFFMNEQS | PTYPRSNA- | ---------- | 539 |
| SEQ_ID_NO_576 | SKFFKG-NFE | RLVSVKTKVD | PQNFFRYEQS | PTRSL---- | ---------- | 528 |
| SEQ_ID_NO_578 | HKYFKETNYK | RLVSVKTKVD | PDNFFRNEQS | PTLSS---- | ---------- | 538 |
| SEQ_ID_NO_579 | HKYFKETNYK | RLTMVKTRVD | PSNFFRNEQS | PTLSSSWK- | ---------- | 540 |
| SEQ_ID_NO_558 | FKYFKD-NFE | KLVKIKSRVD | PDNFFRYEQS | PVLSSH--- | ---------- | 531 |
| SEQ_ID_NO_571 | HKYFKD-NFD | RLVQIKTRVD | PDNFFGYEQS | PTQSSSYRP | DLCAWQQPRK | 542 |

Figure 17 (continued)

| SEQ_ID_NO_559 | VVI- - - - - - - - - - - - - - - - - - - - - - - - - - - - - - - - - - - - - - - - - - - - - - - - - - - - - - - - | 538 |
|---|---|---|
| SEQ_ID_NO_586 | FFLE- - - - - - - - - - - - - - - - - - - - - - - - - - - - - - - - - - - - - - - - - - - - - - - - - - - - - - | 536 |
| SEQ_ID_NO_591 | L- - - - - - - - - - - - - - - - - - - - - - - - - - - - - - - - - - - - - - - - - - - - - - - - - - - - - - - - - | 535 |
| SEQ_ID_NO_581 | - - - - - - - - - - - - - - - - - - - - - - - - - - - - - - - - - - - - - - - - - - - - - - - - - - - - - - - - - | 541 |
| SEQ_ID_NO_588 | - - - - - - - - - - - - - - - - - - - - - - - - - - - - - - - - - - - - - - - - - - - - - - - - - - - - - - - - - | 533 |
| SEQ_ID_NO_589 | - - - - - - - - - - - - - - - - - - - - - - - - - - - - - - - - - - - - - - - - - - - - - - - - - - - - - - - - - | 526 |
| SEQ_ID_NO_590 | - - - - - - - - - - - - - - - - - - - - - - - - - - - - - - - - - - - - - - - - - - - - - - - - - - - - - - - - - | 531 |
| SEQ_ID_NO_584 | - - - - - - - - - - - - - - - - - - - - - - - - - - - - - - - - - - - - - - - - - - - - - - - - - - - - - - - - - | 525 |
| SEQ_ID_NO_583 | - - - - - - - - - - - - - - - - - - - - - - - - - - - - - - - - - - - - - - - - - - - - - - - - - - - - - - - - - | 526 |
| SEQ_ID_NO_585 | - - - - - - - - - - - - - - - - - - - - - - - - - - - - - - - - - - - - - - - - - - - - - - - - - - - - - - - - - | 522 |
| SEQ_ID_NO_560 | - - - - - - - - - - - - - - - - - - - - - - - - - - - - - - - - - - - - - - - - - - - - - - - - - - - - - - - - - | 545 |
| SEQ_ID_NO_577 | - - - - - - - - - - - - - - - - - - - - - - - - - - - - - - - - - - - - - - - - - - - - - - - - - - - - - - - - - | 535 |
| SEQ_ID_NO_569 | - - - - - - - - - - - - - - - - - - - - - - - - - - - - - - - - - - - - - - - - - - - - - - - - - - - - - - - - - | 529 |
| SEQ_ID_NO_575 | - - - - - - - - - - - - - - - - - - - - - - - - - - - - - - - - - - - - - - - - - - - - - - - - - - - - - - - - - | 539 |
| SEQ_ID_NO_576 | - - - - - - - - - - - - - - - - - - - - - - - - - - - - - - - - - - - - - - - - - - - - - - - - - - - - - - - - - | 528 |
| SEQ_ID_NO_578 | - - - - - - - - - - - - - - - - - - - - - - - - - - - - - - - - - - - - - - - - - - - - - - - - - - - - - - - - - | 538 |
| SEQ_ID_NO_579 | - - - - - - - - - - - - - - - - - - - - - - - - - - - - - - - - - - - - - - - - - - - - - - - - - - - - - - - - - | 540 |
| SEQ_ID_NO_558 | - - - - - - - - - - - - - - - - - - - - - - - - - - - - - - - - - - - - - - - - - - - - - - - - - - - - - - - - - | 531 |
| SEQ_ID_NO_571 | RTLGARTSER AWQQHQAADT WRRAVMPYGL GKLARLAKHP KRRFTGPPAW | 592 |

| SEQ_ID_NO_559 | - - - - - - - - - - - - - - - - - - - - - - - - - - - - - - - - - - - - - - - - - - - - - - - - - - - - - - - - - | 538 |
|---|---|---|
| SEQ_ID_NO_586 | - - - - - - - - - - - - - - - - - - - - - - - - - - - - - - - - - - - - - - - - - - - - - - - - - - - - - - - - - | 536 |
| SEQ_ID_NO_591 | - - - - - - - - - - - - - - - - - - - - - - - - - - - - - - - - - - - - - - - - - - - - - - - - - - - - - - - - - | 535 |
| SEQ_ID_NO_581 | - - - - - - - - - - - - - - - - - - - - - - - - - - - - - - - - - - - - - - - - - - - - - - - - - - - - - - - - - | 541 |
| SEQ_ID_NO_588 | - - - - - - - - - - - - - - - - - - - - - - - - - - - - - - - - - - - - - - - - - - - - - - - - - - - - - - - - - | 533 |
| SEQ_ID_NO_589 | - - - - - - - - - - - - - - - - - - - - - - - - - - - - - - - - - - - - - - - - - - - - - - - - - - - - - - - - - | 526 |
| SEQ_ID_NO_590 | - - - - - - - - - - - - - - - - - - - - - - - - - - - - - - - - - - - - - - - - - - - - - - - - - - - - - - - - - | 531 |
| SEQ_ID_NO_584 | - - - - - - - - - - - - - - - - - - - - - - - - - - - - - - - - - - - - - - - - - - - - - - - - - - - - - - - - - | 525 |
| SEQ_ID_NO_583 | - - - - - - - - - - - - - - - - - - - - - - - - - - - - - - - - - - - - - - - - - - - - - - - - - - - - - - - - - | 526 |
| SEQ_ID_NO_585 | - - - - - - - - - - - - - - - - - - - - - - - - - - - - - - - - - - - - - - - - - - - - - - - - - - - - - - - - - | 522 |
| SEQ_ID_NO_560 | - - - - - - - - - - - - - - - - - - - - - - - - - - - - - - - - - - - - - - - - - - - - - - - - - - - - - - - - - | 545 |
| SEQ_ID_NO_577 | - - - - - - - - - - - - - - - - - - - - - - - - - - - - - - - - - - - - - - - - - - - - - - - - - - - - - - - - - | 535 |
| SEQ_ID_NO_569 | - - - - - - - - - - - - - - - - - - - - - - - - - - - - - - - - - - - - - - - - - - - - - - - - - - - - - - - - - | 529 |
| SEQ_ID_NO_575 | - - - - - - - - - - - - - - - - - - - - - - - - - - - - - - - - - - - - - - - - - - - - - - - - - - - - - - - - - | 539 |
| SEQ_ID_NO_576 | - - - - - - - - - - - - - - - - - - - - - - - - - - - - - - - - - - - - - - - - - - - - - - - - - - - - - - - - - | 528 |
| SEQ_ID_NO_578 | - - - - - - - - - - - - - - - - - - - - - - - - - - - - - - - - - - - - - - - - - - - - - - - - - - - - - - - - - | 538 |
| SEQ_ID_NO_579 | - - - - - - - - - - - - - - - - - - - - - - - - - - - - - - - - - - - - - - - - - - - - - - - - - - - - - - - - - | 540 |
| SEQ_ID_NO_558 | - - - - - - - - - - - - - - - - - - - - - - - - - - - - - - - - - - - - - - - - - - - - - - - - - - - - - - - - - | 531 |
| SEQ_ID_NO_571 | VCRHVLWQT PTSGSAATRA WGMCPALLTL QTWALGADSH ARVNCDPHLS | 642 |

Figure 17 (continued)

| | | |
|---|---|---|
| SEQ_ID_NO_559 | .......... .......... .......... .......... .......... | 538 |
| SEQ_ID_NO_586 | .......... .......... .......... .......... .......... | 536 |
| SEQ_ID_NO_591 | .......... .......... .......... .......... .......... | 535 |
| SEQ_ID_NO_581 | .......... .......... .......... .......... .......... | 541 |
| SEQ_ID_NO_588 | .......... .......... .......... .......... .......... | 533 |
| SEQ_ID_NO_589 | .......... .......... .......... .......... .......... | 526 |
| SEQ_ID_NO_590 | .......... .......... .......... .......... .......... | 531 |
| SEQ_ID_NO_584 | .......... .......... .......... .......... .......... | 525 |
| SEQ_ID_NO_583 | .......... .......... .......... .......... .......... | 526 |
| SEQ_ID_NO_585 | .......... .......... .......... .......... .......... | 522 |
| SEQ_ID_NO_560 | .......... .......... .......... .......... .......... | 545 |
| SEQ_ID_NO_577 | .......... .......... .......... .......... .......... | 535 |
| SEQ_ID_NO_569 | .......... .......... .......... .......... .......... | 529 |
| SEQ_ID_NO_575 | .......... .......... .......... .......... .......... | 539 |
| SEQ_ID_NO_576 | .......... .......... .......... .......... .......... | 528 |
| SEQ_ID_NO_578 | .......... .......... .......... .......... .......... | 538 |
| SEQ_ID_NO_579 | .......... .......... .......... .......... .......... | 540 |
| SEQ_ID_NO_558 | .......... .......... .......... .......... .......... | 531 |
| SEQ_ID_NO_571 | RTQEEYIKLG PAQQDPFKLG SALEGPKIAR LDPLALALVA LMGPVLSKTH | 692 |

| | | |
|---|---|---|
| SEQ_ID_NO_559 | .......... . | 538 |
| SEQ_ID_NO_586 | .......... . | 536 |
| SEQ_ID_NO_591 | .......... . | 535 |
| SEQ_ID_NO_581 | .......... . | 541 |
| SEQ_ID_NO_588 | .......... . | 533 |
| SEQ_ID_NO_589 | .......... . | 526 |
| SEQ_ID_NO_590 | .......... . | 531 |
| SEQ_ID_NO_584 | .......... . | 525 |
| SEQ_ID_NO_583 | .......... . | 526 |
| SEQ_ID_NO_585 | .......... . | 522 |
| SEQ_ID_NO_560 | .......... . | 545 |
| SEQ_ID_NO_577 | .......... . | 535 |
| SEQ_ID_NO_569 | .......... . | 529 |
| SEQ_ID_NO_575 | .......... . | 539 |
| SEQ_ID_NO_576 | .......... . | 528 |
| SEQ_ID_NO_578 | .......... . | 538 |
| SEQ_ID_NO_579 | .......... . | 540 |
| SEQ_ID_NO_558 | .......... . | 531 |
| SEQ_ID_NO_571 | QRSLKKKISL M | 703 |

Figure 18

| | | | | | | | |
|---|---|---|---|---|---|---|---|
| SEQ_ID_NO_603 | MAAAT--SSS | AMAVSTPQGV | AERRGIPAAS | FVEDVETYLR | QAGLEVNSAL | 48 |
| SEQ_ID_NO_605 | MAAAA------ | --SASTPQGV | AERRGIPAAA | FVEDVEAYLR | QAGLDVNSAL | 43 |
| SEQ_ID_NO_610 | MAAAAASSSS | SSAAATPQGV | TERRGIPAAS | FVEDVETYLR | QAGLDVNSGL | 50 |
| SEQ_ID_NO_593 | MSSSS------ | --PSGSGSDL | TERRGIPAAK | FIQDVETYLS | QSGLDPNSAL | 43 |
| SEQ_ID_NO_595 | MASSS----S | TAVATATETT | TERRGIPGAQ | FVEDVETYLN | QSGLDVNSAL | 46 |
| SEQ_ID_NO_599 | MASSS------ | -----SESAM | SERRGIPGAQ | FVEDVQTYLT | QSGLDVGSAL | 40 |

| | | | | | | | |
|---|---|---|---|---|---|---|---|
| SEQ_ID_NO_603 | AFLQERLQQY | KMVEMKLLAQ | QRELQAKIPD | EKCLDIVAT | LKAKKALGEA | 98 |
| SEQ_ID_NO_605 | AFLQERLQQY | KIVEMKLLAQ | QRDLQAKIPD | EKCLDIVST | LQAKKDLGEA | 93 |
| SEQ_ID_NO_610 | AFLQERLQQY | KIVEMKLLAQ | QRDLQAKIPD | EKCLDIVAT | LQAKKALGEA | 100 |
| SEQ_ID_NO_593 | AFHQERLQQY | KVVEMKLLAQ | QRDLQAKIPD | IEKCLEVVAT | LEAKKGTGEA | 93 |
| SEQ_ID_NO_595 | SFLQERLQQY | KLVEMKLLAQ | QRDLQAKIPD | EKCLDVVAT | LQAKKGTGEP | 96 |
| SEQ_ID_NO_599 | AFLQERLQQY | KVVEMKLLAQ | QRDLQAKIPD | EKCLDVVAT | LKAKKGTGEE | 90 |

| | | | | | | | |
|---|---|---|---|---|---|---|---|
| SEQ_ID_NO_603 | LIADFELSEG | YSRAKIEDS | DSVCLWLGAN | VMLEYSCDEA | NELLKSNLEN | 148 |
| SEQ_ID_NO_605 | LIADFELSEG | YSCAKIEDT | DSVCLWLGAN | VMLEYSCDEA | NALLKKNLEN | 143 |
| SEQ_ID_NO_610 | LTADFELSEG | YSRAKIEDT | DSVCLWLGAN | VMLEYSCDEA | NALLKKNLEN | 150 |
| SEQ_ID_NO_593 | LLADFEVSEG | YSRACIEDT | DSVCLWLGAN | VMLEYSCEEA | SALLKNNLEN | 143 |
| SEQ_ID_NO_595 | LIADFEVSEG | YSQARIEDA | ESVCLWLGAN | VMLEYSCEEA | NDLLQKNLDN | 146 |
| SEQ_ID_NO_599 | LIADFEVSEG | YSRARIEET | NSVCLWLGAN | VMLEYSLEEA | TGLLQKNLDN | 140 |

| | | | | | | | |
|---|---|---|---|---|---|---|---|
| SEQ_ID_NO_603 | ARASLEVLVG | DLHFLRDQQT | ITQVTIARIF | NWDVHQ-RRS | KQ----SVM | 192 |
| SEQ_ID_NO_605 | AKASLEVLVA | DLQFLRDQQT | ITQVTIARVF | NWDVHH-RRS | KQ-----AV | 186 |
| SEQ_ID_NO_610 | AKASLEVLVA | DLQFLRDQQT | ITQVTIARVF | NWDVHQ-RRS | KQ-----AI | 193 |
| SEQ_ID_NO_593 | AKASLEVLVA | DLQFLRDQVT | VTQVTIARVY | NWDVHQ-RRV | KQVTPTAIAV | 192 |
| SEQ_ID_NO_595 | AKASLEVLVA | DLLFLRDQVT | ITQVTIARVY | NWDVHQKRRM | RE---AVTAE | 193 |
| SEQ_ID_NO_599 | ARASLEVLIA | DLQFLRDQVT | ITQVTIARVY | NWDVHQ-RRV | QQ---AVATT | 186 |

| | | |
|---|---|---|
| SEQ_ID_NO_603 | KET | 195 |
| SEQ_ID_NO_605 | KEP | 189 |
| SEQ_ID_NO_610 | KET | 196 |
| SEQ_ID_NO_593 | ADS | 195 |
| SEQ_ID_NO_595 | KDS | 196 |
| SEQ_ID_NO_599 | AQD | 189 |

Figure 19

```
SEQ_ID_NO_622    ----MAFSNA LRSAAKLVAS SESSLSNSVS RGFHSTGMKR M-GGHGHDE   45
SEQ_ID_NO_613    ----MALSTS IRSVSKIISS SEASVSRSVT RSFHSTGVKK MSGGGHGGYD  46
SEQ_ID_NO_620    ----MALNTG IRSISKIIAF SEASVSRSVS RSFHSTGAKK M-SGGHGHDE  45
SEQ_ID_NO_626    ----MALNTG IRSVSRLIAS SESSVSRSVS RSFHSTGAKK M-SGGHGHDE  45
SEQ_ID_NO_643    ----MAAAAA --------AA GEEE--GEAS RGFHATGVKR M--GGHGHDE  34
SEQ_ID_NO_644    MATATALNRG LRSGIRLLAT GAEAISKTDS RGFHATGVKR M--GGHGHDE  47
SEQ_ID_NO_624    --MATALNRG LRSGIRLLAT GAEAISKPAS RGFHATGVKR M--SGHGHDE  45
SEQ_ID_NO_638    --MATALNRG LRSGIRLLAA GAEAISKPAS RGFHATGVKR M--GGHGHDE  45
SEQ_ID_NO_634    ----MALSRG IRSGLKLLSH SEAALPRSVT HEFHATSMKR M--GGHGHDE  44
SEQ_ID_NO_615    ----MAMIRG ISSGIKLLTS SEAALFRSVT REFHATGMKR M--GGHGHDE  44

SEQ_ID_NO_622    PYYLHAKHMY NLDRMKHQGL KMSLAVFTAF SIGVAVPVYA VIFQQKKTAS  95
SEQ_ID_NO_613    EYYLHAKHMY NLDRMKYQAL KMSLGVFTAF SIGVGVPIFA VVFQQRKTQS  96
SEQ_ID_NO_620    PYYLHAKHMY NLDRMKYQGL KMSLGVFTAF SIGVGVPIFA VVFQQRKTAS  95
SEQ_ID_NO_626    PYYLHAKHMY NLDRMKFQGL KMSLAVFTAF SIGVGVPIFA VVFQQRKTAS  95
SEQ_ID_NO_643    PYYLHAKHMY NLHRMKHQKP KVYLSVLGAV GIGIAVPVYA VVFQQKKTAS  84
SEQ_ID_NO_644    PYYLHAKHMY NLHRMKHQKP KVYLSVLGAV GIGIAVPVYA VVFQQKKTAS  97
SEQ_ID_NO_624    PYYLHAKHMY NLHRMKHQKL TAWTSYLGAV SIGIGVPVFA VVFQQKKTSS  95
SEQ_ID_NO_638    PYYLHAKHMY NLHRMKHQGL KVTLSVLGAV SIGVGVPVYA VIFQQKKTAS  95
SEQ_ID_NO_634    PFYIHAKHMY NLDRMKHQKL KVTLGVLSAF SIGVVVPIYA VIFQQKKAAS  94
SEQ_ID_NO_615    PYYLHAKHMY NLDQMKHQKL KVALSVWSAF GIGMAVPVYA VMFQQKKAAS  94

SEQ_ID_NO_622    S  96
SEQ_ID_NO_613    G  97
SEQ_ID_NO_620    G  96
SEQ_ID_NO_626    G  96
SEQ_ID_NO_643    G  85
SEQ_ID_NO_644    G  98
SEQ_ID_NO_624    G  96
SEQ_ID_NO_638    G  96
SEQ_ID_NO_634    G  95
SEQ_ID_NO_615    A  95
```

Figure 20

| | | | | | | | |
|---|---|---|---|---|---|---|---|
| SEQ_ID_NO_685 | MGFISFVGRV | LFASLFLLSA | YQEFLEFGND | GGPAAKTLKP | KFNLFVKLVS | 50 |
| SEQ_ID_NO_679 | MGFVSFAGRV | LFASVFLLSA | YQEFSEFGAD | GGPAAKALRP | KYNVFTKNIS | 50 |
| SEQ_ID_NO_681 | MGFVSFAGRV | LFASVFLLSA | YQEFSEFGAD | GGPAAKALRP | KYNVFTKNIS | 50 |
| SEQ_ID_NO_668 | MGFVSFVGRV | LFVAAFLLSA | YQEFNEFGAD | GGPAAKALRP | KFNVFVKNVS | 50 |
| SEQ_ID_NO_676 | MGFVSFVGRV | LFVAAFLLSA | YQEFNEFGTD | GGPAAKALQP | KFNVFVKNIS | 50 |
| SEQ_ID_NO_646 | MELASFLGRA | LFVSVFLLSA | WQEFNDFGED | GGRSAKSLKP | KFNAFVNHVT | 50 |
| SEQ_ID_NO_648 | MALVSFVGRV | LFASVFILSA | WQEFNEFGVD | GGPAAKALKP | KFNVFSKTVT | 50 |
| SEQ_ID_NO_656 | MAFTSFLGRV | LFASVFILSA | YQEFNEFGVD | GGPAAKALKP | KFGVFTSHVD | 50 |
| SEQ_ID_NO_660 | MAFASFLGRV | LFASVFILSA | YQEFNEFGVD | GGPAAKALRP | KFDAFTHRVH | 50 |

| | | | | | | | |
|---|---|---|---|---|---|---|---|
| SEQ_ID_NO_685 | KNTGLGVPHI | DIKTVIAATM | FLKGFGGLLF | ESSSFGAFL | LLIYLAFMTP | 100 |
| SEQ_ID_NO_679 | AHLGVAVPHV | ELKHIVAATI | GLKGLGGLLF | LSSSFGAYL | LLIYLAFITP | 100 |
| SEQ_ID_NO_681 | AHLGVAVPHV | ELKHIVAATI | GLKGLGGLLF | LSSSFGAYL | LLIYLAFITP | 100 |
| SEQ_ID_NO_668 | AHLGVAVPHI | ELKHVIAATI | GLKGLGSLLF | LSSSLGAYL | LLLYLALITP | 100 |
| SEQ_ID_NO_676 | SHLGVAVPHI | ELKHVIAATI | ALKGLGGLLF | LSCSLGAYL | LLLYLAIVTP | 100 |
| SEQ_ID_NO_646 | THTGQQLPPV | DMKILVAAAI | ALKGIGGLLF | VFGSSLGAYL | LLHQAVATP | 100 |
| SEQ_ID_NO_648 | AHTGVEVPEF | DIKVLVAAAV | AFKGVGGILF | FGSTIGAYL | LAQOVVTT | 100 |
| SEQ_ID_NO_656 | SHAGIOVPEI | EIKHLVSAAI | FLKGIGGILF | IGSSLGAYL | LIHQLAIP | 100 |
| SEQ_ID_NO_660 | SQVGFQLPEL | DLKFLIAGAI | ALKGLGGVLF | FGSSFGALL | LLHQLATP | 100 |

| | | | | | | | |
|---|---|---|---|---|---|---|---|
| SEQ_ID_NO_685 | IVYDFYNYEM | ESEQFVQLFF | KFTQNLAFIG | ALLFFLGMKN | SIPRRRSK | 148 |
| SEQ_ID_NO_679 | VVYDFYNYNM | EKSEFVQLFM | KFTQNLALFG | ALLFFLGMKN | SIPKRQAK | 148 |
| SEQ_ID_NO_681 | VVYDFYNYDM | EKSEFVQLFM | KFTQNLALFG | ALLFFLGMKN | SIPKRQAK | 148 |
| SEQ_ID_NO_668 | IIHDFYNYDM | EKAEFAGLFA | KFTQDLALIG | ALLFFLGMKN | SIPKROGGK | 149 |
| SEQ_ID_NO_676 | IVHDFYNYDM | EKAEFAQIFG | KFTQDLALIG | ALLFFLGMKN | SIPKRQSK | 148 |
| SEQ_ID_NO_646 | ILYDFYNYDV | DRKEFGQLFS | KFTQSLALLG | GLFFIGMKN | SRKHGRQLR | 149 |
| SEQ_ID_NO_648 | ILYDFYNYDI | EKKEFGLLFS | KFSQNLALLG | ALFFIGMKN | SIPS-RQLK | 148 |
| SEQ_ID_NO_656 | ILYDFYNYDS | EEKEFNQLFI | KFTQNMALYG | ALFFIGMKN | SFPRRQHK | 148 |
| SEQ_ID_NO_660 | IHYDFYNYDS | EDKEFTQLFI | KFTQNMALFG | ALLFFIGMKN | SIPRR-VP | 147 |

| | | |
|---|---|---|
| SEQ_ID_NO_685 | GRTTKTKTN | 157 |
| SEQ_ID_NO_679 | KKAPKSKTN | 157 |
| SEQ_ID_NO_681 | KKAPKSKTN | 157 |
| SEQ_ID_NO_668 | KKAPKAKTN | 158 |
| SEQ_ID_NO_676 | KKAPKAKTN | 157 |
| SEQ_ID_NO_646 | KKAPKAKAN | 158 |
| SEQ_ID_NO_648 | KKAPKTKTV | 157 |
| SEQ_ID_NO_656 | KKVPKTKTG | 157 |
| SEQ_ID_NO_660 | KKAPKTKTY | 156 |

| | | | |
|---|---|---|---|
| SEQ_ID_NO_708 | KSRSREAYEV | VRGAITVDEF | 170 |
| SEQ_ID_NO_728 | KTRSREAYQV | LRDGVLVDKF | 170 |
| SEQ_ID_NO_718 | KTRSRDAYQV | LRAGITVDKF | 170 |
| SEQ_ID_NO_687 | KSRSRDAYEV | QRNGLRVDKF | 170 |
| SEQ_ID_NO_699 | KSRNRDAYEV | LRDGVRADKF | 170 |
| SEQ_ID_NO_689 | ---------- | ---------- | 107 |
| SEQ_ID_NO_691 | KTRDRGAYEV | LRDGVGIDKF | 170 |
| SEQ_ID_NO_703 | KTRSREAYEV | TRXGVCIDKF | 170 |
| SEQ_ID_NO_706 | KTRSREAYDV | TRDGVPVDKF | 170 |
| SEQ_ID_NO_721 | KARNRDAYEV | VRDGVGIDKF | 170 |
| SEQ_ID_NO_712 | KTRSRDAYEV | VRDGIIDKF | 170 |
| SEQ_ID_NO_724 | KTRSRDAYEV | VRDGIPDKF | 170 |

Figure 22

| | | | | | | | |
|---|---|---|---|---|---|---|---|
| SEQ_ID_NO_737 | ··MDEL GGGG | G-···KKGKA | WPWWL GASAA | QI TGAL VWFR | RGKGG SDMTM | | 44 |
| SEQ_ID_NO_738 | ···MEE GGGG | E·····EAER | WPWWA GASAA | QVAAG VAWFR | RGRGG AAFAM | | 42 |
| SEQ_ID_NO_742 | ··MDDR GGGG | G-···GEAER | WPWWA AASAA | QAAAG VAWFR | RGRGG TAVAM | | 44 |
| SEQ_ID_NO_735 | MKMEE AAGSG | N-···SDGGN | KWWWG VASAA | QMGL GI RTFA | KGHGG DSRLM | | 46 |
| SEQ_ID_NO_730 | MEEQNA GTGA | GESSLL DGSG | HWWWAL GSGA | QI MWGI RLIR | RGYAGD VRLM | | 50 |
| SEQ_ID_NO_732 | ···MENGCGG | G-···IETQW | WWWWAMASMA | KFGWGI SAYK | RGFAGD SRLM | | 43 |
| | | | | | | | |
| SEQ_ID_NO_737 | PFRAFAVASL | FVGAGAT TVT | AGVS AAGVGS | VEEMKGL GAR | RKWSR VPPR | | 94 |
| SEQ_ID_NO_738 | PFKAFAI ATL | FVGAGATAVT | AGVL AAGVGS | VDEMKGV GAS | RRWMGA PPR | | 92 |
| SEQ_ID_NO_742 | PFKAFAI ASL | FVGAGATAVS | AGVL AAGVGS | VEEMKGV GAS | RRWMGA PPR | | 94 |
| SEQ_ID_NO_735 | PFKAF VVASL | FVSS AASASV | LLL QANGI HR | VEDL MKAGAN | RAKL GL RPR | | 96 |
| SEQ_ID_NO_730 | PL KAF GVASL | FVGSL ATSSV | AL VRAT GI HT | VQDAI DL GAN | RTNL GV TPQ | | 100 |
| SEQ_ID_NO_732 | PL KAFAVASL | FVGSA ASASI | ASL QASGI HK | VQDLI ELGAN | RTGL GVPPR | | 93 |
| | | | | | | | |
| SEQ_ID_NO_737 | RVE GGE-··· | · | 100 | | | | |
| SEQ_ID_NO_738 | RRVE GGGDP· | · | 101 | | | | |
| SEQ_ID_NO_742 | RAGGSD-··· | · | 100 | | | | |
| SEQ_ID_NO_735 | TQNKNMDDS· | · | 105 | | | | |
| SEQ_ID_NO_730 | I PDKQI TERD | G | 111 | | | | |
| SEQ_ID_NO_732 | VAKE-····· | · | 97 | | | | |

Figure 23

| | | | | | | | |
|---|---|---|---|---|---|---|---|
| SEQ_ID_NO_765 | | MSPMSNPSFD | HSY---E--L | PLRRNLLLL | DLLGRLRFIA | EVLLDRLGVA | 45 |
| SEQ_ID_NO_763 | | MMLSSAYSTP | AADELGGPPP | LPPPPGADVS | VIVGALTGVL | LGLFLFL--- | 47 |
| SEQ_ID_NO_758 | | ------MGFP | VGY--PE--V | SVPNIFLYTL | SLLSFLRSLT | ISFLSLLHLS | 40 |
| SEQ_ID_NO_761 | | ------MGFP | VGY--SE--L | LLPRLLLQVL | LLLGHLHRFL | LMAFHAVGLG | 40 |
| SEQ_ID_NO_762 | | ------MGFP | VGY--SE--L | LLPRLLLQVL | LLLGHLHRFL | LMAFHAVGLG | 40 |
| SEQ_ID_NO_755 | | ------MGFY | AEDPLSG--L | TIGDAIYEVA | LMIAVLRWVL | CLIFRVI--- | 39 |
| SEQ_ID_NO_748 | | ------MGFF | VEE--SG--L | VTHLLYKAA  | LVLAVLRWAL | AMALRFK--- | 37 |
| SEQ_ID_NO_746 | | ------MTFF | IED--TS--L | ISHVLYKTA  | LIITVLRWIF | AMILRYR--- | 37 |
| SEQ_ID_NO_751 | | ------MTFF | IED--TS--L | ISHVLYKTA  | LIITVLRWIF | AMILRYR--- | 37 |
| SEQ_ID_NO_753 | | ------MSFF | IQD--SG--L | VTQLLYQMA  | VFITLLRWIF | SMILRYR--- | 37 |
| SEQ_ID_NO_760 | | ------MSFF | LED--SG--L | VTQLLYQMA  | VLITLLRWIF | TMILRYR--- | 37 |

| | | | | | | | |
|---|---|---|---|---|---|---|---|
| SEQ_ID_NO_765 | | SW-----QG  | EVHLPGQLWG | WGGEHASDAT | LEHFLEARLW | ETGTRSPLTT | 89 |
| SEQ_ID_NO_763 | | ---------- | --IYAKHCRQ | RGRGGARGAA | GGLGLGFRAS | STCDRCRSGV | 85 |
| SEQ_ID_NO_758 | | DL-------- | ---------- | ---------L | DTDFSTTLP  | DSHIHRPTLS | 63 |
| SEQ_ID_NO_761 | | DLIDNPPGLA | ATEQDMMLQG | RGGGMAEGWA | SSSALQHRRP | EFRAIPPM-  | 88 |
| SEQ_ID_NO_762 | | DLIDNPPGLA | ATEQDLMLQG | RGGGMAEGWA | SSSALQHRRP | EFRAIPPM-  | 88 |
| SEQ_ID_NO_755 | | ---------- | ---------- | ---------- | NDRRTTQSDE | TPTPEPCSQM | 59 |
| SEQ_ID_NO_748 | | ---------- | ---------- | ---------N | RTHLASPSND | SLRRSHPVPS | 58 |
| SEQ_ID_NO_746 | | ---------- | ---------- | ---------- | SRSSSSSBS  | SQSSSSPSIS | 57 |
| SEQ_ID_NO_751 | | ---------- | ---------- | ---------- | --SRSSSSSS | SQSSSSPSIS | 55 |
| SEQ_ID_NO_753 | | ---------- | ---------- | ---------- | ------SKS  | RTSSKPPV-S | 49 |
| SEQ_ID_NO_760 | | ---------- | ---------- | ---------- | ----SRSTSS | SSSSTPPI-S | 52 |

| | | | | | | | |
|---|---|---|---|---|---|---|---|
| SEQ_ID_NO_765 | | TRYRRRRVAL | AQPADGKLAA | EGDAEGAA-- | AVCAICVAGL | ESGDLEIVVE | 137 |
| SEQ_ID_NO_763 | | SLSVVDALPV | VRFGD---MG | GAAAAAQP-- | -ECAVCLGTF | DPAADELLRV | 129 |
| SEQ_ID_NO_758 | | AILRQFLPI  | ITFND---LA | EGDSSPPV-- | -GCAVCLNEF | --AGEEEIRC | 105 |
| SEQ_ID_NO_761 | | --AIEEALPV | VRFDE---LV | ASAPAAVCGG | GDCAVCLSGI | --CGRDEVRR | 131 |
| SEQ_ID_NO_762 | | --AIEEALPV | VRFDE---LV | ASAPAAVCGG | GDCAVCLSGI | --CGRDEVRR | 131 |
| SEQ_ID_NO_755 | | TRDKDSILLL | TTFGE---IK | ERLPETE--- | ETCAVCLSQL | --SVEDEVRE | 101 |
| SEQ_ID_NO_748 | | SQQIRDGLIL | TTFGD---VT | ERMPLGVC-- | DTCAVCLSQL | --RDQDEVRE | 100 |
| SEQ_ID_NO_746 | | SQTIKESLAV | FAFRD---AV | ERSPAAIN-- | DMCAVCLGDL | --EDEDEIRE | 100 |
| SEQ_ID_NO_751 | | SQTIKESLAV | SAFRD---AV | ERSPAAIN-- | DMCAVCLGDL | --EDEDEIRE | 98 |
| SEQ_ID_NO_753 | | SQAIKESLSV | TTFHD---AL | ERKPELIS-- | DTCAVCLGDL | --EDGDEVRE | 92 |
| SEQ_ID_NO_760 | | SQTIKESLAV | TTFRD---AA | DRSPELIS-- | DTCAVCLGDL | --EDGDEVRE | 95 |

Figure 23 (continued)

| | | | | | | |
|---|---|---|---|---|---|---|
| SEQ_ID_NO_765 | LCSCSHAFHD | ACIDAWRSG | D- - - - - - - - - | -DDAATCPLC | RAPCCPRRG- | 176 |
| SEQ_ID_NO_763 | LPKCRHAFHA | DCVDTMLEA- | - - - - - - - - - - | - - -HSTCPVC | RRRVGKEDA- | 164 |
| SEQ_ID_NO_758 | MANCRHMFHR | TCVDRWIDHD | - - - - - - - - - - | - - -QKTCPLC | RTHFVPYHK- | 141 |
| SEQ_ID_NO_761 | LSNCRHVFHR | GCLDRWMAHE | - - - - - - - - - - | - - -QRTCPLC | RAPLIPDELL | 168 |
| SEQ_ID_NO_762 | LSNCRHVFHR | GCLDRWMAHE | - - - - - - - - - - | - - -QRTCPLC | RAPLIPDELL | 168 |
| SEQ_ID_NO_755 | LMNCYHVFHR | ECIDRWLEHE | HE- - - - - - - - | -NHSATCPIC | RAPLLSSSC- | 141 |
| SEQ_ID_NO_748 | LRNCCHVFHR | DCIDRWVDHD | HEHD- - - - - - | -ENHNTCPLC | RAPLLTTSQ- | 142 |
| SEQ_ID_NO_746 | LRNCTHVFHR | DCIDRWLDYE | CCGGDD- - - - | -DNHRTCPLC | RTPLLPSFT- | 144 |
| SEQ_ID_NO_751 | LRNCTHVFHR | DCIDRWLDYE | CCGGDD- - - - | -DNHRTCPLC | RTPLLPSFT- | 142 |
| SEQ_ID_NO_753 | LRNCSHVFHR | ECIDRWLDYE | CCGGDGNEGE | EDNHRTCPLC | RTPLLAADT- | 141 |
| SEQ_ID_NO_760 | LRNCSHVFHR | ECIDRWLDYE | CCGGDDNDGE | EDNHRTCPLC | RTPLLAANT- | 144 |

| | | | | | | |
|---|---|---|---|---|---|---|
| SEQ_ID_NO_765 | - - - - - - - - - - | - - - - - - - - - - | TTTGGEQSLS | R- - - -VLKGV | CVSVP | 197 |
| SEQ_ID_NO_763 | - - - - - - - - - - | - - - - -FAVIP | ELEAADADIY | PAREAEMQIV | VRRPA | 194 |
| SEQ_ID_NO_758 | - - - - -MEDYN | QRLWNDAASE | DDIDDDVSLF | SHRHDYYY A | NASL- | 180 |
| SEQ_ID_NO_761 | PAASGLPDPS | DYDLSYYPSP | LPLAPTPTLL | RPHELLLNGL | GGFQ- | 212 |
| SEQ_ID_NO_762 | PAASGLPDPS | DYDLSYYPSP | LPLAPTPTLL | RPHELLLNGL | GGFQ- | 212 |
| SEQ_ID_NO_755 | - - - - - - - - - - | - - - -HHSSAT | CLPPPQPSWA | VERLLYLFGD | DLLPC | 172 |
| SEQ_ID_NO_748 | - - - - - - - - - - | - - - - - - - -SL | ARTRAEPSWA | VERILYLFGD | DLVM- | 168 |
| SEQ_ID_NO_746 | - - - - - - - - - - | - - - - - - - - -D | YSTVTQTSWA | VERLLYLFGD | DLLP- | 169 |
| SEQ_ID_NO_751 | - - - - - - - - - - | - - - - - - - - -D | YSTVTQTSWA | VERLLYLFGD | DLLP- | 167 |
| SEQ_ID_NO_753 | - - - - - - - - - - | - - - - -SSCGD | WPVKTEPSWA | VERLLYLFGD | DLLV- | 170 |
| SEQ_ID_NO_760 | - - - - - - - - - - | - - - - -SSCAD | WPVKNEPSWA | VERLLYLFGD | DLLV- | 173 |

Figure 24

| | | | | | | | |
|---|---|---|---|---|---|---|---|
| SEQ_ID_NO_779 | MVLESIL SS | S--KSPSF-- | ------RRQF | AKHELGSWST | LKRHRFLLF | | 39 |
| SEQ_ID_NO_783 | MVLDSIL SSS | PCLKSPSF-- | ------SRQF | ARHELGSWST | VKRHCFLLS | | 42 |
| SEQ_ID_NO_769 | MVLDGLV SS | PSRRQCL-- | ------KKQW | --DELGSWST | LIQRHQYLLT | | 39 |
| SEQ_ID_NO_777 | MVLDGIV SS | PLRRHQS-- | ------KKQW | --EDLGSCBT | VVNRHRYLLT | | 39 |
| SEQ_ID_NO_773 | MVLDSMI TS | PHRRSPSF-- | ------RKPF | PRDELGSWST | LLRRHRFLLT | | 41 |
| SEQ_ID_NO_771 | MVLDGIV SS | PLRRSAST-- | ------RRQS | SRDEFGSWST | LVERHRFLLT | | 41 |
| SEQ_ID_NO_789 | MVLDSL--SS | PHRRSQNTVF | LASPSKKQQS | GFNEPGSWST | IVERHRFLLT | | 48 |
| SEQ_ID_NO_785 | MVLDSL--SS | PHRRSQNTFF | VSSA-KKPQS | SRDD--SWSA | LVERHRFLLT | | 45 |
| SEQ_ID_NO_790 | MVLDSL--SS | PHRRSQNTFF | LSSP-KKLQS | SKDDVGSWSA | LVERHRFLLT | | 47 |

| | | | | | | | |
|---|---|---|---|---|---|---|---|
| SEQ_ID_NO_779 | ALALLTVLCT | IYLYFAVTFA | AN--DSCSGL | NGPLKDSCHM | EHVKASVAKS | | 87 |
| SEQ_ID_NO_783 | ALALLTVLCT | IYLYFAVTFA | AN--DSCSGL | SGSLRDSCHM | EHVMDSEAKS | | 90 |
| SEQ_ID_NO_769 | ALALLAFLCT | VYLYFAVTLG | ARH-SSCYGL | TGKDKAMCQL | -QLVQALSKG | | 87 |
| SEQ_ID_NO_777 | ALLLGFLCT | VYLYFAVTLD | ARHNSSCYGL | AGKEKAMC-- | ----QAISKG | | 83 |
| SEQ_ID_NO_773 | AFALLAFLCT | IYLYFAVTLG | AT--ESCSGL | TGTKKTLCRL | ELAKDSVGNG | | 89 |
| SEQ_ID_NO_771 | ALGLLAFLCT | IYLYFAVTLG | AT--DTCSGL | KGTEKATCNL | QHVSSTLSHG | | 89 |
| SEQ_ID_NO_789 | MLALLAFLCT | IYLYFAVTLG | AT--GSCSGM | SGAEKALC-- | -QAKSSLHKG | | 93 |
| SEQ_ID_NO_785 | TLLVLAFLCT | VYLYFAVTLG | AS--DACTGL | TGAEREC-- | -QARSVLQHG | | 90 |
| SEQ_ID_NO_790 | TLVLVFLCT | IYLYFAVTLG | AP--DACSGL | AGTEKAVC-- | -RAKSALRHG | | 92 |

| | | |
|---|---|---|
| SEQ_ID_NO_779 | KLKGLRHF | 95 |
| SEQ_ID_NO_783 | KLKGLRHL | 98 |
| SEQ_ID_NO_769 | KLK--FF | 92 |
| SEQ_ID_NO_777 | KLK--LF | 88 |
| SEQ_ID_NO_773 | KLK--FF | 94 |
| SEQ_ID_NO_771 | KLK--F | 94 |
| SEQ_ID_NO_789 | KLK--FF | 98 |
| SEQ_ID_NO_785 | KLK--FR | 95 |
| SEQ_ID_NO_790 | KLK--FF | 97 |

Figure 25

| | | | | | | | |
|---|---|---|---|---|---|---|---|
| SEQ_ID_NO_799 | --MIAE-SM | LLNPTSHIST | N-DSLDDPSP | A-------- | --------- | | 26 |
| SEQ_ID_NO_819 | MMMMGE--- | ---GVSSVPP | N----SHLPV | SGVDVLGGGG | G-------GG | | 32 |
| SEQ_ID_NO_821 | MMMMGE--- | ---GVSSVPP | N----SHLPV | SGVDVLGGGG | G-------GG | | 32 |
| SEQ_ID_NO_810 | MMMMGE--- | ----RAHAPP | N----QHSPA | A-----SGV | T-------DA | | 25 |
| SEQ_ID_NO_816 | MMMMGE--- | ----GAHAPP | WQQQQQQPAA | S-----AGM | V-------DG | | 29 |
| SEQ_ID_NO_801 | -MMI GELSHH | RSNPTVQI PQ | WDPYEEQTTT | SPSLSPI PTS | P--------F | | 41 |
| SEQ_ID_NO_792 | -MMI GE-SHR | GFNPTVHI PP | W-PLSEDLTV | SDI YGSPDGG | S--------- | | 38 |
| SEQ_ID_NO_794 | -MML GE-THR | P-NPTVHVPP | W-PDLDDDQT | DVWYSPI HYN | ATDNNLSSNG | | 46 |
| SEQ_ID_NO_808 | -MML GEPPHR | T-NPTVHVPP | W-PTLNNPTA | E-I FSPLTSN | D-------DY | | 39 |
| SEQ_ID_NO_805 | -MML GE-THR | P-NPTVHVPP | W-------A | PEL FSPYTGN | A-------DY | | 32 |

| | | | | | | | |
|---|---|---|---|---|---|---|---|
| SEQ_ID_NO_799 | -----I SGYF | GTAHVSPLDS | PTAALMDFDS | SLWEDPDLPA | PVDAYSCDQF | | 71 |
| SEQ_ID_NO_819 | DEMTPY-VI A | ALRDYLPAND | VGVGA-DEEE | EAAAMAAI -- | AVDAYACDEF | | 77 |
| SEQ_ID_NO_821 | DEMTPY-VI A | ALRDYLPAND | VGVGA-DEEE | EAAAMAAI -- | AVDAYACDEF | | 77 |
| SEQ_ID_NO_810 | DDASPYALLA | ALQHYLPSNE | V--AAFDEDD | EEAALAAATA | AVDAYACDEF | | 73 |
| SEQ_ID_NO_816 | DDASPYSLLV | ALRHFLPSNE | AAAAAYDEDD | EL----EALA | AVDAYACDEF | | 74 |
| SEQ_ID_NO_801 | TNFNALDSLT | SLHRYLPSNE | PDP---TFED | ELDL------ | PVDAFSCDHF | | 82 |
| SEQ_ID_NO_792 | ---SMMEALA | ELQRYLPSNE | PDP---DSDP | DLSGPDS--- | PI DAYTCDHF | | 79 |
| SEQ_ID_NO_794 | NPFYLHEALS | ALQRYLPSNG | PDV---ELDS | EFPGLDGPDS | PVDAYSCDHF | | 93 |
| SEQ_ID_NO_808 | SQFYMQEALS | AFQHYVNENN | DS----DSDS | EI FPTHE--- | SVDSYSNDHF | | 82 |
| SEQ_ID_NO_805 | SPYSMQEALS | ALQHYESTDA | ------ESDS | EVPSREP-EV | PVDAYSCDHF | | 75 |

| | | | | | | | |
|---|---|---|---|---|---|---|---|
| SEQ_ID_NO_799 | RMYEFKVRSC | ARGRSHDWTK | CPYAHTGEKA | RRRDPRKFNY | SGAECPDLRH | | 121 |
| SEQ_ID_NO_819 | RMYEFKVRRC | ARGRSHDWTE | CPFAHPGEKA | RRRDPRKYHY | SGTACPDFRK | | 127 |
| SEQ_ID_NO_821 | RMYEFKVRRC | ARGRSHDWTE | CPFAHPGEKA | RRRDPRKYHY | SGTACPDFRK | | 127 |
| SEQ_ID_NO_810 | RMYEFKVRRC | GRGRNHDWTA | CPYAHPGEKA | RRRDPRRYHY | SGAACPDFRK | | 123 |
| SEQ_ID_NO_816 | RMYEFKVRRC | GRGRSHDWTD | CPYAHPGEKA | RRRDPRRYHY | SGTACPDYRK | | 124 |
| SEQ_ID_NO_801 | RMYEFKVKRC | ARGRSHDWTE | CPYAHPGEKA | RRRDPRRYHY | SGTACPEFRK | | 132 |
| SEQ_ID_NO_792 | RMYEFKVRRC | ARGRSHDWTE | CPYAHPGEKA | RRRDPRKFHY | SGTACPEFRK | | 129 |
| SEQ_ID_NO_794 | RMYEFKI RRC | ARGRSHDWTE | CPYAHPGEKA | RRRDPRKYHY | SGTACPDFRK | | 143 |
| SEQ_ID_NO_808 | RMFEFKI RRC | ARGRSHDWTE | CPFSHPGEKA | RRRDPRKYNY | SGTSCPDFRK | | 132 |
| SEQ_ID_NO_805 | RMFEFKVRRC | ARCRSHDWTD | CPYAHPGEKA | RRRDPRKYHY | SGTACPDFRK | | 125 |

Figure 25 (continued)

| SEQ_ID | 91-110 | 111-120 | 121-130 | 131-140 | 141-150 | 151-160 | End |
|---|---|---|---|---|---|---|---|
| SEQ_ID_NO_799 | GCCKKGDACE | YAHGTFELNL | HPDRYRTQPC | RDGTGCRRRV | CFFAHTSEQL | | 171 |
| SEQ_ID_NO_819 | GGCKRGDACE | YAHGVFECWL | HPARYRTQPC | KDGTACRRRV | CFFAHTPDQL | | 177 |
| SEQ_ID_NO_821 | GGCKRGDACE | YAHGVFECWL | HPARYRTQPC | KDGTACRRRV | CFFAHTPDQL | | 177 |
| SEQ_ID_NO_810 | GGCKRGDACE | LAHGVFECWL | HPSRYRTQPC | KDGTGCRRRV | CFFAHTPDQL | | 173 |
| SEQ_ID_NO_816 | GGCKRGDACE | FAHGVFECWL | HPSRYRTQPC | KDGTACRRRV | CFFAHTPDXL | | 174 |
| SEQ_ID_NO_801 | GGCKKGDACE | FAHGVFECWL | HPARYRTQPC | KDGPACRRRV | CFFAHTPEQL | | 182 |
| SEQ_ID_NO_792 | GCCKRGDACE | FSHGVFECWL | HPARYRTQPC | KDGGNCRRRV | CFFAHSPDQI | | 179 |
| SEQ_ID_NO_794 | GNCRKGDSCE | FAHGVFECWL | HPARYRTQPC | KDGSGCRRRV | CFFAHTPDQL | | 193 |
| SEQ_ID_NO_808 | GSCKKGDSCE | FAHGVFECWL | HPSRYRTQPC | KDGTSCRRPN | CFFAHTTEQL | | 182 |
| SEQ_ID_NO_805 | GSCKKGDACE | YAHGVFECWL | HPARYRTQPC | KDGTSCRRRV | CFFAHTPDQL | | 175 |

| SEQ_ID | | | | | | | End |
|---|---|---|---|---|---|---|---|
| SEQ_ID_NO_799 | RILPGKQSVR | SPRAREM--- | ---------- | ---------- | ---APAVSS | | 194 |
| SEQ_ID_NO_819 | RVLPAQQS-- | SPRSVAS--S | PLAESYD-GS | PLRRQAFESY | LTKTI-MSSS | | 221 |
| SEQ_ID_NO_821 | RVLPAQQS-- | SPRSVAS--S | PLAESYD-GS | PLRRQAFESY | LTKTI-MSSS | | 221 |
| SEQ_ID_NO_810 | RVPPPRQS-- | SPRGAAAA-S | PLAESYD-GS | PLRRQAFESY | LTKSGIVSSP | | 219 |
| SEQ_ID_NO_816 | RVLPPQQSSA | SPRGAGAAPS | PLAESYD-GS | PLRRQAFESY | LTKTGIMSSS | | 223 |
| SEQ_ID_NO_801 | RLLPQQ---- | SPKGNGSGSG | LGSGEYDFSS | PVIIHPFDSY | MTKAGIFVSS | | 227 |
| SEQ_ID_NO_792 | RVLPNQ---- | SPDR------ | --VDSFDVLS | PTIRRAFQ-- | -----FSIS | | 209 |
| SEQ_ID_NO_794 | RLVSS----- | ---------- | --TDTYD-GS | PL-------- | CGKTLTFMSS | | 216 |
| SEQ_ID_NO_808 | RAPTQQ---- | SPRSVPS--- | --VDSYD-GS | PLRLAFESS | CVKTLDFMSS | | 221 |
| SEQ_ID_NO_805 | RVLPQQ---- | SPRS------ | --ADSYD-GS | PLRHAFESS | CAKSHPFVAS | | 211 |

| SEQ_ID | | | | | | | End |
|---|---|---|---|---|---|---|---|
| SEQ_ID_NO_799 | PTSLLSPSS | ------DSP | PLSPLSP--V | SGG------ | ESLSRLVALM | | 229 |
| SEQ_ID_NO_819 | PTSTLMSPPK | SPPS---ESP | PLSPDGAA-A | RRGSMPGVG | SPVNDYLASF | | 267 |
| SEQ_ID_NO_821 | PTSTLMSPPK | SPPS---ESP | PLSPDGAA-A | RRGSMPGVG | SPVNDYLASF | | 267 |
| SEQ_ID_NO_810 | PTSTLVSPPR | SPPS---ESP | PMSPDAAA-A | LRRGSMPGVG | SPVNEVLASM | | 265 |
| SEQ_ID_NO_816 | PTSTLVSPPR | SPPS---ESP | PMSPDAAAGA | LRRGSMPGVG | SPVNEVVASL | | 270 |
| SEQ_ID_NO_801 | PTSLLTSPPV | SPPS---DSP | PMSPGSP--Q | VIGGSGPGSL | NSMSALLASM | | 272 |
| SEQ_ID_NO_792 | PSSN--SPPV | SPRG------ | --DSDSSCSL | SRSLGSNLG | ---NDVVASL | | 246 |
| SEQ_ID_NO_794 | PGSS--SPPV | SPRAESCSSP | PVSPMAQ--S | LSRSLGSASI | NEM---VTSL | | 259 |
| SEQ_ID_NO_808 | PGSV--SPPV | ------ESP | PMSPMTR--S | LGRSVGS--- | SSVNEMVASL | | 257 |
| SEQ_ID_NO_805 | PGSA--SSPV | ------ESP | PMSPMT---- | ---------- | VSVNEMVASL | | 238 |

Figure 25 (continued)

| SEQ_ID_NO_799 | HSLRLDELK | ......... | ......... | ......... | TNPGVSSF-- | 246 |
| SEQ_ID_NO_819 | RQLRLNKVK | -SSPSGGWSY | PSSS------ | AVYGSPKAA | --TGLYSLPT | 306 |
| SEQ_ID_NO_821 | RQLRLNKVK | -SSPSGGWSY | PSSS------ | AVYGSPKAA | --TGLYSLPT | 306 |
| SEQ_ID_NO_810 | RQLRLGGGS- | PRSAPSGGSF | LGGG------ | YPFGSPKSP- | ---AGLYSLPS | 305 |
| SEQ_ID_NO_816 | RQLRLGGGGS | PRSAPSGGSF | LVG------- | YPFGSPKSP- | ---AALYSLPS | 310 |
| SEQ_ID_NO_801 | RGLQVGKAK | MGSPVGSWGV | QSG------- | FRFGSPRGSS | LRPGFCSLPS | 314 |
| SEQ_ID_NO_792 | RNLQLNKVK | -SSLSSSYNN | QFGGYG---- | SGFGSPRGSV | LGPGFRSLPT | 290 |
| SEQ_ID_NO_794 | RNLQLGKGK | ------SWKT | QVGCCSPSSP | SSFGSPRAAM | IRPGFCSLPS | 302 |
| SEQ_ID_NO_808 | RNLQLGTMK | --SLPSSWNV | QMGS------ | PRFGSPRGPV | IRPGFCSLPS | 298 |
| SEQ_ID_NO_805 | RNLQLGKVK | --SLPSSWNV | -MGS------ | SGFGSPRGPM | RPGFFSLPT | 278 |

| SEQ_ID_NO_799 | SPNL------ | RRSSGAAF- | -DLMDRG--N | EEEPAMERVE | SGRNLRAQMY | 285 |
| SEQ_ID_NO_819 | TPLASTATVT | TASSFMPNL | -EPLDLGLIG | DEEPVLDRVE | SGRALREKVF | 353 |
| SEQ_ID_NO_821 | TPLASTATVT | TASSFMPNL | -EPLDLGLIG | DEEPVLDRVE | SGRALREKVF | 353 |
| SEQ_ID_NO_810 | TPTRPSPVTV | TTASGATVLT | VERLNLGLIG | DEEPVMERVE | SGRALREKVF | 355 |
| SEQ_ID_NO_816 | TPTRPAAVTV | TTPSGATVMT | VERLNLGLIG | DEEPVMERVE | SGRALREMVF | 360 |
| SEQ_ID_NO_801 | TPTR---TM | ASRSGLSQL | -DIMGDGVTC | EEEPAMERVE | SGRDLRAKIY | 358 |
| SEQ_ID_NO_792 | TPTRP----- | ------GFM | -NIWENG--L | EEEPAMERVE | SGRELRAQLF | 325 |
| SEQ_ID_NO_794 | TPTR----NL | -TRPGISYP- | -DSMDKA--C | EEEPVMERVE | SGRDLRAKMF | 343 |
| SEQ_ID_NO_808 | TPTQ----V | PSRGRVNHF- | -DLMDQS--C | EEEPVMERVE | SGRDIRVKMF | 339 |
| SEQ_ID_NO_805 | TPTQ----A | PTRGGVNYF- | -DDMDQS-CC | EEEPVMERVE | SGRSLRARMF | 320 |

| SEQ_ID_NO_799 | AKLMRENSVD | RVRPMISA- | ---------- | GSLN------ | ---------- | 307 |
| SEQ_ID_NO_819 | ERLSRDGAIY | GDATAFATAG | -----VGLDV | DWSDLIN-- | ---------- | 386 |
| SEQ_ID_NO_821 | ERLSRDGAIS | GDATAFATAG | -----VGLDV | DWSDLIN-- | ---------- | 386 |
| SEQ_ID_NO_810 | ERLSKEATVP | SDTAASANVE | GAA--PAPDV | GWSDLIN-- | ---------- | 391 |
| SEQ_ID_NO_816 | ERLSKEATVP | NDAAASANAE | GAAPAAAPDV | GWSDLIN-- | ---------- | 398 |
| SEQ_ID_NO_801 | AKLSKENSVD | RDRGDGGVSG | ------PDV | GWSELYK-- | ---------- | 389 |
| SEQ_ID_NO_792 | EKLSKENQMG | RIEPDPDQGA | G----DTPDV | GWSDLVM-- | ---------- | 359 |
| SEQ_ID_NO_794 | EKLSKENSLE | RVNPDQSSGG | -------PDL | NWSDLGKQA | MGIIVMVDIV | 386 |
| SEQ_ID_NO_808 | EKLSKENSFN | GSGMGSGSGL | GEVV-EDPDV | GWSELVSPF | LGD------- | 381 |
| SEQ_ID_NO_805 | EKLSKENHLD | GSGSGSQIG | ------VPDV | GWSELYSR- | ---------- | 353 |

Figure 25 (continued)

| | | |
|---|---|---|
| SEQ_ID_NO_799 | - - - - - - | 307 |
| SEQ_ID_NO_819 | - - - - - - | 386 |
| SEQ_ID_NO_821 | - - - - - - | 386 |
| SEQ_ID_NO_810 | - - - - - - | 391 |
| SEQ_ID_NO_816 | - - - - - - | 398 |
| SEQ_ID_NO_801 | - - - - - - | 389 |
| SEQ_ID_NO_792 | - - - - - - | 359 |
| SEQ_ID_NO_794 | L F I K Y F | 392 |
| SEQ_ID_NO_808 | - - - - - - | 381 |
| SEQ_ID_NO_805 | - - - - - - | 353 |

Figure 26

| | | | | | | | | |
|---|---|---|---|---|---|---|---|---|
| SEQ_ID_NO_1703 | MA- PPLSSWP | WASLG YKYF | LLGPLVWKVA | QEWAF- -QGG | AP- -GSRML | 45 |
| SEQ_ID_NO_826 | MA- APLSSWP | WTSLGDYKYA | LLGPLAWKVV | QEWREDGQGA | LPLVLGSWML | 49 |
| SEQ_ID_NO_1713 | MA- PPLSSWP | WASLGQYKYV | LFGALVWKVV | QEWRE- -QGG | LP- -LGSWML | 45 |
| SEQ_ID_NO_824 | MAPPPLSSWP | WASLGQYKYV | LLGPLVWKVL | QEWRE- -QAB | LP- -LGSWML | 46 |

| | | | | | | |
|---|---|---|---|---|---|---|
| SEQ_ID_NO_1703 | HLLLLFSARG | LTYQFWFSYS | NMLFLTRRRR | VVPDGVDFRC | VDHEWDW- - | 92 |
| SEQ_ID_NO_826 | HLLLLFVVRG | LTYQFWFTYG | NMLFFTRRRR | VVADGVDFRC | DAEWDW- - | 96 |
| SEQ_ID_NO_1713 | HLLVLFAVRG | LTYQFWFTYG | NMLFFTRRRR | VVADGVDFRC | DAEWDW- - | 92 |
| SEQ_ID_NO_824 | HLLLLFAARG | LTYQFWFSYG | NMLFFTRRRR | VVADGVDFRC | DAEWDWKKI | 96 |

| | | | | | |
|---|---|---|---|---|---|
| SEQ_ID_NO_1703 | .......... | .......... | .......... | .......... | 92 |
| SEQ_ID_NO_826 | .......... | .......... | .......... | .......... | 96 |
| SEQ_ID_NO_1713 | .......... | .......... | .......... | .......... | 92 |
| SEQ_ID_NO_824 | LWI PPPNNQP | WSPSDTGNAQ | AHLAGI GRLF | FLRLVPAFG | 135 |

Figure 27

```
SEQ_ID_NO_828   ---MGRKP-- DAVAKSYHSG GGGAAASS-- ---------- --PRAARKAS   31
SEQ_ID_NO_845   ---MGRKP-- DPSKPHY--- GGGAS----- ---------- --PRAARRTQ   25
SEQ_ID_NO_847   ---MGRKP-- DPSKPHY--- GGGAS----- ---------- --PRAARRTQ   25
SEQ_ID_NO_832   -MLSLLSE-- KPNLALYNQS NGKHYQYHQN IYNDWRWWRS SATQQHRRKV   47
SEQ_ID_NO_837   --MGVVAEVW RSSVRLLTNS PQLNGGSHKS ALWKWRFF-- ---SAQPKRTV   44
SEQ_ID_NO_840   --MKRRKQ-- RSHEKLFLVL QIILHTLIF- ---------- --KRRRRIHH   33
SEQ_ID_NO_842   ---MVLPR-- RRGGHNHH-- ---------- ---------- --PCPRRAVL   21
SEQ_ID_NO_844   ---MGSRR-- RRHHHHHG-- ---------- ---------- --PMLVPAVA   21
SEQ_ID_NO_839   MFMAPRRGLL DGGEDRYGLM SFGTKDI--- ---------- --FTMRRKIR   35
SEQ_ID_NO_850   ---MSEAEKF IYHRKLMEVK GISVGESKAE KLRSY----- --LVSRSRMK   40

SEQ_ID_NO_828   PSP------- VFLGTALFVL GFVSLFTGHV VTDADW---- ARRSRWRPK   70
SEQ_ID_NO_845   PSP------- VFLGTALFVL GFVSLFTGHI VTDADW---- SRRSRWRSK   64
SEQ_ID_NO_847   PSP------- VFLGTALFVL GFVSLFTGHI VTDADW---- SRRSRWRSK   64
SEQ_ID_NO_832   PWS------- LVCGLMLFGL GLVSLFTGHV ASDLEW---- YSQRLVKRSL  66
SEQ_ID_NO_837   MWT------- WVCGFMLFSL GVISLFTGHV VSHLEW---- YSQQLSKRSL  63
SEQ_ID_NO_840   LLP------- LAALTGGIL FFFVLFSPPI TSQHH----- HLINPIWFNN   71
SEQ_ID_NO_842   PAA------- ALLLL--FLL AAVTLLYVSP PPLSDHPALA YSRRRSPHAL   62
SEQ_ID_NO_844   PAA------- AAFAAAGLLL VVWAFHCFLS PPLGDGGGGA RVVRRPNPPF   64
SEQ_ID_NO_839   YWQKQFKQRH LFGGLMVLLL MCVITKFILM NMFSDQ---- LDLDTAIPSN   81
SEQ_ID_NO_850   LWM------- IRAVTILLLW SCVV----HL MALGEFWG-- PRLLKGMPSC   77

SEQ_ID_NO_828   -----QHRNY EP-------- --------D WESKYSSMY YGCSERSASF   99
SEQ_ID_NO_845   -----QVRNN EP-------- --------N IWKSRYSNLY YGCSRRSVNF   93
SEQ_ID_NO_847   -----QVRNN EP-------- --------N IWKSRYSNLY YGCSRRSVNF   93
SEQ_ID_NO_832   FYSRLEGRRR EA-------- --------D IWKSKYSNLF YGCSERGRNF  120
SEQ_ID_NO_837   ----LDMSRR EP-------- --------D VWKSKYSKFF YGCSERGRNF  113
SEQ_ID_NO_840   GTELQMNLQK EH----VFRV PMGGGSLSGD WTSKQSLLY HGCSNSSYKF  117
SEQ_ID_NO_842   LNSSGGGSLV EPGRREISRV PKGGWSATDG LWGSKLASKF YGCSNSSSKF  112
SEQ_ID_NO_844   LLKKPAEVAR SVIGAVDFTV PSGGSKHGQE LWESKATGNF FGCSNATKHF  114
SEQ_ID_NO_839   VVQDEPSPNN WP-------- ------TLE WKHPNSDNY FNCMGRAK--  114
SEQ_ID_NO_850   ---------- ---------- ------FN HHDLPVAAET ASLPMKIA--   97
```

Figure 27 (continued)

| SEQ_ID_NO_828 | RSAVPENSST GYLLIATSGG LNQQRIGITD AVVVAWLNA TLVVPELDHH | 149 |
| --- | --- | --- |
| SEQ_ID_NO_845 | RSAVPENSST GYLLIGTSGG LNQQRIGITD AVVVARILNA TLVVPELDHH | 143 |
| SEQ_ID_NO_847 | RSAVPENSST GYLLIGTSGG LNQQRIGITD AVVVARILNA TLVVPELDHH | 143 |
| SEQ_ID_NO_832 | PPAVRERASN GYLLIAASGG LNQQRTGITD AVVVARILNA TLVVPELDHH | 170 |
| SEQ_ID_NO_837 | LPAVQEQSSN GYLLIAASGG LNQQRTGITD AVVVARILNA TLVVPELDHH | 163 |
| SEQ_ID_NO_840 | PSADVNTHPN RYLMIATSGG LNQQRTGIVD AVVAAHILNA VLVVPKLDQK | 167 |
| SEQ_ID_NO_842 | LDSGVMTHPD RYLMIVTSGG LNQQRTGIID AVVAARILNA TLVVPKLDQT | 162 |
| SEQ_ID_NO_844 | ADAKAVTKLD RYLMIATSGG LNQQRTGIID AVVAARILNA TLVIPKLDEE | 164 |
| SEQ_ID_NO_839 | KDIRQGNNTN GYLLVHANGC LNQMKTGISD MVAIAKIMNA TLVFPTLDHN | 164 |
| SEQ_ID_NO_850 | LPPKRVYKNN GYLMVSCNGC LNQMRAALCD MVTLARYMNV TLIVPELDKT | 147 |

| SEQ_ID_NO_828 | SFWKDDSDFS DIFDVEWFIS HLSKDVTIVK RIPYEVMLSM DKLPWTMRAP | 199 |
| --- | --- | --- |
| SEQ_ID_NO_845 | SFWKDDSDFS DIFDVDWFIS YLSKDVTIVK RIPYEVMMSM DKLPWTMRAP | 193 |
| SEQ_ID_NO_847 | SFWKDDSDFS DIFDVDWFIS YLSKDVTIVK RIPYEVMMSM DKLPWTMRAP | 193 |
| SEQ_ID_NO_832 | SYWKDDSDFV NIFDVDWFIS YLAKDVTIVK RVPDKVMRSM EKPPYTMRVP | 220 |
| SEQ_ID_NO_837 | SYWKDDSDFS DIFDVNWFIS SLAKDVTIVK RVPDRVMRAM EKPPYTTRVP | 213 |
| SEQ_ID_NO_840 | SYWKDSSNFS EIFDVDRFIS HLSKDVKIIR DIPR--IGDK VITPYTTRVP | 215 |
| SEQ_ID_NO_842 | SFWKDASDFA EIFNADWFIS FLSKDVRIVK ELPK--IGGK LWAPHRMRVP | 210 |
| SEQ_ID_NO_844 | SFWNDASDFA QIFDVDSFIY SLSNDVKVIR QLPD--MNGK KLSPYKMRIP | 212 |
| SEQ_ID_NO_839 | SFWIDPSDFK EIFNMKNFVE VLNEDVQVVE SLPPELAAIK P----ALKAP | 210 |
| SEQ_ID_NO_850 | SFWSDPSEFQ DIFDVDHFIT SLRDEVRILK ELPPRLKRRF ELGMYYSFPP | 197 |

| SEQ_ID_NO_828 | RK-SVPEFYI DEVLPILMRR RALQLTKFDY RLTSD-LDED LQKLRCRVNF | 247 |
| --- | --- | --- |
| SEQ_ID_NO_845 | RK-SMPDFYI DEVLPILMRR RALQLTKFDY RLTNE-LDEE LQKLRCRVNF | 241 |
| SEQ_ID_NO_847 | RK-SMPDFYI DEVLPILMRR RALQLTKFDY RLTNE-LDEE LQKLRCRVNF | 241 |
| SEQ_ID_NO_832 | RK-SPPEYYL DQVLPILLRR RVVQLTKFDY RLASN-LDEE LQKLRCRANY | 268 |
| SEQ_ID_NO_837 | RK-STLEYYL DQVLPILTRR HVLQLTKFDY RLAND-LDED MQKLRCRVNY | 261 |
| SEQ_ID_NO_840 | RK-CNAKCYQ TRILPILKKK HAVQLTKFDY RLSNR-LDID MQKLRCRVNF | 263 |
| SEQ_ID_NO_842 | RK-CTQRCYL NRVLPALVKK HVVRLTKFDY RLANR-LDSD LQKLRCRVNY | 258 |
| SEQ_ID_NO_844 | RK-CTPKCYE NRVLPALLKK HVVQLTKFDY RVSNR-LETD LQKLRCRVNY | 260 |
| SEQ_ID_NO_839 | VSWSKASYYR TDMLQLLKKH KVIKFTHTDS RLVNNGLASS IQRVRCRAMY | 260 |
| SEQ_ID_NO_850 | ISWSDISYYS NQILPLVKKY KVVHLNKTDT RLANNGLSLD IQKLRCRVNF | 247 |

Figure 27 (continued)

| | | | | | | | |
|---|---|---|---|---|---|---|---|
| SEQ_ID_NO_828 | HALKFTSSI H | AMGQKLVQKL | RLMNTRYVAI | HLRFEPDMLA | FSGCYYGGGE | 297 |
| SEQ_ID_NO_845 | HALRFTNSI Q | TLGEKLVRKL | RSMSSRYVAV | HLRFEPDMLA | FSGCYYGGGD | 291 |
| SEQ_ID_NO_847 | HALRFTNSI Q | TLGEKLVRKL | RSMSSRYVAV | HLRFEPDMLA | FSGCYYGGGD | 291 |
| SEQ_ID_NO_832 | HALRFTKPI Q | EIGERLVTKM | RKMAKRYIAI | HLRFEPDMLA | FSGCYFGGGE | 318 |
| SEQ_ID_NO_837 | HALRFTKRI Q | SVGMKVVKRM | RKMAKRFIAV | HLRFEPDMLA | FSGCDFGGGE | 311 |
| SEQ_ID_NO_840 | HALKFTDPI I | EMGRKLVERI | RMKSKHFVAL | HLRFEPDMLA | FSGCYYGGGD | 313 |
| SEQ_ID_NO_842 | HALRFTDPI Q | EMGEKIIQRV | RERSTYFIAL | HLRFEPDMLA | FSGCYYGGGE | 308 |
| SEQ_ID_NO_844 | HALQFTDPI L | RMGELLVQRM | KEKSGRFIAL | HLRFEPDMLA | FSGCYYGGGD | 310 |
| SEQ_ID_NO_839 | EALRFAVPI E | ELGKKLVNRL | RENNTPYIAL | HLRYEKDMLA | FTGCSHNLTK | 310 |
| SEQ_ID_NO_850 | NALRFTPQ E | ELGRRVVRI L | REK- GPFLVL | HLRYEMDMLA | FSGCSHGCNP | 296 |

| | | | | | | | |
|---|---|---|---|---|---|---|---|
| SEQ_ID_NO_828 | KERKELGEIR | - - - KRWDILP | ELSAEDERSR | GKCPLTPHEV | GLMLRALGFG | 344 |
| SEQ_ID_NO_845 | KERRELGEIR | - - - KRWDILP | ELSAEDERSR | GKCPLTPQEI | GLMLRALGFS | 338 |
| SEQ_ID_NO_847 | KERRELGEIR | - - - KRWDILP | ELSAEDERSR | GKCPLTPQEI | GLMLRALGFS | 338 |
| SEQ_ID_NO_832 | KERFELGEIR | - - - KRWAILP | DLSPDGERER | GKCPLTPHEV | GLMLRALGFA | 365 |
| SEQ_ID_NO_837 | KERAELAEIR | - - - KRWDILP | DLDPLEERKR | GKCPLTPHEV | GLMLRALGFT | 358 |
| SEQ_ID_NO_840 | KETKELGKIR | - - - KRWKTLH | ATNPDKERRH | GKCPLTPEEI | GLMLRALGFG | 360 |
| SEQ_ID_NO_842 | KEKRELGVIR | - - - KRWKTLH | ASNPEKERRH | GRCPLTPEEV | GLMLRALGYR | 355 |
| SEQ_ID_NO_844 | IERRELGEIR | - - - KRWKTLH | ASNPDRERRH | GKCPLTPEEV | GLMLRALGFG | 357 |
| SEQ_ID_NO_839 | EETQELKKMR | YSVKHMKE- K | EIDSKSKRLK | GSCPMTPREV | AVFLEALGYP | 359 |
| SEQ_ID_NO_850 | DEEEELTRMR | YAYPWMKE- K | VLNSELKRKD | GLCPLTPEET | ALALNALGID | 345 |

| | | | | | | | |
|---|---|---|---|---|---|---|---|
| SEQ_ID_NO_828 | NDTLLYVASG | EIYGGDSTLQ | PLRGLFPNFY | TKEKLAG- DD | LNPFLPFSSR | 393 |
| SEQ_ID_NO_845 | NDTYLYVASG | EIYGGEETLQ | PLRDLFPNYY | TKEMLAG- ND | LKLFLPFSSR | 387 |
| SEQ_ID_NO_847 | NDTYLYVASG | EIYGGEETLQ | PLRDLFPNYY | TKEMLAG- ND | LKPFLPFSSR | 387 |
| SEQ_ID_NO_832 | NDTYLYVASG | EIYGGEETLR | PLRELFPNFY | TKEMLAI- EE | LKSFFPFSSR | 414 |
| SEQ_ID_NO_837 | NDTYIYVASG | EIYGGEKTLK | PLRELFPNFY | TKEMLANI DE | LKPLLPYSSR | 407 |
| SEQ_ID_NO_840 | NDVHIYVASG | EIYGGEETLA | PLKALFPNFY | SKETIASKEE | LAPFSSFSSR | 410 |
| SEQ_ID_NO_842 | KNVHIYVASG | DIYGGAKTLA | PLKALFPNLH | TKETVTSKDE | LAPFSKYSSR | 405 |
| SEQ_ID_NO_844 | KDVHLYVASG | DVYGGEETLA | PLKALFPNFH | SKETLASKEE | LAPFLPYSSR | 407 |
| SEQ_ID_NO_839 | VDTKIYVAAG | VIYGSEG- MK | PLQKKFPNLL | WHSSLATKEE | LQPFEGHLNQ | 408 |
| SEQ_ID_NO_850 | RNVQIYIAAG | EIYGGERRMK | ALAEAFPNVV | RKETLLEPSD | LKFFQNHSSQ | 395 |

Figure 27 (continued)

| | | | | | | |
|---|---|---|---|---|---|---|
| SEQ_ID_NO_828 | LAAIDFIVCD | ESDVFVTNNN | GNMAKVLAGR | RRYMGHKRTI | RPNAKKLNVL | 443 |
| SEQ_ID_NO_845 | LAAIDFIVCD | GSDVFVTNNN | GNMAKVLAGR | RRYMGHKRTI | RPNAKKLNLL | 437 |
| SEQ_ID_NO_847 | LAAIDFIVCD | GSDVFVTNNN | GNMAKVLAGR | RRYMGHKRTI | RPNAKKLNLL | 437 |
| SEQ_ID_NO_832 | MAAIDYIVCD | ESDVFVTNNN | GNMAKILAGR | RRYAGHKRTI | RPNAKKLSAL | 464 |
| SEQ_ID_NO_837 | LAAIDYIVSD | ESDVFITNNN | GNMAKILAGR | RRYMGHKRTI | RPNAKKLSAL | 457 |
| SEQ_ID_NO_840 | MAALDFMVCD | ESDVFVSNNN | GNMARMLAGR | RRYFGHKPTI | RPNAKKLYKL | 460 |
| SEQ_ID_NO_842 | MAALDFIVCD | GSDAFVTNNN | GNMAKILAGR | RRYLGHKRTI | RPNARKLYSL | 455 |
| SEQ_ID_NO_844 | MAALDFIVCD | RSDVFVTNNN | GNMARMLAGR | RRYFGHRRTI | RPNAKKLYSL | 457 |
| SEQ_ID_NO_839 | LAALDYYTV | ESDVFVYSYD | GNMAKAARGH | RKFDGFKKTI | SPDKQRFVRL | 458 |
| SEQ_ID_NO_850 | MAALDYLVSL | ESDIFVPTYD | GNMAKVVEGH | RRFLGFKKTI | LLDRKLLVNL | 445 |

| | | | | | | |
|---|---|---|---|---|---|---|
| SEQ_ID_NO_828 | FQTRNQ-LS | WDTFSRKVQR | VQRGLMGEPD | DI----RPK | QDD-FHEFP | 484 |
| SEQ_ID_NO_845 | FKRRKQ-MG | WDIFSQKVKK | VQRGLMGEPD | DI----RPG | RDD-FNEFP | 478 |
| SEQ_ID_NO_847 | FKRRKQ-MG | WDIFSQKVKK | VQRGLMGEPD | DI----RPG | RDD-FNEFP | 478 |
| SEQ_ID_NO_832 | FKARDR-MD | WDTFAKKVKA | SQRGFMGEPD | EV----RPG | RGD-FHEYP | 505 |
| SEQ_ID_NO_837 | FMDREK-ME | WDTFAKKVKS | CQRGFMGDPD | EF----KPG | RGE-FHEYP | 498 |
| SEQ_ID_NO_840 | FLSRNN--MT | WEEFASQVRT | SQGFMGEPM | EV----KPG | RGE-FHENP | 501 |
| SEQ_ID_NO_842 | FLSRGN--MS | WDAFSSKVHM | AQKGFMGEPK | EL----RPG | RGE-FHENP | 496 |
| SEQ_ID_NO_844 | FLNRTS--MS | WDTFASKVLT | FQKGFMGEPN | EI----KPG | RGE-FHEHP | 498 |
| SEQ_ID_NO_839 | IDQLDNGLIS | WNDFSTKVKS | HAKKKGAPQ | AR-KIHRHPK | FEETFYANPF | 507 |
| SEQ_ID_NO_850 | IDQYTEGLLS | WDEFSSTVKE | VHEDRMGSPK | KRLVIPDKPK | EEDYFYANP | 494 |

| | | | | | | |
|---|---|---|---|---|---|---|
| SEQ_ID_NO_828 | SSCICSRK-- | ---------- | ---------- | ---------- | ---------- | 492 |
| SEQ_ID_NO_845 | SSCICQR-- | ---------- | ---------- | ---------- | ---------- | 486 |
| SEQ_ID_NO_847 | SSCICQR-- | ---------- | ---------- | ---------- | ---------- | 486 |
| SEQ_ID_NO_832 | -SCICEKPFT | DDENRKGEDL | LSDRIHMNLK | ENVDSKYVGE | NQGDKSLQRL | 554 |
| SEQ_ID_NO_837 | QSCICQRP-- | ---------- | ---------- | ---------- | ------FSYD | 510 |
| SEQ_ID_NO_840 | SACICADS-- | ---------- | ---------- | ---------- | ---------- | 509 |
| SEQ_ID_NO_842 | TTCICENT-- | --------D | PKTPTKPNPR | SEQGLINGTE | GRKAITEPTV | 535 |
| SEQ_ID_NO_844 | MDCICAKA-- | ---------- | ---------- | -NGKIGQSRH | HQIKRAGKGA | 525 |
| SEQ_ID_NO_839 | PGCICQK--- | ---------- | ---------- | ---------- | ---------- | 514 |
| SEQ_ID_NO_850 | HECLQLL--- | ---------- | ---------- | ---------- | ---------- | 501 |

Figure 27 (continued)

| | | |
|---|---|---|
| SEQ_ID_NO_828 | .......... .......... .......... .......... .......... | 492 |
| SEQ_ID_NO_845 | .......... .......... .......... .......... .......... | 486 |
| SEQ_ID_NO_847 | .......... .......... .......... .......... .......... | 486 |
| SEQ_ID_NO_832 | KKRSIEEPIS LRENKDVTVI GSANELGLCT GDRYVKVNGT CLVASTKSDL | 604 |
| SEQ_ID_NO_837 | KTSTDDEEED MSEENHNSTS PGHVHLSS.. .......... .......... | 538 |
| SEQ_ID_NO_840 | DANDREDASL FGTHSIISEI DTGSSTNSAR RDMVEVTDGQ ASEEEQEWS- | 558 |
| SEQ_ID_NO_842 | ANHTNEELVG SSAEEDDASV EKEDDTSAEK EDDTSEEKEE IADPEAEDDA | 585 |
| SEQ_ID_NO_844 | ENHSSDGDLD WRDLDYGEHT PLGRDSSNES ESDDIRVGGS .......... | 565 |
| SEQ_ID_NO_839 | .......... .......... .......... .......... .......... | 514 |
| SEQ_ID_NO_850 | .......... .......... .......... .......... .......... | 501 |

| | | |
|---|---|---|
| SEQ_ID_NO_828 | ........PG NISATT.... . | 500 |
| SEQ_ID_NO_845 | ........PV NRSVTARAEN L | 499 |
| SEQ_ID_NO_847 | ........PV NRSVTARAEN L | 499 |
| SEQ_ID_NO_832 | LCHHVLSFST PFLDETGSGM L | 625 |
| SEQ_ID_NO_837 | ........AD NERDEVFPD- - | 549 |
| SEQ_ID_NO_840 | ........DT EYMETELEI- - | 569 |
| SEQ_ID_NO_842 | LVRP....DD PELEEVLSD- - | 600 |
| SEQ_ID_NO_844 | ........DI PELEDMMSD- - | 576 |
| SEQ_ID_NO_839 | ........PT HLMAETNHES L | 527 |
| SEQ_ID_NO_850 | ........DE PLRTTRLSMF L | 514 |

Figure 28

```
SEQ_ID_NO_876    ----MGPVVL TQLATGLGML AGAALVKSVM DQN--TMMGP GSD---RF--  39
SEQ_ID_NO_855    ----MSPIVI TQLATGISVL AGAVFIKSVM DQK-----P  MAG---QF--  35
SEQ_ID_NO_862    ----MGPIVL TQLATGLSVL AGAVLVKSVM DQK-----P  MAG------  33
SEQ_ID_NO_858    ----MVPIVL TQMATGLGVL AGAVFVKSVM DQK-----P  MAG---PF--  35
SEQ_ID_NO_856    ----MFPAVL TQVATGLSVL AGAVLVKSVM DQK-----P  MAG---PF--  35
SEQ_ID_NO_885    MVVVVAPIAV A--SAGLGML AGVAMASRGS NSSSSSGRTS SPAALLRWGA  48
SEQ_ID_NO_868    ---MVSPVVI A--SAGLGML AGVALASRGT GDG-----LP ASS---RWDA  37
SEQ_ID_NO_886    ---MVGPIVI A--SAGLGML AGVAMANRTM GGGGDGRQLP AAS---RWDA  42
SEQ_ID_NO_870    ---MVAPVVI A--SAGLGML AGVAMANRGL GNG-----LP AAS---RWDA  37
SEQ_ID_NO_878    ---MVAPVVI T--SAGLGML AGLAMANRGL GDG-----LP AAS---RWDA  37

SEQ_ID_NO_876    ----PRCSRC NGTGRVSC-L CNRWSD--GD -RGCRTCAGS GRMVCSSCGG  81
SEQ_ID_NO_855    ----PRCPTC NGTGRVTC-F CSRWSD--GD -VGCRRCSGS GRAACSNCGG  77
SEQ_ID_NO_862    ----PLCPSC NGTGRVAC-L CSRWSD--GD -AGCRACSGS GRMACSSCGG  75
SEQ_ID_NO_858    ----QRCPTC NGTGRVSC-L CSRWSD--GD -VGCRTCSGS GRRACSSCGG  77
SEQ_ID_NO_856    ----QRCPTC NGTGRITC-L CTRWSD--GD -IGCRTCAGS GRMACSSCGG  77
SEQ_ID_NO_885    PEPAPRCAAC GGTGREECRL CARWSDARGD CSGCRACAGT RRAPCRSCGG  98
SEQ_ID_NO_868    R---PRCSTC SGTGREEC-L CSRWSD--GD -VGCGTCSGS GRKRCRSCGG  80
SEQ_ID_NO_886    R---PRCATC GGSGRVDC-L CNRWSD--GD -SGCRTCAGS GRMPCRSCGG  85
SEQ_ID_NO_870    R---PRCATC GGSGRVEC-L CNRWSD--GD -SGCRTCAGS GRMPCRSCGG  80
SEQ_ID_NO_878    R---PRCATC GGSGRVEC-L CNRWSD--GD -SGCRTCAGS GRMPCRSCGG  80

SEQ_ID_NO_876    TGTGRPLPVQ SVR------- ---PPNQS-- ---Y-       101
SEQ_ID_NO_855    SGTGRPLPAQ TVQ------- ---PPNRP-- ---Y-       97
SEQ_ID_NO_862    TGTGRPIPVQ SMR------- ---SPNRP-- ---PS       96
SEQ_ID_NO_858    SGTGRPIPVQ LIVR------ ---QPTNR-- ---SF       98
SEQ_ID_NO_856    SGTGRPIPVQ SVR------- ---QPTNR-- ---NS       98
SEQ_ID_NO_885    SGTGRRAPVR VSSS------ ---APPSR-- ------      117
SEQ_ID_NO_868    SGTGRPLPAR LIVQ------ EQKLPTAPGR RGDYN       109
SEQ_ID_NO_886    SGTGRPLPAR LIARGHHHHH NPPSSAPGR GGDYS        120
SEQ_ID_NO_870    SGTGRPLPAR LTVQ---HQ KPPPPPPG- ---YN         107
SEQ_ID_NO_878    SGTGRPLPAR LTVQ---HH K--PPPPAG- ---YN        105
```

Figure 29

```
SEQ_ID_NO_907   ------MAV- --------D SMHVVMPFL AFGHISPFVQ LARKLYAAG-  33
SEQ_ID_NO_912   ---MAAAVVE AD-----DE AMHVALFPFL AFGHISPFAQ LARSLGAVG-  40
SEQ_ID_NO_911   MGSAGAAPVA TAAGGGGGDG DLHVVMFPFL AFGHISPFAQ LARKMAGVGA  50
SEQ_ID_NO_896   ----MPSELA MN-----ND ELHVVMFPFL AFGHISPFVQ LSNKLFSH--  38
SEQ_ID_NO_913   ------MSLK GN-----DK ELHLVMFPFF AFGHITPFVQ LSNKISSLYP  38
SEQ_ID_NO_901   ----MENEMK HS-----ND ALHVVMFPFF AFGHISPFVQ LANKLSSY--  38
SEQ_ID_NO_915   ----MENE-- --------K VLHVVMFPFF AFGHISPFAQ LANKLSSH--  33
SEQ_ID_NO_904   ---MGSQA-- --------T THHMAMYPWF GVGHLTAFFR LANKLASK--  34
SEQ_ID_NO_905   ---MGSQA-- --------T TYHMAMYPWF GVGHLTGFFR LANKLAGK--  34
SEQ_ID_NO_908   ---MGSQA-- --------T TYHMAMYPWF GVGHLTGFFR LANKLAGK--  34
SEQ_ID_NO_891   ------ME-- --------P TFHAFMFPWF AFGHMIPFLH LANKLAEK--  31
SEQ_ID_NO_893   MSDLISKR-- --------S SFRILMFPWF AVGHLTPFLH LSNKLAEK--  37

SEQ_ID_NO_907   GVRVTLLSAA ANVPRVEAML GPAAGAV--A VAPLRLQRVP GLPEGAESTA  81
SEQ_ID_NO_912   GVRVTFLSAA ANVARVEAML PADGTAV--- VAALHLPRNP GLPVGAESTA  87
SEQ_ID_NO_911   GVRVTFLSAA ANVPRVEAML GGTGGTS--T VAALELPRVP GLPEGAESTA  98
SEQ_ID_NO_898   GVHVTFLSAA SNIPRIRST NLNPAIN--- VISLKFPN- ----GITNTA  79
SEQ_ID_NO_913   GVKITFLAAS ASVSRIETML NPSTNTK--- VIPLTLPRVD GLPEGVENTA  85
SEQ_ID_NO_901   GVKVSFFTAS GNASRVKSML NSAPTTH--- VPLTLPHVE GLPPGAESTA  85
SEQ_ID_NO_915   GVKVSFFTAS GNASRLRSML NSAPTTHID  VPLTLPHVE GLPPGSESTA  83
SEQ_ID_NO_904   GHRISFLIPK NTQSKLAS-F NLHPHLV--S FVPITVPSIP GLPPGAETTS  81
SEQ_ID_NO_905   GHRISFLIPK NTQSKLES-F NLHPHLI--S FVPIVVPSIP GLPPGAETTS  81
SEQ_ID_NO_908   GHRISFLIPK NTQSKLES-F NLHPHLI--S FVPIVVPSIP GLPPGAETTS  81
SEQ_ID_NO_891   GHQITFLLPK KAQKQLEH-H NLFPDSI--V FHPLTIPHVN GLPAGAETTS  78
SEQ_ID_NO_893   GCTISFLLPN KAIKLLQH-F NLYPDHI--T FHPVKVPHVE GLPLGTETAS  84

SEQ_ID_NO_907   EVSADGAELL KVAVDGTRPQ VAALLAELRP DALLFDFATP WVTELAAPLR 131
SEQ_ID_NO_912   EVDADGAELL KLALDGTRPQ VEALLARLRP DVVLFDFATP WVADVARQLG 137
SEQ_ID_NO_911   EVSADGAELL KLAVDGTRPQ VEALLARLHP DVVLFDFATP WVDVARPLG 148
SEQ_ID_NO_898   ELPPHLAGNL IHALDLTQDQ VKSLLLELKP HYVEFDFAQH MLPKLASEVG 129
SEQ_ID_NO_913   DASPATIGLL YVAIDLMQPQ KTLLANLKP DFVIFDFVHW MLPEIASELG 135
SEQ_ID_NO_901   ELTPASAELL KVALDLMQPQ KTLLSHLKP HFVLFDFAQE MLPKMANGLG 135
SEQ_ID_NO_915   ELTPVTAELL KVALDLMQPQ KTLLSHLKP HFVLFDFAQE MLPKMADELG 133
SEQ_ID_NO_904   DVPFSSTHLL MEAMDKTQTD EILKNLEV DVVFFDFTH- MLPGLARKIG 130
SEQ_ID_NO_905   DVPFPSTHLL MEAMDKTQND EILKDLKV DVVFYDFTH- MLPSLARKIG 130
SEQ_ID_NO_908   DVPFPSTHLL MEAMDKTQND EILKDLKV DVVFYDFTH- MLPSLARKIG 130
SEQ_ID_NO_891   DISSMDNLL SEALDLTRDQ VEAAVRALRP DLIFFDFAH- MPEIAKEHM 127
SEQ_ID_NO_893   DIPIHLTHFL CVAMDRTRDQ VEKIIRDQKP DFVMYDMAY- MPEVARPLG 133
```

Figure 29 (continued)

| SEQ_ID_NO | Sequence | # |
|---|---|---|
| SEQ_ID_NO_907 | I KAL QF SVF S AVS GAYLMNP ARRL GAG GQL - - P TA DDL TS PP AGF PP SS S | 179 |
| SEQ_ID_NO_912 | AR AA HF SVF T AVT S AYL T VP ARRRL HH G AA SCP T V DDL AT AP V GF PP SS S | 187 |
| SEQ_ID_NO_911 | V KA AL F SVF A AVS G AYVMAP ARRRL P GPWR - - P T V DDL AS AP E GF PP SS P | 196 |
| SEQ_ID_NO_898 | I KSVHF SVY S AI S D AYI T VP S RF ADVE GR N - - I T F EDL KK PPP GYP Q NS N | 177 |
| SEQ_ID_NO_913 | I KTI YF SVY M - - - - AN I VMP S T SKL T GNKP - - S T V EDI K - - - - ALQQ S DG | 175 |
| SEQ_ID_NO_901 | I KTVYYSV VV ALS T AFL T CP AR V L F - PKK Y - - PS L EDM KK PPL GF PQ T SV | 182 |
| SEQ_ID_NO_915 | I KTVFYSVF V ALS T AFL T CP AR V TE - PKK Y - - PT L EDM KK PPL GF PH T SI | 180 |
| SEQ_ID_NO_904 | I KSVFYS T I S P L MHGF AL SP ERRVA - - GKQ - - L T EADMMK AP AS F PDP S I | 176 |
| SEQ_ID_NO_905 | I KSVFYS T I S P L MHGY AL SP ERRVV - GKQ - - L T EADMMK AP AS F PDP S I | 176 |
| SEQ_ID_NO_908 | I KSVFYS T I S P L MHGY AL SP ERRVV - GKQ - - L T EADMMK AP AS F PDP S I | 176 |
| SEQ_ID_NO_891 | I KSV G Y M VS A T T I AYT F AP G - - - - - - - - - - - - GV L GV PPP GYP S SK V | 163 |
| SEQ_ID_NO_893 | I KTI K YSV VS AAA I A I VL VP AR NV V F E GK A - - I T AAEL SV PP T GYP S T SV | 180 |

| SEQ_ID_NO | Sequence | # |
|---|---|---|
| SEQ_ID_NO_907 | I T T VP AYQAA DF SYVF T SF H GEP - CV YDRV LAG V Q AS D AL V I KTC F EMEG | 220 |
| SEQ_ID_NO_912 | L A T VP T YQAA DF TYVF T SF H GMP - S A YDRV AACDK AS D V L V F KTC A EMEG | 236 |
| SEQ_ID_NO_911 | L A T VP AYQAA DF SYVF E SF H GMP - CV YDRV AACHNA C D AL V I KTC A EMEG | 245 |
| SEQ_ID_NO_898 | I - SL KAFEAM DF M F LF T RF G EKN L T G YERV LQS L GE C SF I V F KTCKEI EG | 226 |
| SEQ_ID_NO_913 | L - PV K I T F EAI SLMN V F K SF H - - - - - - D A M DKC I NG C NL M L I KSC R EMEG | 217 |
| SEQ_ID_NO_901 | T - SVR I T F EAR DF L YVF K SF H NGP - T L YDRI QS G L RG C S A I L AKTCS Q MEG | 230 |
| SEQ_ID_NO_915 | T - SVK I T F EAQ DF L YI F K SF N NRP - T V YDRV LS G L KG C S A I L AKTCS Q MEG | 228 |
| SEQ_ID_NO_904 | K - - L HAHEAR GF T ARTVMKF G GDI T F F DRI F T A V SESDG L AYS T CREI EG | 224 |
| SEQ_ID_NO_905 | K - - L HAHEAR GF T ARTVMKF G GDI T F F DRI F T A V SESDG L AYS T CREI EG | 224 |
| SEQ_ID_NO_908 | K - - L HAHEAR GF T ARTVMKF G GDI T F F DRI F T A V SESDG L AYS T CREI EG | 224 |
| SEQ_ID_NO_891 | L - YR EN D AH ALAT I L SI F Y K - - - - RL Y H Q I T T G F KS C DI I AL RTCNEI EG | 207 |
| SEQ_ID_NO_893 | V - L RG H E VR SLLF V S QP V G EGT - T F YER A C I G MKG C D A I AI RSC Y EME E | 227 |

| SEQ_ID_NO | Sequence | # |
|---|---|---|
| SEQ_ID_NO_907 | PYI NYL T AQH GKPV L VTGPV V PEP P QGE - L EERWAR M L S S FPD N AVVF A S | 277 |
| SEQ_ID_NO_912 | PYI EYVA T QY DKPI LVTGPL V PEP P HGE - L EERWE T M L S S FPD N AVVF A S | 285 |
| SEQ_ID_NO_911 | PYI DYI AA E H GKPV L VTGPI V PEP P RGE - L EERWA T M L S S FPD N S VVF A S | 294 |
| SEQ_ID_NO_898 | PYL DYI ET QF RKPV L L SGPL V PEP S TDV - L EEKWSK M L D G FPAK S VI L C S | 275 |
| SEQ_ID_NO_913 | SR I DD V T KQ S TRPVF L I GPV V PEP H SGE - L DE T WAN M L NR FPAK S VI YCS | 266 |
| SEQ_ID_NO_901 | PYI K Y VE A QF NKPV F L I GPV V PDP P SGK - L EEKWA T M L NK F E GGTVI YCS | 279 |
| SEQ_ID_NO_915 | PYI EYVK SQF KKPV LL V GPV V PDP P SGK - L EEKW D A M L NK F E AGTVI YCS | 277 |
| SEQ_ID_NO_904 | QF C DYI ET QF KKPV LL A GPA L PV P SKST - M EQKWSD M L GK F K EGSVI YCA | 273 |
| SEQ_ID_NO_905 | QF C DYI ET QF QKPV LL A GPA L PV P SKST - M EQKWSD M L GK F K EGSVI YCA | 273 |
| SEQ_ID_NO_908 | QF C DYI ET QF QKPV LL A GPA L P Y P SK ST - M EQKWSD M L GK F K EGSVI YCA | 273 |
| SEQ_ID_NO_891 | KF C DYI S SQY HKK V LL TGPM L PE D DTSKP L EEQL S HFLSR FPP R S VVFCA | 257 |
| SEQ_ID_NO_893 | KL CDYI GR QY GKPV F L TGPV L PE S ART P - L EDRWA Q M L NR F E AGSVVFCS | 276 |

Figure 29 (continued)

| | | | | | | |
|---|---|---|---|---|---|---|
| SEQ_ID_NO_907 | FGSETFLPAA | AATELLLGLE | STNRPFFVYL | NFPKGTDTEA | ELAKCTPPGF | 327 |
| SEQ_ID_NO_912 | FGSETFLPTA | AATELLLGLE | ATGDPFVAVL | NFPRSVDAEA | EVKKCMAPGF | 335 |
| SEQ_ID_NO_911 | FGSETFLLHA | AATELLLGLE | ATALPFLAVL | NFPKGTDAEA | ELRKLTPPGL | 344 |
| SEQ_ID_NO_898 | FGSETFLSDY | QIKELASGLE | LTGLPFILVL | NFPSNLSAKA | ELERALPKGY | 325 |
| SEQ_ID_NO_913 | FGSETFLTDD | QIRELALGLE | LTGLPFFLVL | NFPANVDKSA | ELKRTLPDGF | 316 |
| SEQ_ID_NO_901 | FGSETFLTDD | QVKELALGLE | QTGLPFFLVL | NFPANVDVSA | ELNRALPEGF | 329 |
| SEQ_ID_NO_915 | FGSETFLKDD | QIKELALGLE | QTGLPFFLVL | NFPANVDASA | ELNRGLPEGF | 327 |
| SEQ_ID_NO_904 | FGSECTLRKE | QFQELLWGLE | LTGMPFFAAL | KAPFGTDS-- | -IEAAIPEEL | 320 |
| SEQ_ID_NO_905 | FGSECTLRKD | KFQELLWGLE | LTGMPFFAAL | KPPFETES-- | -VEAAIPEEL | 320 |
| SEQ_ID_NO_908 | FGSECTLRKD | KFQELLWGLE | LTGMPFFAAL | KPPFEAES-- | -IEAAIPEEL | 320 |
| SEQ_ID_NO_891 | LGSQIVLEKD | QFQELCLGME | LTGLPFLIAV | KPPRGSST-- | -VEEGLPEGF | 304 |
| SEQ_ID_NO_893 | FGSQLILEKE | QLQELVLGFE | STGLPFLVVL | KPPVGSST-- | -IEEALPEGF | 323 |

| | | | | | | |
|---|---|---|---|---|---|---|
| SEQ_ID_NO_907 | AERTKGRGVV | HTGWQQQHI | LRHRGVGCFV | NHAGLSSVVE | GLVAGCRLVL | 377 |
| SEQ_ID_NO_912 | EERVKGRGVV | HSGWQQQHI | LRHRSVGCYV | NHAGFSSVVE | GLVAGCRLVL | 385 |
| SEQ_ID_NO_911 | EERVKGRGIL | HTGWQQQHI | LRHRSVGCFV | NHSGLSSVVE | GLIAGCRLVL | 394 |
| SEQ_ID_NO_898 | LERVKNRGVV | HSGWFQQQLV | LKHSSVGCYV | CHGSFSSVIE | AMVNECQLVL | 375 |
| SEQ_ID_NO_913 | LERVKDKGIV | HSGWQQRHI | LAHDSVGCYV | FHAGYGSSVIE | GLVNDCQLVM | 366 |
| SEQ_ID_NO_901 | LERVKDKGII | HSGWQQQNI | LAHSSVGCYV | CHAGFSSVIE | ALVNDCQVVM | 379 |
| SEQ_ID_NO_915 | RERVKEKGVI | HSGWQQQHI | LAHTSVGCYV | CHAGFSSVIE | AFMNDCQVVM | 377 |
| SEQ_ID_NO_904 | REKIHGKGIV | HGGWQQQLF | LQHPSVGCFV | SHCGWASLSE | ALVNDCQIVL | 370 |
| SEQ_ID_NO_905 | KEKIQGRGIV | HGEWQQQLF | LQHPSVGCFV | SHCGWASLSE | ALVNDCQIVL | 370 |
| SEQ_ID_NO_908 | KEKIQGRGIV | HGEWQQQLF | LQHPSVGCFV | SHCGWASLSE | ALVNDCQIVL | 370 |
| SEQ_ID_NO_891 | QERVKGRGVV | WGGWQQPLI | LDHPSIGCFV | NHCGPGTIWE | CLMTDCQMVL | 354 |
| SEQ_ID_NO_893 | EERVKGRGVV | WGGWQQLEI | LDHPSIGCFV | NTCGFSSMWE | SLMSDCQIVL | 373 |

| | | | | | | |
|---|---|---|---|---|---|---|
| SEQ_ID_NO_907 | LPMKGDQYLN | AALFARDLRV | GAEVARRDSD | GWFGRGDVSD | AVDTAMAD-- | 425 |
| SEQ_ID_NO_912 | LPMKSDQFFN | AALLARELRV | GTEVARRDGD | GWFGHDAVRD | AVNAAVAD-- | 433 |
| SEQ_ID_NO_911 | LPMKGDQYLN | AALFARELRV | GTEVARRARD | GWFGREDVRD | ALAAAFAG-- | 442 |
| SEQ_ID_NO_898 | LPFKGDQFFN | SKLIANDLKA | GVEVNRSDED | GFFHKEDILE | ALKTVMLEDN | 425 |
| SEQ_ID_NO_913 | LPMKVDQFTN | SKVIALELKA | GVEVNRRDED | GYFGKDDVFE | AVESVMMDTE | 416 |
| SEQ_ID_NO_901 | LPQKGDQILN | AKLVSGDMEA | GVEINRRDED | GYFGKEDIKE | AVEKVMVDVE | 429 |
| SEQ_ID_NO_915 | LPQKGDQLLN | AKLVSGDMKA | GVEVNRRDED | GYFSKDDIEE | AVEKVMVEL- | 425 |
| SEQ_ID_NO_904 | LPQVGDQIIN | ARIMSVSLKV | GVEVEKGEED | GVFSRESVCK | AVKAVM-DEK | 419 |
| SEQ_ID_NO_905 | LPQVGDQIIN | ARIMSVSLKV | GVEVEKGEED | GVFSRESVCK | AVKAVM-DEK | 419 |
| SEQ_ID_NO_908 | LPQVGDQIIN | ARIMSVSLKV | GVEVEKGEED | GVFSRESVCK | AVKAVM-DEK | 419 |
| SEQ_ID_NO_891 | LPFLGDQVLF | TRLMTEEFKV | SVEVSR-EKT | GWFSKEBLSD | AIKSVM-DKD | 402 |
| SEQ_ID_NO_893 | VPHLGDQILN | TRLMAEELKV | AVEVER-DEK | GWFTKENLSN | AIKCVM-DKD | 421 |

Figure 29 (continued)

| SEQ_ID_NO_907 | ···GMEGQG··IKWRDFLMD DAVQKRLADD FVRDFKKFVR A··· | 461 |
|---|---|---|
| SEQ_ID_NO_912 | ···AGGGDDD ERKWREFLTD DAVQRRFVEE FVRELRKLVL ···· | 470 |
| SEQ_ID_NO_911 | ···GEDGGGE EKKWREFLMD DAVQRRFVRE FVAGLRRLKG ···· | 479 |
| SEQ_ID_NO_898 | KEQGKQIREN HMQWSKFLSN KEIQNKFITD LVAQLKSMA- ···· | 464 |
| SEQ_ID_NO_913 | NEPAKSIREN HRKLKEFLQN DEIQKKYIAD FVENLKAL- ···· | 454 |
| SEQ_ID_NO_901 | KDPGKLIREN QKKWKEFLLN KDIQSKYIGN LVNEMTAMAK VSTT | 473 |
| SEQ_ID_NO_915 | ····KVIREN QKKWKEFLLN KDTHSKFVED LVHDMMAMAK LSTT | 465 |
| SEQ_ID_NO_904 | SEIGREVRGN HDKLRGFLLN ADLDSKYMDS FNQKLQDLLG ···· | 459 |
| SEQ_ID_NO_905 | SEIGREVRGN HDKLRGFLMN ADLDSKYMDS FNQKLQDLLG ···· | 459 |
| SEQ_ID_NO_908 | SEIGREVRGN HDKLRGFLLN ADLDSKYMDS FNQKLQDLLG ···· | 459 |
| SEQ_ID_NO_891 | SDLGKLVRSN HAKLKETLGS HGLLTGYVDK FVEELQEYLI ···· | 442 |
| SEQ_ID_NO_893 | SEVGSMKKN HTEWRKLLRS EGFMSSYFDK FFQNMQELVD HK-- | 463 |

Figure 30

```
SEQ_ID_NO_935    MAY--DRRRS-SLFDAFTLS PLPYPVLLIL LMVFLLLSLS WFFDHESFME   47
SEQ_ID_NO_917    MSYYGDRRAE SSIVEAFTLS PLPYPVILVL LMVTLLLGAS WFFTYDDFIE   50
SEQ_ID_NO_925    MSYY-DRRGE SSVLEAFTLS PLPYPVLIL MMVTLLLGAS WFFSYEDFME    49
SEQ_ID_NO_940    MAY--QRGET SSVVEAFTLS PLPYPVLIL LMVMLLGVS WFFTYEDFME      48
SEQ_ID_NO_937    MAYYGDRRPE SSIVEAFTLS PLPYPVLIL LMVSLLLGVS WFFTYEDFIE    50
SEQ_ID_NO_921    MAY--EERRS-SILDSFSLS PLPYPVLLIL AVASVFLSS WYFSLEEAAE     47
SEQ_ID_NO_919    MHY--YRRRS DSIFDAFTLN PLPYPVLLIL AVLSIFLGMS WFFSYEDMVE    48
SEQ_ID_NO_923    MGY--GRSRA SSVLDGFSLN PVPYPVLLIL SLILFLGIS WYLSYEEVVE     48

SEQ_ID_NO_935    ETEEQMSWL LTLPVLILV RWLSSIERL DDTLMGLFRY DRRRPSLYGY     97
SEQ_ID_NO_917    EASQQLSWAL LGVPIALVLL RWSSVDSF EGYLGFYPR ESRWKGRYE-      98
SEQ_ID_NO_925    EASEQFSWFL LGVPIALVLL RWSSVDTF EGYFGFYPT ESRWRG-YP-      96
SEQ_ID_NO_940    EAAEQLSWAL LLVPVALVLL RWSSVDTF DGYFSFYPT ERRWNRWDP-      96
SEQ_ID_NO_937    EAAEQFSWAL LVVPIALVLL RWSSVDSF DGYFFGFYPS ERRWRPGVG-     99
SEQ_ID_NO_921    SAEEQINFAL LLIPLFLIVL VRWLSSMENP DAL-LGWFSS SRRTTYVSPG   96
SEQ_ID_NO_919    TTEEQMGWL LVVPLWLIVI VRWLSSMENP DMI-FVMSPW DKRRRTHHR-    96
SEQ_ID_NO_923    AAEEQLGWML LATPVLILV VRWLSSVDTS EMFFFNSSPW ERRRRTHHF-    97

SEQ_ID_NO_935    SQPQEGSSPW GIAAVLVLLL VMVYF---- ---------- ----------    122
SEQ_ID_NO_917    RGPAEGSSPW GVALLVLLLL VLARAGCGKV VYGNPGRLGR KRRGGDKVKE   148
SEQ_ID_NO_925    AAPSEGSSPW GVAMVVVLLL LLASF---- ---------- ----------    121
SEQ_ID_NO_940    -GPAEGSSPW GVAMVVLLLL VLASF---- ---------- ----------    120
SEQ_ID_NO_937    SAPAEGSSPW GVAMLVLLLI VLASF---- ---------- ----------    124
SEQ_ID_NO_921    AGGDGGSSPW GVAALIVELL VLLQY---- ---------- ----------    121
SEQ_ID_NO_919    --PSEGSSPW GVAAFLVELL VLVKF---- ---------- ----------    119
SEQ_ID_NO_923    --PSEGSSPW GVAALILLVL VLLHY---- ---------- ----------    120

SEQ_ID_NO_935    ---HSSQDM WGP------ ---------- ---------- ----------    132
SEQ_ID_NO_917    QAGDEAAKFP NSGMRLATEK RRRVRRSPSK KGIVLKQKSR KVSLQHRSKK   198
SEQ_ID_NO_925    ---HSTFQDM WKP------ ---------- ---------- ----------    131
SEQ_ID_NO_940    ---HSTFQDM WKP------ ---------- ---------- ----------    130
SEQ_ID_NO_937    ---HETIRDM WRP------ ---------- ---------- ----------    134
SEQ_ID_NO_921    ---QSSFLEM WSG------ ---------- ---------- ----------    131
SEQ_ID_NO_919    ---QSTFLDS MLV------ ---------- ---------- ----------    129
SEQ_ID_NO_923    ---HSTFLDA MFV------ ---------- ---------- ----------    130
```

Figure 30 (continued)

| | | |
|---|---|---|
| SEQ_ID_NO_935 | - - - | 132 |
| SEQ_ID_NO_917 | L K A | 201 |
| SEQ_ID_NO_925 | - - - | 131 |
| SEQ_ID_NO_940 | - - - | 130 |
| SEQ_ID_NO_937 | - - - | 134 |
| SEQ_ID_NO_921 | - - - | 131 |
| SEQ_ID_NO_919 | - - - | 129 |
| SEQ_ID_NO_923 | - - - | 130 |

Figure 31

```
SEQ_ID_NO_947    MGI KFSQGPS NTTIHNRS-- -HQDGEDQRN ETATKLNHDK PQNQSS--SF   45
SEQ_ID_NO_972    MGSL-GPSTI SSMNMAKAAS VVGGKTGVVA VADQQKEVPP KTMNCSSYAF   49
SEQ_ID_NO_967    MGSL-GPAVV VSASAAKM-- ---AGGGQDP STERKETSSA FGGGCCGGGF   44
SEQ_ID_NO_964    MGSLLGPTVT VNVSMTKPDA AAAGGGQQPP --ERKEGGGR CGVLGC--GF   46
SEQ_ID_NO_944    MGSL-GPTVG LSI-MARP-- ----GGQQPA EMERKKDSGV FFGGGC--GF   40
SEQ_ID_NO_946    ---MSGVBCP BSVSSAMP-- -----KDLRP NGYNQHQASK RGTCSC---F   37
SEQ_ID_NO_962    MGSISQPVAN LSLAASAQ-- ---------- --AKQQQRDL H----C---F   29
SEQ_ID_NO_950    MESVTTRPSP NVVGVANS-- ---------- --------K HGVEWCG-HF   28

SEQ_ID_NO_947    QIPLHYPKYT KSDYEKMPEW QLDRLLREYG LPVLGDSYEK RKFAIGAFLW   95
SEQ_ID_NO_972    QMPLHYPRYK KADYESMPEW RVDCLLREYG LPADGDLDSK RKFAMGAFLW   99
SEQ_ID_NO_967    QMPLHYPRYK KADYEAMPEW RVDCLLREYG LPVDGGVEEK RRFAMGAFLW   94
SEQ_ID_NO_964    RMPLHYPRYK KEDYEGMPEW RVDSLLREYG LPADGDLDSK RRFAMGAFLW   96
SEQ_ID_NO_944    RMPLHYPRYK KADYESMPEW RVDCLLREYG LPADGDVDSK RRFAMGAFLW   90
SEQ_ID_NO_946    QMPLHYPRYK KSDYETMPEW RLDCLLKEYG LPAIGDANQK RKFAMGAFLW   87
SEQ_ID_NO_962    RMPLHYPRYT RADYESMPEW KLDCLLREYG LPVTGDVDHK RSFAMGAFLW   79
SEQ_ID_NO_950    QMPLHYPRYT QADYEAMPEW RLDCLLKEYG LPIFGDVESK RKFAMGAFLW   78

SEQ_ID_NO_947    SSENEH      101
SEQ_ID_NO_972    PDQY-       103
SEQ_ID_NO_967    PDQY-       98
SEQ_ID_NO_964    PDQY-       100
SEQ_ID_NO_944    PDQY-       94
SEQ_ID_NO_946    PSENE-      92
SEQ_ID_NO_962    PAH---      82
SEQ_ID_NO_950    IK----      80
```

Figure 32

```
SEQ_ID_NO_976   ------MALH LNTVIDLTVD NYWLFRIPPI TIDFLNKLPQ QSEAPTPASA   44
SEQ_ID_NO_980   MAPSTIYQYH MRQDFSTNVD SN---NSTAP TTDAIIHLQ  FSHVLELCYP   47
SEQ_ID_NO_978   ---------- ---------- -----MARLL FRLLQ ETNSPTPATP            20

SEQ_ID_NO_976   VTAQLTRRFT CSTGDFL-VL VRQPQRVEEM VTAAGLPLEC APSVAEFISL   92
SEQ_ID_NO_980   ETIQIPLNTT NESHLFPRCL FSBHVNRESI VKEILSSMGC SSDFIESAAP   97
SEQ_ID_NO_978   SP-------- --------AL YSDLVF--VV IAALLCALIC VLGLLAVSF-   49

SEQ_ID_NO_976   SVRSNSVRK- ---------- --PVVMTVEV GAPVDEDEDE DEEL------  123
SEQ_ID_NO_980   DISSFALDMV TNPCNASSSE VLTMVLAIHV TTPYDEREEI DRALSESLMQ  147
SEQ_ID_NO_978   --RCVWLRRI ANR------- ---------- SATNSDQPPA NKGLKKKVLK   80

SEQ_ID_NO_976   ---------- ---------- -PPGAVFEEC AICVKEYLVG GATSVKLACS  152
SEQ_ID_NO_980   EASRFKPASK SCIDGLKRMS LEGSCSMKEC MVCLEEFLMG SEV-VCLPCG  196
SEQ_ID_NO_978   SLPKLTYSPD S--------- -PPAEKFAEC AICLMEFAAG DELRVLSQCG  120

SEQ_ID_NO_976   HTFHRKCLDR MTAVNRTCPY CRAPVPVEQD YWDDEDACDN SESESDDIPS  202
SEQ_ID_NO_980   HIFHGDCIVR MLETSHLCPL CRFAMP---- ---------- ----------  222
SEQ_ID_NO_978   HGFHVSCIDT MLGSHSSCPS CRQILV---- ---------- SIARCQKCGG  156

SEQ_ID_NO_976   EEGDDEESEY DDIPSEGGDD EETEHDDIPS EEGDDWESEY EDVPNEEDDG  252
SEQ_ID_NO_980   ---------- ---------- ---------- ---------- ----------  222
SEQ_ID_NO_978   LPGSSSSGPE PDTRIKQDDP NSNNNDNXSX LN-------- ----------  188

SEQ_ID_NO_976   SSPAPDGSSQ EITAASPEFV SSVRDLSLSC LRLD       286
SEQ_ID_NO_980   ---------- ---------- ---------- ----       222
SEQ_ID_NO_978   ---------- ---------- ---------- ----       188
```

Figure 33

| | | | | | | | |
|---|---|---|---|---|---|---|---|
| SEQ_ID_NO_991 | ·MAMGMLEVH | LISGKGLRAH | DPLN------ | ------KPID | PYVEINYKGQ | | 37 |
| SEQ_ID_NO_1032 | ·MAMGMLEVH | LISGKGLQAH | DPLN------ | ------KPID | PYVEINYKGQ | | 37 |
| SEQ_ID_NO_985 | ·MGMGMLEVH | LISGKGLQAH | DPLN------ | ------KPID | PYVDINYKGQ | | 37 |
| SEQ_ID_NO_992 | ·MAMGMLEVH | LISGKGLQAH | DPLN------ | ------KPID | PYVEINYKGQ | | 37 |
| SEQ_ID_NO_1008 | MAGSGVLEVH | LVDAKGLTGN | DFL------- | ------GKID | PYVVVQYRSQ | | 37 |
| SEQ_ID_NO_1001 | ·MPRGTLEVV | LISAKGLEDN | DFL------- | ------SSID | PYVILSYRAQ | | 36 |
| SEQ_ID_NO_1003 | ·MAQGTLEVL | LVGAKGLENT | DYL------- | ------CNMD | PYAVLKCTSQ | | 36 |
| SEQ_ID_NO_1028 | ·MVQGTLEVL | LVGAKGLENT | DYL------- | ------CNMD | PYAVLKCRSQ | | 36 |
| SEQ_ID_NO_984 | ·VPQGKLQVV | LVSAKGLENT | DFL------- | ------CNMD | PYVLLTCRTQ | | 36 |
| SEQ_ID_NO_995 | ·VPEGTIQVV | LVGAKGLENT | DFFNYRVPCN | DVKTYPSNID | PYVLLTCRSQ | | 49 |
| SEQ_ID_NO_982 | ·VPHGTLEVV | LVSAKGLEDS | DFL------- | ------NSMD | PYVLLTCRTQ | | 36 |
| SEQ_ID_NO_996 | ·VPHGTLEVV | LVSAKGLEDA | DFL------- | ------NNMO | PYVQLTCRTQ | | 36 |
| SEQ_ID_NO_1011 | ·MVRGKLEVL | LVSAKGLDDS | DFF------- | ------NSMD | PYVILTCRSH | | 36 |
| SEQ_ID_NO_1023 | ·MVHGKLEVL | LVSAKGLEDT | DFL------- | ------NNMD | PYVILTCRTQ | | 36 |
| SEQ_ID_NO_1026 | ·········· | ·········· | ·········· | ········MD | PYVILTCRTQ | | 12 |

| | | | | | | | |
|---|---|---|---|---|---|---|---|
| SEQ_ID_NO_991 | ERMSKVAKNA | GPDPVMNEKF | KFLAEYPGSG | GDFLLFKVM | DHDVIDGDDY | | 87 |
| SEQ_ID_NO_1032 | ERMSKVAKNA | GPDPVMNEKF | KFLAEYPGSG | GDFLLFKVM | DHDVIDGDDY | | 87 |
| SEQ_ID_NO_985 | ERMSGVAKNG | GPNPLMDEKF | KFLAEYPGSG | GDFHLFKVM | DHDAIDGDDY | | 87 |
| SEQ_ID_NO_992 | ERMSKVAKNA | GPDPLMDEKF | KFLAEYPGSG | GDFHVLFKVM | DHDAIDGDDY | | 87 |
| SEQ_ID_NO_1008 | ERKSSVARDQ | GKNPSMNEVF | KFDINSTAAT | GDHKLFLRLM | DHDTFSRDDF | | 87 |
| SEQ_ID_NO_1001 | EHKSTVQEGA | GSNPQWNETF | LFTV---SD | SASELNLRIM | EKDNFNNDDN | | 82 |
| SEQ_ID_NO_1003 | EQKSTVASGK | GSDPEWNETF | VFTV---SE | NATELVIKLL | DSDGGTDDDS | | 82 |
| SEQ_ID_NO_1028 | EQKSSVASGK | GSDPEWNETF | MFSV---TH | NATELIIKLM | DSDSGTDDDF | | 82 |
| SEQ_ID_NO_984 | EQKSSVASGK | GSEPEWNEDF | FNI---SE | GASELALKIM | DSDAGSQDDF | | 82 |
| SEQ_ID_NO_995 | EQRSSVASGQ | GSEPEWNETF | VFTI---SE | GTSELVLKIV | DHDTLTDDDY | | 95 |
| SEQ_ID_NO_982 | DQKSNVASGQ | GTTPEWNETF | FNV---SE | GTTELKAKIF | DTDVGTEDDP | | 82 |
| SEQ_ID_NO_996 | DQKSNVAEGM | GTTPEWNETF | FTV---SE | GTTELKAKIF | DKDVGTEDDA | | 82 |
| SEQ_ID_NO_1011 | EQKSTVASGA | GSEPEWNETF | FFAV---SS | DSPELRVKIM | DSDALSADDL | | 82 |
| SEQ_ID_NO_1023 | EQKSSVANGE | GSEPEWNETF | FTV---SD | DTPQLNLKIM | DSDFVTNDDF | | 81 |
| SEQ_ID_NO_1026 | EQKSSVAKGA | GSEPEWNETF | VFTV---SD | DVPQLNVKIM | DSDAFSADDF | | 58 |

Figure 33 (continued)

| | | |
|---|---|---|
| SEQ_ID_NO_991  | GDVSIDVKD LLVEGVRKGW SELPPRMYQV AHKLYFKGE EVGVSFKRQ | 137 |
| SEQ_ID_NO_1032 | GDVSIDVKD LLVEGVRKGW SELPPRMYQV AHKLYFKGE EVGVSFKRQ | 137 |
| SEQ_ID_NO_985  | GDVKIDVKD LLAEGVRKGW SEPPPRMYHV AHKIHFKGE EVGVSFKLQ | 137 |
| SEQ_ID_NO_992  | GDVKIDVKD LLAEGVRKGW SEPRPRMYHV AHKIHFKGE EVGVSFKLQ | 137 |
| SEQ_ID_NO_1008 | GEATINNTD LISLGMEHGT WEMSESKHRV LADKIVHGE RVSLTFTAS | 137 |
| SEQ_ID_NO_1001 | GEAIPLEA VFEEG----SLAENAYKL VKEQEYCGE KVALTFTPE | 125 |
| SEQ_ID_NO_1003 | VGEATIPLDG VYTEG----SIPPTVYNV VKDEEYRGE KIGLTFTPE | 125 |
| SEQ_ID_NO_1028 | VGEATISEA YTEG----SIPPTVYNV VKEEEYRGE KVGLTFTPE | 125 |
| SEQ_ID_NO_984  | VEEVAIPLEP VFIER----NIPLTPYTV VKDGEYRGE KFGLTFTPE | 125 |
| SEQ_ID_NO_995  | LGKASIPLEP LFIEG----NLPITAYNV VKDEEYRGE RVGLSFTPE | 138 |
| SEQ_ID_NO_982  | LGEATIPLEA VFLEG----DPPAAYNV VKDEEFKGE IALSFKPS | 125 |
| SEQ_ID_NO_996  | VGEATIPLEP VFMEG----SIPPTAYNV VKDEEYKGE IWALSFKPS | 125 |
| SEQ_ID_NO_1011 | VGEACIPLEA VLQEG----SLPPAVHRV VKDEEYRGE KIALTFTPA | 125 |
| SEQ_ID_NO_1023 | VGEASIPLEA VFQEG----SLPPTVHPV VKEEKYCGE KLALTFTPA | 124 |
| SEQ_ID_NO_1026 | VGEANIPLEP VFLEG----GLPPAVHRV VKEEKYCGE KVALTFTPA | 101 |

| | | |
|---|---|---|
| SEQ_ID_NO_991  | ---------- ---------- ---------- ---------- ---------- | 137 |
| SEQ_ID_NO_1032 | ---------- ---------- ---------- ---------- ---------- | 137 |
| SEQ_ID_NO_985  | ---------- ---------- ---------- ---------- --GGGGCGGC | 145 |
| SEQ_ID_NO_992  | ---------- ---------- ---------- ---------- --GGGGCAGC | 145 |
| SEQ_ID_NO_1008 | ---------- ---------- ---------- ---------- AKAQDHAEQV | 147 |
| SEQ_ID_NO_1001 | ---------- ---------- ---------- ---------- --RNDEEETC | 133 |
| SEQ_ID_NO_1003 | --E------- ---------- ---------- ---------- A RDEDQPEENY | 137 |
| SEQ_ID_NO_1028 | --D------- ---------- ---------- ---------- D RDRGLSEEDI | 137 |
| SEQ_ID_NO_984  | ERE------- ---------- ---------- ---------- S RDFEV-EESF | 138 |
| SEQ_ID_NO_995  | RRT------- ---------- ---------- ---------- S RTFDAGEESY | 152 |
| SEQ_ID_NO_982  | --E------- ---------- ---------- ---------- N RSRGFEEESY | 137 |
| SEQ_ID_NO_996  | --E------- ---------- ---------- ---------- N RSRGMDEESY | 137 |
| SEQ_ID_NO_1011 | ---------- ---------- ---------- ---------- -EENEEEESY | 134 |
| SEQ_ID_NO_1023 | -VE------- ---------- ---------- ---------- T RRPDNEEGTY | 137 |
| SEQ_ID_NO_1026 | AVKTLTSVSC NIDGVVAIVS EHLVGVCDAN VLDTRISSGN SPSSQPRERG | 151 |

Figure 33 (continued)

| | | |
|---|---|---|
| SEQ_ID_NO_991 | -G--------- | 138 |
| SEQ_ID_NO_1032 | -G--------- | 138 |
| SEQ_ID_NO_985 | NPWEN------ | 150 |
| SEQ_ID_NO_992 | YPWEN------ | 150 |
| SEQ_ID_NO_1008 | GGWAHSFRQ--- | 156 |
| SEQ_ID_NO_1001 | GGWKESTRDF-- | 143 |
| SEQ_ID_NO_1003 | GGWNQSS----- | 144 |
| SEQ_ID_NO_1028 | GGWKQSS----- | 144 |
| SEQ_ID_NO_984 | GGWKQSSYTD-- | 148 |
| SEQ_ID_NO_995 | GGWKESAYTD-- | 162 |
| SEQ_ID_NO_982 | GGWKNSEASY-- | 147 |
| SEQ_ID_NO_996 | GGWKNSEASY-- | 147 |
| SEQ_ID_NO_1011 | GGWNQST----- | 141 |
| SEQ_ID_NO_1023 | SSWN------- | 141 |
| SEQ_ID_NO_1026 | GGLQQLELIACY | 163 |

Figure 34

| SEQ_ID_NO | Sequence | # |
|---|---|---|
| SEQ_ID_NO_1058 | MHRFASGLAS - - - - - - - - - - - - - - - - - - - KARL ARKGANQI AS RSSWSRN- - - | 31 |
| SEQ_ID_NO_1077 | - - - MASTFAG MSSAGPLAAP STSSNKLSSV ANI SSTSFGS KRNVALRKSR | 47 |
| SEQ_ID_NO_1078 | - - - MASTFAG MSSAGPLAAP STSSNKLSSV ANI SSTSFGS KRNVALRKSR | 47 |
| SEQ_ID_NO_1075 | - - - MNTQI HP - - HTSLLFFP PN - - - RFNF ISSFSSF- - - - - - - - RRRNP | 33 |
| SEQ_ID_NO_1095 | - - - MTTARGL - - - - - - - - - - - - - - - - SART TRGA- - - - - - - - - - SNRRV | 20 |
| SEQ_ID_NO_1055 | - - - MAQSQLA - - - - - - - - - - - - - - - - KGSR QTTGRPFQNK P- - - - ARAAR | 27 |
| SEQ_ID_NO_1080 | - - - MATIPTT - - GSASLLRG SA - - ALQRD GRSTRPSSAA RPLPGRRARS | 42 |
| SEQ_ID_NO_1086 | - - - MATMPST CASSSSLFLL LR- - - - KDRR SSRSASL- - - - - - - - PGPAR | 35 |
| SEQ_ID_NO_1085 | - - - MATIPTT - - DSALLLGS SA - - - LHRA RRASAARLPG A- - - - NRRRP | 37 |
| SEQ_ID_NO_1097 | - - - MATIPTT - - DSGLLLGS - - - - - - SALL RRTRRAASSA RLPAAARRRP | 39 |
| SEQ_ID_NO_1054 | - - - MASANAI - - STASPFRP LS - - - QGRL - - - - - - - - - - - - - - ATRSQ | 25 |
| SEQ_ID_NO_1088 | - - - MASANAI - - STASLLRS FS - - - SQGRV RRAK- - - - - - - - - - NGRAQ | 31 |
| SEQ_ID_NO_1068 | - - - MASANAL - - SSASVLCS SR- - - - QSKL G- GGNQQQGQ RVSYNKRTIR | 40 |
| SEQ_ID_NO_1072 | - - - MATANAL - - SSPSVLCS SR- - - - QGKL S- GGSQQKGQ RVSY- RKANR | 39 |
| SEQ_ID_NO_1057 | - - - MASANAL - - SSASILCS PN - - - KGSL RRKGNQRQNQ RVNY- RQGNN | 40 |
| SEQ_ID_NO_1061 | - - - MATSNAL - - STASILCS PK- - - - QGGL RRRGNQQNNS RLNY- GLSSR | 40 |
| SEQ_ID_NO_1076 | - - - MASTNAL - - SSTSILRS PTN- - - QAQT SLSKKVKQHG RVNF- RQKPN | 41 |
| SEQ_ID_NO_1092 | - - - MASTNAL - - SSTSILRS PTNN- - QAQT SLSKKAKQHG RVNY- RQNPN | 42 |
| SEQ_ID_NO_1074 | - - - MASTNAL - - SSASILRS PN - - - RQSL TRRANH- - NG RVNY- RKPNN | 38 |
| SEQ_ID_NO_1083 | - - - MASTNAL - - SSASILRS PN - - - HQSL SRRANQ- - NG RVNY- RQPNH | 38 |

| SEQ_ID_NO | Sequence | # |
|---|---|---|
| SEQ_ID_NO_1058 | - - - - - - YAAK DWKFGVEARG - - LMLKGVED LADAVKVTMG PKGRNVVIEQ | 73 |
| SEQ_ID_NO_1077 | RLTL- AAAK ELHFNKDGSA IKKLQNGVNK LADLVGVTLG PKGRNVVLES | 96 |
| SEQ_ID_NO_1078 | RPTL- AAAK ELHFNKDGSA IKKLQNGVNK LADLVGVTLG PKGRNVVLES | 96 |
| SEQ_ID_NO_1075 | QFAVR- ASPK KISFGKECRE - - NLQVGIDK LADAVSLTVG PKGRNVILSE | 80 |
| SEQ_ID_NO_1095 | QVQVR- AEAK KLTFDMASRR - - KIQAGIDK LADAVGVTLG PRGRNVVLEE | 67 |
| SEQ_ID_NO_1055 | RLVI RAADAK EIVFDQESRR - - RLQAGINK VADAVGVTLG PRGRNVVLEQ | 75 |
| SEQ_ID_NO_1080 | LSVVR- ASAK DIAFDQASRS - - ALQAGVEK LAAAVGVTLG PRGRNVVLDE | 89 |
| SEQ_ID_NO_1086 | RLGVVRASAK EIAFDQGSRS - - SLQAGVEK LAAAVATLG PRGRNVVLDE | 83 |
| SEQ_ID_NO_1085 | QALVR- ASAK EIAFDQGARA - - SLQAGVEK LAAAVGVTLG PRGRNVVLDE | 84 |
| SEQ_ID_NO_1097 | QLLVR- ASAK EIAFDQGSRA - - SLQAGVEK LAAAVGVTLG PRGRNVVLDE | 86 |
| SEQ_ID_NO_1054 | RFVVR- ANAK DIAFDQKSRA - - ALQAGVEK LANAVGVTLG PRGRNVVLDE | 72 |
| SEQ_ID_NO_1088 | RLVVR- ADAK DIAFDQKSRA - - ALQAGVEK LANAVGVTLG PRGRNVVLDE | 78 |
| SEQ_ID_NO_1068 | RFSVR- ANVK EIAFDQHSRA - - ALQAGIDK LADCVGLTLG PRGRNVVLDE | 87 |
| SEQ_ID_NO_1072 | RFSLR- ANVK EIAFDQSSRA - - ALQAGIDK LADAVGLTLG PRGRNVVLDE | 86 |
| SEQ_ID_NO_1057 | RFGVK- ACAK EIAFDQSSRA - - AMQAGIDK LADAVGLTLG PRGRNVVLDE | 87 |
| SEQ_ID_NO_1061 | RFSVR- ANAK DIAFDQKSRA - - ALQSGIDK LADAVGLTLG PRGRNVVLDE | 87 |
| SEQ_ID_NO_1076 | RFVVK- AAAK DIAFDQHSRS - - AMQAGIDK LADAVGLTLG PRGRNVVLDE | 88 |
| SEQ_ID_NO_1092 | RFMVK- AAAK DIAFDQHSRR - - AMQAGIDK LADAVGLTLG PRGRNVVLDE | 89 |
| SEQ_ID_NO_1074 | RFSVK- ASAK EIAFDQHSRS - - AMQAGIDK LADAVGLTLG PRGRNVVLDE | 85 |
| SEQ_ID_NO_1083 | RFAVK- ASAK EIAFDQSSRA - - AIQAGIDK LADAVGLTLG PRGRNVVLDE | 85 |

Figure 34 (continued)

| | | | | | | |
|---|---|---|---|---|---|---|
| SEQ_ID_NO_1058 | SYGAPKVTKD | GVTVAKSI EF | KDKVKNVGAS | LVKQVANATN | DVAGDGTTCA | 123 |
| SEQ_ID_NO_1077 | KYGAPKI VND | GVTVAREVEL | EDPVKNI GAK | LVRQAAAKTN | DLAGDGTTTS | 146 |
| SEQ_ID_NO_1078 | KYGAPKI VND | GVTVAREVEL | EDPVENI GAK | LVRQAAAKTN | DLAGDGTTTS | 146 |
| SEQ_ID_NO_1075 | -SGKLKVI ND | GVTI ARSI EL | SDAI ENAGAM | LI QEVASKMN | DLAGDGTSTA | 129 |
| SEQ_ID_NO_1095 | KFGMPQVI ND | GVTI ARAI EL | PDPVENAGAD | LI KEVAGRTN | DSAGDGTTTA | 117 |
| SEQ_ID_NO_1055 | KFGVPQVI ND | GVSI RRAI EL | KDPVENAGAD | LI KEVAGRTN | DAAGDGTTTA | 125 |
| SEQ_ID_NO_1080 | -FGSPKVVND | GVTI ARAI EL | ADPMENAGAA | LI REVASKTN | DSAGDGTTTA | 138 |
| SEQ_ID_NO_1086 | -FGSPKVVND | GVTI ARAI EL | ADPMENAGAA | LI REVASKTN | DSAGDGTTTA | 132 |
| SEQ_ID_NO_1085 | -FGTPKVVND | GVTI ARAI EL | ADPMENAGAS | LI REVASKTN | DSAGDGTTTA | 133 |
| SEQ_ID_NO_1097 | -FGTPKVVND | GVTI ARAI EL | ADPMENAGAA | LI REVASKTN | DSAGDGTTTA | 135 |
| SEQ_ID_NO_1054 | -YGNPKVVND | GVTI ARAI EL | YDPMENAGAA | LI REVASKTN | DSAGDGTTTA | 121 |
| SEQ_ID_NO_1088 | -YGSPKVVND | GVTI ARAI EL | YDPMENAGAA | LI REVASKTN | DSAGDGTTTA | 127 |
| SEQ_ID_NO_1068 | -FGSPKVVND | GVTI ARAI EL | PNAMENAGAA | LI REVASKTN | DSAGDGTTTA | 136 |
| SEQ_ID_NO_1072 | -FGSPKVVND | GVTI ARAI EL | PDAMENAGAA | LI REVASKTN | DSAGDGTTTA | 135 |
| SEQ_ID_NO_1057 | -FGSPKVVND | GVTI ARAI EL | PNAMENAGAA | LI REVASKTN | DSAGDGTTTA | 136 |
| SEQ_ID_NO_1061 | -FGSPKVVND | GVTI ARAI EL | PDPMENAGAA | LI REVASKTN | DSAGDGTTTA | 136 |
| SEQ_ID_NO_1076 | -FGSPKVVND | GVTI ARAI EL | PDPMENAGAA | LI REVASKTN | DSAGDGTTTA | 137 |
| SEQ_ID_NO_1092 | -FGSPKVVND | GVTI ARAI EL | PDPMENAGAA | LI REVASKTN | DSAGDGTTTA | 138 |
| SEQ_ID_NO_1074 | -FGSPKVVND | GVTI ARAI EL | PDPMENAGAA | LI REVASKTN | DSAGDGTTTA | 134 |
| SEQ_ID_NO_1083 | -FGSPKVVND | GVTI ARAI EL | PDAMENAGAA | LI REVASKTN | DSAGDGTTTA | 134 |

| | | | | | | |
|---|---|---|---|---|---|---|
| SEQ_ID_NO_1058 | TI LTRAI FTE | GCKSVAAGMN | AMDLRRGI SM | AVDSVVTNLK | SRARMSTSE | 173 |
| SEQ_ID_NO_1077 | VVLAQGLI AE | GVKVVAAGAN | PVLI TRGI EK | TAKALVAELK | NMSKEVEDS- | 195 |
| SEQ_ID_NO_1078 | VVLAQGLI AE | GVKVVAAGAN | PVLI TRGI EK | TAKALVAELK | NMSKEVEDS- | 195 |
| SEQ_ID_NO_1075 | I I LARAMI KG | GLSAVAFGAN | PI SLKKGMEK | TVKDLVKFLK | KRSI PVEGRD | 179 |
| SEQ_ID_NO_1095 | SVLAREMI KY | GLQSVAAGAN | PVTVKRGMDK | TSEFCRKKLD | ELTI PVRNAA | 167 |
| SEQ_ID_NO_1055 | SVLAREMI HY | GLQSVTAGAN | PI AVKRGLDK | TAEYLVAKLK | EHAKPVKGRD | 175 |
| SEQ_ID_NO_1080 | SVLAREI I KL | GLLSVTSGAN | PVSI KKGI DK | TVQSLVEELE | KKSRPVKGSG | 188 |
| SEQ_ID_NO_1086 | SVLAREI I KL | GLLSVTSGAN | PVSI KKGI DK | TVHSLVEELE | KKSRPVKGSG | 182 |
| SEQ_ID_NO_1085 | SVLAREI I KL | GMLSVTSGAN | PVSI KKGI DK | TVQKLVEELE | KKSRPVKGGG | 183 |
| SEQ_ID_NO_1097 | SVLAREI I KL | GMLSI TSGAN | PVSVKKGI DK | TVQKLVEELE | KKSRPVKGSG | 185 |
| SEQ_ID_NO_1054 | CVLAREI I KL | GLLSVTSGAN | PVSLKKGI DK | TVQGLI QELE | NKSRPI KGGG | 171 |
| SEQ_ID_NO_1088 | SVLAREI I KL | GLLSVTSGAN | PVSLKKGI DK | TVHGLI EELE | KKARPVKGSG | 177 |
| SEQ_ID_NO_1068 | SI LAREI I KH | GLLSVTSGAN | PVSLKRGI DK | TVQGLI EELQ | KKARPVKGRD | 186 |
| SEQ_ID_NO_1072 | SVLAREI I KH | GLLSVTSGAN | PVSLKRGI DK | TVQALI EELE | KRSRPVKGGR | 185 |
| SEQ_ID_NO_1057 | SVLAREI I KL | GLLTVTSGAN | PVSVKRGI DK | TVQSLI EELE | KKARPVKGRD | 186 |
| SEQ_ID_NO_1061 | SVLAREI I KL | GLLSVTSGAN | PVSI KRGI DK | TVQGLVEELE | KKARPVKGRD | 186 |
| SEQ_ID_NO_1076 | SI LAREI I KL | GLLNVTSGAN | PVSI KKGI DK | TVAALVEELE | KLARPVKGGD | 187 |
| SEQ_ID_NO_1092 | SI LAREI I KL | GLLSVTSGAN | PVSI KKGI DK | TVAGLI EELE | KLARPVKGGD | 188 |
| SEQ_ID_NO_1074 | SVLAREI I KL | GLLSVTSGAN | PVSLKRGI DK | TVQGLVEELE | KKARPVKGGD | 184 |
| SEQ_ID_NO_1083 | SVLAREI I KL | GLLSVTSGAN | PVSLKRGI DK | TVQGLVEELE | KRARPVKGGD | 184 |

Figure 34 (continued)

| | | | | | | | |
|---|---|---|---|---|---|---|---|
| SEQ_ID_NO_1058 | EIAQVGTISA | NGEREGELI | AKAMEKVGKE | GVITISDGKT | LFNELEVVEG | 223 |
| SEQ_ID_NO_1077 | ELPDVAAVSA | GNNLEVGSMI | AEPMSTVGRK | GVVTLEEGKS | AENSLRVVEG | 245 |
| SEQ_ID_NO_1078 | ELADVAAVSA | GNNLEVGSMI | AEAMGKVGRK | GVVTLEEGKS | AENSLRVVEG | 245 |
| SEQ_ID_NO_1075 | HIKAVASISA | GNDEYVGNLI | AEAIEKIGFD | GVITIESSRS | SETSYVIEEG | 229 |
| SEQ_ID_NO_1095 | DIRAVASISA | GNNEEGNMI | AEAIEKVGPD | GVLSIETGSG | LETVVEVEEG | 217 |
| SEQ_ID_NO_1055 | DIKNVASISA | GNDNAGEMI | ADALDKVGSN | GVLSIETSNS | TETVVEVQEG | 225 |
| SEQ_ID_NO_1080 | DIKAIAAISA | GNDDFGTMI | AEAINKVGPD | GVLSIESSSS | FETTVEVEEG | 238 |
| SEQ_ID_NO_1086 | DIKAVAAISA | GNDDFVGTMI | AEAIDKVGPD | GVLSIESSSS | FETTVEVEEG | 232 |
| SEQ_ID_NO_1085 | DIKAVAAISA | GNDEFVGTMI | AEAIDKVGPD | GVLSIESSSS | FETTVEVEEG | 233 |
| SEQ_ID_NO_1097 | DIKAVAAISA | GNDEFVGTMI | AEAIDKVGPD | GVLSIESSSS | FETTVEVEEG | 235 |
| SEQ_ID_NO_1054 | DIKAVASISA | GNDEFGSMI | AEAIDKVGPD | GVLSIESSSS | FETTVEVEEG | 221 |
| SEQ_ID_NO_1088 | DIKAVASISA | GNDELGSMI | ADAIDKVGPD | GVLSIESSSS | FETTVDVEEG | 227 |
| SEQ_ID_NO_1068 | DIRAVASISA | GNDDLGSMI | ADAIDKVGPD | GVLSIESSSS | FETTVEVEEG | 236 |
| SEQ_ID_NO_1072 | DIKAVATISA | GNDELGAMI | ADAIDKVGPD | GVSPIESSSS | FETTVEVEEG | 235 |
| SEQ_ID_NO_1057 | DIKAVASISA | GNDDLGTMV | ADAIDKVGPD | GVLSIESSSS | FETTVDVEEG | 236 |
| SEQ_ID_NO_1061 | DIKAVASISA | GNDELGTMI | ADAIDKVGPD | GVLSIESSSS | FETVVEVEEG | 236 |
| SEQ_ID_NO_1076 | DIKAVATISA | GNDELGKMI | AEAIDKVGPD | GVLSIESSNS | FETTVEVEEG | 237 |
| SEQ_ID_NO_1092 | DIKAVASISA | GNDELGKMI | AEAIDKVGPD | GVLSIESSSS | FETTVEVEEG | 238 |
| SEQ_ID_NO_1074 | DIKAVASISA | GNDELGQMI | AEAIDKVGPD | GVLSIESSSS | FETTVEVEEG | 234 |
| SEQ_ID_NO_1083 | DIKAVASISA | GNDELGKMI | AEAIDKVGPD | GVLSIESSSS | FETTVEVEEG | 234 |

| | | | | | | | |
|---|---|---|---|---|---|---|---|
| SEQ_ID_NO_1058 | MKLDRGYISP | YFITNQKNQK | CELDDPLILI | HEKKISSINS | VVKVLELALK | 273 |
| SEQ_ID_NO_1077 | MQFDRGYFAP | YFVTDSEKMS | VEYDNCKLLL | VDKKITNAKD | LVNVLKDAIR | 295 |
| SEQ_ID_NO_1078 | MQFDRGYVSP | YFVTDSEKMS | VEYENCKLLL | VDKKITNARD | LVNVLEDAIR | 295 |
| SEQ_ID_NO_1075 | MKIDRGYMSP | HFITNDEKSI | VEFDNAKVLV | TDQKISSVRE | IVPLLEKAMQ | 279 |
| SEQ_ID_NO_1095 | MEIDRGYISP | QFVNDNERLM | VEYEGCRILI | TDEKIEQVQM | LVPLLEEVSQ | 267 |
| SEQ_ID_NO_1055 | MEIDRGYISP | QFVTNQERLL | VEYDNCRVLV | TDQKIDAIRD | IIPILEQVTR | 275 |
| SEQ_ID_NO_1080 | MEIDRGYISP | QFVTNSEKSV | VEFENARVLV | TDQKISSIKE | ILPLLEQTTQ | 288 |
| SEQ_ID_NO_1086 | MEIDRGYISP | QFVTNPEKSL | VEFENARILV | TDQKISSIKE | IIPLLEQTTQ | 282 |
| SEQ_ID_NO_1085 | MELDRGYISP | QFVTNPEKST | VEFENARILV | TDQKISSIKE | ILPLLEQTTQ | 283 |
| SEQ_ID_NO_1097 | MELDRGYISP | QFVTNPEKST | VEFENARILV | TDQKISSIKE | IIPLLEQTTQ | 285 |
| SEQ_ID_NO_1054 | MEIDRGYISP | QFVTNLEKSI | VEFENCKVLI | TDQKITSIKE | ILPILEKTTQ | 271 |
| SEQ_ID_NO_1088 | MEIDRGYISP | QFVTNLEKSI | VEFENAKVLI | TDQKITSIKE | ILPILEKTTQ | 277 |
| SEQ_ID_NO_1068 | MEIDRGYISP | QFVTNPEKLL | AEFENARVLI | TDQKITAIKD | IPILEKTTQ | 286 |
| SEQ_ID_NO_1072 | MEIDRGYISP | QFVTNPEKLL | VEFENARVLI | TDQKITAIKD | IPILEKTTQ | 285 |
| SEQ_ID_NO_1057 | MEIDRGYISP | QFVTNPEKLL | CEFENARVLV | TDQKITAIKD | IPLLEKTTQ | 286 |
| SEQ_ID_NO_1061 | MEIDRGYISP | QFVTNPEKLL | CEFENARVLI | TDQKITAIKD | IPLLEKTTQ | 286 |
| SEQ_ID_NO_1076 | MEIDRGYISP | QFVTNPEKSI | VEFENARVLI | TDQKISAIKD | IPLLEKTTQ | 287 |
| SEQ_ID_NO_1092 | MEIDRGYISP | QFVTNLEKSI | VEFENARVLI | TDQKISAIKD | IPLLEKTTQ | 288 |
| SEQ_ID_NO_1074 | MEIDRGYISP | QFVTNPEKL | VEFENARVLI | TDQKISAIKD | IPLLEKTTQ | 284 |
| SEQ_ID_NO_1083 | IEIDRGYISP | FVTNLEKSI | VEFENARVLV | TDQKISAIKD | IPLLEKTTQ | 283 |

Figure 34 (continued)

| | | | | | | | |
|---|---|---|---|---|---|---|---|
| SEQ_ID_NO_1058 | RQ- RPLLIVS | EDVESDALAT | LILNKLRAG | KVCAIKAPGF | GENRKAGLHD | 322 |
| SEQ_ID_NO_1077 | NG- SPTLIIA | ENIDQEALAT | LVVNKLRGAL | KVAALKAPGF | GERKSQYLDD | 344 |
| SEQ_ID_NO_1078 | NG- YPILIIA | EDIEQEALAT | LVVNKLRGAL | KVAALKAPGF | GERKSQYLDD | 344 |
| SEQ_ID_NO_1075 | LS- APLLIIA | EDVTAQVLET | LIVNKMQGLL | RVAAVKCPGL | GDGKKALLQD | 328 |
| SEQ_ID_NO_1095 | AGSPPLLIIA | EDITGEALAT | LVVNKMRGVL | KVAAIKAPGF | GERRKALLQD | 317 |
| SEQ_ID_NO_1055 | LN- APLLIIA | EDVSGEALAT | LVVNKLRGVL | NVCAIKAPGF | GERRKSLLQD | 324 |
| SEQ_ID_NO_1080 | LR- APLLIIA | EDVSGEALAT | LVVNKLRGIL | NVAAIKAPGF | GERRKALLQD | 337 |
| SEQ_ID_NO_1086 | LR- APLLIIA | EDVAGEALAT | LVVNKLRGIL | NVAAIKAPGF | GERRKALLQD | 331 |
| SEQ_ID_NO_1085 | LR- APLLIIA | EDVSGEALAT | LVVNKLRGIL | NVAAIKAPGF | GERRKALLQD | 332 |
| SEQ_ID_NO_1097 | LR- APLLIIA | EDVSGEALAT | LVVNKLRGIL | NVAAIKAPGF | GERRKALLQD | 334 |
| SEQ_ID_NO_1054 | LR- APLFIIA | EDITGEALAT | LVVNKLRGIL | NVAAIKAPSF | GERRKAVLQD | 320 |
| SEQ_ID_NO_1088 | LR- APLFIIA | EDITGEALAT | LVVNKLRGIL | NVAAIKAPSF | GERRKAVLQD | 326 |
| SEQ_ID_NO_1068 | LR- APLLIIA | EDVTGEALAT | LVVNKLRGVL | NVMAVKAPGF | GERRKAMLQD | 335 |
| SEQ_ID_NO_1072 | LR- APLLIIA | EDVTGEALAT | LVVNKLRGVL | NVMAVKAPGF | GERRKAMLQD | 334 |
| SEQ_ID_NO_1057 | LR- APLLIIA | EDVTGEALAT | LVVNKLRGIL | NVAAIKAPSF | GERRKAVLQD | 335 |
| SEQ_ID_NO_1061 | LR- APLLIIA | EDVTGEALAT | LVVNKLRGVL | NVAAIKAPGF | GERRKAMLQD | 335 |
| SEQ_ID_NO_1076 | LR- APLLIIS | EDITGEALAT | LVVNKLRGIL | NVAAIKAPGF | GERRKALLQD | 336 |
| SEQ_ID_NO_1092 | LR- APLFIIA | EDITGEALAT | LVVNKLRGIL | NVAAIKAPGF | GERRKALLQD | 337 |
| SEQ_ID_NO_1074 | LR- APLLIIA | EDVTGEALAT | LVVNKLRGIL | NVAAIKAPGF | GERRKALLQD | 333 |
| SEQ_ID_NO_1083 | LR- APLIIIA | EDVTGEALAT | LVVNKLRGIL | NVAAIKAPSF | GERRKAVLQD | 332 |

| | | | | | | | |
|---|---|---|---|---|---|---|---|
| SEQ_ID_NO_1058 | LAVLTGGQLI | TEELGMNLEK | VDLDMLGSCK | KITISKDDTV | LDGAGDKKS | 372 |
| SEQ_ID_NO_1077 | IATLTGGTVI | REELGLTLDK | ADKEVLGHAA | KVVLTKDATT | VGDGSTQEA | 394 |
| SEQ_ID_NO_1078 | IATLTGGTVI | REELGLTLDK | ADKEVLGHAA | KVVLTKDATT | VGDGSTQEA | 394 |
| SEQ_ID_NO_1075 | ALMTGADFL | CGDLGLTLEG | TTSDQLGSAL | KVKITSNATT | FADPNTKAE | 378 |
| SEQ_ID_NO_1095 | AIVTGAQYI | AKDLGLSVQR | ATMDSLGYAR | KVSIAQTTTT | LIADGASKED | 367 |
| SEQ_ID_NO_1055 | AIVTGAEFL | AKDLGMKVEQ | AVVEQLGVAR | KVTVANNTTT | LIADAASKDE | 374 |
| SEQ_ID_NO_1080 | AIVTGAEFQ | AKDLGQLIEQ | TTVEQLGIAR | KVTISGSSTT | IADVATKDE | 387 |
| SEQ_ID_NO_1086 | AIVTGAEFQ | AKDLGLLVES | TTVEQLGIAR | KVTISQSSTT | IADVATKDE | 381 |
| SEQ_ID_NO_1085 | AIVTGAEYQ | SKDLGLLVEK | TTVEQLGIAR | KVTISSSSTT | IADAASKDD | 392 |
| SEQ_ID_NO_1097 | AIVTGAEYQ | SKDLGLLVEN | TTVEQLGIAR | KVTISSSSTT | IADAASKDD | 394 |
| SEQ_ID_NO_1054 | AIVTGAEFL | AKDLGLLVEN | ATEEQLGTAR | KVTIHQTTTT | LIADAASKDE | 370 |
| SEQ_ID_NO_1088 | AIVTGAEFL | AKDLGLLVEN | ATEEQLGTAR | KVTIHQTTTT | LIADAASKDE | 376 |
| SEQ_ID_NO_1068 | AILTGAEYL | AMDMSLLVEN | ATIDQLGIAR | KVTISKDSTT | LIADAASKDE | 385 |
| SEQ_ID_NO_1072 | AILTEPS- T | ALDMGLLVEN | TTIDQLGIAR | KVTISKDSTT | LIADAASKAE | 383 |
| SEQ_ID_NO_1057 | AILTGAEFQ | ANDLGLLIEN | TSVEQLGIAR | KVITKDSTD | IADAASKDE | 385 |
| SEQ_ID_NO_1061 | AILTGAEFQ | ASDLGLSIEN | TSIEQLGLAR | KVTISKDSTT | IADAASKDE | 385 |
| SEQ_ID_NO_1076 | AILTGAEFQ | ASDLGLLVEN | TTIEQLGLAR | KVTISKDSTT | IADAASKDE | 386 |
| SEQ_ID_NO_1092 | AILTGAEYQ | ASDLGLLVEN | TSIEQLGLAR | KVTISKDSTT | IADAASKDE | 387 |
| SEQ_ID_NO_1074 | AILTGAEFQ | ASDLGLLVEN | TSVEQLGLAR | KITISKDSTT | VIADAATKDE | 383 |
| SEQ_ID_NO_1083 | AILTGAEFQ | ASDLGLLVEN | TSIEQLGLAR | KVTISKDSTT | IADAASKDE | 382 |

Figure 34 (continued)

| | | | | | | | |
|---|---|---|---|---|---|---|---|
| SEQ_ID_NO_1058 | I EERCEQI RS | AI ELSI SDYD | KEKL DERLAK | LSGGVAVLKI | GGASEAEVGE | 422 |
| SEQ_ID_NO_1077 | VNKRVAQI KN | LI EAADQDYE | KEKLNERI AK | LSGGVAVI QV | GAQTETELKE | 444 |
| SEQ_ID_NO_1078 | VNKRVAQI KN | LI EAADQDYE | KEKLNERI AK | LSGGVAVI QV | GAQTETELKE | 444 |
| SEQ_ID_NO_1075 | I QARI LQI KK | DLI ETDNANH | SRKLSERI AK | LTGGI AVI KV | GAHI TELELED | 428 |
| SEQ_ID_NO_1095 | I DMRVAQLKQ | ELAETDSVYD | TEKLSERI AK | LAGGVAVI KV | GAATETEMEE | 417 |
| SEQ_ID_NO_1055 | I EMRI AQLKK | ELAETDSVYD | TEKLSERI AK | LSGGVAVI KV | GAATEAELED | 424 |
| SEQ_ID_NO_1080 | I QARI AQLKR | ELSQTDSTYD | SEKLAERI AK | LSGGVAVI KV | GAATETELED | 437 |
| SEQ_ID_NO_1086 | I QARI AQLKR | ELSQTDSAYD | SEKLAERI AK | LSGGVAVI KV | GAATETELED | 431 |
| SEQ_ID_NO_1085 | I QARI AQLKR | ELSQTDSTYD | SEKLAERI AK | LSGGVAVI KV | GASTEAELED | 432 |
| SEQ_ID_NO_1097 | I QARI AQLKR | ELSQTDSAYD | SEKLAERI AK | LSGGVAVI KV | GASTEAELED | 434 |
| SEQ_ID_NO_1054 | I QARI AQLKK | ELAETDSVYD | TEKLAERI AK | LAGGVAVI KV | GAATETELED | 420 |
| SEQ_ID_NO_1088 | I QARVAQLKK | ELSETDSI YD | TEKLAERI AK | LSGGVAVI KV | GAATETELED | 426 |
| SEQ_ID_NO_1068 | LQARI AQLKK | ELFETDSVYD | SEKLAERI AK | LSGGVAVI KV | GAATETELED | 435 |
| SEQ_ID_NO_1072 | LQARI SQLKK | ESFETDSVYD | SEKLAERI AK | LSGGVAVI KV | GAATETELED | 433 |
| SEQ_ID_NO_1057 | I QARVQQLKK | ELAETDSVYD | TEKLAERI AK | LSGGVAVI KV | GAATETELED | 435 |
| SEQ_ID_NO_1061 | LQARI AQLKK | ELSETDSVYD | SEKLAERI AK | LSGGVAVI KV | GAATETELED | 435 |
| SEQ_ID_NO_1076 | LQSRVAQLKK | ELSETDSI YD | SEKLAERI AK | LSGGVAVI KV | GAATETELED | 436 |
| SEQ_ID_NO_1092 | LQSRVAQLKK | ELSETDSVYD | SEKLAERI AK | LSGGVAVI KV | GAATETELED | 437 |
| SEQ_ID_NO_1074 | LQARVAQLKK | ELSQTDSVYD | TEKLAERI AK | LSGGVAVI KV | GAATETELED | 433 |
| SEQ_ID_NO_1083 | LQARVAQLKK | ELAETDAVYD | SMKLAERI TK | LSGGVAVI KV | GAATETELED | 432 |

| | | | | | | | |
|---|---|---|---|---|---|---|---|
| SEQ_ID_NO_1058 | KKDRVTDALN | ATKAAVEEGI | VPGGGVALLY | ASKELDKL - | STANFDQKI G | 470 |
| SEQ_ID_NO_1077 | KKLRVEDALN | ATKAAVERGI | VVGGGCTLLR | LAAKVDAI KG | TLANDEEKVG | 494 |
| SEQ_ID_NO_1078 | KKLRVEDALN | ATKAAVEEGI | VVGGGCTLLR | LAAKVDAI KG | TLANDEEKVG | 494 |
| SEQ_ID_NO_1075 | RKLRI EDAKN | ATFAAI NEGL | VPGGGATYVH | LLDLI PAI KN | SMEDLDEQI G | 478 |
| SEQ_ID_NO_1095 | RKLRI EDAKN | ATFAAVEEGI | VPGGGAALVH | LSKMI DEFI P | TLTSAEERLG | 467 |
| SEQ_ID_NO_1055 | RKLRI EDAKN | ATFAAVEEGI | VPGGGAALLH | LSELVPAFKE | TLTDAEEKLG | 474 |
| SEQ_ID_NO_1080 | RKLRI EDAKN | ATFAAI EEGI | VPGGGAAYVH | LSTFVPAI KE | KLDDPEERLG | 487 |
| SEQ_ID_NO_1086 | RKLRI EDAKN | ATFAAI EEGI | VPGGGAAYVH | LSKFVPAI KE | KLDDPEERLG | 481 |
| SEQ_ID_NO_1085 | RKLRI ENAKN | ATFAAI EEGI | VPGGGAAYVH | LSTFVPAI KE | KLDDPEERLG | 482 |
| SEQ_ID_NO_1097 | RKLRI EDAKN | ATFAAI EEGI | VPGGGAAYVH | LSTFVPAI KE | TLDDPEERLG | 484 |
| SEQ_ID_NO_1054 | RQLRI EDAKN | ATFAAI EEGI | VPGGGAAYVH | LSTVVPKI KE | AI EDPDERLG | 470 |
| SEQ_ID_NO_1088 | RQLRI EDAKN | ATFAAI EEGI | VPGGGTAYVH | LSTTVPAI KE | TI EDHDERLG | 476 |
| SEQ_ID_NO_1068 | RKLRI EDAKN | ATFAAI EEGI | VPGGGAALVH | LSTVI PAI KE | TFEDADERLG | 485 |
| SEQ_ID_NO_1072 | RKLRI EDAKN | ATFAAI EEGI | VPGGGATLVH | LSTVI PAI KE | TFEDADVRLG | 483 |
| SEQ_ID_NO_1057 | RKLRI EDAKN | ATFAAI EEGI | VPGGGAALVH | LSTCVPAI KD | KLEDPEERI G | 485 |
| SEQ_ID_NO_1061 | RKLRI EDAKN | ATFAAI EEGI | VPGGGAALVH | LSTCVPAI KD | KI EDADERLG | 485 |
| SEQ_ID_NO_1076 | RKLRI EDAKN | ATFAAI EEGI | VPGGGTALVH | LSGYVPAI KE | KLEDADERLG | 486 |
| SEQ_ID_NO_1092 | RKLRI EDAKN | ATFAAI EEGI | VPGGGTALVH | LSAYVPAI KE | KLEDADERLG | 487 |
| SEQ_ID_NO_1074 | RKLRI EDAKN | ATFAAI EEGI | VPGGGTALVH | LSTHVPAI KD | KLEDADERLG | 483 |
| SEQ_ID_NO_1083 | RKLRI EDAKN | ATFLAI EVGI | VL - VDTALLH | LSTHVPAI KD | KLEDADERLG | 480 |

Figure 34 (continued)

| | | | | | | | |
|---|---|---|---|---|---|---|---|
| SEQ_ID_NO_1058 | VQIQNALKT | PVHTIASNAG | VEGAVVVGKL | LEQDNPDLGY | DAAKGEYVDM | | 520 |
| SEQ_ID_NO_1077 | ADIVQRALSY | PLKLIAKNAG | VNGSVVSEKV | LSSDDPKFGY | NAATGNYEDL | | 544 |
| SEQ_ID_NO_1078 | ADIVKRALSY | PLKLIAKNAG | VNGSVVSEKV | LSSDDPKFGY | NAATGNYEDL | | 544 |
| SEQ_ID_NO_1075 | ADIVAKALVE | PAKSIAANAG | VDGDVVVEKT | RTFID-MRIGY | NAMTGTYEDL | | 527 |
| SEQ_ID_NO_1095 | AEIVQKALLA | PCRLIGNNAG | VEGDVIVQHV | MEGD-FNYGY | DAMVGEYGDL | | 516 |
| SEQ_ID_NO_1055 | ADIVMKSLRA | PCRLIADNAG | VEGEVIVQRL | LGKP-FEVGY | NAMDKVENL | | 523 |
| SEQ_ID_NO_1080 | ADIIQKALVA | PASLIAHNAG | VEGEVIVEKI | KDSE-MEFGY | NAMTDKHENL | | 536 |
| SEQ_ID_NO_1086 | ADIIQKALVA | PAALIAHNAG | VEGEVIVEKI | KESE-MEVGY | NAMADRHENL | | 530 |
| SEQ_ID_NO_1085 | ADIIQKALVA | PAALIAHNAG | VEGEVIVDKI | KESE-MEYGY | NAMADKHENL | | 531 |
| SEQ_ID_NO_1097 | ADIIQKALVA | PAALIAHNAG | VEGEVIVDKI | RESE-MEFGY | NAMADKHENL | | 533 |
| SEQ_ID_NO_1054 | ADIIQKALVA | PASLIAHNAG | VEGEVVVEKI | KQSD-MEVGY | NAMTDKYENL | | 519 |
| SEQ_ID_NO_1088 | ADIIQKALVA | PASLIAHNAG | VEGEVVVEKI | KQGE-MEVGY | NAMNDKYENL | | 525 |
| SEQ_ID_NO_1068 | ADIVQKALLS | PAALIAQNAG | VEGEVVVEKI | MFSD-MENGY | NAMTDTYENL | | 534 |
| SEQ_ID_NO_1072 | ADIVQKALVA | Q-SLIAQNAG | IEGEVVVEKI | MFSE-MELGY | NAMTDTYENL | | 531 |
| SEQ_ID_NO_1057 | ADIVQKALVA | PASLIAQNAG | MEGEVVVEKV | KNSE-MEIGY | NAMTDTYENL | | 534 |
| SEQ_ID_NO_1061 | ADIVQKALVS | PASLIAQNAG | IEGEVVVEKL | KASE-MEIGY | NAMTDKYENL | | 534 |
| SEQ_ID_NO_1076 | ADIVQKALVA | PAALIAQNAG | IEGEVVVEKI | KNGE-MEVGY | NAMTDTYENL | | 535 |
| SEQ_ID_NO_1092 | ADIVQKALVA | PASLIAQNAG | IEGEVVVEKI | RNGE-MEVGY | NAMTDTYENL | | 536 |
| SEQ_ID_NO_1074 | ADIVQKALIA | PAALIAQNAG | IEGEVVVEKI | KSGE-MEVGY | NAMADRYENL | | 532 |
| SEQ_ID_NO_1083 | ADIVQKALIA | PASLIAQNAG | IEGEVVVEKV | KNGE-MEVGY | NAMTDRYENL | | 529 |
| | | | | | | | |
| SEQ_ID_NO_1058 | -KAGIIDPL | KVIRTALVDA | ASVSSLMTTT | EAIVVELPKD | E---KEVPA | | 565 |
| SEQ_ID_NO_1077 | IMAAGIIDPT | KVVRCCLEHA | ASVAKTFLMS | DCVVVEKEP | E---AAVAG | | 590 |
| SEQ_ID_NO_1078 | -MAAGIIDPT | KVVRCCLEHA | ASVAKTFLMS | DCVVVEKEP | E---AAVAG | | 589 |
| SEQ_ID_NO_1075 | -LNAGVADPS | RVARCALQSA | VSIAGVVLTT | QAILVDKYL- | -----GSN-K | | 569 |
| SEQ_ID_NO_1095 | -IEKGVIDPK | KVTRSGVQNS | CSIAGMVLTT | QAVITELPKK | KRAIGANAGP | | 565 |
| SEQ_ID_NO_1055 | -LDAGVIDPA | KVTRNGLLNS | VSIAGIMLTT | QAVMVEKHKP | SEIPGGMT-A | | 571 |
| SEQ_ID_NO_1080 | -VEAGVIDPA | KVTRCALQNA | ASVAGMVLTT | QAIVVEKPSK | K---APA-P | | 580 |
| SEQ_ID_NO_1086 | -VQAGVIDPA | KVTRCALQNA | ASVAGMVLTT | QAIVVEKPKK | K---ASA-A | | 574 |
| SEQ_ID_NO_1085 | -VEAGVIDPA | KVTRCALQNA | ASVAGMVLTT | QAIVVEKPKK | K---APA-A | | 575 |
| SEQ_ID_NO_1097 | -VEAGVIDPA | KVTRCALQNA | ASVAGMVLTT | QAIVVEKPQK | K---APA-A | | 576 |
| SEQ_ID_NO_1054 | -MEAGVIDPA | KVTRCALQNA | ASVAGMVLTT | QAIVVEKPKP | K---PQV-A | | 563 |
| SEQ_ID_NO_1088 | -IEAGVIDPA | KVTRCALQNA | ASVAGMVLTT | QAIVVEKPKP | K---APV-A | | 569 |
| SEQ_ID_NO_1068 | -FEAGVIDPA | KVTRCALQNA | ASVAGMVLTT | QAIVVDKPKP | K---APA-A | | 578 |
| SEQ_ID_NO_1072 | -LEAGVIDPA | KVTRCALQNA | ASVAGMVLTT | QAIVVDKPKP | K---APA-A | | 575 |
| SEQ_ID_NO_1057 | -LAAGVIDPA | KVTRCALQNA | ASVAGMVLTT | QAIVVEKAKP | K---APA-A | | 578 |
| SEQ_ID_NO_1061 | -MEAGVIDPA | KVTRCALQNS | ASVAGMVLTT | QAIVVEKPKP | K---TPA-A | | 578 |
| SEQ_ID_NO_1076 | -VESGVIDPA | KVTRCALQNA | ASVAGMVLTT | QAIVVEKPKP | K---AAV-A | | 579 |
| SEQ_ID_NO_1092 | -IESGVIDPA | KVTRCALQNA | ASVAGMVLTT | QAIVVEKPKP | R---APV-P | | 580 |
| SEQ_ID_NO_1074 | -VEAGVIDPA | KVTRCALQNA | ASVAGMVLTT | QAIVVEKPKP | K---APV-A | | 576 |
| SEQ_ID_NO_1083 | -VEAGVIDPA | KVTRCALQNA | ASVAGMVLTT | QAIVVEKPKP | K---APT-A | | 573 |

Figure 34 (continued)

| SEQ ID | Sequence | # |
|---|---|---|
| SEQ_ID_NO_1058 | MGGGMGGMDY | 575 |
| SEQ_ID_NO_1077 | NPMDNSGYGY | 600 |
| SEQ_ID_NO_1078 | NPMDNSGYGY | 599 |
| SEQ_ID_NO_1075 | NALTNGKVTV AVSYSWGMMK PMYYKA | 595 |
| SEQ_ID_NO_1095 | MADEEGNFSL | 575 |
| SEQ_ID_NO_1055 | SGMPSG-MTI | 580 |
| SEQ_ID_NO_1080 | AGMPQGMM- | 588 |
| SEQ_ID_NO_1086 | SGAPEGSLAM | 584 |
| SEQ_ID_NO_1085 | AGAPEGSFAM | 585 |
| SEQ_ID_NO_1097 | AAAP- | 580 |
| SEQ_ID_NO_1054 | -EPPEGALTV | 572 |
| SEQ_ID_NO_1088 | -EPAEGTLTV | 578 |
| SEQ_ID_NO_1068 | -AAPEG-LMV | 586 |
| SEQ_ID_NO_1072 | -AAPEG-LMV | 583 |
| SEQ_ID_NO_1057 | -AAPEG-LTI | 586 |
| SEQ_ID_NO_1061 | -AATQGQYAV | 587 |
| SEQ_ID_NO_1076 | -AAPQG-LTI | 587 |
| SEQ_ID_NO_1092 | -GAPQG-LTV | 588 |
| SEQ_ID_NO_1074 | -GAPQG-LTV | 584 |
| SEQ_ID_NO_1083 | -AAPQG-LTI | 581 |

Figure 35

| | | |
|---|---|---|
| SEQ_ID_NO_1106 | MAELNVAPSP PPSTILTLED MLRKLPLPSD ETIRSPATTK MCKIVSHRSS | 50 |
| SEQ_ID_NO_1105 | ---------- ---------- ---------- ---------- ---------M | 1 |
| SEQ_ID_NO_1108 | ---------- ---------- ---------- ---------- ------MREY | 4 |
| SEQ_ID_NO_1109 | --MAAVAPIA MPARVHHHHH HHRRALAASP AALAAAGNGL SATRRVRRSP | 48 |
| SEQ_ID_NO_1101 | ---------- ------MPFA SSSSLIKRRP LL-------- ------RHAN | 20 |
| SEQ_ID_NO_1099 | ---------- ---------- MTRHVILTSE E--------- ------RNSP | 15 |
| SEQ_ID_NO_1103 | ---------- ---------- MTRHVILKSP LLVSSEESTM ------RNSP | 24 |

| | | |
|---|---|---|
| SEQ_ID_NO_1106 | PRHPTTKANK G------FQC AEVAGGTTAG CAALVCC-PC GIVSLLVLAT | 93 |
| SEQ_ID_NO_1105 | TRQNQLQNRR R------SV GEVAGNAIAE CAAICCCVPC AVVDMVALAT | 44 |
| SEQ_ID_NO_1108 | GRGHEEEEGE E--HEPQPGC GEGACQAAAN CAAVCCCCPL ALLDVLLLVT | 52 |
| SEQ_ID_NO_1109 | AVEMRRERER RRAREQQPRC GEVAGGTAAE CAAVFCCFPF AVVELVVLAA | 98 |
| SEQ_ID_NO_1101 | SSGSSCCSGR F--------- GEIAGGTTAE CAAICCCCPC GLVNLLVLTI | 61 |
| SEQ_ID_NO_1099 | PTTMIKHAER R------KV GEVAGGAAAE CAAVMCCGPC AVVNLVVLAV | 58 |
| SEQ_ID_NO_1103 | PSTTSLSKER R------KV GEVAGGAAAE CAAVMCCCPC AVVNLMVLAV | 67 |

| | | |
|---|---|---|
| SEQ_ID_NO_1106 | VKLPAGLCRR ALSQKRRKRV KKR------- -------STTL RSRAMSFVSD | 130 |
| SEQ_ID_NO_1105 | YKVPASLKKK AAINNRKKRL LKQ------- ---------- MKKDMKNFLE | 77 |
| SEQ_ID_NO_1108 | VKLPAGVMRR VRRRRRHRD RVS-----RK KRSAAAAAVE PABPSGSSGK | 97 |
| SEQ_ID_NO_1109 | VRAPAALCRR AVRGGRRRRV RST-----KP KETGAMDIAS PRSLAAAAAK | 143 |
| SEQ_ID_NO_1101 | YKIPAGICRR ALKRKQRKKL IKKGLFPPRG RGYGCGSCDD PELHIHPMAR | 111 |
| SEQ_ID_NO_1099 | YRVPAAVCKK AMRQTKRQRF MRR----RH GLLASAAA-- -ESTVHARLK | 100 |
| SEQ_ID_NO_1103 | YKVPAAVCKK AWRRSKRRRF TRK----RH GLLASATAEG SESTVHARLN | 112 |

| | | |
|---|---|---|
| SEQ_ID_NO_1106 | DEDFGVPSFV PRTPETWPSK SPSVEVAEK- EEEMW-AEFY SAGFWRSPSQ | 178 |
| SEQ_ID_NO_1105 | HEKPGGP--G PETVVVGPTM EELLAQEELP EEDLW-ARFS VNGFWRSSSS | 124 |
| SEQ_ID_NO_1108 | AMIGAAP--S PLEAEFEEAR GEAAAAAEL- EREIMSSRFY GAGFWRSVSS | 144 |
| SEQ_ID_NO_1109 | ARKVDAD--F PAT----PKA EHLVDM--- EKEVW-ASFY GGGFWRSPSQ | 182 |
| SEQ_ID_NO_1101 | VEDSLRE--F DGEL-E-AVKK EEL-AMLRL- EKEMW-ETFY GTGFWRSPSQ | 153 |
| SEQ_ID_NO_1099 | EEDPTAE--I VFEL-E-NVYN VELNDVVVL- EDEMF-ERFY GAGFWRSPSQ | 144 |
| SEQ_ID_NO_1103 | EEDLTAE--I VFEL-ECHVSG GELNDVVRL- ENEML-DRFY GAGFWRSPSQ | 157 |

Figure 35 (continued)

| | | | | |
|---|---|---|---|---|
| SEQ_ID_NO_1106 | ---------- | KESN- ---- | ------------ ------------ --- | 182 |
| SEQ_ID_NO_1105 | -----QKHEP | DELQTGEN-- | ------------ ------------ -NR | 139 |
| SEQ_ID_NO_1108 | ---------- | GCSSSASMRY | Q----------- ------------ --- | 155 |
| SEQ_ID_NO_1109 | REDRRCI AAG | DGAAAAALFF | FSFTTVVGFL AFLLPFLGKR EDR | 225 |
| SEQ_ID_NO_1101 | RELPAKRSSP | RETPNARL-- | ------------ ------------ --- | 171 |
| SEQ_ID_NO_1099 | ---------- | RDTSSGSI-- | ------------ ------------ --- | 152 |
| SEQ_ID_NO_1103 | ---------- | KDTSSGSL-- | ------------ ------------ --- | 165 |

Figure 36

| | | | | | | | |
|---|---|---|---|---|---|---|---|
| SEQ_ID_NO_1112 | MAQNKMVMV | LLSTFLVMA | RSLWVPEEPS | NADD-IRGAC | IEECTKE-NK | | 48 |
| SEQ_ID_NO_1113 | MAQNKTIAVA | LLATLVAV- | ----MGKEPE | TLEETLRAGC | KEECSEQKKK | | 45 |
| SEQ_ID_NO_1114 | MAQNKTIAVA | LLATLVAV- | ----MGKEPE | TLEEAVRAGC | KEECSEQKKK | | 45 |
| | | | | | | | |
| SEQ_ID_NO_1112 | APGDKKTCEV | LC-------- | ---------- | ---------- | ---------T | | 61 |
| SEQ_ID_NO_1113 | APIDEKQCED | FCFIKTKSIF | EAHKGVKDLK | ADRFIDFCNN | ECNAVYKEDP | | 95 |
| SEQ_ID_NO_1114 | APIDEKQCED | FCFIKTKSIF | EAHKGVKDLK | ADRFIDFCNN | ECNAVYKEDP | | 95 |
| | | | | | | | |
| SEQ_ID_NO_1112 | KLTKKPSEEG | KHD------- | ---------- | ----       | | | 74 |
| SEQ_ID_NO_1113 | ATSKKCAESC | EADAKEAEVF | LDKVVAYMQT | MKQA       | | | 129 |
| SEQ_ID_NO_1114 | ATSKKCAESC | EADAKEAEVF | LDKVVAYIQT | TKQA       | | | 129 |

Figure 37

| | | | | | |
|---|---|---|---|---|---|
| SEQ_ID_NO_1138 | M---KRSREA | EEEEEQAA-- | --GAELLLLL | SLSRGDKPA- | ---------- | 32 |
| SEQ_ID_NO_1141 | M------TKH | PRDGEVIS-- | --LSLSLTLG | AAADSGERK- | ---------- | 29 |
| SEQ_ID_NO_1143 | -MAMKR-MRS | EDIVGDKDSL | DDMAKCLMLL | S--HGGGLT- | ---------- | 35 |
| SEQ_ID_NO_1120 | MLLSKVGQAD | HEILTNYR-- | --SAAAAAAA | A--TAGA--- | ---------- | 31 |
| SEQ_ID_NO_1147 | MAKRERAAWE | VEAGAAAD-- | --TARLLMLL | A--QAQQHL | LQQHAHHHHH | 44 |
| SEQ_ID_NO_1132 | -----MAMKR | QRSNEGID-- | --YANCLMLL | S--CPQQ--- | ---------- | 26 |
| SEQ_ID_NO_1134 | MSAMKR-SRE | DRQVEAAA-- | --MANCLMLL | S--KLNDKS- | ---------- | 32 |
| SEQ_ID_NO_1136 | ---------- | ---------- | --MARILLLF | SGHHQHHAH- | ---------- | 17 |
| SEQ_ID_NO_1145 | ---------- | ---------- | --MPMPMPMA | A--RGHR--- | ---------- | 13 |
| SEQ_ID_NO_1144 | MVAI---SEI | KSTVETTA-- | --AANCLMLL | S--RVGQEN- | ---------- | 30 |
| SEQ_ID_NO_1116 | MVAI---SEI | NPTVEAT--- | --AANCLMLL | S--RVGQK-- | ---------- | 28 |
| SEQ_ID_NO_1123 | MVAI---SEI | KSTVDVT--- | --AANCLMLL | S--RVGQEN- | ---------- | 29 |
| SEQ_ID_NO_1140 | -MTIKRSWED | DREVENLA-- | --MANCLMLL | S--RVGQS-- | ---------- | 31 |
| SEQ_ID_NO_1133 | MVMINIPMKR | TREANDFDSI | TTMANCLMLL | SQNRSGEFI- | ---------- | 39 |
| SEQ_ID_NO_1118 | ------MKR | GRDLDAMD-- | --MADCLMLL | S--RVGET-- | ---------- | 25 |
| SEQ_ID_NO_1129 | ------MKR | GREESKLD-- | --MANCLMLL | T--KVGES-- | ---------- | 25 |

| | | | | | | |
|---|---|---|---|---|---|---|
| SEQ_ID_NO_1138 | -----TVRK | K---VRAAEG | ---VFECKIC | SRQFPTFQAL | GGHRTSHNRP | 70 |
| SEQ_ID_NO_1141 | -----KPRR | GSSPAASGSG | ---DFVCKTC | SRAFPSFQAL | GGHRTSHLRG | 70 |
| SEQ_ID_NO_1143 | -----TDTK | ----PKTCPH | PVDVFECKTC | NRQFSSFQAL | GGHRASHKRP | 75 |
| SEQ_ID_NO_1120 | ---------- | ----GAGAGR | ---SFSCKTC | NKNFPSFQAL | GGHRASHKKP | 64 |
| SEQ_ID_NO_1147 | HHHGVGVPPF | PAGRAAVHGR | ---VFECKTC | SRQFPTFQAL | GGHRASHKRP | 91 |
| SEQ_ID_NO_1132 | ---------- | ----KSYENG | ---EVECKTC | NKKFSSFQAL | GGHRASHKRM | 59 |
| SEQ_ID_NO_1134 | -----TSTT | TT--NQDHHN | ---DFECKTC | NKRFSSFQAL | GGHRASHKRP | 71 |
| SEQ_ID_NO_1136 | -----YG-- | -----PSSPER | ---VFECKTC | NRRFPSFQAL | GGHRASHKKP | 52 |
| SEQ_ID_NO_1145 | ---------- | --------APER | ---VFVCKTC | DRVFPSFQAL | GGHRASHKKP | 44 |
| SEQ_ID_NO_1144 | ------VD-- | ----GGSAKR | ---VFTCKTC | LKEFHSFQAL | GGHRASHKKP | 65 |
| SEQ_ID_NO_1116 | ---------- | ----GGDQKR | ---VFTCKTC | LKEFHSFQAL | GGHRASHKKP | 61 |
| SEQ_ID_NO_1123 | ------VD-- | ----GGDQKR | ---VFTCKTC | LKQFHSFQAL | GGHRASHKKP | 64 |
| SEQ_ID_NO_1140 | ---------- | ----GSTPDR | ---VFHCKTC | DKEFKSFQAL | GGHRASHKRP | 64 |
| SEQ_ID_NO_1133 | -----DSTT | SNSSNLNSNR | ---VFECKTC | NRQFPSFQAL | GGHRASHKRP | 80 |
| SEQ_ID_NO_1118 | ---------- | ----DRVAGR | ---VFACKTC | NKKFSSFQAL | GGHRASHKKP | 58 |
| SEQ_ID_NO_1129 | -----ETNY | PISKGSDIG- | ---DFKCKTC | NRRFSSFQAL | GGHRASHKKP | 65 |

Figure 37 (continued)

| | | | | | | |
|---|---|---|---|---|---|---|
| SEQ_ID_NO_1138 | RVDRS----- | -----TS--- | ---------- | ---------- | --RRSVHQCS | 85 |
| SEQ_ID_NO_1141 | RHGLA----L | GLAAATAKET | TKKVQEKPA- | ---------- | --AAATHECH | 103 |
| SEQ_ID_NO_1143 | RLMGE----- | -----EHKVD | RTKLCSSGN- | ---------- | --KPKMHECS | 102 |
| SEQ_ID_NO_1120 | KLKES----- | -----T---- | -GNLKLPNS  | PS-------- | --KPKTHQCS | 89 |
| SEQ_ID_NO_1147 | RVLQQQQLQQ | QQTVVADHAG | QLCLGRQPLQ | LPLPTTTTPQ | QAKPRVHECP | 141 |
| SEQ_ID_NO_1132 | KLAEG----- | ---------- | -EELKEQAKS | LSLWN----- | --KPKMHECS | 86 |
| SEQ_ID_NO_1134 | KLLIG----- | -----A---- | -GEFLVQPS- | ---------- | --SKKMHECS | 93 |
| SEQ_ID_NO_1136 | RLADG----- | ---------- | --AGAEPP-  | ---------- | --KPKVHGCS | 71 |
| SEQ_ID_NO_1145 | RLDDG----- | ---------- | --GDL----  | ---------- | --KPKLHGCS | 60 |
| SEQ_ID_NO_1144 | NNENL----- | -----S---- | -GLMKKTK-- | ---------- | --ASSSHPCP | 86 |
| SEQ_ID_NO_1116 | NNNES----- | --------L  | SGLVKKAK-- | ---------- | --APSSHPCP | 83 |
| SEQ_ID_NO_1123 | NNDAL----- | -----SS--- | -GLMKKV--- | ---------- | --KTSSHPCP | 85 |
| SEQ_ID_NO_1140 | KTSDG----- | ---------- | -SEARTPP-  | ---------- | --KPKTHECP | 84 |
| SEQ_ID_NO_1133 | RLGGD----- | ---------- | -LTLSQIPVA | AA-------- | --KPKTHECS | 104 |
| SEQ_ID_NO_1118 | KLTVG----- | -----DN--- | -EGLAVSP-  | ---K------ | --KPKTHECS | 61 |
| SEQ_ID_NO_1129 | KLMVT----- | -----DL--- | -SCHDELPNP | TMKQ------ | --QPRMHPCP | 93 |

| | | | | | | |
|---|---|---|---|---|---|---|
| SEQ_ID_NO_1138 | CGVEFAMGQ  | ALGGHMRRHK | PMAEDSKRSD | PKK------- | ---------- | 118 |
| SEQ_ID_NO_1141 | CGQGFEMGQ  | ALGGHMRRHR | EEAAAAAAV  | H--------- | ---------- | 134 |
| SEQ_ID_NO_1143 | CGQKFSMGQ  | ALGGHMRRHR | A--NEGLSSI | MNPLDHA--- | ------KVPM | 141 |
| SEQ_ID_NO_1120 | CGLEFPLGQ  | ALGGHMRRHR | APNNVDTTST | SSKDHELAVT | QPPFLPAVPV | 139 |
| SEQ_ID_NO_1147 | VCGLEFAVGQ | ALGGHMRRHR | AEAEAEATEA | PSKVMMR--- | --------PA | 180 |
| SEQ_ID_NO_1132 | CGMGFSLGQ  | ALGGHMRKHR | AVINEGVSSI | NQIIEKF--- | --------PV | 125 |
| SEQ_ID_NO_1134 | CGMEFSLGQ  | ALGGHMRRHR | AAIDEKSKAA | TKAMMIP--- | ---------V | 131 |
| SEQ_ID_NO_1136 | CGLEFAVGQ  | ALGGHMRRHR | AVAAAGPGVG | LGLSLGL--- | --GLGPNEDG | 116 |
| SEQ_ID_NO_1145 | VCGLEFAIGQ | ALGGHMRRHR | AMAAGGGGGV | MPMTPPT--- | -----AAAKE | 103 |
| SEQ_ID_NO_1144 | CGVEFPMGQ  | ALGGHMRRHR | NESG-GAGAL | VTRELLP--- | -----EAALMT | 128 |
| SEQ_ID_NO_1116 | CGVEFPMGQ  | ALGGHMRRHR | NEIG-GGAAL | VTRALLP--- | -----EPTMTT | 125 |
| SEQ_ID_NO_1123 | CGVEFPMGQ  | ALGGHMRRHR | NESGAAGGAL | VTRALLP--- | -----EPTVTT | 128 |
| SEQ_ID_NO_1140 | VCGLEFAIGQ | ALGGHMRRHR | DVGNEK--BG | RPVAARP--- | ---------- | 119 |
| SEQ_ID_NO_1133 | CGLEFAIGQ  | ALGGHMRRHR | AAMSDSASGN | SASPPRDDRT | VVVKKSNIV- | 153 |
| SEQ_ID_NO_1118 | CGLEFAIGQ  | ALGGHMRRHR | AALNDG---L | VTRDLLP--- | ---------E | 116 |
| SEQ_ID_NO_1129 | CGLEFAIGQ  | ALGGHMRKHR | TAINDGLLCG | KPSSSLS--- | ------ILKE | 134 |

Figure 37 (continued)

| SEQ_ID_NO_1138 | | | M DL T MADPEF- | | G DL HR VR- - - - | 135 |
|---|---|---|---|---|---|---|
| SEQ_ID_NO_1141 | | | ----- AP PV- | | | 138 |
| SEQ_ID_NO_1143 | L MK RS NS- - - | - - - T RVV CS L | DL N- - L TPL | | E N- - DL K- L F | 170 |
| SEQ_ID_NO_1120 | L KR SN SS- - - | - - - KRVL C- L | DL S- AL PMY- | | Q ND SEL Q- L EK | 171 |
| SEQ_ID_NO_1147 | HD KT CD Y- - - | - - - AGG I C- L | DL N- - L TPS- | | E NC AK CR S MM | 211 |
| SEQ_ID_NO_1132 | L KR LN S- - - | - - - KRI MG- L | DL N- - L TPL | | E ND- DL M- F G I | 153 |
| SEQ_ID_NO_1134 | L KK SN SS- - - | - - - KRI FC- L | DL N- - L TPR- | | N ED V DL K- L WP | 161 |
| SEQ_ID_NO_1136 | NK KA AA- - - | - - - AAE L A- L | DL N- - EPAL | | E EE PAD R- AM L | 145 |
| SEQ_ID_NO_1145 | HG ES GD DDAV | VGM KR GL W- L | DL N- - HPP CD | EY GAGSESDD | EC GH V D- AAA | 149 |
| SEQ_ID_NO_1144 | L KK SS S- - - | - - - GRL AC- L | DL S- - L GMV- | | E NL- NL K- L EL | 156 |
| SEQ_ID_NO_1116 | L KK SS SG- - - | - - - KRV AC- L | DL S- - L GMV- | | E NL- NL K- L EL | 154 |
| SEQ_ID_NO_1123 | L KK SS SG- - - | - - - KRV AC- L | DL S- - L GMV- | | D NL- NL K- L EL | 157 |
| SEQ_ID_NO_1140 | - - - E S VT- - - | - - - KR G L F- W | DL N- - L TPL | | E N- - DL K- L WS | 144 |
| SEQ_ID_NO_1133 | - - DD DN D- - - | - - - RRV MG- L | DL N- - L TPF- | | E N- - HL E- F QL | 179 |
| SEQ_ID_NO_1118 | MN KS TG D- - - | - - - GRD PS- I | DL G- - L TSW- | | G VDL EL K- L - | 144 |
| SEQ_ID_NO_1129 | SS KD GD Q- - - | - - - KL NL R- L | DL N- - L TPL | | E ED- DL K- L NL | 163 |

| SEQ_ID_NO_1138 | - - - - - - - RTG | SHCQL L QL FV | 148 |
|---|---|---|---|
| SEQ_ID_NO_1141 | - - - - - - - - - - | - - - - L L EL FV | 144 |
| SEQ_ID_NO_1143 | - - - - - - - GKM | APKVD L RL M | 183 |
| SEQ_ID_NO_1120 | - - - - - - - - - - | VARPM L RC F I | 181 |
| SEQ_ID_NO_1147 | LGAAAGQ G V H | KTLAM L DCS L | 231 |
| SEQ_ID_NO_1132 | - - - - - - - KSP | PTPI PL SL F L | 165 |
| SEQ_ID_NO_1134 | - - - - - - - TAP | I SSPV L RI F I | 174 |
| SEQ_ID_NO_1136 | - - - - - - - G L A | VGF RPRGG- - | 156 |
| SEQ_ID_NO_1145 | AGYTF HQF MD | TGT MA V DCV- | 168 |
| SEQ_ID_NO_1144 | - - - - - - - G RP | VC- - - - - - - - | 161 |
| SEQ_ID_NO_1116 | - - - - - - - G RT | VC- - - - - - - - | 159 |
| SEQ_ID_NO_1123 | - - - - - - - G RT | VY- - - - - - - - | 162 |
| SEQ_ID_NO_1140 | - - - - - - - NTV | NTAL A M- - - | 153 |
| SEQ_ID_NO_1133 | - - - - - - - G K I | APT- - N DC F L | 190 |
| SEQ_ID_NO_1118 | - - - - - - - G KV | TPT PV V HC F I | 157 |
| SEQ_ID_NO_1129 | - - - - - - - - - - | - RT PV L NC F I | 172 |

Figure 38

| | | |
|---|---|---|
| SEQ_ID_NO_1162 | MATKIFALLV LLALSASATT AVIIPQCSLA PTAAIIPRFL PPVSAIGFEH | 50 |
| SEQ_ID_NO_1163 | MATKIFVLLA LLALSVSTTT AVIIPQCSLA PNAFLISQFL PPLTLVGFEH | 49 |
| SEQ_ID_NO_1161 | MAAKIFAILA LLALSASVAT ATIIPQCSQL -------QYL SPVTAARFEY | 42 |
| SEQ_ID_NO_1159 | MATKIFSLLM LLALSACVAN ATIFPQCSQA PIASLLPPYL PSMIASVCEN | 50 |
| SEQ_ID_NO_1164 | MAAKIFCFLM LLGLSASVAT ATIFPQCSQA PIASLLPPYL SPAVSSMCEN | 50 |

| | | |
|---|---|---|
| SEQ_ID_NO_1162 | PAVQAYRLQQ ALAASILL-- ----QQPLAD LQQQSSAHLT IQTIAAQQLQ | 92 |
| SEQ_ID_NO_1163 | PALQAYRLQQ ALANSILL-- ----QQPFPQ LQQQSSAHLT VQTIAAQQDQ | 92 |
| SEQ_ID_NO_1161 | PTIQSYRLQE AIAASILRSL ALTVQQPYAL LQQPSLMNLY LQRIAAQQLQ | 92 |
| SEQ_ID_NO_1159 | PALQPYRLQQ AIAASNIPLS PLLFQQSPAL ----SLVQSL VQTIRAQQLQ | 96 |
| SEQ_ID_NO_1164 | PIVQPYRIQQ AIATGLPLS PLFLQQPSAL LQQLPLVHLV AQNIRAQQLQ | 100 |

| | | |
|---|---|---|
| SEQ_ID_NO_1162 | QQFLPSLSQL AAANPTAYLQ QQLLASNPLA VANAIAYQHQ QQLQQLLPAL | 142 |
| SEQ_ID_NO_1163 | QQFLPALSQL ALANPVAYLQ QQLLASNPLA LVNNAAYQ-Q QQLQQVLPVI | 141 |
| SEQ_ID_NO_1161 | QQLLPTINQV VAANLAAYLQ Q--------- ---------- ---QQFLPLF | 119 |
| SEQ_ID_NO_1159 | QLVLPVLNQV ALANLSPYSQ Q--------- ---------- ---QQFLPLF | 123 |
| SEQ_ID_NO_1164 | ------QL VLANLAAYSQ Q--------- ---------- ---HQFLPLF | 119 |

| | | |
|---|---|---|
| SEQ_ID_NO_1162 | SQLAVANPAA YLQ-SQLFPS NPLV-ANAAA YLQQQQLQQI LPVLSQLAVA | 190 |
| SEQ_ID_NO_1163 | SQVAMANPAA YLQ-QQQLAY NPLVAANAAA YLQQQQLQQI LPALSQLALV | 190 |
| SEQ_ID_NO_1161 | NQLAGVNPAA YLQAQQLLPF NQLV-RSPAA FLLQQQL--- LP-FHLQVVA | 164 |
| SEQ_ID_NO_1159 | NQLSTLNPAA YLQ-QQLLPF SQLA----TA YSQQQQL--- LP-FNQLAAL | 164 |
| SEQ_ID_NO_1164 | NQLAALNSAA YLQ-QQLPF SQLV---AA YP--RQF--- LP-FNQLAAL | 157 |

| | | |
|---|---|---|
| SEQ_ID_NO_1162 | DPNSYL-QQQ QLLPFNQVAV ANNAVYEQQH QLLQVNPLA- -----AAFLQ | 233 |
| SEQ_ID_NO_1163 | NPAAYL-QQQ QLLPFNQLAV TNTAAYLQQQ QLLRVNPVVA ANPLAAAFLQ | 239 |
| SEQ_ID_NO_1161 | NIAAFLQQQQ QLLPFYPQVV GNINAFLQQQ QLLPFYPQDV ANN--VAFLQ | 212 |
| SEQ_ID_NO_1159 | NPAAYL-QQQ ILLPFSQLAA ANRASFLTQQ QLLPFYQQFA ANP--ATLLQ | 211 |
| SEQ_ID_NO_1164 | NSAAYL-QQQ QLLPFSQLAD VSPAAFLTQQ QLLPFYLHAM PNA--GTLLQ | 204 |

| | | |
|---|---|---|
| SEQ_ID_NO_1162 | QQQRQLLPFN QMSLNNPALS WQQPIVGGVG F- | 264 |
| SEQ_ID_NO_1163 | QQ-QLLPFN DISLMNPAFS WQQPIVGSAI F- | 268 |
| SEQ_ID_NO_1161 | QQ-QLLPFN QLALTNPTTL LQQPTIGGAI F- | 241 |
| SEQ_ID_NO_1159 | LQ--QLLPFV QLALTDRAAS YQQHIGGAL F- | 240 |
| SEQ_ID_NO_1164 | LQ--QLLPFN QLALTNSTVF YQQPIIGGAL FD | 234 |

Figure 39

| | | | | | | |
|---|---|---|---|---|---|---|
| SEQ_ID_NO_1167 | MAK------ | -NGI NNSVAV | GI AVQSDWDN | RHFSSSLSLN | VRRLFEFLLQ | 42 |
| SEQ_ID_NO_1182 | MGR----GG | --GMGNPVNV | GI AVQADWGN | REFI SNI SLN | VRRLFDFLLR | 43 |
| SEQ_ID_NO_1166 | MGR----GG | --GMGNPVNV | GI AVQADWEN | REFI SNI SLN | VRRLFDFLLR | 43 |
| SEQ_ID_NO_1183 | MAR----AG | GHGMGNPVNV | GI AVQADWEN | REFI SNI SLN | VRRLFDFLLR | 45 |
| SEQ_ID_NO_1173 | MARAGGGGGG | GGGI TNAVNV | GI AVQADWEN | REFI SHI SLN | IRRLFDFLIQ | 50 |
| SEQ_ID_NO_1169 | MSR----GG | GVGI TNAVNV | GI AVQADWEN | REFI SNI SI N | VRRLFDFLIN | 45 |
| SEQ_ID_NO_1177 | MAR----AG | --GI TNAVNV | GI AVQADWEN | REFI SHI SLN | VRRLFDFLVQ | 43 |
| SEQ_ID_NO_1180 | MAR----AG | --GI TNAVNV | GI AVQADWEN | REFI SHI SLN | VRRLFDFLVQ | 43 |
| SEQ_ID_NO_1171 | MAR----AG | --GI TNAVNV | GI AVQADWEN | REFI SHI SLN | VRRLFEFLLQ | 43 |
| SEQ_ID_NO_1175 | MAK----AG | --GI TNAVNV | GI AVQADWEN | REFI SHI SLN | VRRLFEFLVQ | 43 |

| | | | | | | |
|---|---|---|---|---|---|---|
| SEQ_ID_NO_1167 | FESSTRSKLA | TLNEKLTVLE | RQLEFLEADF | STAI NPV-- | --------- | 79 |
| SEQ_ID_NO_1182 | FEATTKSKLA | SLNEKLDI LE | RKLEVLEVQV | SSATTNPSVF | N------ | 84 |
| SEQ_ID_NO_1166 | FEATTKSKLA | SLNEKLDI LE | RKLEVLEVQV | GSATTNPSVF | N------ | 84 |
| SEQ_ID_NO_1183 | FEATTKSKLA | SLNEKLDI LE | RKLEVLEVQV | SSATTNPSVF | N------ | 86 |
| SEQ_ID_NO_1173 | FESTTKSKLS | SLNLKLDTLE | RRLQLLELQV | STATSNPSLF | TSTTTTTA | 98 |
| SEQ_ID_NO_1169 | FEATTKSKLA | SLNEKLDTLE | RRLELLEVQV | GTASANPSLF | TL------ | 86 |
| SEQ_ID_NO_1177 | FEATTKSKLA | SLNEKLDVLE | RRLELLEVQV | GNASANPSLF | AT----- | 85 |
| SEQ_ID_NO_1180 | FEATTKSKLA | SLNEKLDVLE | RRLELLEVQV | GNASANPSLF | AT----- | 85 |
| SEQ_ID_NO_1171 | FEATTKSKLA | SLNEKLDTLE | RRLELLEVQV | GTASANPSLF | ST----- | 85 |
| SEQ_ID_NO_1175 | FESTTKSKLA | SLNEKLDLLE | RRLEMLEVQV | STATANPSLF | AT----- | 85 |

Figure 40

| | | | | | | | |
|---|---|---|---|---|---|---|---|
| SEQ_ID_NO_1187 | MFSWLRGCR | DECSATDQLK | Q---------  ---------A | RDVFVAKEAV | | | 32 |
| SEQ_ID_NO_1185 | MFAWLRGCR | DECSASDQLK | Q---------  ---------A | HDVFKAKEMV | | | 32 |
| SEQ_ID_NO_1189 | MFSWLRGCR | DECSASDQLK | Q---------  ---------A | RDVFMAKEAV | | | 32 |
| SEQ_ID_NO_1190 | MFAWLRGCR | DECSASDQLK | QGVVKEKNRC  WFWGAFSVNA | RDVFVAKEAV | | | 50 |
| SEQ_ID_NO_1191 | MFAWLRGCR | DECSASDQLK | Q---------  ---------A | RDVFVAKEAV | | | 32 |

| | | | | | | | |
|---|---|---|---|---|---|---|---|
| SEQ_ID_NO_1187 | LQKKISQEME | RAKEFKKSGN | KQAAMQCLKR | KRYYESQMNQ | VGSVRLRIDT | | 82 |
| SEQ_ID_NO_1185 | LQKKISQEVE | RAKEFTKSGN | KQAAMQCLKR | KRYYESQMNQ | VGSVQLRINT | | 82 |
| SEQ_ID_NO_1189 | LQKKISQEME | RAKEFTKSGN | KQAAMQCLKR | KKYYESQMSQ | VGSVQLRINT | | 82 |
| SEQ_ID_NO_1190 | LQKKISQEME | RAKEFTKSGN | KQAAMQCLKR | KKYYESQMNQ | VGSVQLRINT | | 100 |
| SEQ_ID_NO_1191 | LQKKISQEME | RAKEFTKSGN | KQAAMQCLKR | KKYYESQMNQ | VGSVQLRINT | | 82 |

| | | | |
|---|---|---|---|
| SEQ_ID_NO_1187 | KEKMIADNMV | N---K | 94 |
| SEQ_ID_NO_1185 | KERMIADHTG | N---K | 94 |
| SEQ_ID_NO_1189 | KEKMIADHMG | N---K | 94 |
| SEQ_ID_NO_1190 | KEKMIADHSG | NKEDK | 115 |
| SEQ_ID_NO_1191 | KEKMIADHSG | NKEDK | 97 |

Figure 41

```
SEQ_ID_NO_1204    ........MVK TRAAATPR.. ............ .....PSGGG GAGAADITAG    26
SEQ_ID_NO_1203    MGEQSLSQPK PQPLSPFPSP PASAAL.... .....PPPAS ASASASASAA    41
SEQ_ID_NO_1205    MESPNPQQVN SMGDQSPLSP NLHPLS.... .....PSPGA AAAAAA....    37
SEQ_ID_NO_1196    MGEQTPSQPQ PQVQSQPPND SSTTTQAQVQ NQSGDPSNTS TAAVSTVTTA    50
SEQ_ID_NO_1202    MGEQTLGQAQ SLIEPQPL.. ............ .....PAPSS TAVPDGATVD    33
SEQ_ID_NO_1194    ...MSLRKTL TAVNQSSL.. ............ .....PPDSL ISAGNLTVBE    30
SEQ_ID_NO_1200    MGKPVTRSHS LLLHEPSS.. ............ .....PPLS. ..........    22

SEQ_ID_NO_1204    .......... .......... ....KISFRS RKIVKSTPAK GKSVATTTTA    52
SEQ_ID_NO_1203    .......... .........S TSRTTSAAAS RPKKKVTN-P SPDRNPAKKP    71
SEQ_ID_NO_1205    .......... .........T PTPAAAAASS RSSRSKKPPH SSDPNQSKKP    68
SEQ_ID_NO_1196    CTAIVACGPT ELVNVPLPTS SPPSKIPSRP RKIRKLSPDL SFDPNASQQA    100
SEQ_ID_NO_1202    .........S ELNNVPRPTT SPATKIPLRP RKIRKVSPDP STSESQTETP    74
SEQ_ID_NO_1194    .......... ........VS GSSSRIRFRP RKIRKVSSDP SPRIIIIASP    62
SEQ_ID_NO_1200    .......... .........T TTSSKISFQS RKIRKLSTNK TTTTTTAITS    53

SEQ_ID_NO_1204    .........  .VLS...... .......... ...PP....P LSSPGELAAA    68
SEQ_ID_NO_1203    .........  .RLT...... .......... ...FSIPGRP LSAVGEVGVA    91
SEQ_ID_NO_1205    .........  .RLT...... .......... ...LTVPGRP LSADGEVAAA    88
SEQ_ID_NO_1196    TTSSSTSLTE QRKTVGRTSK TKLSQHRALA VVAPRIIARS LSDEGEVETA    150
SEQ_ID_NO_1202    .........  KPAKTGGRN TTKAAPPRAL TVVPRIVARS LSDDGEVEIA    113
SEQ_ID_NO_1194    .........  .......... .......... .........P LSTKSTVDIA    73
SEQ_ID_NO_1200    .........  .TSI...... .......... ...PPL.-KP LSHKGEIELA    71

SEQ_ID_NO_1204    LSHLRTADPL LSEVIASTGA PAFISSPSRP AFHSLAHSIL HQQLAPSAAA    118
SEQ_ID_NO_1203    IRYLRAADPA LAAVIDAH-E PPVFDCPHRP -FHSLVRSIL YQQLAFKAAA    139
SEQ_ID_NO_1205    IQHLRAADPA LATVIDAH-D PPAFDCPHRP -FHSLVRSIL YQQLAFKAAA    136
SEQ_ID_NO_1196    IRHLRDADPL LASLIDLH-P PPTFDTFHAP -FLALTRSIL YQQLAFKAGT    198
SEQ_ID_NO_1202    LRYLRNADPV LSPLIDIH-Q PPTFDNFHTP -FLALTRSIL YQQLAYKAGT    161
SEQ_ID_NO_1194    LRHLQSSDEL LGALITTHND PPVFDSSNTP -FLSLARSIL YQQLATKAAK    122
SEQ_ID_NO_1200    LDHLSKSDPL LAPLLNSH-E PPALNPCTSP -FLSLTKSIL FQQLATNAAK    119
```

Figure 41 (continued)

| SEQ_ID_NO | | | | | | | |
|---|---|---|---|---|---|---|---|
| SEQ_ID_NO_1204 | AIYARFLAL | PAAADPDAAV | VNPAAVLALS | AADLRAI GVS | ARKAAYLHDL | | 168 |
| SEQ_ID_NO_1203 | SVYSRFLALL | ----G-GESD | VAPDAVLALT | PHQLRQI GVS | PRKASYLHDL | | 184 |
| SEQ_ID_NO_1205 | SVYSRFLSLL | ----G-GEHN | VLPEAVLALT | TQDLRQI GVS | PRKASYLHDL | | 181 |
| SEQ_ID_NO_1196 | SIYTRFISLC | ----G-GENG | VVPETVLSLT | SQQLRQI GVS | GRKASYLHDL | | 243 |
| SEQ_ID_NO_1202 | SIYTRFIALC | ----G-GENG | VVPETVLALT | PQQLRQI GVS | GRKASYLHDL | | 206 |
| SEQ_ID_NO_1194 | CIYDRFISLF | ----NGGEAG | VFPESVISLS | AVDLRKI GVS | GRKASYLHDL | | 168 |
| SEQ_ID_NO_1200 | SIYTRFLTLC | ----D-GESQ | VNPDTVLSLS | APKLREI GVS | GRKASYLHDL | | 164 |

| SEQ_ID_NO_1204 | AGRFAAGELS | ESAVAAMDEA | ALLAELTKVK | GVGEWIVHMF | MIFSLHRPDV | 218 |
|---|---|---|---|---|---|---|
| SEQ_ID_NO_1203 | ARKYASGILS | DAAIVNMDDR | SLAAMLTMVK | GIGSWSVHMF | MIFSLARPDV | 234 |
| SEQ_ID_NO_1205 | ARKYASGILS | DAAVVNMDDR | SLAAMLTMVK | GIGAWSVHMF | MIFSLNRPDV | 231 |
| SEQ_ID_NO_1196 | ARKYQTGILS | DSAIVNMDDK | SLFTMLTMVN | GIGSWSVHMF | MIFSLHRPDV | 293 |
| SEQ_ID_NO_1202 | ARKYQNGILS | DSAIVNMDDK | SLLTMLTMVN | GIGSWSVHMF | MIFSLHRPDV | 256 |
| SEQ_ID_NO_1194 | ADKYNNGVLS | DELLLKMSDE | ELIDRLTLVK | GIGVMTVHMF | MIFSLHRPDV | 218 |
| SEQ_ID_NO_1200 | AEKYRNGSLS | DSSILEMNDD | MLLNRLTEVK | GIGVWSVHMF | MLFSLHRPDV | 214 |

| SEQ_ID_NO_1204 | LPSGDLGVRK | GVQELYGLPA | LPKPEEMAAL | CERWRPYRSV | GAWYMWRLME | 268 |
|---|---|---|---|---|---|---|
| SEQ_ID_NO_1203 | LPSADLGVRK | GVQMLYALED | VPRPSQMDKL | CERWRPYRSV | GAWYMWRLIE | 284 |
| SEQ_ID_NO_1205 | LPAADLGVRK | GVQHLYGLDA | VPRPSQMEKL | CEQWRPYRSV | GAWYMWRLIE | 281 |
| SEQ_ID_NO_1196 | LPINDLGVRK | GVQLLYNLEE | LPRPSQMDQL | CEKWRPYRSV | ASWYLWRYVE | 343 |
| SEQ_ID_NO_1202 | LPINDLGVRK | GVQLLYNLED | LPRPSQMDQL | CDKWRPYRSV | ASWYMWRFVE | 306 |
| SEQ_ID_NO_1194 | LPVGDLGVRK | GVKDLYGLKN | LPGPLQMEQL | CEKWRPYRSV | GSWYMWRLIE | 268 |
| SEQ_ID_NO_1200 | LPVGDLGVRK | GVQSLYGLKD | LPQALEMEQI | CEKWKPYRSV | GSWYMWRLME | 264 |

| SEQ_ID_NO_1204 | SKGAAAKKAK | SNAIATLPS- | -------SC- | ---------- | ---------- | 289 |
|---|---|---|---|---|---|---|
| SEQ_ID_NO_1203 | SKVPQPAPAI | PVGSLAFPS- | ---------P | DGQSMLQQQE | QQQQQTVIQM | 324 |
| SEQ_ID_NO_1205 | SKAPPPPPAI | PVGPPALTE- | -------HGD | ELMLQQQQHQ | QQQQQSVIQM | 323 |
| SEQ_ID_NO_1196 | AKGAPSSAAA | VAAGASLPP- | ---------- | ----LQQQEE | PQQHQQQPPL | 378 |
| SEQ_ID_NO_1202 | AKGTPSSAVA | VATGAGLQQQ | QHHQHHHQHQ | QQEQQQQQQQ | QQQHPPQPQL | 356 |
| SEQ_ID_NO_1194 | SRKTK----- | ---------- | ---------- | ---------- | ---------- | 273 |
| SEQ_ID_NO_1200 | AKALANKAAK | KA-------- | ---------- | ---------- | ---------- | 276 |

Figure 41 (continued)

| SEQ_ID_NO_1204 | ---------- -------- | 289 |
| SEQ_ID_NO_1203 | IDPLQMLPGM G------ | 335 |
| SEQ_ID_NO_1205 | IDPLQMLPGM G------ | 334 |
| SEQ_ID_NO_1196 | MDPINSILNL G-ACAWGQ | 395 |
| SEQ_ID_NO_1202 | LDPINSMFNL GAACAWGQ | 374 |
| SEQ_ID_NO_1194 | ---------- -------- | 273 |
| SEQ_ID_NO_1200 | ---------- -------- | 276 |

Figure 42

| | | | | | | | |
|---|---|---|---|---|---|---|---|
| SEQ_ID_NO_1241 | MFL VDWFYGV | LASL GLWQKD | AKI LF GLDN | AGKTTLLHML | KDERL VQHQP | 50 |
| SEQ_ID_NO_1229 | MFV DWFYGV | LASL GLWQKE | AKI LF GLDN | AGKTTLLHML | KDERL VQHQP | 50 |
| SEQ_ID_NO_1249 | MFL WDWFYGV | LASL GLWQKE | AKI LF GLDN | AGKTTLLHML | KDERL VQHQP | 50 |
| SEQ_ID_NO_1264 | ---MGI VFTR | LFSSVFGNRE | ARI LVLGLDN | AGKTTI LYRL | QMGEVVSTI P | 47 |
| SEQ_ID_NO_1251 | ---MGI VFTR | LFSSVFGNRE | ARI LVLGLDN | AGKTTI LYRL | QMGEVVSTI P | 47 |
| SEQ_ID_NO_1265 | ---MGI VFTR | LFSSVFGNRE | ARI LVLGLDN | AGKTTI LYRL | QMGEVVSTI P | 47 |
| SEQ_ID_NO_1253 | ---MGI VFTK | LFSSVFGNKE | ARI LVLGLDN | AGKTTI LYRL | QMGEVVSTI P | 47 |
| SEQ_ID_NO_1210 | ---MGI LFTR | MFSSVFGNKE | ARI LVLGLDN | AGKTTI LYRL | QMGEVVSTI P | 47 |
| SEQ_ID_NO_1267 | ---MGI LFTR | MFSSVFGNKE | ARI LVLGLDN | AGKTTI LYRL | QMGEVVSTI P | 47 |
| SEQ_ID_NO_1213 | ---MGI LFTK | MFSNLFGNRE | ARI LVLGLDN | AGKTTI LYRL | QMGEVVSTI P | 47 |
| SEQ_ID_NO_1218 | ---MGI LFSK | MFSSVFGNKE | ARI LVLGLDN | AGKTTI LYRL | QMGEVVSTI P | 47 |
| SEQ_ID_NO_1232 | ---MGL VFTK | LFSSLFGNKE | ARI LVLGLDN | AGKTTI LYRL | QMGEVVSTI P | 47 |
| SEQ_ID_NO_1234 | ---MGL VFTR | LFSSVFGNKE | ARI LVLGLDN | AGKTTI LYRL | QMGEVVSTI P | 47 |
| SEQ_ID_NO_1272 | ---MGL SFTK | LFSRLFAKKE | MRI LMVGLDA | AGKTTI LYKL | KLGEI VTTI P | 47 |
| SEQ_ID_NO_1268 | ---MGI TFAK | LFQRLFSKKE | MRI LMVGLDA | AGKTTI LYKL | KLGEI VTTI P | 47 |
| SEQ_ID_NO_1211 | ---MGL RFTK | ALSRLFGKKE | MRI LMVGLDA | AGKTTI LYKL | KLGEI VTTI P | 47 |
| SEQ_ID_NO_1216 | ---MGL SFTK | LLGRLFSEKE | MRI LMVGLDA | AGKTTI LYKL | KLGEI VTTI P | 47 |
| SEQ_ID_NO_1269 | ---MGL SFTK | LLGRLFSKKE | MRI LMVGLDA | AGKTTI LYKL | KLGEI VTTI P | 47 |
| SEQ_ID_NO_1239 | ---MGL SFTK | LFSRLFAKKE | MRI LMVGLDA | AGKTTI LYQL | KLGEI VTTI P | 47 |
| SEQ_ID_NO_1259 | ---MGL TFTK | LFSRLFAKKE | MRI LMVGLDA | AGKTTI LYKL | KLGEI VTTI P | 47 |
| SEQ_ID_NO_1233 | ---MGL TFTK | LFSRLFAKKE | MRI LMVGLDA | AGKTTI LYKL | KLGEI VTTI P | 47 |
| SEQ_ID_NO_1235 | ---MGL SFTK | LFSRLFAKKE | MRI LMVGLDA | AGKTTI LYKL | KLGEI VTTI P | 47 |
| SEQ_ID_NO_1243 | ---MGL SFTK | LFSRLFAKKE | MRI LMVGLDA | AGKTTI LYKL | KLGEI VTTI P | 47 |
| SEQ_ID_NO_1270 | ---MGL SFTK | LFSRLFAKKE | MRI LMVGLDA | AGKTTI LYKL | KLGEI VTTI P | 47 |
| SEQ_ID_NO_1242 | ---MGL SFGK | LFSRLFAKKE | MRI LMVGLDA | AGKTTI LYKL | KLGEI VTTI P | 47 |
| SEQ_ID_NO_1238 | ---MGL SFTK | LFSRLFAKKE | MRI LMVGLDA | AGKTTI LYKL | KLGEI VTTI P | 47 |
| SEQ_ID_NO_1236 | ---MGL SFTK | LFSRLFAKKE | MRI LMVGLDA | AGKTTI LYKL | KLGEI VTTI P | 47 |
| SEQ_ID_NO_1240 | ---MGL SFGK | LFSRLFAKKE | MRI LMVGLDA | AGKTTI LYKL | KLGEI VTTI P | 47 |

Figure 42 (continued)

| SEQ_ID_NO | | | | | |
|---|---|---|---|---|---|
| SEQ_ID_NO_1241 | T---------- -----QYPT | SEELSIGNIK | FKAFDLGGHQ | IARRVWRDYY | 85 |
| SEQ_ID_NO_1229 | T---------- -----QHPT | SEELSIGKIK | FKAFDLGGHQ | IARRVWKDYY | 85 |
| SEQ_ID_NO_1249 | T---------- -----QHPT | SEELSIGKIK | FKAFDLGGHQ | IARRVWKDYY | 85 |
| SEQ_ID_NO_1264 | SGFPAPDSLI FFLPFA GFN | VETVQYNNIK | FDVWDLGGQT | SIRPYMRCYF | 97 |
| SEQ_ID_NO_1251 | T---------- ------ GFN | VETVQYNNIK | FDVWDLGGQT | SIRPYMRCYF | 82 |
| SEQ_ID_NO_1265 | T---------- ------ GFN | VETVQYNNIK | FDVWDLGGQT | SIRPYMRCYF | 82 |
| SEQ_ID_NO_1253 | T---------- ------ GFN | VETVQYNNIK | FDVWDLGGQT | SIRPYMRCYF | 82 |
| SEQ_ID_NO_1210 | T---------- ------ GFN | VETVQYNNIK | FDVWDLGGQT | SIRPYMRCYF | 82 |
| SEQ_ID_NO_1267 | T---------- ------ GFN | VETVQYNNIK | FDVWDLGGQT | SIRPYMRCYF | 82 |
| SEQ_ID_NO_1213 | T---------- ------ GFN | VETVQYNNIK | FDVWDLGGQT | SIRPYMRCYF | 82 |
| SEQ_ID_NO_1218 | T---------- ------ GFN | VETVQYNNIK | FDVWDLGGQT | SIRPYMRCYF | 82 |
| SEQ_ID_NO_1232 | T---------- ------ GFN | VETVQYNNIK | FDVWDLGGQT | SIRPYMRCYF | 82 |
| SEQ_ID_NO_1234 | T---------- ------ GFN | VETVQYNNIK | FDVWDLGGQT | SIRPYMRCYF | 82 |
| SEQ_ID_NO_1272 | T---------- ------ GFN | VETVEYKNIS | FTVWDVGGQD | KIRPLWRHYF | 82 |
| SEQ_ID_NO_1268 | T---------- ------ GFN | VETVEYKNIS | FTVWDVGGQD | KIRPLWRHYF | 82 |
| SEQ_ID_NO_1211 | T---------- ------ GFN | VETVEYKNIS | FTVWDVGGQD | KIRPLWRHYF | 82 |
| SEQ_ID_NO_1216 | T---------- ------ GFN | VETVEYKNIS | FTVWDVGGQD | KIRPLWRHYF | 82 |
| SEQ_ID_NO_1269 | T---------- ------ GFN | VETVEYKNIS | FTVWDVGGQD | KIRPLWRHYF | 82 |
| SEQ_ID_NO_1239 | T---------- ------ GFN | VETVEYQYS | FTVWDVGGQD | KIRPLWRHYF | 82 |
| SEQ_ID_NO_1259 | T---------- ------ GFN | VETVEYKNIS | FTVWDVGGQD | KIRPLWRHYF | 82 |
| SEQ_ID_NO_1233 | T---------- ------ GFN | VETVEYKNIS | FTVWDVGGQD | KIRPLWRHYF | 82 |
| SEQ_ID_NO_1235 | T---------- ------ GFN | VETVEYKNIS | FTVWDVGGQD | KIRPLWRHYF | 82 |
| SEQ_ID_NO_1243 | T---------- ------ GFN | VETVEYKNIS | FTVWDVGGQD | KIRPLWRHYF | 82 |
| SEQ_ID_NO_1270 | T---------- ------ GFN | VETVEYKNIS | FTVWDVGGQD | KIRPLWRHYF | 82 |
| SEQ_ID_NO_1242 | T---------- ------ GFN | VETVEYKNIS | FTVWDVGGQD | KIRPLWRHYF | 82 |
| SEQ_ID_NO_1239 | T---------- ------ GFN | VETVEYKNIS | FTVWDVGGQD | KIRPLWRHYF | 82 |
| SEQ_ID_NO_1236 | T---------- ------ GFN | VETVEYKNIS | FTVWDVGGQD | KIRPLWRHYF | 82 |
| SEQ_ID_NO_1240 | T---------- ------ GFN | VETVEYKNIS | FTVWDVGGQD | KIRPLWRHYF | 82 |

Figure 42 (continued)

| SEQ_ID | Col1 | Col2 | Col3 | Col4 | Col5 | Col6 | Num |
|---|---|---|---|---|---|---|---|
| SEQ_ID_NO_1241 | AKVDAVVYLV | DANDRERFPE | AKKELDGLLS | DESLTNVPFL | LGNKIDIPY | | 135 |
| SEQ_ID_NO_1229 | AKVDAVVYLV | DAYDKERFAE | SKKELDALLS | DESLATVPFL | LGNKIDIPY | | 135 |
| SEQ_ID_NO_1249 | AKVDAVVYLV | DAYDKERFAE | SKKELDALLS | DDSLANVPFL | LGNKIDIPY | | 135 |
| SEQ_ID_NO_1264 | PNTQAIYVV | DSSDTDRLVF | AKEEFHAILE | EDELKGAVVL | VYANKQDLPG | | 147 |
| SEQ_ID_NO_1251 | PNTQAIYVV | DSSDTDRLVT | AKEEFHSILE | EDELKGAVVL | VYANKQDLPG | | 132 |
| SEQ_ID_NO_1265 | PNTQAIYVV | DSSDTDRLVT | AKEEFHAILE | EDELKGAVVL | VYANKQDLPG | | 132 |
| SEQ_ID_NO_1253 | PNTQAVIYVV | DSSDTDRIGV | AKEEFHAILE | EEELKGAMVL | IFANKQDLPG | | 132 |
| SEQ_ID_NO_1210 | PNTQAVIYVV | DSSDTDRIGV | AKEEFHAILE | EDELKGAVVL | IFANKQDLPG | | 132 |
| SEQ_ID_NO_1267 | PNTQAVIYVV | DSSDTDRIGV | AKEEFHAILE | EEELKGAVVL | IFANKQDLPG | | 132 |
| SEQ_ID_NO_1213 | PNTQAIYVV | DSSDTDRLV | AKEEFHAILE | EEELRGAAVL | IFANKQDLPG | | 132 |
| SEQ_ID_NO_1218 | PNTQAIYVV | DSSDVDRLV | AKDEFHAILE | EEELRGAIVL | IFANKQDLPG | | 132 |
| SEQ_ID_NO_1232 | PNTQAIYVV | DSSDVDRLV | AKEEFHAILE | EEELKGAVVL | IFANKQDLPG | | 132 |
| SEQ_ID_NO_1234 | PNTQAIYVV | DSSDTDRLV | AREEFHAILE | EEELKGAVVL | IFANKQDLPG | | 132 |
| SEQ_ID_NO_1272 | QNTQGLIFVV | DSNDRDRVVE | ARDELHRMLN | EDELRDAVLL | VFANKQDLPN | | 132 |
| SEQ_ID_NO_1268 | QNTQGLIFVV | DSNDRDRVSE | ARDELHRMLN | EDELRDAVLL | VFANKQDLPN | | 132 |
| SEQ_ID_NO_1211 | QNTQGLIFVV | DSNDRERVVE | ARDELHRMLN | EDELRDAVLL | VFANKQDLPN | | 132 |
| SEQ_ID_NO_1216 | QNTQGLIFVV | DSNDRDRVGE | AREELHRMLN | EDELRDAVLL | VFANKQDLPN | | 132 |
| SEQ_ID_NO_1269 | QNTQGLIFVV | DSNDRDRVGE | ARDELHRMLN | EDELRDAVLL | VFANKQDLPN | | 132 |
| SEQ_ID_NO_1239 | QNTQGLIFVV | DSNDRDRVVE | ARDELHRMLN | EDELRDAVLL | VFANKQDLPN | | 132 |
| SEQ_ID_NO_1259 | QNTQGLIFVV | DSNDRDRIVE | AKDELHRMLN | EDELRDAVLL | VFANKQDLPN | | 132 |
| SEQ_ID_NO_1233 | QNTQGLIFVV | DSNDRDRVVE | ARDELHRMLN | EDELRDAVLL | VFANKQDLPN | | 132 |
| SEQ_ID_NO_1235 | QNTQGLIFVV | DSNDRDRVVE | ARDELHRMLN | EDELRDAVLL | VFANKQDLPN | | 132 |
| SEQ_ID_NO_1243 | QNTQGLIFVV | DSNDRDRVVE | ARDELHRMLN | EDELREAVLL | VFANKQDLPN | | 132 |
| SEQ_ID_NO_1270 | QNTQGLIFVV | DSNDRDRVVE | ARDELHRMLN | EDELRDAVLL | VFANKQDLPN | | 132 |
| SEQ_ID_NO_1242 | QNTQGLIFVV | DSNDRDRVVE | ARDELHRMLN | EDELREAVLL | VFANKQDLPN | | 132 |
| SEQ_ID_NO_1238 | QNTQGLIFVV | DSNDRDRVVE | AKDELHRMLN | GDELRDAVLL | VFANKQDLPN | | 132 |
| SEQ_ID_NO_1236 | QNTQGLIFVV | DSNDRDRVVE | ARDELHRMLN | EDELRDAVLL | VFANKQDLPN | | 132 |
| SEQ_ID_NO_1240 | QNTQGLIFVV | DSNDRDRVVE | ARDELHRMLN | EDELRDAVLL | VFANKQDLPN | | 132 |

Figure 42 (continued)

| | | | | | | | |
|---|---|---|---|---|---|---|---|
| SEQ_ID_NO_1241 | AASEDELRYH | LGLTGVTTGK | GNINLAGTNV | RP--IEVFMC | SIVRK--MGY | 181 |
| SEQ_ID_NO_1229 | AASEDELRYH | LGLSNFTTGK | GKVDLVGSNV | RP--LEVFMC | SIVRK--MGY | 181 |
| SEQ_ID_NO_1249 | AASEEELRYH | LGLSSFTTGK | GKVSLCDSNV | RP--LEVFMC | SVVRK--MGY | 181 |
| SEQ_ID_NO_1264 | ALDDAAITES | LELHKIKS-- | ---------- | RQ--WAIFKT | SAIKG--EGL | 181 |
| SEQ_ID_NO_1251 | ALDDAAITES | LELHKIKS-- | ---------- | RQ--WAIFKT | SAIKG--EGL | 166 |
| SEQ_ID_NO_1265 | ALDDAAITES | LELHKIKS-- | ---------- | RQ--WAIFKT | SAIKG--EGL | 166 |
| SEQ_ID_NO_1253 | ALDDAAVTEA | LELHKIKS-- | ---------- | RQ--WAIFKT | CAVKG--EGL | 166 |
| SEQ_ID_NO_1210 | ALDDAAVTEA | LELHKIKS-- | ---------- | RQ--WAIFKT | CAVKG--EGL | 166 |
| SEQ_ID_NO_1267 | ALDDAAVTEA | LELHKIKS-- | ---------- | RQ--WAIFKT | CAVKG--EGL | 166 |
| SEQ_ID_NO_1213 | ALDDAAVTES | LELHKIKN-- | ---------- | RQ--WAIFKT | SAIKG--EGL | 166 |
| SEQ_ID_NO_1218 | ALDDAAVTEA | LELHKIKN-- | ---------- | RQ--WAIFKT | SAIKG--EGL | 166 |
| SEQ_ID_NO_1232 | ALDDAAVTEA | LELHKIKN-- | ---------- | RQ--WAIFKT | SAIKG--EGL | 166 |
| SEQ_ID_NO_1234 | ALDDAAVTES | LELHKIKN-- | ---------- | RQ--WAIFKT | SAIKG--EGL | 166 |
| SEQ_ID_NO_1272 | AMNAAEITDK | LGLHSLRQ-- | ---------- | RPNLWGLINS | PKEVPLVANL | 170 |
| SEQ_ID_NO_1268 | AMSAAEITDK | LGLHSLRQ-- | ---------- | RH--WFIQST | CATSG--EGL | 166 |
| SEQ_ID_NO_1211 | AMNAAEITDK | LGLHSLRQ-- | ---------- | RH--WYIQST | CATSG--EGL | 166 |
| SEQ_ID_NO_1216 | AMNAAEITDK | LGLHSLRQ-- | ---------- | RH--WYIQST | CATSG--EGL | 166 |
| SEQ_ID_NO_1269 | AMNAAEITDK | LGLHSLRQ-- | ---------- | RH--WYIQST | CATSG--EGL | 166 |
| SEQ_ID_NO_1239 | AMNAAEITDK | HGLHSLRQ-- | ---------- | RH--WYIQST | CATSG--EGL | 166 |
| SEQ_ID_NO_1259 | AMNAAEITDK | LGLHSLRQ-- | ---------- | RH--WYIQST | CATSG--EGL | 166 |
| SEQ_ID_NO_1233 | AMNAAEITDK | LGLHSLRQ-- | ---------- | RH--WYIQST | CATSG--EGL | 166 |
| SEQ_ID_NO_1235 | AMNAAEITDK | LGLHSLRQ-- | ---------- | RH--WYIQST | CATSG--EGL | 166 |
| SEQ_ID_NO_1243 | AMNAAEITDK | LGLHSLRQ-- | ---------- | RH--WYIQST | CATSG--EGL | 166 |
| SEQ_ID_NO_1270 | AMNAAEITDK | LGLHSLRQ-- | ---------- | RH--WYIQST | CATSG--EGL | 166 |
| SEQ_ID_NO_1242 | AMNAAEITDK | LGLHSLRQ-- | ---------- | RH--WYIQST | CATSG--EGL | 166 |
| SEQ_ID_NO_1238 | AMNAAEITDK | LGLHSLRQ-- | ---------- | RH--WYIQST | CATSG--EGL | 166 |
| SEQ_ID_NO_1236 | AMNAAEITDK | LGLHSLRQ-- | ---------- | RH--WYIQST | CATSG--EGL | 166 |
| SEQ_ID_NO_1240 | AMNAAEITDK | LGLHSLRQ-- | ---------- | RH--WYIQST | CATSG--EGL | 166 |

Figure 42 (continued)

| | | | |
|---|---|---|---|
| SEQ_ID_NO_1241 | GEGFK- - - - - - - - - - - - - - - - - - - - - - - - - - - - - - - - - -WMSQY | K- - - - - - - - | 193 |
| SEQ_ID_NO_1229 | GEGFK- - - - - - - - - - - - - - - - - - - - - - - - - - - - - - - - - -MLSQY | K- - - - - - - - | 193 |
| SEQ_ID_NO_1249 | GDGFK- - - - - - - - - - - - - - - - - - - - - - - - - - - - - - - - - -WVSQY | N- - - - - - - - | 193 |
| SEQ_ID_NO_1264 | FEGLDCSVLQ HIILQFLPDE CIWEYLMELT YKSLMYLHIE | KNRFVENDE | 231 |
| SEQ_ID_NO_1251 | FEGLN- - - - - - - - - - - - - - - - - - - - - - - - - - - - - - - - - -MLSNA | KSGGS- - - - | 182 |
| SEQ_ID_NO_1265 | FEGLD- - - - - - - - - - - - - - - - - - - - - - - - - - - - - - - - - -MLSNA | KSKSS- - - - | 182 |
| SEQ_ID_NO_1253 | FEGLD- - - - - - - - - - - - - - - - - - - - - - - - - - - - - - - - - -MLSNT | KSGTG- - - - | 182 |
| SEQ_ID_NO_1210 | FEGLD- - - - - - - - - - - - - - - - - - - - - - - - - - - - - - - - - -MLSNT | KSGSG- - - - | 182 |
| SEQ_ID_NO_1267 | FEGLD- - - - - - - - - - - - - - - - - - - - - - - - - - - - - - - - - -MLSNT | KSGSG- - - - | 182 |
| SEQ_ID_NO_1213 | FEGLD- - - - - - - - - - - - - - - - - - - - - - - - - - - - - - - - - -MLSNT | KSGSG- - - - | 182 |
| SEQ_ID_NO_1218 | FEGLD- - - - - - - - - - - - - - - - - - - - - - - - - - - - - - - - - -MLSNT | KSGGG- - - - | 182 |
| SEQ_ID_NO_1232 | FEGLD- - - - - - - - - - - - - - - - - - - - - - - - - - - - - - - - - -MLSNT | KSGGG- - - - | 182 |
| SEQ_ID_NO_1234 | FEGLD- - - - - - - - - - - - - - - - - - - - - - - - - - - - - - - - - -MLSNT | KSGGG- - - - | 182 |
| SEQ_ID_NO_1272 | FLG- - - - - - - - - - - - - - - - - - - - - - - - - - - - - - - - - - - -WKGVL | LGGGPKNLG | 188 |
| SEQ_ID_NO_1268 | YEGLD- - - - - - - - - - - - - - - - - - - - - - - - - - - - - - - - - -MLSSN | SQRA- - - - | 181 |
| SEQ_ID_NO_1211 | YEGLD- - - - - - - - - - - - - - - - - - - - - - - - - - - - - - - - - -MLSNN | ANKT- - - - | 181 |
| SEQ_ID_NO_1216 | YEGLD- - - - - - - - - - - - - - - - - - - - - - - - - - - - - - - - - -MLSNN | ASKA- - - - | 181 |
| SEQ_ID_NO_1269 | YEGLD- - - - - - - - - - - - - - - - - - - - - - - - - - - - - - - - - -MLSNN | SSKA- - - - | 181 |
| SEQ_ID_NO_1239 | YEGLD- - - - - - - - - - - - - - - - - - - - - - - - - - - - - - - - - -MLSNN | ANKA- - - - | 181 |
| SEQ_ID_NO_1259 | YEGLD- - - - - - - - - - - - - - - - - - - - - - - - - - - - - - - - - -MLSNN | ASKA- - - - | 181 |
| SEQ_ID_NO_1233 | YEGLD- - - - - - - - - - - - - - - - - - - - - - - - - - - - - - - - - -MLSNN | ASKA- - - - | 181 |
| SEQ_ID_NO_1235 | YEGLE- - - - - - - - - - - - - - - - - - - - - - - - - - - - - - - - - -MLSNN | ASKA- - - - | 181 |
| SEQ_ID_NO_1243 | YEGLD- - - - - - - - - - - - - - - - - - - - - - - - - - - - - - - - - -MLSNN | ASKA- - - - | 181 |
| SEQ_ID_NO_1270 | YEGLD- - - - - - - - - - - - - - - - - - - - - - - - - - - - - - - - - -MLSNN | ASKG- - - - | 181 |
| SEQ_ID_NO_1242 | YEGLD- - - - - - - - - - - - - - - - - - - - - - - - - - - - - - - - - -MLSNN | SNKA- - - - | 181 |
| SEQ_ID_NO_1238 | YEGLD- - - - - - - - - - - - - - - - - - - - - - - - - - - - - - - - - -MLSNN | ANKA- - - - | 181 |
| SEQ_ID_NO_1236 | YEGLD- - - - - - - - - - - - - - - - - - - - - - - - - - - - - - - - - -MLSNN | ANKA- - - - | 181 |
| SEQ_ID_NO_1240 | YEGLD- - - - - - - - - - - - - - - - - - - - - - - - - - - - - - - - - -MLSNN | ANKA- - - - | 181 |

Figure 42 (continued)

| SEQ ID | Sequence | Number |
|---|---|---|
| SEQ_ID_NO_1241 | . . . . . . . . . . . . . | 193 |
| SEQ_ID_NO_1229 | . . . . . . . . . . . . . | 193 |
| SEQ_ID_NO_1249 | . . . . . . . . . . . . . | 193 |
| SEQ_ID_NO_1264 | QTVRTLGHWW LYP | 244 |
| SEQ_ID_NO_1251 | . . . . . . . . . . . . . | 182 |
| SEQ_ID_NO_1265 | . . . . . . . . . . . . . | 182 |
| SEQ_ID_NO_1253 | . . . . . . . . . . . . . | 182 |
| SEQ_ID_NO_1210 | . . . . . . . . . . . . . | 182 |
| SEQ_ID_NO_1267 | . . . . . . . . . . . . . | 182 |
| SEQ_ID_NO_1213 | . . . . . . . . . . . . . | 182 |
| SEQ_ID_NO_1218 | . . . . . . . . . . . . . | 182 |
| SEQ_ID_NO_1232 | . . . . . . . . . . . . . | 182 |
| SEQ_ID_NO_1234 | . . . . . . . . . . . . . | 182 |
| SEQ_ID_NO_1272 | LLSPKPK--- . . . | 195 |
| SEQ_ID_NO_1268 | . . . . . . . . . . . . . | 181 |
| SEQ_ID_NO_1211 | . . . . . . . . . . . . . | 181 |
| SEQ_ID_NO_1216 | . . . . . . . . . . . . . | 181 |
| SEQ_ID_NO_1269 | . . . . . . . . . . . . . | 181 |
| SEQ_ID_NO_1239 | . . . . . . . . . . . . . | 181 |
| SEQ_ID_NO_1259 | . . . . . . . . . . . . . | 181 |
| SEQ_ID_NO_1233 | . . . . . . . . . . . . . | 181 |
| SEQ_ID_NO_1235 | . . . . . . . . . . . . . | 181 |
| SEQ_ID_NO_1243 | . . . . . . . . . . . . . | 181 |
| SEQ_ID_NO_1270 | . . . . . . . . . . . . . | 181 |
| SEQ_ID_NO_1242 | . . . . . . . . . . . . . | 181 |
| SEQ_ID_NO_1238 | . . . . . . . . . . . . . | 181 |
| SEQ_ID_NO_1236 | . . . . . . . . . . . . . | 181 |
| SEQ_ID_NO_1240 | . . . . . . . . . . . . . | 181 |

Figure 43

| | | | | | | | | |
|---|---|---|---|---|---|---|---|---|
| SEQ_ID_NO_1285 | ---------- | ---------- | ---- | MVGNAF | VEQYYS LHR | DPDQVHRFYH | 26 |
| SEQ_ID_NO_1297 | MAVSDGVQTP | TP-------- | ---- | DVVGNAF | VEQYYS LHQ | DPDQVHKFYH | 39 |
| SEQ_ID_NO_1284 | MALQ-TATPP | TT-------- | PSAQ | VGNAF | VEQYYHI LHH | SPGSVYRFYQ | 41 |
| SEQ_ID_NO_1300 | MAAP-QPAAP | AP-----EAP | PSAQ | VGNAF | VQQYYLVLHQ | SPDLVYRFYQ | 44 |
| SEQ_ID_NO_1294 | MAAP-Q-ASP | S--------- | PSAQ | VGNAF | VQQYYQ LHQ | SPDLVYRFYQ | 39 |
| SEQ_ID_NO_1295 | MAAP-Q-ASP | S--------- | PSAQ | VGNAF | VQQYYQ LHQ | SPDLVYRFYQ | 39 |
| SEQ_ID_NO_1287 | MAAP-TPPPA | AAPAAAPGPT | PPAQ | VGNAF | VQQYYNI LHQ | SPELVFRFYQ | 49 |
| SEQ_ID_NO_1289 | -MAS-QPPPP | AA-AAASGAP | PPAQ | VGNAF | VHQYYNI LHQ | SPELVYRFYQ | 47 |
| SEQ_ID_NO_1291 | MASP-PPPPP | AG-AAAPGSP | PPAQ | VGNAF | VNQYYNI LHQ | SPELVHRFYQ | 48 |
| SEQ_ID_NO_1274 | MAML GAQQVP | AA-----ACT | PL-D | MVGNAF | VPQYYHI LHQ | SPEHVHRFYQ | 43 |
| SEQ_ID_NO_1276 | MASV-EQQVP | AG-----IAT | PTSD | VVGNAF | VHQYYL LHQ | SPELVHRFYH | 44 |
| SEQ_ID_NO_1280 | MAAP-VTQLP | V--------- | PTAD | VVGNAF | AHQYYHI LQQ | SPDLVHRFYQ | 40 |

| | | | | | | | | |
|---|---|---|---|---|---|---|---|---|
| SEQ_ID_NO_1285 | DSSVMSRP- | -EEDGTMTTV | TTTAE DKKI | QSLEYTSFRV | EVLSADAQPS | 73 |
| SEQ_ID_NO_1297 | ESSVLSRP- | -EEDGTMTTV | TTTAE DKKI | QSFDYTSYRV | EVLSADAQPS | 86 |
| SEQ_ID_NO_1284 | DSSVI SRP- | -DSSGVMTSV | TTMKG NEKI | LSLNFKEFKA | EIKTADAQKS | 88 |
| SEQ_ID_NO_1300 | DASRLARPAS | AAGAAGMDSV | TTMEAI SEKI | MEMDVS-KA | EIRTVDSQES | 92 |
| SEQ_ID_NO_1294 | DASRLGRP-P | ADRYGDWSV | TTMEAI NEKI | MAMDMS-RA | EIKTVDSQES | 86 |
| SEQ_ID_NO_1295 | DASRLGRP-P | ADRYGDWSV | TTMEAI NEKI | MAMDMS-RA | EIKTVDSQES | 86 |
| SEQ_ID_NO_1287 | EASRI GRPAT | TGAD--MDTV | TTMEAI NEKI | MSMDA--RA | EIRGVDAQES | 95 |
| SEQ_ID_NO_1289 | EASDLGRPAG | TGADG-MDTV | TTMDAI NDKI | VSMGID--RA | KIKAVDAQES | 94 |
| SEQ_ID_NO_1291 | DASRLGRPAG | AGADG-MDTV | TTMDAI SDKI | VSMGIT--RA | EIKAVDAQES | 95 |
| SEQ_ID_NO_1274 | ELSKLGRP- | -EENGLMSIT | GTLQAI DKKI | MALGYGVI SA | EIATVDTQES | 90 |
| SEQ_ID_NO_1276 | DSSKLGRP- | -EENGGMSIT | TTMQAI NEKI | LSLGYGEFTA | EITTVDAQDS | 91 |
| SEQ_ID_NO_1280 | DGSKFGRP- | -GEDGVMSTT | TTMNAI NEKI | LSLGYGQVRA | EIVTVDSQES | 87 |

| | | | | | | | | |
|---|---|---|---|---|---|---|---|---|
| SEQ_ID_NO_1285 | YNNGVMVVT | GCLTGTDNIK | RKFAQSFFLA | PQDKGFYVLN | DVFRYVDAY- | 122 |
| SEQ_ID_NO_1297 | YNSGVVVVT | GCLTGTDNVK | RKFAQSFFLA | PQDKGFYVLN | DVFRYVDAY- | 135 |
| SEQ_ID_NO_1284 | YKEGVTVLVT | GCLTGKDNLR | RKFAQSFFLA | PQDNGYFVLN | DVFRYVEDH- | 137 |
| SEQ_ID_NO_1300 | LGGGVTVLVT | GHLTGRDSVR | REFSQSFFLA | PQEKGYFVLN | DIFRFYGDL- | 141 |
| SEQ_ID_NO_1294 | LGGGVTVLVT | GHLTVRDGVC | REFSQSFFLA | PQEKGYFVLN | DMFRYVGDG- | 135 |
| SEQ_ID_NO_1295 | LGGGVTVLVT | GHLTVRDGVC | REFSQSFFLA | PQEKGYFVLN | DMFRYVGDG- | 135 |
| SEQ_ID_NO_1287 | LCGGVTVLVT | GHLTGKDDVC | REFAQSFFLA | PQEKGYFVLN | DILRYVGQG- | 144 |
| SEQ_ID_NO_1289 | LCGGVSVLVM | GHLTGRNSVS | RQFVQSFFLA | PQEKGYFVLN | DILRYVGEG- | 143 |
| SEQ_ID_NO_1291 | LGGGVTVLVM | GHLTGRTSVG | REFVQSFFLA | PQEKGYFVLN | DILRYVGDGX | 145 |
| SEQ_ID_NO_1274 | HGSGYIVLVT | GYLTGKDSVR | RTFSQTFFLA | PQETGYFVLN | DMFRFIDEG- | 139 |
| SEQ_ID_NO_1276 | HNGGVLYLVT | GYLTGKDKVK | RKFTQSFFLA | PQDKGYFVLN | DVFRFVDDT- | 140 |
| SEQ_ID_NO_1280 | YKGGVLVLVT | GYLNGNDNLR | QKFITQSFFLA | PQDKGYFVLN | DVFRYVDDS- | 136 |

Figure 43 (continued)

| | | | | | | |
|---|---|---|---|---|---|---|
| SEQ_ID_NO_1285 | ········KS | IDIESVPAND | ADESAPSEA | TPEPEPVHV | PEVIPPTQTV | 164 |
| SEQ_ID_NO_1297 | ·········K | SVDIETVPAN | DADESAPSEA | FTPDPEPIHV | A·······ED | 169 |
| SEQ_ID_NO_1284 | ········EP | SELPPVTGDG | DSAAVTVTPE | EPSHVAD·· | ········SC | 169 |
| SEQ_ID_NO_1300 | ········PA | PTAVEAQPEA | DAVVPPVAAP | LANGTATPAV | EPAIPDDHDA | 183 |
| SEQ_ID_NO_1294 | ·······PTP | AAAAAKAVEV | QPEADAVAPP | LANGTATAPL | QPAAPDY-DG | 177 |
| SEQ_ID_NO_1295 | ··········P | TPAAAAAAEV | QPEADAVAPP | LANGTATAPL | QPAAPDY-DA | 175 |
| SEQ_ID_NO_1287 | ··EADPSLPP | PQQQPPAPEL | DAVVAP-AAA | LANGTVAP·· | VETVPREQEA | 189 |
| SEQ_ID_NO_1289 | ····GGDEGA | EKDPAPEVAA | DAEKTTSAPI | LANGTVGGDA | TTVPQ···DA | 186 |
| SEQ_ID_NO_1291 | GEEGAGHPPP | PPQQPVQETV | TGAEAVPAPI | LANGTVGG-D | NETLPCEQDA | 194 |
| SEQ_ID_NO_1274 | ·········· | ····TVVHGN | QIPVNNVQAP | VNTYQDTAAA | KEIPDDFVQE | 175 |
| SEQ_ID_NO_1276 | ·········· | ····KHQPGG | QDPVNGFEAS | LTHEQGHS·· | ·········· | 164 |
| SEQ_ID_NO_1280 | ·········· | ····THQNGN | QEPASNFEAP | VAPDQDTP·· | ·········· | 160 |

| | | | | | | |
|---|---|---|---|---|---|---|
| SEQ_ID_NO_1285 | IPTAQTVPP | TQTVIADTET | IISKEVSLPL | ENGKLSVT·· | ·········· | 202 |
| SEQ_ID_NO_1297 | IPTIQPVAD | TDTNISK·· | ····EVSLPL | ENGKLSVT·· | ·········· | 200 |
| SEQ_ID_NO_1284 | APEPTNSHVN | KGQTVAE·· | ····NAVELS | NNHERQIPV· | ·········· | 201 |
| SEQ_ID_NO_1300 | VPQQENHVVD | RSPPQPEEED | EA··EVYNPP | PEEVV····· | ·········· | 216 |
| SEQ_ID_NO_1294 | MPQEEPDVVE | HAAVPPEEEE | ····EVYNPP | LEEVEGGAV· | ·········· | 212 |
| SEQ_ID_NO_1295 | MPHEEPDVVE | NVAVPPEEEE | ····EVYNPP | LEEVEGGAV· | ·········· | 210 |
| SEQ_ID_NO_1287 | SPQPELDLSE | SVPHTNEEED | PKE·EVYNPP | NDVEVPV··· | ·········· | 225 |
| SEQ_ID_NO_1289 | SPQPECQVAE | PALNPKEEVL | NG-·EVCNSL | SDVEKPV··· | ·········· | 221 |
| SEQ_ID_NO_1291 | SPQPEQPAAE | SAPPTPEEED | LYGEEVYNPP | NDMEKPV··· | ·········· | 231 |
| SEQ_ID_NO_1274 | KYVQENHAVK | QTEVLSKSTN | EPE·KVFTPS | EDEQVSA··· | ·········· | 211 |
| SEQ_ID_NO_1276 | -PVPENHIEQ | PAA-LPEECN | GP··EVYNSS | ENGDGSIE·· | ·········· | 198 |
| SEQ_ID_NO_1280 | -HTQETHLSE | PTAALSEEVI | GG··EVYNPS | ESGDVSVEVE | EEESGDVSFE | 207 |

| | | | | | | |
|---|---|---|---|---|---|---|
| SEQ_ID_NO_1285 | ENVIPVNHVK | ESSHHVKEPE | QPTS EKVAS | NTQEDTPKKS | FASIVNALKD | 252 |
| SEQ_ID_NO_1297 | ENVIPVNHVK | ESSHQEQMAS | IEKV····PS | NTQEDTPKKS | FASIVSAYKD | 246 |
| SEQ_ID_NO_1284 | ENEGNVESHF | QSNGNDDSQA | TELA·····S | SAQDDAPKKS | YASIVKVQKG | 246 |
| SEQ_ID_NO_1300 | DEEQPVPEVI | NEVPNNVAPM | AATT···VAP | VLQEEAPKKS | YASIVKVMKE | 263 |
| SEQ_ID_NO_1294 | EEEQSVPEVI | NEVPNNVVPV | VAPA···AAP | VSHEEAPKKS | YASIVKVMKE | 259 |
| SEQ_ID_NO_1295 | EEEQSVPEVI | NEVPNNVVPV | VAPA···DAP | VSHEEAPKKS | YASIVKVMKE | 257 |
| SEQ_ID_NO_1287 | VEETLVPEVI | DEVPNNVAAS | IPVS···APP | VPHEEAPKKS | YASIVKVMKA | 272 |
| SEQ_ID_NO_1289 | AEETPVPDVI | NEVPNNVAVA | PPIS···SPP | VPLKEAPKKS | YASIVKVMKE | 268 |
| SEQ_ID_NO_1291 | VDETPVAEVI | NEVPNNVAVA | APSS···SPS | IPIEEAPKKS | YASIVKVMKE | 278 |
| SEQ_ID_NO_1274 | AEEVLVTETV | NEAPIEVQKV | GESD······ | SRTGEIPKRS | YASIVKVMKE | 255 |
| SEQ_ID_NO_1276 | EEESPVAEVV | DEIPDDSKMV | SDSK······ | PEMEELPKKS | YASILKVLKE | 242 |
| SEQ_ID_NO_1280 | EEEFPMPEVV | DEIPPDSQLV | ADSDVVVESS | AKIEDTPKKS | YASVVKVQKE | 257 |

Figure 43 (continued)

| | | | | | | | |
|---|---|---|---|---|---|---|---|
| SEQ_ID_NO_1285 | NSAPFHL--- | -RASPAKPAV | HPP--RVHSV | PAPEAPTPNM | D-PLEKNN-- | | 294 |
| SEQ_ID_NO_1297 | NSAPFLS--- | -RTSPAKPAV | QPP--RVHSV | PAPEAPAPNM | D-PSEKNN-- | | 288 |
| SEQ_ID_NO_1284 | SSVPTKYYV- | -PTNTLKSGP | NKT--ESKVV | ES-VESTEVP | EAALESMSNP | | 291 |
| SEQ_ID_NO_1300 | VPLPA----- | -PAPPTRPAP | PKP--EKQS- | -P-PAPTPVT | DVPPFSSN-P | | 301 |
| SEQ_ID_NO_1294 | APVPAPIPAT | RPAPAARPAP | PKP--EKQSP | AP-PAPAPVA | DATPFSSN-A | | 305 |
| SEQ_ID_NO_1295 | APVPAPIPAT | RPAPAARPAP | PKP--EKQSP | AP-PAPAPVA | DATPFSSN-A | | 303 |
| SEQ_ID_NO_1287 | VLPPN----- | -STVPYRPAP | PKP--EKQA- | -PAPAQSVAV | DAPTFSPN-P | | 311 |
| SEQ_ID_NO_1289 | HRPLA----- | -PAVPSRPAP | P-T--EKQA- | -S-PAPTPVT | EAPAFSPN-P | | 306 |
| SEQ_ID_NO_1291 | YPPPA----- | -PAVPSRPAP | PKP--EKQA- | -P-PAPSLVA | DAPAFSPN-T | | 316 |
| SEQ_ID_NO_1274 | NAAPMSA--- | -SRTPTKVEP | KKD--EDQA- | HI-PLPTPLS | EKSDSGANVA | | 296 |
| SEQ_ID_NO_1276 | NAVPVSAP-- | -TQSPVKSAV | KSQGHPRVAA | PP--SAPNPAS | DAQVSSNN-VT | | 288 |
| SEQ_ID_NO_1280 | YTAPFSSP-- | -TPSPLRSAP | KIQ--EQVTA | AV-SQP-PAA | ESHVSSSNTF | | 300 |

| | | | | | | | |
|---|---|---|---|---|---|---|---|
| SEQ_ID_NO_1285 | ENAGR----- | --AHAIFVAN | LPMSATVEQL | DRAFKKFGP- | KRDGIQVRSN | | 337 |
| SEQ_ID_NO_1297 | ENGGR----- | --AHAIFVAN | LPMTATVEQL | DRVFKKFGTI | KRDGIQVRSN | | 331 |
| SEQ_ID_NO_1284 | ESSDAHE-EV | E-GHSIYIRN | LPLNVTVADL | ELEFKKFGP- | KPGGIQVRNN | | 339 |
| SEQ_ID_NO_1300 | DNSNQEPEV | D-AHAIYVRN | LPLNATETQL | EDEFKKFGTI | KQNGIQVRSN | | 350 |
| SEQ_ID_NO_1294 | ESSNTHEPEV | D-AHAIYVRS | LPLNATTTQL | EDEFKKFGTI | KPDGIQVRSH | | 354 |
| SEQ_ID_NO_1295 | ESSNTHEPEV | D-AHAIYVRS | LPLNATTTQL | EDEFKKFGTI | KPDGIQVRSH | | 352 |
| SEQ_ID_NO_1287 | ESSNQDQEV | D-ALAVYVKN | LPLHATPSQL | EEEFKRFGTI | KHDGIQVRSH | | 360 |
| SEQ_ID_NO_1289 | QSGGFQDPEV | D-AHAIYVRS | LPLNATPQDL | EEEFKRFGTI | KHEGIQVRSN | | 355 |
| SEQ_ID_NO_1291 | QGGSFDDPEV | D-AHAIYVRN | LPLNATPQDL | EEEFKRFGTI | KHEGIQVRSN | | 365 |
| SEQ_ID_NO_1274 | VNENNQENER | ALGPSIYLKG | LPLDATPAL- | ENEFQKFGL- | RTNGIQVRSQ | | 348 |
| SEQ_ID_NO_1276 | ENGNNQDAEA | E-GPSIYVKG | LPLNATPSML | EVEFKKFGP- | KSGGIQVRSQ | | 337 |
| SEQ_ID_NO_1280 | ENGNAQEBE- | E-GPSIYVKG | LPLDATTTLL | ENEFKKFGP- | RNGGVQVRFQ | | 348 |

| | | | | | | | |
|---|---|---|---|---|---|---|---|
| SEQ_ID_NO_1285 | K--GSCFGFV | EFESAASMQS | ALEASPPVML | DNRRLSIEER | RGR------- | | 378 |
| SEQ_ID_NO_1297 | K--GSCFGFV | EFESAASLQS | ALEASPPVML | DNRRLSIEER | RGR------- | | 372 |
| SEQ_ID_NO_1284 | KQQGYCFGFV | EFLSLNSMNS | AIQAS-PVPI | GGRQAVVE-K | RTTTRVGSGI | | 388 |
| SEQ_ID_NO_1300 | KIQGFCYGFV | EFEDSTSVQS | AIEAS-PVT- | GGRQCYVEEK | RTP---GSR- | | 395 |
| SEQ_ID_NO_1294 | KIQGFCYGFV | EFEEATAVQS | AIEAS-PVMI | GGRQCFVEEK | RTP---GSR- | | 399 |
| SEQ_ID_NO_1295 | KIQGFCYGFV | EFEEATAVQS | AIEAS-PVMI | GGRQCFVEEK | RTP---GSR- | | 397 |
| SEQ_ID_NO_1287 | KIQGFCYGFI | EFEDASSVQS | ALAAS-PVT- | DDRPCHVEEK | RTP---GS-- | | 404 |
| SEQ_ID_NO_1289 | KIQGFCYGFV | EFEDASAVQA | AIEAS-PVT- | GEROCFVEEK | RTT---GSRG | | 401 |
| SEQ_ID_NO_1291 | KIQGFCYGFV | EFEDANAVQT | AIEAS-PVMI | SERQCYVEEK | RTT---GSR- | | 410 |
| SEQ_ID_NO_1274 | K--GFCFGFV | EFESASSMQS | AIEAS-PVML | NGHKVVVEEK | RST---A--- | | 389 |
| SEQ_ID_NO_1276 | K--GFCFGFV | EFEMASSVQS | AIEAS-PIN- | GGRKAVVEEK | RST---S--- | | 378 |
| SEQ_ID_NO_1280 | K--GFCFGFV | EFEVASAVQS | ALELIYLFLF | T--------- | ---------- | | 377 |

Figure 43 (continued)

| | | | | | | | | |
|---|---|---|---|---|---|---|---|---|
| SEQ_ID_NO_1285 | SGYR- | ----- | ----NDRND | NFRGRGNFGG | GRGGGFNGRN | DF-ERRGGEF | | 416 |
| SEQ_ID_NO_1297 | GGYR- | ----- | ----NDRND | NFRGRGNFGG | GRGGGFNGRN | DF-DRRG-EF | | 409 |
| SEQ_ID_NO_1284 | NGTGRPR-PS | GRG--GLRND | SFRGRGNYVG | GR-G--YGRN | DY-VSRG-GF | | | 431 |
| SEQ_ID_NO_1300 | GSSRGGRFAP | GRGN-NFRSE | GTRGRGNYGG | GR-G--YGRG | EF-SYRS-DY | | | 439 |
| SEQ_ID_NO_1294 | GSSRGGRFAP | GRGNNNFRAD | GMRGRGNYGG | GR-S--YGRG | DF-SYRS-DY | | | 444 |
| SEQ_ID_NO_1295 | GSSRGGRFAP | GRGNNNFRAD | GMRGRGNYGG | GR-S--YGRG | DF-SYRS-DY | | | 442 |
| SEQ_ID_NO_1287 | RGSSRGRFPP | GRGG-NFRGE | GMRGRGSYTG | GR-G--YGRG | EYNNYRS-DF | | | 449 |
| SEQ_ID_NO_1289 | GGSRGGRFPP | GRGG-NFRGE | GIRGRGTYNG | GR-G--YGRG | EF-SYRS-DY | | | 445 |
| SEQ_ID_NO_1291 | CSNRGGRFAP | GRGG-NFRGE | GLRGRGTYNG | GR-G--YGRG | EF-SYRS-DY | | | 454 |
| SEQ_ID_NO_1274 | RGNYRGRSTF | GVNT-GYRNE | GGRGRGSFGG | GRGG--YGRT | DFNGYGN--  | | | 433 |
| SEQ_ID_NO_1276 | RGN-KGKSSS | VSGA-GYRNE | GARGRGNYGG | GR-G--YSRG | EF------- | | | 415 |
| SEQ_ID_NO_1280 | TGNNRGRFPS | GSGA-GYKSE | GMRGRGNL-G | GK-V--YGRV | EF-GIRT-EF | | | 420 |

| | | | | |
|---|---|---|---|---|
| SEQ_ID_NO_1285 | SGRSRGG-QN | AGR-------- | ------S | 429 |
| SEQ_ID_NO_1297 | SGRPRGG-NN | TGR-------- | ------S | 422 |
| SEQ_ID_NO_1284 | SGRGRGH--- | ---------- | ------- | 438 |
| SEQ_ID_NO_1300 | GGRSGGR-GG | PAR-------- | ------G | 452 |
| SEQ_ID_NO_1294 | GGRGGGR-GG | SAR-------- | ------G | 457 |
| SEQ_ID_NO_1295 | GGRGGGR-GG | SAR-------- | ------G | 455 |
| SEQ_ID_NO_1287 | GGRGGGR-GG | SGR-------- | ------G | 462 |
| SEQ_ID_NO_1289 | GGRGGGR-GG | SLH-------- | ------G | 458 |
| SEQ_ID_NO_1291 | GGRGGGR-GG | SSR-------- | ------G | 467 |
| SEQ_ID_NO_1274 | -NRGNNR-GG | YANRAN---- | ------G | 448 |
| SEQ_ID_NO_1276 | GNRSSNR-GG | YSS-------- | ------R | 428 |
| SEQ_ID_NO_1280 | GNRGGSRGGG | YSNRGGDGYS NRGGGGGGGG DGYSNRGGGG GGDGYSNRGG | | 470 |

| | | | | | |
|---|---|---|---|---|---|
| SEQ_ID_NO_1285 | NGDAVPRSYQ | NG--GGKVAA | RQPPVKVQ-- | ---------- | 455 |
| SEQ_ID_NO_1297 | NGDAAPRSYQ | NG--GGKV-A | RQPPVKAQ-- | ---------- | 447 |
| SEQ_ID_NO_1284 | -GEGYHQG-- | ----RGRG-G | RSSGQKQNAV | SN-------- | 462 |
| SEQ_ID_NO_1300 | ADVGYQRVDH | AGYAGGRG-G | RTAAAGAPAK | ---------- | 481 |
| SEQ_ID_NO_1294 | PDVGYQRVDH | ----GGRG-G | RTSAGPGAPA | K--------- | 482 |
| SEQ_ID_NO_1295 | PDVGYQRVDH | ----GGRG-G | RTSAGPGAPA | K--------- | 480 |
| SEQ_ID_NO_1287 | GDVGYQRVDH | SGT-GGRGGA | RAAAK----- | ---------- | 486 |
| SEQ_ID_NO_1289 | GDVGYQRVDY | SGTSSGRG-A | RAPSAAAAMA | K--------- | 488 |
| SEQ_ID_NO_1291 | -EVGYQRVDH | SGTAGGRG-T | RPASAATAAK | ---------- | 495 |
| SEQ_ID_NO_1274 | DGGGFPRANG | NF--NGRV-R | RGGIDANRA  | TKPVDDAPHV SVTA | 488 |
| SEQ_ID_NO_1276 | GGDGYQRGEH | MSGNGGRV-S | RSGEATFNAS | TKNV--APRV SAPA | 469 |
| SEQ_ID_NO_1280 | GGDGYRRADK | MGNNGGRA-N | RSGGLGLNGT | AKTT--APRV SATA | 511 |

Figure 44

| | | | | | | | |
|---|---|---|---|---|---|---|---|
| SEQ_ID_NO_1327 | MVVTVAATG- | PDTAETLHST | TFASRYVRDQ | LPRYRMPENS | PKEAAYQII | 49 |
| SEQ_ID_NO_1333 | MVVSVAATGA | GTDAEPVTST | FFASRYVRDP | LRRYRMPERS | PREAAYQII | 50 |
| SEQ_ID_NO_1336 | MVVSVAATDS | DTAQPVQYST | FFASRYVRDP | LPRFRMPEQS | PREAAYQII | 50 |
| SEQ_ID_NO_1319 | MVLTTTS-- | RDSEESLHCT | -FASRYVQEP | LPKFKMPKKS | MPKEAAYQIV | 47 |
| SEQ_ID_NO_1302 | MVLATN---- | SDSDEHLHST | -FASRYVRAV | VPRFKMPDHC | MPKDAAYQVI | 45 |
| SEQ_ID_NO_1311 | MVISTAA--- | TDSDENLYST | -FASRYVRTA | LPRFKMPENS | MPKDAAYQVI | 46 |
| SEQ_ID_NO_1317 | MVLTSTATHP | DEQDQSLNYT | -FASRYVREP | PKFKMPEKS | PKDAAYQII | 49 |
| SEQ_ID_NO_1305 | MLAAT----- | NPTEEHVHST | -FASRYVRAP | VPRFKMPEKS | PKDAAYQVI | 44 |
| SEQ_ID_NO_1339 | MALSSA---- | TDSDGSIHST | -FASRYVQES | LPRFQIPSRS | PKDAAYQII | 45 |
| SEQ_ID_NO_1318 | MVLSETA--- | THMDASVHST | -FASRYVRTS | LPRFKMGENS | PKEAAYQII | 46 |
| SEQ_ID_NO_1331 | MVLSNTASSG | SESDLSIHST | -FASRYVRTS | LPRFKMPQES | PKEAAYQII | 49 |
| SEQ_ID_NO_1313 | MVLSKTA--- | SESDVSIHST | -FASRYVRTS | LPRFEMPENS | PKEAAYQII | 46 |
| SEQ_ID_NO_1303 | MVLSKTF--- | SESDESIHST | -FASRYVRNS | LPRFTMPENS | PKEAAYQII | 46 |
| SEQ_ID_NO_1340 | MVLSKTA--- | SESDVSVHST | -FASRYVRAS | LPRFKMPENS | PKEAAFQII | 46 |
| SEQ_ID_NO_1320 | MVLSKTA--- | SESDVSIHST | -FASRYVRTS | LPRFKMPENS | PKEAAYQII | 46 |
| SEQ_ID_NO_1326 | MVLSKTV--- | SQSDVSIHST | -FASRYVRTS | LPRFKMPDNS | PKEAAYQII | 46 |
| SEQ_ID_NO_1334 | MVLSKAV--- | SESDMSVHST | -FASRYVRAS | LPRYRMPENS | PKEAAYQII | 46 |
| SEQ_ID_NO_1330 | MVLSHGV--- | GGSDESVHST | -FASRYVRTS | LPRYRMPEQS | PKEAAYQII | 46 |

| | | | | | | | |
|---|---|---|---|---|---|---|---|
| SEQ_ID_NO_1327 | SDELMLDGNP | RLNLASFVTT | MMEPECGKLI | NDSVNKNYVD | MDEYPVTTEL | 99 |
| SEQ_ID_NO_1333 | NDELMLDGNP | RLNLASFVTT | MMEPECDKLI | MGSINKNYVD | MDEYPVTTEL | 100 |
| SEQ_ID_NO_1336 | NDELMLDGNP | RLNLASFVTT | MMEPECDKLI | NDSVNKNYVD | MDEYPVTTEL | 100 |
| SEQ_ID_NO_1319 | NDELMLDGNP | RLNLASFVST | MMEPECDKLI | MSSINKNYVD | MDEYPVTTEL | 97 |
| SEQ_ID_NO_1302 | NDELMLDGNP | RLNLASFVTT | MMEPECDKLI | NDSVNKNYVD | MDEYPVTTEL | 95 |
| SEQ_ID_NO_1311 | NDELMLDGNP | RLNLASFVTT | MMEPECNDLI | MASINKNYVD | MDEYPVTTEL | 96 |
| SEQ_ID_NO_1317 | NDELMLDGAP | RLNLASFVTT | MMEPECDKLI | MASLNKNYVD | MDEYPVTTEL | 99 |
| SEQ_ID_NO_1305 | HDELMLDGNP | RLNLASFVTT | MMEPECDKLM | MAAINKNYVD | MDEYPVTTEL | 94 |
| SEQ_ID_NO_1339 | SDELMLDGNP | RLNLASFVTT | MMEPECDKLI | MDAINKNYVD | MDEYPVTTEL | 95 |
| SEQ_ID_NO_1318 | NDELMLDGNP | RLNLASFVTT | MMEPECDKLI | MASINKNYVD | MDEYPVTTEL | 96 |
| SEQ_ID_NO_1331 | NDELMLDGNP | RLNLASFVTT | MMEPECDKLI | MASINKNYVD | MDEYPVTTEL | 99 |
| SEQ_ID_NO_1313 | NDELMLDGNP | RLNLASFVTT | MMEPECDKLM | MESINKNYVD | MDEYPVTTEL | 96 |
| SEQ_ID_NO_1303 | NDELMLDGNP | RLNLASFVTT | MMEPECDKLM | MAAINKNYVD | MDEYPVTTEL | 96 |
| SEQ_ID_NO_1340 | NDELMLDGNP | RLNLASFVTT | MMEPECDKLI | ASINKNYVD | MDEYPVTTEL | 96 |
| SEQ_ID_NO_1320 | NDELMLDGNP | RLNLASFVTT | MMEPECNKLM | MDSINKNYVD | MDEYPVTTEL | 96 |
| SEQ_ID_NO_1326 | NDELMLDGNP | RLNLASFVTT | MMEPECDKLM | MDSINKNYVD | MDEYPVTTEL | 96 |
| SEQ_ID_NO_1334 | NDELMLDGNP | RLNLASFVTT | MMEPECDKLI | MAAINKNYVD | MDEYPVTTEL | 96 |
| SEQ_ID_NO_1330 | NDELMLDGNP | RLNLASFVTT | MMEPECDKLI | GASVNKNYVD | MDEYPVTTEL | 96 |

Figure 44 (continued)

| SEQ ID | | | | | | | |
|---|---|---|---|---|---|---|---|
| SEQ_ID_NO_1327 | QDRCVNMIAH | LFNAPIGEDE | TAIGVSTVGS | SEAIMLAGLA | FKRKWANKMK | | 149 |
| SEQ_ID_NO_1333 | QNRCVNMIAH | LFNAPIKEDE | TAVGVGTVGS | SEAIMLAGLA | FKRKWQNKRK | | 150 |
| SEQ_ID_NO_1336 | QNRCVNMIAH | LFNAPIKEDE | TAIGVGTVGS | SEAIMLAGLA | FKRKWQNKRK | | 150 |
| SEQ_ID_NO_1319 | QNRCVNMLAH | LFHAPVGDDE | TAVGVGTVGS | SEAIMLAGLA | FKRKWQSKRK | | 147 |
| SEQ_ID_NO_1302 | QNRCVNMIAN | FFHAPVGEDE | AAIGCGTVGS | SEAIMLAGLA | FKRKWQHRRK | | 145 |
| SEQ_ID_NO_1311 | QNRCVNIIAH | LFNAPVGEKE | TAVGVGTVGS | SEAIMLAGLA | FKRKWQNKRK | | 146 |
| SEQ_ID_NO_1317 | QNRCVNIIAN | LFHAPISDDE | TAVGVGTVGS | SEAIMLAGLA | FKRKWQTKRK | | 149 |
| SEQ_ID_NO_1305 | QNRCVNMIAN | LFHAPVGEEE | TAVGVGTVGS | SEAIMLAGLA | FKRRWQHKRK | | 144 |
| SEQ_ID_NO_1339 | QNRCVNIIAN | LFNAPLGDGE | EAVGVGTVGS | SEAIMLAGLA | FKRKWQNKRK | | 145 |
| SEQ_ID_NO_1318 | QNRCVNMIAH | LFNAPLEDSE | PAVGVGTVGS | SEAIMLAGLA | FKRKWQNRRK | | 146 |
| SEQ_ID_NO_1331 | QNRCVNMIAH | LFNAPLGDSD | L---VGTVGS | SEAIMLAGLA | FKRIWQNRRK | | 146 |
| SEQ_ID_NO_1313 | QNRCVNMIAR | LFNAPLGDGE | AAVGVGTVGS | SEAIMLAGLA | FKRQWQNKRK | | 146 |
| SEQ_ID_NO_1303 | QNRCVNIIAR | LFNAPLEDSE | TAVGVGTVGS | SEAIMLAGLA | FKRKWQNKRK | | 146 |
| SEQ_ID_NO_1340 | QNRCVNMIAH | LFNAPLGDSE | TAVGVGTVGS | SEAIMLAGLA | FKRKWQNKRK | | 146 |
| SEQ_ID_NO_1320 | QNRCVNMIAH | LFNAPLGDGE | TAVGVGTVGS | SEAIMLAGLA | FKRKWQNKMK | | 146 |
| SEQ_ID_NO_1326 | QNRCVNMIAH | LFNAPLEDGE | TAVGVGTVGS | SEAIMLAGLA | FKRKWQNKMK | | 146 |
| SEQ_ID_NO_1334 | QNRCVNMIAH | LFHAPLGEDE | TAVGVGTVGS | SEAIMLAGLA | FKRRWQNKRK | | 146 |
| SEQ_ID_NO_1330 | QNRCVNMIAH | LFNAPLGDAE | TAVGVGTVGS | SEAIMLAGLA | FKRRWQNKMK | | 146 |

| SEQ ID | | | | | | | |
|---|---|---|---|---|---|---|---|
| SEQ_ID_NO_1327 | EQGKPCDKPN | VTGANVQVC | WEKFARYFEV | ELKEVKLTEG | YYVMDPKKAV | | 199 |
| SEQ_ID_NO_1333 | EQGKPYDKPN | VTGANVQVC | WEKFARYFEV | ELKEVKLSEG | YYVMDPVKAV | | 200 |
| SEQ_ID_NO_1336 | EQGKPCDKPN | VTGANVQVC | WEKFARYFEV | ELKEVKLSEG | YYVMDPVKAV | | 200 |
| SEQ_ID_NO_1319 | AEGKPFDKPN | VTGANVQVC | WEKFARYFEV | ELKEVKLKEG | YYVMDPAKAV | | 197 |
| SEQ_ID_NO_1302 | AQGLPIDKPN | VTGANVQVC | WEKFARYFEV | ELKEVKLSED | YYVMDPAKAV | | 195 |
| SEQ_ID_NO_1311 | AEGKPYDKPN | VTGANVQVC | WEKFARYFEV | ELKEVKLTEG | YYVMDPVKAV | | 198 |
| SEQ_ID_NO_1317 | AEGKPYDKPN | VTGANVQVC | WEKFARYFEV | ELKEVKLKEG | YYVMDPAKAV | | 199 |
| SEQ_ID_NO_1305 | TEGKPTDNPN | VTGANVQVC | WEKFARYFEV | GLKEVKLKEG | YYVMDPEQAV | | 194 |
| SEQ_ID_NO_1339 | AEGKPYDKPN | VTGANVQVC | WEKFARYFEV | ELKEVKLKKD | YYIMDPVKAV | | 195 |
| SEQ_ID_NO_1318 | SEGKSCENPN | VTGANVQVC | WEKFARYFEV | ELKEVKLRDG | YYVMDPEKAA | | 196 |
| SEQ_ID_NO_1331 | AEGKPHDKPN | VTGANVQVC | WEKFARYFEV | ELKEVKLSEG | YYVMDPQKAV | | 196 |
| SEQ_ID_NO_1313 | AQGLPYDKPN | VTGANVQVC | WEKFARYFEV | ELKEVKLREG | YYVMDPEKAV | | 196 |
| SEQ_ID_NO_1303 | AEGKPFDKPN | VTGANVQVC | WEKFARYFEV | ELKEVKLSEG | YYVMDPAKAV | | 196 |
| SEQ_ID_NO_1340 | AEGKPYDKPN | VTGANVQVC | WEKFARYFEV | ELKEVKLSDG | YYVMDPEKAV | | 196 |
| SEQ_ID_NO_1320 | AQGKPCDKPN | VTGANVQVC | WEKFARYFEV | ELKEVKLSDG | YYVMDPEKAV | | 196 |
| SEQ_ID_NO_1326 | AQGKPCDKPN | VTGANVQVC | WEKFARYFEV | ELKEVKLSEG | YYVMDPEKAV | | 196 |
| SEQ_ID_NO_1334 | AEGKPFDKPN | ITGANVQVC | WEKFARYFEV | ELKEVKLRDG | YYVMDPEKAV | | 196 |
| SEQ_ID_NO_1330 | AAGKPCDKPN | VTGANVQVC | WEKFARYFEV | ELKEVKLSDG | YYVMDPQKAV | | 196 |

Figure 44 (continued)

| SEQ ID | Col1 | Col2 | Col3 | Col4 | Col5 | Col6 | # |
|---|---|---|---|---|---|---|---|
| SEQ_ID_NO_1327 | EMVDENTICV | AAILGSTLTG | EYEDVKLLND | LLVEKNKETG | MNVPIHVDAA | | 249 |
| SEQ_ID_NO_1333 | DMVDENTICV | AAILGSTLTG | EFEDVKQLND | LLTEKNKETG | MDVPIHVDAA | | 250 |
| SEQ_ID_NO_1336 | EMVDENTICV | AAILGSTLTG | EFEDVKLLNN | LLTEKNKETG | MDVPIHVDAA | | 250 |
| SEQ_ID_NO_1319 | EIVDENTICV | AAILGSTLTG | EFEDVKLLNE | LLTKKNKETG | METPIHVDAA | | 247 |
| SEQ_ID_NO_1302 | EMVDENTICV | AAILGSTLTG | EFEDVKQLND | LLAEKNAETG | METPIHVDAA | | 245 |
| SEQ_ID_NO_1311 | EMVDENTICV | AAILGSTLTG | EFEDVKLLND | LLSKKNKETG | MNTPIHVDAA | | 246 |
| SEQ_ID_NO_1317 | EMVDENTICV | AAILGSTMTG | EFEDVKLLDE | LLTKKNNETG | MDTPIHVDAA | | 249 |
| SEQ_ID_NO_1305 | ELVDENTICV | AAILGSTLTG | EFEDVKTLND | LLMKKNEETG | MGTPIHVDAA | | 244 |
| SEQ_ID_NO_1339 | EMVDENTICV | AAILGSTYNG | EFEDVKLVND | LLIQKNKETG | MDTPIHVDAA | | 245 |
| SEQ_ID_NO_1318 | EMVDENTICV | AAILGSTLNG | EFEDVKRLND | LLVEKNAETG | MDTPIHVDAA | | 246 |
| SEQ_ID_NO_1331 | DLVDENTICV | AAILGSTLNG | EFEDVKRLND | LLIEKNKETG | MDTPIHVDAA | | 246 |
| SEQ_ID_NO_1313 | EMVDENTICV | AAILGSTLTG | EFEDVKLLND | LLVEKNKQTG | MDTGIHVDAA | | 246 |
| SEQ_ID_NO_1303 | EMVDENTICV | AAILGSTLNG | EFEDVKLLND | LLTEKNKETG | MDTPIHVDAA | | 246 |
| SEQ_ID_NO_1340 | QMVDENTICV | AAILGSTLNG | EFEDVKLLND | LLVEKNKSTG | MDTPIHVDAA | | 246 |
| SEQ_ID_NO_1320 | EMVDENTICV | AAILGSTLNG | EFEDVKRLND | LLIEKNKETG | MDTPIHVDAA | | 246 |
| SEQ_ID_NO_1326 | EMVDENTICV | AAILGSTLNG | EFEDVKRLND | LLVEKNKETG | MDTPIHVDAA | | 246 |
| SEQ_ID_NO_1334 | DMVDENTICV | AAILGSTLNG | EFEDVKLLND | LLDKKNKETG | METPIHVDAA | | 246 |
| SEQ_ID_NO_1330 | DMVDENTICV | AAILGSTLNG | EFEDVKLLND | LLTKKNAETG | MDTPIHVDAA | | 246 |

| SEQ ID | Col1 | Col2 | Col3 | Col4 | Col5 | # |
|---|---|---|---|---|---|---|
| SEQ_ID_NO_1327 | SGGFIAPFLQ | PELEWDFRLP | LVKSINVSGH | KYGLVYPGVG | WIWRSKDDL | 299 |
| SEQ_ID_NO_1333 | SGGFIAPFLY | PELEWDFRLP | LVKSINVSGH | KYGLVYAGVG | WIWRSKKDL | 300 |
| SEQ_ID_NO_1336 | SGGFIAPFLY | PELEWDFRLP | LVKSINVSGH | KYGLVYPGVG | WIWRSKEDL | 300 |
| SEQ_ID_NO_1319 | SGGFIAPFLW | PDLEWDFRLP | LVKSINVSGH | KYGLVYAGVG | WIWRSKEDL | 297 |
| SEQ_ID_NO_1302 | SGGFIAPFLY | PDLEWDFRLP | WKSINVSGH | KYGLVYAGVG | WVWRTKDDL | 295 |
| SEQ_ID_NO_1311 | SGGFIAPFIW | PDLEWDFRLP | LVKSINVSGH | KYGLVYAGVG | WVWRTKEDL | 296 |
| SEQ_ID_NO_1317 | SGGFIAPFLY | PDLEWDFRLP | LVKSINVSCH | KYGLVYPGVG | WVWRSKDDL | 299 |
| SEQ_ID_NO_1305 | SGGFIAPFLY | PDLEWDFRLP | LVKSINVSGH | KYGLVYAGVG | WVWRNKEDL | 294 |
| SEQ_ID_NO_1339 | SGGFIAPFLY | PELEWDFRLP | LVKSINVSGH | KYGLVYAGIG | WIWRAKQDL | 295 |
| SEQ_ID_NO_1318 | SGGFIAPFLY | PELVWDFRLS | LVKSINVSGH | KYGLVYAGIG | MIWRSKEDL | 296 |
| SEQ_ID_NO_1331 | SGGFIAPFIY | PELEWDFRLP | LVKSINVSGH | KYGLVYAGIG | WIWRNKEDL | 296 |
| SEQ_ID_NO_1313 | SGGFIAPFLY | PELEWDFRLP | LVKSINVSGH | KYGLVYAGIG | WVWRTKSDL | 296 |
| SEQ_ID_NO_1303 | SGGFIAPFLY | PELEWDFRLP | LVKSINVSGH | KYGLVYAGIG | WVWRNKEDL | 296 |
| SEQ_ID_NO_1340 | SGGFIAPFIY | PELEWDFRLP | LVKSINVSGH | KYGLVYAGIG | WIWRNKEDL | 296 |
| SEQ_ID_NO_1320 | SGGFIAPFLY | PELEWDFRLP | LVKSINVSGH | KYGLVYAGIG | WAWRNKEDL | 296 |
| SEQ_ID_NO_1326 | SGGFIAPFIY | PELEWDFRLP | LVKSINVSGH | KYGLVYAGIG | WVWRNKDDL | 296 |
| SEQ_ID_NO_1334 | SGGFIAPFLY | PELEWDFRLP | WKSINVSGH | KYGLVYAGIG | WCWRNKEDL | 296 |
| SEQ_ID_NO_1330 | SGGFIAPFLY | PELEWDFRLP | LVKSINVSGH | KYGLVYAGIG | WCWRTKVDL | 296 |

Figure 44 (continued)

| SEQ_ID | col1 | col2 | col3 | col4 | col5 | pos |
|---|---|---|---|---|---|---|
| SEQ_ID_NO_1327 | PEELIFHINY | LGADQPTFTL | NFSKGQ-QII | AQYYQLIRLG | FEGYKHIMEN | 348 |
| SEQ_ID_NO_1333 | PEELIFHINY | LGTDQPTFTL | NFSKGSSQII | AQYYQLIRLG | FQGYKNIMEN | 350 |
| SEQ_ID_NO_1336 | PEELIFHINY | LGTDQPTFTL | NFSKGSSQII | AQYYQLIRLG | FEGYKNIMQN | 350 |
| SEQ_ID_NO_1319 | PDELVFHINY | LGSDQPTFTL | NFSKGSYQII | AQYYQLIRLG | FEGYKNVMKN | 347 |
| SEQ_ID_NO_1302 | PEELVFHINY | LGADQPTFTL | NFSKGSSQII | AQYYQFIRLG | FEGYKNIMEN | 345 |
| SEQ_ID_NO_1311 | PDELIFHINY | LGSDQPTFTL | NFSKGSGQII | AQYYQFIRLG | FEGYKRIMEN | 346 |
| SEQ_ID_NO_1317 | PDELVFHINY | LGSDQPTFTL | NFSKGSSQII | AQYYQLIRLG | FEGYKNIMEN | 349 |
| SEQ_ID_NO_1305 | PDDLVFHINY | LGSDQPTFTL | NFSKGSSQII | AQYYQFLRLG | FEGYKNIIEN | 344 |
| SEQ_ID_NO_1339 | PEELIFHINY | LGADQPTFTL | NFSKGASQII | AQYYQLIRLG | FEGYRNIMGN | 345 |
| SEQ_ID_NO_1318 | PEELIFHINY | LGADQPTFTL | NFSKGSSQVI | AQYYQLIRLG | YEGYRNVMEN | 346 |
| SEQ_ID_NO_1331 | PEELIFHINY | LGADQPTFTL | NFSKGSSQII | AQYYQLIRLG | YEGYKHVMEN | 346 |
| SEQ_ID_NO_1313 | PDELIFHINY | LGADQPTFTL | NFSKGSSQVI | AQYYQLIRLG | FEGYRNVMDN | 346 |
| SEQ_ID_NO_1303 | PEELIFHINY | LGADQPTFTL | NFSKGSSQVI | AQYYQLIRLG | FEGYRNVMEN | 346 |
| SEQ_ID_NO_1340 | PEELIFHINY | LGADQPTFTL | NFSKGSSQVI | AQYYQLIRLG | YEGYKNVMEN | 346 |
| SEQ_ID_NO_1320 | PDELIFHINY | LGADQPTFTL | NFSKGSSQVI | AQYYQLIRLG | FEGYKNVMEN | 346 |
| SEQ_ID_NO_1326 | PDELIFHINY | LGADQPTFTL | NFSKGSSQVI | AQYYQLIRLG | YEGYKNVMEN | 346 |
| SEQ_ID_NO_1334 | PEELIFHINY | LGADQPTFTL | NFSKGSSQVI | AQYYQLIRHG | FEGYRNIMEN | 346 |
| SEQ_ID_NO_1330 | PEELIFHINY | LGADQPTFTL | NFSKGSSQVI | AQYYQLIRLG | FEGYKNIMEN | 346 |

| SEQ_ID | col1 | col2 | col3 | col4 | col5 | pos |
|---|---|---|---|---|---|---|
| SEQ_ID_NO_1327 | CKLNAAVLKE | GIDATGRFDV | LSKADGVPLV | ARLKDSTNF | SVFDISENLR | 398 |
| SEQ_ID_NO_1333 | CMENAAILRE | GIAATGRFDI | LSKDAGVPLV | AFSLKDSSRF | SVFDISENLR | 400 |
| SEQ_ID_NO_1336 | CMENTAILRE | GIEATGRFEI | LSKEAGVPLV | AFSLKDSGRY | TVFDISEHLR | 400 |
| SEQ_ID_NO_1319 | CLSNAKVLTE | GITKMGRFDI | VSKDVGVPVV | AFSLRDSSKY | TVFEVSEHLR | 397 |
| SEQ_ID_NO_1302 | CVDNARRLRE | GIEMTGKFNI | VSKDISVPLV | AFSLKDSSKH | TVFEIAESLR | 395 |
| SEQ_ID_NO_1311 | CLENARVLRE | GLEKTGRFDI | VSKDKGVPLV | AFSLKDSSKH | TVFEIAESLR | 396 |
| SEQ_ID_NO_1317 | CMENARVLKE | GIERTGRFNI | ISKDIGVPLV | AFSLQDSSQH | TVFEIADHLR | 399 |
| SEQ_ID_NO_1305 | CMENMKVLKQ | GIENTGRFNI | LSKDIGVPLV | AFSLKDSSKH | TVFEIAENLR | 394 |
| SEQ_ID_NO_1339 | CAANAKALSD | GLVRTGRFNI | LSKEIGVPLV | AFSLKDSSRH | DEYEISDHLR | 395 |
| SEQ_ID_NO_1318 | CRDNMMVLKD | GLEKTERFEI | VSKDEGVPLV | AFTLKDHNNF | NEFQISDMLK | 396 |
| SEQ_ID_NO_1331 | CRDNMLVLKE | GLQKTGRFEI | VSKDNGVPLV | AFTLKDHTHY | NEFQISDSLL | 395 |
| SEQ_ID_NO_1313 | CRENMMVLRE | GLEKTGRFNI | VSKENGVPLV | AFSLKDSSRH | DEFEVAETLR | 396 |
| SEQ_ID_NO_1303 | CHENAMVLKE | GLEKTGRFNI | VSKDEGVPLV | AFSLKDNKRH | DEFEVAELLR | 396 |
| SEQ_ID_NO_1340 | CRDNMLVLKQ | GLEKTGKFNI | VSKDKGVPLV | AFSLKDNSLH | NEFEVSDMLR | 396 |
| SEQ_ID_NO_1320 | CQENARVLRE | GLEKSGRFNI | ISKEIGVPLV | AFSLKDNSQH | NEFEISETLR | 396 |
| SEQ_ID_NO_1326 | CQENASVLRE | GLEKTGRFNI | ISKEIGVPLV | AFSLKDNRQH | NEFEISETLR | 396 |
| SEQ_ID_NO_1334 | CHENAMVLKE | GLVKTGRFDI | VSKDEGVPLV | AFSLKDRSRH | DEFEISDMLR | 396 |
| SEQ_ID_NO_1330 | CQENAIVLKQ | GLEKTGKFNI | VSKDNGVPLV | AFSLKDSSRH | SEFEISDFLR | 396 |

Figure 44 (continued)

| | | | | | | | |
|---|---|---|---|---|---|---|---|
| SEQ_ID_NO_1327 | RFGW VPAYT | MPADAEHVAV | LRI VI REDFN | RSLAQRLL AD | I NKI I GELDA | 448 |
| SEQ_ID_NO_1333 | RFGW VPAYT | MPADAEHVAV | LRVVI REDFS | RTLLERLVGD | VLKI LRELDA | 450 |
| SEQ_ID_NO_1336 | RFGW VPAYT | MPANAEHVAV | LRVVI REDFS | RSLAERLVSD | VKI LHELDA | 450 |
| SEQ_ID_NO_1319 | RFGW VPAYT | MPPDAEHI AV | LRVVI REDFS | HSLAERLVSD | I EKI LSELDT | 447 |
| SEQ_ID_NO_1302 | KFGW I PAYT | MPADAQHI AV | LRVVI REDFS | RGLADRLI TH | I QVLKEI EG | 445 |
| SEQ_ID_NO_1311 | RFGW I PAYT | MPANAQHI AV | LRVVVREDFN | RSLAERLVSH | I DQVMKETDS | 446 |
| SEQ_ID_NO_1317 | KFGW VPAYT | MPPDAQHI AV | LRVVI REDFS | RGLAERLAAD | I EKVVKLLDT | 449 |
| SEQ_ID_NO_1305 | RFGW LPAYT | MPANAQHVAV | LRAVI REDFS | HGLAKRLVAH | I EQVLKEMDG | 444 |
| SEQ_ID_NO_1339 | RFGW VPAYT | MAPDAQEVKL | LRVVVREDFN | RSLAERLVHD | I EKVLHELDT | 445 |
| SEQ_ID_NO_1318 | RHGW I PAYT | MPPDAEHVTV | LRVVI REDFS | RTFAERLVI D | I TRVI HELDL | 446 |
| SEQ_ID_NO_1331 | ---------- | ---------A | LRV........ | ............ | ..........DS | 401 |
| SEQ_ID_NO_1313 | RFGW VPAYT | MPADAQHVTV | LRVVI REDFS | RTLAERLVAD | FEKVL HELDT | 446 |
| SEQ_ID_NO_1303 | RFGW VPAYT | MPADAQHI TV | LRVVI REDFS | RTLAERLVLD | I TKVL HELDS | 446 |
| SEQ_ID_NO_1340 | RFGW VPAYT | MPPDAQHVTV | LRVVI REDFS | RTLAERLVI D | I GKVL HELET | 446 |
| SEQ_ID_NO_1320 | RFGW I PAYT | MPPNAQHVTV | LRVVI REDFS | RTLAERLVI D | I EKVL HELDT | 446 |
| SEQ_ID_NO_1326 | RFGW VPAYT | MPPNAQHI TV | LRVVI REDFS | RTLAERLVRD | I EKVL HELDT | 446 |
| SEQ_ID_NO_1334 | RFGW VPAYT | MPPDAQHVTV | LRVVI REEFS | RTLAERLVLD | I EKVMYQLDA | 446 |
| SEQ_ID_NO_1330 | RFGW VPAYT | MPPDAQHVTV | LRVVI REDFS | RTLAERLVLD | I EKVLHELDA | 446 |

| | | | | | | |
|---|---|---|---|---|---|---|
| SEQ_ID_NO_1327 | HAVHAI KLST | AAAGCDG--- | ---------- | -------A | SKSAVDAATE | 476 |
| SEQ_ID_NO_1333 | CATHAVRVAT | ATAAVQSGDG | GGVVARK--- | -------S | I EI EREVAS | 488 |
| SEQ_ID_NO_1336 | HSAQVLKI SS | AI AKQQSGDD | GVVTKK---- | -------S | VLETEREI FA | 487 |
| SEQ_ID_NO_1319 | QPPRLPTKAV | RVTAEEVRDD | KGDGL HHFHM | -------D | TVETQKDI I K | 488 |
| SEQ_ID_NO_1302 | LPSRI AHLAA | AAAVSGDDEE | VKVK------ | -------T | AKMSLEDI TK | 480 |
| SEQ_ID_NO_1311 | LPSRVAVQAS | RI VTVDETQD | NMDGKKTVKK | -------S | SREI QEFVTL | 487 |
| SEQ_ID_NO_1317 | LPSPLTTKAV | HI TAI TSETG | EKI KK----- | -------A | ALETQKEI AF | 485 |
| SEQ_ID_NO_1305 | LPSGLQHKK- | ---------- | ---------- | -------A | ERETQEEVFR | 464 |
| SEQ_ID_NO_1339 | LPSKI AREVV | ASLVDGHPEL | KEVKDLGI DV | TQFKSSAVFN | EI VNSQKAVK | 495 |
| SEQ_ID_NO_1318 | VPSRVVSTNT | I I VTGGEEDA | DNDGTVTI AN | Q-------S | VLETQRKI TT | 488 |
| SEQ_ID_NO_1331 | AGI QHAPKYS | A--------- | ---------- | -------- | ---------- | 412 |
| SEQ_ID_NO_1313 | LPARVQAKMA | NGNANGVKK- | ---------- | -------T | EEETTREYTA | 476 |
| SEQ_ID_NO_1303 | LPSKVLVPAS | EQNGRNGKK- | ---------- | -------T | EI ETQREVTT | 476 |
| SEQ_ID_NO_1340 | LPSRI SAKI V | LANEEKDAVA | AGKEKK---- | -------D | VQNETREI I T | 483 |
| SEQ_ID_NO_1320 | LPARVNAKLA | VAEANGSGVH | KK-------- | -------T | DREVQLEI TT | 479 |
| SEQ_ID_NO_1326 | LPARVNAKLA | VAEEQAAANG | SEVHKK---- | -------T | DSEVQLEMI T | 483 |
| SEQ_ID_NO_1334 | LPSRLMPPVP | PAPLLVVAKK | ---------- | -------S | ELETQRSVTE | 477 |
| SEQ_ID_NO_1330 | LPARVPSGDL | AALAAAESSE | ---------- | -------R | EMEKQRQVI S | 477 |

Figure 44 (continued)

| | | |
|---|---|---|
| SEQ_ID_NO_1327 | AFKDLAGK- - -KKAGVC- - | 490 |
| SEQ_ID_NO_1333 | RMRDAVSK- - -KKTGPC- - | 502 |
| SEQ_ID_NO_1336 | YMRDQVKK- - -KQTGIC- - | 501 |
| SEQ_ID_NO_1319 | HMRKIAGK- - -KTSGVC- - | 502 |
| SEQ_ID_NO_1302 | YMKRLVEH- - -KRNIVC- - | 494 |
| SEQ_ID_NO_1311 | YMRRLASE- - -KRTGAC- - | 501 |
| SEQ_ID_NO_1317 | YMKRLVDG- - -KRLGAC- - | 499 |
| SEQ_ID_NO_1305 | CMKRLVDR- - -KIAGVC- - | 478 |
| SEQ_ID_NO_1339 | AMKKFVAQ- - -KANRVC- - | 509 |
| SEQ_ID_NO_1318 | AMKKFVMNRK - -KTNGVC- - | 504 |
| SEQ_ID_NO_1331 | - - - - - - - - - - -RDRGPCSH | 420 |
| SEQ_ID_NO_1313 | YMKKFVEAKK -SNKNRIC- - | 493 |
| SEQ_ID_NO_1303 | YMRKFVSERK ANNKNKIC- - | 494 |
| SEQ_ID_NO_1340 | AMRKLVVQRK - -KLNGVC- - | 499 |
| SEQ_ID_NO_1320 | AMKKFVADKK K-KTNGVC- - | 496 |
| SEQ_ID_NO_1326 | AMKKFVEEKK K-KTNRVC- - | 500 |
| SEQ_ID_NO_1334 | AMKKFVLAK- - -RTNGVC- - | 492 |
| SEQ_ID_NO_1330 | LMKRAVLAKK - -KTNGVC- - | 493 |

Figure 45

| | | |
|---|---|---|
| SEQ_ID_NO_1363 | ---------- ---------- ---------- ---MSKTTNQ NRRPSFTSST | 17 |
| SEQ_ID_NO_1373 | ---------- ---------- ---------- ---------- -------MVD | 3 |
| SEQ_ID_NO_1342 | ---------- ---------- ---------- ---------- ---------- | 0 |
| SEQ_ID_NO_1381 | ---------- ---------- ---------- ---------- ---------- | 0 |
| SEQ_ID_NO_1382 | ---------- ---------- ---------- ---------- ---------- | 0 |
| SEQ_ID_NO_1371 | ---------- ---------- ---------- ---------- ---------- | 0 |
| SEQ_ID_NO_1366 | ---------- ---------- ---------- ---------- ---------M | 1 |
| SEQ_ID_NO_1370 | ---------- ---------- ---------- ---------- ---------- | 0 |
| SEQ_ID_NO_1346 | ---------- ---------- ---------- ---------- ---------- | 0 |
| SEQ_ID_NO_1372 | ---------- ---------- ---------- ---------- ---------- | 0 |
| SEQ_ID_NO_1374 | ---------- ---------- ---------- ---------- --MKKQEKEA | 8 |
| SEQ_ID_NO_1355 | ---------- ---------- ---------- ---------- ---------- | 0 |
| SEQ_ID_NO_1364 | ---------- ---------- ---------- ---------- ---------- | 0 |
| SEQ_ID_NO_1378 | MGSRHQVVQQ QNRGDVVPGA IKQKSMAVEK KNRRALGDIG NVV-TVRGVE | 49 |
| SEQ_ID_NO_1377 | ---MNTNRAV LVPHRGEVGG KQKNGQADGR NNRRVLGDIG NLVTGAPVIE | 47 |
| SEQ_ID_NO_1379 | MGSRAVVVPD QQPRGR--GG KQKNGQAEGR -NRRVLRDIG NLV-PVPTVE | 46 |
| SEQ_ID_NO_1380 | ---------- ---------- ---------- ---MAGADEN HGAVKLANFR | 17 |
| SEQ_ID_NO_1383 | ---------- ---------- ---------- ---------- ---------- | 0 |

| | | |
|---|---|---|
| SEQ_ID_NO_1363 | ESSMRKRHGP SSSSSAVK- PISNTAVMVA KKRAPLGNIT ---------- | 55 |
| SEQ_ID_NO_1373 | EENKVPATAA ASRGSNKR- AFDS A TNE NDPLQISERP ---------- | 41 |
| SEQ_ID_NO_1342 | ---------- ---------- ---------- ---------- ---------- | 0 |
| SEQ_ID_NO_1381 | -MADKENSTP ASAARLTRSS AAAGAQAKRS AAAGVADGGA ---------- | 39 |
| SEQ_ID_NO_1382 | -MADKENSTP ASAARLTRSS AAAGAQAKRS AAAGVADGGA ---------- | 39 |
| SEQ_ID_NO_1371 | ---------- ---------- -APSMTTPF- ---------- ---------- | 8 |
| SEQ_ID_NO_1366 | ATSENNSSAR PQREAKKR- AAAA SQIHG N--------- ---------- | 30 |
| SEQ_ID_NO_1370 | MADDDNSTRR PQREAKKR- AVAALCE--- ---------- ---------- | 25 |
| SEQ_ID_NO_1346 | -MAEDENCTR VTRAAKKR- AAALASTEDQ ---------- ---------- | 27 |
| SEQ_ID_NO_1372 | -MADKENCIR VTRLAKKR- AVEAMAASEQ Q--------- ---------- | 28 |
| SEQ_ID_NO_1374 | IMADLENCGR VTRLAKKR- AAEAMASHDQ Q--------- ---------- | 37 |
| SEQ_ID_NO_1355 | MADEKENCVR MTRAATKRKA SMEAAIDKE- ---------- ---------- | 29 |
| SEQ_ID_NO_1364 | -MAENQNSTR MTRAAAKR- KASVTDEN-- ---------- ---------- | 25 |
| SEQ_ID_NO_1378 | GKALPWSRP ITRGFCAQLI ANAEAAAEN NKNSLAVNAK GADGALPIKR | 99 |
| SEQ_ID_NO_1377 | GKPKAQI SRP ATRSFCAQLL ANAQAEKNKV KPLAEVVNKV ---------- | 87 |
| SEQ_ID_NO_1379 | EKPQNQI SRP VTRSLCVQ- PAAAEKKNK KPLAEVVNGG GEVKAAAAAH | 94 |
| SEQ_ID_NO_1380 | ETTNRRALKD IKNFVGAP-- SFPCAANKRD LKEVVCGNND ---------- | 55 |
| SEQ_ID_NO_1383 | -MITGAQGVR QTRSKTTY-- EVPQQQQQQS FEW------- ---------- | 30 |

Figure 45 (continued)

| | | | | | | | |
|---|---|---|---|---|---|---|---|
| SEQ_ID_NO_1363 | - - - - - NQRKD | SRIFPNSSSA | DSAHCPNKSA | KLKLAAPTQP | VCYNACETKS | | 100 |
| SEQ_ID_NO_1373 | - - - - - YPANK | KRVVLGELNN | LGNV- - - - - - | - - IVSTQNSD | LTETHESKRK | | 78 |
| SEQ_ID_NO_1342 | - - - - - - MGYL | WRVRLSSFAA | GAAT- - - - - - | - - ASAAGFFL | LYKDHLLARA | | 36 |
| SEQ_ID_NO_1361 | - - - - - PPAKR | KRVALSDLPT | LSNA- - - - - - | - - VVVAPRQP | HHPVVIKPSS | | 76 |
| SEQ_ID_NO_1362 | - - - - - PPAKR | KRVALSDLPT | LSNA- - - - - - | - - VVVAPRQP | HHPVVIKPSS | | 76 |
| SEQ_ID_NO_1371 | - - - - - PASK | RRVVLGEISN | NSSA- - - - - - | - - VSGNEDLL | CREFEVPKCV | | 44 |
| SEQ_ID_NO_1366 | - - - - - AAKK | KRVVLGDVTN | VSSS- - - - - - | - - - - - - - - - - | - - - - DVAVS | | 53 |
| SEQ_ID_NO_1370 | - - - - - QRKR | KRVALGDITN | DVVS- - - - - - | - - ETEKLVSD | SHSHTQKKKK | | 61 |
| SEQ_ID_NO_1346 | - - - - - PLNK | KRVVLGELPN | LSNA- - - - - - | - - IVSS- - - - | - NEPQKDKAK | | 58 |
| SEQ_ID_NO_1372 | - - - - - RPSK | KRVVLGELKN | LSSN- - - - - - | - - - ISS QTY | DFSSGPDKDQ | | 63 |
| SEQ_ID_NO_1374 | - - - - - HPSK | KRVVLGEIQN | FSNL- - - - - - | - - GVSQIKGL | NTEPKKQPKS | | 73 |
| SEQ_ID_NO_1355 | - - - - - RINK | KRVVLGELPN | LSNI- - - - - - | - - - - - - - - - - | - - - KKSRKA | | 53 |
| SEQ_ID_NO_1364 | - - - - - PVSK | KRVVLGELPN | NGNV- - - - - - | - - - - PAPLIP | LQERETQKPK | | 59 |
| SEQ_ID_NO_1378 | AVAR- - VPVQ | KKFVKSKPQE | IEISPDTEK | KKAPVLEKEI | TGEKSLKKKA | | 147 |
| SEQ_ID_NO_1377 | - - - - - PAKK | KASDKPAVQE | AVIVISPDEE | VKKKTIEKSP | LSKRKAKKTG | | 131 |
| SEQ_ID_NO_1379 | KKHYDPPKPE | TVIVISSDEE | LESE- - - - - - | - - EKKKPVAV | IARKSRVGSS | | 136 |
| SEQ_ID_NO_1380 | - - - - - SVIPR | RPITRQFAST | LASK- - - - - - | - - SQQSHGET | SNKHGQITGN | | 92 |
| SEQ_ID_NO_1383 | - - - - - - GRTS | QRTSHGKPRR | GSVM- - - - - - | - - - - - - GGT | MTTAGADVDM | | 61 |

| | | | | | | | |
|---|---|---|---|---|---|---|---|
| SEQ_ID_NO_1363 | TCEEVVPIE | RKAFSNLCIT | PSSDTTTNVM | SETENKEEKF | MNDNKDDAD | | 150 |
| SEQ_ID_NO_1373 | IKLRKTRNVV | KETVELKTSA | NSSPK- - - - - | - - - - - - - - - - | - - - - - - - - DN | | 105 |
| SEQ_ID_NO_1342 | ADAESNSASY | SPPLATADTA | FSAPP- - - - - | - - - - - - - - - - | RAVAP- - - AD | | 68 |
| SEQ_ID_NO_1361 | KQPEPAAEAA | APSGGGGGSP | VSSAST- - - - | - - - - - - - - - - | STASPSSGWD | | 112 |
| SEQ_ID_NO_1362 | KQPEPAAEAA | APSGGGGGSP | VSSAST- - - - | - - - - - - - - - - | STASPSSGWD | | 112 |
| SEQ_ID_NO_1371 | ADKKRKRGVK | EDVGVDFGEK | F- - - - - - - - - | - - - - - - - - - - | - - - - - - - - DD | | 67 |
| SEQ_ID_NO_1366 | VSKKPVQTHK | NVKLEKPAAP | VAIPE- - - - - | - - - - - - - - - - | - - - KVEERID | | 85 |
| SEQ_ID_NO_1370 | RNIAKSPVPE | KL- - - - - - - - | - - - - - - - - - - | - - - - - - - - - - | - - - - - - - - ED | | 75 |
| SEQ_ID_NO_1346 | AKPKARKGAS | TKKEGVLKED | VDGNP- - - - - | - - - - - - - - - - | - - - - - - - - ED | | 85 |
| SEQ_ID_NO_1372 | KNKNKRKAKE | SLGFEVKEKK | VEEAG- - - - - | - - - - - - - - - - | IDVFSQS- DD | | 97 |
| SEQ_ID_NO_1374 | KQQDSKRKLK | RAVTSKIDKE | ELNVD- - - - - | - - - - - - - - - - | - NVDANY- DD | | 106 |
| SEQ_ID_NO_1355 | TTKDKKKSVS | IPTIETLNSD | IDTRS- - - - - | - - - - - - - - - - | - - - - - - - - DD | | 80 |
| SEQ_ID_NO_1364 | STLFAAKKQT | KTPPIPQTVD | FESGS- - - - - | - - - - - - - - - - | - - - - - - - - SD | | 86 |
| SEQ_ID_NO_1378 | PTLTSTLTAR | SKAASVVRTK | PKEQI- - - - - | - - - - - - - - - - | VDD DAADVNN | | 182 |
| SEQ_ID_NO_1377 | KTLTSTLTAR | SKAACGLSNR | PKNEI- - - - - | - - - - - - - - - - | DDD DAADAAN | | 166 |
| SEQ_ID_NO_1379 | RTMTSILTAR | SKALCGPTTK | PKVPI- - - - - | - - - - - - - - - - | ADD DAADVDN | | 171 |
| SEQ_ID_NO_1380 | EKHNPIIIDE | DVPMVEESEE | MEECELVEEI | TMEDIVIDSA | QDD DIGDVGN | | 142 |
| SEQ_ID_NO_1383 | RESYSTYLER | SSAADVMTDA | L- - - - - - - - - | - - - - - - - - - - | PDD DLYDHDN | | 92 |

Figure 45 (continued)

```
SEQ_ID_NO_1363   PQLYATFACD YNHLRAAEF -AKKQPAVDY METVQKDVNS TMRGILVDWL   198
SEQ_ID_NO_1373   LQKCS-YGPL YQHLHSLEV EERRRPLSNY MEKVQNNVFP SMRTVLVDWL   154
SEQ_ID_NO_1342   LQLSGSYASD YTYLRSLEV DPQRRSRSDY IEAVQADVTA HMRSILVDWL   118
SEQ_ID_NO_1381   PQ---YASD YTYLRSMEV EARRQSAADY IESVQVDVTA NMRAILVDWL   158
SEQ_ID_NO_1382   PQ---YASD YTYLRSMEV EARRQSAADY EAVQVDVTA NMRAILVDWL   158
SEQ_ID_NO_1371   PQMCSAYVSD VYEYLKQMEM ETKRRPMMNY EQVQKDVTS NMRGVLVDWL   117
SEQ_ID_NO_1366   PQLCGPYVSD IYEYLRGMEV DPSKRPLMDY VQKIQRDVNA NMRGVLVDWL   135
SEQ_ID_NO_1370   PQLCEPYVSD HDYLRNLEV DPSKRPLPDY OKVQRDINA NMRGVLVDWL   125
SEQ_ID_NO_1346   PQMCAPYASD IYEYLHKMEV DPKRRPLPDY EKVQKDVSP NMRGILVDWL   135
SEQ_ID_NO_1372   PQMCGAYVSD IYEYLHKMEM ETKRRPLPDY LDKVQKDVTA NMRGVLIDWL   147
SEQ_ID_NO_1374   PQMCSAYVSD IYDYLRKMEI EEKRRPLPDY LEKVQKDLSP NMRGVLVDWL   156
SEQ_ID_NO_1355   PQMCGPYVTS IFEYLRQLEF VKSRPLVDY EKIQKDVTS NMRGVLVDWL   128
SEQ_ID_NO_1364   PQMCGPFVAD ICAYLREMEG KLKQRPLHDY EKVQSDLTP SMRGVLMDWL   136
SEQ_ID_NO_1378   DLAVVEYVED MYKFYKSAEF -NDSRPH-DY MDFSQPEINE KMRAILIDWL   228
SEQ_ID_NO_1377   HLAVVEYVED YNFYKLTEF -DESRVN-NY MEFFQPELNH KMRAILVDWL   212
SEQ_ID_NO_1379   ELAVVEYVED IYKFYKLTEF -GESRVH-DY MDFSQPEINS KMRSILIDWL   217
SEQ_ID_NO_1380   PLAVVDYVDD IYNYYRRVEF -ASSCVHPDY MS-NQFDIND KMRAILIDWL   189
SEQ_ID_NO_1383   PLAVTQYVND YQYWYKVEF -PDTRVSETY ML-QGDINY KMRAILIDWL   139

SEQ_ID_NO_1363   VEVSEEYRLV PETLYLTVNY IDRYLSGNVI SRQKLQLLGV ACMMIAA-KY   247
SEQ_ID_NO_1373   VEVTEEYKLV SDTLYLAVSY DRFLSSHVL AMEKLQLLGV SCMLVAS-KY   203
SEQ_ID_NO_1342   VEVAEEYKLV ADTLYLTISY VDRFLSVNAL GRDKLQLLGV ASMLIAA-KF   167
SEQ_ID_NO_1381   VEVADEYKLV ADTLYLAVSY LDRYLSAHPL RRNRLQLLGV CAMLIAA-KY   207
SEQ_ID_NO_1382   VEVADEYKLV ADTLYLAVSY LDRYLSAHPL RRNRLQLLGV CAMLIAA-KY   207
SEQ_ID_NO_1371   VEVSLEYKLL PETLYLAISY VDRYLSVNVL NRQKLQLLGV SSFLIAS-KY   166
SEQ_ID_NO_1366   VEVAEEYKLV SDTLYFSVAY DRFLSLNIL SRQRLQLLGV ASMLIAS-KY   184
SEQ_ID_NO_1370   VEVAEEYKLV ADTLYFSVSY DRFLSLNDL SRQKLQLLGV SSMLIAS-KY   174
SEQ_ID_NO_1346   VEVAEEYKLV SETLYLTVSY VDRFLSFNVL SRQRLQLLGV SSMLLAS-KY   184
SEQ_ID_NO_1372   VEVAEEYKLL PDTLYLTVSY DRFLSMNAL SRQKLQLLGV SSMLIAS-KY   196
SEQ_ID_NO_1374   VEVAEEYKLL SDTLYLAVSY DRFLSTNV TRQKLQLLGV SSMLISA-KY   205
SEQ_ID_NO_1355   VEVAEEYKLL SDTLYLAVSY DRFLSLKTV NKQRLQLLGV TSMLIAS-KY   177
SEQ_ID_NO_1364   VEVAEEYKLV SDTLYLTVSY VDRFLSAKPL NRQRLQLVGV SAMLIASRKY   186
SEQ_ID_NO_1378   VQVHYKFELS PETLYLTIN VDRYLASKTT SRRELQLLGM SSMLIAS-KY   277
SEQ_ID_NO_1377   LEVHRKFELM PESLYLTIN LDRFLSMKTV PRKELQLVGI SAMLIAC-KY   261
SEQ_ID_NO_1379   TEVHRKFELM PETLYLTIN VDRYLSMNAV PRRELQLVGI SSMLIAC-KY   266
SEQ_ID_NO_1380   VEVHYKFELM EETLYLTVN DRFLSRQAV VRKKLQLVGV TAMLLAC-KY   238
SEQ_ID_NO_1383   VEVHLKFKLM PETLFLTTNL DRFLELKTV TRRNLQLVGV TAMLVAS-KY   188
```

Figure 45 (continued)

| | | | | | | | |
|---|---|---|---|---|---|---|---|
| SEQ_ID_NO_1363 | EEVCAPQVEE | FCYI TDNTYL | KDEVLDMESA | VLNYLKFEMS | APTVKCFLRR | 297 |
| SEQ_ID_NO_1373 | EEI SPPHVED | FCYI TDNTYT | REEVVNMERD | LLSFLNFEIS | SPTTITFLRI | 253 |
| SEQ_ID_NO_1342 | EEI SPPHPED | FCYI TDNTYT | KEELLKMESD | LKLLKFELG | NPTIKTFLRR | 217 |
| SEQ_ID_NO_1381 | EEI SPPHVED | FCYI TDNTYT | RQEVVKMESD | LKLLEFEMG | NPTIKTFLRR | 257 |
| SEQ_ID_NO_1382 | EEI SPPHVED | FCYI TDNTYT | RQEVVKMESD | LKLLEFEMG | NPTIKTFLRR | 257 |
| SEQ_ID_NO_1371 | EEI KPKNVAD | FVDI TDNTYS | QQEVVKMEAD | LLKTLKFEMG | SPTVKTFL-G | 215 |
| SEQ_ID_NO_1365 | EEI KPPEVED | FCYI TDNTYS | KEEVVNMEAE | LKALKFELG | GPTVKTFLRR | 234 |
| SEQ_ID_NO_1370 | EEI KPPEVED | FCYI TDNTYS | KEEVLSMEAE | LKTLKFELG | GPTIKTFLRR | 224 |
| SEQ_ID_NO_1346 | EEI NPPHVED | FCYI TDNTYT | KEEVVKMEAD | LKSLKFEMG | NPTIKTFLRR | 234 |
| SEQ_ID_NO_1372 | EEI SPPHVED | FCYI TDNTYK | KEEVVKMEAD | VLKFLKFEMG | NPTIKTFLRR | 246 |
| SEQ_ID_NO_1374 | EEI SPPHVED | FCYI TDNTYT | KEEVVKMEAD | VLKTLNFEMG | NPTVKTFLRR | 255 |
| SEQ_ID_NO_1355 | EEI TPPNVDD | FCYI TDNTYT | KQEIVKMEAD | LLALQFELG | NPTSNTFLRR | 227 |
| SEQ_ID_NO_1364 | EEI SPPKVED | FVYI TDNTFT | RQDVVSMEAD | LLALQFELG | CPTIKTFLRR | 236 |
| SEQ_ID_NO_1378 | EEI WAPEVND | LVCI SDGSYS | NEQVLRMEKK | LGALEWYLT | VPTPYVFLVR | 327 |
| SEQ_ID_NO_1377 | EEI WAPEVND | FMHI SDNVYI | RDHI LQMEKA | LGKLEWYLT | VPTPYVFLVR | 311 |
| SEQ_ID_NO_1379 | EEI WAPEVSD | FIVI SDNAYV | REQILI MEKA | LGKLEWYLT | VPTPYVFLVR | 316 |
| SEQ_ID_NO_1380 | EEVSVPVVDD | LVTI SDRAYT | RKEVLDMEKS | VKTLQFNTS | VPTPFVFLRR | 288 |
| SEQ_ID_NO_1363 | EEI WAPEVRD | FVYI SDRAYT | RQQILEMEKQ | MLNTLGFHLT | VPTPYCFLNR | 238 |

| | | | | | | | |
|---|---|---|---|---|---|---|---|
| SEQ_ID_NO_1363 | LF-SGCPRVH | EAPCMQLECM | ASYIAELSLL | EYTMLSHPP | SLVAASAIFL | 345 |
| SEQ_ID_NO_1373 | FL-KAAQDNL | SFLTLQFEFL | SCYLAELSLL | DYSCVRFLP | SMTAASAIFL | 301 |
| SEQ_ID_NO_1342 | FI-RSAHEDK | KGSILLMEFL | GSYLAELSLL | DYGCLRFLP | SVVAASVMFV | 265 |
| SEQ_ID_NO_1381 | FT-RSCQEDK | KRSSLLLEFM | GSYLAELSLL | DYSCLRFLP | SVVAASVVFV | 305 |
| SEQ_ID_NO_1382 | FT-RSCQEDK | KRSSLLLEFM | GSYLAELSLL | DYGCLRFLP | SVVAASVVFV | 305 |
| SEQ_ID_NO_1371 | FI-RAVQENP | DVPKLKFEFL | ANYLAELSLL | DYGCLEFVP | SLIAASVTFL | 263 |
| SEQ_ID_NO_1366 | FS-RVGQEGV | DTSDLQFEFL | SCYLAELSLL | DYNCIKFLP | SLVAASVVFL | 282 |
| SEQ_ID_NO_1370 | FTKVGQEGV | DASELQFEFL | CCYLAELSLL | DYNCVKFLP | SMVAASVYFL | 273 |
| SEQ_ID_NO_1346 | FT-RVALEDY | KTSNLQLEFL | GFYLAELSLL | DYNCVKFLP | SLVAASVIFL | 282 |
| SEQ_ID_NO_1372 | LT-RVVQDGD | KNPNLQFEFL | GYYLAELSLL | DYGCVKFLP | SLIASSVIFL | 294 |
| SEQ_ID_NO_1374 | FT-GVAQEDY | KTPNLQLEFL | GYVLAELSIL | DYSCVKYVP | SLLAAVVFL | 303 |
| SEQ_ID_NO_1355 | FT-RVAQEDF | EMSHLQMEFL | CSYLSELSML | DYQSVKFLP | STVAASAVFL | 275 |
| SEQ_ID_NO_1364 | FT-RVAQEDF | NESLLQIECL | CCYLSELSLL | DYSCVKFLP | SMLAASAVFL | 284 |
| SEQ_ID_NO_1378 | FI-KASLPDS | DI---VEKNM | VYFLAELGMM | NYATIWYCP | SMIAAAVYA | 372 |
| SEQ_ID_NO_1377 | YI-KAAMPSD | DQ---EIQNM | AFFAELGLM | NYTTISYCP | SMLAASAVYA | 357 |
| SEQ_ID_NO_1379 | FI-KASVPSN | DHRE-EMENM | VFFLAELGLM | HYPTILYCP | SMIAASAVYA | 364 |
| SEQ_ID_NO_1380 | FL-KAAGSEK | K-----LELL | SSFIELSLV | EYQMLKFQP | SLLAAAAIYT | 331 |
| SEQ_ID_NO_1383 | FF-KAAGGDR | Q-----FQLY | ASYAVECALP | EYGMLKYGG | STLAAGVYI | 281 |

Figure 45 (continued)

| | | | | | | | |
|---|---|---|---|---|---|---|---|
| SEQ_ID_NO_1363 | AKYTLDPTRR | PWNSTLRHYT | QYEAMELRGC | VMDLQRLCSN | AHV---STLP | 392 |
| SEQ_ID_NO_1373 | SRFTVLPEVC | PWTLALQQCT | GYKPSELKDC | VLVIHELQSS | LME---ATGR | 348 |
| SEQ_ID_NO_1342 | ARLTIDPNTN | PWNTKLQKME | GYKVSELKDC | VAIHDLQLN | RKC---PSLT | 312 |
| SEQ_ID_NO_1381 | AKLNIDPYTN | PWSKKMQKLT | GYKVSELKDC | LAIHDLQLR | KKC---SNLT | 352 |
| SEQ_ID_NO_1382 | AKLNIDPYTN | PWSKKMQKLT | GYKVSELKDC | LAIHDLQLR | KKC---SNLT | 352 |
| SEQ_ID_NO_1371 | ARFTIRPNVN | PWSIALQKCS | GYKSKDLKEC | VLLLHDLQMG | RRG---GSLS | 310 |
| SEQ_ID_NO_1366 | ARFMFSTKTH | PWNSALHQLT | RYKPADLKEC | VLNLHDLYLS | RRG---ASLQ | 329 |
| SEQ_ID_NO_1370 | ARFMLNPKSR | PWNSAICQFT | SYKPADLKEC | VLNMHDLYLG | RKG---ATLQ | 320 |
| SEQ_ID_NO_1346 | TRFLMRPKTN | PWSSTLQQYT | GYKAADLREC | VLIIHDLYLS | RRG---GGLQ | 329 |
| SEQ_ID_NO_1372 | SRFTLDPKVH | PWNSLLQHNS | GYKPADLKEC | VLIIHDLQLS | KRG---SSLV | 341 |
| SEQ_ID_NO_1374 | SRFTLDPNTH | PWSLALQQYS | GYKAADLKEC | LILHDLQLS | RRG---GSLA | 350 |
| SEQ_ID_NO_1355 | ARFIIRPKQH | PWNVMLEEYT | RYKAGDLKEC | VAMIHDLYLS | RKC---GALE | 322 |
| SEQ_ID_NO_1364 | ARFIIRPKQR | PWNQMLEEYT | KYKASDLQQP | VGIIHDLYLS | RRG---NSLE | 331 |
| SEQ_ID_NO_1378 | ARCTLNKMPI | -ANETLRMHT | GFSEVQLMDC | AKLLDFHGG | STD---QKLQ | 418 |
| SEQ_ID_NO_1377 | ARGTLNKGPL | -NTPTLQHHT | GYSEEQLMEC | TKQLVSYHKG | AAE---SKLK | 403 |
| SEQ_ID_NO_1379 | ARCTLNSNPL | -NTETLKHHT | GYSEDOLGDC | AKMLARFHSD | GGGVEKSKLK | 413 |
| SEQ_ID_NO_1380 | AQCSLKGFKF | -NTRTCEQYT | MYTEDQLLEC | SKMMWGFHRN | AGS---GKLT | 377 |
| SEQ_ID_NO_1383 | AIRGLQTGS- | -MNHTMEAHT | RLSESEVYPC | ACDMAELMRK | APT---ATLT | 326 |

| | | | | | |
|---|---|---|---|---|---|
| SEQ_ID_NO_1363 | AVRDKYSQHK | YKFVAKKFCP | SILPPDFFK- | ---NSLY- | 425 |
| SEQ_ID_NO_1373 | ALREKYMNHK | YKCVAALHPP | -DIPSCFFD- | ---DA--- | 378 |
| SEQ_ID_NO_1342 | AIRDKYKQHK | FKCVSLILVP | VVIPTSYFE- | ---DLAE- | 345 |
| SEQ_ID_NO_1381 | AIRDKYKQHK | FKCVSTLLPP | VDIPASYLQ- | ---DLTE- | 385 |
| SEQ_ID_NO_1382 | AIRDKYKQHK | FKCVSTLLPP | VDIPASYLQ- | ---DLTE- | 385 |
| SEQ_ID_NO_1371 | AVRDKYKKHK | FKCVSTLSPA | PEIPESIFN- | ---DV--- | 341 |
| SEQ_ID_NO_1366 | AVREKYKQHK | FKCVATTPSP | PEIPLSFFEF | EGQILRQL | 367 |
| SEQ_ID_NO_1370 | AVRDKYKQHK | FKCVATTPSP | PEISLSFFEF | RGADP--- | 355 |
| SEQ_ID_NO_1346 | AVREKYKQHK | FKCVANMPSP | PELPALYFE- | ---EVI-- | 360 |
| SEQ_ID_NO_1372 | AVRDKYKQHK | FKCVSTLTAP | PSIPDEFFE- | ---DI--- | 372 |
| SEQ_ID_NO_1374 | AVRDKYKQHK | FKCVSSLISP | VEIPASFFE- | ---DNRQL | 384 |
| SEQ_ID_NO_1355 | AIREKYKQHK | FKCVATMPVS | PELPLTNFE- | ---DVNI- | 355 |
| SEQ_ID_NO_1364 | AVRNKYKQHK | FKCVATMPVS | PELPQAFFE- | ---DVTIR | 365 |
| SEQ_ID_NO_1378 | GIYRKYSRLE | KGAVALLPQP | LLA------- | -------- | 441 |
| SEQ_ID_NO_1377 | AIYRKFSSPD | RGAVALFPPA | RNLLPTTTT- | ---TTTSS | 437 |
| SEQ_ID_NO_1379 | AVYKKFSSSD | RSSVALFPPA | RSLLLVL--- | -------- | 440 |
| SEQ_ID_NO_1380 | GVHRKYSTSK | FGFAGKSYPA | LFLLDNRL-- | -------- | 405 |
| SEQ_ID_NO_1383 | AVYKKYSSEK | FMKIATLPVP | HDLRL----- | -------- | 351 |

Figure 46

| | | | | | | | |
|---|---|---|---|---|---|---|---|
| SEQ_ID_NO_1404 | -MA------ | ---SEWSKEE | NKLFEQAIAY | YGEGAPDLMH | KVSRAMGGTK | | 39 |
| SEQ_ID_NO_1401 | -MSGSRSSSP | NSKSEWSRKE | NKMFEEALAY | YGEDTPNRWD | KVASAMGGK | | 49 |
| SEQ_ID_NO_1400 | -MAGSQSSSP | NSNSTWSLKE | NKMFEEALAY | YGEGTPNLAD | KVSSAIGGK | | 49 |
| SEQ_ID_NO_1385 | -MSASRSSSP | NSIQWSQKE | NKMFEEALAY | YGEGTSNRWD | KVSRAMGGK | | 49 |
| SEQ_ID_NO_1407 | -MSASRSSSP | NSMSKWSPKE | NKMFEQALAY | YGEGTPNRWD | KVSSAMGGK | | 49 |
| SEQ_ID_NO_1387 | -MSSHQTPR | NSSSWTPRE | NKLFEKALAL | FDKDTPDRWQ | NIAKAVGGVK | | 49 |
| SEQ_ID_NO_1393 | MASSSLSKQK | ASDSSWTPKQ | NKLFEKALAK | YDKDTPDRWQ | NVAKAYGG-K | | 49 |
| SEQ_ID_NO_1390 | MASSSMSSQ- | -SSGSWTAKQ | NKAFEQALAT | YDQDTPNRWQ | NVAKVVGG-K | | 47 |
| SEQ_ID_NO_1395 | --MSSMSSQH | GSSGSWTAKQ | NKAFEKALAV | YDKETRDRWS | NVAKAVGG-K | | 47 |
| SEQ_ID_NO_1398 | MASGSMS--- | ---SSWTAKE | NKMFEKALAV | YDRDTPDRWH | KIARAIGG-K | | 43 |
| SEQ_ID_NO_1396 | -MASTRGSG- | ---RPWSAKE | NKAFERALAV | YDKDTPDRWA | NVARAVEG-R | | 44 |
| SEQ_ID_NO_1394 | MASSSMSAS- | ---GSWSVKE | NKAFERALAV | YDKDTPDRWY | NVAHAYGG-K | | 45 |

| | | | | | | | |
|---|---|---|---|---|---|---|---|
| SEQ_ID_NO_1404 | TADEVRLHFE | LVDDIKLIE | ARRVPFPKYN | TQGAN---- | ---------- | | 75 |
| SEQ_ID_NO_1401 | SAEEIRCHYE | DLTDDVKTIE | SGRVDFPKYK | TQGYWT--- | ---------- | | 85 |
| SEQ_ID_NO_1400 | SAEEVRCHYE | DLVDDVKMIE | SGRVTYPKYK | TQGFWTRG-- | ---------- | | 87 |
| SEQ_ID_NO_1385 | SAEEVRCHYE | DLDYDVKMIE | SGHVPYPKYK | THGFWT--- | ---------- | | 85 |
| SEQ_ID_NO_1407 | SAEEVRCHYE | DLDYDVKMIE | SGHVPYPQYK | TQGFWTRGSL | MPTNYVGSNP | | 99 |
| SEQ_ID_NO_1387 | SAEEMKRHYE | LIEDLKHIE | SGRVPIPNYK | SSRSYSNTNE | EER------ | | 92 |
| SEQ_ID_NO_1393 | SADEVKRHYE | LLEDLRHIE | SGHVPLPKYK | STGSSTNVEE | EERLLKYLKL | | 99 |
| SEQ_ID_NO_1390 | TIEEVKRHYE | LLVQDINSIE | NGHVPFPNYR | TSGGCINGRL | SQEEKRYVLS | | 97 |
| SEQ_ID_NO_1395 | TAEEVKRHYE | LLRDVFFID | NGMVPFPKYK | TTGGSHNSTS | D-------- | | 88 |
| SEQ_ID_NO_1398 | TADEVKRYYD | LLVEDVRRIE | AGQMPYANYR | SSNGRG---- | ---------- | | 79 |
| SEQ_ID_NO_1396 | TPEEVKKHYE | LVEDIKYIE | SGKVPFPNYR | TTGGNMKTDE | KRFRNLKIR- | | 93 |
| SEQ_ID_NO_1394 | TPEEVKKHYE | LLVEDIKHIE | SGKVPFPNYK | KISVSHEEKR | MRNMSLH--- | | 92 |

| | | |
|---|---|---|
| SEQ_ID_NO_1404 | ---------- | 75 |
| SEQ_ID_NO_1401 | ---------- | 85 |
| SEQ_ID_NO_1400 | ---------- | 87 |
| SEQ_ID_NO_1385 | ---------- | 85 |
| SEQ_ID_NO_1407 | SIMTKISYFQ | 109 |
| SEQ_ID_NO_1387 | ---------- | 92 |
| SEQ_ID_NO_1393 | N--------- | 100 |
| SEQ_ID_NO_1390 | ---------- | 97 |
| SEQ_ID_NO_1395 | ---------- | 88 |
| SEQ_ID_NO_1398 | ---------- | 79 |
| SEQ_ID_NO_1396 | ---------- | 93 |
| SEQ_ID_NO_1394 | ---------- | 92 |

Figure 47

```
SEQ_ID_NO_1419    ---------- -----MSFYL F--------- ---------- --FLFITMPL    14
SEQ_ID_NO_1421    ---------- -----MAC-- F--------- ---------- --RSRSRAAA    12
SEQ_ID_NO_1409    ---------- -----MGQRR F--------- ---------- --EDERAALA    14
SEQ_ID_NO_1425    ---------- -----MADC- ---------- ---------- ---TTMRLAS    11
SEQ_ID_NO_1424    MEPWRWQICL VTPRSFLFQA FVRTGFRAMR VSSASSTPPP PAFAAAAMAV    50
SEQ_ID_NO_1413    ---------- -----MNRRF L--------- ---------- --FVLSSLSF    14
SEQ_ID_NO_1418    ---------- -----MRMEH I--------- ---------- --YKFQHWLF    14
SEQ_ID_NO_1415    MEGELKMRGG DLIRPGRFCI L--------- ---------- --SVATISS    29

SEQ_ID_NO_1419    IVFCDF---- ---------- --EMPSGSST QIFHSFHE-- ----------    36
SEQ_ID_NO_1421    VVVVTM---- ---------- -LLLQACSEV SASSSPQF-- ----RKM---    38
SEQ_ID_NO_1409    TVASLL---- ---------- -LILTTAQAA AAAASGRH-- ----LSLPT-    42
SEQ_ID_NO_1425    SVTIIL---- ---------- -LLLVASQAL VVSGESSS-- ----SAM---    37
SEQ_ID_NO_1424    VLLAML---- ------RSD VALAAASGN DDTGLSPLMP PPPPLAAPVP    89
SEQ_ID_NO_1413    AVLFLF---- ---------- LVALFSGQGK NINGSFGL-- ----KLLR--    42
SEQ_ID_NO_1418    FIGLGV---- ---------L LSLSLSVKAN DFEGSNDR-- ----RSIALK    45
SEQ_ID_NO_1415    LLAVFFEDIY HSSMHASSLV SLLLNPVQTQ SLTELFHL-- ----KAVSEI    73

SEQ_ID_NO_1419    -------DKN GSLTVSEKVE HAH------- ---------- -------YTPR    56
SEQ_ID_NO_1421    ---------- -LVSVNASSM SSS------- ---------- -GG-GGHSAE    58
SEQ_ID_NO_1409    --QKAAAARM NDTSSSDMQV ITP------- ---------- -APLAISTAA    72
SEQ_ID_NO_1425    --QSKTLNMN KLLNISED-- HSP------- ---------- -NG-GRHVMQ    64
SEQ_ID_NO_1424    AAVSPAPATP PAVLSPRKLL RPPGADVVGV GFYSGSGGGG GGGGGGDGVR    139
SEQ_ID_NO_1413    --LRINQGNH TLLTPHRKLL RTA------- ---------- ------LAEPN    68
SEQ_ID_NO_1418    A-RSFVSINE NRTALSRKLL LSP------- ---------- -DI-GDGTN    74
SEQ_ID_NO_1415    GSKKPVFYKE NNTNFARKLL QLP------- ---------- -DA---GSTN    102

SEQ_ID_NO_1419    KFWFHGSCTK -RDISISDSK GST--SGIPQ YLVQIVNTCV SG-------    95
SEQ_ID_NO_1421    PLE-LEECSK -DLLEVFQNN APSMAGGMPT YSVEITNTCI -D-------    97
SEQ_ID_NO_1409    RMG-PDGCSG -EDVAVYQSS ANPLPSGIPA YTVRINVCS GG-------    112
SEQ_ID_NO_1425    RMQ-PDSCSE -GNVVVYQNN AEHLPSGIPT YSVEIINVCT -A-------    103
SEQ_ID_NO_1424    TRRVDDGCAG ADDIAIYQGR ATPLPSGVPA YTVDVMNRCA GGGGGGGDEE    189
SEQ_ID_NO_1413    RIW-GEKCSK -ADIVNQGP TAPLPSGIPT YTVEILNVCV SG-------    108
SEQ_ID_NO_1418    RIG--QDCSK -DDIVLFQGS TNPLPSGVPS YTVEIFNSCV SD-------    113
SEQ_ID_NO_1415    RIG--AACSK -DGIDIVQGS TAPLPNGIPS YTVQILNVCV SG-------    141
```

Figure 47 (continued)

| | | | | | | | |
|---|---|---|---|---|---|---|---|
| SEQ_ID_NO_1419 | CAPYDIHLHC | GWFASARIIN | PKLFKRLSVD | DCLVHGGKPL | TSNQIRFTY | | 145 |
| SEQ_ID_NO_1421 | CAVCDVHIAC | SDFASNDVID | PDKFRRLGFN | DCLVNGGGSI | EPSFPVSFQY | | 147 |
| SEQ_ID_NO_1409 | CTVYDVHVSC | SDFASTELVD | PAKFQRVGFN | DCVVKGGGAL | EPSETVSFQY | | 162 |
| SEQ_ID_NO_1425 | CTVYDVHISC | GEFASAELVD | PSQFQRIGFN | DCLVKGGGRL | GPSEAVSFQY | | 153 |
| SEQ_ID_NO_1424 | CAIAGIHVRC | GWFSSVSLVD | PRVFRRLGHD | DCLLNDGRPL | LAGETVSFEY | | 239 |
| SEQ_ID_NO_1413 | CDISGIHLTC | GWFSSARLIN | PKIFKRLRYN | DCLVNDGKPL | INGSTLSFQY | | 158 |
| SEQ_ID_NO_1418 | CNIAEIHVSC | GWFSSVRLVN | PRVFRRLDYD | DCLVNDGQPL | GPGQSLSFQY | | 163 |
| SEQ_ID_NO_1415 | CSISNIHVSC | GWFSSAKLIN | PSVFRRIYYD | DCLVNDGEPL | GPGETLSFQY | | 191 |

| | | | | | | | |
|---|---|---|---|---|---|---|---|
| SEQ_ID_NO_1419 | SNSFMYPLAF | KSARFC---- | ---------- | ---------- | ---------- | | 161 |
| SEQ_ID_NO_1421 | GNSFPYPMTV | ASASCDCN--- | ---------- | ---------- | ---------- | | 165 |
| SEQ_ID_NO_1409 | SNSFSYHLSV | ASVACR---- | ---------- | ---------- | ---------- | | 178 |
| SEQ_ID_NO_1425 | SNSFAYPLAV | ANVACHYSI | VWASMIPCLP | EHACHTASSV | KGLGPRPHA | | 202 |
| SEQ_ID_NO_1424 | TNSFPYKLSV | SVATCVVDPA | AP-------- | ---------- | ---------- | | 261 |
| SEQ_ID_NO_1413 | ANTFLYPLSV | SRRVCS---- | ---------- | ---------- | ---------- | | 174 |
| SEQ_ID_NO_1418 | ANSFSYPLSV | ASVSCF---- | ---------- | ---------- | ---------- | | 179 |
| SEQ_ID_NO_1415 | ANSFLYPLSV | SSVACC---- | ---------- | ---------- | ---------- | | 207 |

Figure 48

| SEQ_ID_NO_1436 | ----------- | --MTRPARFL | ETAATPPQPS | EQ-------- | -------MLA | 23 |
| --- | --- | --- | --- | --- | --- | --- |
| SEQ_ID_NO_1444 | ---------M | GVHARAMSWY | TSPPGSPAPG | SAAEA-QHAL | SSSPRGGDTS | 40 |
| SEQ_ID_NO_1452 | ---------M | GVHGRSMGWY | LGPPGSPAPG | SAVAEAQHAL | SSSPGGGDAS | 41 |
| SEQ_ID_NO_1428 | ----------- | --MHRL--LL | ESHGGGNETS | GSGGG----- | --DGYTRDMN | 29 |
| SEQ_ID_NO_1430 | MMQAKTAMVT | TLYHRPHRLL | LDTQPNASPS | LPNGS----R | TRNAFANEAN | 46 |
| SEQ_ID_NO_1432 | ----------- | --MHRF-RML | DTVPLDVAPA | NGN-----R | THDSYINETN | 30 |
| SEQ_ID_NO_1439 | ----------- | ---------- | -------MPP | SYGGG----N | TSDTFISDAN | 19 |
| SEQ_ID_NO_1442 | ----------- | --MRRLSDAG | EATPL-VTPA | AAAAAGGTLA | SPAAAGSNAN | 37 |
| SEQ_ID_NO_1453 | ----------- | --MRRLGDVV | EAPALVLTPA | SMQQA----- | -GGRGSSGA | 31 |
| SEQ_ID_NO_1457 | ----------- | --MRRLVDVV | EAPALVLTPA | WAATA----S | MQQAGGSSGA | 34 |

| SEQ_ID_NO_1436 | AESDMVVILS | ALLCALICVA | GLAAVVRCAL | -MLRRFTTGE | NSPSANK--- | 68 |
| --- | --- | --- | --- | --- | --- | --- |
| SEQ_ID_NO_1444 | FDTNMVVVLA | ALLFALLFAL | GINSLARCLI | RWARRAPAAE | GGGG------ | 84 |
| SEQ_ID_NO_1452 | FDTNMVIILA | ALLFALLFAL | GLNQLARCLI | RWARRASEGE | AGARGG---- | 87 |
| SEQ_ID_NO_1428 | FDANMVIILA | ALLCALILAL | GLNSILRCAM | RCGFGLSSSA | AAGTVADRAL | 78 |
| SEQ_ID_NO_1430 | FDTNMVIILA | ALLCALICAL | GLNSIMRCTF | RCGRRFGLDA | TEETAARLAA | 96 |
| SEQ_ID_NO_1432 | FDTNMVIILA | ALLCALIGAL | GLNSIVRCLL | RCSSRFALET | TEEAAARLAA | 80 |
| SEQ_ID_NO_1439 | FDTNMVIILA | ALLCALICAL | GLNSIARCAL | RCGRPFGNET | AEDAAARLAG | 69 |
| SEQ_ID_NO_1442 | FDANMVIILA | ALLCVLIFAL | GLNSVIRCVL | HCGRRLAPSS | SLAASATTAR | 87 |
| SEQ_ID_NO_1453 | LDASMVVILA | ALLCVVICAL | GLTSLIRCAL | HCARGLSPTT | ATPTPSVSTA | 81 |
| SEQ_ID_NO_1457 | LDANMVIVLA | ALLCVVICSL | GLSSLIRCAL | HCARGLSPSP | AMATPAAATT | 84 |

| SEQ_ID_NO_1436 | --------G | LKKKALQSLP | RSTFTAAEST | SGTAAEDG-- | -GDSTECAI | 105 |
| --- | --- | --- | --- | --- | --- | --- |
| SEQ_ID_NO_1444 | --------G | FEKRVLRSMP | VEVY------ | -GAAAV---- | --TVADVCAI | 112 |
| SEQ_ID_NO_1452 | --------G | LKRRALRSIP | VEVY------ | -GACGADGAA | A-VAADVCAI | 120 |
| SEQ_ID_NO_1428 | --------G | LKKRELKKFP | VAEY------ | -GSGEVK--- | --AATECAI | 107 |
| SEQ_ID_NO_1430 | AT------G | LKKSALRRLP | VAVY------ | -GSGMD---- | --KATECPI | 126 |
| SEQ_ID_NO_1432 | T-------G | LKKRDLRQIP | VAIY------ | -GAGGS---- | --SATECPI | 109 |
| SEQ_ID_NO_1439 | T-------G | LKRRELSRIP | VAVY------ | -GAAGENT-- | --PATECPI | 100 |
| SEQ_ID_NO_1442 | TTTSVHVQAG | LKRKALRKIP | VEVY------ | -GGAKSSGGA | LPATATECAK | 130 |
| SEQ_ID_NO_1453 | AT-----AG | LKKTELRRIP | VEVY------ | -GAKQAG--- | --VPDGECAI | 113 |
| SEQ_ID_NO_1457 | TG------G | LKKKELRRIT | VEVY------ | -GAKQAG--- | --VPDAECAI | 115 |

Figure 48 (continued)

| | | | | | | | |
|---|---|---|---|---|---|---|---|
| SEQ_ID_NO_1436 | CLSDFADGEE | IRVLPLCGHS | FHVECIDKAL | VSRSSCPXCR | XILRPV--X | 152 |
| SEQ_ID_NO_1444 | CLGEFADGEK | VRVLPRCTHG | FHVRCVDTWL | LSHDSCPTCR | ASVLDG---- | 158 |
| SEQ_ID_NO_1452 | CLGEFADGEK | VRVLPRCAHG | FHVRCVDTWL | LSHDSCPTCR | GTVLEAAAPG | 170 |
| SEQ_ID_NO_1428 | CLGEFADGER | VRVLPPCNHS | FHMSCIDTWL | VSHSSCPNCR | HSLIEV---- | 153 |
| SEQ_ID_NO_1430 | CLGEFMGGEK | VRVLPKCNHG | FHVRCIDTWL | LSHSSCPTCR | QSLLDQA--T | 174 |
| SEQ_ID_NO_1432 | CLGEFVDGEK | VRVLPKCNHG | FHVRCIDTWL | LSHSSCPNCR | HSLLEH---T | 156 |
| SEQ_ID_NO_1439 | CLGEFEKGDR | VRMLPKCNHG | FHVRCIDTWL | LSHSSCPNCR | HSLLEK---- | 146 |
| SEQ_ID_NO_1442 | CLGEFADGEK | VRVLPRCHHG | FHVRCIDMAL | ATHTSCPNCR | ASLAED---- | 176 |
| SEQ_ID_NO_1453 | CLGDFADGDK | VRVLPRCHHG | FHVRCIDTWL | AAHTSCPTCR | DSILSV---- | 159 |
| SEQ_ID_NO_1457 | CLGDFADGDK | VRVLPRCHHG | FHVGCIDTWL | AAHTSCPTCR | DSILSV---- | 161 |

| | | | | | | |
|---|---|---|---|---|---|---|
| SEQ_ID_NO_1436 | CDRCGHASXA | GSOMKDHQHX | QHXSDLTSXX | XTFXP | | 187 |
| SEQ_ID_NO_1444 | --AKAATPAG | GGSRMQGSEA | AAIAVVIR-- | ----- | | 184 |
| SEQ_ID_NO_1452 | KDKAAASAPA | GGSRRQGSEA | AAIAVVIG-- | ----- | | 198 |
| SEQ_ID_NO_1428 | -------HVA | GSE------- | ---------- | ----- | | 159 |
| SEQ_ID_NO_1430 | SSSDGAVEIE | NGIRPIGNSS | GGDQADVPVP | ADEVG | | 209 |
| SEQ_ID_NO_1432 | TDSAAQEVT | GAARPGENDP | GRQARGWP- | -EHGG | | 188 |
| SEQ_ID_NO_1439 | ---PAAAPES | GSGRRSEVVV | VVEQAS---- | ----- | | 169 |
| SEQ_ID_NO_1442 | ----GAAAAN | GGGR------ | ---------- | ----- | | 186 |
| SEQ_ID_NO_1453 | -----HGVVA | GGQT------ | ---------- | ----- | | 168 |
| SEQ_ID_NO_1457 | -----HAGVT | GGQT------ | ---------- | ----- | | 170 |

Figure 49

```
SEQ_ID_NO_1473   ----------  ---MKLVWCP  ETASQAFIAG  VSALSDAEHG  PAGSAG-VAE   36
SEQ_ID_NO_1474   ----------  ----MASKAYIDG  VRALAG--HD  LAGAAADVAE   27
SEQ_ID_NO_1476   MAPPPPPAAQ  VVRMKLVWCP  EMASKAYIDG  VRALAG--HD  LAGAAADVAE   48
SEQ_ID_NO_1471   ----------  ---MKLAWSP  ERASKAYIDT  VQSCQV--FR  ESG----VAE   31
SEQ_ID_NO_1463   ----------  ---MKLVWSP  ETASDAYIDT  VKSCKS--DK  ESG----VAE   31
SEQ_ID_NO_1465   ----------  ---MKLVWTP  DTALKAYVCI  VKTCED--FK  ESS----VAE   31

SEQ_ID_NO_1473   LVSAMVGGWN  AQLVVEAPEV  SAPDSATMSL  ALAAAAGRTG  GRYARVLPDE   86
SEQ_ID_NO_1474   LVSAMAGGWN  ARLVVEAPDS  AAPAAAATSL  ALAAVARRTG  GRYALVLPDR   77
SEQ_ID_NO_1476   LVSAMAGGWN  ARLIVEAPDS  AAPAAAATSL  ALAAAARRTG  GRYALVLPDR   98
SEQ_ID_NO_1471   FISAMAAGWN  SQLIVETWSQ  GGL--ATSV   GLALARSHTC  GRHVCVVPDE   79
SEQ_ID_NO_1463   FLSATAAGWN  ARLIVETWSR  GDP--TTSV   GLAVAATHTG  GRHVCIVPDE   79
SEQ_ID_NO_1465   LLSAMAAGWN  AKLIVESWSK  AGP--ATSI   GLAVAAKHTC  GRHVCVVPDE   79

SEQ_ID_NO_1473   DA--------  ----------  -----DRAMA  ELEGVDFLVV  DARRRDGAAV  113
SEQ_ID_NO_1474   DAAASAAET   -------AEV  VVGEADEAMA  GLHGVDLLVV  DARRRDAAAV  120
SEQ_ID_NO_1476   DAAASAAET   -------AEV  VVGEADEAMA  GLHGVDLLVV  DARRRDAAAV  141
SEQ_ID_NO_1471   RARSEYAERW  GEAGVT-AEI  VVGEPEEVME  GLVGVDFLVV  DSRRKDFTRV  128
SEQ_ID_NO_1463   QSKLEYVLAM  RGFVTTEVVN  VGESVFNTME  EFPGVDFLVV  DSKRREFVRT  129
SEQ_ID_NO_1465   GSRSEYVKAM  HGAGMRETEV  LVGEAEEVMA  GLVGVDFLVA  DCRRRDFVRV  129

SEQ_ID_NO_1473   LAAARPGPRG  MVVV-RHGDE  RRPGIKALEA  SMAAGT-RV   VRSVYLPVDK  160
SEQ_ID_NO_1474   LRAARPGARG  MVVV-RHGDG  RORGAKDLAA  SMAAGT-RV   VRSVYLPIGK  167
SEQ_ID_NO_1476   LRAARPGARG  MVVV-RHGDG  RORGAKDLAA  SMAAGT-RV   VRSVYLPIGK  188
SEQ_ID_NO_1471   LRIAKLSNKG  AVLLCKNANS  NSKGFIARS   LVAKGSSRRV  VRSAFLPVGK  177
SEQ_ID_NO_1463   LRFAKLSNKG  AVLVCKNAMH  RAISGFKMHD  VLKRGT-RV   VRSVFLPVGS  177
SEQ_ID_NO_1465   LRFAKLSHKG  AVLACKNAFQ  DSVSGFKMHG  VLERGT-RV   VKTAYLPVGQ  177

SEQ_ID_NO_1473   GVEVLHVGV-  GKGPSLQCRR  SRSASSRWR   HVDHKTGEEH  LFRRP       204
SEQ_ID_NO_1474   GVEVLHVGV-  GKGPSLQNHR  DRRSTSRWR   HVDHDTGEEH  VFRRQ       211
SEQ_ID_NO_1476   GVEVLHVGV-  GKGPSLQNHR  DRRSTSRWR   HVDHDTGEEH  VFRRQ       232
SEQ_ID_NO_1471   GLDMAHVSAS  GIG----N--  -NSSGHRWK   HVDQHSGDVH  FIRR-       213
SEQ_ID_NO_1463   GLDIVHVGAT  GRG-----D   SRNLRSRWR   HVDHLSGEEH  LFRR-       215
SEQ_ID_NO_1465   GLDMAHIGSN  GIG---DKR   SRGGPSRWK   HIDRKSGEEH  VFRE-       216
```

Figure 50

| | | |
|---|---|---|
| SEQ_ID_NO_1493 | MTFLMPSPEV ---STAFAKI FSNPT-PRHK FLKSCAISKN DDEKVWSKTN | 46 |
| SEQ_ID_NO_1503 | MAFLLPKLTT ---PSCKLPP S--PL-LKPQ LAQPVHGGGK IQGSVFGSVA | 44 |
| SEQ_ID_NO_1508 | MAFLLPKLTT PSGPSCKLPP S--PL-LKPQ LAQPGHSGGK IQGSVSGAGA | 47 |
| SEQ_ID_NO_1501 | MAFLLPKLTT ---PPCRSPP P--SP-LKPQ LGLPSHGGGR ----LHGAGS | 40 |
| SEQ_ID_NO_1504 | MAFLLPKLTT ---PSCKSPP S--PI-LKSQ LGLPGGGKLQ ---------P | 34 |
| SEQ_ID_NO_1505 | MAFLLPKLTT ---PSCKSPP S--PI-LKSQ LGLPGGGKLQ ---------P | 34 |
| SEQ_ID_NO_1495 | MAFLLPNLSF ---PSLLINS KSFKDREKPV LYQTQTLPSH ---------- | 36 |
| SEQ_ID_NO_1499 | MAFLLPNLSF ---PSFLLQT GKSLK-EKPI STHSLSISSS -----SSSSN | 40 |
| SEQ_ID_NO_1491 | MAFLLSNLSS ---PSIHLQT GKYPN-LKPI FSQSLSSSSS ---------V | 37 |

| | | |
|---|---|---|
| SEQ_ID_NO_1493 | ARVGVKDVGS TVSGLSQNLR LYVQFSAPVK -------RGS KSSKEEEEKQ | 89 |
| SEQ_ID_NO_1503 | AQVAAPGHLS LLLLLSASQQ AAAPI-AAKST ATKNR---- GKGGGDPQRS | 89 |
| SEQ_ID_NO_1508 | AQVAAPGHLS LLLLLSAPQQ AADP-ASKST ATKNR---- GKGGGDPQRS | 91 |
| SEQ_ID_NO_1501 | AQAAAPTHLN LPLLLSASQQ EAIPI-TAKSA ETRNRAASGG GGGGDPRRS | 88 |
| SEQ_ID_NO_1504 | AQAVAPSHLN LLLLLGASQQ EAAAVPTPKS RSKNGGGRSG GGGGEDPRRS | 84 |
| SEQ_ID_NO_1505 | AQAVAPSHLN LLLLLGASQQ EAAAVPTPKS RSKNGGGRSG GGGGEDPRRS | 84 |
| SEQ_ID_NO_1495 | -YQTTTTTTS TTTKKPTNTN SSMPPPLQVK T------PPG AQDKEQHQRD | 79 |
| SEQ_ID_NO_1499 | SYEFEEGSLS LLSLPVQAP- -----PAPGA QVKTM--PSE QDKHQQHGKD | 82 |
| SEQ_ID_NO_1491 | SYEFVEENLS TLSLLSIQS- ---PI-PLKDT QVQTR--HSS QDKHNNHDRD | 80 |

| | | |
|---|---|---|
| SEQ_ID_NO_1493 | DYYVNMGYAI RTLRKELPDI FYRELSFDIY RDDIVFKDPL NTFLGIDNYK | 139 |
| SEQ_ID_NO_1503 | DFYLNLGTAV RTLRDDLPDV FVREPNYDIY REDITFVDPL NTFHGIDNYK | 138 |
| SEQ_ID_NO_1508 | DFYLNLGTAV RTLRDDLPDV FDREPNYDIY REDITFVDPL NTFHGIDNYK | 141 |
| SEQ_ID_NO_1501 | DFYLNLGAAV RALRDDLPAV FLREPNYDIY REDITFVDPL NTFHGIDNYK | 138 |
| SEQ_ID_NO_1504 | DYYLNLGTAV RTLRDDLPAV FVREPNYDIY REDITFVDPL NTFHGIDNYK | 134 |
| SEQ_ID_NO_1505 | DYYLNLGTAV RTLRDDLPAV FVREPNYDIY REDITFVDPL NTFHGIDNYK | 134 |
| SEQ_ID_NO_1495 | EFYVNLGLAV RTLREDLPVL FTEDLNYDIY RDDITFIDPL NTFTGIDNYK | 129 |
| SEQ_ID_NO_1499 | EFYINLGLAI RTLREDLPLL FSKDLNYDIY RDDITLVDPK NTFSGIENYK | 132 |
| SEQ_ID_NO_1491 | EFYINLGVAV RTLREDLPLL FTRDLNYDIY RDDITFVDPM NTFTGMDNYK | 130 |

| | | |
|---|---|---|
| SEQ_ID_NO_1493 | SFFSAPRFHG RIFFKALWLD VSVWQPMEN VIMVRWIIHG IPRVPWESHG | 189 |
| SEQ_ID_NO_1503 | TIFWALRFHG RLLFREIGLD VSRIWQLTEN SIVVRWELWG TPRVPWESYG | 188 |
| SEQ_ID_NO_1508 | TIFWALRFHG RLLFREIGLD VSRIWQLTET SIVVRWELWG TPRVPWESYG | 191 |
| SEQ_ID_NO_1501 | TIFWALRFHG RLLFSEIGLD VSRIWQLTET SIVVRWELWG TPRVPWESYG | 188 |
| SEQ_ID_NO_1504 | TIFWALRFHG RLLFREIGLD ISRIWQLTEN SIVVRWELWG TPRVPWESYG | 184 |
| SEQ_ID_NO_1505 | TIFWALRFHG RLLFREIGLD ISRIWQLTEN SIVVRWELWG TPRVPWESYG | 184 |
| SEQ_ID_NO_1495 | LIFWALRFHG KMLFREISLE VYRIWQPSEN VILIRWNLKG VPRVPWEAKG | 179 |
| SEQ_ID_NO_1499 | LIFWALRFHG KILFRDXXXE XYRVWQPSEN MLIRWNXKG VPRVPWEAKG | 182 |
| SEQ_ID_NO_1491 | IIFWALRFHG KILFRDISLE IFRVWQPSEN MLIRWNLKG VPRVPWEAKG | 180 |

Figure 50 (continued)

| | | | | | | | | |
|---|---|---|---|---|---|---|---|---|
| SEQ_ID_NO_1493 | RFDGTSEYKL | DKKGKIYEHR | VDNTALNSPP | KF-HMLAVED | LIRSVGCPST | | | 238 |
| SEQ_ID_NO_1503 | CFSGTSRYKV | DRNGKIYEHK | VDNLALDFPR | SVAKVGSIAD | MV-VATP--S | | | 235 |
| SEQ_ID_NO_1508 | CFSGTSRYKV | DRNGKIYEHK | VDNLALDFPR | SVAKVGSIAD | MV-VATP--S | | | 238 |
| SEQ_ID_NO_1501 | CFSGTSRYKV | DRNGKIYEHK | VDNLALDFPR | PAVKVSSITN | LV-VAAYPPS | | | 237 |
| SEQ_ID_NO_1504 | CFSGTSRYKV | DRNGKIYEHK | VDNLALDFPR | PAAKVGSIAD | IV-VATCPPS | | | 233 |
| SEQ_ID_NO_1505 | CFSGTSRYKV | DRNGKIYEHK | VDNLALDFPR | PAAKVGSIAD | IV-VASCPPS | | | 233 |
| SEQ_ID_NO_1495 | EFQGTSRYKL | DRNGKIYEHK | VDNLAFNFPQ | QLKPAASVLD | LV--AACPAS | | | 227 |
| SEQ_ID_NO_1499 | EFQGTSRYKL | DRNGKIYEHK | VDNLAFNFPH | QLKPATSVLD | LV--TACPAS | | | 230 |
| SEQ_ID_NO_1491 | EFQGTSRYKL | DRNGKIYEHK | VDNLAFNFPQ | QLKPAASVLD | LVTASPASS | | | 229 |

| | | | | | | | | |
|---|---|---|---|---|---|---|---|---|
| SEQ_ID_NO_1493 | PRPTY----- | ---------- | --------F | ESSASPPEK | NI----IKP | | | 259 |
| SEQ_ID_NO_1503 | PNLTF-MNVV | G-TGDGCSWT | KLYEAVLEAV | EREEHSSTGI | GVGALGPVGC | | | 283 |
| SEQ_ID_NO_1508 | PNLTF-MNVV | G-PGDGCSWT | KLYEAVVEAV | EREEHGSTGI | GVGGL-PVPC | | | 285 |
| SEQ_ID_NO_1501 | PNPTF-MDVV | G-TGDGCSWT | KLYRAVLETV | EREGDIPAGI | CMEGL--LTC | | | 283 |
| SEQ_ID_NO_1504 | PNLTF-MDMV | GSTGDGCSWA | NLYQAVVETV | EQEGNDPAGI | AIEGL--LTC | | | 280 |
| SEQ_ID_NO_1505 | PNLTF-MDMV | GSTGDGCSWA | NLYQAVVETV | EREGNDPAGI | AIFGL--LTC | | | 280 |
| SEQ_ID_NO_1495 | PNPTFLMGPA | D--VYSSSW | EFYRAVRETL | DXEN---STN | CFCKM-ATC | | | 270 |
| SEQ_ID_NO_1499 | PNPTFVFGS- | ---SYSSSWI | EFYQAVQRTL | DKQQDQI--M | MQDRF--VLC | | | 272 |
| SEQ_ID_NO_1491 | PNPTFFFSPV | D--SYSSSW | KFYQAVRGTL | ETEDMFVTTD | CL----VTC | | | 272 |

| | | |
|---|---|---|
| SEQ_ID_NO_1493 | P--------- | 260 |
| SEQ_ID_NO_1503 | G----CGCSF | 289 |
| SEQ_ID_NO_1508 | SFGCGCGSSF | 295 |
| SEQ_ID_NO_1501 | S--------- | 284 |
| SEQ_ID_NO_1504 | S--------- | 281 |
| SEQ_ID_NO_1505 | S--------- | 281 |
| SEQ_ID_NO_1495 | S--------- | 271 |
| SEQ_ID_NO_1499 | L--------- | 273 |
| SEQ_ID_NO_1491 | S--------- | 273 |

Figure 51

```
SEQ_ID_NO_1520    MDSLPKLR----------HPSPFPTPL SSSLSFRSLP PPHFPSSSFR                    37
SEQ_ID_NO_1510    MESLGKLQLH HQPFHLSFIH TSSSTFPKNL -----FKSSI QPSSL--LK                 42
SEQ_ID_NO_1512    MESLTKLHCR LQPLHLSFNH QRPSFAKPI SSSVSFRTS- ---SSSSPFK                  45
SEQ_ID_NO_1516    MESVAKLHCR HQPFNLSLNP HRPSFPKPI -ISLSFKTPP PSSSSPFKLS                  48

SEQ_ID_NO_1520    LPSIRASSSP SQNDPAFRTP RNTPSLPPLL QTLTSFLSPL LETTCIMLA                   86
SEQ_ID_NO_1510    SASIKASSSK FQNS---TP LPK------ ST----PFRL FKSTCITLTT                    78
SEQ_ID_NO_1512    LTSIRALSSS SSS---SVP LHQTPKPSLL QT----LAPL LKTTCITITA                   87
SEQ_ID_NO_1516    STSIRASSSS SSR----TP LN-------- KN----LGTI KITSITLTA                    82

SEQ_ID_NO_1520    AAAFFMRFH HT-PAVIAAP LTSPAAETDT -----AFTQE EAERLLEERL                    130
SEQ_ID_NO_1510    AAALLLANLH LKSPAIAAPL APPPSVESKE -----NVTLE EEERALDEHL                    123
SEQ_ID_NO_1512    GAALLFMRFH QK-PALAATP TVTPTVEPAQ TDS-NVSLE DQEKTIEEHL                     134
SEQ_ID_NO_1516    AAALFFTRLN IK-PAIASPL IASSTVDPTE ESSKENVSYE EQERALQDYL                    131

SEQ_ID_NO_1520    STNPRDTEAL HALMEVKIKA RKMDEAFEVL NRLIELEPEE QEWPLLKANM                    180
SEQ_ID_NO_1510    ITHPSDVDAL RSLMEVKIKS RKLTEAVEVI DRLIKLEPEE KEWPVLKANI                    173
SEQ_ID_NO_1512    TQYPNDVEAL QSLMEVRIKS RKLPQAIEVI DRLIQLEPED TEWPMLRAQI                    184
SEQ_ID_NO_1516    SQNPNDIEAL RSLMEVRIKS KKLVEAIEVV DRLIELEPNE DEWPLLKSQI                    181

SEQ_ID_NO_1520    HIYNDDHASA RKLFEEILKK DPLRVEAFHG LVMATAQSNE PLKSLLKRVE                    230
SEQ_ID_NO_1510    FTYSGDLDLA KTGFEEILAK DPLRVEAYHG LLMAYSDAGL DLKEVESRIE                     223
SEQ_ID_NO_1512    HSYSGDFALA KNEFEEILAK DPVRVEAFHG LVMASSESGQ KLKELEKRIE                    234
SEQ_ID_NO_1516    YTYSGDFESA KDGFEAILKK DPLRVEAYHG LVMANSESGG SLEVVLKRIE                    231

SEQ_ID_NO_1520    EAIEVCKKQK KDSDVRDFRL LIAQIKVMEG DYTEALKAYQ ELVKEEPRDF                     280
SEQ_ID_NO_1510    EAMLKCKKEN NQNDFRDFKL LVAQIRVIEG KHSEALKLYQ ELVKEEPRDF                     273
SEQ_ID_NO_1512    GAMEKCKKEK KNKDFRDFKL LIAQIRVIEG DHLEALKVYE GLVKEEPRDF                     284
SEQ_ID_NO_1516    SAMDKCKKEK KTSDLRDFKL LVAQVRVMEE KYLDALKVYE ELVKEEPRDF                     281

SEQ_ID_NO_1520    RPYLCQGIIY TLLRKKDEAD KQFNKFRRLV PKDHPYKDYF EDNMFATKFF                      330
SEQ_ID_NO_1510    RPYLCQGIIY TLLKKKDKAE EQFDNFRKLV PKNHPYREYF MDNMIATKLF                     323
SEQ_ID_NO_1512    RPYLCMGIIY SLMKKKDEAE KHFEKVRKLV PRNHPYREYF VDNMVATKLF                     334
SEQ_ID_NO_1516    RPYLCQGIIY TLLRKKDEAE KKFEQFKKLV PKNHPYREYL VDNMFATKFF                     331
```

Figure 51 (continued)

| | | |
|---|---|---|
| SEQ_ID_NO_1520 | SQKLEREGA···GARG | 343 |
| SEQ_ID_NO_1510 | SEKAQREMAE EMAGSTS | 340 |
| SEQ_ID_NO_1512 | SERAEREGA------- | 343 |
| SEQ_ID_NO_1516 | SDKVERERS------- | 340 |

Figure 52

| | | | | | | | |
|---|---|---|---|---|---|---|---|
| SEQ_ID_NO_1525 | ---------- | MAFPQRKRTP | SFSSSVLDSV | YRSIDESDG | LQSDLKGS N | | 39 |
| SEQ_ID_NO_1535 | ---------- | MALPQRQRTQ | SFSSSVLDSI | YRSIDESDG | LQSDLRGT N | | 39 |
| SEQ_ID_NO_1527 | MYKKERSSRE | STFHPRRRTP | SFSSTLLDSI | YRSIDESNG | -EEQHVLGI K | | 48 |
| SEQ_ID_NO_1534 | MHERSMKEAA | GTCPQRRRTP | SFSSSLLDAI | YRSIDESKSN | LHDDQLGL H | | 50 |

| | | | | | | |
|---|---|---|---|---|---|---|
| SEQ_ID_NO_1525 | EN----VSS | SSSSPSPNKK | DDKLTTLRRA | MDEEHWLYA | RSS------ | 77 |
| SEQ_ID_NO_1535 | SNNNENVSSS | SSSSPSPNKK | DDKLTTLRRA | MDEEHWLYG | RSS---TTT | 85 |
| SEQ_ID_NO_1527 | KQSCNSVSTT | RRDTSFLEEE | KEVSTTLRRA | VR-TESWMEK | KST-RGSMQ | 95 |
| SEQ_ID_NO_1534 | HHD----QTT | HSFTSEKGGK | KERMNLRRA | VMLEDWMEK | HGSHSLNAQL | 94 |

| | | | | | | |
|---|---|---|---|---|---|---|
| SEQ_ID_NO_1525 | ·TTTTNSSDS | SS-------- | --FSSSEAES | -----YRTKR | RLRKLAEQGK | 111 |
| SEQ_ID_NO_1535 | TTTTTNSSDS | SA-------- | --FSSSEAES | -----FRTKR | RLRKLAEQGN | 120 |
| SEQ_ID_NO_1527 | YNSTSSSSDS | SSAGGGGSGS | GVFSSSENES | -------SVR | GNSSSCQQRT | 138 |
| SEQ_ID_NO_1534 | LNSSSSSSEC | SSA-----G | GIFSSSETDT | TTTLTLKKQR | PARLTSEKKK | 138 |

| | | | | | | |
|---|---|---|---|---|---|---|
| SEQ_ID_NO_1525 | RSGDERQRTK | RTVMDNDSRL | FSKSDDDKKP | KAVKILEEL | KRSKQPVSPG | 160 |
| SEQ_ID_NO_1535 | RLGEERQRT | ---------- | --KSDDDIKV | KAVKMFEEL | KRSKQPVSPG | 156 |
| SEQ_ID_NO_1527 | KPLSDKPHQK | PKCEG----- | --GGFHKTKL | RALKIYGEL | KKVKQPISPG | 180 |
| SEQ_ID_NO_1534 | KKQDRIMSSE | KQNKE----- | --SGFTRTKL | RALKIYGELN | QRVKQPISPG | 181 |

| | | | | | | |
|---|---|---|---|---|---|---|
| SEQ_ID_NO_1525 | ARLTSFLNSI | FQSN--AKKV | KLCSVGKTTD | VK------ | -------SSS | 193 |
| SEQ_ID_NO_1535 | ARLTSFLNSI | FQSN--AKKV | KFCSVGKTTD | VK------ | -------SSSS | 190 |
| SEQ_ID_NO_1527 | GRIASFLNSI | FNSASAAKKV | KMCSIGAMDD | VSFERKSKSA | CSSA-TSFS | 228 |
| SEQ_ID_NO_1534 | SRIASFLSSI | FNSQN-VKKR | KMCYAGAVED | VSFEHKSNSP | CFSSPSSFS | 230 |

| | | | | | | |
|---|---|---|---|---|---|---|
| SEQ_ID_NO_1525 | SKSCFSRTRN | KTDNNNNC- | --KKLERSIR | FYPVRVTIDG | DCRDYAQKH | 239 |
| SEQ_ID_NO_1535 | SRSCFSRTRN | KTNNNNNNNN | NFKKLERSIR | FYPVRVTIDG | DCRDYAHKN | 239 |
| SEQ_ID_NO_1527 | -RSCLSKTPP | PRGKPSNG-- | ----TKRSVR | FYPVGVIVDE | DSRPCGHKS- | 270 |
| SEQ_ID_NO_1534 | RRSCMSKTPS | SAKKSNNNE- | ----VKRSVR | FYPVSVILGE | DSEPQSSYHK | 275 |

| | | | | | | |
|---|---|---|---|---|---|---|
| SEQ_ID_NO_1525 | ---TRVRK- | --PIPEFTAK | -KSVKE--- | EIKTNDHTE | FTCITRNI- | 276 |
| SEQ_ID_NO_1535 | ---TR---- | --PIPTKVHQ | TELMKE--- | EIKTVHQTE | LTCITRK- | 274 |
| SEQ_ID_NO_1527 | ---YEDDPG | LMPTPRKVVK | SSSVKELEVA | KGAAADYLRS | YH-QRKNV- | 314 |
| SEQ_ID_NO_1534 | CNILYE--- | --SEPNLGVR | SSSIKELKKN | TARGNENGAE | EAAARGFVKG | 319 |

Figure 52 (continued)

| | | | | | | | |
|---|---|---|---|---|---|---|---|
| SEQ_ID_NO_1525 | ------GLKD | FVRSNKY-EG | KEEEGDAWSH | SSSDLFELDS | YRI GMGRYLK | | 319 |
| SEQ_ID_NO_1535 | ------GLKD | YVRSSNIDEG | KEEEDDVWSY | SSSDLFELDH | YRI GMGRYLK | | 318 |
| SEQ_ID_NO_1527 | ------SEFD | FRGFHNYVAD | DSDSDDEFSC | TSSDLFELDH | LF GI GRYRE | | 356 |
| SEQ_ID_NO_1534 | YRNSGQSEFD | FRGF--YDDD | DEDDDDDVSC | SSSDLFELDH | LF GAARYDE | | 366 |

| | | | | |
|---|---|---|---|---|
| SEQ_ID_NO_1525 | ELPVYETTDF | KTNQAI ARSL | LL | 341 |
| SEQ_ID_NO_1535 | ELPVYETTDF | KINQAI ARGL | LL | 340 |
| SEQ_ID_NO_1527 | ELPVYETTNF | KTNQAI ANGF | FP | 378 |
| SEQ_ID_NO_1534 | ELPVYETTNL | ETNKAI ASGL | CL | 388 |

Figure 53

```
SEQ_ID_NO_1550   MDMNESSEKG ME----GNGS SGPGGGI PVE AQSGFS---G GGFS-A---   38
SEQ_ID_NO_1552   MYSGQQSDQC PS---ANS- ---------- -------G REFSEA---   22
SEQ_ID_NO_1537   MLEGLVSQES LSLNS-MDMS VLER----LK WQQQQQLQ QVVSHS---   41
SEQ_ID_NO_1543   MLESLVSLES MSLSS-MDVS VLER----LK NLQQQ---Q QQVLST---   37
SEQ_ID_NO_1545   MLGYANPSGN LAVD--GDMT VLERQRARMK WQEEQEYFSG NSFNGV---   44
SEQ_ID_NO_1539   MLHC----- ------TDIT VLERQRACIK WQQEQQQQQ VQLQQQEISY   38
SEQ_ID_NO_1548   MLHCLNTSGN LVGGIISDMT VLERQRARKK FQHEHQD-Q QFFMVG---   45

SEQ_ID_NO_1550   HQHQQHPHMM DSFGSGMWS- --------AA SQHGAGFLAP VPGFLPPPGL   79
SEQ_ID_NO_1552   NRNTVTMHQK MGYNSG--- ---------- ---------- ------PYGF   42
SEQ_ID_NO_1537   SNNSPELLQI LGFHGSN--- --------ND ELLESSFSQF Q---MLGSGF   77
SEQ_ID_NO_1543   TNASPELLQF HGTN------ --------ND ELLQNTFSHF Q---MLRSGF   70
SEQ_ID_NO_1545   FSSSSSLHVP DSIMVAADS- ---------G CALAEVVAQA QPRSNKPSA   84
SEQ_ID_NO_1539   FTELTGVFQQ AGFHEGGLSE VVTRSVKPDP GLYDNGWND H---VVGLGV   85
SEQ_ID_NO_1548   CDSALGEVVA NSMKPG--- ---------- ----------   61

SEQ_ID_NO_1550   GGHFPVDSG -FIE----RA ARBSCFVGPG AGGGMVGAGA FGGAGDQQMG   123
SEQ_ID_NO_1552   GP---YNMG -LEE----RP GLYQSSSGTF SQNIQM--- --------S   70
SEQ_ID_NO_1537   GPNYNMGFGP PHES----S RTSSCHMEPV DTMEVL--- ------LKTG   113
SEQ_ID_NO_1543   GPNYSMGFGP SHEAMDGCS ITNSCQMDQA DTVGVM--- ------LKNS   110
SEQ_ID_NO_1545   AP------G -LHANSSSS RTFSCPPALV DPEPKPT--- ---------D   114
SEQ_ID_NO_1539   GPLYDNGSG -FELNYGAS RISSCPPAAV AAVAAATVKG SESVVSDKS   133
SEQ_ID_NO_1548   -----DLG -FEN---- ---------- ---------- ----------   67

SEQ_ID_NO_1550   SAFGEGYLDH RRKEGGDKAE PELAGSGGVP SSEAAGGDCS SKGSDSKKRR   173
SEQ_ID_NO_1552   DEHSGGVKKR KGMD---- ---------- -------DCV AMLQNAGDQQ   97
SEQ_ID_NO_1537   EETRAVALKN KRKP---- ---------- -------EVK TREEQKTEKK   140
SEQ_ID_NO_1543   EENITISLKN KRKS---- ---------- -------EVK TREEEKTEKK   137
SEQ_ID_NO_1545   SSIGKDSFKK RKTD---- ---------- --KPHN-PKV VAENENKDKR   145
SEQ_ID_NO_1539   SGVGRESSKK RKVD---- ---------- --NKQNNSKV DAEEDTRDKR   165
SEQ_ID_NO_1548   ---VEETVKK RKAD---- ---------- -------H KVDMKSKDKR   89
```

Figure 53 (continued)

| | | | | | | | |
|---|---|---|---|---|---|---|---|
| SEQ_ID_NO_1550 | RPSEVMGGDQ | VQSSNVAADS | ANESAQSKDK | GEESSPATGT | TTGGKSKGKG | 223 |
| SEQ_ID_NO_1552 | ----TEGSSQ | PE-------- | ----RNSLEG | NRKISPKMQS | ---KEDSSDG | 128 |
| SEQ_ID_NO_1537 | ----IKVEAE | TESSMK---- | ----GKSNMG | NTEASSDTSK | ---ETSKGAS | 175 |
| SEQ_ID_NO_1543 | ----IKVEAE | TELNMK---- | ----VKSNLS | NTEASSETSK | ---QKSKAAS | 172 |
| SEQ_ID_NO_1545 | ----IKVGAD | DGESKITKCN | T---INTNTN | NKETCTDTSN | ---SKQNSKA | 185 |
| SEQ_ID_NO_1539 | ----IKGCAE | EGESKITEKN | NNKNSRNNNT | NKNNNSNKES | SA-GNSKDNS | 210 |
| SEQ_ID_NO_1548 | ----IKVSVE | EGESKITEQI | KGN-KNTKLK | NRENCDDVGS | ----KENSKG | 130 |

| | | | | | | | |
|---|---|---|---|---|---|---|---|
| SEQ_ID_NO_1550 | AKESSEKEDY | HVRARRGQA | TNSHSLAERL | RREKISERMK | LLQDLVPGCS | 273 |
| SEQ_ID_NO_1552 | DG---TKEDY | VHVRAKQGQA | TNSHSLAERL | RRKKISERMK | LLQDLVPGCS | 175 |
| SEQ_ID_NO_1537 | EN---QKLDY | HVRARRGQA | TDRHSLAERA | RREKISKKMK | YLQDIVPGCN | 222 |
| SEQ_ID_NO_1543 | EN---QKLDY | HVRARRGQA | TDRHSLAERA | RREKISKKMK | YLQDIVPGCN | 219 |
| SEQ_ID_NO_1545 | S----EKPDY | HVRARRGQA | TDSHSLAERV | RREKISERMK | YLQDLVPGCN | 231 |
| SEQ_ID_NO_1539 | KVTEVQKPDY | HVRARRGQA | TDSHSLAERV | RREKISERMK | YLQDLVPGCN | 260 |
| SEQ_ID_NO_1548 | SEIQNHKPDY | HVRARRGQA | TDSHSLAERV | RREKISERMK | YLQDLVPGCN | 180 |

| | | | | | | | |
|---|---|---|---|---|---|---|---|
| SEQ_ID_NO_1550 | KVTGKAVMLD | EIINYVQSLQ | RQVEFLSMKL | ATVNPRLDLN | IEGLLSKDLL | 323 |
| SEQ_ID_NO_1552 | KITGKAVMLD | EIINYVQSLQ | RQVEFLSMKL | ATVNPELGFD | IEQILSKQMM | 225 |
| SEQ_ID_NO_1537 | KVTGKAGMLD | EIINYVQCLQ | RQVEFLSMKL | AVLNPELELA | VEDVSVKQAY | 272 |
| SEQ_ID_NO_1543 | KVTGRAGMLD | EIINYVQSLQ | RQVEFLSMKL | AVLNPELELA | MEDLSVKQ-F | 268 |
| SEQ_ID_NO_1545 | KVTGKAGMLD | EIINYVQSLQ | RQVEFLSMKL | AAVNPRLDFS | MDDLFDKDVF | 281 |
| SEQ_ID_NO_1539 | KITGKAGMLD | EIINYVQSLQ | RQVEFLSMKL | AAVNPRLDFN | FDNLFAREAF | 310 |
| SEQ_ID_NO_1548 | KIAGKAGMLD | EIINYVQSLQ | RQVEFLSMKL | AAVNPRLDFN | IDELFAKEVF | 230 |

| | | | | | | | |
|---|---|---|---|---|---|---|---|
| SEQ_ID_NO_1550 | RF-------- | ---PGVSSSS | MGFSPEMMHP | QLQLSQPGLM | QGGAAAMANS | 362 |
| SEQ_ID_NO_1552 | LSQDRHFAFY | GVDPGSSSLA | SQFSDGIMQP | QM-------- | --MCNISNPA | 265 |
| SEQ_ID_NO_1537 | FTNV------ | ---------VA | SKQSIMVDVP | LFPLDQQGSL | --DLSAINPN | 306 |
| SEQ_ID_NO_1543 | QAYFTNLPVV | ---------VA | SKPSLMVDAP | LFPLDQQGSL | --DLSVINPN | 308 |
| SEQ_ID_NO_1545 | PTCAANFPNI | GMSSTSSDIT | NPAYLPFNSP | QQIFQYDGL- | --DTGINPSD | 328 |
| SEQ_ID_NO_1539 | PACSVNFPTI | GM---SSDMI | NPAYLDFNPA | QDQLVTCCGL | --DMGTDPPD | 355 |
| SEQ_ID_NO_1548 | TQNFQMM--- | -----QSFMS | NPAYLDFNSA | QDQVSCCGGL | INNMGILPPE | 272 |

Figure 53 (continued)

```
SEQ_ID_NO_1550    DVFRRIMQAD ········[]GAKDGSHSQM AHALNGPFSD HVAQMAYPSM    403
SEQ_ID_NO_1552    DVLQGTIHDV ············STMNQI PAMAEGLQN -LPQMNFNPG    299
SEQ_ID_NO_1537    QT········ ············TSIEAP SGSWETQSQS -LYN······    327
SEQ_ID_NO_1543    QA········ ············TTIEAP SASWETQSQS -LYN······    329
SEQ_ID_NO_1545    YGLRRITSAP VS--MPETYL QSSCFTQMLP SSTWEGDFQN -LCNFDVDQA    375
SEQ_ID_NO_1539    MGLKRTTSSP ES--IPETFL DSSCFTQAHP PPAWDADLQN -LYNVAFDQG    402
SEQ_ID_NO_1548    IGVRRNINAP ASASLPEIFL DPSCFTHILP SSTWEGDFQN -LHSVDFDQG    321

SEQ_ID_NO_1550    GSSHSHSQDL S·······[] RPSQDAYQM    424
SEQ_ID_NO_1552    VAADSSANN· ········· -SGSMKIEQ     316
SEQ_ID_NO_1537    ·········· ·········  -TSSLGFHY    335
SEQ_ID_NO_1543    ·········· ·········  -TSSLGFDY    337
SEQ_ID_NO_1545    RATSFPSQLL SGL·····V  EASNLKMEM    398
SEQ_ID_NO_1539    RQTSFPTQPF TGKIKLSCS  EASNLKMEM    431
SEQ_ID_NO_1548    RSTSFPSQPF TGM·····[] EASNLKMEM    344
```

Figure 54

```
SEQ_ID_NO_1571   MAVEAVS---  ------GNGG  EAVAPAPA--  ----------  ----------   19
SEQ_ID_NO_1567   MAEEPQ----  ------PQAA  AAPAAAAT--  ----------  -EVVVAEKAP   27
SEQ_ID_NO_1572   MAEEPQ----  ------PEAA  PAAVAATT--  ----------  -EVAVAEKAP   27
SEQ_ID_NO_1574   MAEEPQ----  ------PEAA  PAAVAATT--  ----------  -EVAVAEKAP   27
SEQ_ID_NO_1555   MAEETQK---  ------PAAA  EAPTSTQP--  ----------  YPEEPAVVPP   29
SEQ_ID_NO_1563   MSQEQDVVVV  TDV---PQAE  KTAPVPPT--  ----------  MPVVVEKEPP   35
SEQ_ID_NO_1575   MAEEPQK---  ------PTEQ  VATTPATS--  ----------  -ETTLEKTPP   28
SEQ_ID_NO_1554   MAEEPTTTTL  VTPEKLPSPS  LTPSEVSEST  QDALPTETET  LEKVTETNPP   50
SEQ_ID_NO_1565   MAQNDSN---  ------PTPP  PEPHVAAE--  ----------  ---------P   20

SEQ_ID_NO_1571   ----------  ------PV  KEVSAK----  ----------  ----VEAKEA   33
SEQ_ID_NO_1567   --AEVEKKAE  EL-----PA  AEAEAE----  ----------  -ETAAVADDG   53
SEQ_ID_NO_1572   VEAEKEKKVE  EET----PA  VEAEAK----  --EEKKDEAA  ---AAGGDEA   63
SEQ_ID_NO_1574   VEAEKEKKVE  EET----PA  VEAEAK----  --EEKKDEAA  AAAAAGGDEA   66
SEQ_ID_NO_1555   PVPAAEIQLP  DSAPAPPQPE  ASPAKP----  --DSVAEVAE  DEKPKASEEF   73
SEQ_ID_NO_1563   V---------  ------PV  PETEEEPMKP  KQVEEGAVET  QVLKPSGGDD   68
SEQ_ID_NO_1575   PQAEEVVAAA  DADAVVPPV  VAEETE----  --KPAEDVKP  ADETAAATDK   72
SEQ_ID_NO_1554   ETADTTTKPE  EETAAEHHPP  TVTETETAST  EKQEVKDEAS  QKEVAEEKKS   100
SEQ_ID_NO_1565   ITEDLVQDKE  EEDDSSKIVI  PVPESE----  ----------  ----------   46

SEQ_ID_NO_1571   AAVTKNASFR  EESNFLDDLK  ESERKALAEL  RDKVEAAILE  GKLFDDGKPE   83
SEQ_ID_NO_1567   GAVEATGSFK  EESNLVADLP  DPEKKALDEF  KELIVAALAA  GEFNLPPPPP   103
SEQ_ID_NO_1572   GAIEGTGSFK  EESNLVADLP  DPEKKALDEF  KQLIAAALAA  CEFNLPPPPP   113
SEQ_ID_NO_1574   GAIEGTGSFK  EESNLVADLP  DPEKKALDEF  KQLIAAALAA  CEFNLPPPPP   116
SEQ_ID_NO_1555   EKISQSVSFK  EESNVVGELP  ESQRKALADL  KVLIQEALNK  HEFTAPPAPL   123
SEQ_ID_NO_1563   EKMPQLVSFK  EESTKVADLL  DSEKKALQEF  KQLVQEALN-  ----------   107
SEQ_ID_NO_1575   KILQSVSFK   EETNVVSELP  ESQKKALDEL  KQLIQEALNK  HEFTAPPPPP   121
SEQ_ID_NO_1554   MIPQNLGSFK  EESSKLSDLS  NSEKKSLDEL  KHLVREALDN  HQFTN-----   145
SEQ_ID_NO_1565   ----SLSLK   EDSNRVSD--  -SEKNAIDEL  KKLLKEELED  ----------   78

SEQ_ID_NO_1571   ----------  ----------  VKEKREAKKK  AEKAPEEKKE  EEEEGKKEPE   113
SEQ_ID_NO_1567   PPKAKTEAAA  EETKTEAPAK  EEAKTEEPAK  AEEPAKEEPK  AEEPAKAEAA   153
SEQ_ID_NO_1572   PPKAKVEAAV  EETKA-----  EESKAEEEPK  AEEPAKEEEP  KAEVAAAAAA   158
SEQ_ID_NO_1574   PPKAKVEAAV  EETKA-----  EETKAEEEPK  AEEPAKEEEP  KAEVAAAAAA   161
SEQ_ID_NO_1555   PPK-----E   EEKPA-----  EEKKEDTEKP  AEQPQIDE-P  AKEPVIEEPP   161
SEQ_ID_NO_1563   ----------  ----------  ----------  ----------  ----------   107
SEQ_ID_NO_1575   PTKAVAEVAE  EKKPE-----  EEEKKTEEVV  AEEKKVEEVV  AEEKKVEEAV   166
SEQ_ID_NO_1554   ----------  ----------  ----------  ----------  ----------   145
SEQ_ID_NO_1565   ----------  ----------  ----------  ----------  ----------   78
```

Figure 54 (continued)

| | | | | | | |
|---|---|---|---|---|---|---|
| SEQ_ID_NO_1571 | AVEKKGEEDD | KKEAEVEGKE | EEEESKKEAE | KEMEDEE--- | ---------- | 150 |
| SEQ_ID_NO_1567 | AAEPAAEEPK | AVVA------ | ----AEAAAE | EPAKEEPK-- | ---AEEAKPA | 188 |
| SEQ_ID_NO_1572 | PPEAGTEEPK | AEASSEEAKT | EEPKAEAAAD | EPAKDESKAE | AAPAEEAKPA | 208 |
| SEQ_ID_NO_1574 | PPEAGTEEPK | AEASSEEAKT | EEPKAEAAAD | EPAKEESKAE | AAPAEEAKPA | 211 |
| SEQ_ID_NO_1555 | KTEAEPEPVT | ETVTVKVEET | ITPHPAPETS | LAPEADEKAA | EPSTVVEKVA | 211 |
| SEQ_ID_NO_1563 | ---------- | ---------- | ---------- | ---------- | ---------- | 107 |
| SEQ_ID_NO_1575 | AEEKKVEEVE | KKEEEKGSSS | EEPKTEAKIE | AEPEAKKEET | VLEVVEKIAT | 216 |
| SEQ_ID_NO_1554 | ---------- | ---------- | ---------- | ---------- | ---------- | 145 |
| SEQ_ID_NO_1565 | ---------- | ---------- | ---------- | ---------- | ---------- | 78 |

| | | | | | | |
|---|---|---|---|---|---|---|
| SEQ_ID_NO_1571 | ---------- | ---------- | ---------- | --AGEAEKVA | AAAEEKPAET | 168 |
| SEQ_ID_NO_1567 | EPKKEEEAVV | VAEE--GTKT | ------AEPV | EEAAAAATTT | EQAAAPEPEA | 230 |
| SEQ_ID_NO_1572 | EPEPEEKTVV | VTEEEAATKT | VEAIEETVYP | AAAAPAAAAT | EEAAAPEPEV | 258 |
| SEQ_ID_NO_1574 | EPEPGGED-- | ---------- | ------RRGH | RGRGGHQDGG | SDRGNRRARC | 243 |
| SEQ_ID_NO_1555 | VIDEDGAKTV | EAIEESVVAV | ------STPP | PEESAPSKEE | AEVEVEAAEA | 255 |
| SEQ_ID_NO_1563 | ---------- | ---------- | ---------- | ---------- | ---------- | 107 |
| SEQ_ID_NO_1575 | STEEDGAKTV | EAIQESIVSV | ------TVTD | GEQPVTETVG | EAVAVAEVE- | 259 |
| SEQ_ID_NO_1554 | ---------- | ---------- | ---------- | ---------- | ---------- | 145 |
| SEQ_ID_NO_1565 | ---------- | ---------- | ---------- | ---------- | ---------- | 78 |

| | | | | | | |
|---|---|---|---|---|---|---|
| SEQ_ID_NO_1571 | AAVVVDKDIA | LWGVPLLPSK | GDE-ATDVVL | LKFLRARDFK | AGAAFEMLRR | 217 |
| SEQ_ID_NO_1567 | E-AAAPEPVF | WGVPLV--  | GDDERTDAVL | LKFLRAREFK | VKEAMAMLRS | 276 |
| SEQ_ID_NO_1572 | QAAAAPEPVL | WGVPLV--  | GDDERTDIVL | LKFLRAREFK | VKEAMAMLRS | 305 |
| SEQ_ID_NO_1574 | CCACCRRHGG | SRGAGTG--- | GDDERTDIVL | LKFLRAREFK | VKEAMAMLRS | 290 |
| SEQ_ID_NO_1555 | VPPPPPEEVF | WGIPLL--  | GDE-RSDVIL | LKFLRARDFK | VKDAFTMIKN | 301 |
| SEQ_ID_NO_1563 | ---------- | ---------- | ----KSDVIL | LKFLRARDFK | VKDAFTMLKS | 133 |
| SEQ_ID_NO_1575 | VTPTTPEEVE | WGIPLL--  | ADE-RSDVIL | LKFLRARDFK | VKEAYTMIKD | 305 |
| SEQ_ID_NO_1554 | ----TPEEVK | WGIPLL--  | EDD-RSDVVL | LKFLRAREFK | VKDSFAMLKN | 187 |
| SEQ_ID_NO_1565 | ------EEVS | WGVPLF--- | KDD-RTDVIL | LKFLRARELK | VKDALVMFQN | 118 |

| | | | | | | |
|---|---|---|---|---|---|---|
| SEQ_ID_NO_1571 | TLRWRRDWPG | FDADADADLP | -EELAGACVL | DGADREGHPV | CYNALRVFAD | 266 |
| SEQ_ID_NO_1567 | AVLWRKRF-G | IESLLEADLA | FPELEKVVFY | RGADREGHPV | CYNVYGEFQD | 325 |
| SEQ_ID_NO_1572 | AVLWRKRF-G | IESLLDADLA | LPELDSVVFY | RGADREGHPV | CYNVYGEFQD | 354 |
| SEQ_ID_NO_1574 | AVLWRKRF-G | IESLLDADLA | LPELDSVVFY | RGADREGHPV | CYNVYGEFQD | 339 |
| SEQ_ID_NO_1555 | TVRWRKQF-D | IEALLDEDLG | -NQMDKVVFS | HGVDREGHPV | CYNVFGEFEN | 349 |
| SEQ_ID_NO_1563 | TIRWRKEF-G | IDELLEQDLG | FDDLGKVVFM | HGLDKEGHPV | CYNVYGEFQN | 182 |
| SEQ_ID_NO_1575 | TVLWRKEF-G | IEALLQEDLG | -TDMDKVVFT | DGYDKEGHPV | YYNVFGEFEN | 353 |
| SEQ_ID_NO_1554 | TIKWRKEF-K | IDELVEEDLV | -DDLDKVVFM | HGHDREGHPV | CYNVYGEFQN | 235 |
| SEQ_ID_NO_1565 | TLRWRKDF-N | IDALLDEDLG | -DHLEKVVFM | HGHGREGHPV | CYNVYGEFQN | 166 |

Figure 54 (continued)

| | | | | | | | | |
|---|---|---|---|---|---|---|---|---|
| SEQ_ID_NO_1571 | DAVYKKALGT | EEGKARFLRW | RVRAMERHV- | AELDLKP-GG | AASLLQVTDL | | | 314 |
| SEQ_ID_NO_1567 | KEVYEKAFGD | EEKRERFLKW | RIQLLERG-L | SQLDFAP-SG | ICSMVQVTDL | | | 374 |
| SEQ_ID_NO_1572 | KDLYEKAFGD | EEKRERFLKW | RIQLLERG-L | SQLDFSP-SG | ICSMVQVTDL | | | 403 |
| SEQ_ID_NO_1574 | KDLYEKAFGD | EEKRERFLKW | RIQLLERG-L | SQLDFSP-SG | ICBMVQVTDL | | | 388 |
| SEQ_ID_NO_1555 | KDLYQITFSD | DEKSLKFLRW | RVQFLEKSI- | RKLDFSP-NG | ISTIVQVNDL | | | 397 |
| SEQ_ID_NO_1563 | KELYKNSFSD | EEKRQRFLRW | RIQFLEKSI- | RTLDFSP-GG | ISTIVQVNDL | | | 230 |
| SEQ_ID_NO_1575 | KELYQNTFSD | DEKRTKFIRW | RIQSLEKSI- | RKLDFTP-SG | ISTIVQVNDL | | | 401 |
| SEQ_ID_NO_1554 | KELYNKTFSD | EEKRKHFLRT | RIQFLERSI- | RKLDFSS-GG | VSTIFQVNDM | | | 283 |
| SEQ_ID_NO_1565 | KDLYHKAFSS | QDNRNKFLRW | RIQLLERSI- | RHLDFTPSSG | INTIFQVNDL | | | 215 |
| | | | | | | | | |
| SEQ_ID_NO_1571 | KNSPGPAKKD | FRVAVKQVLD | LFDDNYPELV | ARNLI NVPF | WYYAFSTLFY | | | 364 |
| SEQ_ID_NO_1567 | KNSPPVLGKH | -RAVTRQAVA | LLQDNYPEFI | AKKVFINVPW | WYLAANKMMS | | | 423 |
| SEQ_ID_NO_1572 | KNSPPVLGKH | -RAVTRQAVA | LLQDNYPEFI | AKKVFINVPW | WYLAANKMMS | | | 452 |
| SEQ_ID_NO_1574 | KNSPPVLGKH | -RAVTRQAVA | LLQDNYPEFI | AKKVFINVPW | WYLAANKMMS | | | 437 |
| SEQ_ID_NO_1555 | KNSPGLTKME | LRNATKRALQ | LFDDNYPEFA | AKQVFINVPW | WYLAVNRMIS | | | 447 |
| SEQ_ID_NO_1563 | KNSPGPAKRE | LRQATRQALQ | LLQDNYPEFV | AKQIFINVPW | WYLTVNRMIS | | | 280 |
| SEQ_ID_NO_1575 | KNSPGLGKKE | LRQATNKALQ | LLQDNYPEFV | AKQVFINVPW | WYLAFSRFLS | | | 451 |
| SEQ_ID_NO_1554 | KNSPGLGKKE | LRSATKQAVE | LLQDNYPEFV | FKQAFINVPW | WYLVFYTVIG | | | 333 |
| SEQ_ID_NO_1565 | KNSPGPAKRE | LRLATKQALQ | LLQDNYPEFV | AKQVFINVPW | WYLAFYTMIN | | | 265 |
| | | | | | | | | |
| SEQ_ID_NO_1571 | PFLTQRTKSK | FVIARPSKVT | ETLLKYIPIE | AIPVKYGGLK | RDD---DTEF | | | 411 |
| SEQ_ID_NO_1567 | PFLTQRTKSK | FVFASQAKSP | ETLFRYIAPE | QVPVQFGGLF | KED---DPDF | | | 470 |
| SEQ_ID_NO_1572 | PFLTQRTKSK | FIFASPAKSA | ETLFRYIAPE | QVPVQFGGLF | KED---DPEF | | | 499 |
| SEQ_ID_NO_1574 | PFLTQRTKSK | FIFASPAKSA | ETLFRYIAPE | QVPVQFGGLF | KED---DPEF | | | 484 |
| SEQ_ID_NO_1555 | PFFTQRTKSK | FVFAGPSKTA | ETLFKYVTPE | QVPVQYGGLS | REG---EQEF | | | 494 |
| SEQ_ID_NO_1563 | PFLTQRTRSK | FVFVGPSKSA | ETLIRYIAAE | QIPVKYGGLS | KDG-----EF | | | 325 |
| SEQ_ID_NO_1575 | AFLTQRTKSK | FVFAGPSKSA | DTLFKYIAPE | QVPVQYGGLS | REG---EQEF | | | 498 |
| SEQ_ID_NO_1554 | PFMTPRSKSK | LVFAGPSRSA | ETLFKYISPE | QVPVQYGGLS | VDPCDCNPDF | | | 383 |
| SEQ_ID_NO_1565 | PFLTSRTKSK | FVFAGPSKSP | DTLFKYIFPE | QVPVQYGGLS | VDFCDCNPDF | | | 315 |
| | | | | | | | | |
| SEQ_ID_NO_1571 | SSADDGEVAE | LTVKGSSTET | IEIEAAEADA | TLTMDLIVLG | WEVNYKEEFV | | | 461 |
| SEQ_ID_NO_1567 | TTSD--SVTE | LTIKASSKET | IEIPVTE-NS | TIVWELRVLG | WEVSHGAEFT | | | 517 |
| SEQ_ID_NO_1572 | TTSD--AVTE | LTIKPSSKET | VEIPVTE-NS | TIGMELRVLG | WEVSYGAEFT | | | 546 |
| SEQ_ID_NO_1574 | TTSD--AVTE | LTIKPSSKET | VEIPVTE-NS | TIGMELRVLG | WEVSYGAEFT | | | 531 |
| SEQ_ID_NO_1555 | SIDD--PVTE | VAIKAATKHT | VEFPISEIPS | LLVWELRVVG | WDVSYGAEFL | | | 541 |
| SEQ_ID_NO_1563 | GSAD--AVTE | ITVKPAAKHT | VEFPVTEITC | LLTMEVRVAG | WDVSYSAEFV | | | 372 |
| SEQ_ID_NO_1575 | TTAD--PATE | VTIKPATKHA | VEFPISE-KS | TLVWEVRVVD | WSVNYGAEFV | | | 545 |
| SEQ_ID_NO_1554 | SLED--SASE | ITVKPGTKQT | VEIIYEIKC | ELVWEIRVTG | WEVSYKAEFV | | | 430 |
| SEQ_ID_NO_1565 | TMSD--PVTE | PIKPTTKQT | VEIAIYEIKC | IVWELRVVG | WEVSYNAEFK | | | 362 |

Figure 54 (continued)

| | | | | | | | | |
|---|---|---|---|---|---|---|---|---|
| SEQ_ID_NO_1571 | PADEGSYTII | VRKGKKMGAG | EEAVLRNSFR | AGEPGKVVLT | VENTSH-KKK | | | 509 |
| SEQ_ID_NO_1567 | PDAEGAYTVI | VQKTRKVPAN | EEPIMKGSFK | AGEAGKIVLT | VSNAAS-KKK | | | 566 |
| SEQ_ID_NO_1572 | PDAEGGYTVI | VQKTRKVPAN | EEPIMKGSFK | VGEPGKIVLT | INNPAS-KKK | | | 595 |
| SEQ_ID_NO_1574 | PDAEGGYTVI | VQKTRKVPAN | EEPIMKGSFK | VGEPGKIVLT | INNPAS-KKK | | | 580 |
| SEQ_ID_NO_1555 | PSAEGGYTVI | VQKTAKLGPA | DEPVISNSYR | VGEAGKIVLT | DNLSSKKKK | | | 591 |
| SEQ_ID_NO_1563 | PSAEDSYTVI | IQKARKVAAT | EEPVVCNSFK | IGEPGKVVLT | DNSTSKKKK | | | 422 |
| SEQ_ID_NO_1575 | PSAEDGYTVI | QKNRKVAPA | DEIISNTFK | GEPGKVILT | DNQSS-KKK | | | 594 |
| SEQ_ID_NO_1554 | PEEKDAYTVV | QKPRKMRPS | DEPVLTHSFK | VNELGKVLLT | VDNPTS-KKK | | | 479 |
| SEQ_ID_NO_1565 | PDVEDAYTVI | QKATKMSPT | DEPVVSNSFK | VVELGKLLLT | DNPTL-KKK | | | 411 |

| | | | |
|---|---|---|---|
| SEQ_ID_NO_1571 | KVLFRHKSKS | AFAKKC----- | 525 |
| SEQ_ID_NO_1567 | KLLYRSKVKC | STGESVEADI P | 587 |
| SEQ_ID_NO_1572 | KLLYRSKVKS | TSESV----- | 610 |
| SEQ_ID_NO_1574 | KLLYRSKVKS | TSESV----- | 595 |
| SEQ_ID_NO_1555 | ILLYRSKTKP | ISD------ | 604 |
| SEQ_ID_NO_1563 | KLLYRLKTKP | ASSD------ | 436 |
| SEQ_ID_NO_1575 | KLLYRSKTIP | ISE------ | 607 |
| SEQ_ID_NO_1554 | KLVYRFNVKP | L--------- | 490 |
| SEQ_ID_NO_1565 | RLLYRFKIKP | YSD------ | 424 |

Figure 55

| | | | | | | | |
|---|---|---|---|---|---|---|---|
| SEQ_ID_NO_1578 | ---------- | ---------- | ---------- | ---------- | ---------- | -MSFYRGTAS | 9 |
| SEQ_ID_NO_1607 | MADNKDGVTP | KSSAAFPLR- | ---------- | N PNVTLNERNF | AAFTNRSAAA | | 40 |
| SEQ_ID_NO_1440 | MDEEMNAVAE | MNAVASKVKE | EY------ | R RAPKLNQRII | SSMSRRSVAA | | 43 |
| SEQ_ID_NO_1648 | ----MSEEAA | TETGSSSVK- | ---------- | R TTPKLNERIL | SSLSRRSVAA | | 36 |
| SEQ_ID_NO_1651 | ---MSQENGA | TNGHLAEEQQ | DVWMEVEPKR | RAPRLNERIL | SSLSRRSVAA | | 47 |
| SEQ_ID_NO_1487 | MSSENGENGH | GAADEVVEPY | QQTP----R | PGPKLNERIL | SSLSRRSVAA | | 45 |
| SEQ_ID_NO_1040 | --MSQEDSTS | AAAAQQPTS- | ---------- | R PAPKLNERIL | SSLSRRGGGA | | 38 |
| SEQ_ID_NO_1485 | ---MSEEDTN | AAAGQP---- | ---------- | R RAPKLNERIL | SSLSRRSVAA | | 34 |
| SEQ_ID_NO_1580 | ----MSEEDK | NEAKVLETP- | ---------- | R KPPRLNERIL | SSMSRRSVAA | | 36 |
| SEQ_ID_NO_1623 | -------MS | NENDDLSPG- | ---------- | R RAPRLNERIL | SSISRRSVAA | | 32 |
| SEQ_ID_NO_1622 | MSEHDDEVQE | VQENVQEIH- | ---------- | R PVPRLNERIL | SSLSRRSVAA | | 40 |
| SEQ_ID_NO_1041 | ----MSDVTK | TQENEVETK- | ---------- | H QAPRLNERIL | SSLSRRTVAA | | 36 |
| SEQ_ID_NO_1590 | ---MSDETKT | QENEVVEAK- | ---------- | R QAPRLNERIL | SSLSRRTVAA | | 37 |
| SEQ_ID_NO_1577 | ---MNGEEVK | TSQPQKKLQ- | ---------- | N PTPRLNERIL | SSLSKRSVAA | | 37 |
| SEQ_ID_NO_1611 | ---MSEEVKE | NQSDKLQ--- | ---------- | R TAPRLNERIL | SSLSRKSVAA | | 35 |
| SEQ_ID_NO_1637 | ---MSEEVKE | NQSGKLQ--- | ---------- | K PTPRLNERIL | SSLSKRSVAA | | 35 |
| SEQ_ID_NO_1627 | -MAPSQEVAA | ATKEPSTNGN | GTQAAAAPKT | KTPALNERIL | SSITRRSVAA | | 49 |
| SEQ_ID_NO_1608 | MAPPLETVQK | VQPPPNA-EP | HVTVHHDH-S | SHPPLNERIL | SSMTRRSIAA | | 49 |
| SEQ_ID_NO_1609 | ---MSPPLES | PAKVAITQH- | ---------S | KPPPLNERII | SSMTRRSVAA | | 37 |
| | | | | | | | |
| SEQ_ID_NO_1578 | HPWHDLHPGN | DAPNFVSCVI | EIPRGSKVKY | ELDKDTGLCF | VDRILYSSVV | | 59 |
| SEQ_ID_NO_1607 | HPWHDLEIGP | EAPAVFNCVV | EISKGGKVKY | ELDKNSGLIK | VDRVLYSSIV | | 90 |
| SEQ_ID_NO_1440 | HPWHDLEIGP | NAPEICNCVV | EIPKGSKVKY | ELDKKTGLIM | VDRILYSSVV | | 93 |
| SEQ_ID_NO_1648 | HPWHDLEIGP | GAPSVVNAVV | EITKGSKVKY | ELDKKTGMIK | VDRVLYSSVV | | 86 |
| SEQ_ID_NO_1651 | HPWHDLEIGP | EAPAVFNVVV | EITKGSKVKY | ELDKKTGLIK | VDRVLYSSVV | | 97 |
| SEQ_ID_NO_1487 | HPWHDLEIGP | DAPAVFNVVV | EITKGSKVKY | ELDKKTGLIK | VDRILYSSVV | | 95 |
| SEQ_ID_NO_1040 | HPWHDLEIGP | GAPAVFNVVV | EITKGSKVKY | ELDKKTGLIK | VDRVLYSSVV | | 88 |
| SEQ_ID_NO_1485 | HPWHDLEIGP | GAPAVFNVVV | EITKGSKVKY | ELDKKTGLIK | VDRVLYSSVV | | 84 |
| SEQ_ID_NO_1580 | HPWHDLEIGP | GAPAIFNCVV | EIPKGSKVKY | ELDKKTGLIK | VDRVLYSSVV | | 86 |
| SEQ_ID_NO_1623 | HPWHDLEIGP | EAPSVFNYVI | EISKGSKVKY | ELDKKTGLIK | VDRILYSSVV | | 82 |
| SEQ_ID_NO_1622 | HPWHDLEIGP | GAPHIFNCVV | EITKGSKVKY | ELDKKTGLIK | VDRILYSSVV | | 90 |
| SEQ_ID_NO_1041 | HPWHDLEIGP | GAPHIFNVVV | EITKGSKVKY | ELDKKTGLIK | VDRILYSSVV | | 86 |
| SEQ_ID_NO_1590 | HPWHDLEIGP | GAPHIFNVVV | EITKGSKVKY | ELDKKTGLIK | VDRILYSSVV | | 87 |
| SEQ_ID_NO_1577 | HPWHDLEIGP | GAPVIFNVVI | EISKGSKVKY | ELDKKTGLIK | VDRILYSSVV | | 87 |
| SEQ_ID_NO_1611 | HPWHDLEIGP | GAPSIFNVVI | EISKGSKVKY | ELDKKTGLIK | VDRILYSSVV | | 85 |
| SEQ_ID_NO_1637 | HPWHDLEIGP | GAPVIFNVVV | EISKGSKVKY | ELDKKTGLIK | VDRILYSSVV | | 85 |
| SEQ_ID_NO_1627 | HPWHDLEIGP | DAPTIFNCVI | EIPKGSKVKY | ELDKKTGLIK | VDRVLYSSVV | | 99 |
| SEQ_ID_NO_1608 | HPWHDLEIGP | GAPKIFNCVI | EIPKGSKVKY | ELDKKTGLIK | GDRILDSSVV | | 99 |
| SEQ_ID_NO_1609 | HPWHDLEIGP | EAPKIFNCVV | EIGKGSKVKY | ELDKKTGLIK | VDRVLYSSVV | | 87 |

Figure 55 (continued)

| | | | | | | | |
|---|---|---|---|---|---|---|---|
| SEQ_ID_NO_1578 | YPHNYGFVPK | TLCEDGDPLD | VLVLMQEPVV | PMCFLRAKPI | GVMQMLDQGE | 109 |
| SEQ_ID_NO_1607 | YPHNYGFIPR | TICEDSDPID | VLVLMQEPVL | TGSFLRARAI | GLMPMIDQGE | 140 |
| SEQ_ID_NO_1440 | YPHNYGFIPR | TLCEDGDPMD | VLVLMQEPVV | PGRFLRARAI | GLMPMIDQGE | 143 |
| SEQ_ID_NO_1648 | YPHNYGFIPR | TLCEDNDPLD | VLILMQEPVL | PGCFLRJRAI | GLMPMIDQGE | 136 |
| SEQ_ID_NO_1651 | YPHNYGFIPR | SLCEDNDPMD | VLVLMQEPVL | PGAFLRARAI | GLMPMIDQGE | 147 |
| SEQ_ID_NO_1487 | YPHNYGFIPR | TLCEDNDPMD | VLVLMQEPVL | PGSFLRARAI | GLMPMIDQGE | 145 |
| SEQ_ID_NO_1040 | YPHNYGFIPR | TLCEDNDPMD | VLVLMQEPVI | PGSFLRARAI | GLMPMIDQGE | 138 |
| SEQ_ID_NO_1485 | YPHNYGFIPR | TLCEDNDPMD | VLVLMQEPVI | PGSFLRARAI | GLMPMIDQGE | 134 |
| SEQ_ID_NO_1580 | YPHNYGFIPR | TLCEDNDPLD | CLVIMQEPVL | PGCFLRARAL | GLMPMIDQGE | 136 |
| SEQ_ID_NO_1623 | YPQNYGFIPR | TLCEDNDPMD | VLVLMQEPVL | PGCFLRARAI | GLMPMIDQGE | 132 |
| SEQ_ID_NO_1622 | YPHNYGFIPR | TLCEDNDPID | VLVLMQEPVL | PGCFLRARAI | GLMPMIDQGE | 140 |
| SEQ_ID_NO_1041 | YPHNYGFIPR | TLCEDNDPLD | VLVLMQEPVL | PGCFLRARAI | GLMPMIDQGE | 136 |
| SEQ_ID_NO_1590 | YPHNYGFIPR | TLCEDNDPLD | VLVLMQEPVL | PGCFLRARAI | GLMPMIDQGE | 137 |
| SEQ_ID_NO_1577 | YPHNYGFVPR | TLCEDNDPID | VLVIMQEPVL | PGCFLRARAI | GLMPMIDQGE | 137 |
| SEQ_ID_NO_1611 | YPHNYGFIPR | TLCEDNDPLD | VLVIMQEPVL | PGCFLRARAI | GLMPMIDQGE | 135 |
| SEQ_ID_NO_1637 | YPHNYGFIPR | TLCEDNDPLD | VLVIMQEPVL | PGCFLRARAI | GLMPMIDQGE | 135 |
| SEQ_ID_NO_1627 | YPHNYGFIPR | TLCDDSDPID | VLVIMQEPVV | PGCFLRAKAI | GLMPMIDQGE | 149 |
| SEQ_ID_NO_1608 | YPHNYGFIPR | TLCEDNDPLG | CLDIMQEPVV | PGCFLRAKAI | GLMPMIDQGE | 149 |
| SEQ_ID_NO_1609 | YPHNYGFIPR | TICEDSDPMD | VLVIMQEPVL | PGCFLRAKAI | GLMPMIDQGE | 137 |

| | | | | | | | |
|---|---|---|---|---|---|---|---|
| SEQ_ID_NO_1578 | RDDKLIAVHA | DDPEYKGFTD | ISQLPPHRLA | EIKRFFEDYK | KNEHKEVVVD | 159 |
| SEQ_ID_NO_1607 | KDDKIIAVCA | DDPEFRHYRD | IKELPPHRLA | EIRRFFEDYK | KNENKKVAVE | 190 |
| SEQ_ID_NO_1440 | KDDKIIAVCA | DDPEVRHYTD | INQLPPHRLA | EIRRFFEDYK | KNENKEVAVN | 193 |
| SEQ_ID_NO_1648 | KDDKIIAVCA | DDPEYRHYTD | IKQLAPHRLA | EIRRFFEDYK | KNENKEVAVN | 186 |
| SEQ_ID_NO_1651 | KDDKIIAVCA | DDPEYRHYND | ISELSPHRLQ | EIRRFFEDYK | KNENKEVAVN | 197 |
| SEQ_ID_NO_1487 | KDDKIIAVCA | DDPEYRHFNN | LSELSPHRLQ | EIRRFFEDYK | KNENKEVAVN | 195 |
| SEQ_ID_NO_1040 | KDDKIIAVCA | DDPEYRHYSI | SVSLPFRLQ | EIKRFLEDYK | KNENKEVAVD | 186 |
| SEQ_ID_NO_1485 | KDDKIIAVCA | DDPEYRHYND | N........ | .......K | KNENKEVAVD | 167 |
| SEQ_ID_NO_1580 | KDDKIIAVCV | DDPEYKHYTD | IKDLPPHRLT | EIRRFFEDYK | KNENKEVAVD | 186 |
| SEQ_ID_NO_1623 | KDDKIIAVCA | DDPEYRHYTD | IKQLPPHRLA | EIRRFFEDYK | KNENKDVAVD | 182 |
| SEQ_ID_NO_1622 | KDDKIIAVCA | DDPEYKHFTD | YKELAPHRIM | EIRRFFEDYK | KNENKEVAVN | 190 |
| SEQ_ID_NO_1041 | KDDKIIAVCA | DDPEYKHYTD | IKELAPHRLS | EIRRFFEDYK | KNENKEVAVN | 186 |
| SEQ_ID_NO_1590 | KDDKIIAVCA | DDPEYKHYTD | IRELAPHRLS | EIRRFFEDYK | KNENKEVAVN | 187 |
| SEQ_ID_NO_1577 | KDDKIIAVCV | DDPEYKHITN | INELPPHRLS | EIRRFFEDYK | KNENKEVAVN | 187 |
| SEQ_ID_NO_1611 | KDDKIIAVCV | DDPEYKHYTD | IKELPPHRLS | EIRRFFEDYK | KNENKEVAVN | 185 |
| SEQ_ID_NO_1637 | KDDKIIAVCV | DDPEYKHYTD | IKELPPHRLT | EIRRFFEDYK | KNENKEVAVN | 185 |
| SEQ_ID_NO_1627 | ADDKIIAVCA | DDPEYRHFND | IKELPPHRLA | EIRRFFEDYK | KNENKEVAVN | 199 |
| SEQ_ID_NO_1608 | KDDQIIAVCA | DDPEYRHYND | IKELPPHRLA | EIRRFFEDYK | KNENKEVAVD | 199 |
| SEQ_ID_NO_1609 | KDDKIIAVCA | DDPEYRHYND | IKELPPHRLA | EIRRFFEDYK | KNENKEVEVH | 187 |

Figure 55 (continued)

| | | | | | | |
|---|---|---|---|---|---|---|
| SEQ_ID_NO_1578 | DFLGAEEAKK | VVKDSLNMYQ | EHYVPRKLRN | VYE | 192 |
| SEQ_ID_NO_1607 | GFLPAQAAID | AIKDSMDLYA | A-YIKAGLQR | --- | 219 |
| SEQ_ID_NO_1440 | EFLPAQIAHD | AIQHSMDLYA | E-YILQTLRR | --- | 222 |
| SEQ_ID_NO_1648 | DFLPSATAHE | AIQYSMDLYA | E-YIMMSLRR | --- | 215 |
| SEQ_ID_NO_1651 | EFLPAEAARE | AIQYSMDLYG | Q-YIMQTLRR | --- | 226 |
| SEQ_ID_NO_1487 | DFLPAPTARE | AIQYSMDLYA | Q-YILQSLKR | --- | 224 |
| SEQ_ID_NO_1040 | AFLPATTARE | AIQYSMDLYA | Q-YILQSLRQ | --- | 215 |
| SEQ_ID_NO_1485 | AFLPANTARD | AIQYSMDLYA | Q-YILQSLRQ | --- | 196 |
| SEQ_ID_NO_1580 | KFLPATAAVE | AVQYSMDLYA | E-YIMQTLRR | --- | 215 |
| SEQ_ID_NO_1623 | DFLPPNSAVN | AIQYSMDLYA | E-YILHSLRK | --- | 211 |
| SEQ_ID_NO_1622 | DFLPPSTAVE | AIQYSMDLYA | E-YILHTLRR | --- | 219 |
| SEQ_ID_NO_1041 | DFLPSNTAVE | AIQYSMDLYA | E-YILHTLRR | --- | 215 |
| SEQ_ID_NO_1590 | DFLPSNSAVE | AIQYSMDLYA | E-YILHTLRR | --- | 216 |
| SEQ_ID_NO_1577 | DFLQPGPAIE | AIQYSMDLYA | E-YILHTLRR | --- | 216 |
| SEQ_ID_NO_1611 | DFLPNGPAVE | AIQYSMDLYA | E-YILHTLRR | --- | 214 |
| SEQ_ID_NO_1637 | DFLPNGPAVE | AIQYSMDLYA | E-YILHTLRR | --- | 214 |
| SEQ_ID_NO_1627 | DFLPSEDAYE | AIQHSMDLYA | T-YICEGLRR | --- | 228 |
| SEQ_ID_NO_1608 | DFLPASTAFD | AIQHSMNLYA | D-YIVESLRR | --- | 228 |
| SEQ_ID_NO_1609 | DFLLATTAMR | AIKHSMTLYA | D-YIVESLRR | --- | 216 |

Figure 56

```
SEQ_ID_NO_361    - - MNGG GDA  LMQP - QHVQ  V - MSS  . . . .  . . . . . . . . .  S  LPMVASTEVA     31
SEQ_ID_NO_443    MDDPGASADP   AARHHLSPQQ   LGGQP - - - -  . . . . . . . . . P  VPRSPTPLDL     36
SEQ_ID_NO_212    - MDDPGAADP  GARP - HHLS   PGQPP - - - -  . . . . . . . . . V  VPRSPTPLDL     33
SEQ_ID_NO_421    . . . . . . . . . .  . . . . . . . . . .  . . . . . . . . . .  . . . . . . . . . .   0
SEQ_ID_NO_1437   MGGGDTTDT    NMMQRVNSSS   GTSSS - - - -  . . . . . . . . .  S  PKHNLHLNP      36
SEQ_ID_NO_740    - MGDTEEANS  EMIQRLQSSF   GTTQSSSTTM   AKQPFSLINQ   DVSQLSLNP      49
SEQ_ID_NO_173    - MEDTEAASS  FKMN - NHME   QLTIP - - - -  . . . . . . . . . Q  FNASSQSQMR     33
SEQ_ID_NO_1461   - MEDTEAASS  FKMN - NHME   QLTIP - - - -  . . . . . . . . . Q  FNASSQSQMR     33

SEQ_ID_NO_361    EPAAAAAA - -  . . . . . . . . . .  . . . . . . . . . .  ANKP - RAAG   - - - - LPPTP     52
SEQ_ID_NO_443    ASAAAASG - -  - YRRLSPS -   - - - LRPPAHP  QARLP - SPYG   - - - - QIPSP      72
SEQ_ID_NO_212    SSAAAAAAAA   SYRRLSPS -   - - - LRPPAHP  QARLP - SPYP   - - - - QIPSSS     73
SEQ_ID_NO_421    . . . . . . . . . .  . . . . . . . . . .  . . . . . MADS  NSKPPMSSQN   . . . . . . . . . .     14
SEQ_ID_NO_1437   ALIRSHHH -    - - - - FRH - -  - - - PFTGAPP  PPIPPISPYS   - - - - QIPAIL    69
SEQ_ID_NO_740    TQMRARHFTN   FSQNFSGDSN   KRVGFPPSHP   NQIPPISPYS   - - - - QIPVSR     95
SEQ_ID_NO_173    TVTRNHHH -    - - - NQRGG -   - - - GIPPSHP  HQIPPISPYS   HMNNQIPVSR     73
SEQ_ID_NO_1461   TVTRNHHH -    - - - NQRGG -   - - - GIPPSHP  HQIPPISPYS   HMNNQIPVSR     73

SEQ_ID_NO_361    . . . . . . . . . .  . . . . . . . . . .  . . . . P - QVFA  AQRAAAAA - -   . . . . . . . . . .     65
SEQ_ID_NO_443    . . . . . . . . . .  - GAGA - HHAR   SLSQP - LFFS   LDSLPPPP -    . . . . . . . . . .     97
SEQ_ID_NO_212    S - - - - - - AAA    AGSSG - HHAR   SLSQP - LFFS   LDSLPPLP -    . . . . . . . . . .    103
SEQ_ID_NO_421    . . . . . . . . . .  FGVGAVSHVR   SLSQS - SFFS   NSCLPPLSPF   PPSEPGMVSG     53
SEQ_ID_NO_1437   . . . . . . . . . .  - - LQP - RHSR   SMSQPSSFFS   FDSLPPLNPS   AP - - - - - - -    98
SEQ_ID_NO_740    PVNQQMGPQG   FSLGP - THSR   SLSQPSSFFS   LDSLPPLSPA   PFRDSSSPSV    144
SEQ_ID_NO_173    P - - - QMPSHS    TSPTP - SHTR   SLSQP - SFFS   LDSLPPLSPC   TFRESSSTSD    118
SEQ_ID_NO_1461   P - - - QMPSHS    TSPTP - SHTR   SLSQP - SFFS   LDSLPPLSPC   TFRESSSTSD    118

SEQ_ID_NO_361    - - - - GGDVCM   EESAQGGGG    . . . . . . . . . .  . . . . . . . . . .  - - GLPPRKA -     87
SEQ_ID_NO_443    - - - - YADL -    - - - - - - GAAP  AVPPSPPP - -  - - STSDPPPL   - - GLPPRRAG    129
SEQ_ID_NO_212    - - - - YADL -    - - - - - - AAPP  AIPPSPPS -   - - SSSDPPPP   - - GLPPRKGG    135
SEQ_ID_NO_421    RSS - LKDISM    EEADVNSQGV   GVVSS - - - -   - - FTRD - - -   - - GLPPRKG     88
SEQ_ID_NO_1437   - - - - SVSVSV    EEKTGAGFSP   SLPPSPFTMC   HSSSSRNAGD   GENLPPRKS     143
SEQ_ID_NO_740    SDPISTDVEM   EEKDGGSHSL   - LPPSPF - -   - - NRGNAPRN   VESLPPRKA     187
SEQ_ID_NO_173    - - - HADVSM    EDRDVTSHSP   - LPP - - - - -   - - FAARNP -    - - SLPPRKS     150
SEQ_ID_NO_1461   - - - HADVSM    EDRDVTSHSP   - LPP - - - - -   - - FAARNP -    - - SLPPRKS     150
```

Figure 56 (continued)

| SEQ_ID | col1 | col2 | col3 | col4 | col5 | col6 | # |
|---|---|---|---|---|---|---|---|
| SEQ_ID_NO_361 | HRRSSSDVPF | GYL-----A | GQHQLLPP- | ---------- | ---------- | ---------- | 109 |
| SEQ_ID_NO_443 | HRRSQSDIPF | GFA-----Q | LSPPLPPP- | ---------- | ---------- | ---------- | 151 |
| SEQ_ID_NO_212 | HRRSQSDIPF | GFS-----H | LSPPLPPP- | ---------- | ---------- | ---------- | 157 |
| SEQ_ID_NO_421 | HRRSNSDVPL | GFSAMI--Q | SSPQLMP- | ---------- | ---------- | --------S | 114 |
| SEQ_ID_NO_1437 | HRRSNSDVTF | GFSSMMSQNQ | KSPPLSSLER | SISGEDT--- | ---------- | -------SD | 182 |
| SEQ_ID_NO_740 | HRRSNSDIPF | GLANVL--Q | CSPPLIPS-R | GSSGLERSMS | GRENLGMA | KP | 233 |
| SEQ_ID_NO_173 | HRRSNSDIPF | GFSTVL--Q | SSPPLIPL-R | GREGV----- | ---------- | -------KP | 183 |
| SEQ_ID_NO_1461 | HRRSNSDIPF | GFSTVL--Q | SSPPLIPL-R | GREGV----- | ---------- | -------KP | 183 |

| SEQ_ID | col1 | col2 | col3 | col4 | col5 | col6 | # |
|---|---|---|---|---|---|---|---|
| SEQ_ID_NO_361 | -----KVEAG | M-----GHL | GACA----GG | AAAADDLFNA | YLNLDGLDGL | | 144 |
| SEQ_ID_NO_443 | --APVKREVT | A-----AAD | GCRSDGGGGD | DAALYDLVNA | YMDLDGLDPL | | 193 |
| SEQ_ID_NO_212 | --APVKREAA | T-----AAE | GCRSD---GD | DFALYDLVNS | YMDLDGMEAL | | 196 |
| SEQ_ID_NO_421 | GDKVLGRAVS | LG----DSN | GKIDERKPKG | ELVTDELLFS | YMNLENIETL | | 158 |
| SEQ_ID_NO_1437 | WSNLVKKE-- | ------PRE | GFYKGRKPEV | EAAMDDVFTA | YMNLDNIDVL | | 223 |
| SEQ_ID_NO_740 | ADSVKK---E | WERGGDSNAE | GMGERKSLEG | ELVVDDLFSA | YMNLDNIDVL | | 278 |
| SEQ_ID_NO_173 | NSSVVKRETN | WEHG--NVE | GSGEKKSPEG | ELVVDDLFSA | YMNLDSFDTL | | 229 |
| SEQ_ID_NO_1461 | NSSVVKRETN | WEHG--NVE | EKKKGLSPEG | ELVVDDLFSA | YMNLDNIDAI | | 228 |

| SEQ_ID | col1 | col2 | col3 | col4 | col5 | # |
|---|---|---|---|---|---|---|
| SEQ_ID_NO_361 | NSSDDRH-DE | GD------- | SRGSSI-KTN | GADSSENESE | ECADDTRGGI | 184 |
| SEQ_ID_NO_443 | NSSEDRH-DD | RD------- | SRASGTRAGS | AAESSENEAE | S--------- | 225 |
| SEQ_ID_NO_212 | NSSEERH-ED | RD------- | SRASGTRTGS | VADSSENEAE | S--------- | 228 |
| SEQ_ID_NO_421 | NGSGTKD-RD | KD------- | SIVSGTLKVT | GSESSNNEAE | SVMKGNNVS- | 197 |
| SEQ_ID_NO_1437 | NSFGGEDGKN | GNENVEEMES | SRGSGTKKTN | GGSSSDSEGD | SSASGNVK-- | 271 |
| SEQ_ID_NO_740 | NSSGTDD-KN | GNENREDLD- | SRASGT-KTN | GGDSSDNEAE | SSVNESGGNL | 325 |
| SEQ_ID_NO_173 | NSSGTDD-KN | GGENRDDLD- | SRACGT-KTN | GGDSSDNEAE | SSVNESGH-- | 274 |
| SEQ_ID_NO_1461 | NDDKNAATDD | --------- | SRASGT-KTN | GGDSSDNEAE | SSVNESG--- | 264 |

| SEQ_ID | col1 | col2 | col3 | col4 | col5 | # |
|---|---|---|---|---|---|---|
| SEQ_ID_NO_361 | RLWS-ADGGE | RREGVKRNAA | GEPATAPLAR | HARSLSMDS- | LIGKFNFTAG | 232 |
| SEQ_ID_NO_443 | ---------- | QSTSADRKDG | GK-----BR | HCRSLSIDS- | FMGKLSFAAG | 258 |
| SEQ_ID_NO_212 | ---------- | HSTPVERKDG | GG----KSR | HCRSLSVDS- | FIEKLNF--- | 259 |
| SEQ_ID_NO_421 | ----IQPTN | LREGTKRSAD | AN--APAAR | HFRSLSMDS- | AIGNFHY--G | 237 |
| SEQ_ID_NO_1437 | -----VALSB | SSSGVKRRAG | GD--APTGR | HYRSVSMDSC | FMGKLNF--G | 312 |
| SEQ_ID_NO_740 | PRAGLSSSTE | KREGIKRSAG | GD--APTTR | HYRSVSMDS- | FMGKLNF--G | 370 |
| SEQ_ID_NO_173 | ------GGSE | KREGMKRSAG | GE--APTTR | HYRSVSMDS- | FIGKLNF--G | 313 |
| SEQ_ID_NO_1461 | ------DSMD | RREGNKRSAG | GD--APTTR | HYRSVSMDS- | FIGKLNF--N | 303 |

Figure 56 (continued)

| | | | | | | |
|---|---|---|---|---|---|---|
| SEQ_ID_NO_361 | TA------- AAAGNGVALG | PN------- | RFSLEFGSGE | FTPSEMKKIM | 266 |
| SEQ_ID_NO_443 | EESPKLPLP SPGGSLTRSG | SGSLEGGAVA | LFNMEFTNGE | FTDSEKKKIM | 307 |
| SEQ_ID_NO_212 | DESPKLPLP SPSGGLSRSG | SGSLDGGAAS | LFSAEFANGE | FTEAEKKKIM | 308 |
| SEQ_ID_NO_421 | DESPNLPT SLMMRSGQLS | PSNSGNESSS | KHNLDFGNSE | FSEAEMKKIM | 285 |
| SEQ_ID_NO_1437 | DESSLKLPP SSSA---KVS | PTNSGEGNSS | AYSVEFGNSE | FTAAEMKKIA | 358 |
| SEQ_ID_NO_740 | NESPKLPP SPGTRPGQLS | PTDSIDGNL- | AFSLDFGNGE | FSGAELKKIM | 416 |
| SEQ_ID_NO_173 | DESPKLPP SPGDRGRLMS | PAGGDGNSA | AFSLEFGSGE | FSGPELKKIM | 361 |
| SEQ_ID_NO_1461 | DESL-KMPP SPGG---LMS | PGNSGDGNNA | AFSLEFGNGE | FSGPELKKIM | 348 |

| | | | | | | |
|---|---|---|---|---|---|---|
| SEQ_ID_NO_361 | ADEKLAEMAL | ADPKRVKRVL | ANRQSAARSK | ERKMRYIAEL | EDKVQLLQSE | 316 |
| SEQ_ID_NO_443 | ANERLAEIAL | TDPKRVKRIL | ANRQSAARSK | ERKMRYIQEL | EHKVQVLQTE | 357 |
| SEQ_ID_NO_212 | ANERLAEIAL | TDPKRVKRIL | ANRQSAARSK | ERKMRYIQEL | EHKVQVLQTE | 358 |
| SEQ_ID_NO_421 | ADERLAEIAV | LDPKRAKRIL | ANRLSAARSK | ERKTRYISEL | EHKVQKLQTE | 335 |
| SEQ_ID_NO_1437 | ADEKLAEIVM | ADPKRVKRIL | ANRVSAARSK | ERKTRYMAEL | EHKVQTLQTE | 408 |
| SEQ_ID_NO_740 | ANEKLAEIAL | ADPKRAKRIL | ANRQSAARSK | ERKMRYISEL | EHKVQTLQTE | 466 |
| SEQ_ID_NO_173 | ANEKLAEIAL | TDPKRAKRIL | ANRQSAARSK | ERKMRYISEL | EHKVQTLQTE | 411 |
| SEQ_ID_NO_1461 | ANEKLAEIAM | ADPKRAKRIL | ANRQSAARSK | ERKMRYISEL | EHKVQTLQTE | 398 |

| | | | | | | |
|---|---|---|---|---|---|---|
| SEQ_ID_NO_361 | ATNLSAQLTM | MQRDSAGLAT | QNNELKFRLH | AMEQQAQLRD | ALNEALTIEV | 366 |
| SEQ_ID_NO_443 | ATTLSAQLTM | LQRDSAGLAT | QNNELKIRLQ | AMEQQAQLRD | ALNEALTAEV | 407 |
| SEQ_ID_NO_212 | ATTLSAQLTM | LQRDSTGLAT | QNNELKIRLQ | AMEQQAQLRD | ALNEALTAEV | 408 |
| SEQ_ID_NO_421 | TTTLSTQVTI | LQKNFVE SS | LNSELKFRIQ | AMEQQAQLRD | ALHEALTAEV | 385 |
| SEQ_ID_NO_1437 | ATTLSAQLTH | LQRDSMGLTN | QNSELKFRLQ | AMEQQAQLRD | ALSEKLNEFV | 458 |
| SEQ_ID_NO_740 | ATTLSAQLTL | LQRDSVGLTN | QNNELKFRIQ | AMEQQAQLRD | ALNEALTAEV | 516 |
| SEQ_ID_NO_173 | ATTLSAQLTL | LQRDSAGLTN | QNSELKFRLQ | SMEQQAKLRD | ALNEALTAEV | 461 |
| SEQ_ID_NO_1461 | ATTLSAQLTL | LQRDSVGLTN | QNSELKFRLQ | SMEQQAKLRD | ALNEALTAEV | 448 |

| | | | | | | |
|---|---|---|---|---|---|---|
| SEQ_ID_NO_361 | QRLKLATAEL | GDSCSSSSLA | QQLQLNAQNQ | MFQL----- | --------QQQ | 403 |
| SEQ_ID_NO_443 | QRLKLATGEV | T-DGRMPKGL | QQQM--NSQ | MLQL----- | --------QQL | 440 |
| SEQ_ID_NO_212 | QRLKLATGEI | T-DGRMSKGL | QQQM--NSQ | LIQL----- | --------- | 438 |
| SEQ_ID_NO_421 | QRLKLAAGEH | REEGRLPNNM | TQQT-PVKHN | IFQM----- | --------- | 418 |
| SEQ_ID_NO_1437 | QRLKLVLGEP | NRRQSGSSSS | ESKMLSLNPE | MFQQ----- | ---------L | 492 |
| SEQ_ID_NO_740 | RRLKIATAEQ | GGDSDPSKSM | VQQQLSINPQ | MYLQQPRPSQ | LGMHQLQQQS | 566 |
| SEQ_ID_NO_173 | QRLKIATAEL | SSDSHGSSCL | PQHSVNPL | MFQQ----- | --------QPP | 497 |
| SEQ_ID_NO_1461 | QRLKIVTAEL | NGESLPSNCM | PQHSVNPM | MFQQ----- | --------- | 481 |

Figure 56 (continued)

| | | | | | | |
|---|---|---|---|---|---|---|
| SEQ_ID_NO_361 | QATQIPFYQL | QQSQ- - - - - | - - - - - - - - - Q | NGAAKNNESK | E | 429 |
| SEQ_ID_NO_443 | QVQQQAPQAQ | QQGQ- - - - - | - - - - - - - - - - | RQQQQQPQKS | A | 465 |
| SEQ_ID_NO_212 | - -QQLQIQQQ | QSSQ- - - - - | - - - - - - - - - - | - - - -TTQQDR | L | 457 |
| SEQ_ID_NO_421 | - -QRQOPSQM | QQLS- - - - - | - - - - - - -VGK | ASAASATPAS | A | 444 |
| SEQ_ID_NO_1437 | SLSQLQHQQM | QHSN- - - - - | - - - - - - - -QC | STMKAKHTSN | D | 519 |
| SEQ_ID_NO_740 | SASQFNMHQR | QRQQQQQQQQ | QSSQPQPQQN | GNTTPKPDSN | Q | 607 |
| SEQ_ID_NO_173 | SASQQNIHLQ | QQQH- - - - - | - - - - - - -RQN | GNANSNSDLK | Q | 525 |
| SEQ_ID_NO_1461 | - - -QHQHQQH | QQQQ- - - - - | - - - - - - -QQN | GNANSKNELK | Q | 506 |

Figure 57

```
SEQ_ID_NO_97     ----MGMKSP NIAAFMLPLL LILFTLSSQL KVVESTGRKL -AWGFSGTPI  45
SEQ_ID_NO_2013   MKKKMGSKSP NIBAFVLPLL LILFTLSSQA RLIESTGRKL AAWGFGGAPI  50
SEQ_ID_NO_2015   ----MGSKSP NIAALVLPLL LILFSLSSQA RLVESSGRKL AAWGFGGAPI  46

SEQ_ID_NO_97     VYTPPSRSCG TSPAVFTSKW RRPRPCRLPP GSY PASDQS P  86
SEQ_ID_NO_2013   WTPPSNSCG ASPAVWYPKP TKRGPCRGPP GIG PTSYQS P  91
SEQ_ID_NO_2015   STPSSNSCG ASPAVWYPKP TKPRPCRRTP GIG PTSHQS P  87
```

NUCLEOTIDE SEQUENCES AND CORRESPONDING POLYPEPTIDES CONFERRING MODIFIED PHENOTYPE CHARACTERISTICS IN PLANTS

CROSS REFERENCES TO RELATED APPLICATIONS

This application is a divisional of co-pending application Ser. No. 15/689,941, filed Aug. 29, 2017, which application is a divisional of application Ser. No. 13/644,359, now U.S. Pat. No. 9,777,287 filed Oct. 4, 2012, which application is a Continuation-in-Part of co-pending application Ser. No. 13/465,846, filed on May 7, 2012, and for which priority is claimed under 35 U.S.C. § 120. Application Ser. No. 13/465, 846 is a Division of application Ser. No. 10/572,827, now U.S. Pat. No. 8,193,409, filed on Mar. 7, 2007. The entire contents of each of which are hereby incorporated by reference, including their sequence listings.

This application is a Continuation-in-Part of co-pending application Ser. No. 11/779,266 filed on Jul. 17, 2007 and for which priority is claimed under 35 U.S.C. § 120. Application Ser. No. 11/779,266 is a Continuation-in-Part of application Ser. No. 11/778,060, now abandoned, filed Jul. 15, 2007. Application Ser. No. 11/778,060 is a Continuation-in-Part of application Ser. No. 11/248,547, now U.S. Pat. No. 7,244,879, filed Oct. 12, 2005. The entire contents of each of which are hereby incorporated by reference, including their sequence listings.

This application is a Continuation-in-Part of co-pending application Ser. No. 12/514,991 filed on Jan. 8, 2010 and for which priority is claimed under 35 U.S.C. § 120. Application Ser. No. 12/514,991 is a national phase under 35 U.S.C. § 371 of PCT International Application No. PCT/US2007/085007 which has the International filing date of Nov. 16, 2007, which designated the United States of America, and which claims priority under 35 U.S.C. § 119(e) of U.S. Provisional Application No. 60/859,467, filed Nov. 16, 2006. The entire contents of each of which are hereby incorporated by reference, including their sequence listings.

This application is a Continuation-in-Part of co-pending application Ser. No. 12/445,005 filed on Jul. 13, 2011 and for which priority is claimed under 35 U.S.C. § 120. Application Ser. No. 12/445,005 is a national phase under 35 U.S.C. § 371 of PCT International Application No. PCT/US2007/081301 which has the International filing date of Oct. 12, 2007, which designated the United States of America, and which claims priority under 35 U.S.C. § 119(e) of U.S. Provisional Application No. 60/851,585, filed Oct. 12, 2006. The entire contents of each of which are hereby incorporated by reference, including their sequence listings.

This application is a Continuation-in-Part of co-pending application Ser. No. 12/515,707 filed on Dec. 16, 2009 and for which priority is claimed under 35 U.S.C. § 120. Application Ser. No. 12/515,707 is a national phase under 35 U.S.C. § 371 of PCT International Application No. PCT/US2007/085439 which has the International filing date of Nov. 21, 2007, which designated the United States of America, and which claims priority under 35 U.S.C. § 119(e) of U.S. Provisional Application No. 60/860,296, filed Nov. 21, 2006. The entire contents of each of which are hereby incorporated by reference, including their sequence listings.

This application is a Continuation-in-Part of co-pending application Ser. No. 12/615,920 filed on Nov. 10, 2009 and for which priority is claimed under 35 U.S.C. § 120. Application Ser. No. 12/615,920 is a Division of application Ser. No. 11/114,963, now U.S. Pat. No. 7,696,409, filed on Apr. 25, 2005. Application Ser. No. 11/114,963 claims priority under 35 U.S.C. § 119(e) of U.S. Provisional Application No. 60/564,659, filed Apr. 23, 2004. The entire contents of each of which are hereby incorporated by reference, including their sequence listings.

This application is a Continuation-in-Part of co-pending application Ser. No. 12/605,261 filed on Oct. 23, 2009 and for which priority is claimed under 35 U.S.C. § 120. Application Ser. No. 12/605,261 is a Division of application Ser. No. 11/298,391, now U.S. Pat. No. 7,663,027, filed on Dec. 8, 2005. Application Ser. No. 11/298,391 claims priority under 35 U.S.C. § 119(e) of U.S. Provisional Application Nos. 60/635,115, filed Dec. 8, 2004 and 60/635,140, filed on Dec. 8, 2004. The entire contents of each of which are hereby incorporated by reference, including their sequence listings.

This application is a Continuation-in-Part of co-pending application Ser. No. 12/377,106 filed on Aug. 13, 2010 and for which priority is claimed under 35 U.S.C. § 120. Application Ser. No. 12/377,106 is a national phase under 35 U.S.C. § 371 of PCT International Application No. PCT/US2007/075747 which has the International filing date of Aug. 10, 2007, which designated the United States of America, and which claims priority under 35 U.S.C. § 119(e) of U.S. Provisional Application No. 60/837,434, filed Aug. 11, 2006. The entire contents of each of which are hereby incorporated by reference, including their sequence listings.

This application is a Continuation-in-Part of co-pending application Ser. No. 12/541,607 filed on Aug. 14, 2009 and for which priority is claimed under 35 U.S.C. § 120. Application Ser. No. 12/541,607 is a Continuation of application Ser. No. 11/140,347, now U.S. Pat. No. 7,576,260, filed on May 27, 2005. Application Ser. No. 11/140,347 claims priority under 35 U.S.C. § 119(e) of U.S. Provisional Application No. 60/575,309, filed May 27, 2004. The entire contents of each of which are hereby incorporated by reference, including their sequence listings.

This application is a Continuation-in-Part of co-pending application Ser. No. 13/184,361 filed on Jul. 15, 2011 and for which priority is claimed under 35 U.S.C. § 120. Application Ser. No. 13/184,361 is a Division of application Ser. No. 11/140,450, now U.S. Pat. No. 8,022,273, filed on May 27, 2005. Application Ser. No. 11/140,450 claims priority under 35 U.S.C. § 119(e) of U.S. Provisional Application No. 60/575,253, filed May 27, 2004. The entire contents of each of which are hereby incorporated by reference, including their sequence listings.

This application is a Continuation-in-Part of co-pending application Ser. No. 11/654,357 filed on Jan. 16, 2007 and for which priority is claimed under 35 U.S.C. § 120. Application Ser. No. 11/654,357 is a Non-Provisional which claims priority under 35 U.S.C. § 119(e) of U.S. Provisional Application Nos. 60/778,568, filed Mar. 1, 2006 and 60/758,831, filed on Jan. 13, 2006. The entire contents of each of which are hereby incorporated by reference, including their sequence listings.

This application is a Continuation-in-Part of co-pending application Ser. No. 13/465,841 filed on May 7, 2012 and for which priority is claimed under 35 U.S.C. § 120. Application Ser. No. 13/465,841 is a Division of application Ser. No. 11/858,117, now abandoned, filed on Sep. 19, 2007. Application Ser. No. 11/858,117 is a Continuation-in-Part of Application No. PCT/US2007/06544 which has the International filing date of Mar. 14, 2007, and which claims priority under 35 U.S.C. § 119(e) of U.S. Provisional Application No. 60/782,735, filed Mar. 14, 2006. The entire contents of each of which are hereby incorporated by reference, including their sequence listings.

This application is a Continuation-in-Part of co-pending application Ser. No. 12/918,309 filed on Nov. 22, 2010 and for which priority is claimed under 35 U.S.C. § 120. Application Ser. No. 12/918,309 is a national phase under 35 U.S.C. § 371 of PCT International Application No. PCT/US2009/034638 which has the International filing date of Feb. 20, 2009, which designated the United States of America, and which claims priority under 35 U.S.C. § 119(e) of U.S. Provisional Application No. 61/030,152, filed Feb. 20, 2008. The entire contents of each of which are hereby incorporated by reference, including their sequence listings.

This application is a Continuation-in-Part of application Ser. No. 12/922,143 filed on Feb. 1, 2011 and for which priority is claimed under 35 U.S.C. § 120. Application Ser. No. 12/922,143 is a national phase under 35 U.S.C. § 371 of PCT International Application No. PCT/US2009/037025 which has the International filing date of Mar. 12, 2009, which designated the United States of America, and which claims priority under 35 U.S.C. § 119(e) of U.S. Provisional Application No. 61/036,396, filed Mar. 13, 2008. The entire contents of each of which are hereby incorporated by reference, including their sequence listings.

This application is a Continuation-in-Part of co-pending application Ser. No. 11/241,685 filed on Sep. 30, 2005 and for which priority is claimed under 35 U.S.C. § 120. Application Ser. No. 11/241,685 is a Non-provisional which claims priority under 35 U.S.C. § 119(e) of U.S. Provisional Application No. 60/615,080, filed on Sep. 30, 2004. The entire contents of each of which are hereby incorporated by reference, including their sequence listings.

This application is a Continuation-in-Part of co-pending application Ser. No. 12/863,773 filed on Nov. 23, 2010 and for which priority is claimed under 35 U.S.C. § 120. Application Ser. No. 12/863,773 is a national phase under 35 U.S.C. § 371 of PCT International Application No. PCT/US2009/031609 which has the International filing date of Jan. 21, 2009, which designated the United States of America, and which claims priority under 35 U.S.C. § 119(e) of U.S. Provisional Application No. 61/022,786, filed Jan. 22, 2008. The entire contents of each of which are hereby incorporated by reference, including their sequence listings.

This application is a Continuation-in-Part of co-pending application Ser. No. 12/282,342 filed on Nov. 17, 2008 and for which priority is claimed under 35 U.S.C. § 120. Application Ser. No. 12/282,342 is a national phase under 35 U.S.C. § 371 of PCT International Application No. PCT/US2007/06544 which has the International filing date of Mar. 14, 2007, which designated the United States of America, and which claims priority under 35 U.S.C. § 119(e) of U.S. Provisional Application No. 60/782,735, filed Mar. 14, 2006. The entire contents of each of which are hereby incorporated by reference, including their sequence listings.

This application is a Continuation-in-Part of co-pending application Ser. No. 12/776,319 filed on May 7, 2010 and for which priority is claimed under 35 U.S.C. § 120. Application Ser. No. 12/776,319 is a Division of application Ser. No. 11/324,093, now U.S. Pat. No. 7,803,983, filed on Dec. 29, 2005. Application Ser. No. 11/324,093 is a Continuation-in-Part of application Ser. No. 11/172,740, now U.S. Pat. No. 7,396,979, filed on Jun. 30, 2005. Application Ser. No. 11/172,740 claims priority under 35 U.S.C. § 119(e) of U.S. Provisional Application Nos. 60/584,829, 60/583,621, and 60/584,800, all filed on Jun. 30, 2004. The entire contents of each of which are hereby incorporated by reference, including their sequence listings.

This application is a Continuation-in-Part of co-pending application Ser. No. 12/911,698 filed on Oct. 25, 2010 and for which priority is claimed under 35 U.S.C. § 120. Application Ser. No. 12/911,698 is a Division of application Ser. No. 11/324,098, now U.S. Pat. No. 7,884,261, filed on Dec. 29, 2005. Application Ser. No. 11/324,098 is a Continuation-in-Part of application Ser. No. 11/172,740, now U.S. Pat. No. 7,396,979, filed on Jun. 30, 2005. Application Ser. No. 11/172,740 claims priority under 35 U.S.C. § 119(e) of U.S. Provisional Application Nos. 60/584,829, 60/583,621, and 60/584,800, all filed on Jun. 30, 2004. The entire contents of each of which are hereby incorporated by reference, including their sequence listings.

This application is a Continuation-in-Part of co-pending application Ser. No. 13/609,176 filed on Sep. 10, 2012 and for which priority is claimed under 35 U.S.C. § 120. Application Ser. No. 13/609,176 is a Division of application Ser. No. 12/139,269, pending, filed on Jun. 13, 2008. Application Ser. No. 12/139,269 is a Division of application Ser. No. 11/172,740, now U.S. Pat. No. 7,396,979, filed on Jun. 30, 2005. Application Ser. No. 11/172,740 claims priority under 35 U.S.C. § 119(e) of U.S. Provisional Application Nos. 60/584,829, 60/583,621, and 60/584,800, all filed on Jun. 30, 2004. The entire contents of each of which are hereby incorporated by reference, including their sequence listings.

TECHNICAL FIELD the present invention relates to methods and materials involved in tolerance of a plant to limiting exogenous nitrogen sources. For example, this document provides plants having increased low-nitrogen tolerance levels as well as materials and methods for making plants and plant products having increased low-nitrogen tolerance levels.

BACKGROUND

Nitrogen is often the rate-limiting element in plant growth, and all field crops have a fundamental dependence on exogenous nitrogen sources.

According to a recent study published in Field Crops Research (Volume 100, Issues 2-3, 1 Feb. 2007, Pages 210-217), Nitrogenous fertilizer, which is usually supplied as ammonium nitrate, potassium nitrate, or urea, typically accounts for 40% of the costs associated with crops, such as corn and wheat in intensive agriculture.

Improving nitrogen use efficiency of crop plants is an important goal towards reducing input costs and reducing the environmental consequences of intensive nitrogen fertilization on the environment. Increased efficiency of nitrogen use by plants should enable the production of higher yields with existing fertilizer inputs and/or enable existing yields of crops to be obtained with lower fertilizer input, or better yields on soils of poorer quality. Also, higher amounts of proteins in the crops could also be produced more cost-effectively.

Plants have a number of means to cope with nutrient deficiencies, such as poor nitrogen availability. One important mechanism senses nitrogen availability in the soil and respond accordingly by modulating gene expression while a second mechanism is to sequester or store nitrogen in times of abundance to be used later. The nitrogen sensing mechanism relies on regulated gene expression and enables rapid physiological and metabolic responses to changes in the supply of inorganic nitrogen in the soil by adjusting nitrogen uptake, reduction, partitioning, remobilization and transport in response to changing environmental conditions. Nitrate acts as a signal to initiate a number of responses that serve to reprogram plant metabolism, physiology and development (Redinbaugh et al. (1991) *Physiol. Plant.* 82, 640-650; Forde (2002) *Annual Review of Plant Biology* 53, 203-224). Nitrogen-inducible gene expression has been characterized for a number of genes in some detail. These include nitrate reductase, nitrite reductase, 6-phosphoglucante dehydrogenase, and nitrate and ammonium transporters (Redinbaugh et al. (1991) *Physiol. Plant.* 82, 640-650; Huber et al. (1994) *Plant Physiol* 106, 1667-1674; Hwang et al. (1997) *Plant Physiol.* 113, 853-862; Redinbaugh et al. (1998) *Plant Science* 134, 129-140; Gazzarrini et al. (1999) *Plant Cell* 11, 937-948; Glass et al. (2002) *J. Exp. Bot.* 53, 855-864; Okamoto et al. (2003) *Plant Cell Physiol.* 44, 304-317).

In the fields of agriculture and forestry, efforts are constantly being made to produce plants with an increased growth potential in order to feed the ever-increasing world population and to guarantee the supply of reproducible raw materials. There is a need for methods of increasing nitrogen use efficiency in plants, which leads to better growth potential and more biomass. This is done conventionally through plant breeding. The breeding process is, however, both time-consuming and labor-intensive. Furthermore, appropriate breeding programs must be performed for each relevant plant species. In addition, although great progresses that have been made about nitrogen utilization and the components involved in nitrogen use efficiency, such as nitrogen uptake, nitrogen assimilation and nitrogen partitioning or remobilization, much is still unknown about many of these complex interactions. Therefore, there is a continuing need for generally applicable processes that improve forest or agricultural plant growth to suit particular needs depending on specific environmental conditions. For example, genes that confer tolerance to growth on low nitrogen supply are valuable product prototypes for manipulating nitrogen use efficiency in plants (Good et al., 2004). One strategy to achieve such desirable traits involves genetic manipulation of plant characteristics through the introduction of exogenous nucleic acids conferring increased efficiency of nitrogen use by plants, which in turn should enable the production of higher yields with existing fertilizer inputs and/or enable existing yields of crops to be obtained with lower fertilizer input, or better yields on soils of poorer quality. Such approaches have the advantage of not usually being limited to one plant species, but instead being transferable among plant species. The present invention relates to a method for increasing growth potential, and/or increasing levels of nitrogen use efficiency in plants, characterized by expression of recombinant DNA molecules stably integrated into the plant genome

SUMMARY

The present invention provides methods and materials related to plants having modulated levels of low-nitrogen tolerance. For example, the present invention provides transgenic plants and plant cells having increased levels of low-nitrogen tolerance, nucleic acids (i.e. isolated polynucleotides), polypeptides encoded thereby used to generate transgenic plants and plant cells having increased levels of low-nitrogen tolerance, and methods for making plants and plant cells having increased levels of low-nitrogen tolerance. Such plants and plant cells can be grown under limiting exogenous nitrogen without stunted growth and diminished yields. Plants having increased low-nitrogen tolerance levels may be useful to produce biomass which may be converted to a liquid fuel or other chemicals and/or to produce food and feed on land that is currently marginally productive, resulting in an overall expansion of arable land.

Methods of producing a plant tissue are provided herein. In one aspect, a method comprises growing a plant cell comprising an exogenous nucleic acid. The exogenous nucleic acid comprises a regulatory region operably linked to a nucleotide sequence encoding a polypeptide. The Hidden Markov Model (HMM) bit score of the amino acid sequence of the polypeptide is greater than about 20, using an HMM generated from the amino acid sequences depicted in one of FIGS. 1-57. The tissue has a difference in the level of low-nitrogen tolerance as compared to the corresponding level in tissue of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence encoding a polypeptide having 80 percent or greater sequence identity to an amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577. A plant and/or plant tissues produced from the plant cell has a difference in the level of low-nitrogen tolerance as compared to the corresponding level of low-nitrogen tolerance of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence having 80 percent or greater sequence identity to a nucleotide sequence, or a fragment thereof, set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576. A plant and/or plant tissues produced from the plant cell has a difference in the level of low-nitrogen tolerance as compared to the corresponding level low-nitrogen tolerance of a control plant that does not comprise the exogenous nucleic acid.

In another aspect, the invention provides a method of producing a plant, the method comprising growing a plant cell comprising an exogenous nucleic acid that is effective for downregulating an endogenous nucleic acid in the plant cell, wherein the endogenous nucleic acid encodes a polypeptide, and wherein the HMM bit score of the amino acid sequence of the polypeptide is greater than about 20, said HMM based on the amino acid sequences depicted in one of FIGS. 1-57

Methods of modulating the level of low-nitrogen tolerance in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than about 20, using an HMM generated from the amino acid sequences depicted in one of FIGS. 1-57. A plant and/or plant tissue produced from the plant cell has a difference in the level of low-nitrogen tolerance as compared to the corresponding level of low-nitrogen tolerance of a control plant that does not comprise the exogenous nucleic acid.

In certain embodiments, the HMM bit score of the amino acid sequence of the polypeptide is greater than about 40, using an HMM generated from the amino acid sequences depicted in one of FIGS. 1-57, wherein the polypeptide comprises a Pfam domain having 70 percent or greater sequence identity to a Pfam domain of any one of the polypeptides in the sequence listing.

In another aspect, a method comprises modulating the level of low-nitrogen tolerance in a plant by introducing into a plant cell an exogenous nucleic acid that comprises a regulatory region operably linked to a nucleotide sequence encoding a polypeptide having 80 percent or greater sequence identity to an amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577, or a fragment thereof. A plant and/or plant tissue produced from the plant cell has a difference in the level of low-nitrogen tolerance as compared to the corresponding level of low-nitrogen tolerance of a control plant that does not comprise the exogenous nucleic acid.

In another aspect, a method comprises modulating the level of low-nitrogen tolerance in a plant by introducing into a plant cell an exogenous nucleic acid, that comprises a regulatory region operably linked to a nucleotide sequence having 80 percent or greater sequence identity to a nucleotide sequence set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576, or a fragment thereof. A plant and/or plant tissue produced from the plant cell has a difference in the level of low-nitrogen tolerance as compared to the corresponding level of low-nitrogen tolerance of a control plant that does not comprise the exogenous nucleic acid.

Plant cells comprising an exogenous nucleic acid are provided herein. In one aspect, the exogenous nucleic acid comprises a regulatory region operably linked to a nucleotide sequence encoding a polypeptide. The HMM bit score of the amino acid sequence of the polypeptide is greater than about 20, using an HMM based on the amino acid sequences depicted in one of FIGS. 1-57. The plant has a difference in the level of low-nitrogen tolerance as compared to the corresponding level of low-nitrogen tolerance of a control plant that does not comprise the exogenous nucleic acid. In another aspect, the exogenous nucleic acid comprises a regulatory region operably linked to a nucleotide sequence encoding a polypeptide having 80 percent or greater sequence identity to an amino acid sequence selected from the group consisting of SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. A plant and/or plant tissue produced from the plant cell has a difference in the level of low-nitrogen tolerance as compared to the corresponding level of low-nitrogen tolerance of a control plant that does not comprise the exogenous nucleic acid. In another aspect, the exogenous nucleic acid comprises a regulatory region operably linked to a nucleotide sequence having 80 percent or greater sequence identity to a nucleotide sequence selected from the group consisting of SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576, or a fragment thereof. A plant and/or plant tissue of a plant produced from the plant cell has a difference in the level of low-nitrogen tolerance as compared to the corresponding level of low-nitrogen tolerance of a control plant that does not comprise the exogenous nucleic acid. A transgenic plant comprising such a plant cell is also provided.

Isolated nucleic acids are also provided. In one aspect, an isolated nucleic acid comprises a nucleotide sequence having 80% or greater sequence identity to the nucleotide sequence set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576. In another aspect, an isolated nucleic acid comprises a nucleotide sequence encoding a polypeptide having 80% or greater sequence identity to the amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577.

In another aspect, methods of identifying a genetic polymorphism associated with variation in the level of low-nitrogen tolerance are provided. The methods include providing a population of plants, and determining whether one or more genetic polymorphisms in the population are genetically linked to the locus for a polypeptide selected from the group consisting of the polypeptides depicted in FIGS. 1-57, SEQ ID NO:556, SEQ ID NO:853, SEQ ID NO:1157, and functional homologs thereof, such as those in the Sequence Listing. The correlation between variation in the level of low-nitrogen tolerance in a tissue in plants of the population and the presence of the one or more genetic polymorphisms in plants of the population is measured, thereby permitting identification of whether or not the one or more genetic polymorphisms are associated with such variation.

In another aspect, the invention provides a method of making a plant line, said method comprising:
a) determining whether one or more genetic polymorphisms in a population of plants is associated with the locus for a polypeptide selected from the group consisting of the polypeptides depicted in FIGS. 1-57, SEQ ID NO: 556, SEQ ID NO: 853, and SEQ ID NO: 1157 and functional homologs thereof;
b) identifying one or more plants in said population in which the presence of at least one allele at said one or more genetic polymorphisms is associated with variation in a trait;
c) crossing each said one or more identified plants with itself or a different plant to produce seed;
d) crossing at least one progeny plant grown from said seed with itself or a different plant; and
e) repeating steps c) and d) for an additional 0-5 generations to make said plant line, wherein said at least one allele is present in said plant line.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is an alignment of Ceres SEEDLINE No. ME00919 (SEQ ID NO:3) with homologous and/or orthologous amino acid sequences GI No. 5921925 (SEQ ID NO:4), CeresClone: 1929222 (SEQ ID NO:6), CeresAnnot: 1471370 (SEQ ID NO:10), GI No. 84380741 (SEQ ID NO:21), GI No. 5921926 (SEQ ID NO:22), GI No. 84514161 (SEQ ID NO:25), CeresClone: 779234 (SEQ ID NO:27), CeresClone: 1600726 (SEQ ID NO:29), GI No. 78183420 (SEQ ID NO:36), CeresClone: 1877346 (SEQ ID NO:38), GI No. 125562440 (SEQ ID NO:39), GI No. 115477665 (SEQ ID NO:40), GI No. 1173624 (SEQ ID NO:46), and GI No. 84468276 (SEQ ID NO:47). In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE version 3.52.

FIG. 2 is an alignment of ME01312 (SEQ ID NO:49) with homologous and/or orthologous amino acid sequences CeresClone: 1869410 (SEQ ID NO:51), CeresAnnot: 1540549 (SEQ ID NO:53), CeresClone: 978708 (SEQ ID NO:58), CeresClone: 1623097 (SEQ ID NO:60), GI No. 92873064 (SEQ ID NO:63), GI No. 37051131 (SEQ ID NO:64), GI No. 3341468 (SEQ ID NO:65), CeresClone: 937560 (SEQ ID NO:67), CeresClone: 456844 (SEQ ID NO:69), GI No. 125564100 (SEQ ID NO:70), GI No. 52077334 (SEQ ID NO:71), GI No. 113205234 (SEQ ID NO:73), and CeresAnnot: 6100272 (SEQ ID NO:75).

FIG. 3 is an alignment of ME01463 (SEQ ID NO:77) with homologous and/or orthologous amino acid sequences GI No. 2811029 (SEQ ID NO:78), CeresClone: 1853284 (SEQ ID NO:80), CeresAnnot: 1476446 (SEQ ID NO:82), CeresClone: 527024 (SEQ ID NO:87), GI No. 27527063 (SEQ ID NO:88), CeresClone: 913632 (SEQ ID NO:90), CeresClone: 1386710 (SEQ ID NO:92), GI No. 115461885 (SEQ ID NO:93), and CeresAnnot: 6054519 (SEQ ID NO:95)

FIG. 4 is an alignment of ME01910 (SEQ ID NO:100) with homologous and/or orthologous amino acid sequences GI No. 585238 (SEQ ID NO:101), GI No. 90704789 (SEQ ID NO:102), CeresClone: 1895729 (SEQ ID NO:104), CeresAnnot: 1442808 (SEQ ID NO:108), CeresClone: 1104700 (SEQ ID NO:113), GI No. 32966575 (SEQ ID NO:116), GI No. 4996567 (SEQ ID NO:117), GI No. 62286644 (SEQ ID NO:118), GI No. 2623960 (SEQ ID NO:119), GI No. 585241 (SEQ ID NO:120), GI No. 790929 (SEQ ID NO:122), CeresClone: 579112 (SEQ ID NO:125), CeresClone: 244199 (SEQ ID NO:137), CeresClone: 1725848 (SEQ ID NO:144), GI No. 6474950 (SEQ ID NO:145), GI No. 125546057 (SEQ ID NO:146), GI No. 115455945 (SEQ ID NO:147), GI No. 2641211 (SEQ ID NO:149), and GI No. 30024108 (SEQ ID NO:150).

FIG. 5 is an alignment of ME02538 (SEQ ID NO:152) with homologous and/or orthologous amino acid sequences CeresClone: 1843642 (SEQ ID NO:154), CeresAnnot: 1459112 (SEQ ID NO:158), CeresClone: 953633 (SEQ ID NO:162), and CeresClone: 587957 (SEQ ID NO:164).

FIG. 6 is an alignment of ME02603 (SEQ ID NO:166) with homologous and/or orthologous amino acid sequences CeresClone: 1857256 (SEQ ID NO:168), CeresAnnot: 1442042 (SEQ ID NO:170), GI No. 89257469 (SEQ ID NO:174), CeresClone: 389818 (SEQ ID NO:177), CeresClone: 2019147 (SEQ ID NO:181), GI No. 125537720 (SEQ ID NO:182), GI No. 115443697 (SEQ ID NO:183), and GI No. 20340241 (SEQ ID NO:184).

FIG. 7 is an alignment of ME02613 (SEQ ID NO:186) with homologous and/or orthologous amino acid sequences CeresAnnot: 1490274 (SEQ ID NO:188), CeresClone: 873093 (SEQ ID NO:193), GI No. 6635384 (SEQ ID NO:194), CeresClone: 663726 (SEQ ID NO:196), GI No. 92881411 (SEQ ID NO:197), CeresClone: 686525 (SEQ ID NO:199), CeresClone: 1524364 (SEQ ID NO:201), CeresClone: 1742159 (SEQ ID NO:203), and GI No. 125543535 (SEQ ID NO:204).

FIG. 8 is an alignment of ME02801 (SEQ ID NO:208) with homologous and/or orthologous amino acid sequences CeresClone: 981621 (SEQ ID NO:214) and CeresClone: 564714 (SEQ ID NO:216).

FIG. 9 is an alignment of ME03123 (SEQ ID NO:218) with homologous and/or orthologous amino acid sequences CeresClone: 1899168 (SEQ ID NO:220), CeresAnnot: 1494669 (SEQ ID NO:222), CeresClone: 1017441 (SEQ ID NO:225), CeresClone: 1065937 (SEQ ID NO:227), CeresClone: 1822919 (SEQ ID NO:229), GI No. 125553329 (SEQ ID NO:230), GI No. 115439053 (SEQ ID NO:231), and CeresAnnot: 6040744 (SEQ ID NO:1052).

FIG. 10 is an alignment of ME04204 (SEQ ID NO:234) with homologous and/or orthologous amino acid sequences CeresAnnot: 1519952 (SEQ ID NO:236), CeresClone: 234768 (SEQ ID NO:241), GI No. 108707052 (SEQ ID NO:242), and GI No. 55978030 (SEQ ID NO:244).

FIG. 11 is an alignment of ME04477 (SEQ ID NO:246) with homologous and/or orthologous amino acid sequences CeresClone: 1620215 (SEQ ID NO:248), GI No. 38016527 (SEQ ID NO:249), CeresClone: 1798756 (SEQ ID NO:251), CeresAnnot: 1460527 (SEQ ID NO:255), GI No. 119720772 (SEQ ID NO:260), CeresClone: 708446 (SEQ ID NO:262), GI No. 92896423 (SEQ ID NO:265), GI No. 113196593 (SEQ ID NO:267), GI No. 75133829 (SEQ ID NO:268), CeresClone: 1030374 (SEQ ID NO:270), CeresClone: 1387149 (SEQ ID NO:274), GI No. 5031281 (SEQ ID NO:277), CeresClone: 1775820 (SEQ ID NO:279), GI No. 35187687 (SEQ ID NO:286), GI No. 115468934 (SEQ ID NO:290), GI No. 118424243 (SEQ ID NO:296), and CeresAnnot: 6063957 (SEQ ID NO:298).

FIG. 12 is an alignment of ME04507 (SEQ ID NO:300) with homologous and/or orthologous amino acid sequences CeresAnnot: 1513514 (SEQ ID NO:302), CeresClone: 923483 (SEQ ID NO:310), CeresClone: 304357 (SEQ ID NO:312), CeresClone: 1902716 (SEQ ID NO:316), GI No. 116309713 (SEQ ID NO:319), GI No. 38345408 (SEQ ID NO:321), and CeresAnnot: 6017635 (SEQ ID NO:325).

FIG. 13 is an alignment of ME04587 (SEQ ID NO:332) with homologous and/or orthologous amino acid sequences Ceres ANNOT ID no. 1474882 (SEQ ID NO:334), Ceres ANNOT ID no. 553243 (SEQ ID NO:338), Public GI ID no. 5514645 (SEQ ID NO:339), Ceres CLONE ID no. 464376 (SEQ ID NO:341), Public GI ID no. 1345643 (SEQ ID NO:346), Public GI ID no. 5832707 (SEQ ID NO:347), Public GI ID no. 81157968 (SEQ ID NO:348), Public GI ID no. 6118407 (SEQ ID NO:349), Public GI ID no. 5081817 (SEQ ID NO:351), Public GI ID no. 125556057 (SEQ ID NO:353), Public GI ID no. 115468946 (SEQ ID NO:354), Public GI ID no. 5915860 (SEQ ID NO:356), Public GI ID no. 6979544 (SEQ ID NO:358), Public GI ID no. 5832709 (SEQ ID NO:359), Public GI ID no. 6979542 (SEQ ID NO:360), Public GI ID no. 14278923 (SEQ ID NO:364), Public GI ID no. 81157970 (SEQ ID NO:365), Public GI ID no. 81157972 (SEQ ID NO:366), Public GI ID no. 169793907 (SEQ ID NO:2541), Public GI ID no. 84514153 (SEQ ID NO:2543), Public GI ID no. 184202209 (SEQ ID NO:2544), Ceres ANNOT ID no. 8459850 (SEQ ID NO:2546), Ceres ANNOT ID no. 8743452 (SEQ ID NO:2548), Public GI ID no. 157327290 (SEQ ID NO:2549), Public GI ID no. 148839039 (SEQ ID NO:2550), Public GI ID no. 197209782 (SEQ ID NO:2551), Public GI ID no. 171906244 (SEQ ID NO:2553).

FIG. 14 is an alignment of ME04753 (SEQ ID NO:368) with homologous and/or orthologous amino acid sequences GI No. 21388658 (SEQ ID NO:369), GI No. 4704605 (SEQ ID NO:371), GI No. 90704785 (SEQ ID NO:372), GI No. 115529229 (SEQ ID NO:373), GI No. 20152613 (SEQ ID NO:374), CeresClone: 1916226 (SEQ ID NO:376), CeresAnnot: 1460836 (SEQ ID NO:392), GI No. 83032218 (SEQ ID NO:420), GI No. 1346180 (SEQ ID NO:422), CeresClone: 621487 (SEQ ID NO:425), GI No. 6273331 (SEQ ID NO:433), GI No. 92874469 (SEQ ID NO:434), GI No. 1778374 (SEQ ID NO:436), GI No. 18076086 (SEQ ID NO:437), GI No. 2674201 (SEQ ID NO:438), GI No. 2267567 (SEQ ID NO:440), GI No. 544426 (SEQ ID NO:441), GI No. 6911144 (SEQ ID NO:444), GI No. 469071 (SEQ ID NO:447), GI No. 1934994 (SEQ ID NO:450), GI No. 82623423 (SEQ ID NO:451), GI No. 90265701 (SEQ ID NO:454), GI No. 544423 (SEQ ID NO:455), CeresClone: 1320097 (SEQ ID NO:458), CeresClone: 1469740 (SEQ ID NO:465), CeresClone: 1740834 (SEQ ID NO:473), GI No. 2226370 (SEQ ID NO:474), GI No. 27527723 (SEQ ID NO:475), CeresClone: 1762613 (SEQ ID NO:477), GI No. 125545195 (SEQ ID NO:488), GI No. 108710322 (SEQ ID NO:494), GI No. 34851124 (SEQ ID NO:504), GI No. 111162637 (SEQ ID NO:505), GI No. 7024451 (SEQ ID NO:506), and GI No. 1229138 (SEQ ID NO:507).

FIG. 15 is an alignment of ME04772 (SEQ ID NO:510) with homologous and/or orthologous amino acid sequences GI No. 38016521 (SEQ ID NO:511), CeresClone: 1895044 (SEQ ID NO:513), CeresAnnot: 1512198 (SEQ ID NO:517), CeresClone: 682503 (SEQ ID NO:521), CeresClone: 685324 (SEQ ID NO:523), CeresClone: 1384414 (SEQ ID NO:525), CeresClone: 1739919 (SEQ ID NO:527), CeresClone: 2002832 (SEQ ID NO:529), GI No. 125531563 (SEQ ID NO:530), and GI No. 115478344 (SEQ ID NO:531).

FIG. 16 is an alignment of ME04909 (SEQ ID NO:533) with homologous and/or orthologous amino acid sequences CeresClone: 1839156 (SEQ ID NO:535), GI No. 56605378 (SEQ ID NO:536), CeresAnnot: 1467946 (SEQ ID NO:538), GI No. 110931704 (SEQ ID NO:539), GI No. 92869601 (SEQ ID NO:542), GI No. 12005328 (SEQ ID NO:543), GI No. 119331596 (SEQ ID NO:546), GI No. 7705206 (SEQ ID NO:547), GI No. 18874263 (SEQ ID NO:548), CeresClone: 753605 (SEQ ID NO:550), CeresClone: 291733 (SEQ ID NO:552), and GI No. 21902114 (SEQ ID NO:553).

FIG. 17 is an alignment of ME05194 (SEQ ID NO:558) with homologous and/or orthologous amino acid sequences GI No. 400972 (SEQ ID NO:559), GI No. 81158002 (SEQ ID NO:560), CeresClone: 1834135 (SEQ ID NO:569), CeresAnnot: 1467218 (SEQ ID NO:571), CeresClone: 1104143 (SEQ ID NO:575), GI No. 87240745 (SEQ ID NO:576), GI No. 13161397 (SEQ ID NO:577), GI No. 18652400 (SEQ ID NO:578), GI No. 18652398 (SEQ ID NO:579), CeresClone: 778892 (SEQ ID NO:581), CeresClone: 222523 (SEQ ID NO:583), GI No. 82492267 (SEQ ID NO:584), GI No. 41393750 (SEQ ID NO:585), GI No. 4335857 (SEQ ID NO:586), CeresClone: 1776394 (SEQ ID NO:588), GI No. 125555681 (SEQ ID NO:589), GI No. 115468460 (SEQ ID NO:590), and GI No. 51980210 (SEQ ID NO:591).

FIG. 18 is an alignment of ME05267 (SEQ ID NO:593) with homologous and/or orthologous amino acid sequences CeresAnnot: 1511954 (SEQ ID NO:595), CeresClone: 560687 (SEQ ID NO:599), CeresClone: 579724 (SEQ ID NO:603), CeresClone: 286197 (SEQ ID NO:605), and GI No. 115489090 (SEQ ID NO:610).

FIG. 19 is an alignment of ME05300 (SEQ ID NO:613) with homologous and/or orthologous amino acid sequences CeresAnnot: 6431448 (SEQ ID NO:615), CeresClone: 969084 (SEQ ID NO:620), CeresClone: 471052 (SEQ ID NO:622), CeresClone: 733048 (SEQ ID NO:624), CeresClone: 1062332 (SEQ ID NO:626), CeresClone: 1743166 (SEQ ID NO:634), CeresClone: 1778589 (SEQ ID NO:638), GI No. 125548354 (SEQ ID NO:643), and GI No. 115458464 (SEQ ID NO:644).

FIG. 20 is an alignment of ME05341 (SEQ ID NO:646) with homologous and/or orthologous amino acid sequences CeresClone: 1808421 (SEQ ID NO:648), CeresAnnot: 1452653 (SEQ ID NO:656), CeresClone: 1660955 (SEQ ID NO:660), CeresClone: 1287179 (SEQ ID NO:668), CeresClone: 1770929 (SEQ ID NO:676), GI No. 125542421 (SEQ ID NO:679), GI No. 115450741 (SEQ ID NO:681), and CeresAnnot: 6063505 (SEQ ID NO:685).

FIG. 21 is an alignment of ME05392 (SEQ ID NO:687) with homologous and/or orthologous amino acid sequences CeresClone: 1841531 (SEQ ID NO:689), CeresAnnot: 1507382 (SEQ ID NO:691), CeresClone: 978410 (SEQ ID NO:699), CeresClone: 527314 (SEQ ID NO:703), GI No. 92893019 (SEQ ID NO:706), CeresClone: 638935 (SEQ ID NO:708), CeresClone: 1437744 (SEQ ID NO:712), CeresClone: 1728293 (SEQ ID NO:718), GI No. 125526460 (SEQ ID NO:721), GI No. 115463325 (SEQ ID NO:724), and GI No. 40642817 (SEQ ID NO:728).

FIG. 22 is an alignment of ME05429 (SEQ ID NO:730) with homologous and/or orthologous amino acid sequences CeresAnnot: 1539629 (SEQ ID NO:732), CeresClone: 682471 (SEQ ID NO:735), CeresClone: 729869 (SEQ ID NO:737), GI No. 115459766 (SEQ ID NO:738), and CeresAnnot: 6026765 (SEQ ID NO:742).

FIG. 23 is an alignment of ME05493 (SEQ ID NO:746) with homologous and/or orthologous amino acid sequences CeresAnnot: 1455092 (SEQ ID NO:748), GI No. 15229284 (SEQ ID NO:751), CeresClone: 961796 (SEQ ID NO:753), CeresClone: 706956 (SEQ ID NO:755), GI No. 87162911 (SEQ ID NO:758), CeresClone: 1061446 (SEQ ID NO:760), GI No. 125540686 (SEQ ID NO:761), GI No. 115447931 (SEQ ID NO:762), GI No. 20152976 (SEQ ID NO:763), and CeresAnnot: 6007280 (SEQ ID NO:765).

FIG. 24 is an alignment of ME05885 (SEQ ID NO:769) with homologous and/or orthologous amino acid sequences CeresClone: 1808741 (SEQ ID NO:771), CeresAnnot: 1437729 (SEQ ID NO:773), CeresClone: 952789 (SEQ ID NO:777), CeresClone: 724313 (SEQ ID NO:779), CeresClone: 791239 (SEQ ID NO:783), CeresClone: 208975 (SEQ ID NO:785), CeresClone: 1727075 (SEQ ID NO:789), and GI No. 115475611 (SEQ ID NO:790).

FIG. 25 is an alignment of ME07344 (SEQ ID NO:792) with homologous and/or orthologous amino acid sequences CeresClone: 1843695 (SEQ ID NO:794), GI No. 56605376 (SEQ ID NO:799), CeresAnnot: 1508502 (SEQ ID NO:801), CeresClone: 1239229 (SEQ ID NO:805), GI No. 92893962 (SEQ ID NO:808), CeresClone: 327364 (SEQ ID NO:810), CeresClone: 1820378 (SEQ ID NO:816), GI No. 125524748 (SEQ ID NO:819), and GI No. 115435036 (SEQ ID NO:821).

FIG. 26 is an alignment of ME07859 (SEQ ID NO:824) with homologous amino acid sequence Fragment_of_Ceres ANNOT ID no. 6007357 (SEQ ID NO:826), Fragment_of_Ceres CLONE ID no. 771707 (SEQ ID NO:1708), and Fragment_of_Ceres CLONE ID no. 1790436 (SEQ ID NO:1713).

FIG. 27 is an alignment of ME08464 (SEQ ID NO:828) with homologous and/or orthologous amino acid sequences CeresAnnot: 1499777 (SEQ ID NO:832), GI No. 22328730 (SEQ ID NO:837), GI No. 92886131 (SEQ ID NO:839), GI No. 559921 (SEQ ID NO:840), CeresClone: 910787 (SEQ ID NO:842), CeresClone: 1797432 (SEQ ID NO:844), GI No. 116310135 (SEQ ID NO:845), GI No. 38345464 (SEQ ID NO:847), and GI No. 90657544 (SEQ ID NO:850).

FIG. 28 is an alignment of ME11735 (SEQ ID NO:855) with homologous and/or orthologous amino acid sequences GI No. 35187445 (SEQ ID NO:856), CeresClone: 1798230 (SEQ ID NO:858), CeresAnnot: 1500963 (SEQ ID NO:862), CeresClone: 567542 (SEQ ID NO:868), CeresClone: 702251 (SEQ ID NO:870), CeresClone: 1606777 (SEQ ID NO:876), CeresClone: 1789146 (SEQ ID NO:878), GI No. 116309500 (SEQ ID NO:885), and GI No. 115446281 (SEQ ID NO:886).

FIG. 29 is an alignment of ME12910 (SEQ ID NO:891) with homologous and/or orthologous amino acid sequences CeresAnnot: 1466353 (SEQ ID NO:893), CeresClone: 519143 (SEQ ID NO:898), GI No. 2501497 (SEQ ID NO:901), GI No. 119394507 (SEQ ID NO:904), GI No. 62857206 (SEQ ID NO:905), CeresClone: 766529 (SEQ ID NO:907), GI No. 62857204 (SEQ ID NO:908), GI No. 125534279 (SEQ ID NO:911), GI No. 115485437 (SEQ ID NO:912), GI No. 23955910 (SEQ ID NO:913), and GI No. 22759895 (SEQ ID NO:915).

FIG. 30 is an alignment of ME12927 (SEQ ID NO:917) with homologous and/or orthologous amino acid sequences CeresAnnot: 1503548 (SEQ ID NO:919), CeresClone: 37778 (SEQ ID NO:921), CeresClone: 681297 (SEQ ID NO:923), CeresClone: 575835 (SEQ ID NO:925), CeresClone: 1714750 (SEQ ID NO:935), CeresClone: 1721907 (SEQ ID NO:937), and GI No. 115451923 (SEQ ID NO:940).

FIG. 31 is an alignment of ME12929 (SEQ ID NO:944) with homologous and/or orthologous amino acid sequences CeresAnnot: 1447562 (SEQ ID NO:946), GI No. 98962139 (SEQ ID NO:947), CeresClone: 641607 (SEQ ID NO:950), CeresClone: 1715150 (SEQ ID NO:962), CeresClone: 1873767 (SEQ ID NO:964), GI No. 115468306 (SEQ ID NO:967), and CeresAnnot: 6059980 (SEQ ID NO:972).

FIG. 32 is an alignment of ME12954 (SEQ ID NO:976) with homologous and/or orthologous amino acid sequences CeresClone: 957229 (SEQ ID NO:978) and CeresAnnot: 1496202 (SEQ ID NO:980).

FIG. 33 is an alignment of ME12970 (SEQ ID NO:982) with homologous and/or orthologous amino acid sequences CeresClone: 1935438 (SEQ ID NO:984), GI No. 117573664 (SEQ ID NO:985), GI No. 68349002 (SEQ ID NO:991), GI No. 68348998 (SEQ ID NO:992), CeresAnnot: 1497170 (SEQ ID NO:995), GI No. 15221718 (SEQ ID NO:996), GI No. 3860331 (SEQ ID NO:1001), CeresClone: 1075911 (SEQ ID NO:1003), GI No. 2920839 (SEQ ID NO:1008), CeresClone: 698452 (SEQ ID NO:1011), CeresClone: 2019456 (SEQ ID NO:1023), GI No. 90399071 (SEQ ID NO:1026), GI No. 115459588 (SEQ ID NO:1028), and GI No. 68349016 (SEQ ID NO:1032).

FIG. 34 is an alignment of ME13021 (SEQ ID NO:1054) with homologous and/or orthologous amino acid sequences GI No. 2493647 (SEQ ID NO:1055), CeresClone: 1924252 (SEQ ID NO:1057), GI No. 461736 (SEQ ID NO:1058), CeresAnnot: 1542060 (SEQ ID NO:1061), GI No. 15226314 (SEQ ID NO:1068), GI No. 464727 (SEQ ID NO:1072), CeresClone: 480644 (SEQ ID NO:1074), GI No. 124301264 (SEQ ID NO:1075), GI No. 1710807 (SEQ ID NO:1076), GI No. 110349923 (SEQ ID NO:1077), GI No. 1762130 (SEQ ID NO:1078), CeresClone: 706098 (SEQ ID NO:1080), GI No. 3790441 (SEQ ID NO:1083), CeresClone: 1795282 (SEQ ID NO:1085), GI No. 125546535 (SEQ ID NO:1086), GI No. 115488160 (SEQ ID NO:1088), GI No. 84468456 (SEQ ID NO:1092), GI No. 116060917 (SEQ ID NO:1095), and CeresAnnot: 6039555 (SEQ ID NO:1097).

FIG. 35 is an alignment of ME13064 (SEQ ID NO:1099) with homologous and/or orthologous amino acid sequences CeresAnnot: 1528508 (SEQ ID NO:1101), CeresClone: 9248 (SEQ ID NO:1103), GI No. 87240560 (SEQ ID NO:1105), GI No. 19453 (SEQ ID NO:1106), CeresClone: 1795329 (SEQ ID NO:1108), and GI No. 108862979 (SEQ ID NO:1109).

FIG. 36 is an alignment of ME13071 (SEQ ID NO:1112) with homologous and/or orthologous amino acid sequences GI No. 125541485 (SEQ ID NO:1113), and GI No. 115449245 (SEQ ID NO:1114).

FIG. 37 is an alignment of ME13087 (SEQ ID NO:1116) with homologous and/or orthologous amino acid sequences CeresClone: 100062822 (SEQ ID NO:1118), CeresAnnot: 1440025 (SEQ ID NO:1120), GI No. 15238538 (SEQ ID NO:1123), GI No. 69111473 (SEQ ID NO:1129), GI No. 92873741 (SEQ ID NO:1132), GI No. 55734106 (SEQ ID NO:1133), GI No. 2346974 (SEQ ID NO:1134), CeresClone: 569852 (SEQ ID NO:1136), CeresClone: 1715326 (SEQ ID NO:1138), CeresClone: 1608104 (SEQ ID NO:1140), GI No. 115456237 (SEQ ID NO:1141), GI No. 68655289 (SEQ ID NO:1143), GI No. 81022807 (SEQ ID NO:1144), GI No. 75706704 (SEQ ID NO:1145), and CeresAnnot: 6016055 (SEQ ID NO:1147).

FIG. 38 is an alignment of ME13107 (SEQ ID NO:1159) with homologous and/or orthologous amino acid sequences CeresClone: 1371824 (SEQ ID NO:1161), GI No. 22585 (SEQ ID NO:1162), GI No. 22208482 (SEQ ID NO:1163), and GI No. 16073 (SEQ ID NO:1164).

FIG. 39 is an alignment of ME13108 (SEQ ID NO:1166) with homologous and/or orthologous amino acid sequences GI No. 99109436 (SEQ ID NO:1167), CeresClone: 1627939 (SEQ ID NO:1169), CeresClone: 1840433 (SEQ ID NO:1171), CeresAnnot: 1524198 (SEQ ID NO:1173), CeresClone: 1650 (SEQ ID NO:1175), CeresClone: 691979 (SEQ ID NO:1177), GI No. 92876897 (SEQ ID NO:1180), CeresClone: 1774130 (SEQ ID NO:1182), and GI No. 115450018 (SEQ ID NO:1183).

FIG. 40 is an alignment of ME13110 (SEQ ID NO:1185) with homologous and/or orthologous amino acid sequences CeresClone: 737317 (SEQ ID NO:1187), CeresClone: 1880853 (SEQ ID NO:1189), GI No. 125558381 (SEQ ID NO:1190), and GI No. 115472157 (SEQ ID NO:1191).

FIG. 41 is an alignment of ME13125 (SEQ ID NO:1194) with homologous and/or orthologous amino acid sequences CeresClone: 1938817 (SEQ ID NO:1196), CeresAnnot: 1457245 (SEQ ID NO:1200), CeresClone: 577910 (SEQ ID NO:1202), Public PUBLICCLONE ID no. 100736184 (SEQ ID NO:1203), GI No. 125553355 (SEQ ID NO:1204), and GI No. 5091600 (SEQ ID NO:1205).

FIG. 42 is an alignment of ME13149 (SEQ ID NO:1210) with homologous and/or orthologous amino acid sequences GI No. 1703374 (SEQ ID NO:1211), CeresClone: 1846330 (SEQ ID NO:1213), GI No. 29124979 (SEQ ID NO:1216), CeresAnnot: 1531725 (SEQ ID NO:1218), GI No. 3334321 (SEQ ID NO:1229), CeresClone: 571410 (SEQ ID NO:1232), GI No. 39653273 (SEQ ID NO:1233), GI No. 92875403 (SEQ ID NO:1234), GI No. 11131026 (SEQ ID NO:1235), GI No. 77812440 (SEQ ID NO:1236), GI No. 89475524 (SEQ ID NO:1238), GI No. 3182919 (SEQ ID NO:1239), GI No. 7643794 (SEQ ID NO:1240), GI No. 1710851 (SEQ ID NO:1241), GI No. 115501471 (SEQ ID NO:1242), GI No. 77999251 (SEQ ID NO:1243), GI No. 3450893 (SEQ ID NO:1249), CeresClone: 704589 (SEQ ID NO:1251), CeresClone: 1384151 (SEQ ID NO:1253), CeresClone: 1713894 (SEQ ID NO:1259), GI No. 125560752 (SEQ ID NO:1264), GI No. 115475543 (SEQ ID NO:1265), GI No. 3182922 (SEQ ID NO:1267), GI No. 145353078 (SEQ ID NO:1268), GI No. 11131023 (SEQ ID NO:1269), GI No. 47026845 (SEQ ID NO:1270), and GI No. 38353642 (SEQ ID NO:1272).

FIG. 43 is an alignment of ME13151 (SEQ ID NO:1274) with homologous and/or orthologous amino acid sequences CeresClone: 1884601 (SEQ ID NO:1276), CeresAnnot: 1445717 (SEQ ID NO:1280), CeresClone: 527903 (SEQ ID NO:1284), GI No. 92891722 (SEQ ID NO:1285), CeresClone: 790881 (SEQ ID NO:1287), CeresClone: 299417 (SEQ ID NO:1289), CeresClone: 1993894 (SEQ ID NO:1291), GI No. 125539547 (SEQ ID NO:1294), GI No. 48716424 (SEQ ID NO:1295), GI No. 84468278 (SEQ ID NO:1297), and CeresAnnot: 6036303 (SEQ ID NO:1300).

FIG. 44 is an alignment of ME13153 (SEQ ID NO:1302) with homologous and/or orthologous amino acid sequences GI No. 70609690 (SEQ ID NO:1303), CeresClone: 1927524 (SEQ ID NO:1305), CeresAnnot: 1467310 (SEQ ID NO:1311), GI No. 45935270 (SEQ ID NO:1313), CeresClone: 718446 (SEQ ID NO:1317), GI No. 92875133 (SEQ ID NO:1318), GI No. 1706318 (SEQ ID NO:1319), GI No. 3252856 (SEQ ID NO:1320), GI No. 1169238 (SEQ ID NO:1326), GI No. 31296711 (SEQ ID NO:1327), CeresClone: 1468893 (SEQ ID NO:1330), GI No. 51587340 (SEQ ID NO:1331), CeresClone: 1796201 (SEQ ID NO:1333), GI No. 125543034 (SEQ ID NO:1334), GI No. 115476804 (SEQ ID NO:1336), GI No. 75268060 (SEQ ID NO:1339), and GI No. 75268007 (SEQ ID NO:1340).

FIG. 45 is an alignment of ME13177 (SEQ ID NO:1342) with homologous and/or orthologous amino acid sequences CeresAnnot: 1443786 (SEQ ID NO:1346), GI No. 15239172 (SEQ ID NO:1355), GI No. 562190 (SEQ ID NO:1363), GI No. 83032266 (SEQ ID NO:1364), CeresClone: 602910 (SEQ ID NO:1366), GI No. 7242793 (SEQ ID NO:1370), GI No. 116167 (SEQ ID NO:1371), GI No. 2190259 (SEQ ID NO:1372), GI No. 5420278 (SEQ ID NO:1373), GI No. 1064931 (SEQ ID NO:1374), GI No. 6093215 (SEQ ID NO:1377), GI No. 461726 (SEQ ID NO:1378), GI No. 89111295 (SEQ ID NO:1379), GI No. 82949283 (SEQ ID NO:1380), GI No. 125537180 (SEQ ID NO:1381), GI No. 115489300 (SEQ ID NO:1382), and GI No. 55978000 (SEQ ID NO:1383).

FIG. 46 is an alignment of ME13200 (SEQ ID NO:1385) with homologous and/or orthologous amino acid sequences CeresAnnot: 1503394 (SEQ ID NO:1387), GI No. 4914437 (SEQ ID NO:1390), CeresClone: 638126 (SEQ ID NO:1393), GI No. 124360540 (SEQ ID NO:1394), GI No. 7981380 (SEQ ID NO:1395), GI No. 118137433 (SEQ ID NO:1396), CeresClone: 1723374 (SEQ ID NO:1398), CeresClone: 1785379 (SEQ ID NO:1400), GI No. 125553354 (SEQ ID NO:1401), GI No. 115471859 (SEQ ID NO:1404), and CeresAnnot: 6040771 (SEQ ID NO:1407).

FIG. 47 is an alignment of ME13204 (SEQ ID NO:1409) with homologous and/or orthologous amino acid sequences CeresClone: 1939206 (SEQ ID NO:1413), CeresAnnot: 1453316 (SEQ ID NO:1415), GI No. 79319075 (SEQ ID NO:1418), GI No. 124359953 (SEQ ID NO:1419), CeresClone: 891431 (SEQ ID NO:1421), GI No. 125536578 (SEQ ID NO:1424), and GI No. 20270065 (SEQ ID NO:1425).

FIG. 48 is an alignment of ME14649 (SEQ ID NO:1428) with homologous and/or orthologous amino acid sequences CeresClone: 1978733 (SEQ ID NO:1430), CeresAnnot: 1476165 (SEQ ID NO:1432), CeresClone: 871529 (SEQ ID NO:1436), CeresClone: 1043344 (SEQ ID NO:1439), CeresClone: 786542 (SEQ ID NO:1442), CeresClone: 346115 (SEQ ID NO:1444), CeresClone: 1821683 (SEQ ID NO:1452), GI No. 125533171 (SEQ ID NO:1453), and GI No. 77553492 (SEQ ID NO:1457)

FIG. 49 is an alignment of ME16546 (SEQ ID NO:1463) with homologous and/or orthologous amino acid sequences CeresAnnot: 1444102 (SEQ ID NO:1465), CeresClone: 582439 (SEQ ID NO:1471), CeresClone: 579953 (SEQ ID NO:1473), GI No. 125539335 (SEQ ID NO:1474), and GI No. 115445987 (SEQ ID NO:1476).

FIG. 50 is an alignment of ME17567 (SEQ ID NO:1491) with homologous and/or orthologous amino acid sequences CeresClone: 1895876 (SEQ ID NO:1493), CeresAnnot: 1464522 (SEQ ID NO:1495), CeresClone: 968434 (SEQ ID NO:1499), CeresClone: 686479 (SEQ ID NO:1501), CeresClone: 1564962 (SEQ ID NO:1503), GI No. 125549699 (SEQ ID NO:1504), GI No. 125591612 (SEQ ID NO:1505), and CeresAnnot: 6006969 (SEQ ID NO:1508).

FIG. 51 is an alignment of ME17932 (SEQ ID NO:1510) with homologous and/or orthologous amino acid sequences CeresClone: 1842178 (SEQ ID NO:1512), CeresAnnot: 1475265 (SEQ ID NO:1516) and CeresClone: 1044646 (SEQ ID NO:1520).

FIG. 52 is an alignment of ME17936 (SEQ ID NO:1525) with homologous and/or orthologous amino acid sequences CeresAnnot: 1454324 (SEQ ID NO:1527), CeresClone: 1652842 (SEQ ID NO:1534), and GI No. 75214620 (SEQ ID NO:1535).

FIG. 53 is an alignment of ME18275 (SEQ ID NO:1537) with homologous and/or orthologous amino acid sequences CeresAnnot: 1514086 (SEQ ID NO:1539), CeresClone: 1087909 (SEQ ID NO:1543), CeresClone: 1359070 (SEQ ID NO:1545), GI No. 92880913 (SEQ ID NO:1548), CeresClone: 932449 (SEQ ID NO:1550), and CeresClone: 1788695 (SEQ ID NO:1552).

FIG. 54 is an alignment of ME18924 (SEQ ID NO:1554) with homologous and/or orthologous amino acid sequences GI No. 82469976 (SEQ ID NO:1555), CeresAnnot: 1533704 (SEQ ID NO:1563), CeresClone: 524404 (SEQ ID NO:1565), CeresClone: 846541 (SEQ ID NO:1567), CeresClone: 1769321 (SEQ ID NO:1571), GI No. 125528559 (SEQ ID NO:1572), GI No. 125572823 (SEQ ID NO:1574), and GI No. 84453208 (SEQ ID NO:1575).

FIG. 55 is an alignment of ME19182 (SEQ ID NO:1577) with homologous and/or orthologous amino acid sequences GI No. 4033417 (SEQ ID NO:1040), GI No. 5669924 (SEQ ID NO:1041), GI No. 40642617 (SEQ ID NO:1440), GI No. 90399018 (SEQ ID NO:1485), GI No. 115464117 (SEQ ID NO:1487), GI No. 75164812 (SEQ ID NO:1578), CeresClone: 1794223 (SEQ ID NO:1580), CeresAnnot: 1471422 (SEQ ID NO:1590), CeresClone: 968096 (SEQ ID NO:1607), GI No. 6752884 (SEQ ID NO:1608), GI No. 47775656 (SEQ ID NO:1609), CeresClone: 1020799 (SEQ ID NO:1611), GI No. 87240865 (SEQ ID NO:1622), GI No. 2500047 (SEQ ID NO:1623), CeresClone: 705340 (SEQ ID NO:1627), CeresClone: 1430456 (SEQ ID NO:1637), GI No. 84619270 (SEQ ID NO:1648), and CeresClone: 1821143 (SEQ ID NO:1651).

FIG. 56 is an alignment of ME20628 (SEQ ID NO:1437) with homologous and/or orthologous amino acid sequences GI No. 113367236 (SEQ ID NO:173), GI No. 115477615 (SEQ ID NO:212), GI No. 125542223 (SEQ ID NO:361), GI No. 1838976 (SEQ ID NO:421), CeresClone: 1547185 (SEQ ID NO:443), CeresAnnot: 1450452 (SEQ ID NO:740), and GI No. 92870675 (SEQ ID NO:1461).

FIG. 57 is an alignment of ME01821 (SEQ ID NO:97) with homologous and/or orthologous amino acid sequences Public GI ID no. 167480754 (SEQ ID NO:2013) and Public GI ID no. 83830869 (SEQ ID NO:2015).

DETAILED DESCRIPTION

The invention provides methods and materials related to modulating low-nitrogen tolerance levels in plants. In some embodiments, the plants may also have modulated levels of low-nitrogen tolerance. The methods can include transforming a plant cell with a nucleic acid encoding a low nitrogen tolerance-modulating polypeptide, wherein expression of the polypeptide results in a modulated level of low-nitrogen tolerance. Plant cells produced using such methods can be grown to produce plants having an increased tolerance to conditions with limiting exogenous nitrogen sources. Such plants can be used for the production of higher yields and biomasses with existing fertilizer inputs, and/or enable existing yields and biomass of crops to be obtained with lower fertilizer input, or better yields and biomasses on soils of poorer quality.

I. Definitions

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Low Nitrogen Conditions" as used herein refers to nitrogen concentrations which lead to nitrogen deficiency symptoms such as pale green leaf color, chlorosis and reduced growth and vigor. Typically, low nitrogen conditions lead to a reduction of at least 20%, 25%, 30%, 35%, 40%, 45%, 50%, 60%, 70%, 80% or 90% in growth and/or vigor.

"Modulation" of the level of low-nitrogen tolerance refers to the change in the level of tolerance of a plant to limiting exogenous nitrogen sources that is observed as a result of expression of, or transcription from, an exogenous nucleic acid in a plant cell. The change in low-nitrogen tolerance level is measured by changes in plant size and greenness as well as greater photosynthesis efficiency, relative to the corresponding level in control plants in an environment with limiting nitrogen supply.

"Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al. (1989) *The Plant Cell,* 1:977-984.

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. Polypeptides

Polypeptides described herein include low nitrogen tolerance-modulating polypeptides. Low nitrogen tolerance-modulating polypeptides can be effective to modulate low-nitrogen tolerance levels when expressed in a plant or plant cell. Such polypeptides typically contain at least one domain indicative of low nitrogen tolerance-modulating polypeptides, as described in more detail herein. Low nitrogen tolerance-modulating polypeptides typically have an HMM bit score that is greater than 20, as described in more detail herein. In some embodiments, low nitrogen tolerance-modulating polypeptides have greater than 80% identity to SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577, as described in more detail herein.

A. Domains Indicative of Low Nitrogen Tolerance-Modulating Polypeptides

A low nitrogen tolerance-modulating polypeptide can contain a P450 domain, which is characteristic of polypeptides belonging to the Cytochrome P450 superfamily. Cytochrome P450s are haem-thiolate proteins involved in the oxidative degradation of various compounds. They are particularly well known for their role in the degradation of environmental toxins and mutagens. In plants, these proteins are important for the biosynthesis of several compounds such as hormones, defensive compounds and fatty acids. Sequence conservation is relatively low within the family—there are only 3 absolutely conserved residues—but their general topography and structural fold are highly conserved. The conserved core is composed of a coil termed the 'meander', a four-helix bundle, helices J and K, and two sets of beta-sheets. These constitute the haem-binding loop, the proton-transfer groove and the conserved EXXR motif in helix K. While prokaryotic P450s are soluble proteins, most eukaryotic P450s are associated with microsomal membranes. Their general enzymatic function is to catalyse regiospecific and stereospecific oxidation of non-activated hydrocarbons at physiological temperatures. SEQ ID NO:3 and SEQ ID NO:332 set forth the amino acid sequence of *Arabidopsis* clones, identified herein as ME00919 (SEQ ID NO:3) and ME04587 (SEQ ID NO:332) respectively, that are predicted to encode polypeptides containing a Cytochrome P450 domain.

A low nitrogen tolerance-modulating polypeptide can contain a zf-Dof domain, which is conserved in several DNA-binding proteins of higher plants. Dof domain is a zinc finger DNA-binding domain that shows resemblance to the Cys2 zinc finger, although it has a longer putative loop where an extra Cys residue is typically conserved. The motif is also present in SEQ ID NO:49, which sets forth the amino acid sequence of an *Arabidopsis* clone, identified herein as Ceres ME01312 (SEQ ID NO:49), that is predicted to encode a polypeptide containing a zf-Dof domain.

A low nitrogen tolerance-modulating polypeptide can contain an Aminotran_3 domain characteristic of polypeptides belonging to the aminotransferase Class-III family. Aminotransferases share certain mechanistic features with other pyridoxalphosphate-dependent enzymes, such as the covalent binding of the pyridoxalphosphate group to a lysine residue. Class-III aminotransferases include acetylornithine aminotransferase, which catalyzes the transfer of an amino group from acetylornithine to alpha-ketoglutarate, yielding N-acetyl-glutamic-5-semi-aldehyde and glutamic acid; ornithine aminotransferase, which catalyzes the transfer of an amino group from ornithine to alpha-ketoglutarate, yielding glutamic-5-semi-aldehyde and glutamic acid; omega-amino acid-pyruvate aminotransferase, which catalyzes transamination between a variety of omega-amino acids, mono- and diamines, and pyruvate; 4-aminobutyrate aminotransferase; GABA transaminase, which catalyzes the transfer of an amino group from GABA to alpha-ketoglutarate, yielding succinate semialdehyde and glutamic acid; DAPA aminotransferase, a bacterial enzyme (bioA), which catalyzes an intermediate step in the biosynthesis of biotin, the transamination of 7-keto-8-aminopelargonic acid to form 7,8-diaminopelargonic acid; 2,2-dialkylglycine decarboxylase, a *Burkholderia cepacia* (*Pseudomonas cepacia*) enzyme (dgdA) that catalyzes the decarboxylating amino transfer of 2,2-dialkylglycine and pyruvate to dialkyl ketone, alanine and carbon dioxide; glutamate-1-semialdehyde aminotransferase (GSA); *Bacillus subtilis* aminotransferases yhxA and yodT; *Haemophilus influenzae* aminotransferase HI0949; and *Caenorhabditis elegans* aminotransferase. On the basis of sequence similarity, these various enzymes can be grouped into subfamilies. The aminotran_3 domain is also present in SEQ ID NO:77, which set forth the amino acid sequences of *Arabidopsis* clone, identified herein as Ceres ME01463 (SEQ ID NO:77), that is predicted to encode polypeptides containing an aminotran_3 domain.

A low nitrogen tolerance-modulating polypeptide can contain a linker histone domain characteristic of polypeptides belonging to the linker histone H1 and H5 family. Linker histone H1 is an essential component of chromatin structure. H1 links nucleosomes into higher order structures. Histone H5 performs the same function as histone H1, and replaces H1 in certain cells. The structure of GH5, the globular domain of the linker histone H5 fold is similar to the DNA-binding domain of the catabolite gene activator protein, CAP, thus providing a possible model for the binding of GH5 to DNA. The domain is also present in SEQ ID NO:100, which sets forth the amino acid sequence of an *Arabidopsis* clone, identified herein as Ceres ME01910 (SEQ ID NO:100), that is predicted to encode a polypeptide containing a linker histone domain.

A low nitrogen tolerance-modulating polypeptide can contain a zf-C3HC4 domain, which is predicted to be characteristic of proteins belonging to the C3HC4 type zinc-finger (RING finger) protein family. The C3HC4 type zinc-finger (RING finger) is a cysteine-rich domain of approximately 40 to 60 residues that coordinates two zinc ions, and is probably involved in mediating protein-protein interactions. Members of the C3HC4 type zinc-finger (RING finger) protein family contain the loosely conserved sequence: C-X2-C-X(9-39)-C-X(1-3)-H-X(2-3)-C-X2-C-X (4-48)-C-X2-C where X is any amino acid. The domain is also present in SEQ ID NOs:166, 746, 976, 1428, which set forth the amino acid sequences of *Arabidopsis* clones, identified herein as Ceres ME02603 (SEQ ID NO:166), ME05493 (SEQ ID NO:746), ME12954 (SEQ ID NO:976), ME14649 (SEQ ID NO:1428) respectively, that are predicted to encode polypeptides containing a zf-C3HC4 domain.

A low nitrogen tolerance-modulating polypeptide can contain a Gal_Lectin domain characteristic of a galactose binding lectin domain protein. SEQ ID NO:208 sets forth the amino acid sequence of an *Arabidopsis* clone, identified herein as Ceres ME02801 (SEQ ID NO:208), that is predicted to encode a polypeptide containing a galactose binding lectin domain.

A low nitrogen tolerance-modulating polypeptide can contain a TRP_1 domain characteristic of tetratricopeptide repeat (TPR) domain protein. The tetratricopeptide repeat is a structural motif present in a wide range of proteins identified in various different organisms, ranging from bacteria to humans. It mediates protein-protein interactions and the assembly of multiprotein complexes. Sequence alignment of the TPR domains reveals a consensus sequence defined by a pattern of small and large amino acids. Proteins containing TPRs are involved in a variety of biological processes, such as cell cycle regulation, transcriptional control, mitochondrial and peroxisomal protein transport, neurogenesis and protein folding. The X-ray structure of a domain containing three TPRs from protein phosphatase 5 revealed that TPR adopts a helixturnhelix arrangement, with adjacent TPR motifs packing in a parallel fashion, resulting in a spiral of repeating anti-parallel alpha-helices. The two helices are denoted helix A and helix B. The packing angle between helix A and helix B is ~24° within a single TPR and generates a right-handed superhelical shape. Helix A interacts with helix B and with helix A' of the next TPR. Two protein surfaces are generated: the inner concave surface is contributed to mainly by residue on helices A, and the other surface presents residues from both helices A and B.

A low nitrogen tolerance-modulating polypeptide can contain a TRP_2 tetratricopeptide repeat domain, which is predicted to be characteristic of scaffold-proteins in multiprotein complexes. The TPR_2 domain consists of approximately 34-amino-acid motif with a loose consensus and is present, usually as multiple tandem repeats, in proteins with many cellular functions, including mitosis, transcription, protein transport, and development. Structural analysis of the TPR-2 domain demonstrates that it forms two α-helical regions separated by a turn, such that apposed bulky and small side chains form a "knob and hole" structure. In general, the hydrophobic surface of this structure mediates protein-protein interactions between TPR- and non-TPR-containing proteins.

SEQ ID NO:234 sets forth the amino acid sequence of *Arabidopsis* clone, identified herein as Ceres ME04204 (SEQ ID NO:234), that is predicted to encode a polypeptide containing a TRP_1 tetratricopeptide repeat domain and a TRP_2 tetratricopeptide repeat domain. SEQ ID NO:1510 sets forth the amino acid sequence of *Arabidopsis* clone, identified herein as Ceres ME17932 (SEQ ID NO:1510), that is predicted to encode a polypeptide containing a TRP_2 tetratricopeptide repeat domain.

A low nitrogen tolerance-modulating polypeptide can contain a zf-AN1 domain characteristic of polypeptides belonging to the AN1-like Zinc finger domain protein family. The AN1-like Zinc finger domain was first identified as a zinc finger at the C-terminus of An1 a ubiquitin-like protein in *Xenopus laevis*. The following pattern describes the zinc finger: C-X2-C-X(9-12)-C-X(1-2)-C-X4-C-X2-H-X5-H—X—C, where X can be any amino acid, and numbers in brackets indicate the number of residues.

A low nitrogen tolerance-modulating polypeptide can contain a zf-A20 domain, which is characteristic of A20— (an inhibitor of cell death)-like zinc fingers. In animals, A20-like zinc fingers are believed to mediate self-association in A20. These fingers also mediate IL-1-induced NF-kappa B activation. SEQ ID NO: 246 sets forth the amino acid sequence of *Arabidopsis* clone, identified herein as Ceres ME04477 (SEQ ID NO:246), that is predicted to encode a polypeptide containing an AN1-like Zinc finger domain and zf-A20 domain.

A low nitrogen tolerance-modulating polypeptide can contain an Aa_trans domain, or transmembrane amino acid transporter domain, which is predicted to be characteristic of amino acid transporters and amino acid permeases. The domain is also present in SEQ ID NO:300, which sets forth the amino acid sequence of an *Arabidopsis* clone, identified herein as Ceres ME04507 (SEQ ID NO:300), that is predicted to encode a polypeptide containing an transmembrane amino acid transporter domain.

A low nitrogen tolerance-modulating polypeptide can contain an RNA recognition motif (as known as RRM_1, RRM, RBD, or RNP domain), which is characteristic of polypeptides belonging to the single strand RNA-binding protein superfamily. RRM proteins have a variety of RNA binding preferences and functions, and include heterogeneous nuclear ribonucleoproteins (hnRNPs), proteins implicated in regulation of alternative splicing, protein components of small nuclear ribonucleoproteins, and proteins that regulate RNA stability and translation. The RRM in heterodimeric splicing factor U2 snRNP auxiliary factor (U2AF) appears to have two RRM-like domains with specialized features for protein recognition. The motif also appears in a few single stranded DNA binding proteins. The typical RRM consists of four anti-parallel beta-strands and two alpha-helices arranged in a beta-alpha-beta-beta-alpha-beta fold with side chains that stack with RNA bases. Specificity of RNA binding is determined by multiple contacts with surrounding amino acids. A third helix is present during RNA binding in some cases. The motif is also present in SEQ ID NO:368 and SEQ ID NO:1274, which set forth the amino acid sequences of *Arabidopsis* clones, identified herein as Ceres ME04753 (SEQ ID NO:368) and ME13151 (SEQ ID NO:1274) respectively, that are predicted to encode polypeptides containing an RNA recognition motif.

A low nitrogen tolerance-modulating polypeptide can contain an NTF2 domain characteristic of a nuclear transport factor 2 (NTF2) polypeptide. NTF2 is a homodimer of approximately 14 kDa subunits which stimulates efficient nuclear import of a cargo protein. NTF2 binds to both RanGDP and FxFG repeat-containing nucleoporins. NTF2 binds to RanGDP sufficiently strongly for the complex to remain intact during transport through nucleopore complexes (NPCs), but the interaction between NTF2 and FxFG nucleoporins is much more transient, which would enable NTF2 to move through the NPC by hopping from one repeat to another. NTF2 folds into a cone with a deep hydrophobic cavity, the opening of which is surrounded by several negatively charged residues. RanGDP binds to NTF2 by inserting a conserved phenylalanine residue into the hydrophobic pocket of NTF2 and making electrostatic interactions with the conserved negatively charged residues that surround the cavity. A structurally similar domain appears in other nuclear import proteins. SEQ ID NO:1274, which sets forth the amino acid sequence of an *Arabidopsis* clone, identified herein as Ceres ME13151 (SEQ ID NO:1274), that is predicted to encode a polypeptide containing a NTF2 domain.

A low nitrogen tolerance-modulating polypeptide can contain a DUF1218 domain. SEQ ID NO:510, which sets forth the amino acid sequence of an *Arabidopsis* clone, identified herein as Ceres ME04772 (SEQ ID NO:510), that is predicted to encode a polypeptide containing a DUF1218 domain.

A low nitrogen tolerance-modulating polypeptide can contain a Myb-like DNA-binding domain characteristic of polypeptides belonging to a protein family whose members contain the DNA binding domains from Myb proteins, as well as the SANT domain family. SEQ ID NO:533, which sets forth the amino acid sequence of an *Arabidopsis* clone, identified herein as Ceres ME04909 (SEQ ID NO:533), that is predicted to encode a polypeptide containing a Myb-like DNA-binding domain.

A low nitrogen tolerance-modulating polypeptide can contain a FAD_binding_4 domain. This domain is predicted to be characteristic of polypeptides belonging to a family of enzymes that use FAD (flavin adenine dinucleotide) as a co-factor, most of the enzymes are similar to oxygen oxidoreductase, containing a covalently bound FAD group which is attached to a histidine via an 8-alpha-(N3-histidyl)-riboflavin linkage.

A low nitrogen tolerance-modulating polypeptide can contain a BBE domain, which is predicted to be characteristic of a berberine bridge and berberine bridge-like enzyme. BBE enzymes are typically involved in the biosynthesis of numerous isoquinoline alkaloids. They catalyse the transformation of the N-methyl group of (S)-reticuline into the C-8 berberine bridge carbon of (S)-scoulerine. SEQ ID NO:558 sets forth the amino acid sequence of an *Arabidopsis* clone, identified herein as Ceres ME05194 (SEQ ID NO:558), that is predicted to encode a polypeptide containing an FAD_binding_4 domain and a BBE domain.

A low nitrogen tolerance-modulating polypeptide can contain a prefoldin (PFD) domain characteristic of polypeptides belonging to the prefoldin subunit family. Prefoldin (PFD) is a chaperone that typically interacts with type II chaperonins, hetero-oligomers lacking an obligate co-chaperonin that are found in eukaryotes (chaperonin-containing T-complex polypeptide-1 (CCT)) and archaea. Eukaryotic PFD can typically bind both actin and tubulin co-translationally. The chaperone can then delivers the target protein to CCT, interacting with the chaperonin through the tips of the coiled coils. SEQ ID NO:593 sets forth the amino acid sequence of an *Arabidopsis* clone, identified herein as Ceres ME05267 (SEQ ID NO:593), that is predicted to encode a polypeptide containing a prefoldin domain.

A low nitrogen tolerance-modulating polypeptide can contain an HR-lesion domain characteristic of polypeptides belonging to a family of plant proteins can be associated with the hypersensitive response (HR) pathway of defense against plant pathogens. The domain is also present in SEQ ID NO: 646, which sets forth the amino acid sequence of an *Arabidopsis* clone, identified herein as Ceres ME05341 (SEQ ID NO: 646), that is predicted to encode a polypeptide containing an HR-lesion domain.

A low nitrogen tolerance-modulating polypeptide can contain a DUF538 domain. SEQ ID NO:687 sets forth the amino acid sequence of an *Arabidopsis* clone, identified herein as Ceres ME05392 (SEQ ID NO:687), that is predicted to encode a polypeptide containing a DUF538 domain.

A low nitrogen tolerance-modulating polypeptide can contain a zinc finger C-x8-C-x5-C-x3-H type domain (zf-CCCH), which is characteristic of polypeptides belonging to the zinc finger protein superfamily. Members of zinc finger domains proteins are thought to be involved in DNA-binding, and exist as different types. Proteins containing zinc finger domains of the C-x8-C-x5-C-x3-H type include zinc finger proteins from eukaryotes involved in cell cycle or growth phase-related regulation. It has been shown that different CCCH zinc finger proteins interact with the 3' untranslated region of various mRNA. SEQ ID NO:792 sets forth the amino acid sequence of an *Arabidopsis* clone, identified herein as Ceres ME07344 (SEQ ID NO:792), that is predicted to encode a polypeptide containing a zf-CCCH domain.

A low nitrogen tolerance-modulating polypeptide can contain a DUF246 domain. SEQ ID NO:828 sets forth the amino acid sequence of an *Arabidopsis* clone, identified herein as Ceres ME08464 (SEQ ID NO:828), that is predicted to encode a polypeptide containing a DUF246 domain.

A low nitrogen tolerance-modulating polypeptide can contain a C2 domain. The C2 domain is a Ca2+-dependent membrane-targeting module found in many cellular proteins involved in signal transduction or membrane trafficking. C2 domains are unique among membrane targeting domains in that they typically show wide range of lipid selectivity for the major components of cell membranes, including phosphatidylserine and phosphatidylcholine. SEQ ID NO:982 sets forth the amino acid sequence of an *Arabidopsis* clone, identified herein as Ceres ME12970 (SEQ ID NO:982), that is predicted to encode a polypeptide containing an C2 domain.

A low nitrogen tolerance-modulating polypeptide can contain a Cpn60_TCP1 domain characteristic of polypeptides belonging to the TCP-1/cpn60 chaperonin family. This family includes members from the HSP60 chaperone family and the TCP-1 (T-complex protein) family. Chaperonins, a subfamily of molecular chaperones, are typically essential for the correct folding and assembly of polypeptides into oligomeric structures. Chaperonins are typically found in abundance in prokaryotes, chloroplasts and mitochondria. They are typically required for normal cell growth, and are stress-induced, acting to stabilize or protect disassembled polypeptides under heat-shock conditions. SEQ ID NO: 1054 sets forth the amino acid sequence of an *Arabidopsis* clone, identified herein as Ceres ME13021 (SEQ ID NO: 1054), that is predicted to encode a polypeptide containing a Cpn60_TCP1 domain.

A low nitrogen tolerance-modulating polypeptide can contain a zf-C2H2 domain characteristic of a C2H2 zinc finger domain polypeptide. Zinc finger domains are nucleic acid-binding protein structures composed of 25 to 30 amino-acid residues including 2 conserved Cys and 2 conserved His residues in a C-2-C-12-H-3-H type motif. The 12 residues separating the second Cys and the first His are mainly polar and basic, implicating this region in particular in nucleic acid binding. They have the ability to bind to both RNA and DNA, and it has been suggested that the zinc finger may thus represent the original nucleic acid binding protein. It has also been suggested that a Zn-centered domain could be used in a protein interaction, e.g. in protein kinase C. Many classes of zinc fingers are characterized according to the number and positions of the histidine and cysteine residues involved in the zinc atom coordination. In C2H2 zinc finger class, the first pair of zinc coordinating residues are cysteines, while the second pair are histidines. The motif is also present in SEQ ID NO:1116, which sets forth the amino acid sequence of an *Arabidopsis* clone, identified herein as Ceres ME13087 (SEQ ID NO:1116), that is predicted to encode a polypeptide containing a zf-C2H2 domain.

A low nitrogen tolerance-modulating polypeptide can contain a zein domain characteristic of polypeptides belonging to the zein family of seed storage proteins. SEQ ID NO:1159, which sets forth the amino acid sequence of an *Arabidopsis* clone, identified herein as Ceres ME13107 (SEQ ID NO: 1159), that is predicted to encode a polypeptide containing a zein domain.

A low nitrogen tolerance-modulating polypeptide can contain a snf7 domain characteristic of polypeptides belonging to a family of eukaryotic proteins related to yeast SNF7. SEQ ID NO:1185 sets forth the amino acid sequence of an *Arabidopsis* clone, identified herein as Ceres ME13110 (SEQ ID NO:1185), that is predicted to encode a polypeptide containing a snf7 domain.

A low nitrogen tolerance-modulating polypeptide can contain an HhH-GPD domain characteristic of polypeptides belonging to the HhH-GPD base excision DNA repair protein superfamily. Members of the HhH-GPD base excision DNA repair protein superfamily contain helix-hairpin-helix and Gly/Pro rich loop followed by a conserved aspartate. This domain is found in a diverse range of structurally related DNA repair proteins. The domain is also present in SEQ ID NO:1194 sets forth the amino acid sequence of an *Arabidopsis* clone, identified herein as Ceres ME13125 (SEQ ID NO:1194), that is predicted to encode a polypeptide containing an HhH-GPD domain.

A low nitrogen tolerance-modulating polypeptide can contain an Arf domain characteristic of polypeptides belonging to the ADP-ribosylation factor family. The small ADP ribosylation factor (Arf) GTP-binding proteins are major regulators of vesicle biogenesis in intracellular traffic. They are the founding members of a growing family that includes Arl (Arf-like), Arp (Arf-related proteins) and the remotely related Sar (Secretion-associated and Ras-related) proteins. Arf proteins cycle between inactive GDP-bound and active GTP-bound forms that bind selectively to effectors. The classical structural GDP/GTP switch is characterized by conformational changes at the so-called switch 1 and switch 2 regions, which bind tightly to the gamma-phosphate of GTP but poorly or not at all to the GDP nucleotide. Structural studies of Arf1 and Arf6 have revealed that although these proteins feature the switch 1 and 2 conformational changes, they depart from other small GTP-binding proteins in that they use an additional, unique switch to propagate structural information from one side of the protein to the other. The GDP/GTP structural cycles of human Arf1 and Arf6 feature a unique conformational change that affects the beta2beta3 strands connecting switch 1 and switch 2 (inter-switch) and also the amphipathic helical N-terminus. SEQ ID NO: 1210 sets forth the amino acid sequence of an *Arabidopsis* clone, identified herein as Ceres ME13149 (SEQ ID NO:1210), that is predicted to encode a polypeptide containing an Arf domain.

A low nitrogen tolerance-modulating polypeptide can contain a Pyridoxal_deC domain characteristic of pyridoxal-dependent decarboxylase polypeptide. Pyridoxal-dependent decarboxylases typically share regions of sequence similarity, particularly in the vicinity of a conserved lysine residue, which provides the attachment site for the pyridoxal-phosphate (PLP) group. Pyridoxal phosphate is the active form of vitamin B6 (pyridoxine or pyridoxal). PLP is a versatile catalyst, acting as a coenzyme in a multitude of reactions, including decarboxylation, deamination and transamination. PLP-dependent enzymes, including pyridoxal-dependent decarboxylases, are involved in the biosynthesis of amino acids and amino acid-derived metabolites, but they are also found in the biosynthetic pathways of amino sugars and in the synthesis or catabolism of neurotransmitter. SEQ ID NO:1302 sets forth the amino acid sequence of an *Arabidopsis* clone, identified herein as Ceres ME13153 (SEQ ID NO:1302), that is predicted to encode a polypeptide containing a Pyridoxal_deC domain.

A low nitrogen tolerance-modulating polypeptide can contain a Cyclin_C domain, which is characteristic to the C-terminal domain of polypeptides belonging to the Cyclin family. Cyclins are eukaryotic proteins that play an active role in controlling nuclear cell division cycles, and regulate cyclin dependent kinases (CDKs). Cyclins, together with the p34 (cdc2) or cdk2 kinases, form the Maturation Promoting Factor (MPF). There are two main groups of cyclins, G1/S cyclins, which play a role in the control of the cell cycle at the G1/S (start) transition, and G2/M cyclins, which play a role in the control of the cell cycle at the G2/M (mitosis) transition. G2/M cyclins accumulate steadily during G2 and are abruptly destroyed as cells exit from mitosis (at the end of the M-phase). Cyclins typically contain two domains of similar all-alpha fold, of which this family corresponds with the C-terminal domain.

A low nitrogen tolerance-modulating polypeptide can contain a Cyclin_N domain, which defines the N-terminal domain of polypeptides belonging to the Cyclin family. SEQ ID NO: 1342 sets forth the amino acid sequence of an *Arabidopsis* clone, identified herein as Ceres ME13177 (SEQ ID NO: 1342), that is predicted to encode a polypeptide containing a Cyclin_C domain and a Cyclin_N domain A low nitrogen tolerance-modulating polypeptide can contain a DUF1442 domain. SEQ ID NO:1463, which sets forth the amino acid sequence of an *Arabidopsis* clone, identified herein as Ceres ME16546 (SEQ ID NO:1463), that is predicted to encode a polypeptide containing a DUF1442 domain.

A low nitrogen tolerance-modulating polypeptide can contain an HLH domain characteristic of polypeptides belonging to the Helix-loop-helix DNA-binding domain superfamily. Basic helix-loop-helix proteins (bHLH) are a group of eukaryotic transcription factors that can exert a determinative influence in a variety of developmental pathways. These transcription factors are characterized by a conserved bHLH domain that mediates specific dimerization. They can facilitate the conversion of inactive monomers to trans-activating dimers at appropriate stages of development. Members of this superfamily can be classified into discrete categories according to dimerization, DNA binding and expression characteristics. SEQ ID NO:1537 sets forth the amino acid sequence of an *Arabidopsis* clone, identified herein as Ceres ME18275 (SEQ ID NO:1537), that is predicted to encode a polypeptide containing an HLH domain.

A low nitrogen tolerance-modulating polypeptide can contain a CRAL_TRIO domain characteristic of the C-terminal of retinaldehyde/retinal-binding protein family. In animals, retinaldehyde/retinal-binding proteins may be functional components of the visual cycle. Cellular retinaldehyde-binding protein (CRALBP) may function as a substrate carrier protein that modulates interaction of these retinoids with visual cycle enzymes. The multidomain protein Trio can bind the LAR transmembrane tyrosine phosphatase, contains a protein kinase domain, and has separate rac-specific and rho-specific guanine nucleotide exchange factor domains. Trio is a multifunctional protein that can integrate and amplify signals involved in coordinating actin remodeling, which is necessary for cell migration and growth. Other members of the family are transfer proteins that include, guanine nucleotide exchange factor that may function as an effector of RAC1, phosphatidylinositol/phosphatidylcholine transfer protein that is required for the transport of secretory proteins from the Golgi complex and alpha-tocopherol transfer protein that enhances the transfer of the ligand between separate membranes.

A low nitrogen tolerance-modulating polypeptide can contain a CRAL_TRIO_N which defines the N-terminal of retinaldehyde/retinal-binding protein family.

A low nitrogen tolerance-modulating polypeptide can contain an EMP24_GP25L domain characteristic of polypeptides belonging to the emp24/gp25L/p24 family/GOLD gene family. Members of this family are implicated in bringing cargo forward from the ER and binding to coat proteins by their cytoplasmic domains. This domain corresponds closely to the beta-strand rich GOLD domain. The GOLD domain is often found combined with lipid- or membrane-association domains. p24 proteins are major membrane components of COPI- and COPII-coated vesicles and are implicated in cargo selectivity of ER to Golgi transport. Multiple members of the p24 family are found in all eukaryotes, from yeast to mammals. Members of the p24 family are type I membrane proteins with a signal peptide at the amino terminus, a lumenal coiled-coil (extracytosolic) domain, a single transmembrane domain with conserved amino acids, and a short cytoplasmic tail. They may be grouped into at least three subfamilies based on primary sequence. One subfamily comprises yeast Emp24p and mammalian p24A. Another subfamily comprises yeast Erv25p and mammalian Tmp21, and the third subfamily comprises mammalian gp25L proteins. SEQ ID NO:1554 sets forth the amino acid sequence of an *Arabidopsis* clone, identified herein as Ceres ME18924 (SEQ ID NO:1554), that is predicted to encode a polypeptide containing a CRAL_TRIO domain, a CRAL_TRIO_N domain, and a EMP24_GP25L domain.

A low nitrogen tolerance-modulating polypeptide can contain a Pyrophosphatase domain, which is predicted to be characteristic of an inorganic pyrophosphatase (PPase). PPase is the enzyme responsible for the hydrolysis of pyrophosphate (PPi) which is formed principally as the product of the many biosynthetic reactions that utilize ATP. PPases may require the presence of divalent metal cations, with magnesium conferring the highest activity. Among other residues, a lysine has been postulated to be part of or close to the active site. The sequences of PPases share some regions of similarities, among which is a region that contains three conserved aspartates that are involved in the binding of cations. SEQ ID NO:1577 sets forth the amino acid sequence of an *Arabidopsis* clone, identified herein as Ceres ME19182 (SEQ ID NO:1577), that is predicted to encode a polypeptide containing a Pyrophosphatase domain.

A low nitrogen tolerance-modulating polypeptide can contain a bZIP_1 domain characteristic of polypeptides belonging to the superfamily of basic ZIP transcription factors. Members of the eukaryotic bZIP transcription factor superfamily contain a basic region mediating sequence-specific DNA-binding followed by a leucine zipper region required for dimerization. SEQ ID NO: 1437 sets forth the amino acid sequence of an *Arabidopsis* clone, identified herein as Ceres ME20628 (SEQ ID NO: 1437), that is predicted to encode a polypeptide containing a bZIP_1 domain.

B. Functional Homologs Identified by Reciprocal BLAST

In some embodiments, one or more functional homologs of a reference low nitrogen tolerance-modulating polypeptide defined by one or more of the Pfam descriptions indicated above are suitable for use as low nitrogen tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a low nitrogen tolerance-modulating polypeptide, or by combining domains from the coding sequences for different naturally-occurring low nitrogen tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of low nitrogen tolerance-modulating polypeptides. Sequence analysis can involve BLAST, Reciprocal BLAST, or PSI-BLAST analysis of nonredundant databases using a low nitrogen tolerance-modulating polypeptide amino acid sequence as the reference sequence Amino acid sequence is, in some instances, deduced from the nucleotide sequence. Those polypeptides in the database that have greater than 20% sequence identity are candidates for further evaluation for suitability as a low nitrogen tolerance-modulating polypeptide Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in low nitrogen tolerance-modulating polypeptides, e.g., conserved functional domains.

Conserved regions can be identified by locating a region within the primary amino acid sequence of a low nitrogen tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. A description of the information included at the Pfam database is described in Sonnhammer et al. (1998) *Nucl. Acids Res.*, 26:320-322; Sonnhammer et al. (1997) *Proteins*, 28:405-420; and Bateman et al. (1999) *Nucl. Acids Res.*, 27:260-262. Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 20% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 1:
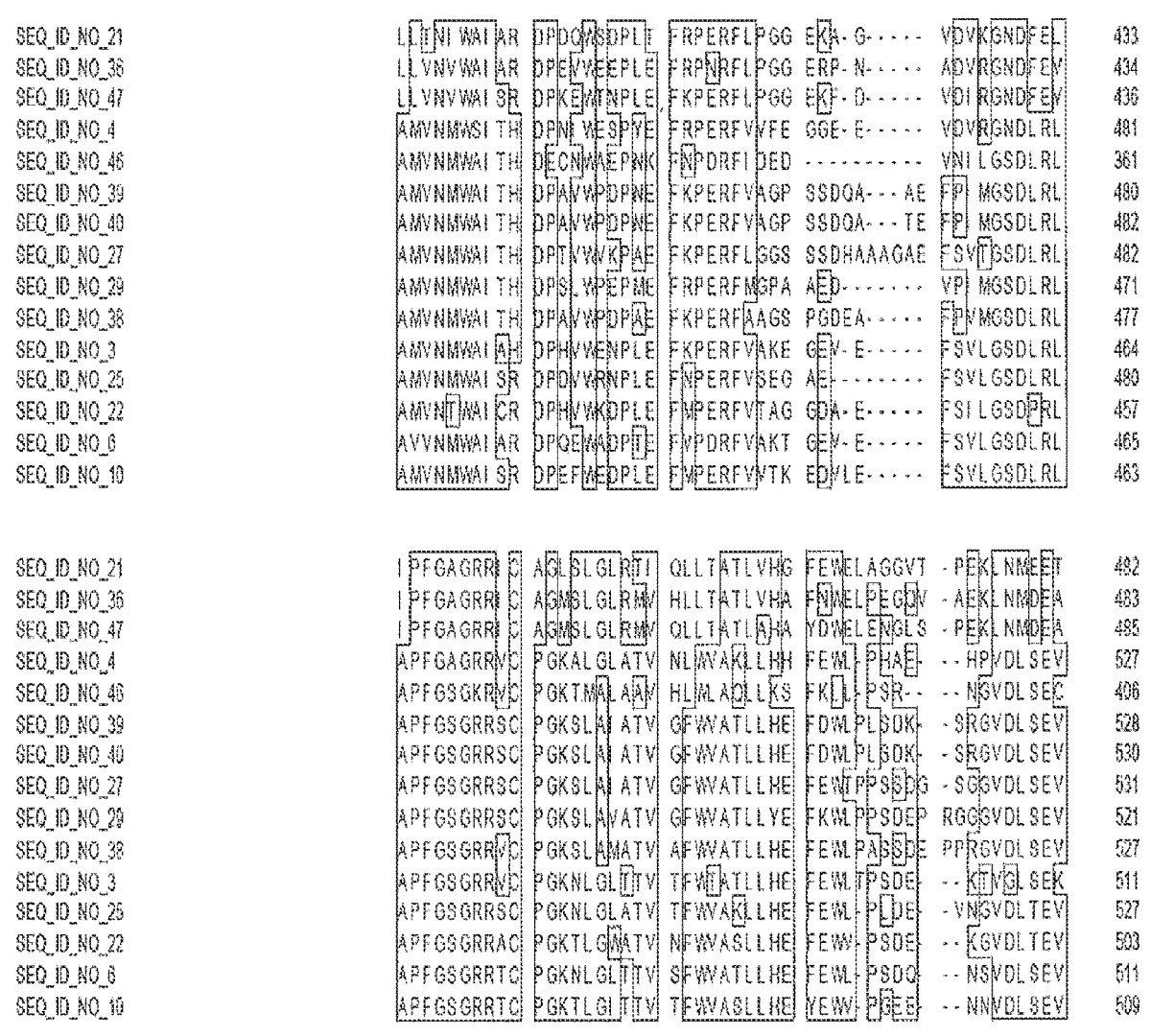

Examples of amino acid sequences of functional homologs of the polypeptide set forth in SEQ ID NO:3 are provided in FIG. 1 and in the Sequence Listing. Such functional homologs include SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some cases, a functional homolog of SEQ ID NO:3 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:3.

Examples of amino acid sequences of functional homologs of the polypeptide set forth in SEQ ID NO:49 are provided in FIG. 2 and in the Sequence Listing. Such functional homologs include SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75. In some cases, a functional homolog of SEQ ID NO:49 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:49.

Examples of amino acid sequences of functional homologs of the polypeptide set forth in SEQ ID NO:77 are provided in FIG. 3 and in the Sequence Listing. Such functional homologs include SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, and CeresAnnot: 839064 (SEQ ID NO:1479). In some cases, a functional homolog of SEQ ID NO:77 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:77.

Examples of amino acid sequences of functional homologs of the polypeptide set forth in SEQ ID NO:100 are provided in FIG. 4 and in the Sequence Listing. Such functional homologs include SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150. In some cases, a functional homolog of SEQ ID NO:100 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:100.

Examples of amino acid sequences of functional homologs of the polypeptide set forth in SEQ ID NO:152 are provided in FIG. 5 and in the Sequence Listing. Such functional homologs include SEQ ID NO:154, SEQ ID NO:156, SEQ ID NO:158, SEQ ID NO:160, SEQ ID NO:162, and SEQ ID NO:164. In some cases, a functional homolog of SEQ ID NO:152 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:152.

Examples of amino acid sequences of functional homologs of the polypeptide set forth in SEQ ID NO:166 are provided in FIG. 6 and in the Sequence Listing. Such functional homologs include SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, and SEQ ID NO:184. In some cases, a functional homolog of SEQ ID NO:166 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:166.

Examples of amino acid sequences of functional homologs of the polypeptide set forth in SEQ ID NO:186 are provided in FIG. 7 and in the Sequence Listing. Such functional homologs include SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206. In some cases, a functional homolog of SEQ ID NO:186 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:186.

Examples of amino acid sequences of functional homologs of the polypeptide set forth in SEQ ID NO:208 are provided in FIG. 8 and in the Sequence Listing. Such functional homologs include SEQ ID NO:209, SEQ ID NO:210, SEQ ID NO:214, and SEQ ID NO:216. In some cases, a functional homolog of SEQ ID NO:208 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:208.

Examples of amino acid sequences of functional homologs of the polypeptide set forth in SEQ ID NO:218 are provided in FIG. 9 and in the Sequence Listing. Such functional homologs include SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052. In some cases, a functional homolog of SEQ ID NO:218 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:218.

Examples of amino acid sequences of functional homologs of the polypeptide set forth in SEQ ID NO:234 are provided in FIG. 10 and in the Sequence Listing. Such functional homologs include SEQ ID NO:236, SEQ ID NO:238, SEQ ID NO:239, SEQ ID NO:241, SEQ ID NO:242, SEQ ID NO:243, and SEQ ID NO:244. In some cases, a functional homolog of SEQ ID NO:234 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:234.

Examples of amino acid sequences of functional homologs of the polypeptide set forth in SEQ ID NO:246 are provided in FIG. 11 and in the Sequence Listing. Such functional homologs include SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298. In some cases, a functional homolog of SEQ ID NO:246 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:246.

Examples of amino acid sequences of functional homologs of the polypeptide set forth in SEQ ID NO:300 are provided in FIG. 12 and in the Sequence Listing. Such functional homologs include SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329. In some cases, a functional homolog of SEQ ID NO:300 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:300.

Examples of amino acid sequences of functional homologs of the polypeptide set forth in SEQ ID NO:332 are provided in FIG. 13 and in the Sequence Listing. Such functional homologs include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553. In some cases, a functional homolog of SEQ ID NO:332 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:332.

Examples of amino acid sequences of functional homologs of the polypeptide set forth in SEQ ID NO:368 are provided in FIG. 14 and in the Sequence Listing. Such functional homologs include SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508. In some cases, a functional homolog of SEQ ID NO:368 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:368.

Examples of amino acid sequences of functional homologs of the polypeptide set forth in SEQ ID NO:510 are provided in FIG. 15 and in the Sequence Listing. Such functional homologs include SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531. In some cases, a functional homolog of SEQ ID NO:510 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:510.

Examples of amino acid sequences of functional homologs of the polypeptide set forth in SEQ ID NO:533 are provided in FIG. 16 and in the Sequence Listing. Such functional homologs include SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554. In some cases, a functional homolog of SEQ ID NO:533 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:533.

Figure 17:
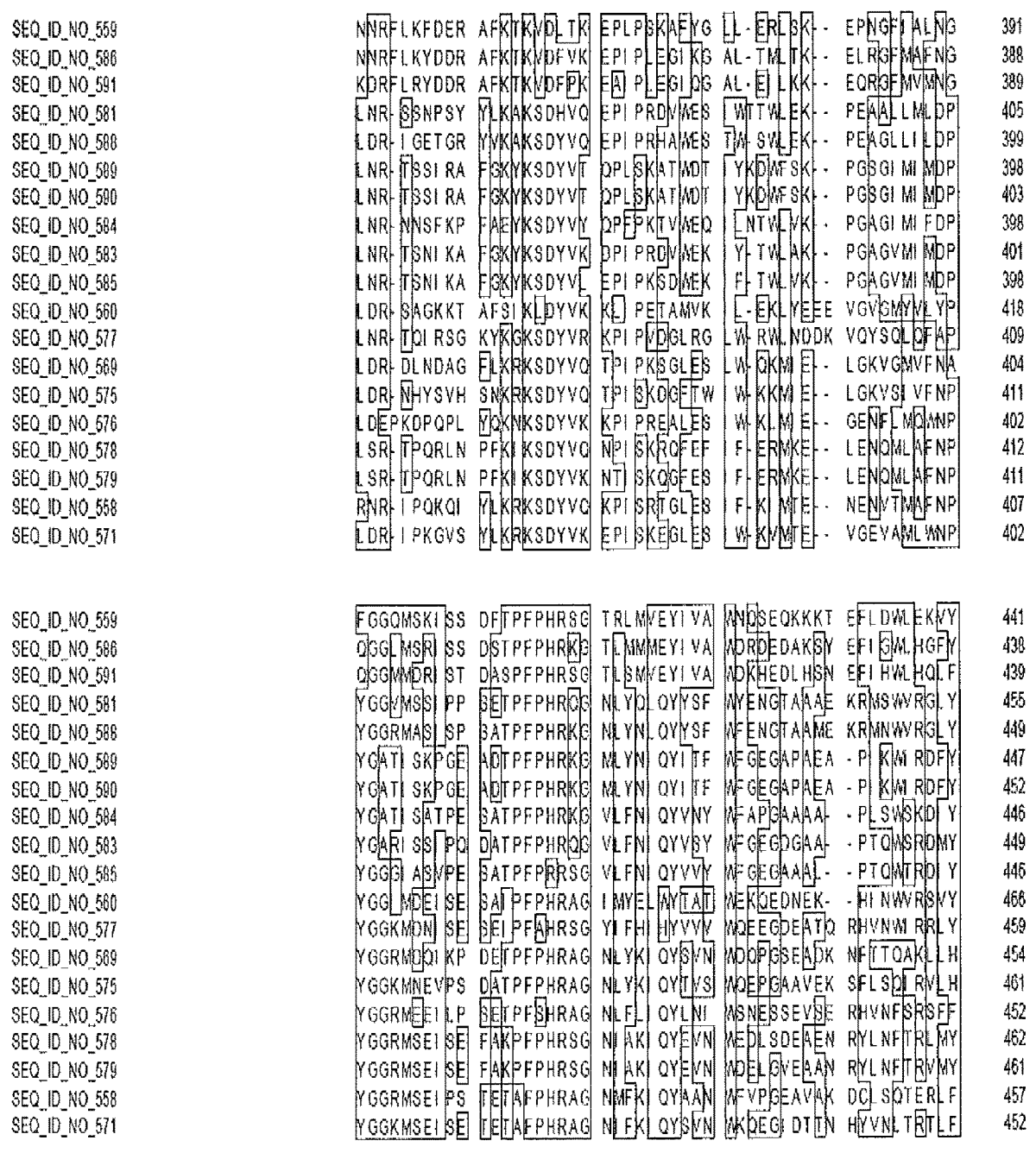

Examples of amino acid sequences of functional homologs of the polypeptide set forth in SEQ ID NO:558 are provided in FIG. 17 and in the Sequence Listing. Such functional homologs include SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591. In some cases, a functional homolog of SEQ ID NO:558 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:558.

Examples of amino acid sequences of functional homologs of the polypeptide set forth in SEQ ID NO:593 are provided in FIG. 18 and in the Sequence Listing. Such functional homologs include SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611. In some cases, a functional homolog of SEQ ID NO:593 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:593.

Examples of amino acid sequences of functional homologs of the polypeptide set forth in SEQ ID NO:613 are provided in FIG. 19 and in the Sequence Listing. Such functional homologs include SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644. In some cases, a functional homolog of SEQ ID NO:613 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:613.

Examples of amino acid sequences of functional homologs of the polypeptide set forth in SEQ ID NO:646 are provided in FIG. 20 and in the Sequence Listing. Such functional homologs include SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685. In some cases, a functional homolog of SEQ ID NO:646 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:646.

Figure 21:
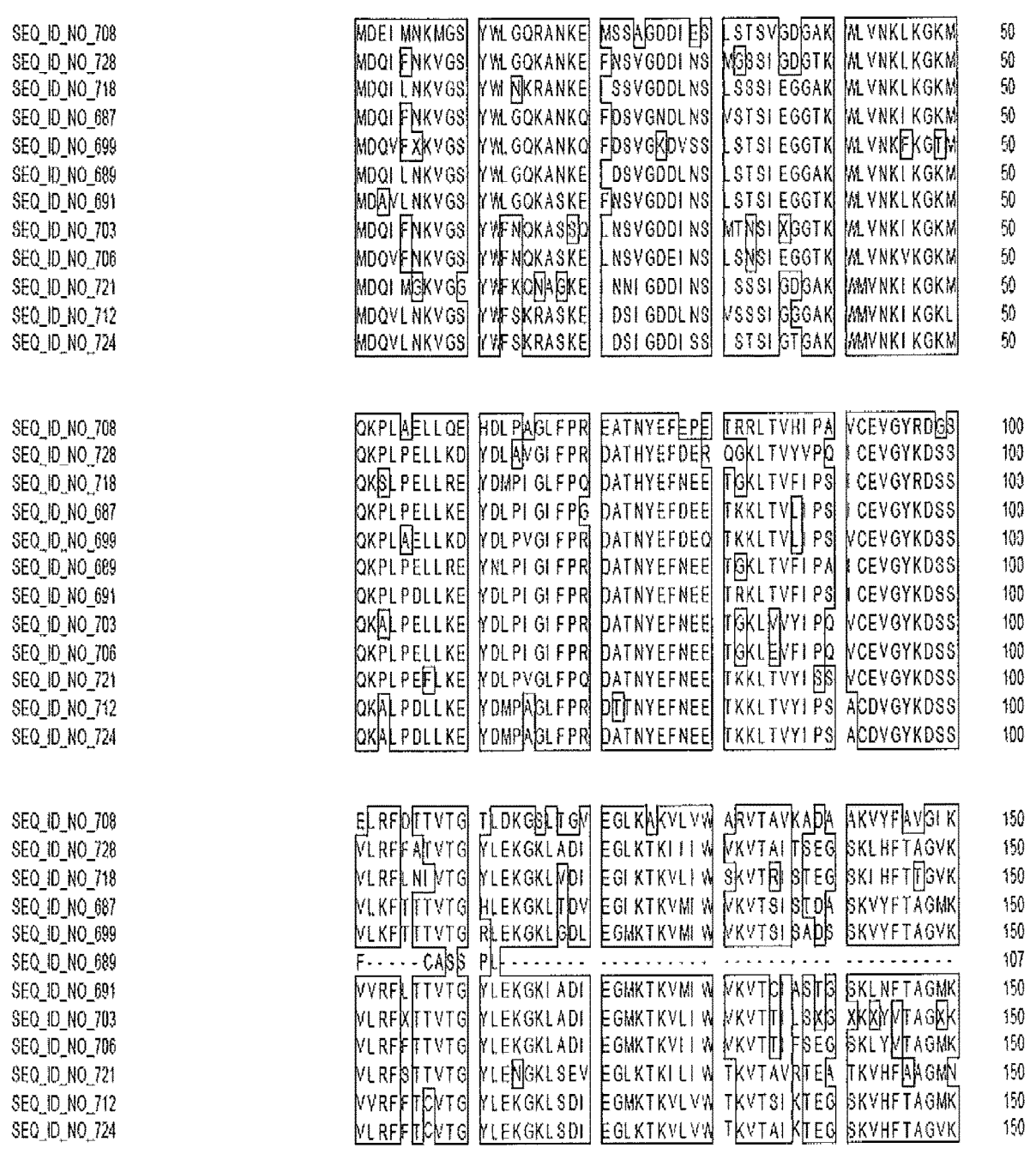

Examples of amino acid sequences of functional homologs of the polypeptide set forth in SEQ ID NO:687 are provided in FIG. 21 and in the Sequence Listing. Such functional homologs include SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728. In some cases, a functional homolog of SEQ ID NO:687 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:687.

Examples of amino acid sequences of functional homologs of the polypeptide set forth in SEQ ID NO:730 are provided in FIG. 22 and in the Sequence Listing. Such functional homologs include SEQ ID NO:732, SEQ ID NO:733, SEQ ID NO:735, SEQ ID NO:737, SEQ ID NO:738, and SEQ ID NO:742. In some cases, a functional homolog of SEQ ID NO:730 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:730.

Examples of amino acid sequences of functional homologs of the polypeptide set forth in SEQ ID NO:746 are provided in FIG. 23 and in the Sequence Listing. Such functional homologs include SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767. In some cases, a functional homolog of SEQ ID NO:746 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:746.

Examples of amino acid sequences of functional homologs of the polypeptide set forth in SEQ ID NO:769 are provided in FIG. 24 and in the Sequence Listing. Such functional homologs include SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790. In some cases, a functional homolog of SEQ ID NO:769 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:769.

Examples of amino acid sequences of functional homologs of the polypeptide set forth in SEQ ID NO:792 are provided in FIG. 25 and in the Sequence Listing. Such functional homologs include SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO:821, and SEQ ID NO:822. In some cases, a functional homolog of SEQ ID NO:792 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:792.

Examples of amino acid sequences of functional homologs of the polypeptide set forth in SEQ ID NO:824 are provided in FIG. 26 and in the Sequence Listing. Such functional homologs include, but not limited to, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716. In some cases, a functional homolog of SEQ ID NO:824 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:824.

Examples of amino acid sequences of functional homologs of the polypeptide set forth in SEQ ID NO:828 are provided in FIG. 27 and in the Sequence Listing. Such functional homologs include SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851. In some cases, a functional homolog of SEQ ID NO:828 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:828.

Examples of amino acid sequences of functional homologs of the polypeptide set forth in SEQ ID NO:855 are provided in FIG. 28 and in the Sequence Listing. Such functional homologs include SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889. In some cases, a functional homolog of SEQ ID NO:855 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:855.

Examples of amino acid sequences of functional homologs of the polypeptide set forth in SEQ ID NO:891 are provided in FIG. 29 and in the Sequence Listing. Such functional homologs include SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915. In some cases, a functional homolog of SEQ ID NO:891 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:891.

Examples of amino acid sequences of functional homologs of the polypeptide set forth in SEQ ID NO:917 are provided in FIG. 30 and in the Sequence Listing. Such functional homologs include SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940. In some cases, a functional homolog of SEQ ID NO:917 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:917.

Examples of amino acid sequences of functional homologs of the polypeptide set forth in SEQ ID NO:944 are provided in FIG. 31 and in the Sequence Listing. Such functional homologs include SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974. In some cases, a functional homolog of SEQ ID NO:944 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:944.

Examples of amino acid sequences of functional homologs of the polypeptide set forth in SEQ ID NO:976 are provided in FIG. 32 and in the Sequence Listing. Such functional homologs include, but not limited to, SEQ ID NO:978 and SEQ ID NO:980. In some cases, a functional homolog of SEQ ID NO:976 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:976.

Examples of amino acid sequences of functional homologs of the polypeptide set forth in SEQ ID NO:982 are provided in FIG. 33 and in the Sequence Listing. Such functional homologs include SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033. In some cases, a functional homolog of SEQ ID NO:982 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:982.

Examples of amino acid sequences of functional homologs of the polypeptide set forth in SEQ ID NO:1054 are provided in FIG. 34 and in the Sequence Listing. Such functional homologs include SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097. In some cases, a functional homolog of SEQ ID NO:1054 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1054.

Examples of amino acid sequences of functional homologs of the polypeptide set forth in SEQ ID NO:1099 are provided in FIG. 35 and in the Sequence Listing. Such functional homologs include SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110. In some cases, a functional homolog of SEQ ID NO:1099 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1099.

Examples of amino acid sequences of functional homologs of the polypeptide set forth in SEQ ID NO:1112 are provided in FIG. 36 and in the Sequence Listing. Such functional homologs include SEQ ID NO:1113 and SEQ ID NO:1114. In some cases, a functional homolog of SEQ ID NO:1112 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1112.

Examples of amino acid sequences of functional homologs of the polypeptide set forth in SEQ ID NO:1116 are provided in FIG. 37 and in the Sequence Listing. Such functional homologs include SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155. In some cases, a functional homolog of SEQ ID NO:1116 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1116.

Examples of amino acid sequences of functional homologs of the polypeptide set forth in SEQ ID NO:1159 are provided in FIG. 38 and in the Sequence Listing. Such functional homologs include SEQ ID NO:1161, SEQ ID NO:1162, SEQ ID NO:1163, and SEQ ID NO:1164. In some cases, a functional homolog of SEQ ID NO:1159 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1159.

Examples of amino acid sequences of functional homologs of the polypeptide set forth in SEQ ID NO:1166 are provided in FIG. 39 and in the Sequence Listing. Such functional homologs include SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183. In some cases, a functional homolog of SEQ ID NO:1166 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1166.

Examples of amino acid sequences of functional homologs of the polypeptide set forth in SEQ ID NO:1185 are provided in FIG. 40 and in the Sequence Listing. Such functional homologs include SEQ ID NO:1187, SEQ ID NO:1189, SEQ ID NO:1190, SEQ ID NO:1191, and SEQ ID NO:1192. In some cases, a functional homolog of SEQ ID NO:1185 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1185.

Examples of amino acid sequences of functional homologs of the polypeptide set forth in SEQ ID NO:1194 are provided in FIG. 41 and in the Sequence Listing. Such functional homologs include SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208. In some cases, a functional homolog of SEQ ID NO:1194 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1194.

Examples of amino acid sequences of functional homologs of the polypeptide set forth in SEQ ID NO:1210 are provided in FIG. 42 and in the Sequence Listing. Such functional homologs include SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272. In some cases, a functional homolog of SEQ ID NO:1210 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1210.

Examples of amino acid sequences of functional homologs of the polypeptide set forth in SEQ ID NO:1274 are provided in FIG. 43 and in the Sequence Listing. Such functional homologs include SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300. In some cases, a functional homolog of SEQ ID NO:1274 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1274.

Examples of amino acid sequences of functional homologs of the polypeptide set forth in SEQ ID NO:1302 are provided in FIG. 44 and in the Sequence Listing. Such functional homologs include SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340. In some cases, a functional homolog of SEQ ID NO:1302 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1302.

Examples of amino acid sequences of functional homologs of the polypeptide set forth in SEQ ID NO:1342 are provided in FIG. 45 and in the Sequence Listing. Such functional homologs include SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383. In some cases, a functional homolog of SEQ ID NO:1342 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1342.

Examples of amino acid sequences of functional homologs of the polypeptide set forth in SEQ ID NO:1385 are provided in FIG. 46 and in the Sequence Listing. Such functional homologs include SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID NO:1402, SEQ ID NO:1403, SEQ ID NO:1404, SEQ ID NO:1405, and SEQ ID NO:1407. In some cases, a functional homolog of SEQ ID NO:1385 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1385.

Examples of amino acid sequences of functional homologs of the polypeptide set forth in SEQ ID NO:1409 are provided in FIG. 47 and in the Sequence Listing. Such functional homologs include SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, and SEQ ID NO:1426. In some cases, a functional homolog of SEQ ID NO:1409 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1409.

Examples of amino acid sequences of functional homologs of the polypeptide set forth in SEQ ID NO:1428 are provided in FIG. 48 and in the Sequence Listing. Such functional homologs include SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459. In some cases, a functional homolog of SEQ ID NO:1428 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1428.

Examples of amino acid sequences of functional homologs of the polypeptide set forth in SEQ ID NO:1463 are provided in FIG. 49 and in the Sequence Listing. Such functional homologs include SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477. In some cases, a functional homolog of SEQ ID NO:1463 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1463.

Examples of amino acid sequences of functional homologs of the polypeptide set forth in SEQ ID NO:1491 are provided in FIG. 50 and in the Sequence Listing. Such functional homologs include SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508. In some cases, a functional homolog of SEQ ID NO:1491 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1491.

Examples of amino acid sequences of functional homologs of the polypeptide set forth in SEQ ID NO:1510 are provided in FIG. 51 and in the Sequence Listing. Such functional homologs include SEQ ID NO:1512, SEQ ID NO:1514, SEQ ID NO:1516, SEQ ID NO:1518, SEQ ID NO:1520, SEQ ID NO:1522, and SEQ ID NO:1523. In some cases, a functional homolog of SEQ ID NO:1510 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1510.

Examples of amino acid sequences of functional homologs of the polypeptide set forth in SEQ ID NO:1525 are provided in FIG. 52 and in the Sequence Listing. Such functional homologs include SEQ ID NO:1527, SEQ ID NO:1529, SEQ ID NO:1530, SEQ ID NO:1532, SEQ ID NO:1534, and SEQ ID NO:1535. In some cases, a functional homolog of SEQ ID NO:1525 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1525.

Examples of amino acid sequences of functional homologs of the polypeptide set forth in SEQ ID NO:1537 are provided in FIG. 53 and in the Sequence Listing. Such functional homologs include SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392. In some cases, a functional homolog of SEQ ID NO:1537 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1537.

Examples of amino acid sequences of functional homologs of the polypeptide set forth in SEQ ID NO:1554 are provided in FIG. 54 and in the Sequence Listing. Such functional homologs include SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575. In some cases, a functional homolog of SEQ ID NO:1554 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1554.

Examples of amino acid sequences of functional homologs of the polypeptide set forth in SEQ ID NO:1577 are provided in FIG. 55 and in the Sequence Listing. Such functional homologs include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, and SEQ ID NO:1653. In some cases, a functional homolog of SEQ ID NO:1577 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1577.

Examples of amino acid sequences of functional homologs of the polypeptide set forth in SEQ ID NO:1437 are provided in FIG. 56 and in the Sequence Listing. Such functional homologs include SEQ ID NO:173, SEQ ID NO:212, SEQ ID NO:361, SEQ ID NO:421, SEQ ID NO:443, SEQ ID NO:740, SEQ ID NO:744, SEQ ID NO:942, and SEQ ID NO:1461. In some cases, a functional homolog of SEQ ID NO:1437 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1437.

Examples of amino acid sequences of functional homologs of the polypeptide set forth in SEQ ID NO:97 are provided in FIG. 57 and in the Sequence Listing. Such functional homologs include SEQ ID NO:2010, SEQ ID NO:2011, SEQ ID NO:2013, SEQ ID NO:2015, SEQ ID NO:2017. In some cases, a functional homolog of SEQ ID NO:97 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:97.

The identification of conserved regions in a low nitrogen tolerance-modulating polypeptide facilitates production of variants of low nitrogen tolerance-modulating polypeptides. Variants of low nitrogen tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIG. 1-57 and/or homologs identified in the Sequence Listing. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

C. Functional Homologs Identified by HMMER

In some embodiments, useful low nitrogen tolerance-modulating polypeptides include those that fit a Hidden Markov Model based on the polypeptides set forth in any one of FIGS. 1-57. A Hidden Markov Model (HMM) is a statistical model of a consensus sequence for a group of functional homologs. See, Durbin et al. (1998) *Biological Sequence Analysis: Probabilistic Models of Proteins and Nucleic Acids*, Cambridge University Press, Cambridge, UK. An HMM is generated by the program HMMER 2.3.2 with default program parameters, using the sequences of the group of functional homologs as input. The multiple sequence alignment is generated by ProbCons (Do et al. (2005) Genome Res., 15(2):330-40) version 1.11 using a set of default parameters: -c, --consistency REPS of 2; -ir, --iterative-refinement REPS of 100; -pre, --pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as hmmer janelia.org; hmmer wustl.edu; and fr.com/hmmer232/. Hmmbuild outputs the model as a text file.

The HMM for a group of functional homologs can be used to determine the likelihood that a candidate low nitrogen tolerance-modulating polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the Prob-Cons program. Nevertheless, such HMM bit score variation is minor.

The low nitrogen tolerance-modulating polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a low nitrogen tolerance-modulating polypeptide discussed below is about 50%, 60%, 70%, 80%, 90%, or 95% of the HMM bit score of a functional homolog provided the Sequence Listing of this application. In some embodiments, a low nitrogen tolerance-modulating polypeptide discussed below fits the indicated HMM with an HMM bit score greater than 20, and has a domain indicative of a low nitrogen tolerance-modulating polypeptide. In some embodiments, a low nitrogen tolerance-modulating polypeptide discussed below fits the indicated HMM with an HMM bit score greater than 20, and has 70% or greater sequence identity (e.g., 75%, 80%, 85%, 90%, 95%, or 100% sequence identity) to an amino acid sequence shown in any one of FIGS. 1-57.

Examples of polypeptides are shown in the sequence listing that have HMM bit scores greater than 800 when fitted to an HMM generated from the amino acid sequences set forth in FIG. 1 are identified in the Sequence Listing of this application. Such polypeptides include SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47.

Examples of polypeptides are shown in the sequence listing that have HMM bit scores greater than 150 when fitted to an HMM generated from the amino acid sequences set forth in FIG. 2 are identified in the Sequence Listing of this application. Such polypeptides include SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75.

Examples of polypeptides are shown in the sequence listing that have HMM bit scores greater than 540 when fitted to an HMM generated from the amino acid sequences set forth in FIG. 3 are identified in the Sequence Listing of this application. Such polypeptides include SEQ ID NO:77, SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, and SEQ ID NO:1479.

Examples of polypeptides are shown in the sequence listing that have HMM bit scores greater than 210 when fitted to an HMM generated from the amino acid sequences set forth in FIG. 4 are identified in the Sequence Listing of this application. Such polypeptides include SEQ ID NO:100, SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150.

Examples of polypeptides are shown in the sequence listing that have HMM bit scores greater than 90 when fitted to an HMM generated from the amino acid sequences set forth in FIG. 5 are identified in the Sequence Listing of this application. Such polypeptides include SEQ ID NO:152, SEQ ID NO:154, SEQ ID NO:156, SEQ ID NO:158, SEQ ID NO:160, SEQ ID NO:162, and SEQ ID NO:164.

Examples of polypeptides are shown in the sequence listing that have HMM bit scores greater than 230 when fitted to an HMM generated from the amino acid sequences set forth in FIG. 6 are identified in the Sequence Listing of this application. Such polypeptides include SEQ ID NO:166, SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, and SEQ ID NO:184.

Examples of polypeptides are shown in the sequence listing that have HMM bit scores greater than 90 when fitted to an HMM generated from the amino acid sequences set forth in FIG. 7 are identified in the Sequence Listing of this application. Such polypeptides include SEQ ID NO:186, SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206.

Examples of polypeptides are shown in the sequence listing that have HMM bit scores greater than 380 when fitted to an HMM generated from the amino acid sequences set forth in FIG. 8 are identified in the Sequence Listing of this application. Such polypeptides include SEQ ID NO:208, SEQ ID NO:209, SEQ ID NO:210, SEQ ID NO:214, and SEQ ID NO:216.

Examples of polypeptides are shown in the sequence listing that have HMM bit scores greater than 110 when fitted to an HMM generated from the amino acid sequences set forth in FIG. 9 are identified in the Sequence Listing of this application. Such polypeptides include SEQ ID NO:218, SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052.

Examples of polypeptides are shown in the sequence listing that have HMM bit scores greater than 220 when fitted to an HMM generated from the amino acid sequences set forth in FIG. 10 are identified in the Sequence Listing of this application. Such polypeptides include SEQ ID NO:234, SEQ ID NO:236, SEQ ID NO:238, SEQ ID NO:239, SEQ ID NO:241, SEQ ID NO:242, SEQ ID NO:243, and SEQ ID NO:244.

Examples of polypeptides are shown in the sequence listing that have HMM bit scores greater than 150 when fitted to an HMM generated from the amino acid sequences set forth in FIG. 11 are identified in the Sequence Listing of this application. Such polypeptides include SEQ ID NO:246, SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298.

Examples of polypeptides are shown in the sequence listing that have HMM bit scores greater than 950 when fitted to an HMM generated from the amino acid sequences set forth in FIG. 12 are identified in the Sequence Listing of this application. Such polypeptides include SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329.

Examples of polypeptides are shown in the sequence listing that have HMM bit scores greater than 460 when fitted to an HMM generated from the amino acid sequences set forth in FIG. 13 are identified in the Sequence Listing of this application. Such polypeptides include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553.

Examples of polypeptides are shown in the sequence listing that have HMM bit scores greater than 150 when fitted to an HMM generated from the amino acid sequences set forth in FIG. 14 are identified in the Sequence Listing of this application. Such polypeptides include SEQ ID NO:368, SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508.

Examples of polypeptides are shown in the sequence listing that have HMM bit scores greater than 410 when fitted to an HMM generated from the amino acid sequences set forth in FIG. 15 are identified in the Sequence Listing of this application. Such polypeptides include SEQ ID NO:510, SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531.

Examples of polypeptides are shown in the sequence listing that have HMM bit scores greater than 520 when fitted to an HMM generated from the amino acid sequences set forth in FIG. 16 are identified in the Sequence Listing of this application. Such polypeptides include SEQ ID NO:533, SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554.

Examples of polypeptides are shown in the sequence listing that have HMM bit scores greater than 1150 when fitted to an HMM generated from the amino acid sequences set forth in FIG. 17 are identified in the Sequence Listing of this application. Such polypeptides include SEQ ID NO:558, SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591.

Examples of polypeptides are shown in the sequence listing that have HMM bit scores greater than 340 when fitted to an HMM generated from the amino acid sequences set forth in FIG. 18 are identified in the Sequence Listing of this application. Such polypeptides include SEQ ID NO:593, SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611.

Examples of polypeptides are shown in the sequence listing that have HMM bit scores greater than 140 when fitted to an HMM generated from the amino acid sequences set forth in FIG. 19 are identified in the Sequence Listing of this application. Such polypeptides include SEQ ID NO:613, SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644.

Examples of polypeptides are shown in the sequence listing that have HMM bit scores greater than 250 when fitted to an HMM generated from the amino acid sequences set forth in FIG. 20 are identified in the Sequence Listing of this application. Such polypeptides include SEQ ID NO:646, SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685.

Examples of polypeptides are shown in the sequence listing that have HMM bit scores greater than 170 when fitted to an HMM generated from the amino acid sequences set forth in FIG. 21 are identified in the Sequence Listing of this application. Such polypeptides include SEQ ID NO:687, SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728.

Examples of polypeptides are shown in the sequence listing that have HMM bit scores greater than 210 when fitted to an HMM generated from the amino acid sequences set forth in FIG. 22 are identified in the Sequence Listing of this application. Such polypeptides include SEQ ID NO:730, SEQ ID NO:732, SEQ ID NO:733, SEQ ID NO:735, SEQ ID NO:737, SEQ ID NO:738, and SEQ ID NO:742.

Examples of polypeptides are shown in the sequence listing that have HMM bit scores greater than 230 when fitted to an HMM generated from the amino acid sequences set forth in FIG. 23 are identified in the Sequence Listing of this application. Such polypeptides include SEQ ID NO:746, SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767.

Examples of polypeptides are shown in the sequence listing that have HMM bit scores greater than 180 when fitted to an HMM generated from the amino acid sequences set forth in FIG. 24 are identified in the Sequence Listing of this application. Such polypeptides include SEQ ID NO:769, SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790.

Examples of polypeptides are shown in the sequence listing that have HMM bit scores greater than 300 when fitted to an HMM generated from the amino acid sequences set forth in FIG. 25 are identified in the Sequence Listing of this application. Such polypeptides include SEQ ID NO:792, SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO:821, and SEQ ID NO:822.

Examples of polypeptides are shown in the sequence listing that have HMM bit scores greater than 190 when fitted to an HMM generated from the amino acid sequences set forth in FIG. 26 are identified in the Sequence Listing of this application. Such polypeptides include SEQ ID NO:824, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716.

Examples of polypeptides are shown in the sequence listing that have HMM bit scores greater than 630 when fitted to an HMM generated from the amino acid sequences set forth in FIG. 27 are identified in the Sequence Listing of this application. Such polypeptides include SEQ ID NO:828, SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851.

Examples of polypeptides are shown in the sequence listing that have HMM bit scores greater than 95 when fitted to an HMM generated from the amino acid sequences set forth in FIG. 28 are identified in the Sequence Listing of this application. Such polypeptides include SEQ ID NO:855, SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889.

Examples of polypeptides are shown in the sequence listing that have HMM bit scores greater than 850 when fitted to an HMM generated from the amino acid sequences set forth in FIG. 29 are identified in the Sequence Listing of this application. Such polypeptides include SEQ ID NO:891, SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915.

Examples of polypeptides are shown in the sequence listing that have HMM bit scores greater than 300 when fitted to an HMM generated from the amino acid sequences set forth in FIG. 30 are identified in the Sequence Listing of this application. Such polypeptides include SEQ ID NO:917, SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940.

Examples of polypeptides are shown in the sequence listing that have HMM bit scores greater than 60 when fitted to an HMM generated from the amino acid sequences set forth in FIG. 31 are identified in the Sequence Listing of this application. Such polypeptides include SEQ ID NO:944, SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974.

Examples of polypeptides are shown in the sequence listing that have HMM bit scores greater than 340 when fitted to an HMM generated from the amino acid sequences set forth in FIG. 32 are identified in the Sequence Listing of this application. Such polypeptides include SEQ ID NO:976, SEQ ID NO:978, and SEQ ID NO:980.

Examples of polypeptides are shown in the sequence listing that have HMM bit scores greater than 180 when fitted to an HMM generated from the amino acid sequences set forth in FIG. 33 are identified in the Sequence Listing of this application. Such polypeptides include SEQ ID NO:982, SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033.

Examples of polypeptides are shown in the sequence listing that have HMM bit scores greater than 1060 when fitted to an HMM generated from the amino acid sequences set forth in FIG. 34 are identified in the Sequence Listing of this application. Such polypeptides include SEQ ID NO:1054, SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097.

Examples of polypeptides are shown in the sequence listing that have HMM bit scores greater than 260 when fitted to an HMM generated from the amino acid sequences set forth in FIG. 35 are identified in the Sequence Listing of this application. Such polypeptides include SEQ ID NO:1099, SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110.

Examples of polypeptides are shown in the sequence listing that have HMM bit scores greater than 150 when fitted to an HMM generated from the amino acid sequences set forth in FIG. 36 are identified in the Sequence Listing of this application. Such polypeptides include SEQ ID NO:1112, SEQ ID NO:1113, and SEQ ID NO:1114.

Examples of polypeptides are shown in the sequence listing that have HMM bit scores greater than 40 when fitted to an HMM generated from the amino acid sequences set forth in FIG. 37 are identified in the Sequence Listing of this application. Such polypeptides include SEQ ID NO:1116, SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155.

Examples of polypeptides are shown in the sequence listing that have HMM bit scores greater than 450 when fitted to an HMM generated from the amino acid sequences set forth in FIG. 38 are identified in the Sequence Listing of this application. Such polypeptides include SEQ ID NO:1159, SEQ ID NO:1161, SEQ ID NO:1162, SEQ ID NO:1163, and SEQ ID NO:1164.

Examples of polypeptides are shown in the sequence listing that have HMM bit scores greater than 160 when fitted to an HMM generated from the amino acid sequences set forth in FIG. 39 are identified in the Sequence Listing of this application. Such polypeptides include SEQ ID NO:1166, SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183.

Examples of polypeptides are shown in the sequence listing that have HMM bit scores greater than 180 when fitted to an HMM generated from the amino acid sequences set forth in FIG. 40 are identified in the Sequence Listing of this application. Such polypeptides include SEQ ID NO:1185, SEQ ID NO:1187, SEQ ID NO:1189, SEQ ID NO:1190, SEQ ID NO:1191, and SEQ ID NO:1192.

Examples of polypeptides are shown in the sequence listing that have HMM bit scores greater than 670 when fitted to an HMM generated from the amino acid sequences set forth in FIG. 41 are identified in the Sequence Listing of this application. Such polypeptides include SEQ ID NO:1194, SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208.

Examples of polypeptides are shown in the sequence listing that have HMM bit scores greater than 280 when fitted to an HMM generated from the amino acid sequences set forth in FIG. 42 are identified in the Sequence Listing of this application. Such polypeptides include SEQ ID NO:1210, SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272.

Examples of polypeptides are shown in the sequence listing that have HMM bit scores greater than 700 when fitted to an HMM generated from the amino acid sequences set forth in FIG. 43 are identified in the Sequence Listing of this application. Such polypeptides include SEQ ID NO:1274, SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300.

Examples of polypeptides are shown in the sequence listing that have HMM bit scores greater than 920 when fitted to an HMM generated from the amino acid sequences set forth in FIG. 44 are identified in the Sequence Listing of this application. Such polypeptides include SEQ ID NO:1302, SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340.

Examples of polypeptides are shown in the sequence listing that have HMM bit scores greater than 510 when fitted to an HMM generated from the amino acid sequences set forth in FIG. 45 are identified in the Sequence Listing of this application. Such polypeptides include SEQ ID NO:1342, SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383.

Examples of polypeptides are shown in the sequence listing that have HMM bit scores greater than 140 when fitted to an HMM generated from the amino acid sequences set forth in FIG. 46 are identified in the Sequence Listing of this application. Such polypeptides include SEQ ID NO:1385, SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID NO:1402, SEQ ID NO:1403, SEQ ID NO:1404, SEQ ID NO:1405, and SEQ ID NO:1407.

Examples of polypeptides are shown in the sequence listing that have HMM bit scores greater than 150 when fitted to an HMM generated from the amino acid sequences set forth in FIG. 47 are identified in the Sequence Listing of this application. Such polypeptides include SEQ ID NO:1409, SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, SEQ ID NO:1426.

Examples of polypeptides are shown in the sequence listing that have HMM bit scores greater than 190 when fitted to an HMM generated from the amino acid sequences set forth in FIG. 48 are identified in the Sequence Listing of this application. Such polypeptides include SEQ ID NO:1428, SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459.

Examples of polypeptides are shown in the sequence listing that have HMM bit scores greater than 450 when fitted to an HMM generated from the amino acid sequences set forth in FIG. 49 are identified in the Sequence Listing of this application. Such polypeptides include SEQ ID NO:1463, SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477.

Examples of polypeptides are shown in the sequence listing that have HMM bit scores greater than 580 when fitted to an HMM generated from the amino acid sequences set forth in FIG. 50 are identified in the Sequence Listing of this application. Such polypeptides include SEQ ID NO:1491, SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508.

Examples of polypeptides are shown in the sequence listing that have HMM bit scores greater than 100 when fitted to an HMM generated from the amino acid sequences set forth in FIG. 51 are identified in the Sequence Listing of this application. Such polypeptides include SEQ ID NO:1510, SEQ ID NO:1512, SEQ ID NO:1514, SEQ ID NO:1516, SEQ ID NO:1518, SEQ ID NO:1520, SEQ ID NO:1522, and SEQ ID NO:1523.

Examples of polypeptides are shown in the sequence listing that have HMM bit scores greater than 800 when fitted to an HMM generated from the amino acid sequences set forth in FIG. 52 are identified in the Sequence Listing of this application. Such polypeptides include SEQ ID NO:1525, SEQ ID NO:1527, SEQ ID NO:1529, SEQ ID NO:1530, SEQ ID NO:1532, SEQ ID NO:1534, and SEQ ID NO:1535.

Examples of polypeptides are shown in the sequence listing that have HMM bit scores greater than 490 when fitted to an HMM generated from the amino acid sequences set forth in FIG. 53 are identified in the Sequence Listing of this application. Such polypeptides include SEQ ID NO:1537, SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392.

Examples of polypeptides are shown in the sequence listing that have HMM bit scores greater than 690 when fitted to an HMM generated from the amino acid sequences set forth in FIG. 54 are identified in the Sequence Listing of this application. Such polypeptides include SEQ ID NO:1554, SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575.

Examples of polypeptides are shown in the sequence listing that have HMM bit scores greater than 380 when fitted to an HMM generated from the amino acid sequences set forth in FIG. 55 are identified in the Sequence Listing of this application. Such polypeptides include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1577, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, and SEQ ID NO:1653.

Examples of polypeptides are shown in the sequence listing that have HMM bit scores greater than 870 when fitted to an HMM generated from the amino acid sequences set forth in FIG. 56 are identified in the Sequence Listing of this application. Such polypeptides include SEQ ID NO:173, SEQ ID NO:212, SEQ ID NO:361, SEQ ID NO:421, SEQ ID NO:443, SEQ ID NO:740, SEQ ID NO:744, SEQ ID NO:942, SEQ ID NO:1437, and SEQ ID NO:1461.

Examples of polypeptides are shown in the sequence listing that have HMM bit scores greater than 140 when fitted to an HMM generated from the amino acid sequences set forth in FIG. 57 are identified in the Sequence Listing of this application. Such polypeptides include SEQ ID NO:97, SEQ ID NO:2010, SEQ ID NO:2011, SEQ ID NO:2013, SEQ ID NO:2015, and SEQ ID NO:2017.

D. Percent Identity

In some embodiments, a low nitrogen tolerance-modulating polypeptide has an amino acid sequence with at least 20% sequence identity, e.g., at least 50%, 52%, 56%, 59%, 61%, 65%, 70%, 75%, 80%, 85%, 90%, 95%, 97%, 98%, or 99% sequence identity, to one of the amino acid sequences set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. Polypeptides having such a percent sequence identity often have a domain indicative of a low nitrogen tolerance-modulating polypeptide and/or have an HMM bit score that is greater than 20, as discussed above. Amino acid sequences of low nitrogen tolerance-modulating polypeptides having at least 20% sequence identity to one of the amino acid sequences set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577 are provided in FIGS. 1-57 and in the Sequence Listing.

"Percent sequence identity" refers to the degree of sequence identity between any given reference sequence, e.g., SEQ ID NO:3, and a candidate low nitrogen tolerance-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al. (2003) *Nucleic Acids Res.*, 31(13): 3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a low nitrogen tolerance-modulating polypeptide has an amino acid sequence with sequence similarity to the amino acid sequence set forth in SEQ ID NO:3, and preferably has at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:3 Amino acid sequences of polypeptides having greater than 20% sequence identity to the polypeptide set forth in SEQ ID NO:3 are provided in FIG. 1 and in the Sequence Listing. Examples of such polypeptides include SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47.

In some cases, a low nitrogen tolerance-modulating polypeptide has an amino acid sequence with sequence similarity to the amino acid sequence set forth in SEQ ID NO:49, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:49 Amino acid sequences of polypeptides having greater than 45% sequence identity to the polypeptide set forth in SEQ ID NO:49 are provided in FIG. 2 and in the Sequence Listing. Examples of such polypeptides include SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75.

In some cases, a low nitrogen tolerance-modulating polypeptide has an amino acid sequence with sequence similarity to the amino acid sequence set forth in SEQ ID NO:77, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:77 Amino acid sequences of polypeptides having greater than 45% sequence identity to the polypeptide set forth in SEQ ID NO:77 are provided in FIG. 3 and in the Sequence Listing. Examples of such polypeptides include SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, SEQ ID NO:1479.

In some cases, a low nitrogen tolerance-modulating polypeptide has an amino acid sequence with sequence similarity to the amino acid sequence set forth in SEQ ID NO:100, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:100. Amino acid sequences of polypeptides having greater than 45% sequence identity to the polypeptide set forth in SEQ ID NO: 100 are provided in FIG. 4 and in the Sequence Listing. Examples of such polypeptides include SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150.

In some cases, a low nitrogen tolerance-modulating polypeptide has an amino acid sequence with sequence similarity to the amino acid sequence set forth in SEQ ID NO:152, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:152. Amino acid sequences of polypeptides having greater than 45% sequence identity to the polypeptide set forth in SEQ ID NO:152 are provided in FIG. 5 and in the Sequence Listing. Examples of such polypeptides include SEQ ID NO:154, SEQ ID NO:156, SEQ ID NO:158, SEQ ID NO:160, SEQ ID NO:162, and SEQ ID NO:164.

In some cases, a low nitrogen tolerance-modulating polypeptide has an amino acid sequence with sequence similarity to the amino acid sequence set forth in SEQ ID NO:166, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:166. Amino acid sequences of polypeptides having greater than 45% sequence identity to the polypeptide set forth in SEQ ID NO:166 are provided in FIG. 6 and in the Sequence Listing. Examples of such polypeptides include SEQ ID NO:166, SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, SEQ ID NO:184.

In some cases, a low nitrogen tolerance-modulating polypeptide has an amino acid sequence with sequence similarity to the amino acid sequence set forth in SEQ ID NO:186, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:186. Amino acid sequences of polypeptides having greater than 45% sequence identity to the polypeptide set forth in SEQ ID NO:186 are provided in FIG. 7 and in the Sequence Listing. Examples of such polypeptides include SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206.

In some cases, a low nitrogen tolerance-modulating polypeptide has an amino acid sequence with sequence similarity to the amino acid sequence set forth in SEQ ID NO:208, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:208. Amino acid sequences of polypeptides having greater than 45% sequence identity to the polypeptide set forth in SEQ ID NO:208 are provided in FIG. 8 and in the Sequence Listing. Examples of such polypeptides include SEQ ID NO:209, SEQ ID NO:210, SEQ ID NO:214, and SEQ ID NO:216.

In some cases, a low nitrogen tolerance-modulating polypeptide has an amino acid sequence with sequence similarity to the amino acid sequence set forth in SEQ ID NO:218, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:218. Amino acid sequences of polypeptides having greater than 45% sequence identity to the polypeptide set forth in SEQ ID NO:218 are provided in FIG. 9 and in the Sequence Listing. Examples of such polypeptides include SEQ ID NO:218, SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052.

In some cases, a low nitrogen tolerance-modulating polypeptide has an amino acid sequence with sequence similarity to the amino acid sequence set forth in SEQ ID NO:234, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:234. Amino acid sequences of polypeptides having greater than 45% sequence identity to the polypeptide set forth in SEQ ID NO:234 are provided in FIG. 10 and in the Sequence Listing. Examples of such polypeptides include SEQ ID NO:236, SEQ ID NO:238, SEQ ID NO:239, SEQ ID NO:241, SEQ ID NO:242, SEQ ID NO:243, and SEQ ID NO:244.

In some cases, a low nitrogen tolerance-modulating polypeptide has an amino acid sequence with sequence similarity to the amino acid sequence set forth in SEQ ID NO:246, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:246. Amino acid sequences of polypeptides having greater than 45% sequence identity to the polypeptide set forth in SEQ ID NO:246 are provided in FIG. 11 and in the Sequence Listing. Examples of such polypeptides include SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298.

In some cases, a low nitrogen tolerance-modulating polypeptide has an amino acid sequence with sequence similarity to the amino acid sequence set forth in SEQ ID NO:300, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:300. Amino acid sequences of polypeptides having greater than 45% sequence identity to the polypeptide set forth in SEQ ID NO:300 are provided in FIG. 12 and in the Sequence Listing. Examples of such polypeptides include SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329.

In some cases, a low nitrogen tolerance-modulating polypeptide has an amino acid sequence with sequence similarity to the amino acid sequence set forth in SEQ ID NO:332, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:332. Amino acid sequences of polypeptides having greater than 45% sequence identity to the polypeptide set forth in SEQ ID NO:332 are provided in FIG. 13 and in the Sequence Listing. Examples of such polypeptides include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553.

In some cases, a low nitrogen tolerance-modulating polypeptide has an amino acid sequence with sequence similarity to the amino acid sequence set forth in SEQ ID NO:368, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:368. Amino acid sequences of polypeptides having greater than 45% sequence identity to the polypeptide set forth in SEQ ID NO:368 are provided in FIG. 14 and in the Sequence Listing. Examples of such polypeptides include SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508.

In some cases, a low nitrogen tolerance-modulating polypeptide has an amino acid sequence with sequence similarity to the amino acid sequence set forth in SEQ ID NO:510, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:510. Amino acid sequences of polypeptides having greater than 45% sequence identity to the polypeptide set forth in SEQ ID NO:510 are provided in FIG. 15 and in the Sequence Listing. Examples of such polypeptides include SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531.

In some cases, a low nitrogen tolerance-modulating polypeptide has an amino acid sequence with sequence similarity to the amino acid sequence set forth in SEQ ID NO:533, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:533. Amino acid sequences of polypeptides having greater than 45% sequence identity to the polypeptide set forth in SEQ ID NO:533 are provided in FIG. 16 and in the Sequence Listing. Examples of such polypeptides include SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554.

In some cases, a low nitrogen tolerance-modulating polypeptide has an amino acid sequence with sequence similarity to the amino acid sequence set forth in SEQ ID NO:558, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:558. Amino acid sequences of polypeptides having greater than 45% sequence identity to the polypeptide set forth in SEQ ID NO:558 are provided in FIG. 17 and in the Sequence Listing. Examples of such polypeptides include SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591.

In some cases, a low nitrogen tolerance-modulating polypeptide has an amino acid sequence with sequence similarity to the amino acid sequence set forth in SEQ ID NO:593, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:593. Amino acid sequences of polypeptides having greater than 45% sequence identity to the polypeptide set forth in SEQ ID NO:593 are provided in FIG. 18 and in the Sequence Listing. Examples of such polypeptides include SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611.

In some cases, a low nitrogen tolerance-modulating polypeptide has an amino acid sequence with sequence similarity to the amino acid sequence set forth in SEQ ID NO:613, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:613. Amino acid sequences of polypeptides having greater than 45% sequence identity to the polypeptide set forth in SEQ ID NO:613 are provided in FIG. 19 and in the Sequence Listing. Examples of such polypeptides include SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644.

In some cases, a low nitrogen tolerance-modulating polypeptide has an amino acid sequence with sequence similarity to the amino acid sequence set forth in SEQ ID NO:646, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:646. Amino acid sequences of polypeptides having greater than 45% sequence identity to the polypeptide set forth in SEQ ID NO:646 are provided in FIG. 20 and in the Sequence Listing. Examples of such polypeptides include SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685.

In some cases, a low nitrogen tolerance-modulating polypeptide has an amino acid sequence with sequence similarity to the amino acid sequence set forth in SEQ ID NO:687, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:687. Amino acid sequences of polypeptides having greater than 45% sequence identity to the polypeptide set forth in SEQ ID NO:687 are provided in FIG. 21 and in the Sequence Listing. Examples of such polypeptides include SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728.

In some cases, a low nitrogen tolerance-modulating polypeptide has an amino acid sequence with sequence similarity to the amino acid sequence set forth in SEQ ID NO:730, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:730. Amino acid sequences of polypeptides having greater than 45% sequence identity to the polypeptide set forth in SEQ ID NO:730 are provided in FIG. 22 and in the Sequence Listing. Examples of such polypeptides include SEQ ID NO:732, SEQ ID NO:733, SEQ ID NO:735, SEQ ID NO:737, SEQ ID NO:738, and SEQ ID NO:742.

In some cases, a low nitrogen tolerance-modulating polypeptide has an amino acid sequence with sequence similarity to the amino acid sequence set forth in SEQ ID NO:746, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:746. Amino acid sequences of polypeptides having greater than 45% sequence identity to the polypeptide set forth in SEQ ID NO:746 are provided in FIG. 23 and in the Sequence Listing. Examples of such polypeptides include SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767.

In some cases, a low nitrogen tolerance-modulating polypeptide has an amino acid sequence with sequence similarity to the amino acid sequence set forth in SEQ ID NO:769, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:769. Amino acid sequences of polypeptides having greater than 45% sequence identity to the polypeptide set forth in SEQ ID NO:769 are provided in FIG. 24 and in the Sequence Listing. Examples of such polypeptides include SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790.

In some cases, a low nitrogen tolerance-modulating polypeptide has an amino acid sequence with sequence similarity to the amino acid sequence set forth in SEQ ID NO:792, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:792. Amino acid sequences of polypeptides having greater than 20% sequence identity to the polypeptide set forth in SEQ ID NO:792 are provided in FIG. 25 and in the Sequence Listing. Examples of such polypeptides include SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO:821, and SEQ ID NO:822.

In some cases, a low nitrogen tolerance-modulating polypeptide has an amino acid sequence with sequence similarity to the amino acid sequence set forth in SEQ ID NO:824, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:824. Amino acid sequences of polypeptides having greater than 45% sequence identity to the polypeptide set forth in SEQ ID NO:824 are provided in FIG. 26 and in the Sequence Listing. Such polypeptides include, but not limited to, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716.

In some cases, a low nitrogen tolerance-modulating polypeptide has an amino acid sequence with sequence similarity to the amino acid sequence set forth in SEQ ID NO:828, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:828. Amino acid sequences of polypeptides having greater than 20% sequence identity to the polypeptide set forth in SEQ ID NO:828 are provided in FIG. 27 and in the Sequence Listing. Examples of such polypeptides include SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851.

In some cases, a low nitrogen tolerance-modulating polypeptide has an amino acid sequence with sequence similarity to the amino acid sequence set forth in SEQ ID NO:855, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:855. Amino acid sequences of polypeptides having greater than 20% sequence identity to the polypeptide set forth in SEQ ID NO:855 are provided in FIG. 28 and in the Sequence Listing. Examples of such polypeptides include SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889.

In some cases, a low nitrogen tolerance-modulating polypeptide has an amino acid sequence with sequence similarity to the amino acid sequence set forth in SEQ ID NO:891, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:891. Amino acid sequences of polypeptides having greater than 20% sequence identity to the polypeptide set forth in SEQ ID NO:891 are provided in FIG. 29 and in the Sequence Listing. Examples of such polypeptides include SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915.

In some cases, a low nitrogen tolerance-modulating polypeptide has an amino acid sequence with sequence similarity to the amino acid sequence set forth in SEQ ID NO:917, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:917. Amino acid sequences of polypeptides having greater than 20% sequence identity to the polypeptide set forth in SEQ ID NO:917 are provided in FIG. 30 and in the Sequence Listing. Examples of such polypeptides include SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940.

In some cases, a low nitrogen tolerance-modulating polypeptide has an amino acid sequence with sequence similarity to the amino acid sequence set forth in SEQ ID NO:944, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:944. Amino acid sequences of polypeptides having greater than 20% sequence identity to the polypeptide set forth in SEQ ID NO:944 are provided in FIG. 31 and in the Sequence Listing. Examples of such polypeptides include SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974.

In some cases, a low nitrogen tolerance-modulating polypeptide has an amino acid sequence with sequence similarity to the amino acid sequence set forth in SEQ ID NO:976, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:976. Amino acid sequences of polypeptides having greater than 45% sequence identity to the polypeptide set forth in SEQ ID NO:976 are provided in FIG. 32 and in the Sequence Listing. Examples of such polypeptides include SEQ ID NO:978 and SEQ ID NO:980.

In some cases, a low nitrogen tolerance-modulating polypeptide has an amino acid sequence with sequence similarity to the amino acid sequence set forth in SEQ ID NO:982, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:982. Amino acid sequences of polypeptides having greater than 20% sequence identity to the polypeptide set forth in SEQ ID NO:982 are provided in FIG. 33 and in the Sequence Listing. Examples of such polypeptides include SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033.

In some cases, a low nitrogen tolerance-modulating polypeptide has an amino acid sequence with sequence similarity to the amino acid sequence set forth in SEQ ID NO:1054, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1054 Amino acid sequences of polypeptides having greater than 20% sequence identity to the polypeptide set forth in SEQ ID NO:1054 are provided in FIG. 34 and in the Sequence Listing. Examples of such polypeptides include SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097.

In some cases, a low nitrogen tolerance-modulating polypeptide has an amino acid sequence with sequence similarity to the amino acid sequence set forth in SEQ ID NO:1099, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1099 Amino acid sequences of polypeptides having greater than 20% sequence identity to the polypeptide set forth in SEQ ID NO:1099 are provided in FIG. 35 and in the Sequence Listing. Examples of such polypeptides include SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110.

In some cases, a low nitrogen tolerance-modulating polypeptide has an amino acid sequence with sequence similarity to the amino acid sequence set forth in SEQ ID NO:1112, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1112 Amino acid sequences of polypeptides having greater than 20% sequence identity to the polypeptide set forth in SEQ ID NO:1112 are provided in FIG. 36 and in the Sequence Listing. Examples of such polypeptides include SEQ ID NO:1113 and SEQ ID NO:1114.

In some cases, a low nitrogen tolerance-modulating polypeptide has an amino acid sequence with sequence similarity to the amino acid sequence set forth in SEQ ID NO:1116, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1116 Amino acid sequences of polypeptides having greater than 20% sequence identity to the polypeptide set forth in SEQ ID NO:1116 are provided in FIG. 37 and in the Sequence Listing. Examples of such polypeptides include SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155.

In some cases, a low nitrogen tolerance-modulating polypeptide has an amino acid sequence with sequence similarity to the amino acid sequence set forth in SEQ ID NO:1159, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1159 Amino acid sequences of polypeptides having greater than 20% sequence identity to the polypeptide set forth in SEQ ID NO:1159 are provided in FIG. 38 and in the Sequence Listing. Examples of such polypeptides include SEQ ID NO:1161, SEQ ID NO:1162, SEQ ID NO:1163, and SEQ ID NO:1164.

In some cases, a low nitrogen tolerance-modulating polypeptide has an amino acid sequence with sequence similarity to the amino acid sequence set forth in SEQ ID NO:1166, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1166 Amino acid sequences of polypeptides having greater than 20% sequence identity to the polypeptide set forth in SEQ ID NO:1166 are provided in FIG. 39 and in the Sequence Listing. Examples of such polypeptides include SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183.

In some cases, a low nitrogen tolerance-modulating polypeptide has an amino acid sequence with sequence similarity to the amino acid sequence set forth in SEQ ID NO:1185, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1185 Amino acid sequences of polypeptides having greater than 20% sequence identity to the polypeptide set forth in SEQ ID NO:1185 are provided in FIG. 40 and in the Sequence Listing. Examples of such polypeptides include SEQ ID NO:1187, SEQ ID NO:1189, SEQ ID NO:1190, SEQ ID NO:1191, and SEQ ID NO:1192.

In some cases, a low nitrogen tolerance-modulating polypeptide has an amino acid sequence with sequence similarity to the amino acid sequence set forth in SEQ ID NO:1194, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1194 Amino acid sequences of polypeptides having greater than 20% sequence identity to the polypeptide set forth in SEQ ID NO:1194 are provided in FIG. 41 and in the Sequence Listing. Examples of such polypeptides include SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208.

In some cases, a low nitrogen tolerance-modulating polypeptide has an amino acid sequence with sequence similarity to the amino acid sequence set forth in SEQ ID NO:1210, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1210 Amino acid sequences of polypeptides having greater than 20% sequence identity to the polypeptide set forth in SEQ ID NO:1210 are provided in FIG. 42 and in the Sequence Listing. Examples of such polypeptides include SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272.

In some cases, a low nitrogen tolerance-modulating polypeptide has an amino acid sequence with sequence similarity to the amino acid sequence set forth in SEQ ID NO:1274, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1274 Amino acid sequences of polypeptides having greater than 20% sequence identity to the polypeptide set forth in SEQ ID NO:1274 are provided in FIG. 43 and in the Sequence Listing. Examples of such polypeptides include SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300.

In some cases, a low nitrogen tolerance-modulating polypeptide has an amino acid sequence with sequence similarity to the amino acid sequence set forth in SEQ ID NO:1302, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1302 Amino acid sequences of polypeptides having greater than 20% sequence identity to the polypeptide set forth in SEQ ID NO:1302 are provided in FIG. 44 and in the Sequence Listing. Examples of such polypeptides include SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340.

In some cases, a low nitrogen tolerance-modulating polypeptide has an amino acid sequence with sequence similarity to the amino acid sequence set forth in SEQ ID NO:1342, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1342 Amino acid sequences of polypeptides having greater than 20% sequence identity to the polypeptide set forth in SEQ ID NO:1342 are provided in FIG. 45 and in the Sequence Listing. Examples of such polypeptides include SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383.

In some cases, a low nitrogen tolerance-modulating polypeptide has an amino acid sequence with sequence similarity to the amino acid sequence set forth in SEQ ID NO:1385, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1385 Amino acid sequences of polypeptides having greater than 20% sequence identity to the polypeptide set forth in SEQ ID NO:1385 are provided in FIG. 46 and in the Sequence Listing. Examples of such polypeptides include SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID NO:1402, SEQ ID NO:1403, SEQ ID NO:1404, SEQ ID NO:1405, and SEQ ID NO:1407.

In some cases, a low nitrogen tolerance-modulating polypeptide has an amino acid sequence with sequence similarity to the amino acid sequence set forth in SEQ ID NO:1409, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1409 Amino acid sequences of polypeptides having greater than 20% sequence identity to the polypeptide set forth in SEQ ID NO:1409 are provided in FIG. 47 and in the Sequence Listing. Examples of such polypeptides include SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, and SEQ ID NO:1426.

In some cases, a low nitrogen tolerance-modulating polypeptide has an amino acid sequence with sequence similarity to the amino acid sequence set forth in SEQ ID NO:1428, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1428 Amino acid sequences of polypeptides having greater than 20% sequence identity to the polypeptide set forth in SEQ ID NO:1428 are provided in FIG. 48 and in the Sequence Listing. Examples of such polypeptides include SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459.

In some cases, a low nitrogen tolerance-modulating polypeptide has an amino acid sequence with sequence similarity to the amino acid sequence set forth in SEQ ID NO:1463, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1463 Amino acid sequences of polypeptides having greater than 20% sequence identity to the polypeptide set forth in SEQ ID NO:1463 are provided in FIG. 49 and in the Sequence Listing. Examples of such polypeptides include SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477.

In some cases, a low nitrogen tolerance-modulating polypeptide has an amino acid sequence with sequence similarity to the amino acid sequence set forth in SEQ ID NO:1491, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1491 Amino acid sequences of polypeptides having greater than 20% sequence identity to the polypeptide set forth in SEQ ID NO:1491 are provided in FIG. 50 and in the Sequence Listing. Examples of such polypeptides include SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508.

In some cases, a low nitrogen tolerance-modulating polypeptide has an amino acid sequence with sequence similarity to the amino acid sequence set forth in SEQ ID NO:1510, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1510 Amino acid sequences of polypeptides having greater than 20% sequence identity to the polypeptide set forth in SEQ ID NO:1510 are provided in FIG. 51 and in the Sequence Listing. Examples of such polypeptides include SEQ ID NO:1512, SEQ ID NO:1514, SEQ ID NO:1516, SEQ ID NO:1518, SEQ ID NO:1520, SEQ ID NO:1522, and SEQ ID NO:1523.

In some cases, a low nitrogen tolerance-modulating polypeptide has an amino acid sequence with sequence similarity to the amino acid sequence set forth in SEQ ID NO:1525, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1525 Amino acid sequences of polypeptides having greater than 20% sequence identity to the polypeptide set forth in SEQ ID NO:1525 are provided in FIG. 52 and in the Sequence Listing. Examples of such polypeptides include SEQ ID NO:1527, SEQ ID NO:1529, SEQ ID NO:1530, SEQ ID NO:1532, SEQ ID NO:1534, and SEQ ID NO:1535.

In some cases, a low nitrogen tolerance-modulating polypeptide has an amino acid sequence with sequence similarity to the amino acid sequence set forth in SEQ ID NO:1537, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1537 Amino acid sequences of polypeptides having greater than 20% sequence identity to the polypeptide set forth in SEQ ID NO:1537 are provided in FIG. 53 and in the Sequence Listing. Examples of such polypeptides include SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392.

In some cases, a low nitrogen tolerance-modulating polypeptide has an amino acid sequence with sequence similarity to the amino acid sequence set forth in SEQ ID NO:1554, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1554 Amino acid sequences of polypeptides having greater than 20% sequence identity to the polypeptide set forth in SEQ ID NO:1554 are provided in FIG. 54 and in the Sequence Listing. Examples of such polypeptides include SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575.

In some cases, a low nitrogen tolerance-modulating polypeptide has an amino acid sequence with sequence similarity to the amino acid sequence set forth in SEQ ID NO:1577, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1577 Amino acid sequences of polypeptides having greater than 20% sequence identity to the polypeptide set forth in SEQ ID NO:1577 are provided in FIG. 55 and in the Sequence Listing. Examples of such polypeptides include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, SEQ ID NO:1653.

In some cases, a low nitrogen tolerance-modulating polypeptide has an amino acid sequence with sequence similarity to the amino acid sequence set forth in SEQ ID NO:1437, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1437 Amino acid sequences of polypeptides having greater than 20% sequence identity to the polypeptide set forth in SEQ ID NO:1437 are provided in FIG. 56 and in the Sequence Listing. Examples of such polypeptides include SEQ ID NO:173, SEQ ID NO:212, SEQ ID NO:361, SEQ ID NO:421, SEQ ID NO:443, SEQ ID NO:740, SEQ ID NO:744, SEQ ID NO:942, SEQ ID NO:1461.

In some cases, a low nitrogen tolerance-modulating polypeptide has an amino acid sequence with sequence similarity to the amino acid sequence set forth in SEQ ID NO:97, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:97 Amino acid sequences of polypeptides having greater than 20% sequence identity to the polypeptide set forth in SEQ ID NO:1437 are provided in FIG. 57 and in the Sequence Listing. Examples of such polypeptides include SEQ ID NO:2010, SEQ ID NO:2011, SEQ ID NO:2013, SEQ ID NO:2015, and SEQ ID NO:2017

E. Other Sequences

It should be appreciated that a low nitrogen tolerance-modulating polypeptide can include additional amino acids that are not involved in low nitrogen tolerance-modulation, and thus such a polypeptide can be longer than would otherwise be the case. For example, a low nitrogen tolerance-modulating polypeptide can include a purification tag, a chloroplast transit peptide, a mitochondrial transit peptide, an amyloplast peptide, or a leader sequence added to the amino or carboxy terminus. In some embodiments, a low nitrogen tolerance-modulating polypeptide includes an amino acid sequence that functions as a reporter, e.g., a green fluorescent protein or yellow fluorescent protein.

III. Nucleic Acids

Nucleic acids described herein include nucleic acids that are effective to modulate low-nitrogen tolerance levels when transcribed in a plant or plant cell. Such nucleic acids include, without limitation, those that encode a low nitrogen tolerance-modulating polypeptide and those that can be used to inhibit expression of low nitrogen tolerance-modulating polypeptide via a nucleic acid based method.

A. Nucleic Acids Encoding Low Nitrogen Tolerance-Modulating Polypeptides

Nucleic acids encoding low nitrogen tolerance-modulating polypeptides are described herein. Examples of such nucleic acids include SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576, as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576.

A low nitrogen tolerance-modulating nucleic acid can comprise the nucleotide sequence set forth in SEQ ID NO:1. Alternatively, a low nitrogen tolerance-modulating nucleic acid can be a variant of the nucleic acid having the nucleotide sequence set forth in SEQ ID NO:2. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:2.

A low nitrogen tolerance-modulating nucleic acid can comprise the nucleotide sequence set forth in SEQ ID NO: 48. Alternatively, a low nitrogen tolerance-modulating nucleic acid can be a variant of the nucleic acid having the nucleotide sequence set forth in SEQ ID NO: 48. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 48.

A low nitrogen tolerance-modulating nucleic acid can comprise the nucleotide sequence set forth in SEQ ID NO:76. Alternatively, a low nitrogen tolerance-modulating nucleic acid can be a variant of the nucleic acid having the nucleotide sequence set forth in SEQ ID NO:76. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:76.

A low nitrogen tolerance-modulating nucleic acid can comprise the nucleotide sequence set forth in SEQ ID NO:96. Alternatively, a low nitrogen tolerance-modulating nucleic acid can be a variant of the nucleic acid having the nucleotide sequence set forth in SEQ ID NO:96. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:96.

A low nitrogen tolerance-modulating nucleic acid can comprise the nucleotide sequence set forth in SEQ ID NO:99. Alternatively, a low nitrogen tolerance-modulating nucleic acid can be a variant of the nucleic acid having the nucleotide sequence set forth in SEQ ID NO:99. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:99.

A low nitrogen tolerance-modulating nucleic acid can comprise the nucleotide sequence set forth in SEQ ID NO:151. Alternatively, a low nitrogen tolerance-modulating nucleic acid can be a variant of the nucleic acid having the nucleotide sequence set forth in SEQ ID NO:151. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:151.

A low nitrogen tolerance-modulating nucleic acid can comprise the nucleotide sequence set forth in SEQ ID NO:165. Alternatively, a low nitrogen tolerance-modulating nucleic acid can be a variant of the nucleic acid having the nucleotide sequence set forth in SEQ ID NO:165. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:165.

A low nitrogen tolerance-modulating nucleic acid can comprise the nucleotide sequence set forth in SEQ ID NO:175. Alternatively, a low nitrogen tolerance-modulating nucleic acid can be a variant of the nucleic acid having the nucleotide sequence set forth in SEQ ID NO:175. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:175.

A low nitrogen tolerance-modulating nucleic acid can comprise the nucleotide sequence set forth in SEQ ID NO:185. Alternatively, a low nitrogen tolerance-modulating nucleic acid can be a variant of the nucleic acid having the nucleotide sequence set forth in SEQ ID NO:185. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:185.

A low nitrogen tolerance-modulating nucleic acid can comprise the nucleotide sequence set forth in SEQ ID NO:207. Alternatively, a low nitrogen tolerance-modulating nucleic acid can be a variant of the nucleic acid having the nucleotide sequence set forth in SEQ ID NO:207. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:207.

A low nitrogen tolerance-modulating nucleic acid can comprise the nucleotide sequence set forth in SEQ ID NO:217. Alternatively, a low nitrogen tolerance-modulating nucleic acid can be a variant of the nucleic acid having the nucleotide sequence set forth in SEQ ID NO:217. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:217.

A low nitrogen tolerance-modulating nucleic acid can comprise the nucleotide sequence set forth in SEQ ID NO:233. Alternatively, a low nitrogen tolerance-modulating nucleic acid can be a variant of the nucleic acid having the nucleotide sequence set forth in SEQ ID NO:233. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:233.

A low nitrogen tolerance-modulating nucleic acid can comprise the nucleotide sequence set forth in SEQ ID NO:245. Alternatively, a low nitrogen tolerance-modulating nucleic acid can be a variant of the nucleic acid having the nucleotide sequence set forth in SEQ ID NO:245. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:245.

A low nitrogen tolerance-modulating nucleic acid can comprise the nucleotide sequence set forth in SEQ ID NO:299. Alternatively, a low nitrogen tolerance-modulating nucleic acid can be a variant of the nucleic acid having the nucleotide sequence set forth in SEQ ID NO:299. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:299.

A low nitrogen tolerance-modulating nucleic acid can comprise the nucleotide sequence set forth in SEQ ID NO:331. Alternatively, a low nitrogen tolerance-modulating nucleic acid can be a variant of the nucleic acid having the nucleotide sequence set forth in SEQ ID NO:331. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:331.

A low nitrogen tolerance-modulating nucleic acid can comprise the nucleotide sequence set forth in SEQ ID NO:367. Alternatively, a low nitrogen tolerance-modulating nucleic acid can be a variant of the nucleic acid having the nucleotide sequence set forth in SEQ ID NO:367. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:367.

A low nitrogen tolerance-modulating nucleic acid can comprise the nucleotide sequence set forth in SEQ ID NO:509. Alternatively, a low nitrogen tolerance-modulating nucleic acid can be a variant of the nucleic acid having the nucleotide sequence set forth in SEQ ID NO:509. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:509.

A low nitrogen tolerance-modulating nucleic acid can comprise the nucleotide sequence set forth in SEQ ID NO:532. Alternatively, a low nitrogen tolerance-modulating nucleic acid can be a variant of the nucleic acid having the nucleotide sequence set forth in SEQ ID NO:532. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:532.

A low nitrogen tolerance-modulating nucleic acid can comprise the nucleotide sequence set forth in SEQ ID NO:555. Alternatively, a low nitrogen tolerance-modulating nucleic acid can be a variant of the nucleic acid having the nucleotide sequence set forth in SEQ ID NO:555. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:555.

A low nitrogen tolerance-modulating nucleic acid can comprise the nucleotide sequence set forth in SEQ ID NO:557. Alternatively, a low nitrogen tolerance-modulating nucleic acid can be a variant of the nucleic acid having the nucleotide sequence set forth in SEQ ID NO:557. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:557.

A low nitrogen tolerance-modulating nucleic acid can comprise the nucleotide sequence set forth in SEQ ID NO:592. Alternatively, a low nitrogen tolerance-modulating nucleic acid can be a variant of the nucleic acid having the nucleotide sequence set forth in SEQ ID NO:592. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:592.

A low nitrogen tolerance-modulating nucleic acid can comprise the nucleotide sequence set forth in SEQ ID NO:612. Alternatively, a low nitrogen tolerance-modulating nucleic acid can be a variant of the nucleic acid having the nucleotide sequence set forth in SEQ ID NO:612. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:612.

A low nitrogen tolerance-modulating nucleic acid can comprise the nucleotide sequence set forth in SEQ ID NO:645. Alternatively, a low nitrogen tolerance-modulating nucleic acid can be a variant of the nucleic acid having the nucleotide sequence set forth in SEQ ID NO:645. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:645.

A low nitrogen tolerance-modulating nucleic acid can comprise the nucleotide sequence set forth in SEQ ID NO:686. Alternatively, a low nitrogen tolerance-modulating nucleic acid can be a variant of the nucleic acid having the nucleotide sequence set forth in SEQ ID NO:686. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:686.

A low nitrogen tolerance-modulating nucleic acid can comprise the nucleotide sequence set forth in SEQ ID NO:729. Alternatively, a low nitrogen tolerance-modulating nucleic acid can be a variant of the nucleic acid having the nucleotide sequence set forth in SEQ ID NO:729. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:729.

A low nitrogen tolerance-modulating nucleic acid can comprise the nucleotide sequence set forth in SEQ ID NO:745. Alternatively, a low nitrogen tolerance-modulating nucleic acid can be a variant of the nucleic acid having the nucleotide sequence set forth in SEQ ID NO:745. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:745.

A low nitrogen tolerance-modulating nucleic acid can comprise the nucleotide sequence set forth in SEQ ID NO:768. Alternatively, a low nitrogen tolerance-modulating nucleic acid can be a variant of the nucleic acid having the nucleotide sequence set forth in SEQ ID NO:768. For example, a low nitrogen tolerance-modulating nucleic acid can have a nucleotide sequence with at least 80% sequence A low nitrogen tolerance-modulating nucleic acid can comprise the nucleotide sequence set forth in SEQ ID NO:791. Alternatively, a low nitrogen tolerance-modulating nucleic acid can be a variant of the nucleic acid having the nucleotide sequence set forth in SEQ ID NO:791. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:791.

A low nitrogen tolerance-modulating nucleic acid can comprise the nucleotide sequence set forth in SEQ ID NO:823. Alternatively, a low nitrogen tolerance-modulating nucleic acid can be a variant of the nucleic acid having the nucleotide sequence set forth in SEQ ID NO:823. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:823.

A low nitrogen tolerance-modulating nucleic acid can comprise the nucleotide sequence set forth in SEQ ID NO:827. Alternatively, a low nitrogen tolerance-modulating nucleic acid can be a variant of the nucleic acid having the nucleotide sequence set forth in SEQ ID NO:827. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:827.

A low nitrogen tolerance-modulating nucleic acid can comprise the nucleotide sequence set forth in SEQ ID NO:852. Alternatively, a low nitrogen tolerance-modulating nucleic acid can be a variant of the nucleic acid having the nucleotide sequence set forth in SEQ ID NO:852. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:852.

A low nitrogen tolerance-modulating nucleic acid can comprise the nucleotide sequence set forth in SEQ ID NO:854. Alternatively, a low nitrogen tolerance-modulating nucleic acid can be a variant of the nucleic acid having the nucleotide sequence set forth in SEQ ID NO:854. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:854.

A low nitrogen tolerance-modulating nucleic acid can comprise the nucleotide sequence set forth in SEQ ID NO:890. Alternatively, a low nitrogen tolerance-modulating nucleic acid can be a variant of the nucleic acid having the nucleotide sequence set forth in SEQ ID NO:890. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:890.

A low nitrogen tolerance-modulating nucleic acid can comprise the nucleotide sequence set forth in SEQ ID NO:916. Alternatively, a low nitrogen tolerance-modulating nucleic acid can be a variant of the nucleic acid having the nucleotide sequence set forth in SEQ ID NO:916. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:916.

A low nitrogen tolerance-modulating nucleic acid can comprise the nucleotide sequence set forth in SEQ ID NO:943. Alternatively, a low nitrogen tolerance-modulating nucleic acid can be a variant of the nucleic acid having the nucleotide sequence set forth in SEQ ID NO:943. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:943.

A low nitrogen tolerance-modulating nucleic acid can comprise the nucleotide sequence set forth in SEQ ID NO:975. Alternatively, a low nitrogen tolerance-modulating nucleic acid can be a variant of the nucleic acid having the nucleotide sequence set forth in SEQ ID NO:975. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:975.

A low nitrogen tolerance-modulating nucleic acid can comprise the nucleotide sequence set forth in SEQ ID NO:981. Alternatively, a low nitrogen tolerance-modulating nucleic acid can be a variant of the nucleic acid having the nucleotide sequence set forth in SEQ ID NO:981. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:981.

A low nitrogen tolerance-modulating nucleic acid can comprise the nucleotide sequence set forth in SEQ ID NO: 1034. Alternatively, a low nitrogen tolerance-modulating nucleic acid can be a variant of the nucleic acid having the nucleotide sequence set forth in SEQ ID NO: 1034. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1034.

A low nitrogen tolerance-modulating nucleic acid can comprise the nucleotide sequence set forth in SEQ ID NO:1053. Alternatively, a low nitrogen tolerance-modulating nucleic acid can be a variant of the nucleic acid having the nucleotide sequence set forth in SEQ ID NO:1053. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1053.

A low nitrogen tolerance-modulating nucleic acid can comprise the nucleotide sequence set forth in SEQ ID NO:1098. Alternatively, a low nitrogen tolerance-modulating nucleic acid can be a variant of the nucleic acid having the nucleotide sequence set forth in SEQ ID NO:1098. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1098.

A low nitrogen tolerance-modulating nucleic acid can comprise the nucleotide sequence set forth in SEQ ID NO:1111. Alternatively, a low nitrogen tolerance-modulating nucleic acid can be a variant of the nucleic acid having the nucleotide sequence set forth in SEQ ID NO:1111. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1111.

A low nitrogen tolerance-modulating nucleic acid can comprise the nucleotide sequence set forth in SEQ ID NO:1115. Alternatively, a low nitrogen tolerance-modulating nucleic acid can be a variant of the nucleic acid having the nucleotide sequence set forth in SEQ ID NO:1115. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1115.

A low nitrogen tolerance-modulating nucleic acid can comprise the nucleotide sequence set forth in SEQ ID NO:1156. Alternatively, a low nitrogen tolerance-modulating nucleic acid can be a variant of the nucleic acid having the nucleotide sequence set forth in SEQ ID NO:1156. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1156.

A low nitrogen tolerance-modulating nucleic acid can comprise the nucleotide sequence set forth in SEQ ID NO:1158. Alternatively, a low nitrogen tolerance-modulating nucleic acid can be a variant of the nucleic acid having the nucleotide sequence set forth in SEQ ID NO:1158. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1158.

A low nitrogen tolerance-modulating nucleic acid can comprise the nucleotide sequence set forth in SEQ ID NO:1165. Alternatively, a low nitrogen tolerance-modulating nucleic acid can be a variant of the nucleic acid having the nucleotide sequence set forth in SEQ ID NO:1165. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1165.

A low nitrogen tolerance-modulating nucleic acid can comprise the nucleotide sequence set forth in SEQ ID NO:1184. Alternatively, a low nitrogen tolerance-modulating nucleic acid can be a variant of the nucleic acid having the nucleotide sequence set forth in SEQ ID NO:1184. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1184.

A low nitrogen tolerance-modulating nucleic acid can comprise the nucleotide sequence set forth in SEQ ID NO:1193. Alternatively, a low nitrogen tolerance-modulating nucleic acid can be a variant of the nucleic acid having the nucleotide sequence set forth in SEQ ID NO:1193. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1193.

A low nitrogen tolerance-modulating nucleic acid can comprise the nucleotide sequence set forth in SEQ ID NO: 1209. Alternatively, a low nitrogen tolerance-modulating nucleic acid can be a variant of the nucleic acid having the nucleotide sequence set forth in SEQ ID NO: 1209. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1209.

A low nitrogen tolerance-modulating nucleic acid can comprise the nucleotide sequence set forth in SEQ ID NO:1273. Alternatively, a low nitrogen tolerance-modulating nucleic acid can be a variant of the nucleic acid having the nucleotide sequence set forth in SEQ ID NO:1273. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1273.

A low nitrogen tolerance-modulating nucleic acid can comprise the nucleotide sequence set forth in SEQ ID NO:1301. Alternatively, a low nitrogen tolerance-modulating nucleic acid can be a variant of the nucleic acid having the nucleotide sequence set forth in SEQ ID NO:1301. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1301.

A low nitrogen tolerance-modulating nucleic acid can comprise the nucleotide sequence set forth in SEQ ID NO:1341. Alternatively, a low nitrogen tolerance-modulating nucleic acid can be a variant of the nucleic acid having the nucleotide sequence set forth in SEQ ID NO:1341. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1341.

A low nitrogen tolerance-modulating nucleic acid can comprise the nucleotide sequence set forth in SEQ ID NO:1384. Alternatively, a low nitrogen tolerance-modulating nucleic acid can be a variant of the nucleic acid having the nucleotide sequence set forth in SEQ ID NO:1384. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1384.

A low nitrogen tolerance-modulating nucleic acid can comprise the nucleotide sequence set forth in SEQ ID NO:1408. Alternatively, a low nitrogen tolerance-modulating nucleic acid can be a variant of the nucleic acid having the nucleotide sequence set forth in SEQ ID NO:1408. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1408.

A low nitrogen tolerance-modulating nucleic acid can comprise the nucleotide sequence set forth in SEQ ID NO:1427. Alternatively, a low nitrogen tolerance-modulating nucleic acid can be a variant of the nucleic acid having the nucleotide sequence set forth in SEQ ID NO:1427. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1427.

A low nitrogen tolerance-modulating nucleic acid can comprise the nucleotide sequence set forth in SEQ ID NO:1462. Alternatively, a low nitrogen tolerance-modulating nucleic acid can be a variant of the nucleic acid having the nucleotide sequence set forth in SEQ ID NO:1462. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1462.

A low nitrogen tolerance-modulating nucleic acid can comprise the nucleotide sequence set forth in SEQ ID NO:1490. Alternatively, a low nitrogen tolerance-modulating nucleic acid can be a variant of the nucleic acid having the nucleotide sequence set forth in SEQ ID NO:1490. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1490.

A low nitrogen tolerance-modulating nucleic acid can comprise the nucleotide sequence set forth in SEQ ID NO:1509. Alternatively, a low nitrogen tolerance-modulating nucleic acid can be a variant of the nucleic acid having the nucleotide sequence set forth in SEQ ID NO:1509. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1509.

A low nitrogen tolerance-modulating nucleic acid can comprise the nucleotide sequence set forth in SEQ ID NO:1524. Alternatively, a low nitrogen tolerance-modulating nucleic acid can be a variant of the nucleic acid having the nucleotide sequence set forth in SEQ ID NO:1524. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1524.

A low nitrogen tolerance-modulating nucleic acid can comprise the nucleotide sequence set forth in SEQ ID NO:1536. Alternatively, a low nitrogen tolerance-modulating nucleic acid can be a variant of the nucleic acid having the nucleotide sequence set forth in SEQ ID NO:1536. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1536.

A low nitrogen tolerance-modulating nucleic acid can comprise the nucleotide sequence set forth in SEQ ID NO:1553. Alternatively, a low nitrogen tolerance-modulating nucleic acid can be a variant of the nucleic acid having the nucleotide sequence set forth in SEQ ID NO:1553. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1553.

A low nitrogen tolerance-modulating nucleic acid can comprise the nucleotide sequence set forth in SEQ ID NO:1576. Alternatively, a low nitrogen tolerance-modulating nucleic acid can be a variant of the nucleic acid having the nucleotide sequence set forth in SEQ ID NO:1576. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1576.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Low Nitrogen Tolerance-Modulating Polypeptide A nucleic acid encoding one of the low nitrogen tolerance-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular low nitrogen tolerance-modulating polypeptide; i.e., for many amino acids, there is more than one nucleotide triplet that serves as the codon for the amino acid. Thus, codons in the coding sequence for a given low nitrogen tolerance-modulating polypeptide can be modified such that optimal expression in a particular plant species is obtained, using appropriate codon bias tables for that species.

In some cases, expression of a low nitrogen tolerance-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a Low Nitrogen Tolerance-Modulating Polypeptide

Polynucleotides and recombinant constructs described herein can be used to inhibit expression of a low nitrogen tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); Dorsett and Tuschl, *Nature Reviews Drug Discovery* 3: 318-329 (2004); and *Nature Reviews RNA interference collection*, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding low nitrogen tolerance-modulating polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al. (1995) *Proc. Natl. Acad. Sci. USA*, 92(13):6175-6179; de Feyter and Gaudron, Methods in Molecular Biology, Vol. 74, Chapter 43, "Expressing Ribozymes in Plants", Edited by Turner, P. C., Humana Press Inc., Totowa, NJ RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a low nitrogen tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the low nitrogen tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a low nitrogen tolerance-modulating polypeptide, and the other strand of the stem portion of the double stranded RNA comprises a sequence that is similar or identical to the sequence that is complementary to the 3' or 5' untranslated region, respectively, or a fragment thereof, of the mRNA encoding the low nitrogen tolerance-modulating polypeptide. In other embodiments, one strand of the stem portion of a double stranded RNA comprises a sequence that is similar or identical to the sequence of an intron, or a fragment thereof, in the pre-mRNA encoding a low nitrogen tolerance-modulating polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of a low nitrogen tolerance-modulating polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a low nitrogen tolerance-modulating polypeptide, or a fragment of such sequences. In some embodiments, the sense or antisense sequence is identical or complementary to a sequence of the regulatory region that drives transcription of the gene encoding a low nitrogen tolerance-modulating polypeptide. In each case, the sense sequence is the sequence that is complementary to the antisense sequence.

The sense and antisense sequences can be any length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a low nitrogen tolerance-modulating polypeptide described herein. The sense sequence complementary to the antisense sequence can be a sequence present within the mRNA of the low nitrogen tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.,* 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.,* 7:187-195; Hyrup et al. (1996) *Bioorgan. Med. Chem.,* 4:5-23. In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate low-nitrogen tolerance levels. A recombinant nucleic acid construct can comprise a nucleic acid encoding a low nitrogen tolerance-modulating polypeptide as described herein, operably linked to a regulatory region suitable for expressing the low nitrogen tolerance-modulating polypeptide in the plant or cell. Thus, a nucleic acid can comprise a coding sequence that encodes any of the low nitrogen tolerance-modulating polypeptides as set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. Examples of nucleic acids encoding low nitrogen tolerance-modulating polypeptides are set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576. The low nitrogen tolerance-modulating polypeptide encoded by a recombinant nucleic acid can be a native low nitrogen tolerance-modulating polypeptide, or can be heterologous to the cell. In some cases, the recombinant construct contains a nucleic acid that inhibits expression of a low nitrogen tolerance-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, 3-glucuronidase (GUS), green fluorescent protein (GFP), glutathione S-transferase (GST), polyhistidine, c-myc, hemagglutinin, or Flag™ tag (Kodak, New Haven, CT) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al. (1989) *Plant Cell*, 1:855-866; Bustos et al. (1989) *Plant Cell*, 1:839-854; Green et al. (1988) *EMBO J.*, 7:4035-4044; Meier et al. (1991) *Plant Cell*, 3:309-316; and Zhang et al. (1996) *Plant Physiology*, 110:1069-1079.

Examples of various classes of regulatory regions are described below. Some of the regulatory regions indicated below as well as additional regulatory regions are described in more detail in U.S. Patent Application Ser. Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al. (1989) *Proc. Natl. Acad. Sci. USA*, 86:7890-7894), root cell specific promoters reported by Conkling et al. (1990) *Plant Physiol.*, 93:1203-1211, and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al. (1989) *Plant Cell,* 1(9):839-853), the soybean trypsin inhibitor promoter (Riggs et al. (1989) *Plant Cell*, 1(6):609-621), the ACP promoter (Baerson et al. (1993) *Plant Mol. Biol.*, 22(2):255-267), the stearoyl-ACP desaturase promoter (Slocombe et al. (1994) *Plant Physiol.*, 104(4):167-176), the soybean a' sub-unit of β-conglycinin promoter (Chen et al. (1986) *Proc. Natl. Acad. Sci. USA*, 83:8560-8564), the oleosin promoter (Hong et al. (1997) *Plant Mol. Biol.*, 34(3):549-555), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al. (1993) *Mol. Cell Biol.*, 13:5829-5842), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmycl (see, Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics,* 142: 1009-1020); maize Cat3 (see, GenBank No. L05934; Abler (1993) *Plant Mol. Biol.*, 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp 1) promoter (*Plant Cell Rep* (2001) 20:647-654), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al. (1994) *Plant Cell Physiol.*, 35:773-778), the Cab-1 promoter from wheat (Fejes et al. (1990) *Plant Mol. Biol.*, 15:921-932), the CAB-1 promoter from spinach (Lubberstedt et al. (1994) *Plant Physiol.*, 104:997-1006), the cab1R promoter from rice (Luan et al. (1992) *Plant Cell*, 4:971-981), the pyruvate orthophosphate dikinase (PPDK) promoter from corn (Matsuoka et al. (1993) *Proc. Natl. Acad. Sci. USA*, 90:9586-9590), the tobacco Lhcb1*2 promoter (Cerdan et al. (1997) *Plant Mol. Biol.*, 33:245-255), the *Arabidopsis thaliana* SUC2 sucrose-H+ symporter promoter (Truernit et al. (1995) *Planta*, 196:564-570), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner (1991) *Plant Cell*, 3(10):1051-1061), the *Commelina* yellow mottle virus (CoYMV) promoter (Medberry et al. (1992) *Plant Cell*, 4(2):185-192), and the rice tungro bacilliform virus (RTBV) promoter (Dai et al. (2004) *Proc. Natl. Acad. Sci. USA*, 101(2):687-692).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) *Nature Biotech* 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and CryIA(b) and CryIA(c) (Braga et al. 2003, Journal of New Seeds 5:209-221).

xii. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a low nitrogen tolerance-modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. Transgenic Plants and Plant Cells

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous low nitrogen tolerance-modulating polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a low nitrogen tolerance-modulating polypeptide or nucleic acid. Physical and biochemical methods can be used to identify expression levels. These include Southern analysis or PCR amplification for detection of a polynucleotide; Northern blots, 51 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of low-nitrogen tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in low nitrogen tolerance level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

Suitable species include *Panicum* spp. or hybrid thereof, *Sorghum* spp. or hybrid thereof, sudangrass, *Miscanthus* spp. or hybrid thereof, *Saccharum* spp. or hybrid thereof, Erianthus spp., *Populus* spp., *Andropogon* gerardii (big bluestem), *Pennisetum purpureum* (elephant grass)) or hybrid thereof (e.g., *Pennisetum purpureum* x *Pennisetum typhoidum*), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed) or hybrid thereof, *Secale cereale* (rye), *Salix* spp. (willow), *Eucalyptus* spp. (*eucalyptus*), Triticosecale (*triticum*-wheat X rye), Tripsicum *dactyloides* (Eastern gammagrass), *Leymus cinereus* (basin wildrye), *Leymus condensates* (giant wildrye) and bamboo.

In some embodiments, a suitable species can be a wild, weedy, or cultivated *sorghum* species such as, but not limited to, *Sorghum almum, Sorghum amplum, Sorghum angustum, Sorghum arundinaceum, Sorghum bicolor* (such as *bicolor, guinea, caudatum, kafir,* and *durra*), *Sorghum brachypodum, Sorghum bulbosum, Sorghum burmahicum, Sorghum controversum, Sorghum drummondii, Sorghum* ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare, or hybrids such as Sorghum x almum, Sorghum x sudangrass or Sorghum x drummondii.

Suitable species also include Helianthus annuus (sunflower), Carthamus tinctorius (safflower), Jatropha curcas (jatropha), Ricinus communis (castor), Elaeis guineensis (palm), Linum usitatissimum (flax), and Brassica juncea.

Suitable species also include Beta vulgaris (sugarbeet), and Manihot esculenta (cassava).

Suitable species also include Lycopersicon esculentum (tomato), Lactuca sativa (lettuce), Musa paradisiaca (banana), Solanum tuberosum (potato), Brassica oleracea (broccoli, cauliflower, Brussels sprouts), Camellia sinensis (tea), Fragaria ananassa (strawberry), Theobroma cacao (cocoa), Coffea arabica (coffee), Vitis vinifera (grape), Ananas comosus (pineapple), Capsicum annum (hot & sweet pepper), Allium cepa (onion), Cucumis melo (melon), Cucumis sativus (cucumber), Cucurbita maxima (squash), Cucurbita moschata (squash), Spinacea oleracea (spinach), Citrullus lanatus (watermelon), Abelmoschus esculentus (okra), and Solanum melongena (eggplant).

Suitable species also include Papaver somniferum (opium poppy), Papaver orientale, Taxus baccata, Taxus brevifolia, Artemisia annua, Cannabis sativa, Camptotheca acuminata, Catharanthus roseus, Vinca rosea, Cinchona officinalis, Colchicum autumnale, Veratrum californica, Digitalis lanata, Digitalis purpurea, Dioscorea spp., Andrographis paniculata, Atropa belladonna, Datura stomonium, Berberis spp., Cephalotaxus spp., Ephedra sinica, Ephedra spp., Erythroxylum coca, Galanthus wornorii, Scopolia spp., Lycopodium serratum (=Huperzia serrata), Lycopodium spp., Rauwolfia serpentina, Rauwolfia spp., Sanguinaria canadensis, Hyoscyamus spp., Calendula officinalis, Chrysanthemum parthenium, Coleus forskohlii, and Tanacetum parthenium.

Suitable species also include Parthenium argentatum (guayule), Hevea spp. (rubber), Mentha spicata (mint), Mentha piperita (mint), Bixa orellana, and Alstroemeria spp.

Suitable species also include Rosa spp. (rose), Dianthus caryophyllus (carnation), Petunia spp. (petunia) and Poinsettia pulcherrima (poinsettia).

Suitable species also include Nicotiana tabacum (tobacco), Lupinus albus (lupin), Uniola paniculata (oats), bentgrass (Agrostis spp.), Populus tremuloides (aspen), Pinus spp. (pine), Abies spp. (fir), Acer spp. (maple), Hordeum vulgare (barley), Poa pratensis (bluegrass), Lolium spp. (ryegrass) and Phleum pratense (timothy).

Thus, the methods and compositions can be used over a broad range of plant species, including species from the dicot genera Brassica, Carthamus, Glycine, Gossypium, Helianthus, Jatropha, Parthenium, Populus, and Ricinus; and the monocot genera Elaeis, Festuca, Hordeum, Lolium, Oryza, Panicum, Pennisetum, Phleum, Poa, Saccharum, Secale, Sorghum, Triticosecale, Triticum, and Zea. In some embodiments, a plant is a member of the species Panicum virgatum (switchgrass), Sorghum bicolor (sorghum, sudangrass), Miscanthus giganteus (miscanthus), Saccharum sp. (energycane), Populus balsamifera (poplar), Zea mays (corn), Glycine max (soybean), Brassica napus (canola), Triticum aestivum (wheat), Gossypium hirsutum (cotton), Oryza sativa (rice), Helianthus annuus (sunflower), Medicago sativa (alfalfa), Beta vulgaris (sugarbeet), or Pennisetum glaucum (pearl millet).

In certain embodiments, the polynucleotides and vectors described herein can be used to transform a number of monocotyledonous and dicotyledenous plants and plant cell systems, wherein such plants are hybrids of different species or varieties of a specific species (e.g., Saccharum sp. X Miscanthus sp., Panicum virgatum x Panicum amarum, Panicum virgatum x Panicum amarulum, and Pennisetum purpureum x Pennisetum typhoidum).

D. Transgenic Plant Phenotypes

In some embodiments, a plant in which expression of a low nitrogen tolerance-modulating polypeptide is modulated can have increased levels of photosynthetic efficiency in seedlings. For example, a low nitrogen tolerance-modulating polypeptide described herein can be expressed in a transgenic plant, resulting in increased levels of photosynthetic efficiency in growth conditions with low nitrogen sources. The level of photosynthetic efficiency can be increased by at least 0.25 percent, e.g., 0.25, 1, 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of photosynthetic efficiency in a corresponding control plant that does not express the transgene. In some embodiments, a plant in which expression of a low nitrogen tolerance-modulating polypeptide is modulated can have decreased levels of photosynthetic efficiency. The level of photosynthetic efficiency can be decreased by at least 0.25 percent, e.g., 0.25, 1, 2, 3, 4, 5, 10, 15, 20, 25, 30, 35, or more than 35 percent, as compared to the level of photosynthetic in a corresponding control plant that does not express the transgene.

In some embodiments, a plant in which expression of a low nitrogen tolerance-modulating polypeptide is modulated can have increased or decreased levels of photosynthetic efficiency in one or more green tissues, e.g., leaves, stems, bulbs, flowers, fruits, young seeds. For example, the level of photosynthetic efficiency can be increased by at least 0.25 percent, e.g., 0.25, 1, 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of photosynthetic efficiency in a corresponding control plant that does not express the transgene. In some embodiments, a plant in which expression of a low nitrogen tolerance-modulating polypeptide is modulated can have decreased levels of photosynthetic efficiency in one or more green tissues. The level of photosynthetic efficiency can be decreased by at least 0.25 percent, e.g., 0.25, 1, 2, 3, 4, 5, 10, 15, 20, 25, 30, 35, or more than 35 percent, as compared to the level of photosynthetic efficiency in a corresponding control plant that does not express the transgene.

Increases in photosynthetic efficiency in low-nitrogen growth conditions in such plants can provide improved plant growth in geographic locales where plant's intake of nitrogenous fertilizers is often insufficient. Decreases in photosynthetic efficiency, and hence less tolerance to low-nitrogen growth conditions in such plants can be useful for removing weeds and such from the environment, by applying to weeds and such. For example, a plant capable of inducing the decrease in photosynthetic efficiency can be prepared to apply for land improvements and such.

Typically, a difference in the level of photosynthetic efficiency in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the level of photosynthetic is statistically significant at $p<0.01$, $p<0.005$, or p<0.001. A statistically significant difference in, for example, the level of photosynthetic efficiency in a transgenic plant compared to the amount in cells of a control plant indicates that the recombinant nucleic acid present in the transgenic plant results in altered levels of photosynthetic efficiency.

In some embodiments, a plant in which expression of a low nitrogen tolerance-modulating polypeptide is modulated can have increased growth rates in seedlings. For example, a low nitrogen tolerance-modulating polypeptide described herein can be expressed in a transgenic plant, resulting in increased growth rate in growth conditions of limiting nitrogen sources. The growth rate can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the growth rate in a corresponding control plant that does not express the transgene. In some embodiments, a plant in which expression of a low nitrogen tolerance-modulating polypeptide is modulated can have decreased growth rates. The growth rate can be decreased by at least 2 percent, e.g., 2, 3, 4, 5, 10, 15, 20, 25, 30, 35, or more than 35 percent, as compared to the growth rate in a corresponding control plant that does not express the transgene. Growth rate can be measured in seedlings, developing, or mature plants and measured for periods of time such as about 1 hour, 3 hours, 6 hours, 12 hours, 1 day, 3 days, 5 days, 10 days, 1 month, 3 months, 6 months, 12 months, or the entire lifespan of a plant.

In some embodiments, a plant in which expression of a low nitrogen tolerance-modulating polypeptide is modulated can have increased or decreased growth rates in one or more vegetative and reproductive tissues, e.g., leaves, stems, flowers, bulbs, fruits, young seeds. For example, the growth rate can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the growth rate in a corresponding control plant that does not express the transgene. In some embodiments, a plant in which expression of a low nitrogen tolerance-modulating polypeptide is modulated can have decreased levels of growth rate in one or more vegetative tissues. The growth rate can be decreased by at least 2 percent, e.g., 2, 3, 4, 5, 10, 15, 20, 25, 30, 35, or more than 35 percent, as compared to the growth rate in a corresponding control plant that does not express the transgene.

Increases in growth rate in low-nitrogen conditions in such plants can provide improved plant growth and initial establishment in geographic locales where plant's intake of nitrogenous fertilizers is often insufficient. Decreases in growth rate, and hence less tolerance to low-nitrogen growth conditions in such plants can be useful for engineering slow-growing plants, by applying to ornamentals and such. For example, a plant capable of inducing the decrease in growth rate can be prepared to apply for land improvements and such.

Typically, a difference in the growth rate of a transgenic plant or cell relative to a control plant or cell is considered statistically significant at p≤0.05 with an appropriate parametric or non-parametric statistic, e.g., Chi-square test, Student's t-test, Mann-Whitney test, or F-test. In some embodiments, a difference in the growth rate is statistically significant at p<0.01, p<0.005, or p<0.001. A statistically significant difference in, for example, the growth rate of a transgenic plant compared to the growth rate of a control plant indicates that the recombinant nucleic acid present in the transgenic plant results in altered growth rates.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, Si RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

V. Plant Breeding

Genetic polymorphisms are discrete allelic sequence differences in a population. Typically, an allele that is present at 1% or greater is considered to be a genetic polymorphism. The discovery that polypeptides disclosed herein can modulate photosynthetic efficiency and/or nitrogen content is useful in plant breeding, because genetic polymorphisms exhibiting a degree of linkage with loci for such polypeptides are more likely to be correlated with variation in a low-nitrogen tolerance trait. For example, genetic polymorphisms linked to the loci for such polypeptides are more likely to be useful in marker-assisted breeding programs to create lines having a desired modulation in the low-nitrogen tolerance trait.

Thus, one aspect of the invention includes methods of identifying whether one or more genetic polymorphisms are associated with variation in a low-nitrogen tolerance trait. Such methods involve determining whether genetic polymorphisms in a given population exhibit linkage with the locus for one of the polypeptides depicted in FIGS. 1-57, SEQ ID NO:556, SEQ ID NO:853, SEQ ID NO:1157 and/or a functional homolog thereof, such as, but not limited to those identified in the Sequence Listing of this application. The correlation is measured between variation in the low-nitrogen tolerance trait in plants of the population and the presence of the genetic polymorphism(s) in plants of the population, thereby identifying whether or not the genetic polymorphism(s) are associated with variation for the trait. If the presence of a particular allele is statistically significantly correlated with a desired modulation in the low-nitrogen tolerance trait, the allele is associated with variation for the trait and is useful as a marker for the trait. If, on the other hand, the presence of a particular allele is not significantly correlated with the desired modulation, the allele is not associated with variation for the trait and is not useful as a marker.

Such methods are applicable to populations containing the naturally occurring endogenous polypeptide rather than an exogenous nucleic acid encoding the polypeptide, i.e., populations that are not transgenic for the exogenous nucleic acid. It will be appreciated, however, that populations suitable for use in the methods may contain a transgene for another, different trait, e.g., herbicide resistance.

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. If the probes flank an SSR in the population, PCR products of different sizes will be produced. See, e.g., U.S. Pat. No. 5,766,847. Alternatively, SSR polymorphisms can be identified by using PCR product(s) as a probe against Southern blots from different individuals in the population. See, U. H. Refseth et al. (1997) *Electrophoresis* 18: 1519. The identification of RFLPs is discussed, for example, in Alonso-Blanco et al. (Methods in Molecular Biology, vol. 82, "*Arabidopsis* Protocols", pp. 137-146, J. M. Martinez-Zapater and J. Salinas, eds., c. 1998 by Humana Press, Totowa, NJ); Burr ("Mapping Genes with Recombinant Inbreds", pp. 249-254, in Freeling, M. and V. Walbot (Ed.), The Maize Handbook, c. 1994 by Springer-Verlag New York, Inc.: New York, NY, USA; Berlin Germany; Burr et al. (1998) *Genetics* 118: 519; and Gardiner, J. et al. (1993) *Genetics* 134: 917). The identification of AFLPs is discussed, for example, in EP 0 534 858 and U.S. Pat. No. 5,878,215.

In some embodiments, the methods are directed to breeding a plant line. Such methods use genetic polymorphisms identified as described above in a marker assisted breeding program to facilitate the development of lines that have a desired alteration in the low-nitrogen tolerance trait. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VI. Articles of Manufacture

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought or limiting nitrogen sources. In some embodiments, plants described herein have a composition that permits more efficient processing into free sugars, and subsequently ethanol, for energy production. In some embodiments, such plants provide higher yields of ethanol, butanol, dimethyl ether, other biofuel molecules, and/or sugar-derived co-products per kilogram of plant material, relative to control plants. Such processing efficiencies are believed to be derived from the nitrogenous composition of the plant material. By providing higher yields at an equivalent or even decreased cost of production, the transgenic plants described herein improve profitability for farmers and processors as well as decrease costs to consumers[RCL2].

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

The invention will be further described in the following examples, which do not limit the scope of the invention described in the claims.

VII. Examples

Example 1—Transgenic *Arabidopsis* Plants

The following symbols are used in the Examples with respect to *Arabidopsis* transformation: $T_1$: first generation transformant; $T_2$: second generation, progeny of self-pollinated $T_1$ plants; $T_3$: third generation, progeny of self-pollinated $T_2$ plants; $T_4$: fourth generation, progeny of self-pollinated $T_3$ plants. Independent transformations are referred to as events.

The following is a list of nucleic acids that were isolated from *Arabidopsis thaliana* plants, CeresClone: 29661 (SEQ ID NO:1), CeresClone: 251343 (SEQ ID NO:48), CeresClone: 19586 (SEQ ID NO:76), CeresClone: 25136 (SEQ ID NO:96), CeresClone: 1820 (SEQ ID NO:99), CeresClone: 13102 (SEQ ID NO:151), CeresClone: 15457 (SEQ ID NO:165), Ceres Annot: 859276 (SEQ ID NO:175), CeresClone: 17883 (SEQ ID NO:185), CeresClone: 251590 (SEQ ID NO:207), CeresClone: 4898 (SEQ ID NO:217), CeresClone: 148977 (SEQ ID NO:233), CeresClone: 24255 (SEQ ID NO:245), CeresClone: 38432 (SEQ ID NO:299), Ceres Annot: 553243 (SEQ ID NO:331), CeresClone: 1011900 (SEQ ID NO:367), CeresClone: 5232 (SEQ ID NO:509), CeresClone: 29302 (SEQ ID NO:532), CeresClone: 93971 (SEQ ID NO:555), Ceres Annot: 12669619_cDNA (SEQ ID NO:557), CeresClone: 21608 (SEQ ID NO:592), CeresClone: 2031 (SEQ ID NO:612), CeresClone: 94503 (SEQ ID NO:645), CeresClone: 21740 (SEQ ID NO:686), CeresClone: 5609 (SEQ ID NO:729), CeresClone: 3137 (SEQ ID NO:745), CeresClone: 32430 (SEQ ID NO:768), CeresClone: 101255 (SEQ ID NO:791), Ceres Annot: 573161 (SEQ ID NO:854), Ceres Annot: 552727 (SEQ ID NO:890), CeresClone: 732 (SEQ ID NO:1193), CeresClone: 2267 (SEQ ID NO:1209), CeresClone: 39358 (SEQ ID NO:1273), CeresClone: 115046 (SEQ ID NO:1301), Ceres Annot: 850581 (SEQ ID NO:1427), Ceres Annot: 862321 (SEQ ID NO:1462), Ceres Annot: 839064 (SEQ ID NO:1478), Ceres Annot: 864666 (SEQ ID NO:1490), Ceres Annot: 875012 (SEQ ID NO:1509), Ceres Annot: 874016 (SEQ ID NO:1524), Ceres Annot: 827304 (SEQ ID NO:1536), Ceres Annot: 869192 (SEQ ID NO:1553), and Ceres Annot: 876419 (SEQ ID NO:1576). The nucleic acid designated Ceres Clone:

968180 (SEQ ID NO:1115) was isolated from the species *Brassica napus*. The nucleic acid designated Ceres Clone: 1017441 (SEQ ID NO:224) was isolated from the species *Triticum aesticum*. The following is a list of nucleic acids that were isolated from *Zea mays* plants, CeresClone: 1387146 (SEQ ID NO:981), CeresClone: 1408950 (SEQ ID NO:1098, CeresClone: 208453 (SEQ ID NO:1111), Ceres-Clone: 208995 (SEQ ID NO:943), CeresClone: 225681 (SEQ ID NO:975), CeresClone: 239806 (SEQ ID NO:916), CeresClone: 244306 (SEQ ID NO:1053), CeresClone: 276809 (SEQ ID NO:823), CeresClone: 324216 (SEQ ID NO:852), CeresClone: 339439 (SEQ ID NO:1341), Ceres-Clone: 424522 (SEQ ID NO:827), CeresClone: 896483 (SEQ ID NO:1384), CeresClone: 986438 (SEQ ID NO:1156), CeresClone: 988083 (SEQ ID NO:1184), Ceres-Clone: 995409 (SEQ ID NO:1408), CeresClone: 996227 (SEQ ID NO:1158), and CeresClone: 996263 (SEQ ID NO:1165).

With the exception of Ceres Clone: 29661 (SEQ ID NO:1), each isolated nucleic acid described above was cloned into a Ti plasmid vector, CRS338, containing a phosphinothricin acetyltransferase gene which confers FINALE™ resistance to transformed plants. Constructs were made using CRS338 that contained SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576, each operably linked to a 35S promoter. Ceres Clone: 29661 (SEQ ID NO:1) was cloned into a Ti plasmid vector, CRS 311, containing a phosphinothricin acetyltransferase gene, which confers FINALE™ resistance to transformed plants. SEQ ID NO:1 was operably linked to a p32449 promoter in the constructs made using the CRS 331 vector. Wild-type *Arabidopsis thaliana* ecotype Wassilewskija (Ws) plants were transformed separately with each construct. The transformations were performed essentially as described in Bechtold et al. (1993) *C.R. Acad. Sci. Paris*, 316:1194-1199.

Transgenic *Arabidopsis* lines containing SEQ ID NO:1, SEQ ID NO:48, SEQ ID NO:76, SEQ ID NO:96, SEQ ID NO:99, SEQ ID NO:151, SEQ ID NO:165, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:224, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1478, SEQ ID NO:1490, SEQ ID NO:1509, SEQ ID NO:1524, SEQ ID NO:1536, SEQ ID NO:1553, SEQ ID NO:1576, or SEQ ID NO:175 were designated ME00919, ME01312, ME01463, ME01821, ME01910, ME02538, ME02603, ME02613, ME02801, ME03123, ME04204, ME04477, ME04507, ME04587, ME04753, ME04772, ME04909, ME05033, ME05194, ME05267, ME05300, ME05341, ME05392, ME05429, ME05493, ME05885, ME07344, ME07859, ME08464, ME09939, ME11735, ME12910, ME12927, ME12929, ME12954, ME12970, ME13006, ME13021, ME13064, ME13071, ME13087, ME13106, ME13107, ME13108, ME13110, ME13125, ME13149, ME13151, ME13153, ME13177, ME13200, ME13204, ME14649, ME16546, ME17457, ME17567, ME17932, ME17936, ME18275, ME18924, ME19182, or ME20628, respectively. The presence of each vector containing a nucleic acid described above in the respective transgenic *Arabidopsis* line transformed with the vector was confirmed by FINALE™ resistance, PCR amplification from green leaf tissue extract, and/or sequencing of PCR products. As controls, wild-type *Arabidopsis* ecotype Ws plants were transformed with the empty vector, either CRS338 or CRS311.

Example 2—Screening for Transgenic Plants Tolerant to Low-Nitrogen Growth Conditions A low-nitrogen tolerance screen was carried out on seedlings in order to identify transgenic lines that showed increased photosynthesis efficiency or seedling size or greenness under limiting nitrogen conditions relative to the internal control plants. The media used for the low-nitrogen tolerance assay contained 0.5% sucrose, 0.5×MS without nitrogen media (PhytoTech), 0.05% MES Hydrate, and 0.8% Phytagar. In addition, for low ammonium nitrate assay, 240 µM NH4NO3 was used as nitrogen source. For low nitrate assay, nitrogen source was 300 µM KNO3. pH of the media was adjusted to pH 5.7 using 10N KOH. Sterilized seeds were plated on agar plates and stratified for 2 days in the dark at 4° C. to promote uniform germination. Agar plates with germinating seedlings were placed horizontally in a CONVIRON® growth chamber set at 22° C., 16:8 hour light:dark cycle, 70% humidity with a combination of incandescent and fluorescent lamps emitting a light intensity of ~100µ Einsteins. The control plates were placed randomly within the set. Screen the seedlings daily starting at 14 days. In this screen, seedlings that were larger or greener relative to the internal controls on low nitrogen growth media were selected. As they were found each day, candidate seedlings were aseptically transplanted to standard MS germination plates for recovery. This intermediate recovery step was necessary before transplanting to soil to minimize the overall candidate mortality rate. The scoring and transplanting of candidates were continued until all remaining plants were small and yellowed from nitrogen stress. On the very last day of scoring, each plate was scanned for photosynthetic efficiency (Fv/Fm) on the chlorophyll fluorescence (CF) imager and scored as candidates and transplanted any extreme outliers on the high end of Fv/Fm scores. Fv/Fm ratio typically provides an estimate of the photosystem II (PSII) maximum efficiency within dark-adapted material where Fv is variable fluorescence, i.e. difference between minimum (Fo) and maximum (Fm) fluorescence signal, from dark-adapted material. This could be done visually by looking at the false color image for each seedling using the CF image analysis software (plants with high end Fv/Fm scores appear red). This step was typically done at ~24 days after germination. Seven days after being transferred to MS recovery plates, candidates were transplanted to soil (standard Sunshine:vermiculite 3:2 mix; Osmocote; Marathon). Five days after being transplanted to soil, candidates were sprayed with FINALE® [5 mL FINALE®/48 oz. water] to eliminate non-transgenics from the population. Two days after spraying with FINALE®, cauline leaf tissue of each candidate was collected for genomic DNA extraction, PCR, and sequencing to determine the identity of the transgene for each candidate.

Example 3—Validation Plate Assay

This assay was designed to validate transgenic lines that showed increased photosynthesis or size under limiting nitrogen conditions relative to the internal control. The media used for the low-nitrogen tolerance assay contained 0.5% sucrose, 0.5×MS without nitrogen media (PhytoTech), 0.05% MES Hydrate, and 0.8% Phytagar. pH of the media was adjusted to pH 5.7 using 10N KOH. In addition, for low ammonium nitrate assay, 240 µM $NH_4NO_3$ was used as nitrogen source. For low nitrate assay, nitrogen source was 300 µM $KNO_3$. Sterilized seeds were plated on agar plates and stratified for 2 days in the dark at 4° C. to promote uniform germination. Agar plates with germinating seedlings were placed horizontally in a CONVIRON® growth chamber set at 22° C., 16:8 hour light:dark cycle, 70% humidity with a combination of incandescent and fluorescent lamps emitting a light intensity of ~100 µEinsteins. The control plates were placed randomly within the set. Plates were scanned every other day using the CF Imager (after 45 minute of dark-acclimation) and were completed after all wild-type plants have completely yellowed. After the plates were scanned on the last day, they were sprayed with FINALE® (10 mL FINALE® into 48 oz. full-strength MS liquid media). Two days after spraying, each plate was dark-acclimated for 45 minutes and scanned for Fv/Fm on the CF imager and scored for each of the plants at each time point. For each separate time point, the data for all the $T_2$ transgenic plants across an event was pooled and a one-tailed t-test was used to compare both the Fv/Fm ratios and rosette areas relative to the pooled non-transgenics across the same plate. Whenever possible, this process was repeated for the $T_3$ generation plants. A low nitrogen tolerant candidate was confirmed when the transgenic Fv/Fm ratio and/or rosette area was greater than the wild-type segregants with a p-value ≤0.05 in 2 or more events in both generations Example 4—Validation Soil Assay A Low, Medium, and High Nitrogen experiment on soil was carried out to assess phenotypic characteristics at a mature point in the life cycle of *Arabidopsis*, as compared to seedling screens. The lines to be tested were originally identified through superpool screens for low nitrate and low ammonium nitrate tolerance. These lines were later individually assayed as seedlings on low nitrate and low ammonium nitrate agar. For this assay, MetroMix200 soil was mixed with vermiculite and Marathon™ (MetroMix200: vermiculite 3:2 mix; Osmocote; Marathon) autoclaved and cooled before use. Experimental plants and controls were randomized across the flats. Prior to sowing seed, each flat was watered with 3 L filtered water. Flats with 24 wells were filled with the following 3:2 ratios of MetroMix200 to Thermorock vermiculite. At the beginning of the experiment no nitrogen was provided until 2 weeks after germination when ¼ Hoaglands supplemented with $KNO_3$ at 25 ppm, 250 ppm, and 1500 ppm were used to water the flats from beneath.

Seeds were stratified on soil and in the dark at 4° C. for 3 days. After the cold treatment, flats were transferred to the growth chamber. Plants were grown for approximately 5 weeks, or until full grown/mature. Plants were then dark-acclimated for one hour. Chlorophyll fluorescence images were taken using a CF-Imager (Technologica, UK) according to the manufacturer's protocol to measure the performance and efficiency of photosystem II: 1) Fv/Fm, maximum photosystem II efficiency 2) Fq'/Fm', operating efficiency and 3) non-photochemical quenching (NPQ).

One week after watering with ¼ Hoaglands supplemented with various $KNO_3$ concentrations, plant rosette area measurements were taken using the WhinRhizo imaging software (Reagent Instruments, Canada). The plants were then collected in manila envelopes, placed in a 125° C. drying oven for 1-2 days and weighed.

Example 5—Analysis of ME00919 Events

ME00919 contains Ceres Clone: 29661 (At3g61880, SEQ ID NO:1) from *Arabidopsis thaliana*, which encodes a 534 amino acid cytochrome P450 protein. Evaluation of low-nitrogen tolerance for ME00919 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -03, showed significantly increased photosynthetic efficiency relative to the internal controls in both generations at p≤0.05 using a one-tailed t-test assuming unequal variance. A summary of photosynthetic efficiency of ME00919 seedlings on low ammonium nitrate-containing media are shown in Table 1. Events -01 and -03 segregated 15:1 and 3:1 (R:S), respectively, for FINALE™ resistance in the $T_2$ generation. ME00919 events were also tested for enhanced growth on the low ammonium nitrate media. No significant differences between the transgenics and the controls were observed.

TABLE 1 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME00919 | ME00919-01 ($T_2$) | 0.65641304 | 46 | 0.595818 | 11 | $2.48 \times 10^{-2}$ |
| ME00919 | ME00919-01 ($T_3$) | 0.66348780 | 41 | 0.595818 | 11 | $1.55 \times 10^{-2}$ |
| ME00919 | ME00919-03 ($T_2$) | 0.67212195 | 41 | 0.634026 | 38 | $3.35 \times 10^{-3}$ |
| ME00919 | ME00919-03 ($T_3$) | 0.69278947 | 19 | 0.634026 | 38 | $2.39 \times 10^{-5}$ |

Events -01 and -03 of ME00919 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 6—Analysis of ME01312 Events

ME01312 contains Ceres Clone: 251343 (At3g21270, SEQ ID NO:48) from *Arabidopsis thaliana*, which encodes a 204 amino acid Dof zinc finger protein. Ceres Clone: 251343 shares approximately 40% amino acid identity to the corn Dof1 gene, which when overexpressed in *Arabidopsis*, has shown to confer tolerance to plants receiving low nitrogen stress (Yanagisawa et al., 2004). Evaluation of low-nitrogen tolerance for ME01312 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -11, showed significantly enhanced photosynthetic efficiency on either low nitrate or low ammonium nitrate-containing media after 16 and 17 days compared to the internal controls in both generations at $p \leq 0.05$ using a one-tailed t-test assuming unequal variance. Event -03 had a slightly greater p-value than 0.05 in the $T_3$ generation for the low nitrate screen, significant at $p \leq 0.10$. A summary of photosynthetic efficiency of ME01312 seedlings on either low nitrate or low ammonium nitrate-containing media is shown in Table 2. Events -03 and -11 segregated 3:1 (R:S), respectively, for FINALE™ resistance in the $T_2$ generation.

TABLE 2

| Line | Events | Transgenic Fv/Fm | n | Pooled Non-Transgenics Fv/Fm | n | t-test p-value |
|---|---|---|---|---|---|---|
| A. T-test comparison of photosynthetic efficiency between transgenic seedlings and pooled non-transgenic segregants after 16 days of growth on low nitrate. | | | | | | |
| ME01312 | ME01312-03 ($T_2$) | 0.63 | 38 | 0.60 | 58 | 0.03 |
| ME01312 | ME01312-03 ($T_3$) | 0.63 | 38 | 0.60 | 58 | 0.07 |
| ME01312 | ME01312-11 ($T_2$) | 0.64 | 41 | 0.60 | 58 | 0.019 |
| ME01312 | ME01312-11 ($T_3$) | 0.64 | 47 | 0.60 | 58 | $9.89 \times 10^{-3}$ |
| B. T-test comparison of photosynthetic efficiency between transgenic seedlings and pooled non-transgenic segregants after 17 days of growth on low ammonium nitrate. | | | | | | |
| ME01312 | ME01312-03 ($T_2$) | 0.64 | 36 | 0.61 | 88 | $2.64 \times 10^{-3}$ |
| ME01312 | ME01312-03 ($T_3$) | 0.66 | 27 | 0.61 | 88 | $1.87 \times 10^{-5}$ |
| ME01312 | ME01312-11 ($T_2$) | 0.65 | 35 | 0.61 | 88 | $7.06 \times 10^{-4}$ |
| ME01312 | ME01312-11 ($T_3$) | 0.64 | 37 | 0.61 | 88 | 0.011 |

Events -03-11 of ME01312 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 7—Analysis of ME01463 Events

ME01463 contains Ceres Clone: 19586 (At1g80600, SEQ ID NO:76) from *Arabidopsis thaliana*, which encodes a 457 acetylornithine aminotransferase, a member of the Class-III aminotransferase family. Evaluation of low-nitrogen tolerance for ME01463 in two generations was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -06, and -10, showed significantly increased photosynthetic efficiency on low ammonium nitrate containing-media relative to the internal controls in both generations at $p \leq 0.05$ using a one-tailed t-test assuming unequal variance. A summary of photosynthetic efficiency of ME01463 seedlings is shown in Table 3. Events -02, -06, and -10 segregated 2:1, 2:1 and 3:1 (R:S), respectively, for FINALE™ resistance in the $T_2$ generation. ME01463 events were also tested for enhanced growth on the low ammonium nitrate media. No significant differences between the transgenics and the controls were observed (data not shown).

TABLE 3

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME01463 | ME01463-02 ($T_3$) | 0.6815 | 26 | 0.6376 | 122 | $2.47 \times 10^{-4}$ |
| ME01463 | ME01463-02 ($T_4$) | 0.6701 | 41 | 0.6376 | 122 | $1.57 \times 10^{-3}$ |
| ME01463 | ME01463-06 ($T_3$) | 0.6615 | 31 | 0.6376 | 122 | $2.37 \times 10^{-2}$ |
| ME01463 | ME01463-06 ($T_4$) | 0.6881 | 35 | 0.6376 | 122 | $5.85 \times 10^{-6}$ |
| ME01463 | ME01463-10 ($T_2$) | 0.6699 | 33 | 0.6376 | 122 | $2.25 \times 10^{-3}$ |
| ME01463 | ME01463-10 ($T_3$) | 0.6809 | 18 | 0.6376 | 122 | $4.60 \times 10^{-4}$ |

Events -02, -06, and -10 of ME01463 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 8—Analysis of ME01821 Events

ME01821 contains Ceres Clone: 25136 (At1g65500, SEQ ID NO:96) from *Arabidopsis thaliana*, which encodes a 86 amino acid protein of unknown function. Evaluation of low-nitrogen tolerance for ME01821 in $T_2$ generation was conducted under the same conditions as described in Examples 2 and 3. In this study, the seedling photosynthetic efficiency was measured as Fv/Fm comparing transgenic plants within an event to non-transgenic segregants pooled across the same plate. Three events, -01, -04 and -05, showed significantly increased photosynthetic efficiency on low nitrate-containing media relative to the internal controls in $T_2$ generation. Two events, -04 and -05, showed significantly increased photosynthetic efficiency on low ammonium nitrate-containing media relative to the internal controls in $T_2$ generation at p≤0.05 using a one-tailed t-test assuming unequal variance. A summary of photosynthetic efficiency of ME01821 seedlings is shown in Table 4.

TABLE 4

| Line | Events | Transgenic Fv/Fm | n | Pooled Non-Transgenics Fv/Fm | n | t-test p-value |
|---|---|---|---|---|---|---|
| A. T-test comparison of seedling photosynthetic efficiency between transgenic seedlings and pooled non-transgenic segregants after 14 days of growth on low nitrate. | | | | | | |
| ME01821 | ME01821-01 ($T_2$) | 0.6745 | 15 | 0.6520 | 33 | $3.76 \times 10^{-2}$ |
| ME01821 | ME01821-04 ($T_2$) | 0.6826 | 17 | 0.6614 | 14 | $2.76 \times 10^{-2}$ |
| ME01821 | ME01821-05 ($T_2$) | 0.6826 | 20 | 0.6614 | 14 | $3.74 \times 10^{-2}$ |
| B. T-test comparison of seedling photosynthetic efficiency between transgenic seedlings and pooled non-transgenic segregants after 18 days of growth on low ammonium nitrate. | | | | | | |
| ME01821 | ME01821-04 ($T_2$) | 0.7422 | 13 | 0.7166 | 21 | $5.20 \times 10^{-3}$ |
| ME01821 | ME01821-05 ($T_2$) | 0.7426 | 19 | 0.7166 | 21 | $6.07 \times 10^{-3}$ |

A summary of the enhanced growth of ME01812 events on either low nitrate- or low ammonium nitrate-containing media is shown in Table 5. For two events -01 and -05, transgenic seedlings were found significantly larger than the pooled non-transgenic segregants after 14 days of growth on low nitrate-containing media (Table 5A). Transgenic seedlings of two events -02 and -05 were found significantly larger than the pooled non-transgenic segregants after 14 days of growth on low ammonium nitrate-containing media (Table 5B). In this study, the seedling area for transgenic plants within an event was compared to the seedling area for non-transgenic segregants pooled across the same line.

TABLE 5A

T-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME01821 | ME01821-01 ($T_2$) | 0.0608 | 15 | 0.0555 | 33 | $3.97 \times 10^{-2}$ |
| ME01821 | ME01821-05 ($T_2$) | 0.0666 | 20 | 0.0530 | 14 | $3.05 \times 10^{-6}$ |

TABLE 5B

T-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME01821 | ME01821-02 ($T_2$) | 0.0750 | 19 | 0.0567 | 21 | $8.94 \times 10^{-5}$ |
| ME01821 | ME01821-05 ($T_2$) | 0.0680 | 19 | 0.0567 | 21 | $7.89 \times 10^{-3}$ |

Example 9—Analysis of ME01910 Events

ME01910 contains Ceres Clone: 1820 (At2g30620, SEQ ID NO:99) from *Arabidopsis thaliana*, which encodes a 273 amino acid linker histone H1 and H5 family protein. Evaluation of low-nitrogen tolerance for ME01910 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency relative to the internal controls in both generations at p≤0.05 using a one-tailed t-test assuming unequal variance. A summary of photosynthetic efficiency of ME01910 seedlings is shown in Table 6. Events -01 and -02 segregated 3:1 (R:S) for FINALE™ resistance in the $T_2$ generation. ME01910 events were also tested for enhanced growth on the low ammonium nitrate media. No significant differences between the transgenics and the controls were observed.

TABLE 6 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME01910 | ME01910-01 ($T_2$) | 0.60433 | 39 | 0.56396 | 27 | $2.03 \times 10^{-2}$ |
| ME01910 | ME01910-01 ($T_3$) | 0.61274 | 31 | 0.56396 | 27 | $9.23 \times 10^{-3}$ |
| ME01910 | ME01910-02 ($T_2$) | 0.62705 | 37 | 0.58083 | 29 | $7.39 \times 10^{-3}$ |
| ME01910 | ME01910-02 ($T_3$) | 0.64146 | 24 | 0.58083 | 29 | $9.23 \times 10^{-4}$ |

Events -01 and -02 of ME01910 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 10—Analysis of ME02538 Events

ME02538 contains Ceres Clone: 13102 (At1g67920, SEQ ID NO:151) from *Arabidopsis thaliana*, which encodes a 67 amino acid protein of unknown function. Evaluation of low-nitrogen tolerance for ME02538 in $T_2$ generation was conducted under the same conditions as described in Example 2. In this study, the seedling photosynthetic efficiency was measured as Fv/Fm comparing transgenic plants within an event to non-transgenic segregants pooled across the same plate. Two events, --04 and -05, showed significantly increased photosynthetic efficiency relative to the internal controls in $T_2$ generation on both low nitrate-containing and ammonium nitrate-containing media at p≤0.05 using a one-tailed t-test assuming unequal variance. A summary of photosynthetic efficiency of ME01821 seedlings is shown in Table 7.

TABLE 7

| Line | Events | Transgenic Fv/Fm | n | Pooled Non-Transgenics Fv/Fm | n | t-test p-value |
|---|---|---|---|---|---|---|
| A. T-test comparison of seedling photosynthetic efficiency between transgenic seedlings and pooled non-transgenic segregants after 14 days of growth on low nitrate. | | | | | | |
| ME02538 | ME02538-04 ($T_2$) | 0.6686 | 15 | 0.6171 | 24 | $1.92 \times 10^{-4}$ |
| ME02538 | ME02538-05 ($T_2$) | 0.6420 | 20 | 0.6171 | 24 | $4.84 \times 10^{-2}$ |

TABLE 7-continued

| | | Transgenic | | Pooled Non-Transgenics | | t-test |
|---|---|---|---|---|---|---|
| Line | Events | Fv/Fm | n | Fv/Fm | n | p-value |
| B. T-test comparison of seedling photosynthetic efficiency between transgenic seedlings and pooled non-transgenic segregants after 18 days of growth on low ammonium nitrate. | | | | | | |
| ME02538 | ME02538-04 ($T_2$) | 0.7345 | 13 | 0.7080 | 22 | $4.45 \times 10^{-3}$ |
| ME02538 | ME02538-05 ($T_2$) | 0.7356 | 20 | 0.7080 | 22 | $5.93 \times 10^{-3}$ |

ME02538 events were also tested for enhanced growth on the low ammonium nitrate media. A summary of the growth assay performed on ME01812 events is shown in Table 8. Transgenic seedlings of two events -01 and -02 were found significantly larger than the pooled non-transgenic segregants on both low nitrate—(Table 8A) and low ammonium nitrate-containing media (Table 8B).

TABLE 8A

T-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME02538 | ME02538-01 ($T_2$) | 0.0655 | 16 | 0.0558 | 36 | $2.80 \times 10^{-4}$ |
| ME02538 | ME02538-02 ($T_2$) | 0.0651 | 13 | 0.0601 | 20 | $1.32 \times 10^{-2}$ |

TABLE 8B

T-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME02538 | ME02538-01 ($T_2$) | 0.0856 | 15 | 0.0737 | 39 | $8.60 \times 10^{-3}$ |
| ME02538 | ME02538-02 ($T_2$) | 0.0864 | 14 | 0.0776 | 22 | $3.13 \times 10^{-2}$ |

Example 11—Analysis of ME02603 Events

ME02603 contains Ceres Clone: 15457 (At5g47610, SEQ ID NO:165) from *Arabidopsis thaliana*, which encodes a 166 amino acid zinc ion binding protein. Evaluation of low-nitrogen tolerance for ME02603 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME02603 seedlings is shown in Table 9. Events -01 and -04 segregated 3:1 (R:S) for FINALE™ resistance in the $T_2$ generation. Transgenic plants of two events -01 and -04—were also tested for enhanced photosynthetic efficiency on the low nitrate media. No significant differences between the transgenics and the controls were observed.

TABLE 9

T-test comparison of photosynthetic efficiency between transgenic seedlings and pooled non-transgenic segregants after 17 days (21 days for the $T_2$ generation of ME02603-01) of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME02603 | ME02603-01 ($T_2$) | 0.61 | 10 | 0.54 | 32 | $9.00 \times 10^{-4}$ |
| ME02603 | ME02603-01 ($T_3$) | 0.67 | 28 | 0.65 | 62 | $6.11 \times 10^{-3}$ |
| ME02603 | ME02603-04 ($T_2$) | 0.69 | 25 | 0.65 | 62 | $4.45 \times 10^{-5}$ |
| ME02603 | ME02603-04 ($T_3$) | 0.68 | 24 | 0.65 | 62 | $7.53 \times 10^{-3}$ |

Events -01 and -04 of ME02603 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 12—Analysis of ME02613 Events

ME02613 contains Ceres Clone: 17883 (At3g13910, SEQ ID NO:185) from *Arabidopsis thaliana*, which encodes a 102 amino acid protein of unknown function. Evaluation of low-nitrogen tolerance for ME02613 in $T_2$ generation was conducted under the same conditions as described in Examples 2 and 3. In this study, the seedling photosynthetic efficiency was measured as Fv/Fm comparing transgenic plants within an event to non-transgenic segregants pooled across the same plate. In $T_2$ generation, two events, -01 and -04, showed significantly increased photosynthetic efficiency on low nitrate containing-media relative to the internal controls in $T_2$ generation at p≤0.05 using a one-tailed t-test assuming unequal variance. Two events, -03 and -04, showed significantly increased photosynthetic efficiency on low ammonium nitrate containing-media relative to the internal controls in $T_2$ generation at p≤0.05 using a one-tailed t-test assuming unequal variance. A summary of photosynthetic efficiency of ME02613 seedlings is shown in Table 10.

TABLE 10

| | | Transgenic | | Pooled Non-Transgenics | | t-test |
|---|---|---|---|---|---|---|
| Line | Events | Fv/Fm | n | Fv/Fm | n | p-value |
| A. T-test comparison of seedling photosynthetic efficiency between transgenic seedlings and pooled non-transgenic segregants after 18 days of growth on low ammonium nitrate. | | | | | | |
| ME02613 | ME02613-01 ($T_2$) | 0.6979 | 16 | 0.6630 | 21 | $1.45 \times 10^{-2}$ |
| ME02613 | ME02613-04 ($T_2$) | 0.7046 | 13 | 0.6630 | 21 | $5.73 \times 10^{-4}$ |
| B. T-test comparison of seedling photosynthetic efficiency between transgenic seedlings and pooled non-transgenic segregants after 18 days of growth on low ammonium nitrate. | | | | | | |
| ME02613 | ME02613-03 ($T_2$) | 0.7270 | 9 | 0.7068 | 29 | $4.34 \times 10^{-2}$ |
| ME02613 | ME02613-04 ($T_2$) | 0.7485 | 15 | 0.7068 | 29 | $7.09 \times 10^{-5}$ |

A summary of the enhanced growth of ME02613 events on either low nitrate- or low ammonium nitrate-containing media is shown in Table 11. For two events -01 and -03, transgenic seedlings were found significantly larger than the pooled non-transgenic segregants after 14 days of growth on low nitrate-containing media (Table 11A). Transgenic seedlings of two events -02 and -03 were found significantly larger than the pooled non-transgenic segregants after 14 days of growth on low ammonium nitrate-containing media (Table 11B).

TABLE 11A

T-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME02613 | ME02613-01 ($T_2$) | 0.05706 | 16 | 0.05259 | 31 | $4.71 \times 10^{-2}$ |
| ME02613 | ME02613-03 ($T_2$) | 0.06236 | 12 | 0.05789 | 29 | $2.39 \times 10^{-2}$ |

TABLE 1

T-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME02613 | ME02613-02 ($T_2$) | 0.08324 | 14 | 0.07018 | 29 | $2.72 \times 10^{-4}$ |
| ME02613 | ME02613-03 ($T_2$) | 0.08273 | 9 | 0.07018 | 29 | $1.41 \times 10^{-2}$ |

Example 13—Analysis of ME02801 Events

ME02801 contains Ceres Clone: 251590 (At3g53080, SEQ ID NO:207) from *Arabidopsis thaliana*, which encodes a 155 amino acid protein of unknown function. Evaluation of low-nitrogen tolerance for ME02801 in $T_2$ and $T_3$ was conducted under the same conditions as described in Example 2 and 3. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at p≤0.05 using a one-tailed t-test assuming unequal variance. A summary of photosynthetic efficiency of ME02801 seedlings is shown in Table 12. Events -02 and -04 segregated 3:1 (R:S) for FINALE™ resistance in the $T_2$ generation. ME02801 events were also tested for enhanced growth on the low nitrate media and enhanced photosynthetic efficiency and growth on low ammonium nitrate media. No significant differences between the transgenics and the controls were observed.

TABLE 12 t-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME02801 | ME02801-02 ($T_2$) | 0.536385 | 39 | 0.465903 | 113 | $5.49 \times 10^{-7}$ |
| ME02801 | ME02801-02 ($T_3$) | 0.536465 | 43 | 0.465903 | 113 | $5.11 \times 10^{-7}$ |

TABLE 12-continued t-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME02801 | ME02801-04 ($T_2$) | 0.532419 | 31 | 0.465903 | 113 | $1.28 \times 10^{-5}$ |
| ME02801 | ME02801-04 ($T_3$) | 0.510406 | 32 | 0.465903 | 113 | $1.74 \times 10^{-2}$ |

Events -02 and -04 of ME02801 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 14—Analysis of ME03123 Events

ME03123 contains Ceres Clone: 4898 (At1g29970, SEQ ID NO:217) from *Arabidopsis thaliana*, which encodes a 158 amino acid protein of unknown function. Evaluation of low-nitrogen tolerance for ME03123 in $T_2$ and/or $T_3$ was conducted under the same conditions as described in Examples 2 and 3. In this study, the seedling photosynthetic efficiency was measured as Fv/Fm comparing transgenic plants within an event to non-transgenic segregants pooled across the same plate. A summary of photosynthetic efficiency of ME03123 seedlings is shown in Table 13. Two events, -01 and -10, showed significantly increased photosynthetic efficiency on low nitrate- or low ammonium nitrate-containing media relative to the internal controls in $T_2$ or $T_3$ generation at p≤0.05 using a one-tailed t-test assuming unequal variance.

TABLE 13

A.
T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME03123 | ME03123-01 ($T_2$) | 0.6282 | 15 | 0.5732 | 26 | $6.60 \times 10^{-5}$ |
| ME03123 | ME03123-10 ($T_3$) | 0.6069 | 12 | 0.5732 | 26 | $1.05 \times 10^{-2}$ |

B.
T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME03123 | ME03123-01 ($T_2$) | 0.6736 | 17 | 0.6315 | 16 | $1.74 \times 10^{-2}$ |

TABLE 13-continued

| | | | | | | |
|---|---|---|---|---|---|---|
| ME03123 | ME03123-10 (T$_3$) | 0.6699 | 20 | 0.6315 | 16 | $1.60 \times 10^{-2}$ |

ME03123 events were also tested for enhanced growth on the low ammonium nitrate media. In this assay, transgenic seedlings of ME03123-02 and ME03123-04 (T$_2$) were significantly larger than the pooled non-transgenic segregants after 14 days of growth on low nitrate (Table 14).

TABLE 14

T-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME03123 | ME03123-02 (T$_2$) | 0.07235 | 19 | 0.05623 | 20 | $1.41 \times 10^{-6}$ |
| ME03123 | ME03123-04 (T$_3$) | 0.06571 | 7 | 0.05729 | 41 | $7.74 \times 10^{-3}$ |

Example 15—Analysis of ME04204 Events

ME04204 contains Ceres Clone: 148977 (At1g78770, SEQ ID NO:233) from *Arabidopsis thaliana*, which encodes a 159 amino acid anaphase promoting complex/cyclosome subunit protein. However, it is also possible that this is natural variant transcript produced by the plant, because multiple annotations for locus At1g78770 were found in public domain. Evaluation of low-nitrogen tolerance for ME04204 in T$_2$ and T$_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency relative to the internal controls in both generations at p≤0.05 using a one-tailed t-test assuming unequal variance. A summary of photosynthetic efficiency of ME04204 seedlings is shown in Table 15. Events -01 and -05 segregated 3:1 (R:S) for FINALE™ resistance in the T$_2$ generation. ME04204 events were also tested for enhanced growth on the low nitrate media. No significant differences between the transgenics and the controls were observed.

TABLE 15

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME04204 | ME04204-01 (T$_2$) | 0.623676 | 34 | 0.585504 | 121 | $2.15 \times 10^{-4}$ |
| ME04204 | ME04204-01 (T$_3$) | 0.627706 | 17 | 0.585504 | 121 | $8.22 \times 10^{-5}$ |
| ME04204 | ME04204-05 (T$_2$) | 0.615857 | 35 | 0.585504 | 121 | $9.41 \times 10^{-3}$ |
| ME04204 | ME04204-05 (T$_3$) | 0.611419 | 43 | 0.585504 | 121 | $1.25 \times 10^{-2}$ |

Events -01 and -05 of ME04204 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 16—Analysis of ME04477 Events

ME04477 contains Ceres Clone: 24255 (At2g36320, SEQ ID NO:245) from *Arabidopsis thaliana*, which encodes a 161 amino acid DNA binding/zinc ion binding protein. Evaluation of low-nitrogen tolerance for ME04477 in T$_2$ and T$_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at p≤0.05 using a one-tailed t-test assuming unequal variance. A summary of photosynthetic efficiency of ME04477 seedlings is shown in Table 16. Events -01 and -05 segregated 3:1 (R:S) for FINALE™ resistance in the T$_2$ generation. ME04477 events were also tested for enhanced growth on the low nitrate media. No significant differences between the transgenics and the controls were observed.

TABLE 16

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME04204 | ME04204-01 (T$_2$) | 0.623676 | 34 | 0.585504 | 121 | $2.15 \times 10^{-4}$ |
| ME04204 | ME04204-01 (T$_3$) | 0.627706 | 17 | 0.585504 | 121 | $8.22 \times 10^{-5}$ |
| ME04204 | ME04204-05 (T$_2$) | 0.615857 | 35 | 0.585504 | 121 | $9.41 \times 10^{-3}$ |
| ME04204 | ME04204-05 (T$_3$) | 0.611419 | 43 | 0.585504 | 121 | $1.25 \times 10^{-2}$ |

Events -01 and -05 of ME04477 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 17—Analysis of ME04507 Events

ME04507 contains Ceres Clone: 38432 (At4g38250, SEQ ID NO:299) from *Arabidopsis thaliana*, which encodes a 436 amino acid transmembrane amino acid transporter protein. Evaluation of low-nitrogen tolerance for ME04507 in T$_2$ and T$_3$ was conducted under the same conditions as described in Example 2. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low nitrate-containing media relative to the internal controls in both generations at p≤0.05 using a one-tailed t-test assuming unequal variance. A summary of photosynthetic efficiency of ME04507 seedlings is shown in Table 17. Events -03 and -04 segregated 15:1 and 3:1 (R:S), respectively, for FINALE™ resistance in the $T_2$ generation. ME04507 events were also tested for enhanced growth on the low nitrate media. No significant differences between the transgenics and the controls were observed.

TABLE 17

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME04507 | ME04507-03 ($T_2$) | 0.57753 | 40 | 0.53084 | 103 | 4.90 × 10$^{-4}$ |
| ME04507 | ME04507-03 ($T_3$) | 0.56318 | 39 | 0.53084 | 103 | 2.64 × 10$^{-2}$ |
| ME04507 | ME04507-04 ($T_2$) | 0.57708 | 38 | 0.53084 | 103 | 6.12 × 10$^{-3}$ |
| ME04507 | ME04507-04 ($T_3$) | 0.57277 | 22 | 0.53084 | 103 | 2.35 × 10$^{-2}$ |

Events -03 and -04 of ME04507 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 18—Analysis of ME04587 Events

ME04587 contains Ceres Annot: 553243 (At2g27010, SEQ ID NO:331) from *Arabidopsis thaliana*, which encodes a 516 amino acid cytochrome P450 protein. Evaluation of low-nitrogen tolerance for ME04587 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at p≤0.05 using a one-tailed t-test assuming unequal variance. A summary of photosynthetic efficiency of ME04587 seedlings is shown in Table 18. In $T_2$ generation, events -01 and -02 segregated 1:1 and 47:1 respectively (R:S) for FINALE™ resistance. These two events segregated 2:1 and 7:1 respectively (R:S) for FINALE® resistance in the $T_3$ generation.

TABLE 18

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME04587 | ME04587-01 ($T_2$) | 0.6424 | 10 | 0.5437 | 30 | 2.48 × 10$^{-3}$ |
| ME04587 | ME04587-01 ($T_3$) | 0.6165 | 25 | 0.5437 | 30 | 1.24 × 10$^{-2}$ |
| ME04587 | ME04587-02 ($T_2$) | 0.6022 | 47 | 0.5437 | 30 | 3.08 × 10$^{-2}$ |
| ME04587 | ME04587-02 ($T_3$) | 0.6310 | 43 | 0.5437 | 30 | 3.68 × 10$^{-3}$ |

ME04587 events were also tested for enhanced growth on the low ammonium nitrate media. In addition, these events were tested on low nitrate media for increased seedling area and photosynthetic efficiency. No statistically significant differences between the transgenics and the controls were observed.

Events -01 and -02 of ME04587 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 19—Analysis of ME04753 Events

ME04753 contains Ceres Clone: 1011900 (At2g21660, SEQ ID NO:367) from *Arabidopsis thaliana*, which encodes a 130 amino acid glycine-rich RNA binding protein. Evaluation of low-nitrogen tolerance for ME04753 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low nitrate-containing media relative to the internal controls in both generations at p≤0.05 using a one-tailed t-test assuming unequal variance. A summary of photosynthetic efficiency of ME04753 seedlings is shown in Table 19. Events -01 and -02 segregated 3:1 and 2:1 respectively (R:S) for FINALE™ resistance in the $T_2$ generation. ME04753 events were also tested for enhanced growth on the low nitrate media. No significant differences between the transgenics and the controls were observed.

TABLE 19

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME04753 | ME04753-01 ($T_2$) | 0.49323 | 39 | 0.45917 | 66 | 3.17 × 10$^{-2}$ |

TABLE 19-continued

T-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME04753 | ME04753-01 ($T_3$) | 0.50942 | 26 | 0.45917 | 66 | $1.80 \times 10^{-2}$ |
| ME04753 | ME04753-02 ($T_2$) | 0.49856 | 34 | 0.45917 | 66 | $2.43 \times 10^{-2}$ |
| ME04753 | ME04753-02 ($T_3$) | 0.51274 | 27 | 0.45917 | 66 | $1.15 \times 10^{-2}$ |

Events -01 and -02 of ME04753 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 20—Analysis of ME04772 Events

ME04772 contains Ceres Clone: 5232 (At1g13380, SEQ ID NO:509) from *Arabidopsis thaliana*, which encodes a 188 amino acid protein of unknown function. Evaluation of low-nitrogen tolerance for ME04772 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at $p \leq 0.05$ using a one-tailed t-test assuming unequal variance. A summary of photosynthetic efficiency of ME04772 seedlings is shown in Table 20. Events -02 and -04 segregated 2:1 and 3:1 respectively (R:S) for FINALE™ resistance in the $T_2$ generation. ME04772 events were also tested for enhanced growth on the low nitrate media. No significant differences between the transgenics and the controls were observed.

TABLE 20

T-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME04772 | ME04772-02 ($T_2$) | 0.53708 | 25 | 0.46204 | 53 | $3.36 \times 10^{-5}$ |
| ME04772 | ME04772-02 ($T_3$) | 0.53121 | 34 | 0.46204 | 53 | $1.27 \times 10^{-4}$ |
| ME04772 | ME04772-04 ($T_2$) | 0.52921 | 34 | 0.46204 | 53 | $3.71 \times 10^{-4}$ |
| ME04772 | ME04772-04 ($T_3$) | 0.50272 | 36 | 0.46204 | 53 | $2.73 \times 10^{-2}$ |

Events -02 and -04 of ME04772 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 21—Analysis of ME04772 Events

ME04909 contains Ceres Clone: 29302 (At1g49010, SEQ ID NO:532) from *Arabidopsis thaliana*, which encodes a 314 amino acid Myb-like DNA-binding domain protein. Evaluation of low-nitrogen tolerance for ME04909 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low nitrate-containing media relative to the internal controls in both generations at $p \leq 0.05$ using a one-tailed t-test assuming unequal variance. A summary of photosynthetic efficiency of ME04909 seedlings is shown in Table 21. Events -01 and -03 segregated 15:1 (R:S) for FINALE™ resistance in the $T_2$ generation. ME04909 events were also tested for enhanced growth on the low nitrate media. No significant differences between the transgenics and the controls were observed.

TABLE 21 t-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME04909 | ME04909-01 ($T_2$) | 0.587774 | 31 | 0.550342 | 111 | $1.36 \times 10^{-2}$ |
| ME04909 | ME04909-01 ($T_3$) | 0.607452 | 31 | 0.550342 | 111 | $1.28 \times 10^{-3}$ |
| ME04909 | ME04909-03 ($T_2$) | 0.581537 | 41 | 0.550342 | 111 | $1.8 \times 10^{-2}$ |
| ME04909 | ME04909-03 ($T_3$) | 0.609806 | 31 | 0.550342 | 111 | $4.3 \times 10^{-5}$ |

Events -01 and -03 of ME04909 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 22—Analysis of ME05033 Events

ME05033 contains Ceres Clone: 93971 (At4g19095, SEQ ID NO:555) from *Arabidopsis thaliana*, which encodes a 188 amino acid protein of unknown function. Evaluation of low-nitrogen tolerance for ME05033 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -03 and -05, showed significantly increased photosynthetic efficiency on low nitrate-containing media relative to the internal controls in both generations at p≤0.05 using a one-tailed t-test assuming unequal variance. A summary of photosynthetic efficiency of ME05033 seedlings is shown in Table 22. Events -03 and -05 segregated 15:1 and 2:1 respectively (R:S) for FINALE™ resistance in the $T_2$ generation. ME05033 events were also tested for enhanced growth on the low nitrate media. No significant differences between the transgenics and the controls were observed.

TABLE 22

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME05033 | ME05033-03 ($T_2$) | 0.65717 | 46 | 0.62621 | 132 | $9.20 \times 10^{-5}$ |
| ME05033 | ME05033-03 ($T_3$) | 0.64956 | 39 | 0.62621 | 132 | $4.52 \times 10^{-3}$ |
| ME05033 | ME05033-05 ($T_2$) | 0.64448 | 29 | 0.62621 | 132 | $3.46 \times 10^{-2}$ |
| ME05033 | ME05033-05 ($T_3$) | 0.65537 | 30 | 0.62621 | 132 | $2.38 \times 10^{-4}$ |

Events -03 and -05 of ME05033 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 23—Analysis of ME05194 Events

ME05194 contains Ceres cDNA: 12669619 (At1g30710, SEQ ID NO:557) from *Arabidopsis thaliana*, which encodes a 531 amino acid electron carrier protein. Evaluation of low-nitrogen tolerance for ME05194 in $T_2$ and $T_3$ was conducted under the same conditions as described in Examples 2 and 3. Two events, -03 and -05, showed significantly enhanced growth on low nitrate-containing media relative to the internal controls in both generations at p≤0.05 using a one-tailed t-test assuming unequal variance. In this study, the seedling area at 14 days for transgenic plants within an event was compared to the seedling area for non-transgenic segregants pooled across the same line. A summary of enhanced growth under low nitrate growth conditions of ME05194 seedlings is shown in Table 23. Events -03 and -05 segregated 1:1 (R:S) for FINALE™ resistance in the $T_2$ generation. ME05194 events were also tested for increased photosynthetic efficiency on the low nitrate media. No significant differences between the transgenics and the controls were observed.

TABLE 23 t-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME05194 | ME05194-03 ($T_2$) | 0.051216 | 38 | 0.040874 | 82 | $2.54 \times 10^{-5}$ |
| ME05194 | ME05194-03 ($T_3$) | 0.047042 | 45 | 0.040874 | 82 | $2.61 \times 10^{-2}$ |
| ME05194 | ME05194-05 ($T_2$) | 0.048746 | 26 | 0.040874 | 82 | $6.15 \times 10^{-3}$ |
| ME05194 | ME05194-05 ($T_3$) | 0.048457 | 14 | 0.040874 | 82 | $3.03 \times 10^{-2}$ |

Events -03 and -05 of ME05194 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 24—Analysis of ME05267 Events

ME05267 contains Ceres Clone: 21608 (At5g49510, SEQ ID NO:592) from *Arabidopsis thaliana*, which encodes a 195 amino acid von Hippel-Lindau binding protein. Evaluation of low-nitrogen tolerance for ME05267 in $T_2$ and $T_3$ was conducted under the same conditions as described in Examples 2 and 3. Two events, -01 and -04, showed significantly enhanced growth on low nitrate-containing media relative to the internal controls in both generations at p≤0.05 using a one-tailed t-test assuming unequal variance. In this study, the seedling area at 14 days for transgenic plants within an event was compared to the seedling area for non-transgenic segregants pooled across the same line. A summary of enhanced growth under low nitrate growth conditions of ME05194 seedlings is shown in Table 24. Events -01 and -04 segregated 15:1 (R:S) for FINALE™ resistance in the $T_2$ generation. ME05267 events were also tested for increased photosynthetic efficiency on the low nitrate media. No significant differences between the transgenics and the controls were observed.

TABLE 24 t-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME05267 | ME05267-01 ($T_2$) | 0.053263 | 46 | 0.0450197 | 122 | $4.4 \times 10^{-5}$ |
| ME05267 | ME05267-01 ($T_3$) | 0.051135 | 26 | 0.0450197 | 122 | $5.0 \times 10^{-2}$ |
| ME05267 | ME05267-04 ($T_2$) | 0.049977 | 44 | 0.0450197 | 122 | $6.4 \times 10^{-3}$ |
| ME05267 | ME05267-04 ($T_3$) | 0.053084 | 38 | 0.0450197 | 122 | $8.4 \times 10^{-4}$ |

Events -01 and -04 of ME05267 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 25—Analysis of ME05300 Events

ME05300 contains Ceres Clone: 2031 (At1g72020, SEQ ID NO:612) from *Arabidopsis thaliana*, which encodes a 97 amino acid protein of unknown function. Evaluation of low-nitrogen tolerance for ME05300 in $T_2$ generation was conducted under the same conditions as described in Examples 2 and 3. A summary of photosynthetic efficiency of ME05300 seedlings is shown in Table 25. Two events, -04 and -05, showed significantly increased photosynthetic efficiency on low nitrate- and low ammonium nitrate-containing media relative to the internal controls in $T_2$ generation at $p \leq 0.05$ using a one-tailed t-test assuming unequal variance. In this study, the seedling photosynthetic efficiency was measured as Fv/Fm comparing transgenic plants within an event to non-transgenic segregants pooled across the same plate. In addition, two events, -01 and -05, showed significantly enhanced growth on low nitrate- and low ammonium nitrate-containing media relative to the internal controls in $T_2$ generation at $p \leq 0.05$ using a one-tailed t-test assuming unequal variance. In this study, the seedling area for transgenic plants within an event was compared to the seedling area for non-transgenic segregants pooled across the same line. A summary of enhanced growth under low nitrate and low ammonium nitrate growth conditions of ME05300 seedlings is shown in Table 26.

TABLE 25

A.
T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME05300 | ME05300-04 ($T_2$) | 0.6867 | 7 | 0.6488 | 27 | $1.65 \times 10^{-2}$ |
| ME05300 | ME05300-05 ($T_2$) | 0.6839 | 16 | 0.6488 | 27 | $2.50 \times 10^{-3}$ |

B.
T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME05300 | ME05300-04 ($T_2$) | 0.6767 | 6 | 0.6323 | 32 | $1.68 \times 10^{-2}$ |
| ME05300 | ME05300-05 ($T_2$) | 0.6934 | 11 | 0.6323 | 32 | $7.04 \times 10^{-4}$ |

TABLE 26

A.
T-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME05300 | ME05300-01 ($T_2$) | 0.0737 | 18 | 0.0588 | 21 | $3.80 \times 10^{-3}$ |
| ME05300 | ME05300-05 ($T_2$) | 0.0655 | 16 | 0.0570 | 27 | $1.59 \times 10^{-2}$ |

B.
T-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME05300 | ME05300-01 ($T_2$) | 0.0987 | 17 | 0.0776 | 29 | $3.89 \times 10^{-3}$ |
| ME05300 | ME05300-05 ($T_2$) | 0.1082 | 11 | 0.0776 | 29 | $1.57 \times 10^{-3}$ |

Example 26—Analysis of ME05341 Events

ME05341 contains Ceres Clone: 94503 (At4g14420, SEQ ID NO:645) from *Arabidopsis thaliana*, which encodes a 158 amino acid elicitor-like protein. Evaluation of low-nitrogen tolerance for ME05341 in $T_2$ and $T_3$ was conducted under the same conditions as described in Examples 2 and 3. Two events, -01 and -02, showed significantly enhanced growth on low nitrate-containing media relative to the internal controls in both generations at $p \leq 0.05$ using a one-tailed t-test assuming unequal variance. In this study, the seedling area at 14 days for transgenic plants within an event was compared to the seedling area for non-transgenic segregants pooled across the same line. A summary of photosynthetic efficiency of ME05341 seedlings is shown in Table 27. Events -01 and -02 segregated 15:1 (R:S) for FINALE™ resistance in the $T_2$ generation. ME05341 events were also tested for increased photosynthetic efficiency on the low nitrate media. No significant differences between the transgenics and the controls were observed.

TABLE 27 t-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME05341 | ME05341-01 ($T_2$) | 0.06253 | 46 | 0.04988 | 143 | $4.17 \times 10^{-10}$ |
| ME05341 | ME05341-01 ($T_3$) | 0.05876 | 38 | 0.04988 | 143 | $4.13 \times 10^{-4}$ |
| ME05341 | ME05341-02 ($T_2$) | 0.06152 | 46 | 0.04988 | 143 | $2.91 \times 10^{-7}$ |
| ME05341 | ME05341-02 ($T_3$) | 0.05572 | 48 | 0.04988 | 143 | $2.90 \times 10^{-3}$ |

Events -01 and -02 of ME05341 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 27—Analysis of ME05392 Events

ME05392 contains Ceres Clone: 21740 (At5g01610, SEQ ID NO:686) from *Arabidopsis thaliana*, which encodes a 170 amino acid protein of unknown function. Evaluation of low-nitrogen tolerance for ME05392 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low nitrate-containing media relative to the internal controls in both generations at p≤0.05 using a one-tailed t-test assuming unequal variance. A summary of photosynthetic efficiency of ME05392 seedlings is shown in Table 20. Events -01 and -03 segregated 2:1 (R:S) for FINALE™ resistance in the $T_2$ generation. ME05392 events were also tested for enhanced growth on the low nitrate media. No significant differences between the transgenics and the controls were observed.

TABLE 28

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME05392 | ME05392-01 ($T_2$) | 0.61759 | 32 | 0.60093 | 107 | $3.70 \times 10^{-2}$ |
| ME05392 | ME05392-01 ($T_3$) | 0.63388 | 40 | 0.60093 | 107 | $5.05 \times 10^{-5}$ |
| ME05392 | ME05392-03 ($T_2$) | 0.64335 | 23 | 0.60093 | 107 | $5.81 \times 10^{-5}$ |
| ME05392 | ME05392-03 ($T_3$) | 0.63397 | 36 | 0.60093 | 107 | $4.30 \times 10^{-5}$ |

Events -01 and -03 of ME05392 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 28—Analysis of ME05429 Events

ME05429 contains Ceres Clone: 5609 (At3g60480, SEQ ID NO:729) from *Arabidopsis thaliana*, which encodes a 188 amino acid protein of unknown function. Evaluation of low-nitrogen tolerance for ME05429 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -06 and -08, showed significantly increased photosynthetic efficiency on low ammonium nitrate-containing media relative to the internal controls in both generations at p≤0.05 using a one-tailed t-test assuming unequal variance. A summary of photosynthetic efficiency of ME05429 seedlings is shown in Table 29. Events -06 and -08 segregated 3:1 and 2:1 respectively (R:S) for FINALE™ resistance in the $T_2$ generation. ME05429 events were tested for enhanced growth on the low ammonium nitrate media. In addition, these events were also tested for enhanced growth and photosynthetic efficiency on low nitrate media. No significant differences between the transgenics and the controls were observed.

TABLE 29 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME05429 | ME05429-06 ($T_2$) | 0.62521 | 28 | 0.59991 | 78 | $2.85 \times 10^{-2}$ |
| ME05429 | ME05429-06 ($T_3$) | 0.63031 | 39 | 0.59991 | 78 | $8.49 \times 10^{-3}$ |
| ME05429 | ME05429-08 ($T_2$) | 0.64526 | 23 | 0.59991 | 78 | $1.67 \times 10^{-3}$ |
| ME05429 | ME05429-08 ($T_3$) | 0.65076 | 17 | 0.59991 | 78 | $2.76 \times 10^{-4}$ |

Events -06 and -08 of ME05429 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 29—Analysis of ME05493 Events

ME05493 contains Ceres Clone: 3137 (At3g43430, SEQ ID NO:745) from *Arabidopsis thaliana*, which encodes a 169 amino acid zinc finger family protein. Evaluation of low-nitrogen tolerance for ME05493 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at p≤0.05 using a one-tailed t-test assuming unequal variance. A summary of photosynthetic efficiency of ME05493 seedlings is shown in Table 30. Events -01 and -05 segregated 15:1 (R:S) for FINALE™ resistance in the $T_2$ generation. ME05493 events were also tested for enhanced growth on the low nitrate media. No significant differences between the transgenics and the controls were observed.

TABLE 30 t-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME05493 | ME05493-01 ($T_2$) | 0.64121 | 32 | 0.61097 | 92 | $1.13 \times 10^{-3}$ |
| ME05493 | ME05493-01 ($T_3$) | 0.64250 | 46 | 0.61097 | 92 | $3.03 \times 10^{-4}$ |
| ME05493 | ME05493-05 ($T_2$) | 0.62865 | 43 | 0.61097 | 92 | $1.75 \times 10^{-2}$ |
| ME05493 | ME05493-05 ($T_3$) | 0.63936 | 42 | 0.61097 | 92 | $1.21 \times 10^{-4}$ |

Events -01 and -05 of ME05493 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 30—Analysis of ME05885 Events

ME05885 contains Ceres Clone: 32430 (At1g16170, SEQ ID NO:768) from *Arabidopsis thaliana*, which encodes a 92 amino acid protein of unknown function. Evaluation of low-nitrogen tolerance for ME05885 in $T_3$ generation was conducted under the same conditions as described in Examples 2 and 3. A summary of photosynthetic efficiency of ME05885 seedlings is shown in Table 31. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media and low ammonium nitrate-containing media relative to the internal controls in $T_3$ generation at p≤0.05 using a one-tailed t-test assuming unequal variance.

TABLE 31

| Line | Events | Transgenic Fv/Fm | n | Pooled Non-Transgenics Fv/Fm | n | t-test p-value |
|---|---|---|---|---|---|---|
| A. T-test comparison of seedling photosynthetic efficiency between transgenic seedlings and pooled non-transgenic segregants after 14 days of growth on low nitrate. | | | | | | |
| ME05885 | ME05885-01 ($T_3$) | 0.6759 | 12 | 0.6533 | 28 | $4.32 \times 10^{-2}$ |
| ME05885 | ME05885-05 ($T_3$) | 0.6831 | 7 | 0.6530 | 52 | $3.68 \times 10^{-6}$ |
| B. T-test comparison of seedling photosynthetic efficiency between transgenic seedlings and pooled non-transgenic segregants after 18 days of growth on low ammonium nitrate. | | | | | | |
| ME05885 | ME05885-01 ($T_3$) | 0.6490 | 13 | 0.6135 | 30 | $3.06 \times 10^{-2}$ |
| ME05885 | ME05885-05 ($T_3$) | 0.6810 | 9 | 0.6133 | 43 | $6.77 \times 10^{-5}$ |

ME05885 events were also tested for enhanced growth on the low nitrate and low ammonium nitrate media. A summary of enhanced growth under low nitrate and low ammonium nitrate growth conditions of ME05885 seedlings in $T_3$ generation is shown in Table 32. Two events, -03 and -05, showed significantly enhanced growth on low nitrate-containing media. Two events, -02 and -05, showed significantly enhanced growth on low ammonium nitrate-containing media relative to the internal controls at p≤0.05 using a one-tailed t-test assuming unequal variance. In this study, the seedling area for transgenic plants within an event was compared to the seedling area for non-transgenic segregants pooled across the same line.

TABLE 32

| Line | Events | Transgenic Area | n | Pooled Non-Transgenics Area | n | t-test p-value |
|---|---|---|---|---|---|---|
| A. T-test comparison of seedling area between transgenic seedlings and pooled non-transgenic segregants after 14 days of growth on low nitrate. | | | | | | |
| ME05885 | ME05885-03 ($T_3$) | 0.06245 | 6 | 0.05286 | 14 | $1.42 \times 10^{-2}$ |
| ME05885 | ME05885-05 ($T_3$) | 0.05893 | 7 | 0.04725 | 12 | $5.61 \times 10^{-3}$ |
| B. T-test comparison of seedling area between transgenic seedlings and pooled non-transgenic segregants after 18 days of growth on low ammonium nitrate. | | | | | | |
| ME05885 | ME05885-02 ($T_3$) | 0.0744 | 14 | 0.05595 | 6 | $3.28 \times 10^{-5}$ |
| ME05885 | ME05885-05 ($T_3$) | 0.0753 | 9 | 0.06179 | 11 | $5.08 \times 10^{-3}$ |

Example 31—Analysis of ME07344 Events

ME07344 contains Ceres Clone: 101255 (At2g19810, SEQ ID NO:791) from *Arabidopsis thaliana*, which encodes a 359 amino acid CCCH-type zinc finger protein. Evaluation of low-nitrogen tolerance for ME07344 in $T_2$ and $T_3$ was conducted under the same conditions as described in Example 4. In this study, the $4^{th}$ true leaf from each plant was collected on day 38 and analyzed on the CF imager for its Fv/Fm value. Transgenic plants within an event were compared to all non-transgenic plants, including the non-transgenic segregants and external controls. Two events, -02 and -03, showed significantly increased photosynthetic efficiency relative to the internal controls in both generations at p≤0.05 using a one-tailed t-test assuming unequal variance. A summary of photosynthetic efficiency of ME07344 seedlings is shown in Table 33. Events -02 and -03 segregated 3:1 (R:S) for FINALE™ resistance in the $T_2$ generation. ME07344 events were also tested for enhanced growth on the low nitrate media. No significant differences between the transgenics and the controls were observed.

TABLE 33

T-test comparison of photosynthetic efficiency between transgenic plants and non-transgenic controls after 38 days of growth on nitrogen-depleted soil.

| Line | Events | Transgenic Fv/Fm | n | Non-Transgenic Controls Fv/Fm | n | t-test p-value |
|---|---|---|---|---|---|---|
| ME07344 | ME07344-02 ($T_2$) | 0.752 | 17 | 0.729 | 50 | $2.86 \times 10^{-4}$ |
| ME07344 | ME07344-02 ($T_3$) | 0.750 | 16 | 0.729 | 50 | $1.11 \times 10^{-4}$ |
| ME07344 | ME07344-03 ($T_2$) | 0.741 | 13 | 0.729 | 50 | 0.018 |
| ME07344 | ME07344-03 ($T_3$) | 0.754 | 17 | 0.729 | 50 | $4.62 \times 10^{-6}$ |

Events -02 and -03 of ME07344 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 32—Analysis of ME07859 Events

ME07859 contains Ceres Clone: 276809 (SEQ ID NO:823) from *Zea mays*, which encodes a 135 amino acid sterol desaturase protein. Evaluation of low-nitrogen tolerance for ME07859 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at p≤0.05 using a one-tailed t-test assuming unequal variance. A summary of photosynthetic efficiency of ME07859 seedlings is shown in Table 34. Events -02 and -04 segregated 1:1 and 2:1 respectively (R:S) for FINALE™ resistance in the $T_2$ generation. ME07859 events were also tested for enhanced growth on the low nitrate media as well as for enhanced growth and photosynthetic efficiency on low ammonium nitrate media. No significant differences between the transgenics and the controls were observed.

TABLE 34 t-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME07859 | ME07859-02 ($T_2$) | 0.6598 | 24 | 0.6378 | 127 | 0.03 |
| ME07859 | ME07859-02 ($T_3$) | 0.6825 | 14 | 0.6378 | 127 | $1.3 \times 10^{-3}$ |
| ME07859 | ME07859-04 ($T_2$) | 0.6539 | 33 | 0.6378 | 127 | 0.05 |
| ME07859 | ME07859-04 ($T_3$) | 0.6601 | 17 | 0.6378 | 127 | 0.05 |

Events -02 and -04 of ME07859 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 33—Analysis of ME08464 Events

ME08464 contains Ceres Clone: 424522 (SEQ ID NO:827) from *Zea mays*, which encodes a 500 amino acid unknown protein. Evaluation of low-nitrogen tolerance for ME08464 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME07859 seedlings is shown in Table 35. Events -02 and -03 segregated 3:1 (R:S) for FINALE™ resistance in the $T_2$ generation. ME08464 events were also tested for increased photosynthetic efficiency on the low nitrate media. No significant differences between the transgenics and the controls were observed.

TABLE 35

T-test comparison of photosynthetic efficiency between transgenic seedlings and pooled non-transgenic segregants after 15 days of growth on low ammonium nitrate.

| Line | Events | Transgenic Fv/Fm | n | Pooled Non-Transgenics Fv/Fm | n | t-test p-value |
|---|---|---|---|---|---|---|
| ME08464 | ME08464-02 ($T_2$) | 0.65 | 41 | 0.62 | 40 | 0.015 |
| ME08464 | ME08464-02 ($T_3$) | 0.67 | 32 | 0.62 | 40 | $2.32 \times 10^{-4}$ |
| ME08464 | ME08464-03 ($T_2$) | 0.65 | 43 | 0.62 | 40 | 0.013 |
| ME08464 | ME08464-03 ($T_3$) | 0.65 | 42 | 0.62 | 40 | $6.85 \times 10^{-3}$ |

Events -02 and -03 of ME08464 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 34—Analysis of ME09939 Events

ME09939 contains Ceres Clone: 324216 (SEQ ID NO:852) from *Zea mays*, which encodes a 38 amino acid protein of unknown function. Evaluation of low-nitrogen tolerance for ME09939 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME09939 seedlings is shown in Table 36. Events -04 and -05 segregated 15:1 and 3:1 respectively (R:S) for FINALE™ resistance in the $T_2$ generation. ME09939 events were also tested for enhanced growth on the low ammonium nitrate media. No significant differences between the transgenics and the controls were observed.

TABLE 36

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME09939 | ME09939-04 ($T_2$) | 0.49285 | 40 | 0.38571 | 7 | 0.05 |
| ME09939 | ME09939-04 ($T_3$) | 0.50697 | 34 | 0.38571 | 7 | $3.50 \times 10^{-2}$ |
| ME09939 | ME09939-05 ($T_2$) | 0.53487 | 39 | 0.47492 | 24 | $1.19 \times 10^{-2}$ |
| ME09939 | ME09939-05 ($T_3$) | 0.55341 | 32 | 0.47492 | 24 | $1.82 \times 10^{-3}$ |

Events -04 and -05 of ME09939 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 35—Analysis of ME11735 Events

ME11735 contains Ceres Annot: 573161 (At5g43260, SEQ ID NO:854) from *Arabidopsis thaliana*, which encodes a 97 amino acid DnaJ-related chaperone protein. Evaluation of low-nitrogen tolerance for ME11735 in $T_2$ and $T_3$ was conducted under the same conditions as described in Example 2 and 3. A summary of the enhanced growth of ME11735 events on low nitrate-containing media is shown in Table 37. In this study, the seedling area for transgenic plants within an event was compared to the seedling area for non-transgenic segregants pooled across the same line. Two events, -04 and -05, were found significantly larger than the pooled non-transgenic segregants after 14 days of growth on low nitrate-containing media relative to the internal controls in both generations at p≤0.05 using a one-tailed t-test assuming unequal variance. ME11735 events were also tested for increased photosynthetic efficiency on the low nitrate media. No significant differences between the transgenics and the controls were observed. Events -04 and -05 segregated 40:1 and 4:1 respectively (R:S) for FINALE™ resistance in the $T_2$ generation.

TABLE 37 t-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME11735 | ME11735-04 ($T_2$) | 0.05820 | 41 | 0.04994 | 127 | $5.91 \times 10^{-5}$ |
| ME11735 | ME11735-04 ($T_3$) | 0.05553 | 42 | 0.04994 | 127 | $1.26 \times 10^{-2}$ |
| ME11735 | ME11735-05 ($T_2$) | 0.05788 | 37 | 0.04994 | 127 | $1.59 \times 10^{-3}$ |
| ME11735 | ME11735-05 ($T_3$) | 0.06011 | 13 | 0.04994 | 127 | $1.64 \times 10^{-2}$ |

Events -04 and -05 of ME11735 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 36—Analysis of ME12910 Events

ME12910 contains Ceres Annot: 552727 (At2g22930, SEQ ID NO:890) from *Arabidopsis thaliana*, which encodes a 442 amino acid UDP-glucoronosyl and UDP-glucosyl transferase family protein. Evaluation of low-nitrogen tolerance for ME12910 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME12910 seedlings is shown in Table 38. ME12910 events were also tested for enhanced growth on the low ammonium nitrate media. No significant differences between the transgenics and the controls were observed.

TABLE 38 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME12910 | ME12910-03 ($T_2$) | 0.5851 | 39 | 0.5191 | 29 | $1.54 \times 10^{-3}$ |
| ME12910 | ME12910-03 ($T_3$) | 0.5861 | 22 | 0.5191 | 29 | $2.17 \times 10^{-3}$ |
| ME12910 | ME12910-05 ($T_2$) | 0.5523 | 44 | 0.4251 | 7 | $1.23 \times 10^{-2}$ |
| ME12910 | ME12910-05 ($T_3$) | 0.5600 | 42 | 0.4251 | 7 | $9.62 \times 10^{-3}$ |

Events -03 and -05 segregated 3:1 and 15:1 respectively (R:S) for FINALE™ resistance in the $T_2$ generation.

Events -03 and -05 of ME12910 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 37—Analysis of ME12927 Events

ME12927 contains Ceres Clone: 239806 (SEQ ID NO:916) from *Zea mays*, which encodes a 201 amino acid lipoprotein amino terminal region. Evaluation of low-nitrogen tolerance for ME12927 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -03 and -05, showed significantly increased photosynthetic efficiency on low ammonium nitrate-containing media relative to the internal controls in both generations at p≤0.05, using a one-tailed t-test assuming unequal variance. A summary of photosynthetic efficiency of ME12927 seedlings is shown in Table 39.

TABLE 39 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME12927 | ME12927-02 ($T_2$) | 0.60843 | 44 | 0.47813 | 8 | $4.88 \times 10^{-3}$ |
| ME12927 | ME12927-02 ($T_3$) | 0.60867 | 36 | 0.47813 | 8 | $5.23 \times 10^{-3}$ |
| ME12927 | ME12927-03 ($T_2$) | 0.61906 | 32 | 0.57929 | 38 | $8.96 \times 10^{-3}$ |
| ME12927 | ME12927-03 ($T_3$) | 0.63437 | 19 | 0.57929 | 38 | $5.35 \times 10^{-4}$ |
| ME12927 | ME12927-05 ($T_2$) | 0.60581 | 43 | 0.53982 | 22 | $7.26 \times 10^{-3}$ |
| ME12927 | ME12927-05 ($T_3$) | 0.63145 | 29 | 0.53982 | 22 | $5.83 \times 10^{-4}$ |

ME12927 events were also tested for enhanced growth on the low ammonium nitrate media. A summary of the enhanced growth of ME11735 events on low ammonium nitrate-containing media is shown in Table 40. In this study, the seedling area for transgenic plants within an event was compared to the seedling area for non-transgenic segregants pooled across the same line. Three events, -02, -03 and -05, were found significantly larger than the pooled non-transgenic segregants after 18 days of growth on low ammonium nitrate-containing media relative to the internal controls in both generations at p≤0.05, using a one-tailed t-test assuming unequal variance.

TABLE 40 t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME12927 | ME12927-02 ($T_2$) | 0.066920 | 44 | 0.056585 | 117 | $1.65 \times 10^{-4}$ |
| ME12927 | ME12927-02 ($T_3$) | 0.062119 | 36 | 0.056585 | 117 | $3.51 \times 10^{-2}$ |
| ME12927 | ME12927-03 ($T_2$) | 0.068972 | 32 | 0.056585 | 117 | $1.18 \times 10^{-5}$ |
| ME12927 | ME12927-03 ($T_3$) | 0.063716 | 19 | 0.056585 | 117 | $1.98 \times 10^{-2}$ |
| ME12927 | ME12927-05 ($T_2$) | 0.069972 | 43 | 0.056585 | 117 | $4.25 \times 10^{-6}$ |
| ME12927 | ME12927-05 ($T_3$) | 0.064014 | 29 | 0.056585 | 117 | $8.49 \times 10^{-3}$ |

Events 02, -03 and -05 segregated 15:1, 2:1 and 15:1 respectively (R:S) for FINALE™ resistance in the $T_2$ generation.

Events 02, -03 and -05 of ME12927 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in $T_1$ generation.

Example 38—Analysis of ME12929 Events

ME12929 contains Ceres Clone: 208995 (SEQ ID NO:943) from *Zea mays*, which encodes a 94 amino acid protein of unknown function. Evaluation of low-nitrogen tolerance for ME12929 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME12929 seedlings is shown in Table 41. ME12929 events were also tested for enhanced growth on the low ammonium nitrate media. No significant differences between the transgenics and the controls were observed. Events -03 and -04 segregated 1:1 and 3:1 respectively (R:S) for FINALE™ resistance in the $T_2$ generation.

Events -03 and -04 of ME12929 exhibited no statistically relevant negative phenotypes. That is, there was no detectable reduction in germination rate, the transgenic

TABLE 41 t-test comparison of seedling photosynthetic
efficiency between transgenic seedlings and
pooled non-transgenic segregants after 14 days
of growth on low ammonium nitrate.

| Line | Events | Transgenic Fv/Fm | n | Pooled Non-Transgenics Fv/Fm | n | t-test p-value |
|---|---|---|---|---|---|---|
| ME12929 | ME12929-03 ($T_2$) | 0.6410 | 33 | 0.5736 | 24 | $9.44 \times 10^{-4}$ |
| ME12929 | ME12929-03 ($T_3$) | 0.6610 | 41 | 0.5736 | 24 | $4.38 \times 10^{-5}$ |
| ME12929 | ME12929-04 ($T_2$) | 0.6544 | 47 | 0.5790 | 9 | $3.68 \times 10^{-2}$ |
| ME12929 | ME12929-04 ($T_3$) | 0.6663 | 43 | 0.5790 | 9 | $2.15 \times 10^{-2}$ | plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 39—Analysis of ME12954 Events

ME12954 contains Ceres Clone: 225681 (SEQ ID NO:975) from *Zea mays*, which encodes a 286 amino acid protein of unknown function. Evaluation of low-nitrogen tolerance for ME12954 in $T_2$ and $T_3$ was conducted under the same conditions as described in Examples 2 and 3. Two events, -04 and -05, showed significantly increased photosynthetic efficiency on low ammonium nitrate-containing media relative to the internal controls in both generations at $p \leq 0.05$ using a one-tailed t-test assuming unequal variance. In this study, the seedling photosynthetic efficiency was measured as Fv/Fm comparing transgenic plants within an event to non-transgenic segregants pooled across the same plate. A summary of photosynthetic efficiency of ME12954 seedlings is shown in Table 42.

TABLE 42 t-test comparison of seedling photosynthetic
efficiency between transgenic seedlings and
pooled non-transgenic segregants after 18 days
of growth on low ammonium nitrate.

| Line | Events | Transgenic Fv/Fm | n | Pooled Non-Transgenics Fv/Fm | n | t-test p-value |
|---|---|---|---|---|---|---|
| ME12954 | ME12954-04 ($T_2$) | 0.6236 | 40 | 0.5973 | 152 | $6.61 \times 10^{-3}$ |
| ME12954 | ME12954-04 ($T_3$) | 0.6200 | 39 | 0.5973 | 152 | $1.97 \times 10^{-2}$ |
| ME12954 | ME12954-05 ($T_2$) | 0.6280 | 45 | 0.5973 | 152 | $1.79 \times 10^{-2}$ |
| ME12954 | ME12954-05 ($T_3$) | 0.6315 | 35 | 0.5973 | 152 | $2.85 \times 10^{-2}$ |

ME12954 events were also tested for enhanced growth on the low ammonium nitrate media. A summary of the enhanced growth of ME12954 events on low ammonium nitrate-containing media is shown in Table 43. In this study, the seedling area for transgenic plants within an event was compared to the seedling area for non-transgenic segregants pooled across the same line. Two events, -02 and -04, were found significantly larger than the pooled non-transgenic segregants after 18 days of growth on low ammonium nitrate-containing media relative to the internal controls in both generations at $p \leq 0.05$, using a one-tailed t-test assuming unequal variance.

TABLE 43 t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME12954 | ME12954-02 ($T_2$) | 0.06883 | 31 | 0.05579 | 152 | $1.86 \times 10^{-5}$ |
| ME12954 | ME12954-02 ($T_3$) | 0.06604 | 26 | 0.05579 | 152 | $1.48 \times 10^{-3}$ |
| ME12954 | ME12954-04 ($T_2$) | 0.06469 | 40 | 0.05579 | 152 | $1.95 \times 10^{-4}$ |
| ME12954 | ME12954-04 ($T_3$) | 0.06301 | 39 | 0.05579 | 152 | $3.32 \times 10^{-3}$ |

Events -02, -04 and -05 segregated 2:1, 3:1 and 15:1 respectively (R:S) for FINALE™ resistance in the T2 generation.

Events -02, -04 and -05 of ME12954 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 40—Analysis of ME12970 Events

ME12970 contains Ceres Clone: 1387146 (SEQ ID NO:981) from *Zea mays*, which encodes a 147 amino acid C2 domain-containing protein. Evaluation of low-nitrogen tolerance for ME12970 in $T_2$ and $T_3$ was conducted under the same conditions as described in Examples 2 and 3. Two events, -02 and -03, showed significantly increased photosynthetic efficiency on low ammonium nitrate-containing media relative to the internal controls in both generations at $p \leq 0.05$ using a one-tailed t-test assuming unequal variance. In this study, the seedling photosynthetic efficiency was measured as Fv/Fm comparing transgenic plants within an event to non-transgenic segregants pooled across the same plate. A summary of photosynthetic efficiency of ME12970 seedlings is shown in Table 44. ME12970 events were also tested for enhanced growth on the low ammonium nitrate media. No significant differences between the transgenics and the controls were observed.

TABLE 44 t-test comparison of seedling photosynthetic efficiency between transgenic seedlings and pooled non-transgenic segregants after 18 days of growth on low ammonium nitrate.

| Line | Events | Transgenic | | Pooled Non-Transgenics | | t-test |
| --- | --- | --- | --- | --- | --- | --- |
| | | Fv/Fm | n | Fv/Fm | n | p-value |
| ME12970 | ME12970-02 ($T_2$) | 0.55136 | 44 | 0.52401 | 108 | $3.78 \times 10^{-2}$ |
| ME12970 | ME12970-02 ($T_3$) | 0.58305 | 43 | 0.52401 | 108 | $1.89 \times 10^{-5}$ |
| ME12970 | ME12970-03 ($T_2$) | 0.58759 | 37 | 0.52401 | 108 | $2.14 \times 10^{-6}$ |
| ME12970 | ME12970-03 ($T_3$) | 0.59131 | 29 | 0.52401 | 108 | $3.05 \times 10^{-6}$ |

Events -02 and -03 segregated 15:1 and 3:1 respectively (R:S) for FINALE™ resistance in the T2 generation.

Events -02 and -03 of ME12970 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 41—Analysis of ME13006 Events

ME13006 contains Ceres Clone: 1017441 (SEQ ID NO:224) from *Triticum aestivum*, which encodes a 143 amino acid polypeptide, predicted to be a homolog of Ceres Clone: 4898 (ME03123, SEQ ID NO:217). Evaluation of low-nitrogen tolerance for ME13006 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13006 seedlings is shown in Table 45. ME13006 events were also tested for enhanced growth on the low nitrate media. No significant differences between the transgenics and the controls were observed.

TABLE 45 t-test comparison of seedling area between transgenic seedlings and pooled non-transgenic segregants after 14 days of growth on low ammonium nitrate.

| Line | Events | Transgenic Area | n | Pooled Non-Transgenics Area | n | t-test p-value |
|---|---|---|---|---|---|---|
| ME13006 | ME13006-01 ($T_2$) | 0.0777 | 42 | 0.0648 | 7 | $3.29 \times 10^{-2}$ |
| ME13006 | ME13006-01 ($T_3$) | 0.0660 | 28 | 0.0540 | 19 | $1.49 \times 10^{-3}$ |
| ME13006 | ME13006-03 ($T_2$) | 0.0706 | 21 | 0.0601 | 29 | $4.83 \times 10^{-3}$ |
| ME13006 | ME13006-03 ($T_3$) | 0.0758 | 14 | 0.0617 | 33 | $2.60 \times 10^{-3}$ |

Events -01 and -03 segregated 3:1 and 1:1 respectively (R:S) for FINALE™ resistance in the $T_2$ generation.

Events -01 and -03 of ME13006 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 42—Analysis of ME13021 Events

ME13021 contains Ceres Clone: 244306 (SEQ ID NO:1053) from *Zea mays*, which encodes a 572 amino acid TCP-1/cpn60 chaperonin family protein. Evaluation of low-nitrogen tolerance for ME13021 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13021 seedlings is shown in Table 46. ME13021 events were also tested for enhanced growth on the low ammonium nitrate media. No significant differences between the transgenics and the controls were observed.

Events -04 and -05 segregated 3:1 and 2:1 respectively (R:S) for FINALE™ resistance in the T2 generation.

Events -04 and -05 of ME13021 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 43—Analysis of ME13064 Events

ME13064 contains Ceres Clone: 1408950 (SEQ ID NO:1098) from *Zea mays*, which encodes a 152 amino acid protein of unknown function. Evaluation of low-nitrogen tolerance for ME13064 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME13064 seedlings is shown in Table 47. ME13064 events were also tested for enhanced growth on the low ammonium nitrate media. No significant differences between the transgenics and the controls were observed.

TABLE 46 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13021 | ME13021-04 ($T_2$) | 0.56697 | 39 | 0.49440 | 10 | $2.47 \times 10^{-2}$ |
| ME13021 | ME13021-04 ($T_3$) | 0.59916 | 37 | 0.48685 | 13 | $1.54 \times 10^{-3}$ |
| ME13021 | ME13021-05 ($T_2$) | 0.60575 | 32 | 0.50344 | 18 | $6.05 \times 10^{-4}$ |
| ME13021 | ME13021-05 ($T_3$) | 0.64400 | 23 | 0.55638 | 26 | $3.86 \times 10^{-6}$ |

TABLE 47 t-test comparison of seedling photosynthetic efficiency between transgenic seedlings
and pooled non-transgenic segregants after 18 days of growth on low ammonium nitrate.

| Line | Events | Transgenic | | Pooled Non-Transgenics | | t-test |
| --- | --- | --- | --- | --- | --- | --- |
| | | Fv/Fm | n | Fv/Fm | n | p-value |
| ME13064 | ME13064-03 ($T_2$) | 0.59444 | 27 | 0.54793 | 28 | $5.84 \times 10^{-3}$ |
| ME13064 | ME13064-03 ($T_3$) | 0.59676 | 29 | 0.54793 | 28 | $1.25 \times 10^{-2}$ |
| ME13064 | ME13064-04 ($T_2$) | 0.58577 | 31 | 0.51053 | 40 | $2.05 \times 10^{-3}$ |
| ME13064 | ME13064-04 ($T_3$) | 0.59128 | 25 | 0.51053 | 40 | $8.93 \times 10^{-4}$ |

Events -03 and -04 segregated 2:1 (R:S) for FINALE™ resistance in the T2 generation.

Events -03 and -04 of ME13064 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 44—Analysis of ME13071 Events

ME13071 contains Ceres Clone: 208453 (SEQ ID NO:1111) from *Zea mays*, which encodes a 74 amino acid protein of unknown function. Evaluation of low-nitrogen tolerance for ME13071 in $T_2$ and $T_3$ was conducted under the same conditions as described in Examples 2 and 3. Two events, -03 and -05, showed significantly enhanced growth on low nitrate- and low ammonium nitrate-containing media relative to the internal controls in $T_2$ generation at p≤0.05 using a one-tailed t-test assuming unequal variance. In this study, the seedling area for transgenic plants within an event was compared to the seedling area for non-transgenic segregants pooled across the same line. A summary of enhanced growth under low ammonium nitrate growth conditions of ME13071 seedlings is shown in Table 48. ME13071 events were also tested for photosynthetic efficiency on the low ammonium nitrate media. No significant differences between the transgenics and the controls were observed.

Events -03 and -05 segregated 1:1 and 2:1 respectively (R:S) for FINALE™ resistance in the T2 generation.

Events -03 and -05 of ME13071 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 45—Analysis of ME13087 Events

ME13087 contains Ceres Clone: 968180 (SEQ ID NO:1115) from *Brassica napus*, which encodes a 159 amino acid zinc finger protein. Evaluation of low-nitrogen tolerance for ME13087 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -01, -02, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME13087 seedlings is shown in Table 49. ME13087 events were also tested for enhanced growth on the low ammonium nitrate media. No significant differences between the transgenics and the controls were observed.

TABLE 48 t-test comparison of seedling area between transgenic seedlings and pooled non-transgenic segregants after 18 days of growth on low ammonium nitrate.

| Line | Events | Transgenic | | Pooled Non-Transgenics | | t-test |
| --- | --- | --- | --- | --- | --- | --- |
| | | Area | n | Area | n | p-value |
| ME13071 | ME13071-03 ($T_2$) | 0.06694 | 26 | 0.05915 | 19 | $3.55 \times 10^{-3}$ |
| ME13071 | ME13071-03 ($T_3$) | 0.07787 | 24 | 0.07040 | 22 | $3.65 \times 10^{-2}$ |
| ME13071 | ME13071-05 ($T_2$) | 0.06232 | 32 | 0.05491 | 16 | $2.07 \times 10^{-3}$ |
| ME13071 | ME13071-05 ($T_3$) | 0.06335 | 22 | 0.05626 | 28 | $1.09 \times 10^{-2}$ |

TABLE 49 t-test comparison of seedling photosynthetic efficiency between transgenic seedlings and pooled non-transgenic segregants after 18 days of growth on low ammonium nitrate.

| Line | Events | Transgenic | | Pooled Non-Transgenics | | t-test |
|---|---|---|---|---|---|---|
| | | Fv/Fm | n | Fv/Fm | n | p-value |
| ME13087 | ME13087-01 ($T_2$) | 0.59761 | 23 | 0.56163 | 38 | $9.61 \times 10^{-3}$ |
| ME13087 | ME13087-01 ($T_3$) | 0.61247 | 15 | 0.56163 | 38 | $5.99 \times 10^{-4}$ |
| ME13087 | ME13087-02 ($T_2$) | 0.63400 | 39 | 0.58532 | 34 | $9.30 \times 10^{-3}$ |
| ME13087 | ME13087-02 ($T_3$) | 0.63442 | 26 | 0.58532 | 34 | $1.22 \times 10^{-2}$ |
| ME13087 | ME13087-03 ($T_2$) | 0.61429 | 38 | 0.55533 | 24 | $5.04 \times 10^{-3}$ |
| ME13087 | ME13087-03 ($T_3$) | 0.62283 | 35 | 0.55533 | 24 | $3.31 \times 10^{-3}$ |
| ME13087 | ME13087-04 ($T_2$) | 0.62714 | 28 | 0.60068 | 56 | $3.02 \times 10^{-2}$ |
| ME13087 | ME13087-04 ($T_3$) | 0.64543 | 7 | 0.60068 | 56 | $9.04 \times 10^{-3}$ |

Events -01, -02, -03 and -04 segregated 2:1, 3:1, 3:1 and 2:1 respectively (R:S) for FINALE™ resistance in the T2 generation.

Events -01, -02, -03 and -04 of ME13087 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 46—Analysis of ME13106 Events

ME13106 contains Ceres Clone: 986438 (SEQ ID NO:1156) from *Zea mays*, which encodes a 188 amino acid protein of unknown function. Evaluation of low-nitrogen tolerance for ME13106 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13106 seedlings is shown in Table 50. ME13106 events were also tested for enhanced growth on the low ammonium nitrate media. No significant differences between the transgenics and the controls were observed.

Events -03 and -04 segregated 1:1 and 3:1 respectively (R:S) for FINALE™ resistance in the $T_2$ generation.

Events -03 and -04 of ME13106 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 47—Analysis of ME13107 Events

ME13107 contains Ceres Clone: 996227 (SEQ ID NO:1158) from *Zea mays*, which encodes a 240 amino acid zein seed storage protein. Evaluation of low-nitrogen tolerance for ME13107 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -04 and -05, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13107 seedlings is shown in Table 51.

TABLE 50 t-test comparison of seedling photosynthetic efficiency between transgenic seedlings and pooled non-transgenic segregants after 18 days of growth on low ammonium nitrate.

| Line | Events | Transgenic | | Pooled Non-Transgenics | | t-test |
|---|---|---|---|---|---|---|
| | | Fv/Fm | n | Fv/Fm | n | p-value |
| ME13106 | ME13106-03 ($T_2$) | 0.62726 | 27 | 0.58600 | 43 | $1.50 \times 10^{-2}$ |
| ME13106 | ME13106-03 ($T_3$) | 0.65163 | 30 | 0.58600 | 43 | $1.69 \times 10^{-4}$ |
| ME13106 | ME13106-04 ($T_2$) | 0.60836 | 36 | 0.55876 | 25 | $2.62 \times 10^{-2}$ |
| ME13106 | ME13106-04 ($T_3$) | 0.64250 | 38 | 0.55876 | 25 | $5.01 \times 10^{-4}$ |

TABLE 51 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13107 | ME13107-02 ($T_2$) | 0.63122 | 37 | 0.56643 | 21 | $1.07 \times 10^{-2}$ |
| ME13107 | ME13107-02 ($T_3$) | 0.63848 | 29 | 0.56643 | 21 | $6.03 \times 10^{-3}$ |
| ME13107 | ME13107-04 ($T_2$) | 0.62948 | 27 | 0.55918 | 50 | $2.07 \times 10^{-5}$ |
| ME13107 | ME13107-04 ($T_3$) | 0.63019 | 21 | 0.55918 | 50 | $6.72 \times 10^{-5}$ |
| ME13107 | ME13107-05 ($T_2$) | 0.61952 | 29 | 0.54440 | 48 | $7.85 \times 10^{-5}$ |
| ME13107 | ME13107-05 ($T_3$) | 0.62185 | 20 | 0.54440 | 48 | $4.02 \times 10^{-5}$ |

ME13107 events were also tested for enhanced growth on the low ammonium nitrate media. Two events, -02 and -04, showed significantly enhanced growth on low ammonium nitrate-containing media relative to the internal controls in $T_2$ generation at p≤0.05 using a one-tailed t-test assuming unequal variance. In this study, the seedling area for transgenic plants within an event was compared to the seedling area for non-transgenic segregants pooled across the same line. A summary of enhanced growth under low ammonium nitrate growth conditions of ME13071 seedlings is shown in Table 52.

TABLE 2 t-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME13107 | ME13107-02 ($T_2$) | 0.07738 | 37 | 0.06919 | 203 | $3.63 \times 10^{-4}$ |
| ME13107 | ME13107-02 ($T_3$) | 0.07688 | 29 | 0.06919 | 203 | $4.60 \times 10^{-2}$ |
| ME13107 | ME13107-04 ($T_2$) | 0.07514 | 27 | 0.06919 | 203 | $3.18 \times 10^{-2}$ |
| ME13107 | ME13107-04 ($T_3$) | 0.07585 | 21 | 0.06919 | 203 | $2.27 \times 10^{-2}$ |

Events -02, -04 and -05 segregated 3:1, 1:1 and 2:1 respectively (R:S) for FINALE™ resistance in the $T_2$ generation.

Events -02, -04 and -05 of ME13107 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 48—Analysis of ME13108 Events

ME13108 contains Ceres Clone: 996263 (SEQ ID NO:1165) from *Zea mays*, which encodes an 84 amino acid BRICK1 protein. Evaluation of low-nitrogen tolerance for ME13108 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -01, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13108 seedlings is shown in Table 53. ME13108 events were also tested for enhanced growth on the low ammonium nitrate media. No significant differences between the transgenics and the controls were observed.

TABLE 53 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13108 | ME13108-01 ($T_2$) | 0.56703 | 36 | 0.53932 | 195 | $1.97 \times 10^{-2}$ |
| ME13108 | ME13108-01 ($T_3$) | 0.59250 | 26 | 0.53932 | 195 | $3.64 \times 10^{-4}$ |
| ME13108 | ME13108-04 ($T_2$) | 0.60032 | 37 | 0.53932 | 195 | $3.37 \times 10^{-7}$ |
| ME13108 | ME13108-04 ($T_3$) | 0.60463 | 30 | 0.53932 | 195 | $4.10 \times 10^{-5}$ |
| ME13108 | ME13108-05 ($T_2$) | 0.60727 | 30 | 0.53932 | 195 | $4.97 \times 10^{-9}$ |
| ME13108 | ME13108-05 ($T_3$) | 0.61850 | 32 | 0.53932 | 195 | $2.35 \times 10^{-9}$ |

Events -01, -04 and -05 segregated 3:1 (R:S) for FINALE™ resistance in the $T_2$ generation.

Events -01, -04 and -05 of ME13108 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 49—Analysis of ME13110 Events

ME13110 contains Ceres Clone: 988083 (SEQ ID NO:1184) from *Zea mays*, which encodes a 188 amino acid protein of unknown function. Evaluation of low-nitrogen tolerance for ME13110 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -03, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13110 seedlings is shown in Table 54. ME13110 events were also tested for enhanced growth on the low ammonium nitrate media. No significant differences between the transgenics and the controls were observed.

TABLE 54 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13110 | ME13110-03 ($T_2$) | 0.5721 | 34 | 0.3948 | 16 | $8.92 \times 10^{-3}$ |
| ME13110 | ME13110-03 ($T_3$) | 0.5773 | 24 | 0.4583 | 26 | $4.58 \times 10^{-4}$ |
| ME13110 | ME13110-04 ($T_2$) | 0.5651 | 35 | 0.4243 | 15 | $4.34 \times 10^{-2}$ |
| ME13110 | ME13110-04 ($T_3$) | 0.6000 | 10 | 0.4594 | 40 | $3.29 \times 10^{-3}$ |
| ME13110 | ME13110-05 ($T_2$) | 0.5143 | 28 | 0.3809 | 22 | $2.24 \times 10^{-2}$ |
| ME13110 | ME13110-05 ($T_3$) | 0.5278 | 28 | 0.3688 | 21 | $1.28 \times 10^{-2}$ |

Events -03, -04 and -05 segregated 3:1, 1:1 and 3:1 respectively (R:S) for FINALE™ resistance in the $T_2$ generation.

Events -03, -04 and -05 of ME13110 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 50—Analysis of ME13125 Events

ME13125 contains Ceres Clone: 732 (At3g50880, SEQ ID NO:1193) from *Arabidopsis thaliana*, which encodes a 188 amino acid protein of unknown function. Evaluation of low-nitrogen tolerance for ME13125 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -01, -03 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13125 seedlings is shown in Table 55. ME13125 events were also tested for enhanced growth on the low ammonium nitrate media. No significant differences between the transgenics and the controls were observed.

TABLE 55 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13125 | ME13125-01 ($T_2$) | 0.61129 | 42 | 0.53829 | 125 | $4.82 \times 10^{-7}$ |
| ME13125 | ME13125-01 ($T_3$) | 0.61929 | 38 | 0.53829 | 125 | $1.96 \times 10^{-7}$ |
| ME13125 | ME13125-03 ($T_2$) | 0.63360 | 45 | 0.53829 | 125 | $3.05 \times 10^{-13}$ |
| ME13125 | ME13125-03 ($T_3$) | 0.62218 | 44 | 0.53829 | 125 | $3.81 \times 10^{-9}$ |
| ME13125 | ME13125-05 ($T_2$) | 0.61565 | 31 | 0.53829 | 125 | $4.12 \times 10^{-8}$ |
| ME13125 | ME13125-05 ($T_3$) | 0.58469 | 16 | 0.53829 | 125 | 0.05 |

Events -01, -03 and -05 segregated 3:1, 15:1 and 2:1 respectively (R:S) for FINALE™ resistance in the $T_2$ generation.

Events -01, -03 and -05 of ME13125 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 51—Analysis of ME13149 Events

ME13149 contains Ceres Clone: 2267 (At2g24765, SEQ ID NO:1209) from *Arabidopsis thaliana*, which encodes a 182 amino acid ADP-ribosylation factor 3 protein. Evaluation of low-nitrogen tolerance for ME13149 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME13149 seedlings is shown in Table 56. ME13149 events were also tested for enhanced growth on the low ammonium nitrate media. No significant differences between the transgenics and the controls were observed.

or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 52—Analysis of ME13151 Events

ME13151 contains Ceres Clone: 39358 (At3g25150, SEQ ID NO:1273) from *Arabidopsis thaliana*, which encodes a 488 amino acid nuclear transport factor 2 (NTF2) domain protein. Evaluation of low-nitrogen tolerance for ME13151 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at p≤0.05 using a one-tailed t-test assuming unequal variance. A summary of photosynthetic efficiency of ME13151 seedlings is shown in Table 57. ME13151 events were also tested for enhanced growth on the low ammonium nitrate media. No significant differences between the transgenics and the controls were observed.

TABLE 56 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13149 | ME13149-02 ($T_2$) | 0.55623 | 30 | 0.51138 | 55 | $2.29 \times 10^{-2}$ |
| ME13149 | ME13149-02 ($T_3$) | 0.54818 | 17 | 0.51138 | 55 | $4.56 \times 10^{-2}$ |
| ME13149 | ME13149-03 ($T_2$) | 0.55998 | 42 | 0.51138 | 55 | $5.11 \times 10^{-3}$ |
| ME13149 | ME13149-03 ($T_3$) | 0.58450 | 24 | 0.51138 | 55 | $2.77 \times 10^{-4}$ |

Events -02 and -03 segregated 2:1 and 15:1 respectively (R:S) for FINALE™ resistance in the $T_2$ generation.

Events -02 and -03 of ME13149 exhibited no statistically relevant negative phenotypes. That is, there was no detectable reduction in germination rate, the transgenic plants appeared wild type in all instances; there was no observable

TABLE 57

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13151 | ME13151-01 ($T_2$) | 0.62593 | 44 | 0.53141 | 17 | $8.58 \times 10^{-4}$ |
| ME13151 | ME13151-01 ($T_3$) | 0.59936 | 33 | 0.53141 | 17 | $1.21 \times 10^{-2}$ |
| ME13151 | ME13151-02 ($T_2$) | 0.59879 | 39 | 0.46956 | 16 | $3.08 \times 10^{-5}$ |
| ME13151 | ME13151-02 ($T_3$) | 0.59566 | 32 | 0.46956 | 16 | $4.28 \times 10^{-5}$ |

Events -01 and -02 segregated 9:1 and 6:1 respectively (R:S) for FINALE™ resistance in the T2 generation.

Events -01 and -02 of ME13151 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 53—Analysis of ME13153 Events

ME13153 contains Ceres Clone: 115046 (At3g17760, SEQ ID NO:1301) from *Arabidopsis thaliana*, which encodes a 494 amino acid glutamate decarboxylase. Evaluation of low-nitrogen tolerance for ME13153 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13153 seedlings is shown in Table 58. ME13153 events were also tested for increased photosynthetic efficiency on the low nitrate media. No significant differences between the transgenics and the controls were observed.

the rosette area 7 days post-bolting. Events -03 and -04 yielded slightly less seed per plant compared to the controls, but these differences are not significant at $p \leq 0.10$.

Example 54—Analysis of ME13177 Events

ME13177 contains Ceres Clone: 339439 (SEQ ID NO:1341) from *Zea mays*, which encodes a 345 amino acid cyclin C-terminal domain protein. Evaluation of low-nitrogen tolerance for ME13177 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13177 seedlings is shown in Table 59. ME13177 events were also tested for enhanced growth on the low ammonium nitrate media. No significant differences between the transgenics and the controls were observed.

TABLE 58

T-test comparison of seedling photosynthetic efficiency between transgenic seedlings and non-transgenic segregants after 14 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13153 | ME13153-03 ($T_2$) | 0.62 | 34 | 0.56 | 16 | $3.0 \times 10^{-2}$ |
| ME13153 | ME13153-03 ($T_3$) | 0.60 | 19 | 0.54 | 22 | $2.9 \times 10^{-2}$ |
| ME13153 | ME13153-04 ($T_2$) | 0.57 | 32 | 0.50 | 18 | $4.3 \times 10^{-2}$ |
| ME13153 | ME13153-04 ($T_3$) | 0.61 | 24 | 0.55 | 24 | $2.1 \times 10^{-2}$ |

Events -03 and -04 segregated 3:1 (R:S) for FINALE™ resistance in the $T_2$ generation.

Events -03 and -04 of ME13153 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of

TABLE 59 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13177 | ME13177-01 ($T_2$) | 0.6315 | 32 | 0.6112 | 175 | $2.43 \times 10^{-2}$ |
| ME13177 | ME13177-01 ($T_3$) | 0.6407 | 29 | 0.6112 | 175 | $7.33 \times 10^{-3}$ |
| ME13177 | ME13177-02 ($T_2$) | 0.6400 | 41 | 0.6112 | 175 | $1.23 \times 10^{-3}$ |
| ME13177 | ME13177-02 ($T_3$) | 0.6499 | 20 | 0.6112 | 175 | $6.47 \times 10^{-3}$ |

Events -01 and -02 segregated 2:1 and 3:1 respectively (R:S) for FINALE™ resistance in the $T_2$ generation.

Events -01 and -02 of ME13177 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 55—Analysis of ME13200 Events

ME13200 contains Ceres Clone: 896483 (SEQ ID NO:1384) from Zea mays, which encodes an 85 amino acid myb family transcription factor. Evaluation of low-nitrogen tolerance for ME13200 in $T_2$ and $T_3$ was conducted under the same conditions as described in Examples 2 and 3. A summary of the enhanced growth of ME13200 events on low ammonium nitrate-containing media is shown in Table 60. In this study, the seedling area for transgenic plants within an event was compared to the seedling area for non-transgenic segregants pooled across the same line. Two events, -03 and -04, were found significantly larger than the pooled non-transgenic segregants after 18 days of growth on low ammonium nitrate-containing media relative to the internal controls in both generations at p≤0.05 using a one-tailed t-test assuming unequal variance. ME13200 events were also tested for increased photosynthetic efficiency on the low ammonium nitrate media as well as for enhanced photosynthesis and growth on low nitrate media. No significant differences between the transgenics and the controls were observed.

Example 56—Analysis of ME13204 Events

ME13204 contains Ceres Clone: 995409 (SEQ ID NO:1408) from Zea mays, which encodes a 178 amino acid protein of unknown function. Evaluation of low-nitrogen tolerance for ME13204 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at p≤0.05 using a one-tailed t-test assuming unequal variance. A summary of photosynthetic efficiency of ME13204 seedlings is shown in Table 61. ME13204 events were also tested for enhanced growth on the low nitrate media as well as for enhanced growth and photosynthetic efficiency on low ammonium nitrate media. No significant differences between the transgenics and the controls were observed.

TABLE 60 t-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME13200 | ME13200-03 ($T_2$) | 0.07366 | 43 | 0.06342 | 35 | $4.09 \times 10^{-4}$ |
| ME13200 | ME13200-03 ($T_3$) | 0.08193 | 34 | 0.06342 | 35 | $2.37 \times 10^{-5}$ |
| ME13200 | ME13200-04 ($T_2$) | 0.07377 | 48 | 0.06342 | 35 | $4.87 \times 10^{-4}$ |
| ME13200 | ME13200-04 ($T_3$) | 0.07530 | 47 | 0.06342 | 35 | $1.88 \times 10^{-4}$ |

Events -03 and -04 segregated 3:1 and 15:1 respectively (R:S) for FINALE™ resistance in the $T_2$ generation.

Events -03 and -04 of ME13200 exhibited no statistically relevant negative phenotypes. That is, there was no detect-

TABLE 61

T-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME13204 | ME13204-01 ($T_2$) | 0.5874 | 45 | 0.5354 | 46 | $1.41 \times 10^{-2}$ |
| ME13204 | ME13204-01 ($T_3$) | 0.5932 | 36 | 0.5354 | 46 | $9.85 \times 10^{-3}$ |
| ME13204 | ME13204-05 ($T_2$) | 0.5855 | 34 | 0.5354 | 46 | $2.00 \times 10^{-2}$ |
| ME13204 | ME13204-05 ($T_3$) | 0.5998 | 20 | 0.5354 | 46 | $5.58 \times 10^{-3}$ | able reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Events -01 and -05 segregated 9:1 and 3:1 respectively (R:S) for FINALE™ resistance in the $T_2$ generation.

Events -01 and -05 of ME13204 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 57—Analysis of ME14649 Events

ME14649 contains Ceres Annot: 850581 (At5g01880, SEQ ID NO:1427) from *Arabidopsis thaliana*, which encodes a 159 amino acid zinc finger protein. Evaluation of low-nitrogen tolerance for ME14649 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME14649 seedlings is shown in Table 62. ME14649 events were also tested for enhanced growth on the low ammonium nitrate media. No significant differences between the transgenics and the controls were observed.

Example 58—Analysis of ME16546 Events

ME16546 contains Ceres Annot: 862321 (At2g45360, SEQ ID NO:1462) from *Arabidopsis thaliana*, which encodes a 215 amino acid protein of unknown function. Evaluation of low-nitrogen tolerance for ME16546 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME16546 seedlings is shown in Table 63. ME16546 events were also tested for enhanced growth on the low ammonium nitrate media. No significant differences between the transgenics and the controls were observed.

TABLE 62 t-test comparison of seedling photosynthetic efficiency between transgenic seedlings and pooled non-transgenic segregants after 18 days of growth on low ammonium nitrate.

| Line | Events | Transgenic | | Pooled Non-Transgenics | | t-test |
| | | Fv/Fm | n | Fv/Fm | n | p-value |
| --- | --- | --- | --- | --- | --- | --- |
| ME14649 | ME14649-02 ($T_2$) | 0.59789 | 35 | 0.54533 | 30 | $1.54 \times 10^{-4}$ |
| ME14649 | ME14649-02 ($T_3$) | 0.58154 | 26 | 0.54533 | 30 | $3.42 \times 10^{-2}$ |
| ME14649 | ME14649-03 ($T_2$) | 0.61875 | 28 | 0.56539 | 33 | $2.03 \times 10^{-3}$ |
| ME14649 | ME14649-03 ($T_3$) | 0.62630 | 27 | 0.56539 | 33 | $9.18 \times 10^{-4}$ |

Events -02 and -03 segregated 3:1 and 2:1 respectively (R:S) for FINALE™ resistance in the $T_2$ generation.

Events -02 and -03 of ME14649 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

TABLE 63 t-test comparison of seedling photosynthetic efficiency between transgenic seedlings and pooled non-transgenic segregants after 18 days of growth on low ammonium nitrate.

| Line | Events | Transgenic | | Pooled Non-Transgenics | | t-test |
| | | Fv/Fm | n | Fv/Fm | n | p-value |
| --- | --- | --- | --- | --- | --- | --- |
| ME16546 | ME16546-04 ($T_2$) | 0.59891 | 33 | 0.56124 | 130 | $2.21 \times 10^{-4}$ |
| ME16546 | ME16546-04 ($T_3$) | 0.57924 | 41 | 0.56124 | 130 | $3.77 \times 10^{-2}$ |
| ME16546 | ME16546-05 ($T_2$) | 0.58861 | 36 | 0.56124 | 130 | $7.17 \times 10^{-3}$ |
| ME16546 | ME16546-05 ($T_3$) | 0.61763 | 27 | 0.56124 | 130 | $3.25 \times 10^{-6}$ |

Events -04 and -05 segregated 2:1 and 3:1 respectively (R:S) for FINALE™ resistance in the $T_2$ generation.

Events -04 and -05 of ME16546 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 59—Analysis of ME17457 Events

ME17457 contains Ceres Annot: 839064 (At1g80600, SEQ ID NO:1478) from *Arabidopsis thaliana*, which encodes a 457 acetylornithine aminotransferase, a member of the Class-III aminotransferase family. This is a homolog of Ceres Clone: 19586 (ME01463, SEQ ID NO:76). Evaluation of low-nitrogen tolerance for ME17457 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -02, -03, -05 and -06, showed significantly increased photosynthetic efficiency on low ammonium nitrate-containing media relative to the internal controls in both generations at p≤0.05 using a one-tailed t-test assuming unequal variance. A summary of photosynthetic efficiency of ME17457 seedlings is shown in Table 64. ME17457 events were also tested for enhanced growth on the low ammonium nitrate media. No significant differences between the transgenics and the controls were observed.

Example 60—Analysis of ME17567 Events

ME17567 contains Ceres Annot: 864666 (At1g16320, SEQ ID NO:1490) from *Arabidopsis thaliana*, which encodes a 273 amino acid protein of unknown function. Evaluation of low-nitrogen tolerance for ME17567 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -04, showed significantly increased photosynthetic efficiency on low nitrate-containing media relative to the internal controls in both generations at p≤0.05 using a one-tailed t-test assuming unequal variance. A summary of photosynthetic efficiency of ME17567 seedlings is shown in Table 65. ME17567 events were also tested for enhanced growth on the low nitrate media as well as enhanced photosynthetic efficiency and growth on low ammonium nitrate media. No significant differences between the transgenics and the controls were observed.

TABLE 64 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME17457 | ME17457-02 ($T_2$) | 0.60800 | 21 | 0.50878 | 46 | $6.99 \times 10^{-4}$ |
| ME17457 | ME17457-02 ($T_3$) | 0.59539 | 18 | 0.50878 | 46 | $9.02 \times 10^{-3}$ |
| ME17457 | ME17457-03 ($T_2$) | 0.55164 | 11 | 0.49673 | 45 | $3.45 \times 10^{-2}$ |
| ME17457 | ME17457-03 ($T_3$) | 0.57356 | 18 | 0.49673 | 45 | $2.49 \times 10^{-3}$ |
| ME17457 | ME17457-05 ($T_2$) | 0.52928 | 18 | 0.42672 | 32 | $2.23 \times 10^{-3}$ |
| ME17457 | ME17457-05 ($T_3$) | 0.56660 | 25 | 0.42672 | 32 | $5.97 \times 10^{-5}$ |
| ME17457 | ME17457-06 ($T_2$) | 0.54088 | 33 | 0.47350 | 30 | $3.59 \times 10^{-4}$ |
| ME17457 | ME17457-06 ($T_3$) | 0.52210 | 21 | 0.47350 | 30 | $2.03 \times 10^{-2}$ |

Events -02, -03 and -05 segregated 1:1, and Event -06 segregated 3:1 (R:S) for FINALE™ resistance in the $T_2$ generation.

Events -02, -03, -05 and -06 of ME17457 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was

TABLE 65 t-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME17567 | ME17567-01 ($T_2$) | 0.605455 | 33 | 0.474791 | 67 | $9.69 \times 10^{-10}$ |
| ME17567 | ME17567-01 ($T_3$) | 0.6244 | 20 | 0.474791 | 67 | $6.79 \times 10^{-13}$ |
| ME17567 | ME17567-04 ($T_2$) | 0.57727 | 37 | 0.474791 | 67 | $1.22 \times 10^{-7}$ |
| ME17567 | ME17567-04 ($T_3$) | 0.615143 | 35 | 0.474791 | 67 | $5.95 \times 10^{-13}$ |

Events -01 and -04 segregated 2:1 and 3:1 respectively (R:S) for FINALE™ resistance in the $T_2$ generation.

Events -01 and -04 of ME17567 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 61—Analysis of ME17932 Events

ME17932 contains Ceres Annot: 875012 (At3g53560, SEQ ID NO:1509) from *Arabidopsis thaliana*, which encodes a 340 amino acid chloroplast lumen common family protein. Evaluation of low-nitrogen tolerance for ME17932 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -01, -02, -03 and -05, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME17932 seedlings is shown in Table 66. ME17932 events were also tested for enhanced growth on the low ammonium nitrate media. No significant differences between the transgenics and the controls were observed.

Example 62—Analysis of ME17936 Events

ME17936 contains Ceres Annot: 874016 (At3g42800, SEQ ID NO:1524) from *Arabidopsis thaliana*, which encodes a 341 amino acid protein of unknown function. Evaluation of low-nitrogen tolerance for ME17936 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at $p \leq 0.05$ using a one-tailed t-test assuming unequal variance. A summary of photosynthetic efficiency of ME17936 seedlings is shown in Table 67. ME17936 events were also tested for enhanced growth on the low nitrate media as well as for increased photosynthetic efficiency and enhanced growth on low ammonium nitrate media. No significant differences between the transgenics and the controls were observed.

TABLE 66 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME17932 | ME17932-01 ($T_2$) | 0.6292 | 36 | 0.6094 | 194 | 0.050 |
| ME17932 | ME17932-01 ($T_3$) | 0.6640 | 22 | 0.6094 | 194 | $2.82 \times 10^{-6}$ |
| ME17932 | ME17932-02 ($T_2$) | 0.6351 | 32 | 0.6094 | 194 | $1.05 \times 10^{-2}$ |
| ME17932 | ME17932-02 ($T_3$) | 0.6373 | 20 | 0.6094 | 194 | $2.82 \times 10^{-2}$ |
| ME17932 | ME17932-03 ($T_2$) | 0.6504 | 45 | 0.6094 | 194 | $1.80 \times 10^{-5}$ |
| ME17932 | ME17932-03 ($T_3$) | 0.6708 | 20 | 0.6094 | 194 | $8.38 \times 10^{-4}$ |
| ME17932 | ME17932-05 ($T_2$) | 0.6349 | 24 | 0.6094 | 194 | $3.23 \times 10^{-2}$ |
| ME17932 | ME17932-05 ($T_3$) | 0.6615 | 11 | 0.6094 | 194 | $1.16 \times 10^{-3}$ |

Events -01, -02, -03 and -05 segregated 3:1, 2:1, 15:1 and 1:1 respectively (R:S) for FINALE™ resistance in the $T_2$ generation.

Events -01, -02, -03 and -05 of ME17932 exhibited no statistically relevant negative phenotypes. That is, there was no detectable reduction in germination rate, the transgenic plants appeared wild type in all instances; there was no

TABLE 67 t-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME17936 | ME17936-01 ($T_2$) | 0.64778 | 36 | 0.61762 | 39 | $4.68 \times 10^{-3}$ |
| ME17936 | ME17936-01 ($T_3$) | 0.66081 | 21 | 0.61762 | 39 | $4.33 \times 10^{-5}$ |
| ME17936 | ME17936-05 ($T_2$) | 0.63189 | 35 | 0.61444 | 50 | $2.73 \times 10^{-2}$ |
| ME17936 | ME17936-05 ($T_3$) | 0.64257 | 14 | 0.61444 | 50 | $2.56 \times 10^{-2}$ |

Events -01 and -05 segregated 3:1 (R:S) for FINALE™ resistance in the $T_2$ generation.

Events -01 and -05 of ME17936 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 63—Analysis of ME18275 Events

ME18275 contains Ceres Annot: 827304 (At2g18300, SEQ ID NO:1536) from *Arabidopsis thaliana*, which encodes a 335 amino acid helix-loop-helix DNA-binding domain. Evaluation of low-nitrogen tolerance for ME18275 in $T_2$ and $T_3$ was conducted under the same conditions as described in Examples 2 and 3. A summary of the enhanced growth of ME18275 events on low nitrate-containing media is shown in Table 68. In this study, the seedling area for transgenic plants within an event was compared to the seedling area for non-transgenic segregants pooled across the same line. Three events, -01, -02 and -03, were found significantly larger than the pooled non-transgenic segregants after 14 days of growth on low nitrate-containing media relative to the internal controls in both generations at $p \leq 0.05$, using a one-tailed t-test assuming unequal variance. ME18275 events were also tested for photosynthetic efficiency on the low nitrate media as well as for increased photosynthetic efficiency and enhanced growth on low ammonium nitrate media. No significant differences between the transgenics and the controls were observed.

TABLE 68 t-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME18275 | ME18275-01 ($T_2$) | 0.09574 | 40 | 0.05961 | 10 | $3.24 \times 10^{-10}$ |
| ME18275 | ME18275-01 ($T_3$) | 0.07807 | 32 | 0.05142 | 15 | $3.71 \times 10^{-4}$ |
| ME18275 | ME18275-02 ($T_2$) | 0.11903 | 33 | 0.05884 | 16 | $6.21 \times 10^{-14}$ |
| ME18275 | ME18275-02 ($T_3$) | 0.08552 | 22 | 0.04208 | 24 | $2.82 \times 10^{-5}$ |
| ME18275 | ME18275-03 ($T_2$) | 0.10281 | 39 | 0.06789 | 9 | $9.48 \times 10^{-8}$ |
| ME18275 | ME18275-03 ($T_3$) | 0.09136 | 20 | 0.05646 | 26 | $9.46 \times 10^{-4}$ |

Events -01, -02 and -03 segregated 3:1 (R:S) for FINALE™ resistance in the $T_2$ generation.

Events -01, -02 and -03 of ME18275 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 64—Analysis of ME18924 Events

ME18924 contains Ceres Annot: 869192 (At1g72160, SEQ ID NO:1553) from *Arabidopsis thaliana*, which encodes a 490 amino acid emp24/gp25L/p24 family protein. Evaluation of low-nitrogen tolerance for ME18924 in $T_2$ and $T_3$ was conducted under the same conditions as described in Examples 2 and 3. A summary of photosynthetic efficiency of ME18924 seedlings is shown in Table 69. In this study, the seedling photosynthetic efficiency was measured as Fv/Fm comparing transgenic plants within an event to non-transgenic segregants pooled across the same plate. Three events, -02, -04 and -05, showed significantly increased photosynthetic efficiency on low ammonium nitrate-containing media relative to the internal controls in both generations at $p \leq 0.05$, using a one-tailed t-test assuming unequal variance.

TABLE 69 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME18924 | ME18924-02 ($T_2$) | 0.6515 | 46 | 0.6223 | 138 | $6.43 \times 10^{-3}$ |
| ME18924 | ME18924-02 ($T_3$) | 0.6639 | 45 | 0.6223 | 138 | $1.52 \times 10^{-4}$ |
| ME18924 | ME18924-04 ($T_2$) | 0.6489 | 33 | 0.6223 | 138 | $2.72 \times 10^{-3}$ |
| ME18924 | ME18924-04 ($T_3$) | 0.6517 | 21 | 0.6223 | 138 | $1.58 \times 10^{-2}$ |
| ME18924 | ME18924-05 ($T_2$) | 0.6602 | 35 | 0.6223 | 138 | $5.55 \times 10^{-5}$ |
| ME18924 | ME18924-05 ($T_3$) | 0.6488 | 31 | 0.6223 | 138 | $4.25 \times 10^{-2}$ |

ME18924 events were also tested for enhanced growth on the low ammonium nitrate media. A summary of the enhanced growth of ME18924 events on low nitrate-containing media is shown in Table 70. In this study, the seedling area for transgenic plants within an event was compared to the seedling area for non-transgenic segregants pooled across the same line. Two events, -01 and -04, were found significantly larger than the pooled non-transgenic segregants after 18 days of growth on low ammonium nitrate-containing media relative to the internal controls in both generations at p≤0.05, using a one-tailed t-test assuming unequal variance.

TABLE 70 t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME18924 | ME18924-01 ($T_2$) | 0.06881 | 37 | 0.06311 | 138 | $1.31 \times 10^{-2}$ |
| ME18924 | ME18924-01 ($T_3$) | 0.07164 | 34 | 0.06311 | 138 | $7.43 \times 10^{-3}$ |
| ME18924 | ME18924-04 ($T_2$) | 0.08401 | 33 | 0.06311 | 138 | $5.64 \times 10^{-8}$ |
| ME18924 | ME18924-04 ($T_3$) | 0.07365 | 21 | 0.06311 | 138 | $3.82 \times 10^{-2}$ |

Events -01, -02, -04 and -05 segregated 3:1, 15:1, 2:1 and 2:1 respectively (R:S) for FINALE™ resistance in the $T_2$ generation.

Events -01, -02, -04 and -05 of ME18924 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 65—Analysis of ME19182 Events

ME19182 contains Ceres Annot: 876419 (At4g01480, SEQ ID NO:1576) from *Arabidopsis thaliana*, which encodes a 216 amino acid inorganic pyrophosphatase protein. Evaluation of low-nitrogen tolerance for ME19182 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME19182 seedlings is shown in Table 71. ME19182 events were also tested for enhanced growth on the low ammonium nitrate media. No significant differences between the transgenics and the controls were observed.

TABLE 71 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME19182 | ME19182-01 ($T_2$) | 0.64938 | 24 | 0.61988 | 154 | $2.47 \times 10^{-2}$ |
| ME19182 | ME19182-01 ($T_3$) | 0.65546 | 13 | 0.61988 | 154 | $1.08 \times 10^{-2}$ |
| ME19182 | ME19182-03 ($T_2$) | 0.64797 | 37 | 0.61988 | 154 | $3.84 \times 10^{-3}$ |
| ME19182 | ME19182-03 ($T_3$) | 0.65388 | 26 | 0.61988 | 154 | $3.15 \times 10^{-3}$ |

Events -01 and -03 segregated 2:1 and 3:1 respectively (R:S) for FINALE™ resistance in the T2 generation.

Events -01 and -03 of ME19182 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 66—Analysis of ME20628 Events

ME20628 contains Ceres Annot: 859276 (At2g21230, SEQ ID NO:175) from *Arabidopsis thaliana*, which encodes a 188 amino acid protein of unknown function. Evaluation of low-nitrogen tolerance for ME20628 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low nitrate-containing media relative to the internal controls in both generations at p≤0.05 using a one-tailed t-test assuming unequal variance. A summary of photosynthetic efficiency of ME20628 seedlings is shown in Table 72. ME20628 events were also tested for enhanced growth on the low nitrate media as well as for increased photosynthetic efficiency and enhanced growth on low ammonium nitrate media. No significant differences between the transgenics and the controls were observed.

TABLE 72 t-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME20628 | ME20628-03 ($T_2$) | 0.62771 | 42 | 0.58957 | 7 | $9.94 \times 10^{-3}$ |
| ME20628 | ME20628-03 ($T_3$) | 0.64375 | 20 | 0.61914 | 28 | $2.97 \times 10^{-2}$ |
| ME20628 | ME20628-04 ($T_2$) | 0.62439 | 38 | 0.59667 | 12 | $4.78 \times 10^{-2}$ |
| ME20628 | ME20628-04 ($T_3$) | 0.64768 | 22 | 0.61360 | 25 | $9.93 \times 10^{-4}$ |

Events -03 and -04 segregated 3:1 (R:S) for FINALE™ resistance in the $T_2$ generation.

Events -03 and -04 of ME20628 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 67—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al. (1998) *Proc. Natl. Acad. Sci. USA*, 95:6239-6244) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Missouri, USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NO:3, SEQ ID NO:49, SEQ ID NO:77, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1463, SEQ ID NO:1491, SEQ ID NO:1510, SEQ ID NO:1525, SEQ ID NO:1537, SEQ ID NO:1554, SEQ ID NO:1577, and SEQ ID NO:1437 are shown in FIGS. 1-57, respectively. Additional exemplary homologs are correlated to certain Figures in the Sequence Listing.

Example 68—Determination of Functional Homologs by Hidden Markov Models

Hidden Markov Models (HMMs) were generated by the program HMMER 2.3.2. To generate each HMM, the default HMMER 2.3.2 program parameters, configured for global alignments, were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO:3.

The procedure above was repeated and an HMM was generated for each group of sequences shown in FIGS. 2-57, using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

VIII. Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy sequence listing. A copy of the sequence listing is available in electronic form from the USPTO web site (https://seqdata.uspto.gov/?pageRequest=docDetail&DocID=US11981906B2). An electronic copy of the sequence listing will also be available from the USPTO upon request and payment of the fee set forth in 37 CFR 1.19(b)(3).

What is claimed is:

1. A method of increasing level of low-nitrogen tolerance in a plant, said method comprising
growing plant cells transformed with an exogenous nucleic acid molecule, said exogenous nucleic acid molecule comprising a heterologous promoter operably linked to a polynucleotide sequence encoding a polypeptide having 95 percent or greater amino acid sequence identity to the amino acid sequence of SEQ ID NO: 186; and
producing plants from said transformed plant cells; and
selecting for a transformed plant from said transformed plants that overexpresses said polypeptide and exhibits an increased level of low-nitrogen tolerance as compared to the corresponding level of low-nitrogen tolerance of a control plant of the same species that does not comprise said exogenous nucleic acid molecule.

2. The method of claim 1, wherein the polynucleotide sequence has 95 percent or greater nucleotide sequence identity to the nucleotide sequence of SEQ ID NO: 185.

3. The method of claim 1, wherein said polypeptide comprises the amino acid sequence of SEQ ID NO:186.

4. A transgenic plant cell transformed with an exogenous nucleic acid molecule, said exogenous nucleic acid molecule comprising a heterologous promoter operably linked to a polynucleotide sequence encoding a polypeptide having 95 percent or greater amino acid sequence identity to the amino acid sequence of SEQ ID NO:186, wherein a transformed plant comprising said transformed plant cell has been obtained and selected for having an increased level of low-nitrogen tolerance as compared to the corresponding level of low-nitrogen tolerance of a control plant of the same species that does not comprise said nucleic acid molecule.

5. The plant cell of claim 4, wherein the polynucleotide sequence has 95 percent or greater nucleotide sequence identity to the nucleotide sequence of SEQ ID NO:185.

6. A transgenic plant comprising the transformed plant cell of claim 4.

7. The transgenic plant of claim 6, wherein said plant is a member of a species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), and *Pennisetum glaucum* (pearl millet).

8. A product comprising a transgenic plant tissue from the transgenic plant according to claim 7, and wherein said product comprises said exogenous nucleic acid molecule.

9. A transgenic seed produced by the transgenic plant of claim 6, and wherein said transgenic seed comprises said exogenous nucleic acid molecule.

\* \* \* \* \*